(12) United States Patent
Colloca et al.

(10) Patent No.: US 11,254,710 B2
(45) Date of Patent: Feb. 22, 2022

(54) ADENOVIRUS POLYNUCLEOTIDES AND POLYPEPTIDES

(71) Applicant: GLAXOSMITHKLINE BIOLOGICALS, SA, Rixensart (BE)

(72) Inventors: Stefano Colloca, Rome (IT); Virginia Ammendola, Rome (IT); Fabiana Grazioli, Rome (IT); Alessandra Franz Vitelli, Rome (IT); Alfredo Nicosia, Naples (IT); Riccardo Cortese, Basel (IT)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 0 days.

(21) Appl. No.: 15/735,839

(22) PCT Filed: Jun. 10, 2016

(86) PCT No.: PCT/EP2016/063329
§ 371 (c)(1),
(2) Date: Dec. 12, 2017

(87) PCT Pub. No.: WO2016/198621
PCT Pub. Date: Dec. 15, 2016

(65) Prior Publication Data
US 2018/0170972 A1 Jun. 21, 2018

(30) Foreign Application Priority Data

Jun. 12, 2015 (GB) ...................................... 1510357
Aug. 19, 2015 (GB) ...................................... 1514772

(51) Int. Cl.
| | |
|---|---|
| C07H 21/04 | (2006.01) |
| C07K 14/005 | (2006.01) |
| C12N 15/86 | (2006.01) |
| C07K 14/075 | (2006.01) |
| C07K 14/75 | (2006.01) |
| A61K 39/12 | (2006.01) |
| C12N 15/861 | (2006.01) |
| A61K 39/155 | (2006.01) |
| A61K 39/21 | (2006.01) |
| C12N 7/00 | (2006.01) |
| A61K 39/00 | (2006.01) |

(52) U.S. Cl.
CPC ............ *C07K 14/005* (2013.01); *A61K 39/12* (2013.01); *A61K 39/155* (2013.01); *A61K 39/21* (2013.01); *C07K 14/075* (2013.01); *C07K 14/75* (2013.01); *C12N 7/00* (2013.01); *C12N 15/86* (2013.01); *C12N 15/861* (2013.01); *A61K 2039/5256* (2013.01); *C12N 2710/10321* (2013.01); *C12N 2710/10322* (2013.01); *C12N 2710/10343* (2013.01); *C12N 2710/10371* (2013.01); *C12N 2740/16234* (2013.01); *C12N 2750/14134* (2013.01); *C12N 2750/14143* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 2003/0147920 A1 | 8/2003 | Mossman et al. | |
| 2005/0227943 A1 | 10/2005 | Johnson et al. | |
| 2009/0104226 A1 | 10/2009 | Perri et al. | |
| 2010/0260799 A1* | 10/2010 | Roy | C12N 7/00 424/233.1 |
| 2012/0027788 A1* | 2/2012 | Colloca | A61K 39/235 424/186.1 |
| 2012/0321694 A1 | 12/2012 | Larocque et al. | |
| 2014/0314834 A1 | 10/2014 | Paya Cuenca et al. | |

FOREIGN PATENT DOCUMENTS

| | | |
|---|---|---|
| CN | 102131920 A | 7/2011 |
| CN | 102300872 A | 12/2011 |
| CN | 103442731 A | 12/2013 |
| CN | 104334188 A | 2/2015 |
| JP | 2007-518414 A | 7/2007 |
| JP | 2011-504751 A | 2/2011 |
| JP | 2011-521985 A | 7/2011 |
| JP | 2012-516679 A | 7/2012 |
| JP | 2014-504500 A | 2/2014 |
| WO | WO 03/000283 A1 | 1/2003 |

(Continued)

OTHER PUBLICATIONS

Furtado et al. Journal of Viorology, 1989, vol. 63, No. 8, pp. 3423-3434. (Year: 1989).*

Roberts, et al., "Hexon-chimaeric adenovirus serotype 5 vectors circumvent pre-existing anti-vector immunity." 2006, vol. 441, pp. 239-243.

(Continued)

*Primary Examiner* — Celine X Qian
(74) *Attorney, Agent, or Firm* — Birch, Stewart, Kolasch & Birch, LLP

(57) ABSTRACT

There is provided inter alia an isolated polynucleotide, wherein the polynucleotide encodes a polypeptide selected from the group consisting of:

(a) a polypeptide having the amino acid sequence according to SEQ ID NO: 1,
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polypeptide having the amino acid sequence according to SEQ ID NO: 3.

12 Claims, 15 Drawing Sheets
Specification includes a Sequence Listing.

(56) References Cited

FOREIGN PATENT DOCUMENTS

| WO | 2005071093 A2 | 8/2005 |
|---|---|---|
| WO | WO 2008/107370 A1 | 9/2008 |
| WO | 2009105084 A2 | 8/2009 |
| WO | 2009136977 A2 | 11/2009 |
| WO | 2009146902 A1 | 12/2009 |
| WO | 2010085984 A1 | 8/2010 |
| WO | 2010086189 A2 | 8/2010 |
| WO | WO 2011/150249 A1 | 12/2011 |
| WO | WO 2012/089231 A1 | 7/2012 |
| WO | WO 2013/006842 A2 | 1/2013 |
| WO | WO 2013/052799 A2 | 4/2013 |
| WO | WO 2013/116965 A1 | 8/2013 |
| WO | WO 2013/139911 A1 | 9/2013 |
| WO | WO 2014/019718 A1 | 2/2014 |
| WO | WO 2014/079642 A1 | 5/2014 |
| WO | WO 2015/189425 A1 | 12/2015 |
| WO | WO 2016/198599 A1 | 12/2016 |

OTHER PUBLICATIONS

Youil et al. "Hexon gene switch strategy . . . ", Human Gene Therapy, 13: 311-320, Jan. 2002.
Astray, R M, et al., "Rabies vaccine development by expression of recombinant viral glycoprotein", Archives of Virology, Springer Wien, AT, vol. 162, No. 2, Oct. 31, 2016, pp. 323-332.
Colloca, et al., "Vaccine Vectors Derived from a Large Collection of Simian Adenoviruses Induce Potent Cellular Immunity Across Multiple Species", Science Translational Medicine, American Association for the Advancement of Science (A A A S), US, vol. 4, No. 115, Jan. 1, 2012, pp. 47-55 XP009166675.
Connors M., et al., "Respiratory Syncytial Virus (RSV) F, G, M2 (22K), and N Proteins Each Induce Resistance to RSV Challenge, but Resistance Induced by M2 and N Proteins Is Relatively Short-Lived" Journal of Virology, vol. 65, No. 3, Mar. 1, 1991, pp. 1634-1637.
Database Geneseq [Online], XP-002778171, Sep. 24, 2015 (Sep. 24, 2015).
Ertl, H., et al., "Novel Vaccines to Human Rabies", PLOS Neglected Tropical Diseases, vol. 3, No. 9, Sep. 29, 2009 (Sep. 29, 2009), p. e515.
European Communication pursuant to Article 94(3) EPC for European Application No. 16730773.5, dated May 7, 2020.
Hennessy, et al., "Targeting Toll-like receptors: emerging therapeutics?", Nature reviews Drug discovery, vol. 9, Issue 4; Apr. 1, 2010, pp. 293-307.
Hsu et al., "Efficacy of adenovirus-vectored respiratory syncytial virus vaccines in a new ferret model," Vaccine, vol. 12, No. 7, 1994, pp. 607-612.
Indian Office Action for Indian Application No. 201717043018, dated May 24, 2021, with English translation.
Mossman, et al., "Development of a CTL vaccine for Her-2/neu usingpeptide-microspheres and adjuvants", Vaccine vol. 23, Issue 27, May 20, 2005, pp. 3545-3554.
Pierantoni A. et al., "Mucosal delivery of a vectored RSV vaccine is safe and elicitsprotective immunity in rodents and nonhuman primates." Molecular Therapy—Methods & Clinical Development, May 20, 2015, vol. 2, No. 15018 pp. 1-11.
Roy, et al., "Complete nucleotide sequences and genome organization of four chimpanzee adenoviruses", Virology, vol. 324, 2004, pp. 361-372.
Roy, et al., "Creation of a panel of vectors based on ape adenovirus isolates", The Journal of Gene Medicine, vol. 13, Dec. 17, 2010, pp. 17-25.
Tatsis, et al., "Adenoviruses as vaccine vectors", Molecular Therapy, 2004, vol. 10, No. 4, Oct. 2004, p. 616-629.
Xiang Z.Q. et al., "Protection of non-human primates against rabies with an adenovirus recombinant vaccine", Virology, vol. 450, Jan. 9, 2014 (Jan. 9, 2014), pp. 243-249.
Yu et al., "Toll-like receptors expressed in tumor cells: targets for therapy", Cancer Immunol Immunother, vol. 57, Issue 9; pp. 1271-1278; Feb. 7, 2008.
Zhou, et al., "A Chimpanzee-Origin Adenovirus Vector Expressing the Rabies Virus Glycoprotein as an Oral Vaccine against Inhalation Infection with Rabies Virus", Molecular Therapy, vol. 14, No. 5, Nov. 2006, pp. 662-672.
Wang, D., "A complex adenovirus vaccine against chikungunya virus provides complete protection against viraemia and arthritis" Vaccine, Mar. 24, 2011, 29(15), pp. 2803-2809.

* cited by examiner

ADENOVIRUS POLYNUCLEOTIDES AND POLYPEPTIDES

FIELD OF THE INVENTION

The present invention relates to isolated polynucleotide and polypeptide sequences derived from novel chimp adenovirus ChAd155, as well as to recombinant polynucleotides, vectors, adenoviruses, cells and compositions comprising said polynucleotide and polypeptide sequences.

BACKGROUND OF THE INVENTION

Adenovirus has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Recombinant adenoviruses are useful in gene therapy and as vaccines. Viral vectors based on chimpanzee adenovirus represent an alternative to the use of human derived Ad vectors for the development of genetic vaccines. Adenoviruses isolated from chimpanzees are closely related to adenoviruses isolated from humans as demonstrated by their efficient propagation in cells of human origin. However, since human and chimp adenoviruses are close relatives, serologic cross reactivity between the two virus species is possible.

There is a demand for vectors which effectively deliver molecules to a target and minimize the effect of pre-existing immunity to selected adenovirus serotypes in the population. One aspect of pre-existing immunity that is observed in humans is humoral immunity, which can result in the production and persistence of antibodies that are specific for adenoviral proteins. The humoral response elicited by adenovirus is mainly directed against the three major structural capsid proteins: fiber, penton and hexon.

Vectors, compositions and methods of the present invention may have one or more following improved characteristics over the prior art, including but not limited to higher productivity, improved immunogenicity and increased transgene expression.

SUMMARY OF THE INVENTION

There is provided an isolated polynucleotide, wherein the polynucleotide encodes a polypeptide selected from the group consisting of:
(a) a polypeptide having the amino acid sequence according to SEQ ID NO: 1,
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polypeptide having the amino acid sequence according to SEQ ID NO: 3.

Also provided is a recombinant polynucleotide comprising a polynucleotide selected from the group consisting of:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polynucleotide which encodes a polypeptide having the amino acid sequence according to SEQ ID NO: 3.

Also provided is a recombinant vector comprising a polynucleotide selected from the group consisting of:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polynucleotide which encodes a polypeptide having the amino acid sequence according to SEQ ID NO: 3.

Also provided is a recombinant adenovirus comprising at least one polynucleotide or polypeptide selected from the group consisting of:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(f) a polypeptide having the amino acid sequence according to SEQ ID NO: 3.

Also provided is a composition comprising at least one of the following:
(a) a polynucleotide which encodes a polypeptide having the amino acid sequence according to SEQ ID NO: 1,
(b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(f) a polypeptide having the amino acid sequence according to SEQ ID NO: 3,
(g) a vector comprising a polynucleotide as described in (a), (b) or (c) above, and
(h) a recombinant adenovirus comprising a polynucleotide as described in (a), (b) or (c) above, and a pharmaceutically acceptable excipient.

Also provided is a cell comprising at least one of the following:
(a) a polynucleotide which encodes a polypeptide having the amino acid sequence according to SEQ ID NO: 1, (b) a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(c) a polynucleotide which encodes a polypeptide having the amino acid sequence according to SEQ ID NO: 3,
(d) a polypeptide having the amino acid sequence according to SEQ ID NO: 1,
(e) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1,
(f) a polypeptide having the amino acid sequence according to SEQ ID NO: 3,
(g) a vector comprising a polynucleotide as described in (a), (b) or (c) above, and
(h) a recombinant adenovirus comprising a polynucleotide as described in (a), (b) or (c) above,
and a pharmaceutically acceptable excipient.

Also provided is an isolated adenoviral polypeptide selected from the group consisting of:
(a) a polypeptide having the amino acid sequence according to SEQ ID NO: 1,
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1, and
(c) a polypeptide having the amino acid sequence according to SEQ ID NO: 3.

Also provided is an isolated polynucleotide, vector, recombinant adenovirus, composition or cell comprising or consisting of the sequence according to SEQ ID NO: 6.

DESCRIPTION OF THE FIGURES

FIG. 1A-C—Alignment of fiber protein sequences from the indicated simian adenoviruses.
  ChAd3 (SEQ ID NO:27)
  PanAd3 (SEQ ID NO:28)
  ChAd17 (SEQ ID NO:29)
  ChAd19 (SEQ ID NO:30)
  ChAd24 (SEQ ID NO:31)
  ChAd155 (SEQ ID NO:1)
  ChAd11 (SEQ ID NO:32)
  ChAd20 (SEQ ID NO:33)
  ChAd31 (SEQ ID NO:34)
  PanAd1 (SEQ ID NO:35)
  PanAd2 (SEQ ID NO:36)
FIG. 2—Flow diagram for production of specific ChAd155 BAC and plasmid vectors
FIG. 3—Species C BAC Shuttle #1365 schematic
FIG. 4—pArsChAd155 Ad5E4orf6-2 (#1490) schematic
FIG. 5—pChAd155/RSV schematic
FIG. 6—BAC ChAd155/RSV schematic
FIG. 7—Productivity of ChAd3 and ChAd155 vectors expressing an HIV Gag transgene (Experiment 1)
FIG. 8—Productivity of ChAd3 and ChAd155 vectors expressing an HIV Gag transgene (Experiment 2)
FIG. 9—Productivity of PanAd3 and ChAd155 vectors expressing RSV transgene
FIG. 10—Expression levels of ChAd3 and ChAd155 vectors expressing an HIV Gag transgene
FIG. 11—Expression levels of PanAd3 and ChAd155 vectors expressing an HIV Gag transgene—Western Blot
FIG. 12—Immunogenicity of ChAd3 and ChAd155 vectors expressing an HIV Gag transgene—IFN-gamma ELISpot
FIG. 13—Immunogenicity of PanAd3 and ChAd155 vectors expressing an HIV Gag transgene—IFN-gamma ELISpot

DESCRIPTION OF THE SEQUENCES

Figure 2:
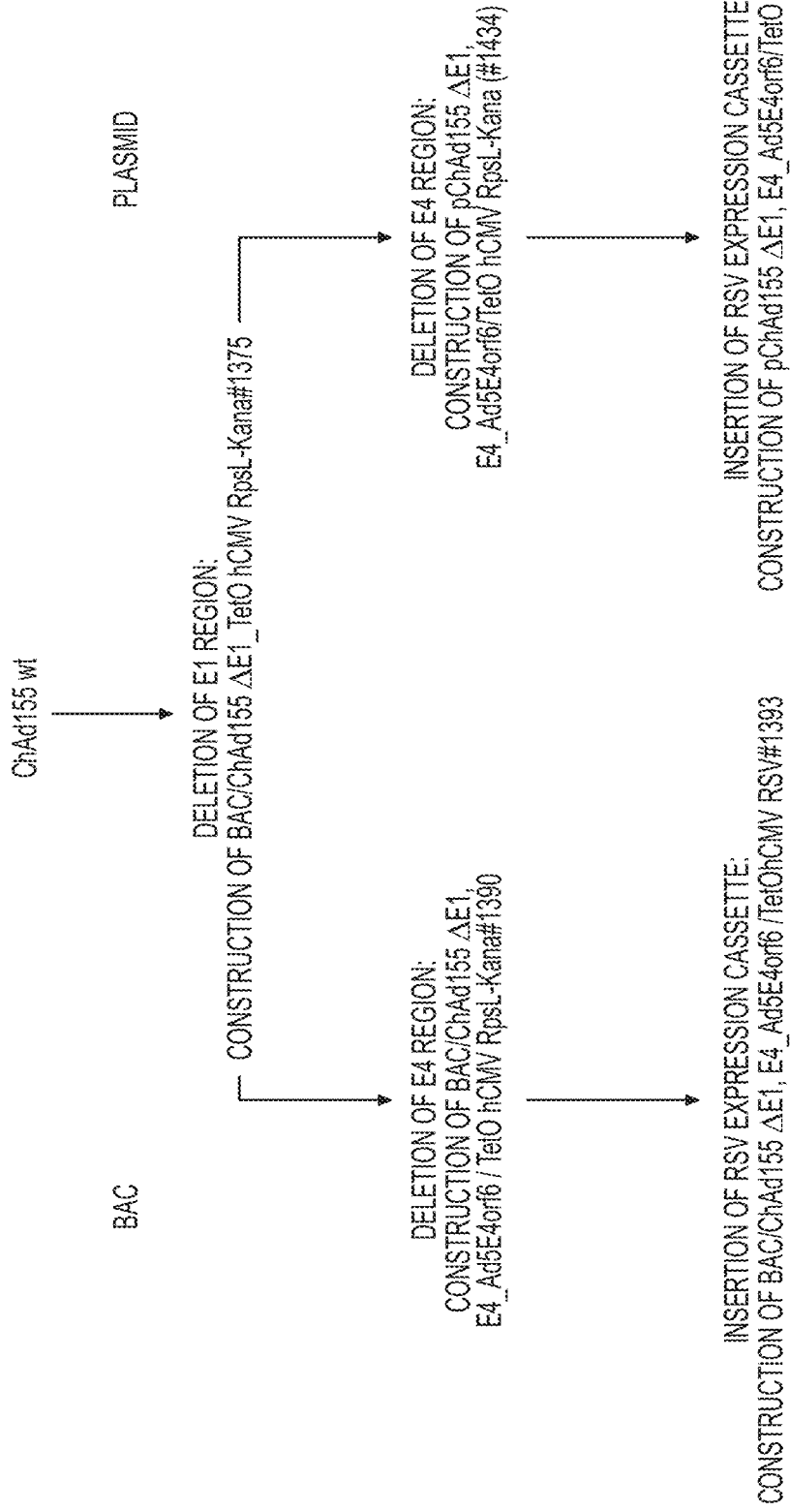

SEQ ID NO: 1—Polypeptide sequence of ChAd155 fiber
SEQ ID NO: 2—Polynucleotide sequence encoding ChAd155 fiber
SEQ ID NO: 3—Polypeptide sequence of ChAd155 penton
SEQ ID NO: 4—Polynucleotide sequence encoding ChAd155 penton
SEQ ID NO: 5—Polypeptide sequence of ChAd155 hexon
SEQ ID NO: 6—Polynucleotide sequence encoding ChAd155 hexon
SEQ ID NO: 7—Polynucleotide sequence encoding ChAd155#1434
SEQ ID NO: 8—Polynucleotide sequence encoding ChAd155#1390
SEQ ID NO: 9—Polynucleotide sequence encoding ChAd155#1375
SEQ ID NO: 10—Polynucleotide sequence encoding wild type ChAd155
SEQ ID NO: 11—Polynucleotide sequence encoding ChAd155/RSV
SEQ ID NO: 12—Polynucleotide sequence encoding the CASI promoter
SEQ ID NO: 13—Ad5orf6 primer 1 polynucleotide sequence
SEQ ID NO: 14—Ad5orf6 primer 2 polynucleotide sequence
SEQ ID NO: 15—BAC/CHAd155 ΔE1_TetO hCMV RpsL-Kana primer 1 polynucleotide sequence
SEQ ID NO: 16—BAC/CHAd155 ΔE1_TetO hCMV RpsL-Kana (#1375) primer 2 polynucleotide sequence
SEQ ID NO: 17—1021-FW E4 Del Step1 primer polynucleotide sequence
SEQ ID NO: 18—1022-RW E4 Del Step1 primer polynucleotide sequence
SEQ ID NO: 19—1025-FW E4 Del Step2 primer polynucleotide sequence
SEQ ID NO: 20—1026-RW E4 Del Step2 primer polynucleotide sequence
SEQ ID NO: 21—91-SubMonte FW primer polynucleotide sequence
SEQ ID NO: 22—890-BghPolyA RW primer polynucleotide sequence
SEQ ID NO: 23—CMVfor primer polynucleotide sequence
SEQ ID NO: 24—CMVrev primer polynucleotide sequence
SEQ ID NO: 25—CMVFAM-TAM RA qPCR probe polynucleotide sequence
SEQ ID NO: 26—Woodchuck Hepatitis Virus Posttranscriptional Regulatory Element (WPRE) polynucleotide sequence
SEQ ID NO: 27—Amino acid sequence for the fiber protein of ChAd3
SEQ ID NO: 28—Amino acid sequence for the fiber protein of PanAd3
SEQ ID NO: 29—Amino acid sequence for the fiber protein of ChAd17
SEQ ID NO: 30—Amino acid sequence for the fiber protein of ChAd19
SEQ ID NO: 31—Amino acid sequence for the fiber protein of ChAd24

SEQ ID NO: 32—Amino acid sequence for the fiber protein of ChAd11

SEQ ID NO: 33—Amino acid sequence for the fiber protein of ChAd20

SEQ ID NO: 34—Amino acid sequence for the fiber protein of ChAd31

SEQ ID NO: 35—Amino acid sequence for the fiber protein of PanAd1

SEQ ID NO: 36—Amino acid sequence for the fiber protein of PanAd2

SEQ ID NO: 37—RSV FΔTM amino acid sequence

SEQ ID NO: 38—HIV Gag polynucleotide sequence

DETAILED DESCRIPTION OF THE INVENTION

Adenovirus

Adenoviruses have a characteristic morphology with an icosahedral capsid comprising three major proteins, hexon (II), penton base (III) and a knobbed fiber (IV), along with a number of other minor proteins, VI, VIII, IX, IIIa and IVa2. The virus genome is a linear, double-stranded DNA. The virus DNA is intimately associated with the highly basic protein VII and a small peptide pX (formerly termed mu). Another protein, V, is packaged with this DNA-protein complex and provides a structural link to the capsid via protein VI. The virus also contains a virus-encoded protease, which is necessary for processing of some of the structural proteins to produce mature infectious virus.

The adenoviral genome is well characterized. There is general conservation in the overall organization of the adenoviral genome with respect to specific open reading frames being similarly positioned, e.g. the location of the E1A, E1B, E2A, E2B, E3, E4, L1, L2, L3, L4 and L5 genes of each virus. Each extremity of the adenoviral genome comprises a sequence known as an inverted terminal repeat (ITR), which is necessary for viral replication. The virus also comprises a virus-encoded protease, which is necessary for processing some of the structural proteins required to produce infectious virions. The structure of the adenoviral genome is described on the basis of the order in which the viral genes are expressed following host cell transduction. More specifically, the viral genes are referred to as early (E) or late (L) genes according to whether transcription occurs prior to or after onset of DNA replication. In the early phase of transduction, the E1A, E1B, E2A, E2B, E3 and E4 genes of adenovirus are expressed to prepare the host cell for viral replication. During the late phase of infection, expression of the late genes L1-L5, which encode the structural components of the virus particles, is activated.

Adenoviruses are species-specific and different serotypes, i.e., types of viruses that are not cross-neutralized by antibodies, have been isolated from a variety of mammalian species. For example, more than 50 serotypes have been isolated from humans which are divided into six subgroups (A-F; B is subdivided into B1 and B2) based on sequence homology and on their ability to agglutinate red blood cells (Tatsis and Ertl *Molecular Therapy* (2004) 10:616-629). Numerous adenoviruses have been isolated from nonhuman simians such as chimpanzees, bonobos, rhesus macaques and gorillas, and they are classified into the same human groups based on phylogenetic relationships based on hexon or fiber sequences (Colloca et al. (2012) Science Translational Medicine 4:1-9; Roy et al. (2004) *Virology* 324: 361-372; Roy et al. (2010) *Journal of Gene Medicine* 13:17-25).

Adenovirus Capsid Proteins Including the Fiber Protein and Polynucleotides Encoding these Proteins As outlined above, the adenoviral capsid comprises three major proteins, hexon, penton and fiber. The hexon accounts for the majority of the structural components of the capsid, which consists of 240 trimeric hexon capsomeres and 12 penton bases. The hexon has three conserved double barrels, while the top has three towers, each tower containing a loop from each subunit that forms most of the capsid. The base of hexon is highly conserved between adenoviral serotypes, while the surface loops are variable (Tatsis and Ertl *Molecular Therapy* (2004) 10:616-629).

Penton is another adenoviral capsid protein that forms a pentameric base to which fiber attaches. The trimeric fiber protein protrudes from the penton base at each of the 12 vertices of the capsid and is a knobbed rod-like structure. A remarkable difference in the surface of adenovirus capsids compared to that of most other icosahedral viruses is the presence of the long, thin fiber protein. The primary role of the fiber protein is the tethering of the viral capsid to the cell surface via its interaction with a cellular receptor.

The fiber proteins of many adenovirus serotypes share a common architecture: an N-terminal tail, a central shaft made of repeating sequences, and a C-terminal globular knob domain (or "head"). The central shaft domain consists of a variable number of beta-repeats. The beta-repeats connect to form an elongated structure of three intertwined spiraling strands that is highly rigid and stable. The shaft connects the N-terminal tail with the globular knob structure, which is responsible for interaction with the target cellular receptor. The globular nature of the adenovirus knob domain presents large surfaces for binding the receptor laterally and apically. The effect of this architecture is to project the receptor-binding site far from the virus capsid, thus freeing the virus from steric constraints presented by the relatively flat capsid surface.

Although fibers of many adenovirus serotypes have the same overall architecture, they have variable amino acid sequences that influence their function as well as structure. For example, a number of exposed regions on the surface of the fiber knob present an easily adaptable receptor binding site. The globular shape of the fiber knob allows receptors to bind at the sides of the knob or on top of the fiber knob. These binding sites typically lie on surface-exposed loops connecting beta-strands that are poorly conserved among human adenoviruses. The exposed side chains on these loops give the knob a variety of surface features while preserving the tertiary and quaternary structure. For example, the electrostatic potential and charge distributions at the knob surfaces can vary due to the wide range of isoelectric points in the fiber knob sequences, from pI approximately 9 for Ad 8, Ad 19, and Ad 37 to approximately 5 for subgroup B adenoviruses. As a structurally complex virus ligand, the fiber protein allows the presentation of a variety of binding surfaces (knob) in a number of orientations and distances (shaft) from the viral capsid.

One of the most obvious variations between some serotypes is fiber length. Studies have shown that the length of the fiber shaft strongly influences the interaction of the knob and the virus with its target receptors. Further, fiber proteins between serotypes can also vary in their ability to bend. Although beta-repeats in the shaft form a highly stable and regular structure, electron microscopy (EM) studies have shown distinct hinges in the fiber. Analysis of the protein sequence from several adenovirus serotype fibers pinpoints a disruption in the repeating sequences of the shaft at the third beta-repeat from the N-terminal tail, which correlates strongly with one of the hinges in the shaft, as seen by EM. The hinges in the fiber allow the knob to adopt a variety of orientations relative to the virus capsid, which may circumvent steric hindrances to receptor engagement requiring the correct presentation of the receptor binding site on the knob. For example, the rigid fibers of subgroup D Ads thus require a flexible receptor or one prepositioned for virus attachment, as they are unable to bend themselves. (Nicklin et al *Molecular Therapy* 2005 12:384-393)

The identification of specific cell receptors for different Ad serotypes and the knowledge of how they contribute to tissue tropism have been achieved through the use of fiber pseudotyping technology. Although Ads of some subgroups use CAR as a primary receptor, it is becoming clear that many Ads use alternate primary receptors, leading to vastly different tropism in vitro and in vivo. The fibers of these serotypes show clear differences in their primary and tertiary structures, such as fiber shaft rigidity, the length of the fiber shaft, and the lack of a CAR binding site and/or the putative HSPG binding motif, together with the differences in net charge within the fiber knob. Pseudotyping Ad 5 particles with an alternate fiber shaft and knob therefore provides an opportunity to remove important cell binding domains and, in addition, may allow more efficient (and potentially more cell-selective) transgene delivery to defined cell types compared to that achieved with Ad 5. Neutralization of fiber-pseudotyped Ad particles may also be reduced if the fibers used are from Ads with lower seroprevalence in humans or experimental models, a situation that favours successful administration of the vector (Nicklin et al *Molecular Therapy* (2005) 12:384-393). Furthermore, full length fiber as well as isolated fiber knob regions, but not hexon or penton alone, are capable of inducing dendritic cell maturation and are associated with induction of a potent CD8+ T cell response (Molinier-Frenkel et al. *J. Biol. Chem.* (2003) 278:37175-37182). Taken together, adenoviral fiber plays an important role in at least receptor-binding and immunogenicity of adenoviral vectors.

Figure 1A:
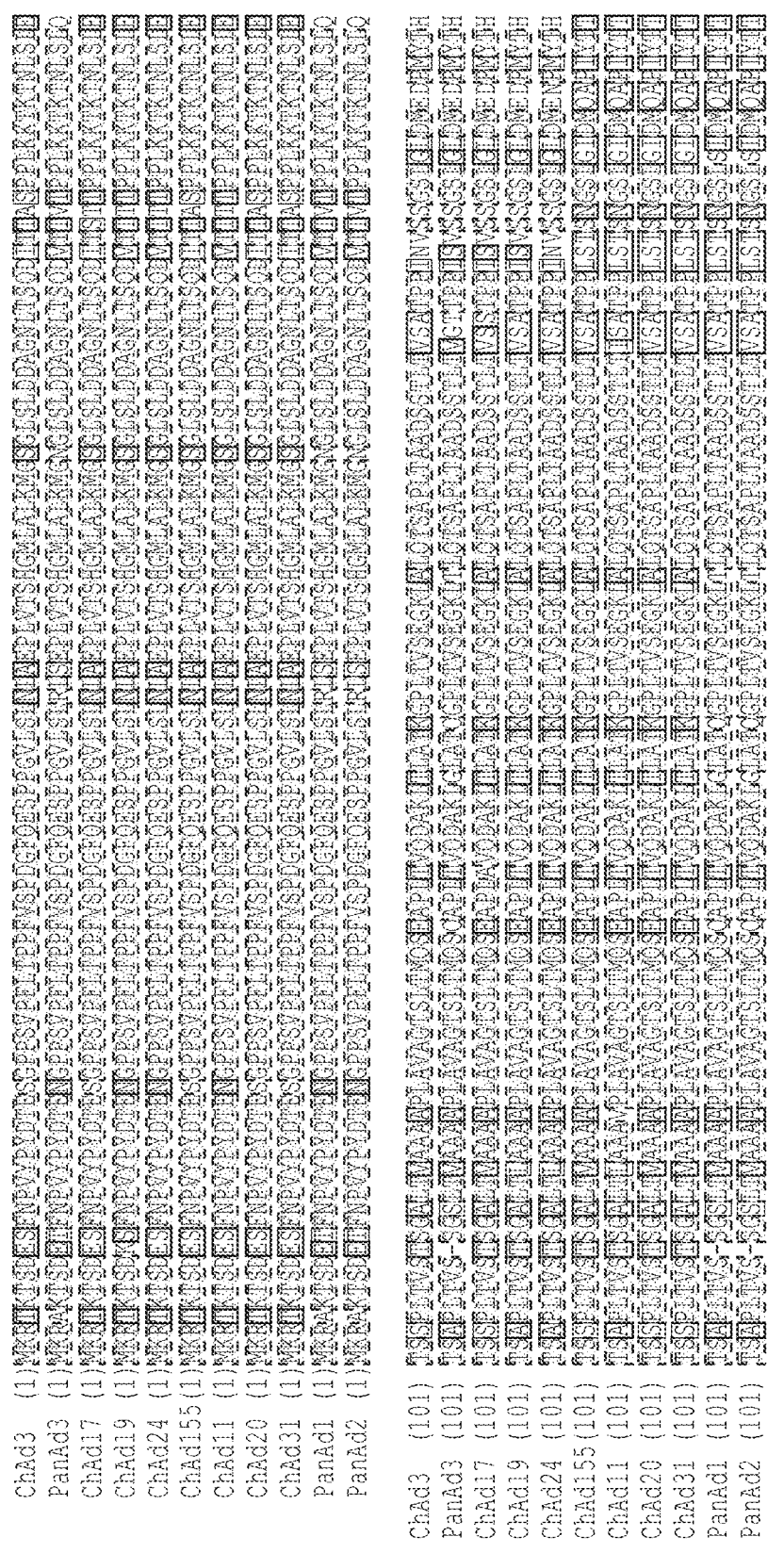
Figure 1B:
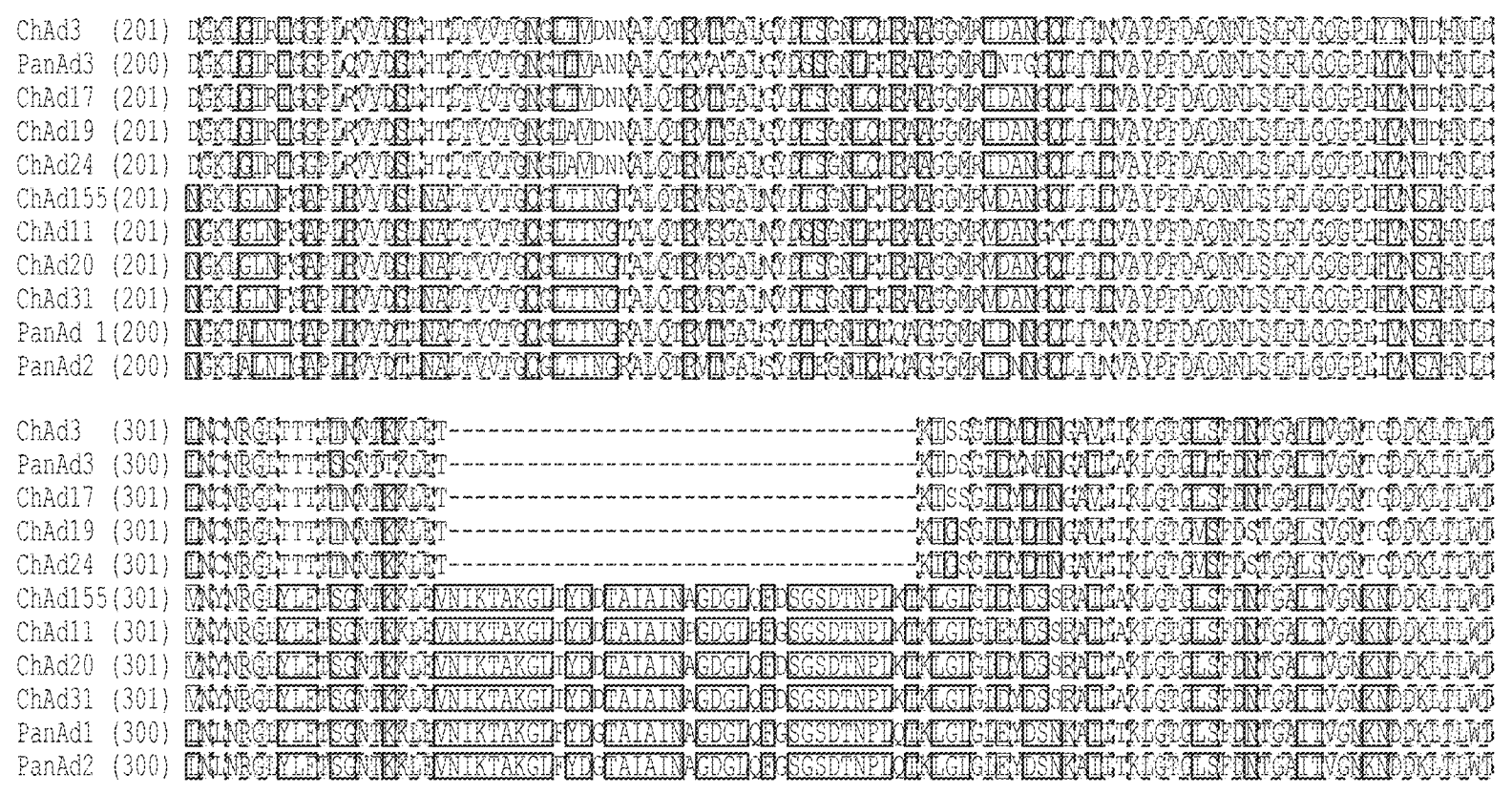
Figure 1C:
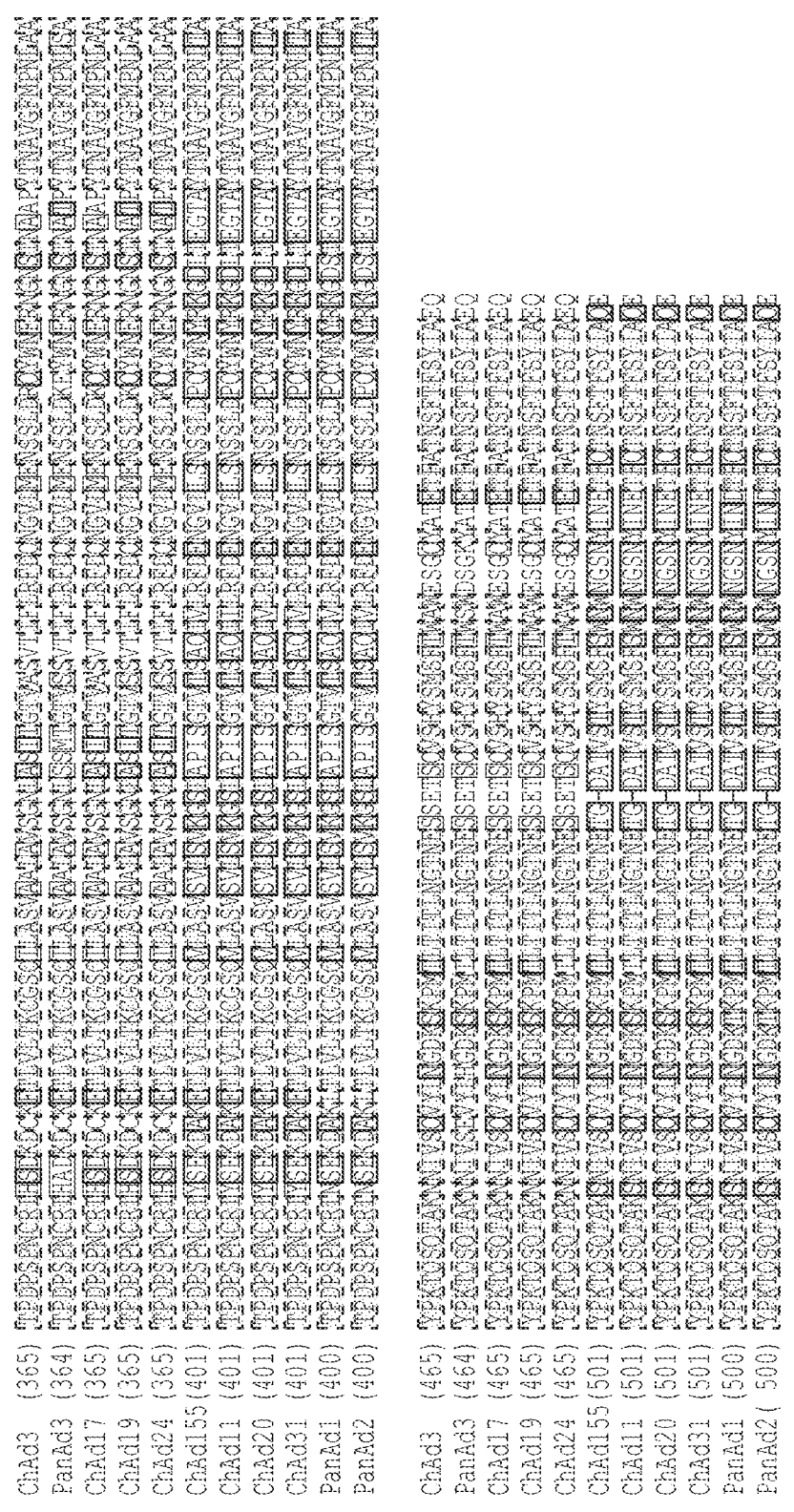

Illustrating the differences between the fiber proteins of Group C simian adenoviruses is the alignment provided in FIG. 1. A striking feature is that the fiber sequences of these adenoviruses can be broadly grouped into having a long fiber, such as ChAd155, or a short fiber, such as ChAd3. This length differential is due to a 36 amino acid deletion at approximately position 321 in the short fiber relative to the long fiber. In addition, there are a number of amino acid substitutions that differ between the short versus long fiber subgroup yet are consistent within each subgroup. While the exact function of these differences have not yet been elucidated, given the function and immunogenicity of fiber, they are likely to be significant. It has been shown that one of the determinants of viral tropism is the length of the fiber shaft. It has been demonstrated that an Ad5 vector with a shorter shaft has a lower efficiency of binding to CAR receptor and a lower infectivity (Ambriović-Ristov A. et al.: Virology. (2003) 312(2):425-33): It has been speculated that this impairment is the results of an increased rigidity of the shorter fiber leading to a less efficient attachment to the cell receptor (Wu, E et al.: J Virol. (2003) 77(13): 7225-7235). These studies may explain the improved properties of ChAd155 carrying a longer and more flexible fiber in comparison with the previously described ChAd3 and PanAd3 carrying a fiber with a shorter shaft.

In one aspect of the invention there is provided isolated fiber, penton and hexon capsid polypeptides of chimp adenovirus ChAd155 and isolated polynucleotides encoding the fiber, penton and hexon capsid polypeptides of chimp adenovirus ChAd155.

All three capsid proteins are expected to contribute to low seroprevalence and can, thus, be used independently from each other or in combination to suppress the affinity of an adenovirus to preexisting neutralizing antibodies, e.g. to manufacture a recombinant adenovirus with a reduced seroprevalence. Such a recombinant adenovirus may be a chimeric adenovirus with capsid proteins from different serotypes with at least a fiber protein from ChAd155.

The ChAd155 fiber polypeptide sequence is provided in SEQ ID NO: 1.

The ChAd155 penton polypeptide sequence is provided in SEQ ID NO: 3.

The ChAd155 hexon polypeptide sequence is provided in SEQ ID NO: 5.

Polypeptides, Recombinant Adenoviruses, Compositions or Cells Comprising Polypeptide Sequences of ChAd155 Fiber or a Functional Derivative Thereof Suitably the isolated polypeptide, recombinant adenovirus, composition or cell of the invention comprises a polypeptide having the amino acid sequence according to SEQ ID NO: 1.

Suitably the polypeptide, recombinant adenovirus, composition or cell of the invention comprises a polypeptide which is a functional derivative of a polypeptide having the amino acid sequence according to SEQ ID NO: 1, wherein the functional derivative has an amino acid sequence which is at least 80% identical over its entire length to the amino acid sequence of SEQ ID NO: 1. Suitably the functional derivative of a polypeptide having the amino acid sequence according to SEQ ID NO: 1 has an amino acid sequence which is at least 80% identical, such as at least 85.0% identical, such as at least 90% identical, such as at least 91.0% identical, such as at least 93.0% identical, such as at least 95.0% identical, such as at least 97.0% identical, such as at least 98.0% identical, such as at least 99.0% identical, such as at least 99.2% identical, such as at least 99.4% identical, such as 99.5% identical, such as at least 99.6% identical, such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 1.

Suitably the polypeptide, recombinant adenovirus, composition or cell according to the invention further comprises:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 50.0% identical over its entire length to the amino acid sequence of SEQ ID NO: 3, and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of a polypeptide having the amino acid sequence according to SEQ ID NO: 3 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 3. Alternatively the functional derivative has no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 3.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 5.

Polypeptides, Recombinant Adenoviruses, Compositions or Cells Comprising Polypeptide Sequences of ChAd155 Penton Suitably the polypeptide, recombinant adenovirus, composition or cell of the invention comprises a polypeptide having the amino acid sequence according to SEQ ID NO: 3.

Suitably the polypeptide, recombinant adenovirus, composition or cell of the invention further comprises:
(a) a polypeptide having the amino acid sequence according to SEQ ID NO: 1; or
(b) a functional derivative of a polypeptide having the amino acid sequence according to SEQ ID NO: 1, wherein the functional derivative has an amino acid sequence which is at least 80% identical over its entire length to the amino acid sequence of SEQ ID NO: 1 and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 60% identical over its entire length to the amino acid sequence of SEQ ID NO: 5.

Suitably the functional derivative of a polypeptide having the amino acid sequence according to SEQ ID NO: 1 has an amino acid sequence which is at least 60.0% identical, such as at least 70.0% identical, such as at least 80.0% identical, such as at least 85.0% identical, such as at least 87.0% identical, such as at least 89.0% identical, such as at least 91.0% identical, such as at least 93.0% identical, such as at least 95.0% identical, such as at least 97.0% identical, such as at least 98.0% identical, such as at least 99.0% identical, such as at least 99.2%, such as at least 99.4%, such as 99.5% identical, such as at least 99.6%, such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 1.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 99.0%, such as at least 99.0%, such as at least 99.2%, such as at least 99.4%, such as 99.5% identical, such as at least 99.6%, such as at least 99.8% identical, such as 99.9% identical over its entire length to the amino acid sequence of SEQ ID NO:5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 5.

Isolated Polynucleotides, Vectors, Recombinant Adenoviruses, Compositions or Cells Comprising Polynucleotides Encoding ChAd155 Fiber or a Functional Derivative Thereof Suitably the isolated polynucleotide, vector, recombinant adenovirus, composition or cell of the invention comprises a polynucleotide which encodes a polypeptide having the amino acid sequence according to SEQ ID NO: 1. Suitably the polynucleotide has a sequence according to SEQ ID NO: 2.

Alternatively, the polynucleotide, vector, recombinant adenovirus, composition or cell of the invention comprises a polynucleotide which encodes a functional derivative of a polypeptide having the amino acid sequence according to SEQ ID NO: 1, wherein the functional derivative has an amino acid sequence which is at least 80% identical over its entire length to the amino acid sequence of SEQ ID NO: 1. Suitably the functional derivative of a polypeptide having the amino acid sequence according to SEQ ID NO: 1 has an amino acid sequence which is at least 80% identical, such as at least 85.0% identical, such as at least 90% identical, such as at least 91.0% identical, such as at least 93.0% identical, such as at least 95.0% identical, such as at least 97.0% identical, such as at least 98.0% identical, such as at least 99.0% identical, such as at least 99% identical, such as at least 99.4% identical, such as at least 99.6% identical, such as at least 99.8% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 1.

Suitably the polynucleotide, vector, recombinant adenovirus, composition or cell of the invention further comprises a polynucleotide encoding:
(a) a polypeptide having the amino acid sequence according to SEQ ID NO: 3; or
(b) a functional derivative of a polypeptide having the amino acid sequence according to SEQ ID NO: 3, wherein the functional derivative has an amino acid sequence which is at least 50.0% identical over its entire length to the amino acid sequence of SEQ ID NO: 3, and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of the polypeptide having the amino acid sequence according to SEQ ID NO: 3 has an amino acid sequence which is at least 60.0%, such as at least 70.0%, such as at least 80.0%, such as at least 85.0%, such as at least 90.0%, such as at least 91.0% identical, such as at least 93.0% identical, such as at least 95.0% identical, such as at least 97.0% identical, such as at least 98.0% identical, such as at least 99.0%, such as at least 99%, such as at least 99.4%, such as at least 99.6%, such as at least 99.8% identical over its entire length to the amino acid sequence of SEQ ID NO: 3. Alternatively the functional derivative has no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 3.

Suitably the functional derivative of the polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 98.0%, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 5.

Isolated Polynucleotides, Vectors, Recombinant Adenoviruses, Compositions or Cells Comprising Polynucleotides Encoding ChAd155 Penton Suitably the isolated polynucleotide, vector, recombinant adenovirus, composition or cell of the invention comprises a polynucleotide which encodes a polypeptide having the amino acid sequence according to SEQ ID NO: 3. Suitably the polynucleotide has a sequence according to SEQ ID NO: 4.

Suitably the polynucleotide, vector, recombinant adenovirus, composition or cell of the invention further comprises a polynucleotide encoding:
(a) a polypeptide having the amino acid sequence according to SEQ ID NO: 1; or
(b) a functional derivative of a polypeptide having the amino acid sequence according to SEQ ID NO: 1, wherein the functional derivative has an amino acid sequence which is at least 50% identical over its entire length to the amino acid sequence of SEQ ID NO: 1 and/or
(a) a polypeptide having the amino acid sequence according to SEQ ID NO: 5; or
(b) a functional derivative of a polypeptide having the amino acid sequence according to SEQ ID NO: 5, wherein the functional derivative has an amino acid sequence which is at least 50% identical over its entire length to the amino acid sequence of SEQ ID NO: 5.

Suitably the functional derivative of a polypeptide having the amino acid sequence according to SEQ ID NO: 1 has an amino acid sequence which is at least 60.0% identical, such as at least 70.0% identical, such as at least 80.0% identical, such as at least 85.0% identical, such as at least 87.0% identical, such as at least 89.0% identical, such as at least 91.0% identical, such as at least 93.0% identical, such as at least 95.0% identical, such as at least 97.0% identical, such as at least 98.0% identical, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 1. Alternatively the functional derivative has no more than 130, more suitably no more than 120, more suitably no more than 110, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 1.

Suitably the functional derivative of a polypeptide having the amino acid sequence according to SEQ ID NO: 5 has an amino acid sequence which is at least 60.0%, such as at least 70.0%, such as at least 80.0%, such as at least 85.0%, such as at least 90.0%, such as at least 95.0%, such as at least 97.0%, such as at least 98.0%, such as at least 99.0%, such as at least 99.2%, such as at least 99.4%, such as 99.5% identical, such as at least 99.6%, such as 99.7% identical such as at least 99.8% identical, such as 99.9% identical over its entire length to the amino acid sequence of SEQ ID NO: 5. Alternatively the functional derivative has no more than 500, more suitably no more than 400, more suitably no more than 450, more suitably no more than 300, more suitably no more than 250, more suitably no more than 200, more suitably no more than 150, more suitably no more than 125, more suitably no more than 100, more suitably no more than 90, more suitably no more than 80, more suitably no more than 70, more suitably no more than 60, more suitably no more than 50, more suitably no more than 40, more suitably no more than 30, more suitably no more than 20, more suitably no more than 10, more suitably no more than 5, more suitably no more than 4, more suitably no more than 3, more suitably no more than 2, more suitably no more than 1 addition(s), deletion(s) or substitutions(s) compared to SEQ ID NO: 5.

ChAd155 Backbones

The invention provides isolated polynucleotide sequences of chimp adenovirus ChAd155, including that of wild type, unmodified ChAd155 (SEQ ID NO: 10) and modified backbone constructs of ChAd155. These modified backbone constructs include ChAd155#1434 (SEQ ID NO: 7), ChAd155#1390 (SEQ ID NO: 8) and ChAd155#1375 (SEQ ID NO: 9). ChAd155 backbones may be used in the construction of recombinant replication-competent or replication-incompetent adenoviruses for example for the delivery of transgenes.

Annotation of the ChAd155 wild type sequence (SEQ ID NO: 10) sequence is provided below.

| LOCUS | ChAd155 | 37830 bp | DNA | linear |
|---|---|---|---|---|
| 10-JUN-2015 | | | | |
| DEFINITION | Chimp adenovirus 155, complete genome. | | | |
| COMMENT | Annotation according to alignment of ChAd155 against the human Adenovirus 2 reference strain NC_001405 Two putative ORFs in the E3 region added manually | | | |
| FEATURES | Location/Qualifiers | | | |
| source | 1..37830 | | | |
| | /organism = "Chimpanzee adenovirus 155" | | | |
| | /mol_type = "genomic DNA" | | | |
| | /acronym = "ChAd155" | | | |
| repeat_region | 1..101 | | | |
| | /standard_name = "ITR" | | | |
| | /rpt_type = inverted | | | |

-continued

| gene | 466..1622 |
|---|---|
| | /gene = "E1A" |
| TATA_signal | 466..471 |
| | /gene = "E1A" |
| prim_transcript | 497..1622 |
| | /gene = "E1A" |
| CDS | join(577..1117, 1231..1532) |
| | /gene = "E1A" |
| | /product = "E1A_280R" |
| CDS | join(577..979, 1231..1532) |
| | /gene = "E1A" |
| | /product = "E1A_243R" |
| polyA_signal | 1600..1605 |
| | /gene = "E1A" |
| gene | 1662..4131 |
| | /gene = "E1B" |
| TATA_signal | 1662..1667 |
| | /gene = "E1B" |
| prim_transcript | 1692..4131 |
| | /gene = "E1B" |
| CDS | 1704..2267 |
| | /gene = "E1B" |
| | /product = "E1B_19K" |
| CDS | 2009..3532 |
| | /gene = "E1B" |
| | /product = "E1B_55K" |
| gene | 3571..4131 |
| | /gene = "IX" |
| TATA_signal | 3571..3576 |
| | /gene = "IX" |
| prim_transcript | 3601..4131 |
| | /gene = "IX" |
| CDS | 3628..4092 |
| | /gene = "IX" |
| | /product = "IX" |
| polyA_signal | 4097..4102 |
| | /note = "E1B, IX" |
| gene | complement(4117..27523) |
| | /gene = "E2B" |
| prim_transcript | complement(4117..27494) |
| | /gene = "E2B" |
| gene | complement(4117..5896) |
| | /gene = "IVa2" |
| prim_transcript | complement(4117..5896) |
| | /gene = "IVa2" |
| CDS | complement(join(4151..5487, 5766..5778)) |
| | /gene = "IVa2" |
| | /product = "E2B_IVa2" |
| polyA_signal | complement(4150..4155) |
| | /note = "IVa2, E2B" |
| CDS | complement(join(5257..8838, 14209..14217)) |
| | /gene = "E2B" |
| | /product = "E2B_polymerase" |
| gene | 6078..34605 |
| | /gene = "L5" |
| gene | 6078..28612 |
| | /gene = "L4" |
| gene | 6078..22658 |
| | /gene = "L3" |
| gene | 6078..18164 |
| | /gene = "L2" |
| gene | 6078..14216 |
| | /gene = "L1" |
| TATA_signal | 6078..6083 |
| | /note = "L" |
| prim_transcript | 6109..34605 |
| | /gene = "L5" |
| prim_transcript | 6109..28612 |
| | /gene = "L4" |
| prim_transcript | 6109..22658 |
| | /gene = "L3" |
| prim_transcript | 6109..18164 |
| | /gene = "L2" |
| prim_transcript | 6109..14216 |
| | /gene = "L1" |
| CDS | join(8038..8457, 9722..9742) |
| | /gene = "L1" |
| | /product = "L1_13.6K" |

| | | |
|---|---|---|
| CDS | complement(join(8637..10640, 14209..14217)) | |
| | /gene = "E2B" | |
| | /product = "E2B_pTP" | |
| gene | 10671..10832 | |
| | /gene = "VAI" | |
| misc_RNA | 10671..10832 | |
| | /gene = "VAI" | |
| | /product = "VAI" | |
| gene | 10902..11072 | |
| | /gene = "VAII" | |
| misc_RNA | 10902..11072 | |
| | /gene = "VAII" | |
| | /product = "VAII" | |
| CDS | 11093..12352 | |
| | /gene = "L1" | |
| | /product = "L1_52K" | |
| CDS | 12376..14157 | |
| | /gene = "L1" | |
| | /product = "L1_pIIIa" | |
| polyA_signal | 14197..14202 | |
| | /gene = "L1" | |
| CDS | 14254..16035 | |
| | /gene = "L2" | |
| | /product = "L2_penton" | |
| CDS | 16050..16646 | |
| | /gene = "L2" | |
| | /product = "L2_pVII" | |
| CDS | 16719..17834 | |
| | /gene = "L2" | |
| | /product = "L2_V" | |
| CDS | 17859..18104 | |
| | /gene = "L2" | |
| | /product = "L2_pX" | |
| polyA_signal | 18143..18148 | |
| | /gene = "L2" | |
| CDS | 18196..18951 | |
| | /gene = "L3" | |
| | /product = "L3_pVI" | |
| CDS | 19063..21945 | |
| | /gene = "L3" | |
| | /product = "L3_hexon" | |
| CDS | 21975..22604 | |
| | /gene = "L3" | |
| | /product = "L3_protease" | |
| polyA_signal | 22630..22635 | |
| | /gene = "L3" | |
| gene | complement(22632..27523) | |
| | /gene = "E2A" | |
| prim_transcript | complement(22632..27494) | |
| | /gene = "E2A" | |
| gene | complement(22632..26357) | |
| | /gene = "E2A-L" | |
| prim_transcript | complement(22632..26328) | |
| | /gene = "E2A-L" | |
| polyA_signal | complement(22649..22654) | |
| | /note = "E2A, E2A-L" | |
| CDS | complement(22715..24367) | |
| | /gene = "E2A" | |
| | /note = "DBP; genus-common; DBP family" | |
| | /codon_start = 1 | |
| | /product = "E2A" | |
| CDS | 24405..26915 | |
| | /gene = "L4" | |
| | /product = "L4_100k" | |
| TATA_signal | complement(26352..26357) | |
| | /gene = "E2A-L" | |
| CDS | join(26602..26941, 27147..27529) | |
| | /gene = "L4" | |
| | /product = "L4_33K" | |
| CDS | 26602..27207 | |
| | /gene = "L4" | |
| | /product = "L4_22K" | |
| TATA_signal | complement(27518..27523) | |
| | /note = "E2A, E2B; nominal" | |
| CDS | 27604..28287 | |
| | /gene = "L4" | |
| | /product = "L4_pVIII" | |
| gene | 27969..32686 | |
| | /gene = "E3B" | |
| gene | 27969..31611 | |
| | /gene = "E3A" | |
| TATA_signal | 27969..27974 | |
| | /note = "E3A, E3B" | |
| prim_transcript | 27998..32686 | |
| | /gene = "E3B" | |
| prim_transcript | 27998..31611 | |
| | /gene = "E3A" | |
| CDS | 28288..28605 | |
| | /gene = "E3A" | |
| | /product = "E3 ORF1" | |
| polyA_signal | 28594..28599 | |
| | /gene = "L4" | |
| CDS | 29103..29303 | |
| | /gene = "E3A" | |
| | /product = "E3 ORF2" | |
| CDS | 29300..29797 | |
| | /gene = "E3A" | |
| | /product = "E3 ORF3" | |
| CDS | 29826..30731 | |
| | /gene = "E3A" | |
| | /product = "E3 ORF4" | |
| CDS | 30728..31579 | |
| | /gene = "E3A" | |
| | /product = "E3 ORF5" | |
| CDS | 31283..31579 | |
| | /gene = "E3A" | |
| | /product = "E3 ORF6" | |
| polyA_signal | 31578..31584 | |
| | /gene = "E3A" | |
| CDS | 31591..31863 | |
| | /gene = "E3B" | |
| | /product = "E3 ORF7" | |
| CDS | 31866..32264 | |
| | /gene = "E3B" | |
| | /product = "E3 ORF8" | |
| CDS | 32257..32643 | |
| | /gene = "E3B" | |
| | /product = "E3 ORF9" | |
| polyA_signal | 32659..32664 | |
| | /gene = "E3B" | |
| gene | complement(<32678..32838) | |
| | /gene = "U" | |
| CDS | complement(<32678..32838) | |
| | /gene = "U" | |
| | /note = "exon encoding C terminus unidentified; genus-common" | |
| | /product = "protein U" | |
| CDS | 32849..34585 | |
| | /gene = "L5" | |
| | /product = "L5_fiber" | |
| polyA_signal | 34581..34586 | |
| | /gene = "L5" | |
| gene | complement(34611..37520) | |
| | /gene = "E4" | |
| prim_transcript | complement(34611..37490) | |
| | /gene = "E4" | |
| polyA_signal | complement(34625..34630) | |
| | /gene = "E4" | |
| CDS | complement(join(34794..35069, 35781..35954)) | |
| | /gene = "E4" | |
| | /product = "E4 ORF7" | |
| CDS | complement(35070..35954) | |
| | /gene = "E4" | |
| | /product = "E4 ORF6" | |
| CDS | complement(35875..36219) | |
| | /gene = "E4" | |
| | /product = "E4 ORF4" | |
| CDS | complement(36235..36582) | |
| | /gene = "E4" | |
| | /product = "E4 ORF3" | |
| CDS | complement(36579..36971) | |
| | /gene = "E4" | |
| | /product = "E4 ORF2" | |
| CDS | complement(37029..37415) | |
| | /gene = "E4" | |
| | /product = "E4 ORF1" | |

| | |
|---|---|
| TATA_signal | complement(37515..37520) /gene = "E4" |
| repeat_region | 37740..37830 /standard_name = "ITR" /rpt_type = inverted |

In one embodiment, fragments of the sequences of SEQ ID NO: 7, 8, 9, 10 and their complementary strands, cDNA and RNA complementary thereto are provided. Suitably, fragments are at least 15 nucleotides in length, more suitably 30 nucleotides in length, more suitably 60 nucleotides in length, more suitably 120 nucleotides in length, more suitably 240, more suitably 480 nucleotides in length and encompass functional fragments, i.e., fragments which are of biological interest. For example, a functional fragment can express a desired adenoviral product or may be useful in production of recombinant viral vectors. Such fragments include the gene sequences listed above.

Gene products of the ChAd155 adenovirus, such as proteins, enzymes, and fragments thereof, which are encoded by the adenoviral nucleic acids described herein are provided. Such proteins include those encoded by the open reading frames identified above and the proteins encoded by the polynucleotides provided in the Sequence Listing.

Further ChAd155 Polynucleotides and Polypeptides

In some embodiments the polynucleotide of the invention comprises a polynucleotide encoding a fiber polypeptide; a penton polypeptide; a hexon polypeptide and penton polypeptide; a hexon polypeptide and fiber polypeptide; penton polypeptide and fiber polypeptide; or hexon polypeptide, penton polypeptide and fiber polypeptide of the invention; and may further comprise additional adenoviral polynucleotides, suitably ChAd155 polynucleotides. Thus, suitably the polynucleotide according to the invention comprises one or more of the following, the sequence coordinates relative to SEQ ID NO:10 provided in the previous annotation:
  (a) an adenoviral 5'-inverted terminal repeat (ITR);
  (b) an adenoviral E1A region, or a fragment thereof selected from among the E1A_280R and E1A_243R regions;
  (c) an adenoviral E1B or IX region, or a fragment thereof selected from among the group consisting of the E1B_19K, E1B_55K and IX regions;
  (d) an adenoviral E2B region; or a fragment thereof selected from among the group consisting of the E2B_pTP, E2B_polymerase and E2B_IVa2 regions;
  (e) an adenoviral L1 region, or a fragment thereof, said fragment encoding an adenoviral protein selected from the group consisting of the L1_13.6K, L1_52K and L1_pIIIa protein;
  (f) an adenoviral L2 region or a L2 region comprising a polynucleotide encoding the penton protein of the invention, or a fragment thereof, said fragment encoding an adenoviral protein selected from the group consisting of the L2_penton protein, the L2_pVII protein, the L2_V protein and the L2_pX protein;
  (g) an adenoviral L3 region or a L3 region comprising a polynucleotide encoding the hexon protein of the invention, or a fragment thereof, said fragment encoding an adenoviral protein selected from the group consisting of the L3_pVI protein, the L3_hexon protein and the L3_protease protein;
  (h) an adenoviral E2A region;
  (i) an adenoviral L4 region, or a fragment thereof said fragment encoding an adenoviral protein selected from the group consisting of the L4_100 k protein, the L4_33K protein, the L4_22K protein and protein L4_VIII;
  (j) an adenoviral E3 region, or a fragment thereof selected from the group consisting of E3 ORF1, E3 ORF2, E3 ORF3, E3 ORF4, E3 ORF5, E3 ORF6, E3 ORF7, E3 ORF8, and E3 ORF9;
  (k) an adenoviral L5 region or a L5 region comprising a polynucleotide encoding the L5_fiber fiber polypeptide of the invention
  (l) an adenoviral (such as Ad5) E4 region, or a fragment thereof selected from the group consisting of E4 ORF7, E4 ORF6, E4 ORF4, E4 ORF3, E4 ORF2, and E4 ORF1; in particular ORF6 of said E4 region;
  (m) an adenoviral 3'-ITR; and/or
  (n) an adenoviral VAI or VAII RNA region, preferably an adenoviral VAI or VAII RNA region from an adenovirus other than ChAd155, more preferably from Ad5.

Definitions

Suitably the polynucleotides or polypeptides of the invention are isolated. An "isolated" polynucleotide is one that is removed from its original environment. For example, a naturally-occurring polynucleotide is isolated if it is separated from some or all of the coexisting materials in the natural system. A polynucleotide is considered to be isolated if, for example, it is cloned into a vector that is not a part of its natural environment or if it is comprised within cDNA.

Suitably the polynucleotides of the invention are recombinant. Recombinant means that the polynucleotide is the product of at least one of cloning, restriction or ligation steps, or other procedures that result in a polynucleotide that is distinct from a polynucleotide found in nature. A recombinant adenovirus is an adenovirus comprising a recombinant polynucleotide. A recombinant vector is a vector comprising a recombinant polynucleotide. 'A recombinant virus' includes progeny of the original recombinant virus. 'A recombinant vector' includes replicates of the original recombinant vector. 'A recombinant polynucleotide' includes replicates of the original recombinant polynucleotide.

Suitably, the polypeptide sequence of the present invention contains at least one alteration with respect to a native sequence. Suitably, the polynucleotide sequences of the present invention contain at least one alteration with respect to a native sequence. For example, a polynucleotide introduced by genetic engineering techniques into a plasmid or vector derived from a different species (and often a different genus, subfamily or family) is a heterologous polynucleotide. A promoter removed from its native coding sequence and operatively linked to a coding sequence with which it is not naturally found linked is a heterologous promoter. A specific recombination site that has been cloned into a genome of a virus or viral vector, wherein the genome of the virus does not naturally contain it, is a heterologous recombination site. A heterologous nucleic acid sequence also includes a sequence naturally found in an adenoviral genome, but located at a non-native position within the adenoviral vector.

Typically, "heterologous" means derived from a genotypically distinct entity from that of the rest of the entity to which it is being compared. A heterologous nucleic acid sequence refers to any nucleic acid sequence that is not isolated from, derived from, or based upon a naturally occurring nucleic acid sequence of the adenoviral vector. "Naturally occurring" means a sequence found in nature and not synthetically prepared or modified. A sequence is "derived" from a source when it is isolated from a source but modified (e.g., by deletion, substitution (mutation), insertion, or other modification), suitably so as not to disrupt the normal function of the source gene.

A "functional derivative" of a polypeptide suitably refers to a modified version of a polypeptide, e.g. wherein one or more amino acids of the polypeptide may be deleted, inserted, modified and/or substituted. A derivative of an unmodified adenoviral capsid protein is considered functional if, for example:

(a) an adenovirus comprising the derivative capsid protein within its capsid retains substantially the same or a lower seroprevalence compared to an adenovirus comprising the unmodified capsid protein and/or (b) an adenovirus comprising the derivative capsid protein within its capsid retains substantially the same or a higher host cell infectivity compared to an adenovirus comprising the unmodified capsid protein and/or (c) an adenovirus comprising the derivative capsid protein within its capsid retains substantially the same or a higher immunogenicity compared to an adenovirus comprising the unmodified capsid protein and or (d) an adenovirus comprising the derivative capsid protein within its capsid retains substantially the same or a higher level of transgene productivity compared to an adenovirus comprising the unmodified capsid protein.

Properties (a)-(d) above may suitably be measured using the methods described in the Examples section below.

Suitably, the polypeptide, vector or recombinant adenovirus has a low seroprevalence in a human population. "Low seroprevalence" may mean having a reduced pre-existing neutralizing antibody level as compared to human adenovirus 5 (Ad5). Similarly or alternatively, "low seroprevalence" may mean less than about 20% seroprevalence, less than about 15% seroprevalence, less than about 10% seroprevalence, less than about 5% seroprevalence, less than about 4% seroprevalence, less than about 3% seroprevalence, less than about 2% seroprevalence, less than about 1% seroprevalence or no detectable seroprevalence. Seroprevalence can be measured as the percentage of individuals having a clinically relevant neutralizing titre (defined as a 50% neutralisation titer >200) using methods as described in Aste-Amézaga et al., Hum. Gene Ther. (2004) 15(3):293-304.

The terms polypeptide, peptide and protein are used interchangeably herein.

The term "simian" is typically meant to encompass non-human primates, for example Old World monkeys, New World monkeys, apes and gibbons. In particular, simian may refer to nonhuman apes such as chimpanzees (*Pan troglodyte*), bonobos (*Pan paniscus*) and gorillas (genus *Gorilla*). Non-ape simians may include rhesus macaques (*Macaca mulatta*)

Sequence Comparison

For the purposes of comparing two closely-related polynucleotide or polypeptide sequences, the "% identity" between a first sequence and a second sequence may be calculated using an alignment program, such as BLAST® (available at blast.ncbi.nlm.nih.gov, last accessed 9 Mar. 2015) using standard settings. The % identity is the number of identical residues divided by the number of residues in the reference sequence, multiplied by 100. The % identity figures referred to above and in the claims are percentages calculated by this methodology. An alternative definition of % identity is the number of identical residues divided by the number of aligned residues, multiplied by 100. Alternative methods include using a gapped method in which gaps in the alignment, for example deletions in one sequence relative to the other sequence, are accounted for in a gap score or a gap cost in the scoring parameter. For more information, see the BLAST® fact sheet available at ftp.ncbi.nlm.nih.gov/pub/factsheets/HowTo_BLASTGuide.pdf, last accessed on 9 Mar. 2015.

Sequences that preserve the functionality of the polynucleotide or a polypeptide encoded thereby are likely to be more closely identical. Polypeptide or polynucleotide sequences are said to be the same as or identical to other polypeptide or polynucleotide sequences, if they share 100% sequence identity over their entire length.

A "difference" between sequences refers to an insertion, deletion or substitution of a single amino acid residue in a position of the second sequence, compared to the first sequence. Two polypeptide sequences can contain one, two or more such amino acid differences. Insertions, deletions or substitutions in a second sequence which is otherwise identical (100% sequence identity) to a first sequence result in reduced percent sequence identity. For example, if the identical sequences are 9 amino acid residues long, one substitution in the second sequence results in a sequence identity of 88.9%. If the identical sequences are 17 amino acid residues long, two substitutions in the second sequence results in a sequence identity of 88.2%. If the identical sequences are 7 amino acid residues long, three substitutions in the second sequence results in a sequence identity of 57.1%. If first and second polypeptide sequences are 9 amino acid residues long and share 6 identical residues, the first and second polypeptide sequences share greater than 66% identity (the first and second polypeptide sequences share 66.7% identity). If first and second polypeptide sequences are 17 amino acid residues long and share 16 identical residues, the first and second polypeptide sequences share greater than 94% identity (the first and second polypeptide sequences share 94.1% identity). If first and second polypeptide sequences are 7 amino acid residues long and share 3 identical residues, the first and second polypeptide sequences share greater than 42% identity (the first and second polypeptide sequences share 42.9% identity).

Alternatively, for the purposes of comparing a first, reference polypeptide sequence to a second, comparison polypeptide sequence, the number of additions, substitutions and/or deletions made to the first sequence to produce the second sequence may be ascertained. An addition is the addition of one amino acid residue into the sequence of the first polypeptide (including addition at either terminus of the first polypeptide). A substitution is the substitution of one amino acid residue in the sequence of the first polypeptide with one different amino acid residue. A deletion is the deletion of one amino acid residue from the sequence of the first polypeptide (including deletion at either terminus of the first polypeptide).

For the purposes of comparing a first, reference polynucleotide sequence to a second, comparison polynucleotide sequence, the number of additions, substitutions and/or deletions made to the first sequence to produce the second sequence may be ascertained. An addition is the addition of one nucleotide residue into the sequence of the first polynucleotide (including addition at either terminus of the first polynucleotide). A substitution is the substitution of one nucleotide residue in the sequence of the first polynucleotide with one different nucleotide residue. A deletion is the deletion of one nucleotide residue from the sequence of the first polynucleotide (including deletion at either terminus of the first polynucleotide).

Suitably substitutions in the sequences of the present invention may be conservative substitutions. A conservative substitution comprises the substitution of an amino acid with another amino acid having a chemical property similar to the amino acid that is substituted (see, for example, Stryer et al, *Biochemistry*, 5*th* Edition 2002, pages 44-49). Preferably, the conservative substitution is a substitution selected from the group consisting of: (i) a substitution of a basic amino acid with another, different basic amino acid; (ii) a substitution of an acidic amino acid with another, different acidic amino acid; (iii) a substitution of an aromatic amino acid with another, different aromatic amino acid; (iv) a substitution of a non-polar, aliphatic amino acid with another, different non-polar, aliphatic amino acid; and (v) a substitution of a polar, uncharged amino acid with another, different polar, uncharged amino acid. A basic amino acid is preferably selected from the group consisting of arginine, histidine, and lysine. An acidic amino acid is preferably aspartate or glutamate. An aromatic amino acid is preferably selected from the group consisting of phenylalanine, tyrosine and tryptophane. A non-polar, aliphatic amino acid is preferably selected from the group consisting of glycine, alanine, valine, leucine, methionine and isoleucine. A polar, uncharged amino acid is preferably selected from the group consisting of serine, threonine, cysteine, proline, asparagine and glutamine. In contrast to a conservative amino acid substitution, a non-conservative amino acid substitution is the exchange of one amino acid with any amino acid that does not fall under the above-outlined conservative substitutions (i) through (v).

Vectors and Recombinant Adenovirus

The ChAd155 sequences of the invention are useful as therapeutic agents and in construction of a variety of vector systems, recombinant adenovirus and host cells. Suitably the term "vector" refers to a nucleic acid that has been substantially altered (e.g., a gene or functional region that has been deleted and/or inactivated) relative to a wild type sequence and/or incorporates a heterologous sequence, i.e., nucleic acid obtained from a different source (also called an "insert"), and replicating and/or expressing the inserted polynucleotide sequence, when introduced into a cell (e.g., a host cell). For example, the insert may be all or part of the ChAd155 sequences described herein. In addition or alternatively, a ChAd155 vector may be a ChAd155 adenovirus comprising one or more deletions or inactivations of viral genes, such as E1 or other viral gene or functional region described herein. Such a ChAd155, which may or may not comprise a heterologous sequence, is often called a "backbone" and may be used as is or as a starting point for additional modifications to the vector.

A vector may be any suitable nucleic acid molecule including naked DNA, a plasmid, a virus, a cosmid, phage vector such as lambda vector, an artificial chromosome such as a BAC (bacterial artificial chromosome), or an episome. Alternatively, a vector may be a transcription and/or expression unit for cell-free in vitro transcription or expression, such as a T7-compatible system. The vectors may be used alone or in combination with other adenoviral sequences or fragments, or in combination with elements from non-adenoviral sequences. The ChAd155 sequences are also useful in antisense delivery vectors, gene therapy vectors, or vaccine vectors. Thus, further provided are gene delivery vectors, and host cells which contain the ChAd155 sequences.

The term "replication-competent" adenovirus refers to an adenovirus which can replicate in a host cell in the absence of any recombinant helper proteins comprised in the cell. Suitably, a "replication-competent" adenovirus comprises the following intact or functional essential early genes: E1A, E1B, E2A, E2B, E3 and E4. Wild type adenoviruses isolated from a particular animal will be replication competent in that animal.

The term "replication-incompetent" or "replication-defective" adenovirus refers to an adenovirus which is incapable of replication because it has been engineered to comprise at least a functional deletion (or "loss-of-function" mutation), i.e. a deletion or mutation which impairs the function of a gene without removing it entirely, e.g. introduction of artificial stop codons, deletion or mutation of active sites or interaction domains, mutation or deletion of a regulatory sequence of a gene etc, or a complete removal of a gene encoding a gene product that is essential for viral replication, such as one or more of the adenoviral genes selected from E1A, E1B, E2A, E2B, E3 and E4 (such as E3 ORF1, E3 ORF2, E3 ORF3, E3 ORF4, E3 ORF5, E3 ORF6, E3 ORF7, E3 ORF8, E3 ORF9, E4 ORF7, E4 ORF6, E4 ORF4, E4 ORF3, E4 ORF2 and/or E4 ORF1). Particularly suitably E1 and optionally E3 and/or E4 are deleted. If deleted, the aforementioned deleted gene region will suitably not be considered in the alignment when determining % identity with respect to another sequence.

The present invention provides vectors such as recombinant adenovirus that deliver a protein, suitably a heterologous protein, to cells, either for therapeutic or vaccine purposes. A vector may include any genetic element including naked DNA, a phage, transposon, cosmid, episome, plasmid, or a virus. Such vectors contain DNA of ChAd155 as disclosed herein and a minigene. By "minigene" (or "expression cassette") is meant the combination of a selected heterologous gene (transgene) and the other regulatory elements necessary to drive translation, transcription and/or expression of the gene product in a host cell.

Typically, a ChAd155-derived adenoviral vector is designed such that the minigene is located in a nucleic acid molecule which contains other adenoviral sequences in the region native to a selected adenoviral gene. The minigene may be inserted into an existing gene region to disrupt the function of that region, if desired. Alternatively, the minigene may be inserted into the site of a partially or fully deleted adenoviral gene. For example, the minigene may be located in the site of a mutation, insertion or deletion which renders non-functional at least one gene of a genomic region selected from the group consisting of E1A, E1B, E2A, E2B, E3 and E4. The term "renders non-functional" means that a sufficient amount of the gene region is removed or otherwise disrupted, so that the gene region is no longer capable of producing functional products of gene expression. If desired, the entire gene region may be removed (and suitably replaced with the minigene).

For example, for a production vector useful for generation of a recombinant virus, the vector may contain the minigene and either the 5' end of the adenoviral genome or the 3' end of the adenoviral genome, or both the 5' and 3' ends of the adenoviral genome. The 5' end of the adenoviral genome contains the 5' cis-elements necessary for packaging and replication; i.e., the 5' ITR sequences (which function as origins of replication) and the native 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation. Suitably, a recombinant adenovirus contains both 5' and 3' adenoviral cis-elements and the minigene (suitably containing a transgene) is located between the 5' and 3' adenoviral sequences. A ChAd155-based adenoviral vector may also contain additional adenoviral sequences.

Suitably, ChAd155-based vectors contain one or more adenoviral elements derived from the adenoviral ChAd155 genome of the invention. In one embodiment, the vectors contain adenoviral ITRs from ChAd155 and additional adenoviral sequences from the same adenoviral serotype. In another embodiment, the vectors contain adenoviral sequences that are derived from a different adenoviral serotype than that which provides the ITRs.

As defined herein, a pseudotyped adenovirus refers to an adenovirus in which the capsid proteins of the adenovirus are from a different adenovirus than the adenovirus which provides the ITRs.

Further, chimeric or hybrid adenoviruses may be constructed using the adenoviruses described herein using techniques known to those of skill in the art (e.g., U.S. Pat. No. 7,291,498).

ITRs and any other adenoviral sequences present in the vector of the present invention may be obtained from many sources. A variety of adenovirus strains are available from the American Type Culture Collection, Manassas, Va., or available by request from a variety of commercial and institutional sources. Further, the sequences of many such strains are available from a variety of databases including, e.g., PubMed and GenBank. Homologous adenovirus vectors prepared from other chimp or from human adenoviruses are described in the published literature (for example, U.S. Pat. No. 5,240,846). The DNA sequences of a number of adenovirus types are available from GenBank, including type Ad5 (GenBank Accession Number M73370). The adenovirus sequences may be obtained from any known adenovirus serotype, such as serotypes 2, 3, 4, 7, 12 and 40, and further including any of the presently identified human types. Similarly adenoviruses known to infect nonhuman animals (e.g., simians) may also be employed in the vector constructs of this invention (e.g., U.S. Pat. No. 6,083,716). The viral sequences, helper viruses (if needed), and recombinant viral particles, and other vector components and sequences employed in the construction of the vectors described herein may be obtained as described below.

Sequence, Vector and Adenovirus Production

The sequences of the invention may be produced by any suitable means, including recombinant production, chemical synthesis, or other synthetic means. Suitable production techniques are well known to those of skill in the art. Alternatively, peptides can also be synthesized by well known solid phase peptide synthesis methods.

The adenoviral plasmids (or other vectors) may be used to produce adenoviral vectors. In one embodiment, the adenoviral vectors are adenoviral particles which are replication-incompetent. In one embodiment, the adenoviral particles are rendered replication-incompetent by deletions in the E1A and/or E1B genes. Alternatively, the adenoviruses are rendered replication-incompetent by another means, optionally while retaining the E1A and/or E1B genes. Similarly, in some embodiments, reduction of an immune response to the vector may be accomplished by deletions in the E2B and/or DNA polymerase genes. The adenoviral vectors can also contain other mutations to the adenoviral genome, e.g., temperature-sensitive mutations or deletions in other genes. In other embodiments, it is desirable to retain an intact E1A and/or E1B region in the adenoviral vectors. Such an intact E1 region may be located in its native location in the adenoviral genome or placed in the site of a deletion in the native adenoviral genome (e.g., in the E3 region).

In the construction of adenovirus vectors for delivery of a gene to a mammalian (such as human) cell, a range of modified adenovirus nucleic acid sequences can be employed in the vectors. For example, all or a portion of the adenovirus delayed early gene E3 may be eliminated from the adenovirus sequence which forms a part of the recombinant virus. The function of E3 is believed to be irrelevant to the function and production of the recombinant virus particle. Adenovirus vectors may also be constructed having a deletion of at least the ORF6 region of the E4 gene, and more desirably because of the redundancy in the function of this region, the entire E4 region. Still another vector of the invention contains a deletion in the delayed early gene E2A. Deletions may also be made in any of the late genes L1 to L5 of the adenovirus genome. Similarly, deletions in the intermediate genes IX and IVa2 may be useful for some purposes. Other deletions may be made in the other structural or non-structural adenovirus genes. The above discussed deletions may be used individually, i.e., an adenovirus sequence for use as described herein may contain deletions in only a single region. Alternatively, deletions of entire genes or portions thereof effective to destroy their biological activity may be used in any combination. For example, in one exemplary vector, the adenovirus sequence may have deletions of the E1 genes and the E4 gene, or of the E1, E2A and E3 genes, or of the E1 and E3 genes, or of E1, E2A and E4 genes, with or without deletion of E3, and so on. Any one or more of the E genes may suitably be replaced with an E gene (or one or more E gene open reading frames) sourced from a different strain of adenovirus. Particularly suitably the ChAd155 E1 and E3 genes are deleted and the ChAd155E4 gene is replaced with E4Ad5orf6. As discussed above, such deletions and/or substitutions may be used in combination with other mutations, such as temperature-sensitive mutations, to achieve a desired result.

An adenoviral vector lacking one or more essential adenoviral sequences (e.g., E1A, E1B, E2A, E2B, E4 ORF6, L1, L2, L3, L4 and L5) may be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell.

Complementation of Replication-Incompetent Vectors

To generate recombinant adenoviruses deleted in any of the genes described above, the function of the deleted gene region, if essential to the replication and infectivity of the virus, must be supplied to the recombinant virus by a helper virus or cell line, i.e., a complementation or packaging cell line.

Helper Viruses

Depending upon the adenovirus gene content of the viral vectors employed to carry the minigene, a helper adenovirus or non-replicating virus fragment may be used to provide sufficient adenovirus gene sequences necessary to produce an infective recombinant viral particle containing the minigene. Useful helper viruses contain selected adenovirus gene sequences not present in the adenovirus vector construct and/or not expressed by the packaging cell line in which the vector is transfected. In one embodiment, the helper virus is replication-defective and contains adenovirus genes in addition, suitably, to one or more of the sequences described herein. Such a helper virus is suitably used in combination with an E1 expressing (and optionally additionally E3 expressing) cell line.

A helper virus may optionally contain a reporter gene. A number of such reporter genes are known to the art as well as described herein. The presence of a reporter gene on the helper virus which is different from the transgene on the adenovirus vector allows both the adenoviral vector and the helper virus to be independently monitored. This reporter is used to enable separation between the resulting recombinant virus and the helper virus upon purification.

Complementation Cell Lines

In many circumstances, a cell line expressing the one or more missing genes which are essential to the replication and infectivity of the virus, such as human E1, can be used to transcomplement a chimp adenoviral vector. This is particularly advantageous because, due to the diversity between the chimp adenovirus sequences of the invention and the human adenovirus sequences found in currently available packaging cells, the use of the current human E1-containing cells prevents the generation of replication-competent adenoviruses during the replication and production process.

Alternatively, if desired, one may utilize the sequences provided herein to generate a packaging cell or cell line that expresses, at a minimum, the E1 gene from ChAd155 under the transcriptional control of a promoter for expression in a selected parent cell line. Inducible or constitutive promoters may be employed for this purpose. Examples of such promoters are described in detail elsewhere in this document. A parent cell is selected for the generation of a novel cell line expressing any desired ChAd155 gene. Without limitation, such a parent cell line may be HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209.

Such E1-expressing cell lines are useful in the generation of recombinant adenovirus E1 deleted vectors. Additionally, or alternatively, cell lines that express one or more adenoviral gene products, e.g., E1A, E1B, E2A, E3 and/or E4, can be constructed using essentially the same procedures as used in the generation of recombinant viral vectors. Such cell lines can be utilised to transcomplement adenovirus vectors deleted in the essential genes that encode those products, or to provide helper functions necessary for packaging of a helper-dependent virus (e.g., adeno-associated virus). The preparation of a host cell involves techniques such as assembly of selected DNA sequences.

In another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells.

Host cells may be selected from among any mammalian species, including, without limitation, cells such as A549, WEHI, 3T3, 10T1/2, HEK 293 cells or Per.C6 (both of which express functional adenoviral E1) [Fallaux, F J et al, (1998), Hum Gene Ther, 9:1909-1917], Saos, C2C12, L cells, HT1080, HepG2 and primary fibroblast, hepatocyte and myoblast cells derived from mammals including human, monkey, mouse, rat, rabbit, and hamster.

A particularly suitable complementation cell line is the Procell92 cell line. The Procell92 cell line is based on HEK 293 cells which express adenoviral E1 genes, transfected with the Tet repressor under control of the human phosphoglycerate kinase-1 (PGK) promoter, and the G418-resistance gene (Vitelli et al. *PLOS One* (2013) 8(e55435):1-9). Procell92.S is adapted for growth in suspension conditions and is useful for producing adenoviral vectors expressing toxic proteins (www.okairos.com/e/inners.php?m=00084, last accessed 13 Apr. 2015).

Assembly of a Viral Particle and Transfection of a Cell Line

Generally, when delivering the vector comprising the minigene by transfection, the vector is delivered in an amount from about 5 µg to about 100 µg DNA, and preferably about 10 to about 50 µg DNA to about $1 \times 10^4$ cells to about $1 \times 10^{13}$ cells, and preferably about $10^5$ cells. However, the relative amounts of vector DNA to host cells may be adjusted, taking into consideration such factors as the selected vector, the delivery method and the host cells selected.

Introduction into the host cell of the vector may be achieved by any means known in the art, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently.

Introduction of vectors into the host cell may also be accomplished using techniques known to the skilled person. Suitably, standard transfection techniques are used, e.g., CaPC transfection or electroporation.

Assembly of the selected DNA sequences of the adenovirus (as well as the transgene and other vector elements) into various intermediate plasmids, and the use of the plasmids and vectors to produce a recombinant viral particle are all achieved using conventional techniques. Such techniques include conventional cloning techniques of cDNA, use of overlapping oligonucleotide sequences of the adenovirus genomes, polymerase chain reaction, and any suitable method which provides the desired nucleotide sequence. Standard transfection and co-transfection techniques are employed, e.g., CaPC precipitation techniques. Other conventional methods employed include homologous recombination of the viral genomes, plaquing of viruses in agar overlay, methods of measuring signal generation, and the like.

For example, following the construction and assembly of the desired minigene-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The resulting recombinant adenoviruses are useful in transferring a selected transgene to a selected cell. In in vivo experiments with the recombinant virus grown in the packaging cell lines, the E1-deleted recombinant adenoviral vectors of the invention demonstrate utility in transferring a transgene to a non-simian mammal, preferably a human, cell.

Transgenes

The transgene is a nucleic acid sequence, heterologous to the vector sequences flanking the transgene, which encodes a protein of interest. The nucleic acid coding sequence is operatively linked to regulatory components in a manner which permits transgene transcription, translation, and/or expression in a host cell.

The composition of the transgene sequence will depend upon the use to which the resulting vector will be put. For example, the transgene may be a therapeutic transgene or an immunogenic transgene. Alternatively, a transgene sequence may include a reporter sequence, which upon expression produces a detectable signal. Such reporter sequences include, without limitation, DNA sequences encoding β-lactamase, β-galactosidase (LacZ), alkaline phosphatase, thymidine kinase, green fluorescent protein (GFP), chloramphenicol acetyltransferase (CAT), luciferase, membrane bound proteins including, for example, CD2, CD4, CD8, the influenza hemagglutinin protein, and others well known in the art, to which high affinity antibodies directed thereto exist or can be produced by conventional means, and fusion proteins comprising a membrane bound protein appropriately fused to an antigen tag domain from, among others, hemagglutinin or Myc. These coding sequences, when associated with regulatory elements which drive their expression, provide signals detectable by conventional means, including enzymatic, radiographic, colorimetric, fluorescence or other spectrographic assays, fluorescent activating cell sorting assays and immunological assays, including enzyme linked immunosorbent assay (ELISA), radioimmunoassay (RIA) and immunohistochemistry.

In one embodiment, the transgene is a non-marker sequence encoding a product which is useful in biology and medicine, such as a therapeutic transgene or an immunogenic transgene such as proteins, RNA, enzymes, or catalytic RNAs. Desirable RNA molecules include tRNA, dsRNA, ribosomal RNA, catalytic RNAs, and antisense RNAs. One example of a useful RNA sequence is a sequence which extinguishes expression of a targeted nucleic acid sequence in the treated animal.

The transgene may be used for treatment, e.g., of genetic deficiencies, as a cancer therapeutic or vaccine, for induction of an immune response, and/or for prophylactic vaccine purposes. As used herein, induction of an immune response refers to the ability of a protein to induce a T cell and/or a humoral immune response to the protein.

Regulatory Elements

In addition to the transgene the vector also includes conventional control elements which are operably linked to the transgene in a manner that permits its transcription, translation and/or expression in a cell transfected with the plasmid vector or infected with the virus produced by the invention. As used herein, "operably linked" sequences include both expression control sequences that are contiguous with the gene of interest and expression control sequences that act in trans or at a distance to control the gene of interest.

Expression control sequences include appropriate transcription initiation, termination, promoter and enhancer sequences; efficient RNA processing signals such as splicing and polyadenylation (poly A) signals including rabbit beta-globin polyA; sequences that stabilize cytoplasmic mRNA; sequences that enhance translation efficiency (e.g., Kozak consensus sequence); sequences that enhance protein stability; and when desired, sequences that enhance secretion of the encoded product. Among other sequences, chimeric introns may be used.

In some embodiments, the Woodchuck Hepatitis Virus Posttranscriptional Regulatory Element (WPRE) (Zuffrey et al. (1999) J Virol; 73(4):2886-9) may be operably linked to the transgene. An exemplary WPRE is provided in SEQ ID NO: 26.

A "promoter" is a nucleotide sequence that permits binding of RNA polymerase and directs the transcription of a gene. Typically, a promoter is located in the 5' non-coding region of a gene, proximal to the transcriptional start site of the gene. Sequence elements within promoters that function in the initiation of transcription are often characterized by consensus nucleotide sequences. Examples of promoters include, but are not limited to, promoters from bacteria, yeast, plants, viruses, and mammals (including humans). A great number of expression control sequences, including promoters which are internal, native, constitutive, inducible and/or tissue-specific, are known in the art and may be utilized.

Examples of constitutive promoters include, without limitation, the TBG promoter, the retroviral Rous sarcoma virus LTR promoter (optionally with the enhancer), the cytomegalovirus (CMV) promoter (optionally with the CMV enhancer, see, e.g., Boshart et al, Cell, 41:521-530 (1985)), the CASI promoter, the SV40 promoter, the dihydrofolate reductase promoter, the β-actin promoter, the phosphoglycerol kinase (PGK) promoter, and the EF1a promoter (Invitrogen).

In some embodiments, the promoter is a CASI promoter (see, for example, WO2012/115980). The CASI promoter is a synthetic promoter which contains a portion of the CMV enhancer, a portion of the chicken beta-actin promoter, and a portion of the UBC enhancer. In some embodiments, the CASI promoter can include a nucleic acid sequence having at least about 90%, at least about 95%, at least about 96%, at least about 97%, at least about 98%, at least about 99%, or more, sequence identity to SEQ ID NO: 12. In some embodiments, the promoter comprises or consists of a nucleic acid sequence of SEQ ID NO: 12.

Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. Inducible promoters and inducible systems are available from a variety of commercial sources, including, without limitation, Invitrogen, Clontech and Ariad. Many other systems have been described and can be readily selected by one of skill in the art. For example, inducible promoters include the zinc-inducible sheep metallothionine (MT) promoter and the dexamethasone (Dex)-inducible mouse mammary tumor virus (MMTV) promoter. Other inducible systems include the T7 polymerase promoter system (WO 98/10088); the ecdysone insect promoter (No et al, Proc. Natl. Acad. Sci. USA, 93:3346-3351 (1996)), the tetracycline-repressible system (Gossen et al, Proc. Natl. Acad. Sci. USA, 89:5547-5551 (1992)), the tetracycline-inducible system (Gossen et al, Science, 378:1766-1769 (1995), see also Harvey et al, Curr. Opin. Chem. Biol, 2:512-518 (1998)). Other systems include the FK506 dimer, VP16 or p65 using castradiol, diphenol murislerone, the RU486-inducible system (Wang et al, Nat. Biotech., 15:239-243 (1997) and Wang et al, Gene Ther., 4:432-441 (1997)) and the rapamycin-inducible system (Magari et al, J. Clin. Invest., 100:2865-2872 (1997)). The effectiveness of some inducible promoters increases over time. In such cases one can enhance the effectiveness of such systems by inserting multiple repressors in tandem, e.g., TetR linked to a TetR by an IRES.

In another embodiment, the native promoter for the transgene will be used. The native promoter may be preferred when it is desired that expression of the transgene should mimic the native expression. The native promoter may be used when expression of the transgene must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

The transgene may be operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al, Nat. Biotech., 17:241-245 (1999)). Examples of promoters that are tissue-specific are known for liver (albumin, Miyatake et al, J. Virol, 71:5124-32 (1997); hepatitis B virus core promoter, Sandig et al, Gene Ther., 3:1002-9 (1996); alpha-fetoprotein (AFP), Arbuthnot et al., Hum. Gene Ther., 7: 1503-14 (1996)), bone osteocalcin (Stein et al, Mol. Biol. Rep., 24:185-96 (1997)); bone sialoprotein (Chen et al., J. Bone Miner. Res., 11:654-64 (1996)), lymphocytes (CD2, Hansal et al, J. Immunol, 161:1063-8 (1998); immunoglobulin heavy chain; T cell receptor chain), neuronal such as neuron-specific enolase (NSE) promoter (Andersen et al, Cell. Mol. Neurobiol, 13:503-15 (1993)), neurofilament light-chain gene (Piccioli et al, Proc. Natl. Acad. Sci. USA, 88:5611-5 (1991)), and the neuron-specific vgf gene (Piccioli et al, Neuron, 15:373-84 (1995)), among others.

Optionally, vectors carrying transgenes encoding therapeutically useful or immunogenic products may also include selectable markers or reporter genes which may include sequences encoding geneticin, hygromicin or purimycin resistance, among others. Such selectable reporters or marker genes (preferably located outside the viral genome to be packaged into a viral particle) can be used to signal the presence of the plasmids in bacterial cells, such as ampicillin resistance. Other components of the vector may include an origin of replication.

These vectors are generated using the techniques and sequences provided herein, in conjunction with techniques known to those of skill in the art. Such techniques include conventional cloning techniques of cDNA such as those described in texts, use of overlapping oligonucleotide sequences of the adenovirus genomes, polymerase chain reaction, and any suitable method which provides the desired nucleotide sequence.

Therapeutics and Prophylaxis

The recombinant ChAd155-based vectors are useful for gene transfer to a human or non-simian mammal in vitro, ex vivo, and in vivo.

The recombinant adenovirus vectors described herein can be used as expression vectors for the production of the products encoded by the heterologous transgenes in vitro. For example, the recombinant replication-incompetent adenovirus containing a transgene may be transfected into a complementation cell line as described above.

A ChAd155-derived recombinant adenoviral vector provides an efficient gene transfer vehicle that can deliver a selected transgene to a selected host cell in vivo or ex vivo even where the organism has neutralizing antibodies to one or more adenovirus serotypes. In one embodiment, the vector and the cells are mixed ex vivo; the infected cells are cultured using conventional methodologies; and the transduced cells are re-infused into the patient. These techniques are particularly well suited to gene delivery for therapeutic purposes and for immunisation, including inducing protective immunity.

Immunogenic Transgenes

The recombinant ChAd155 vectors may also be as administered in immunogenic compositions. An immunogenic composition as described herein is a composition comprising one or more recombinant ChAd155 vector capable of inducing an immune response, for example a humoral (e.g., antibody) and/or cell-mediated (e.g., a cytotoxic T cell) response, against a transgene product delivered by the vector following delivery to a mammal, suitably a human. A recombinant adenovirus may comprise (suitably in any of its gene deletions) a gene encoding a desired immunogen and may therefore be used in a vaccine. The recombinant adenoviruses can be used as prophylactic or therapeutic vaccines against any pathogen for which the antigen(s) crucial for induction of an immune response and able to limit the spread of the pathogen has been identified and for which the cDNA is available.

Such vaccine or other immunogenic compositions may be formulated in a suitable delivery vehicle. Generally, doses for the immunogenic compositions are in the range defined below under 'Delivery Methods and Dosage'. The levels of immunity of the selected gene can be monitored to determine the need, if any, for boosters. Following an assessment of antibody titers in the serum, optional booster immunizations may be desired.

Optionally, a vaccine or immunogenic composition of the invention may be formulated to contain other components, including, e.g., adjuvants, stabilizers, pH adjusters, preservatives and the like. Examples of suitable adjuvants are provided below under 'Adjuvants'. Such an adjuvant can be administered with a priming DNA vaccine encoding an antigen to enhance the antigen-specific immune response compared with the immune response generated upon priming with a DNA vaccine encoding the antigen only. Alternatively, such an adjuvant can be administered with a polypeptide antigen which is administered in an administration regimen involving the ChAd155 vectors of the invention (as described below under 'Administration Regimens').

The recombinant adenoviruses are administered in an immunogenic amount, that is, an amount of recombinant adenovirus that is effective in a route of administration to transfect the desired target cells and provide sufficient levels of expression of the selected gene to induce an immune response. Where protective immunity is provided, the recombinant adenoviruses are considered to be vaccine compositions useful in preventing infection and/or recurrent disease.

The recombinant vectors described herein are expected to be highly efficacious at inducing cytolytic T cells and antibodies directed to the inserted heterologous antigenic protein expressed by the vector.

Immunogens expressed by the inventive vectors which are useful to immunize a human or non-human animal against other pathogens include, e.g., bacteria, fungi, parasitic microorganisms or multicellular parasites which infect human and non-human vertebrates, or from a cancer cell or tumor cell. For example, immunogens may be selected from a variety of viral families. Examples of viral families against which an immune response would be desirable include respiratory viruses such as respiratory syncytial virus (RSV) and other paramyxoviruses such as human metapneumovirus, hMPV and parainfluenza viruses (PIV).

Suitable antigens of RSV which are useful as immunogens to immunize a human or non-human animal can be selected from: the fusion protein (F), the attachment protein (G), the matrix protein (M2) and the nucleoprotein (N). The term "F protein" or "fusion protein" or "F protein polypeptide" or "fusion protein polypeptide" refers to a polypeptide or protein having all or part of an amino acid sequence of an RSV Fusion protein polypeptide. Similarly, the term "G protein" or "G protein polypeptide" refers to a polypeptide or protein having all or part of an amino acid sequence of an RSV Attachment protein polypeptide. The term "M protein"

or "matrix protein" or "M protein polypeptide" refers to a polypeptide or protein having all or part of an amino acid sequence of an RSV Matrix protein and may include either or both of the M2-1 (which may be written herein as M2.1) and M2-2 gene products. Likewise, the term "N protein" or "Nucleocapsid protein" or "N protein polypeptide" refers to a polypeptide or protein having all or part of an amino acid sequence of an RSV Nucleoprotein.

Two groups of human RSV strains have been described, the A and B groups, based mainly on differences in the antigenicity of the G glycoprotein. Numerous strains of RSV have been isolated to date, any of which are suitable in the context of the antigens of the immunogenic combinations disclosed herein. Exemplary strains indicated by GenBank and/or EMBL Accession number can be found in US published application number 2010/0203071 (WO2008114149), which is incorporated herein by reference for the purpose of disclosing the nucleic acid and polypeptide sequences of RSV F and G proteins suitable for use in present invention. In an embodiment, the RSV F protein can be an ectodomain of an RSV F Protein (FΔTM).

Exemplary M and N protein nucleic acids and protein sequences can be found, e.g., in US published application number 2014/0141042 (WO2012/089833), which is incorporated herein for purpose of disclosing the nucleic acid and polypeptide sequences of RSV M and N proteins suitable for use in present invention.

Suitably, for use with in present invention, a nucleic acid encodes an RSV F antigen and RSV, M and N antigens. More specifically, the nucleic acid encodes an RSV FΔTM antigen and RSV M2-1 and N antigens, wherein a self-cleavage site is included between the RSV FΔTM antigen and the RSV M2-1 and a flexible linker is included between the RSV M2-1 and N antigens. In one embodiment a suitable nucleic acid encodes the polypeptide represented by SEQ ID NO:37

In one embodiment, the immunogen may be from a retrovirus, for example a lentivirus such as the Human Immunodeficiency Virus (HIV). In such an embodiment, immunogens may be derived from HIV-1 or HIV-2.

The HIV genome encodes a number of different proteins, each of which can be immunogenic in its entirety or as a fragment when expressed by vectors of the present invention. Envelope proteins include gp120, gp41 and Env precursor gp160, for example. Non-envelope proteins of HIV include for example internal structural proteins such as the products of the gag and pol genes and other non-structural proteins such as Rev, Nef, Vif and Tat. In an embodiment the vector of the invention encodes one or more polypeptides comprising HIV Gag.

The Gag gene is translated as a precursor polyprotein that is cleaved by protease to yield products that include the matrix protein (p17), the capsid (p24), the nucleocapsid (p9), p6 and two space peptides, p2 and p1, all of which are examples of fragments of Gag.

The Gag gene gives rise to the 55-kilodalton (kD) Gag precursor protein, also called p55, which is expressed from the unspliced viral mRNA. During translation, the N terminus of p55 is myristoylated, triggering its association with the cytoplasmic aspect of cell membranes. The membrane-associated Gag polyprotein recruits two copies of the viral genomic RNA along with other viral and cellular proteins that triggers the budding of the viral particle from the surface of an infected cell. After budding, p55 is cleaved by the virally encoded protease (a product of the pol gene) during the process of viral maturation into four smaller proteins designated MA (matrix [p17]), CA (capsid [p24]), NC (nucleocapsid [p9]), and p6, all of which are examples of fragments of Gag. In one embodiment, the vectors of the present invention comprise a Gag polypeptide of SEQ ID NO: 38.

Adjuvants

An "adjuvant" as used herein refers to a composition that enhances the immune response to an immunogen. Examples of such adjuvants include but are not limited to inorganic adjuvants (e.g. inorganic metal salts such as aluminium phosphate or aluminium hydroxide), organic adjuvants (e.g. saponins, such as QS21, or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immunostimulatory complexes (ISCOMS), liposomes, or biodegradable microspheres), virosomes, bacterial adjuvants (e.g. monophosphoryl lipid A, such as 3-de-O-acylated monophosphoryl lipid A (3D-MPL), or muramyl peptides), synthetic adjuvants (e.g. non-ionic block copolymers, muramyl peptide analogues, or synthetic lipid A), synthetic polynucleotides adjuvants (e.g polyarginine or polylysine) and immunostimulatory oligonucleotides containing unmethylated CpG dinucleotides ("CpG").

One suitable adjuvant is monophosphoryl lipid A (MPL), in particular 3-de-O-acylated monophosphoryl lipid A (3D-MPL). Chemically it is often supplied as a mixture of 3-de-O-acylated monophosphoryl lipid A with either 4, 5, or 6 acylated chains. It can be purified and prepared by the methods taught in GB 2122204B, which reference also discloses the preparation of diphosphoryl lipid A, and 3-O-deacylated variants thereof. Other purified and synthetic lipopolysaccharides have been described (U.S. Pat. No. 6,005,099 and EP 0 729 473 B1; Hilgers et al., 1986, Int. Arch. Allergy. Immunol., 79(4):392-6; Hilgers et al., 1987, Immunology, 60(1):141-6; and EP 0 549 074 B1I).

Saponins are also suitable adjuvants (see Lacaille-Dubois, M and Wagner H, A review of the biological and pharmacological activities of saponins. Phytomedicine vol 2 pp 363-386 (1996)). For example, the saponin Quil A (derived from the bark of the South American tree Quillaja Saponaria Molina), and fractions thereof, are described in U.S. Pat. No. 5,057,540 and Kensil, Crit. Rev. Ther. Drug Carrier Syst., 1996, 12:1-55; and EP 0 362 279 B1. Purified fractions of Quil A are also known as immunostimulants, such as QS21 and QS17; methods of their production is disclosed in U.S. Pat. No. 5,057,540 and EP 0 362 279 B1. Also described in these references is QS7 (a non-haemolytic fraction of Quil-A). Use of QS21 is further described in Kensil et al. (1991, J. Immunology, 146: 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Another adjuvant is an immunostimulatory oligonucleotide containing unmethylated CpG dinucleotides ("CpG") (Krieg, Nature 374:546 (1995)). CpG is an abbreviation for cytosine-guanosine dinucleotide motifs present in DNA. CpG is known as an adjuvant when administered by both systemic and mucosal routes (WO 96/02555, EP 468520, Davis et al, J. Immunol, 1998, 160:870-876; McCluskie and Davis, J. Immunol., 1998, 161:4463-6). CpG, when formulated into vaccines, may be administered in free solution together with free antigen (WO 96/02555) or covalently conjugated to an antigen (WO 98/16247), or formulated with a carrier such as aluminium hydroxide (Brazolot-Millan et al., Proc. Natl. Acad. Sci., USA, 1998, 95:15553-8).

Adjuvants such as those described above may be formulated together with carriers, such as liposomes, oil in water emulsions, and/or metallic salts (including aluminum salts such as aluminum hydroxide). For example, 3D-MPL may be formulated with aluminum hydroxide (EP 0 689 454) or oil in water emulsions (WO 95/17210); QS21 may be formulated with cholesterol containing liposomes (WO 96/33739), oil in water emulsions (WO 95/17210) or alum (WO 98/15287); CpG may be formulated with alum (Brazolot-Millan, supra) or with other cationic carriers.

Combinations of adjuvants may be utilized in the present invention, in particular a combination of a monophosphoryl lipid A and a saponin derivative (see, e.g., WO 94/00153; WO 95/17210; WO 96/33739; WO 98/56414; WO 99/12565; WO 99/11241), more particularly the combination of QS21 and 3D-MPL as disclosed in WO 94/00153, or a composition where the QS21 is quenched in cholesterol-containing liposomes (DQ) as disclosed in WO 96/33739. Alternatively, a combination of CpG plus a saponin such as QS21 is an adjuvant suitable for use in the present invention. A potent adjuvant formulation involving QS21, 3D-MPL & tocopherol in an oil in water emulsion is described in WO 95/17210 and is another formulation for use in the present invention. Saponin adjuvants may be formulated in a liposome and combined with an immunostimulatory oligonucleotide. Thus, suitable adjuvant systems include, for example, a combination of monophosphoryl lipid A, preferably 3D-MPL, together with an aluminium salt (e.g. as described in WO00/23105). A further exemplary adjuvant comprises QS21 and/or MPL and/or CpG. QS21 may be quenched in cholesterol-containing liposomes as disclosed in WO 96/33739.

Other suitable adjuvants include alkyl Glucosaminide phosphates (AGPs) such as those disclosed in WO9850399 or U.S. Pat. No. 6,303,347 (processes for preparation of AGPs are also disclosed), or pharmaceutically acceptable salts of AGPs as disclosed in U.S. Pat. No. 6,764,840. Some AGPs are TLR4 agonists, and some are TLR4 antagonists. Both are thought to be useful as adjuvants.

It has been found (WO 2007/062656, which published as US 2011/0293704 and is incorporated by reference for the purpose of disclosing invariant chain sequences) that the fusion of the invariant chain to an antigen which is comprised by an expression system used for vaccination increases the immune response against said antigen, if it is administered with an adenovirus. Accordingly, in one embodiment of the invention, the immunogenic transgene may be co-expressed with invariant chain in a recombinant ChAd155 viral vector.

In another embodiment, the invention provides the use of the capsid of ChAd155 (optionally an intact or recombinant viral particle or an empty capsid is used) to induce an immunomodulatory effect response, or to enhance or adjuvant a cytotoxic T cell response to another active agent by delivering a ChAd155 capsid to a subject. The ChAd155 capsid can be delivered alone or in a combination regimen with an active agent to enhance the immune response thereto. Advantageously, the desired effect can be accomplished without infecting the host with an adenovirus.

Administration Regimens

Commonly, the ChAd155 recombinant adenoviral vectors will be utilized for delivery of therapeutic or immunogenic molecules (such as proteins). It will be readily understood for both applications, that the recombinant adenoviral vectors of the invention are particularly well suited for use in regimens involving repeat delivery of recombinant adenoviral vectors. Such regimens typically involve delivery of a series of viral vectors in which the viral capsids are alternated. The viral capsids may be changed for each subsequent administration, or after a pre-selected number of administrations of a particular serotype capsid (e.g. one, two, three, four or more). Thus, a regimen may involve delivery of a recombinant adenovirus with a first capsid, delivery with a recombinant adenovirus with a second capsid, and delivery with a recombinant adenovirus with a third capsid. A variety of other regimens which use the adenovirus capsids of the invention alone, in combination with one another, or in combination with other adenoviruses (which are preferably immunologically non-crossreactive) will be apparent to those of skill in the art. Optionally, such a regimen may involve administration of recombinant adenovirus with capsids of other non-human primate adenoviruses, human adenoviruses, or artificial sequences such as are described herein.

The adenoviral vectors of the invention are particularly well suited for therapeutic regimens in which multiple adenoviral-mediated deliveries of transgenes are desired, e.g., in regimens involving redelivery of the same transgene or in combination regimens involving delivery of other transgenes. Such regimens may involve administration of a ChAd155 adenoviral vector, followed by re-administration with a vector from the same serotype adenovirus. Particularly desirable regimens involve administration of a ChAd155 adenoviral vector, in which the source of the adenoviral capsid sequences of the vector delivered in the first administration differs from the source of adenoviral capsid sequences of the viral vector utilized in one or more of the subsequent administrations. For example, a therapeutic regimen involves administration of a ChAd155 vector and repeat administration with one or more adenoviral vectors of the same or different serotypes.

In another example, a therapeutic regimen involves administration of an adenoviral vector followed by repeat administration with a ChAd155 vector which has a capsid which differs from the source of the capsid in the first delivered adenoviral vector, and optionally further administration with another vector which is the same or, preferably, differs from the source of the adenoviral capsid of the vector in the prior administration steps. These regimens are not limited to delivery of adenoviral vectors constructed using the ChAd155 sequences. Rather, these regimens can readily utilize other adenoviral sequences, including, without limitation, other adenoviral sequences including other non-human primate adenoviral sequences, or human adenoviral sequences, in combination with the ChAd155 vectors.

In a further example, a therapeutic regimen may involve either simultaneous (such as co-administration) or sequential (such as a prime-boost) delivery of (i) one or more ChAd155 adenoviral vectors and (ii) a further component such as non-adenoviral vectors, non-viral vectors, and/or a variety of other therapeutically useful compounds or molecules such as antigenic proteins optionally simultaneously administered with adjuvant. Examples of co-administration include homo-lateral co-administration and contra-lateral co-administration (further described below under 'Delivery Methods and Dosage').

Suitable non-adenoviral vectors for use in simultaneous or particularly in sequential delivery (such as prime-boost) with one or more ChAd155 adenoviral vectors include one or more poxviral vectors. Suitably, the poxviral vector belongs to the subfamily chordopoxvirinae, more suitably to a genus in said subfamily selected from the group consisting of orthopox, parapox, yatapox, avipox (suitably canarypox (ALVAC) or fowlpox (FPV)) and molluscipox. Even more suitably, the poxviral vector belongs to the orthopox and is selected from the group consisting of vaccinia virus, NYVAC (derived from the Copenhagen strain of vaccinia), Modified Vaccinia Ankara (MVA), cowpoxvirus and monkeypox virus. Most suitably, the poxviral vector is MVA.

"Simultaneous" administration suitably refers to the same ongoing immune response. Preferably both components are administered at the same time (such as simultaneous administration of both DNA and protein), however, one component could be administered within a few minutes (for example, at the same medical appointment or doctor's visit), within a few hours. Such administration is also referred to as co-administration. In some embodiments, co-administration may refer to the administration of an adenoviral vector, an adjuvant and a protein component. In other embodiments, co-administration refers to the administration of an adenoviral vector and another viral vector, for example a second adenoviral vector or a poxvirus such as MVA. In other embodiments, co-administration refers to the administration of an adenoviral vector and a protein component, which is optionally adjuvanted.

A prime-boost regimen may be used. Prime-boost refers to two separate immune responses: (i) an initial priming of the immune system followed by (ii) a secondary or boosting of the immune system many weeks or months after the primary immune response has been established.

Such a regimen may involve the administration of a recombinant ChAd155 vector to prime the immune system to second, booster, administration with a traditional antigen, such as a protein (optionally co-administered with adjuvant), or a recombinant virus carrying the sequences encoding such an antigen (e.g., WO 00/11140). Alternatively, an immunization regimen may involve the administration of a recombinant ChAd155 vector to boost the immune response to a vector (either viral or DNA-based) encoding an antigen. In another alternative, an immunization regimen involves administration of a protein followed by booster with a recombinant ChAd155 vector encoding the antigen. In one example, the prime-boost regimen can provide a protective immune response to the virus, bacteria or other organism from which the antigen is derived. In another embodiment, the prime-boost regimen provides a therapeutic effect that can be measured using conventional assays for detection of the presence of the condition for which therapy is being administered.

Preferably, a boosting composition is administered about 2 to about 27 weeks after administering the priming composition to the subject. The administration of the boosting composition is accomplished using an effective amount of a boosting composition containing or capable of delivering the same antigen or a different antigen as administered by the priming vaccine. The boosting composition may be composed of a recombinant viral vector derived from the same viral source or from another source. Alternatively, the boosting composition can be a composition containing the same antigen as encoded in the priming vaccine, but in the form of a protein, which composition induces an immune response in the host. The primary requirements of the boosting composition are that the antigen of the composition is the same antigen, or a cross-reactive antigen, as that encoded by the priming composition.

Delivery Methods and Dosage

The vector may be prepared for administration by being suspended or dissolved in a pharmaceutically or physiologically acceptable carrier such as isotonic saline; isotonic salts solution or other formulations that will be apparent to those skilled in the art. The appropriate carrier will be evident to those skilled in the art and will depend in large part upon the route of administration. The compositions described herein may be administered to a mammal in a sustained release formulation using a biodegradable biocompatible polymer, or by on-site delivery using micelles, gels and liposomes.

In some embodiments, the recombinant adenovirus of the invention is administered to a subject by intramuscular injection, intravaginal injection, intravenous injection, intraperitoneal injection, subcutaneous injection, epicutaneous administration, intradermal administration, nasal administration or oral administration.

If the therapeutic regimen involves co-administration of one or more ChAd155 adenoviral vectors and a further component, each formulated in different compositions, they are favourably administered co-locationally at or near the same site. For example, the components can be administered (e.g. via an administration route selected from intramuscular, transdermal, intradermal, sub-cutaneous) to the same side or extremity ("co-lateral" administration) or to opposite sides or extremities ("contra-lateral" administration).

Dosages of the viral vector will depend primarily on factors such as the condition being treated, the age, weight and health of the patient, and may thus vary among patients. For example, a therapeutically effective adult human or veterinary dosage of the viral vector generally contains $1 \times 10^5$ to $1 \times 10^{15}$ viral particles, such as from $1 \times 10^8$ to $1 \times 10^{12}$ (e.g., $1 \times 10^8$, $2.5 \times 10^8$, $5 \times 10^8$, $1 \times 10^9$, $1.5 \times 10^9$, $2.5 \times 10^9$, $5 \times 10^9$, $1 \times 10^{10}$, $1.5 \times 10^{10}$, $2.5 \times 10^{10}$, $5 \times 10^{10}$, $1 \times 10^{11}$, $1.5 \times 10^{11}$, $2.5 \times 10^{11}$, $5 \times 10^{11}$, $1 \times 10^{12}$ particles). Alternatively, a viral vector can be administered at a dose that is typically from $1 \times 10^5$ to $1 \times 10^{10}$ plaque forming units (PFU), such as $1 \times 10^5$ PFU, $2.5 \times 10^5$ PFU, $5 \times 10^5$ PFU, $1 \times 10^6$ PFU, $2.5 \times 10^6$ PFU, $5 \times 10^6$ PFU; $1 \times 10^7$ PFU, $2.5 \times 10^7$ PFU, $5 \times 10^7$ PFU, $1 \times 10^8$ PFU, $2.5 \times 10^8$ PFU, $5 \times 10^8$ PFU, $1 \times 10^9$ PFU, $2.5 \times 10^9$ PFU, $5 \times 10^9$ PFU, or $1 \times 10^{10}$ PFU. Dosages will vary depending upon the size of the animal and the route of administration. For example, a suitable human or veterinary dosage (for about an 80 kg animal) for intramuscular injection is in the range of about $1 \times 10^9$ to about $5 \times 10^{12}$ particles per mL, for a single site. Optionally, multiple sites of administration may be used. In another example, a suitable human or veterinary dosage may be in the range of about $1 \times 10^{11}$ to about $1 \times 10^{15}$ particles for an oral formulation.

The viral vector can be quantified by Quantitative PCR Analysis (Q-PCR), for example with primers and probe designed on CMV promoter region using as standard curve serial dilution of plasmid DNA containing the vector genome with expression cassette including HCMV promoter. The copy number in the test sample is determined by the parallel line analysis method. Alternative methods for vector particle quantification can be analytical HPLC or spectrophotometric method based on A260 nm.

An immunologically effective amount of a nucleic acid may suitably be between 1 ng and 100 mg. For example, a suitable amount can be from 1 µg to 100 mg. An appropriate amount of the particular nucleic acid (e.g., vector) can readily be determined by those of skill in the art. Exemplary effective amounts of a nucleic acid component can be between 1 ng and 100 µg, such as between 1 ng and 1 µg (e.g., 100 ng-1 µg), or between 1 µg and 100 µg, such as 10 ng, 50 ng, 100 ng, 150 ng, 200 ng, 250 ng, 500 ng, 750 ng, or 1 µg. Effective amounts of a nucleic acid can also include from 1 µg to 500 µg, such as between 1 µg and 200 µg, such as between 10 and 100 µg, for example 1 µg, 2 µg, 5 µg, 10 µg, 20 µg, 50 µg, 75 µg, 100 µg, 150 µg, or 200 µg. Alternatively, an exemplary effective amount of a nucleic acid can be between 100 µg and 1 mg, such as from 100 µg to 500 μg, for example, 100 μg, 150 μg, 200 μg, 250 μg, 300 μg, 400 μg, 500 μg, 600 μg, 700 μg, 800 μg, 900 μg or 1 mg.

Generally a human dose will be in a volume of between 0.1 ml and 2 ml. Thus the composition described herein can be formulated in a volume of, for example 0.1, 0.15, 0.2, 0.5, 1.0, 1.5 or 2.0 ml human dose per individual or combined immunogenic components.

One of skill in the art may adjust these doses, depending on the route of administration and the therapeutic or vaccine application for which the recombinant vector is employed. The levels of expression of the transgene, or for an adjuvant, the level of circulating antibody, can be monitored to determine the frequency of dosage administration.

If one or more priming and/or boosting steps are used, this step may include a single dose that is administered hourly, daily, weekly or monthly, or yearly. As an example, mammals may receive one or two doses containing between about 10 μg to about 50 μg of plasmid in carrier. The amount or site of delivery is desirably selected based upon the identity and condition of the mammal.

The therapeutic levels of, or level of immune response against, the protein encoded by the selected transgene can be monitored to determine the need, if any, for boosters. Following an assessment of CD8+ T cell response, or optionally, antibody titers, in the serum, optional booster immunizations may be desired. Optionally, the recombinant ChAd155 vectors may be delivered in a single administration or in various combination regimens, e.g., in combination with a regimen or course of treatment involving other active ingredients or in a prime-boost regimen.

The present invention will now be further described by means of the following non-limiting examples.

EXAMPLES

Example 1: Isolation of ChAd155

Wild type chimpanzee adenovirus type 155 (ChAd155) was isolated from a healthy young chimpanzee housed at the New Iberia Research Center facility (New Iberia Research Center; The University of Louisiana at Lafayette) using standard procedures as described in Colloca et al. (2012) and WO 2010086189, which is hereby incorporated by reference for the purpose of describing adenoviral isolation and characterization techniques

Example 2: ChAd155 Vector Construction

The ChAd155 viral genome was then cloned in a plasmid or in a BAC vector and subsequently modified (FIG. 2) to carry the following modifications in different regions of the ChAd155 viral genome:
a) deletion of the E1 region (from bp 449 to bp 3529) of the viral genome;
b) deletion of the E4 region (from bp 34731 to bp 37449) of the viral genome;
c) insertion of the E4orf6 derived from human Ad5.

2.1: Deletion of E1 Region: Construction of BAC/ChAd155 ΔE1 TetO hCMV RpsL-Kana#1375

Figure 3:
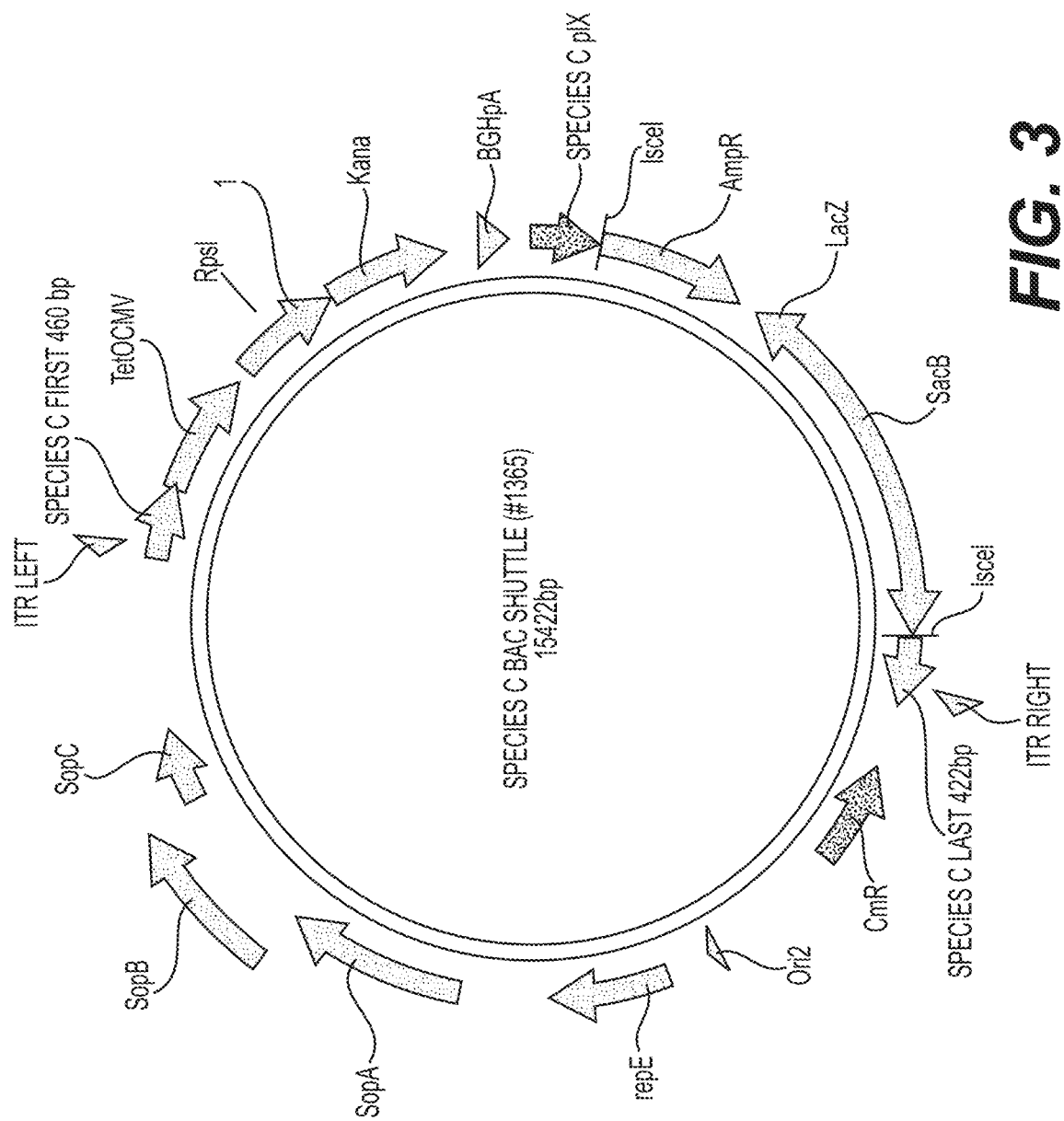

The ChAd155 viral genome was cloned into a BAC vector by homologous recombination in *E. coli* strain BJ5183 electroporation competent cells (Stratagene catalog no. 2000154) co-transformed with ChAd155 viral DNA and Subgroup C BAC Shuttle (#1365). As shown in the schematic of FIG. 3, the Subgroup C Shuttle is a BAC vector derived from pBeloBAC11 (GenBank U51113, NEB) and which is dedicated to the cloning of ChAd belonging to species C and therefore contains the pIX gene and DNA fragments derived from right and left ends (including right and left ITRs) of species C ChAd viruses.

The Species C BAC Shuttle also contains a RpsL-Kana cassette inserted between left end and the pIX gene. In addition, an Amp-LacZ-SacB selection cassette, flanked by IScel restriction sites, is present between the pIX gene and right end of the viral genome. In particular, the BAC Shuttle comprised the following features: Left ITR: bp 27 to 139, hCMV(tetO) RpsL-Kana cassette: bp 493 to 3396, pIX gene: bp 3508 to 3972, IScel restriction sites: bp 3990 and 7481, Amp-LacZ-SacB selection cassette: bp 4000 to 7471, Right ITR: bp 7805 to 7917.

BJ5183 cells were co-transformed by electroporation with ChAd155 purified viral DNA and Subgroup C BAC Shuttle vector digested with IScel restriction enzyme and then purified from gel. Homologous recombination occurring between pIX gene and right ITR sequences (present at the ends of Species C BAC Shuttle linearized DNA) and homologous sequences present in ChAd155 viral DNA lead to the insertion of ChAd155 viral genomic DNA in the BAC shuttle vector. At the same time, the viral E1 region was deleted and substituted by the RpsL-Kana cassette, generating BAC/ChAd155 ΔE1/TetO hCMV RpsL-Kana#1375.

2.2: Plasmid Construction by Homologous Recombination in *E. coli* BJ5183

2.2.1: Deletion of E4 Region—Construction of pChAd155 ΔE1, E4_Ad5E4orf6/TetO hCMV RpsL-Kana (#1434)

To improve propagation of the vector, a deletion of the E4 region spanning from nucleotide 34731-37449 (ChAd155 wild type sequence) was introduced in the vector backbone by replacing the native E4 region with Ad5 E4orf6 coding sequence using a strategy involving several steps of cloning and homologous recombination in *E. coli*. The E4 coding region was completely deleted while the E4 native promoter and polyadenylation signal were conserved. To this end, a shuttle vector was constructed to allow the insertion of Ad5orf6 by replacing the ChAd155 native E4 region by homologous recombination in *E. coli* BJ5183 as detailed below.

Construction of pARS SpeciesC Ad5E4orf6-1

A DNA fragment containing Ad5orf6 was obtained by PCR using Ad5 DNA as template, with the oligonucleotides 5'-ATACGGACTAGTGGAGAAGTACTCGCCTACATG-3' (SEQ ID NO: 13) and 5'-ATACGGAAGATCTAA-GACTTCAGGAAATATGACTAC-3' (SEQ ID NO: 14). The PCR fragment was digested with BglII and SpeI and cloned into Species C RLD-EGFP shuttle digested with BglII and SpeI, generating the plasmid pARS Species C Ad5orf6-1. Details regarding the shuttle can be found in Colloca et al, Sci. Transl. Med. (2012) 4:115ra.

Construction of pARS SpeciesC Ad5E4orf6-2

Figure 4:
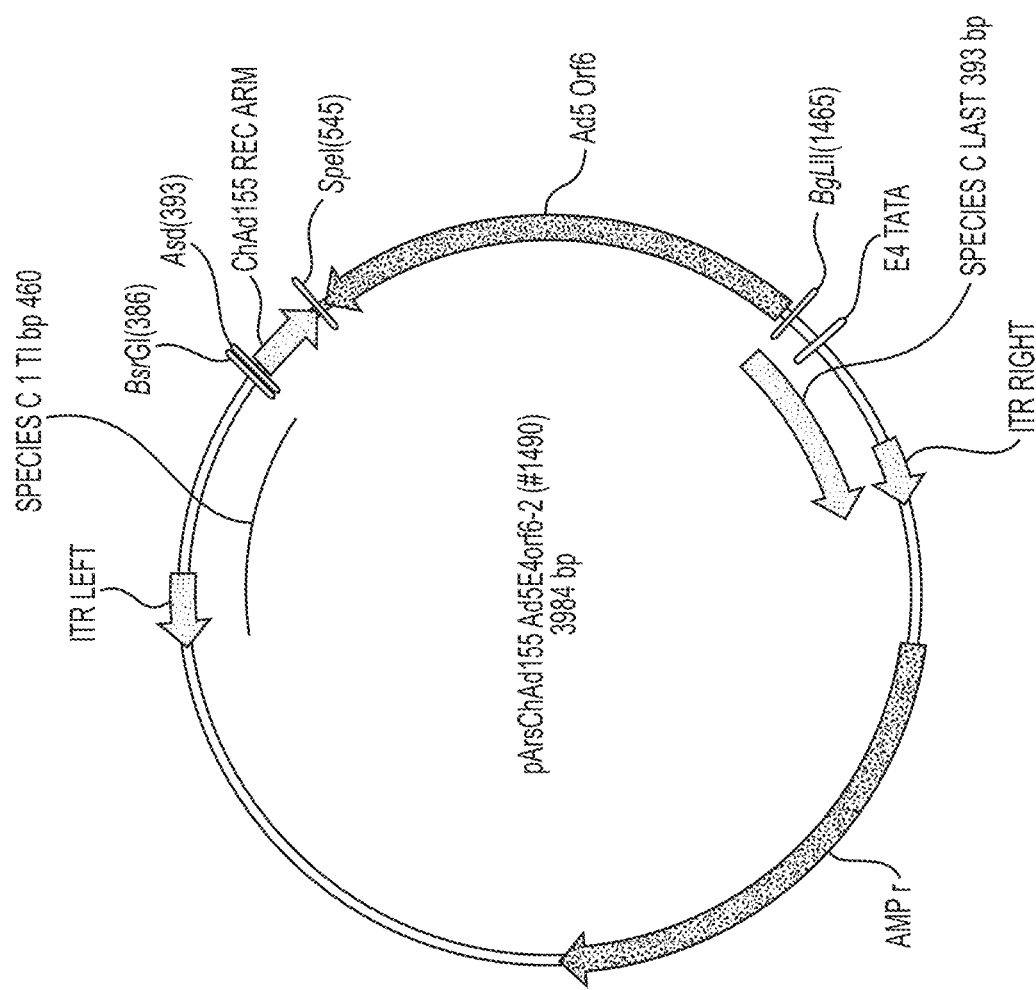

To delete the E4 region, a 177 bp DNA fragment spanning bp 34586 to bp 34730 of the ChAd155 wt sequence (SEQ ID NO: 10) was amplified by PCR using the plasmid BAC/ChAd155 ΔE1_TetO hCMV RpsL-Kana (#1375) as a template with the following oligonucleotides: 5'-AT-TCAGTGTACAGGCGCGCCAAAGCATGACGCTGTTG ATTTGATTC-3' (SEQ ID NO: 15) and 5'-ACT-AGGACTAGTTATAAGCTAGAATGGGGCTTTGC-3' (SEQ ID NO: 16). The PCR fragment was digested with BsrGI and SpeI and cloned into pARS SubGroupC Ad5orf6-1 digested with BsrGI and SpeI, generating the plasmid pARS SpeciesC Ad5orf6-2 (#1490). A schematic diagram of this shuttle plasmid is provided in FIG. 4. In particular, the shuttle plasmid comprised the following features: Left ITR: bp 1 to 113, Species C first 460 bp: bp 1 to 460, ChAd155 wt (bp 34587 to bp 34724 of SEQ ID NO:10): bp 516 to 650, Ad5 orf6: bp 680 and 1561, Species C last 393 bp: bp 1567 to 1969, Right ITR: bp 1857 to 1969. Construction of pChAd155 ΔE1, E4 Ad5E4orf6/TetO hCMV RpsL-Kana (#1434)

The resulting plasmid pARS SubGroupC Ad5orf6-2 was then used to replace the E4 region within the ChAd155 backbone with Ad5orf6. To this end the plasmid BAC/ChAd155 ΔE1_TetO hCMV RpsL-Kana (#1375) was digested with PacI/PmeI and co-transformed into BJ5183 cells with the digested plasmid pARS SubGroupC Ad5orf6-2 BsrGI/AscI, to obtain the pChAd155 ΔE1, E4_Ad5E4orf6/TetO hCMV RpsL-Kana (#1434) pre-adeno plasmid.

Figure 5:
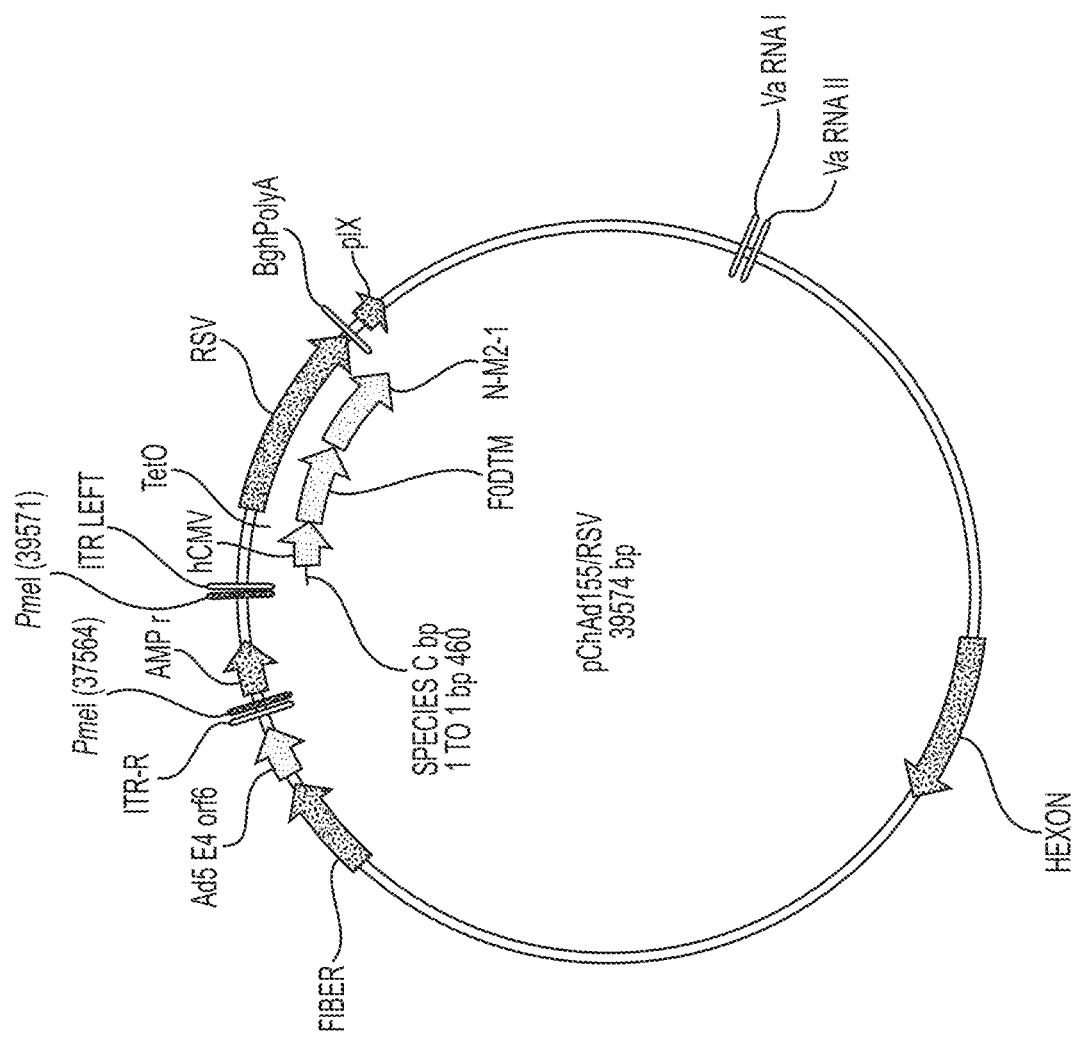

2.2.2: Insertion of RSV Expression Cassette—Construction of pChAd155 ΔE1, E4 Ad5E4orf6/TetO hCMV RSV An RSV cassette was cloned into a linearised pre-adeno acceptor vector via homologous recombination in *E. coli* by exploiting the homology existing between HCMV promoter and BGH polyA sequences. The plasmid pvjTetOhCMV-bghpolyA_RSV was cleaved with SfiI and SpeI to excise the 4.65 Kb fragment containing the HCMV promoter with tetO, RSV and BGHpolyA sequence. The resulting RSV 4.65 Kb fragment was cloned by homologous recombination into the pChAd155 ΔE1, E4_Ad5E4orf6/TetO hCMV RpsL-Kana (#1434) acceptor vector carrying the RpsL-Kana selection cassette under control of HCMV and BGHpA. The acceptor pre-adeno plasmid was linearized with the restriction endonuclease SnaBI. The resulting construct was the pChAd155 ΔE1, E4_Ad5E4orf6/TetO hCMV RSV vector (FIG. 5).

2.3: BAC Vector Construction by Recombineering
2.3.1: Deletion of E4 Region—Construction of BAC/ChAd155 ΔE1, E4_Ad5E4orf6/TetO hCMV RpsL-Kana#1390

A deletion of the E4 region spanning from nucleotide 34731-37449 of the ChAd155 wt sequence was introduced in the vector backbone by replacing this native E4 region with the Ad5 E4orf6 coding sequence using a strategy involving two different steps of recombineering in *E. Coli* SW102 competent cells.

The first step resulted in insertion of a selection cassette including the suicide gene SacB, ampicillin-R gene and lacZ (Amp-LacZ-SacB selection cassette) in the E4 region of ChAd155, for the purpose of positive/negative selection of recombinants.

First Step—Substitution of ChAd155 Native E4 Region with Amp-LacZ-SacB Selection Cassette The Amp-LacZ-SacB selection cassette was amplified by PCR using the oligonucleotides provided below containing E4 flanking sequences to allow homologous recombination:

```
1021-FW E4 Del Step1
                                    (SEQ ID NO: 17)
(5'-TTAATAGACACAGTAGCTTAATAGACCCAGTAGTGCAAAGCCCCAT
TCTAGCTTATAACCCCTATTTGITTATTITTCT-3')
and 1022-RW E4 Del Step1
                                    (SEQ ID NO: 18)
(5-ATATATACTCTCTCGGCACTTGGCCTTTTACACTGCGAAGTGTTGGT
GCTGGTGCTGCGTTGAGAGATCTTTATTTGTTAACTGTTAATTGTC-3').
```

The PCR product was used to transform *E. Coli* SW102 competent cells containing the pAdeno plasmid BAC/ChAd155 (DE1) tetO hCMV—RpsLKana#1375. The transformation of SW102 cells allowed the insertion of the selection cassette in the E4 region of ChAd155 via lambda (A) Red-mediated homologous recombination, thus obtaining BAC/ChAd155 (DE1) TetOhCMV—RpsL Kana #1379 (including Amp-LacZ-SacB cassette by substituting ChAd155 native E4 region).

Second Step—Substitution of Amp-lacZ-SacB Selection Cassette with Ad5E4orf6 Region The resulting plasmid BAC/ChAd155 (DE1) TetOhCMV—RpsL Kana #1379 (with Amp-LacZ-SacB cassette in place of ChAd155 E4 region) was then manipulated to replace the Amp-lacZ-SacB selection cassette with Ad5orf6 within the ChAd155 backbone. To this end, a DNA fragment containing the Ad5orf6 region was obtained by PCR, using the oligonucleotides 1025-FW E4 Del Step2 (5'-TTAATAGACACAGTAGCTTAATA-3') (SEQ ID NO: 19) and 1026-RW E4 Del Step2 (5'-GGAAGG-GAGTGTCTAGTGTT-3') (SEQ ID NO: 20). The resulting DNA fragment was introduced into *E. coli* SW102 competent cells containing the pAdeno plasmid BAC/ChAd155 (DE1) TetOhCMV—RpsL Kana)#1379, resulting in a final plasmid BAC/ChAd155 (ΔE1, E4 Ad5E4orf6) TetOhCMV—RpsL Kana#1390 containing Ad5orf6 substituting the native ChAd155 E4 region.

2.3.2: Insertion of RSV Expression Cassette: Construction of BAC/ChAd155 ΔE1, E4_Ad5E4orf6/TetOhCMV RSV#1393

An RSV transgene was cloned into the BAC/ChAd155 ΔE1, E4_Ad5E4orf6/TetOhCMV RSV#1393 vector by substituting the RpsL-Kana selection cassette. The construction strategy was based on two different steps of recombineering in *E. Coli* SW102 competent cells.

First Step—Substitution of RpsL-Kana Cassette with Amp-LacZ-SacB Selection Cassette The Amp-LacZ-SacB selection cassette was obtained from plasmid BAC/ChAd155 (DE1) TetO hCMV Amp-LacZ-SacB#1342 by PCR using the oligonucleotides 91-SubMonte FW (5'-CAATGGGCGTGGA-TAGCGGTTTGAC-3') (SEQ ID NO: 21) and 890-Bgh-PolyA RW (5'-CAGCATGCCTGCTATTGTC-3') (SEQ ID NO: 22). The product was transformed into *E. Coli* SW102 competent cells containing the pAdeno plasmid BAC/ChAd155 (DE1, E4 Ad5E4orf6) TetOhCMV—RpsL Kana#1390, resulting in BAC/ChAd155 (DE1, E4 Ad5E4orf6) TetOhCMV—Amp-LacZ-SacB#1386.

Second Step—Substitution of Amp-lacZ-SacB Selection Cassette with RSV Transgene

Figure 6:
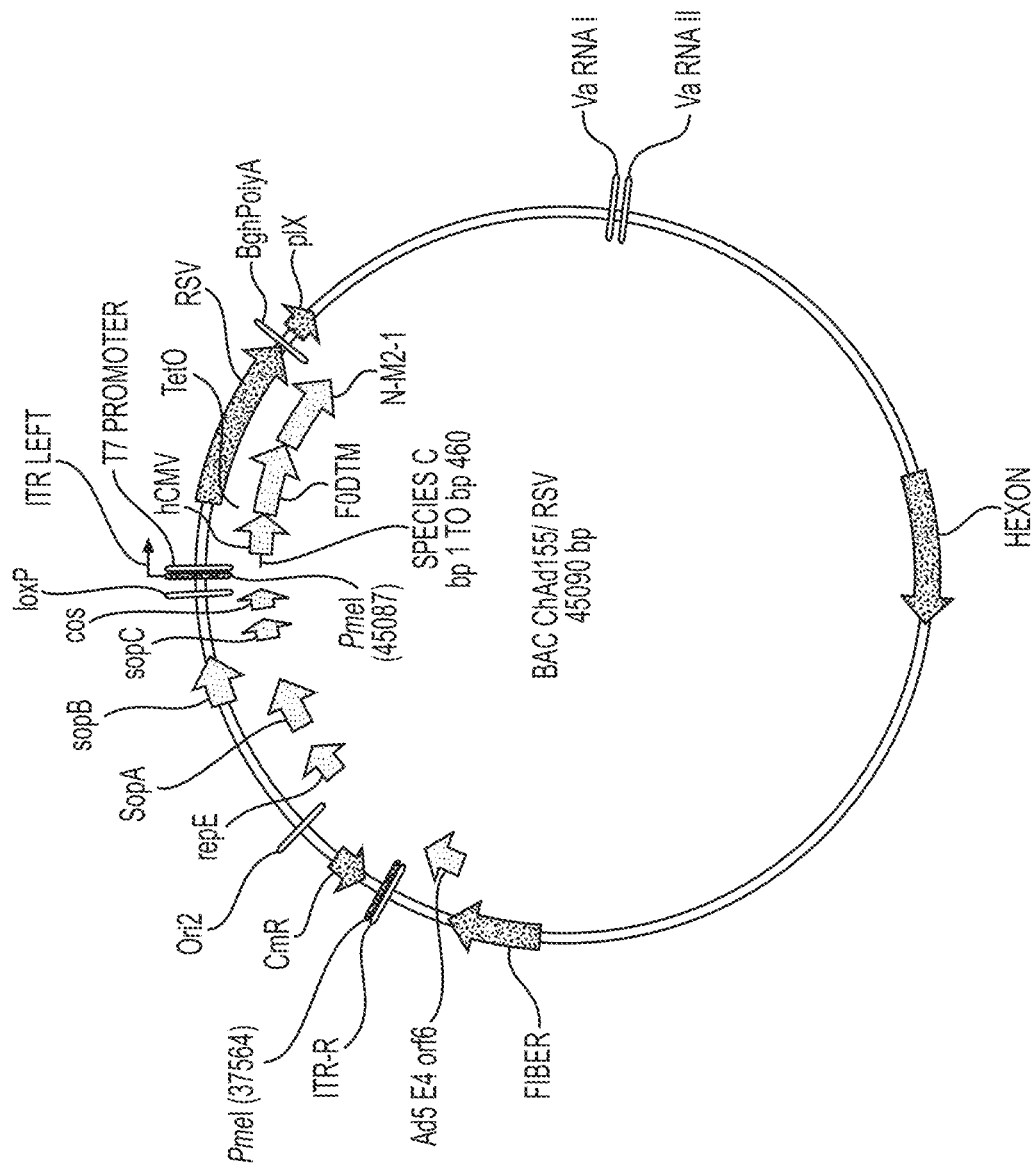

The RSV transgene was inserted in plasmid BAC/ChAd155 (DE1, E4 Ad5E4orf6) TetOhCMV—Amp-LacZ-SacB#1386 by replacing the Amp-lacZ-SacB selection cassette by homologous recombination. To this end, the plasmid pvjTetOhCMV—bghpolyA_RSV#1080 (containing an RSV expression cassette) was cleaved with SpeI and SfiI to excise the 4.4 Kb fragment including the HCMV promoter, RSV and BGHpolyA. The resulting RSV 4.4 Kb fragment was transformed into *E. Coli* SW102 competent cells containing the pAdeno plasmid BAC/ChAd155 (DE1, E4 Adr5E4orf6) TetOhCMV—Amp-LacZ-SacB#1386, resulting in the final plasmid BAC/ChAd155 ΔE1, E4_Ad5E4orf6/TetO hCMV Kana#1390. The structure of the BAC carrying ChAd155/RSV (SEQ ID NO: 11) is illustrated in FIG. 6. In particular, ChAd155/RSV comprised the following features: Species C Left ITR: bp 1 to 113, hCMV(tetO) bp 467 to 1311, RSV gene: bp 1348 to 4785, bghpolyA: bp 4815 to 5032, Ad5E4orf6: bp 36270 to 37151, Species C Right ITR: bp 37447 to 37559.

Example 3: Vector Production

The productivity of ChAd155 was evaluated in comparison to ChAd3 and PanAd3 in the Procell 92 cell line.

3.1: Production of Vectors Comprising an HIV Gag Transgene

Figure 7:
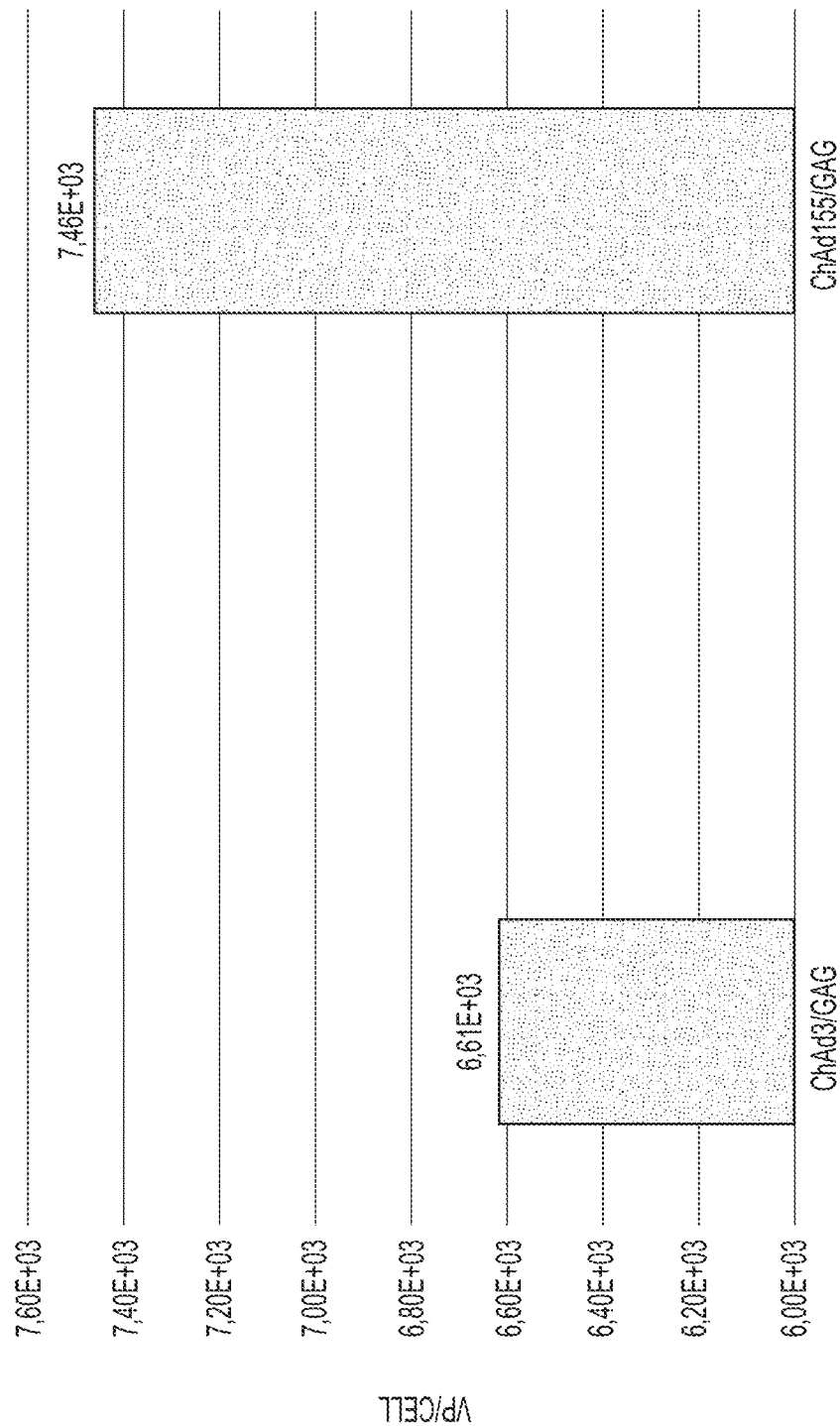

Vectors expressing the HIV Gag protein were prepared as described above (ChAd155/GAG) or previously (ChAd3/GAG Colloca et al, Sci. Transl. Med. (2012) 4:115ra). ChAd3/GAG and ChAd155/GAG were rescued and amplified in Procell 92 until passages 3 (P3); P3 lysates were used to infect 2 T75 flasks of Procell 92 cultivated in monolayer with each vector. A multiplicity of infection (MOI) of 100 vp/cell was used for both infection experiments. The infected cells were harvested when full CPE was evident (72 hours post-infection) and pooled; the viruses were released from the infected cells by 3 cycles of freeze/thaw (−70°/37° C.) then the lysate was clarified by centrifugation. The clarified lysates were quantified by Quantitative PCR Analysis with primers and probe complementary to the CMV promoter region. The oligonucleotide sequences are the following: CMVfor 5'-CATCTACGTATTAGTCATCGCTATTACCA-3' (SEQ ID NO: 23), CMVrev 5'-GACTTGGAAATCCCCGTGAGT-3' (SEQ ID NO: 24), CMVFAM-TAMRA probe 5'-ACATCAATGGGCGTGGATAGCGGTT-3' (SEQ ID NO: 25) (QPCRs were run on ABI Prism 7900 Sequence detector—Applied Biosystem). The resulting volumetric titers (vp/ml) measured on clarified lysates and the specific productivity expressed in virus particles per cell (vp/cell) are provided in Table 1 below and illustrated in FIG. 7.

TABLE 1

Vector productivity from P3 lysates.

| Vector | vp/ml | Total vp (20 ml conc.) | vp/cell |
|---|---|---|---|
| ChAd3/GAG | 9.82E+09 | 1.96E+11 | 6.61E+03 |
| ChAd155/GAG | 1.11E+10 | 2.22E+11 | 7.46E+03 |

Figure 8:
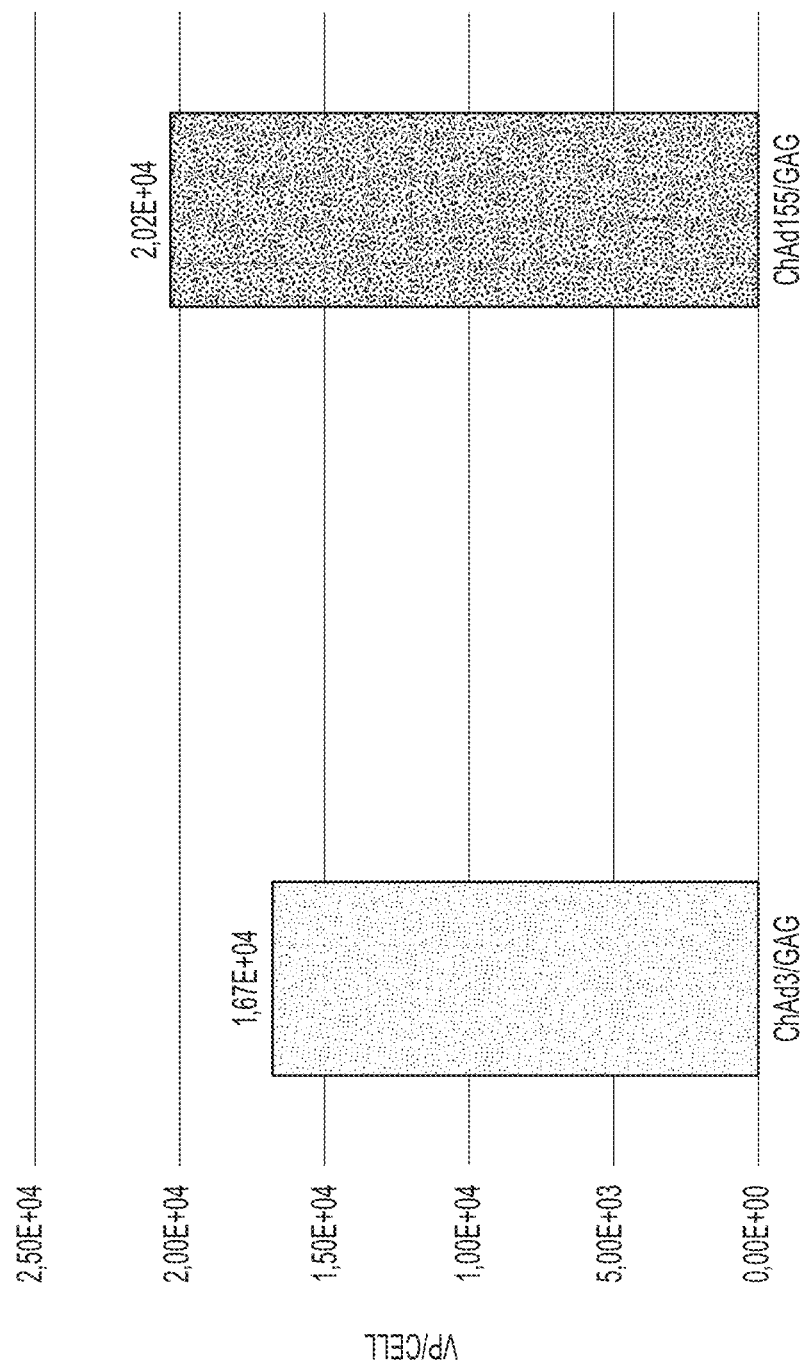

To confirm the higher productivity of the ChAd155 vector expressing HIV Gag transgene, a second experiment was performed by using purified viruses as inoculum. To this end, Procell 92 cells were seeded in a T25 Flask and infected with ChAd3/GAG and ChAd155/GAG when the confluence of the cells was about 80%, using a MOI=100 vp/cell of infection. The infected cells were harvested when full CPE was evident; the viruses were released from the infected cells by freeze/thaw and clarified by centrifugation. The clarified lysates were quantified by Quantitative PCR Analysis by using following primers and probe: CMVfor 5'-CATCTACGTATTAGTCATCGCTATTACCA-3' (SEQ ID NO: 23), CMV rev GACTTGGAAATCCCCGTGAGT (SEQ ID NO: 24), CMV FAM-TAMRA probe 5'-ACATCAATGGGCGTGGATAGCGGTT-3' (SEQ ID NO: 25) complementary to the CMV promoter region (samples were analysed on an ABI Prism 7900 Sequence detector-Applied Biosystems). The resulting volumetric titers (vp/ml) measured on clarified lysates and the specific productivity expressed in virus particles per cell (vp/cell) are provided in Table 2 below and illustrated in FIG. 8.

TABLE 2

Vector productivity from purified viruses.

| Vector | vp/ml | Total vp/T25 flask (5 ml of lysate) | vp/cell |
|---|---|---|---|
| ChAd3/GAG | 1.00E+10 | 5.00E+10 | 1.67E+04 |
| ChAd155/GAG | 1.21E+10 | 6.05E+10 | 2.02E+04 |

3.2: Production of Vectors Comprising an RSV Transgene

Figure 9:
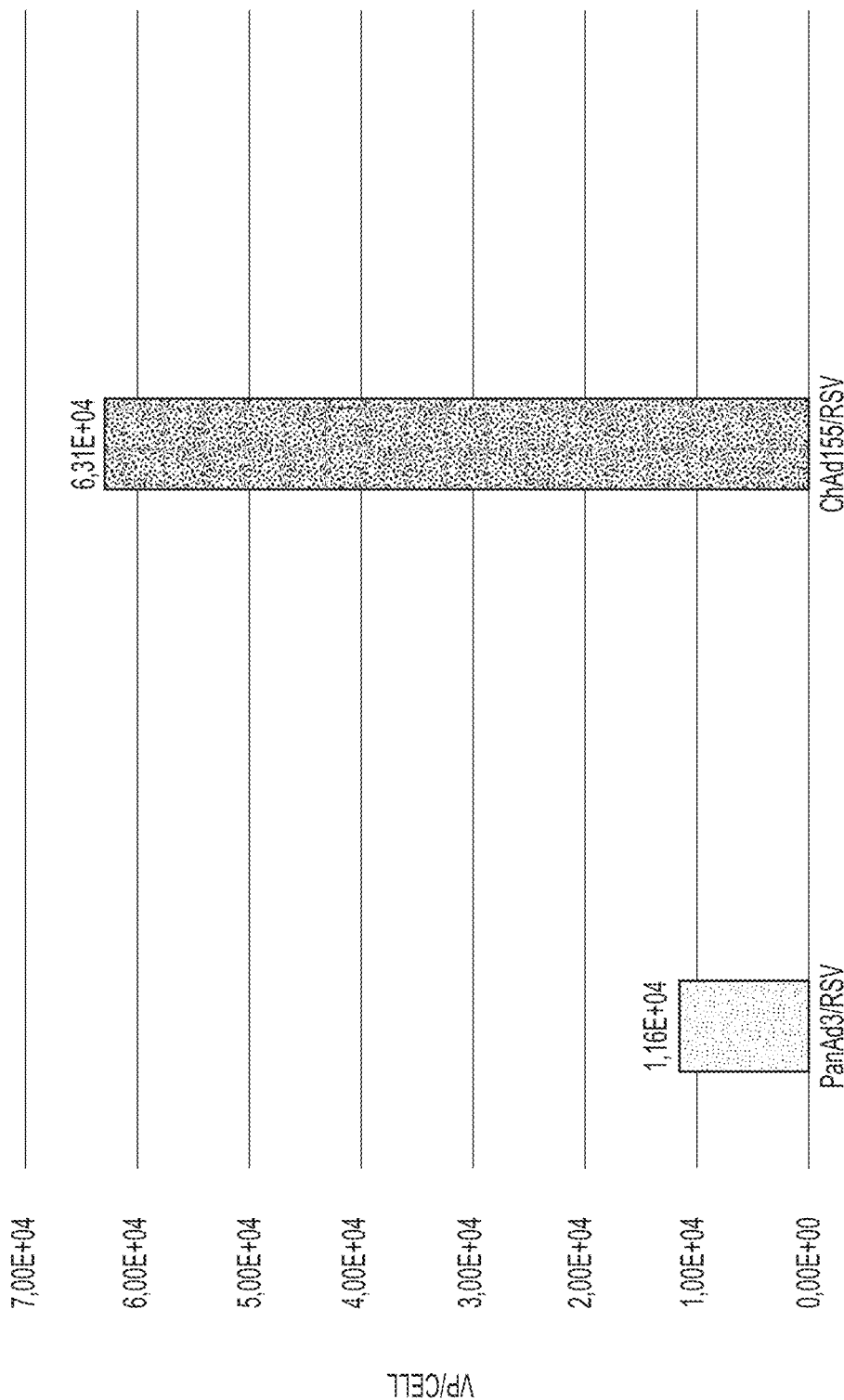

A different set of experiments were performed to evaluate the productivity of RSV vaccine vectors in Procell 92.S cultivated in suspension. The experiment compared PanAd3/RSV (described in WO2012/089833) and Chad155/RSV in parallel by infecting Procell 92.S at a cell density of $5 \times 10^5$ cells/ml. The infected cells were harvested 3 days post infection; the virus was released from the infected cells by 3 cycles of freeze/thaw and the lysate was clarified by centrifugation. The clarified lysates were then quantified by Quantitative PCR Analysis as reported above. The volumetric productivity and the cell specific productivity are provided in Table 3 below and illustrated in FIG. 9.

TABLE 3

| Virus | Volumetric productivity (Vp/ml) | Total vp | Cell specific productivity (vp/cell) |
|---|---|---|---|
| PanAd3/RSV | 5.82E+09 | 2.91E+11 | 1.16E+4 |
| ChAd155/RSV | 3.16E+10 | 1.58E+12 | 6.31E+04 |

Example 4: Transgene Expression Levels

4.1: Expression Level of HIV Gag Transgene

Figure 10:
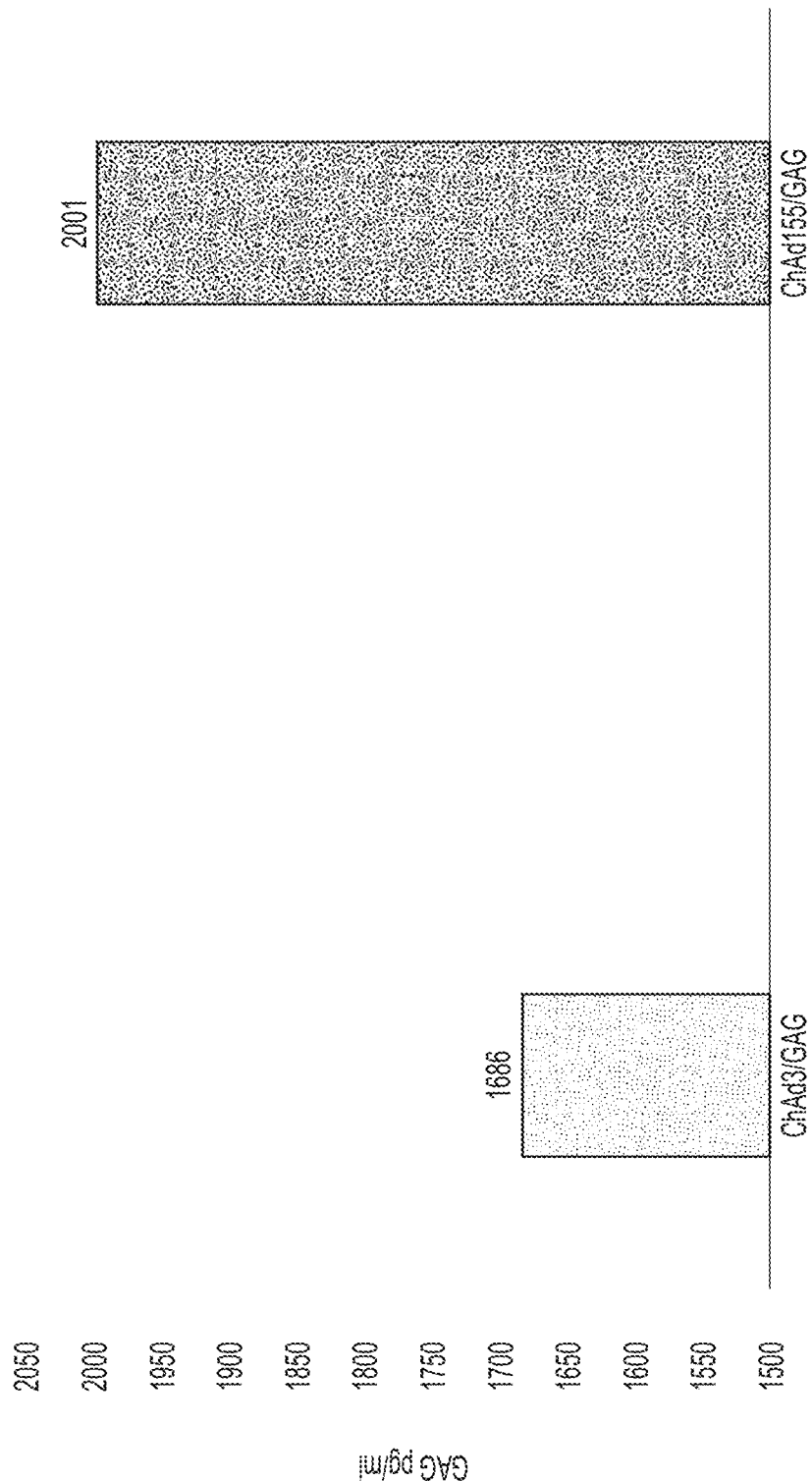

Expression levels were compared in parallel experiments by infecting HeLa cells with ChAd3 and ChAd155 vectors comprising an HIV Gag transgene. HeLa cells were seeded in 24 well plates and infected in duplicate with ChAd3/GAG and ChAd155/GAG purified viruses using a MOI=250 vp/cell. The supernatants of HeLa infected cells were harvested 48 hours post-infection, and the production of secreted HIV GAG protein was quantified by using a commercial ELISA Kit (HIV-1 p24 ELISA Kit, PerkinElmer Life Science). The quantification was performed according to the manufacturer's instruction by using an HIV-1 p24 antigen standard curve. The results, expressed in pg/ml of GAG protein, are illustrated in FIG. 10.

4.1: Expression Level of RSV F Transgene

Expression levels were compared in parallel experiments by infecting HeLa cells with the above-described PanAd3 and ChAd155 vectors comprising an RSV F transgene. To this end, HeLa cells were seeded in 6 well plates and infected in duplicate with PanAd3/RSV and ChAd155/RSV purified viruses using a MOI=500 vp/cell. The supernatants were harvested 48 hours post-infection, and the production of secreted RSV F protein was quantified by ELISA. Five different dilutions of the supernatants were transferred to microplate wells which are coated with a commercial mouse anti-RSV F monoclonal antibody. The captured antigen was revealed using a secondary anti-RSV F rabbit antiserum followed by Biotin-conjugated anti-rabbit IgG, then by adding Streptavidin-AP conjugate (BD Pharmingen cat. 554065). The quantification was performed by using an RSV F protein (Sino Biological cat. 11049-V08B) standard curve. The results obtained, expressed as ug/ml of RSV F protein, are provided in Table 4 below.

TABLE 4

| Sample | μg/ml RSV F protein |
|---|---|
| ChAd155/RSV | 5.9 |
| PanAd3/RSV | 4 |

Figure 11:
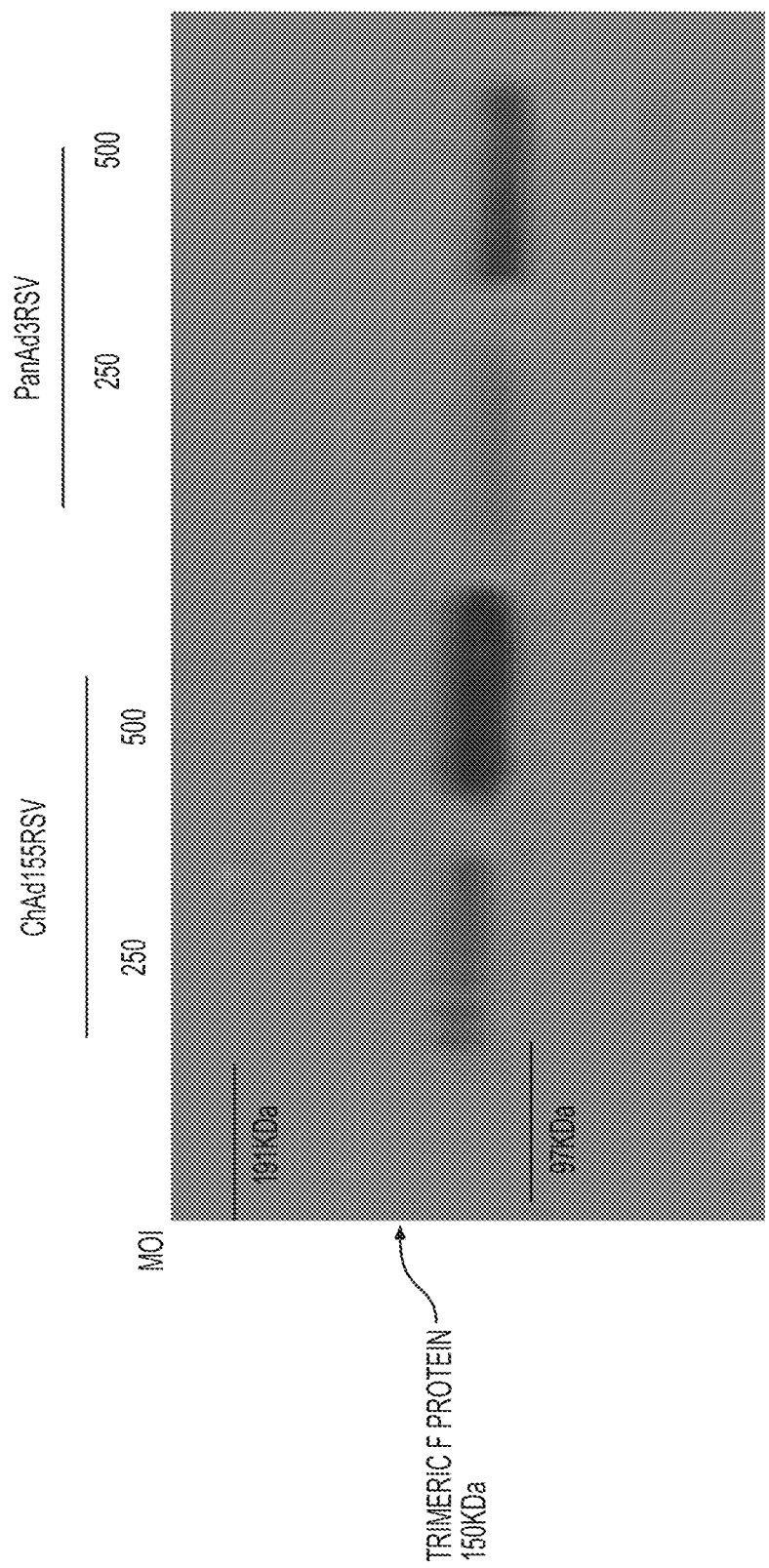

A western blot analysis was also performed to confirm the higher level of transgene expression provided by the ChAd155 RSV vector relative to the PanAd3 RSV vector. HeLa cells plated in 6 well plates were infected with PanAd3/RSV and ChAd155/RSV purified viruses using MOI=250 and 500 vp/cell. The supernatants of HeLa infected cells were harvested and the production of secreted RSV F protein were analysed by non-reducing SDS gel followed by Western Blot analysis. Equivalent quantities of supernatants were loaded on non-reducing SDS gel; after electrophoresis separation, the proteins were transferred to a nitrocellulose membrane to be probed with an anti-RSV F mouse monoclonal antibody (clone RSV-F-3 catalog no: ABIN308230 available at antibodies-online.com (last accessed 13 Apr. 2015). After the incubation with primary antibody, the membrane was washed and then incubated with anti-mouse HRP conjugate secondary antibody. Finally the assay was developed by electrochemiluminescence using standard techniques (ECL detection reagents Pierce catalog no W3252282). The Western Blot results are shown in FIG. 11. A band of about 170 kD indicated by the arrow was revealed by monoclonal antibody mAb 13 raised against the F protein, which corresponds to the expected weight of trimeric F protein. It can be seen that the ChAd155 RSV vector produced a darker band at both MOI=250 and 500 vp/cell.

Example 5: Evaluation of Immunological Potency by Mouse Immunization Experiments

5.1: Immunogenicity of Vectors Comprising the HIV Gag Transgene

Figure 12:
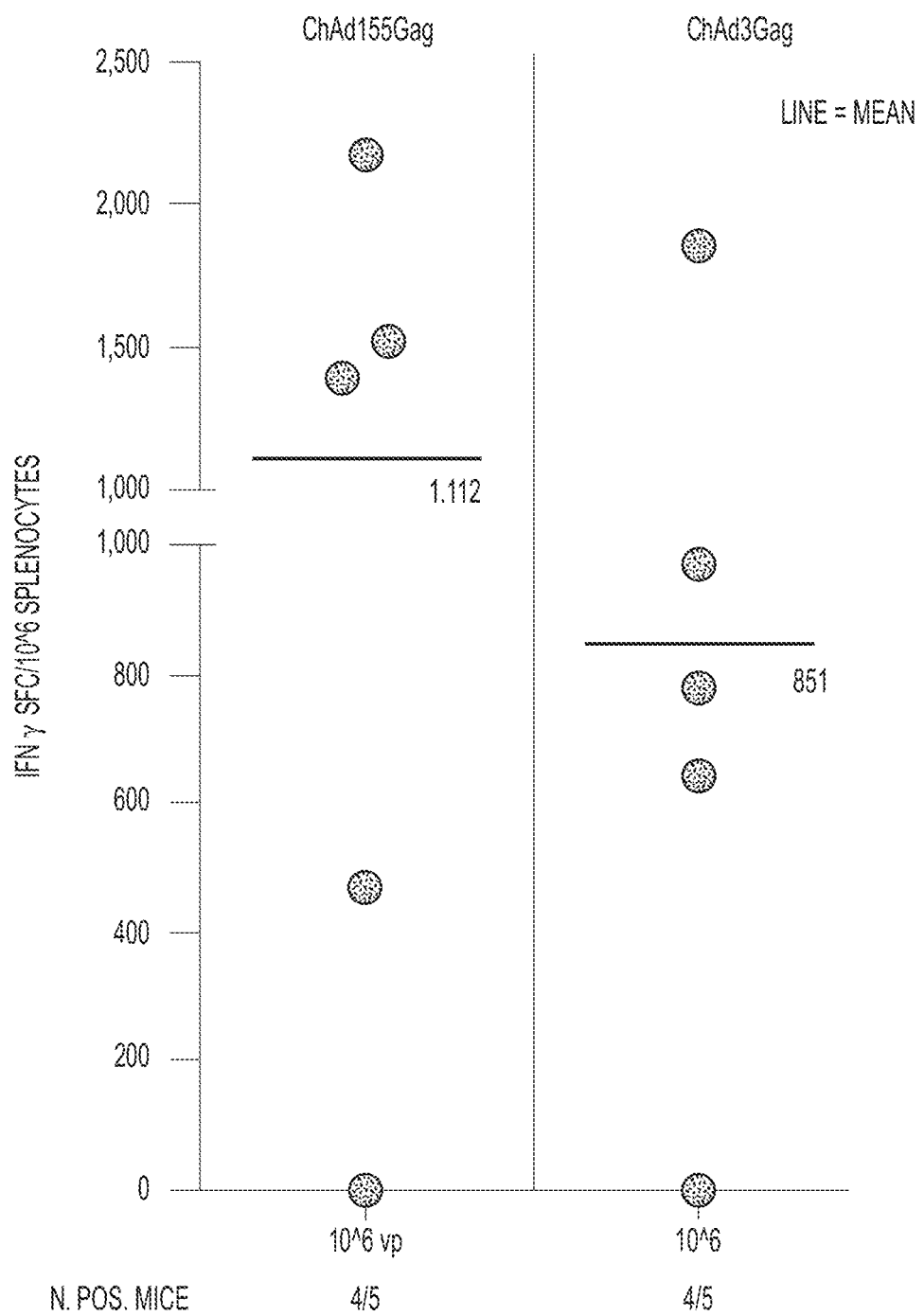

The immunogenicity of the ChAd155/GAG vector was evaluated in parallel with the ChAd3/GAG vector in BALB/c mice (5 per group). The experiment was performed by injecting $10^6$ viral particles intramuscularly. T-cell response was measured 3 weeks after the immunization by ex vivo IFN-gamma enzyme-linked immunospot (ELISpot) using a GAG CD8+ T cell epitope mapped in BALB/c mice. The results are shown in FIG. 12, expressed as IFN-gamma Spot Forming Cells (SFC) per million of splenocytes. Each dot represents the response in a single mouse, and the line corresponds to the mean for each dose group. Injected dose in number of virus particles and frequency of positive mice to the CD8 immunodominant peptide are shown on the x axis.

5.2 Immunogenicity of Vectors Comprising the RSV Transgene

Figure 13:
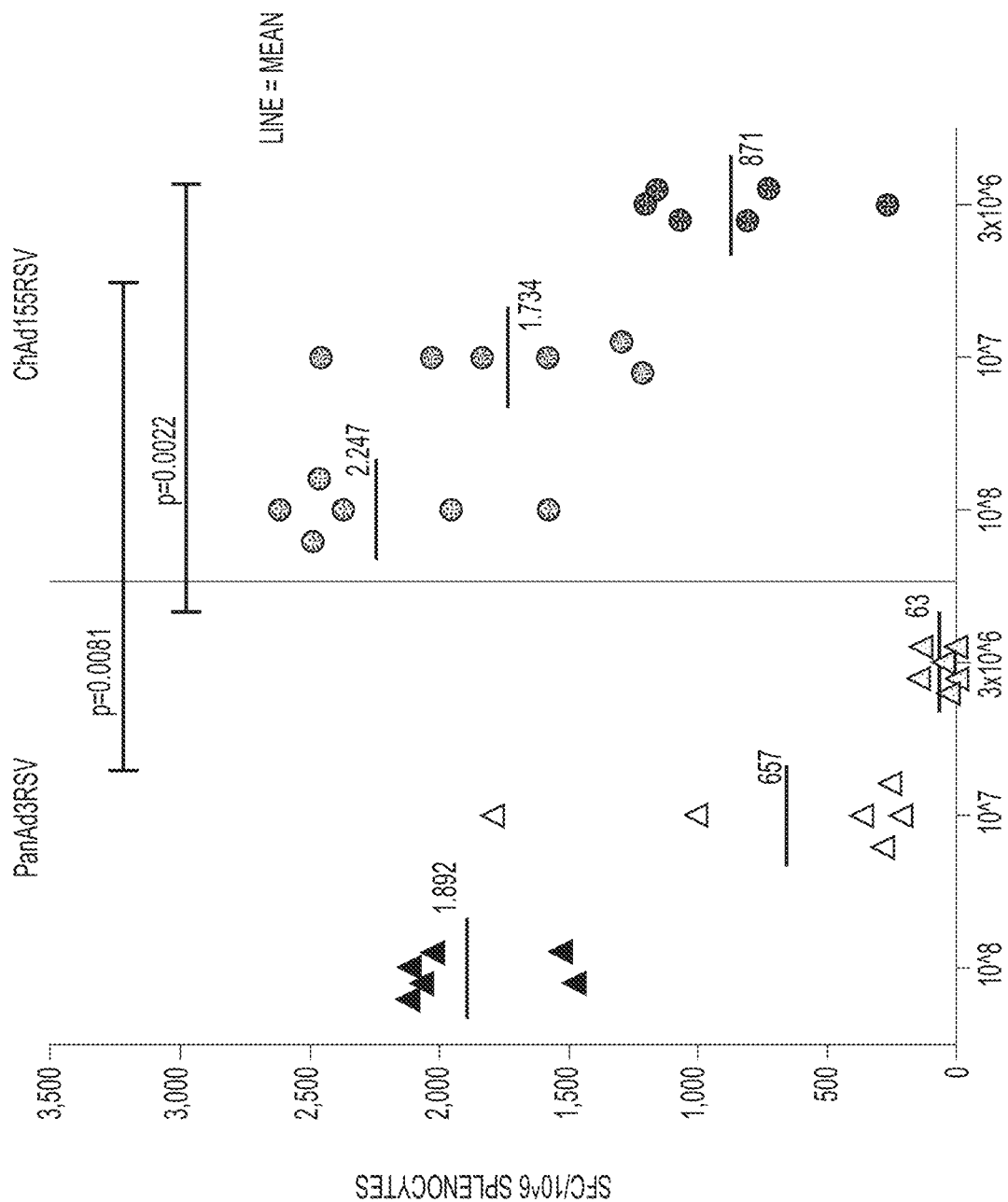

The immunological potency of the PanAd3/RSV and ChAd155/RSV vectors was evaluated in BALB/c mice. Both vectors were injected intramuscularly at doses of $10^8$, $10^7$ and $3\times10^6$vp. Three weeks after vaccination the splenocytes of immunized mice were isolated and analyzed by IFN-gamma-ELISpot using as antigens immunodominant peptide F and M epitopes mapped in BALB/c mice. The levels of immune-responses were reduced in line with decreasing dosage (as expected) but immune responses were clearly higher in the groups of mice immunized with ChAd155/RSV vector compared to the equivalent groups of mice immunized with PanAd3/RSV vaccine (FIG. 13). In FIG. 13, symbols show individual mouse data, expressed as IFN-gamma Spot Forming Cells (SFC)/million splenocytes, calculated as the sum of responses to the three immunodominant epitopes ($F_{51-66}$ $F_{85-93}$ and $M2-1_{282-290}$) and corrected for background. Horizontal lines represent the mean number of IFN-gamma SFC/million splenocytes for each dose group.

CONCLUSION

Taken together the results reported above demonstrated that ChAd155 is an improved adenoviral vector in comparison to ChAd3 and PanAd3 vectors. ChAd155 was shown to be more productive therefore facilitating the manufacture process, able to express higher level of transgene in vitro and also in vivo providing a stronger T-cell response against the antigens expressed in animal models.

---

DESCRIPTION OF THE SEQUENCES

```
SEQ ID NO: 1-Polypeptide sequence of ChAd155 fiber
MKRTKTSDESFNPVYPYDFESGPPSVPFLTPPFVSPDGFQESPPGVLSLNLAEPLVTSHGMLALKMGS
GLSLDDAGNLTSQDITTASPPLKKTKTNLSLETSSPLTVSTSGALTVAAAAPLAVAGTSLTMQSEAPL
TVQDAKLTLATKGPLTVSEGKLALQTSAPLTAADSSTLTVSATPPLSTSNGSLGIDMQAPIYTTNGKL
GLNFGAPLHVVDSLNALTVVTGQGLTINGTALQTRVSGALNYDTSGNLELRAAGGMRVDANGQLIL
DVAYPFDAQNNLSLRLGQGPLFVNSAHNLDVNYNRGLYLFTSGNTKKLEVNIKTAKGLIYDDTAIAI
NAGDGLQFDSGSDTNPLKTKLGLGLDYDSSRAIIAKLGTGLSFDNTGAITVGNKNDDKLTLWTTPDP
SPNCRIYSEKDAKFTLVLTKCGSQVLASVSVLSVKGSLAPISGTVTSAQIVLRFDENGVLLSNSSLDPQ
YWNYRKGDLTEGTAYTNAVGFMPNLTAYPKTQSQTAKSNIVSQVYLNGDKSKPMTLTITLNGTNET
GDATVSTYSMSFSWNWNGSNYINETFQTNSFTFSYIAQE SEQ ID NO: 2-Polynucleotide sequence encoding ChAd155 fiber
ATGAAGCGCACCAAAACGTCTGACGAGAGCTTCAACCCCGTGTACCCCTATGACACGGAAAGCG
GCCCTCCCTCCGTCCCTTTCCTCACCCCTCCCTTCGTGTCTCCCGATGGATTCCAAGAAAGTCCCC
CCGGGGTCCTGTCTCTGAACCTGGCCGAGCCCCTGGTCACTTCCCACGGCATGCTCGCCCTGAAA
ATGGGAAGTGGCCTCTCCCTGGACGACGCTGGCAACCTCACCTCTCAAGATATCACCACCGCTA
GCCCTCCCCTCAAAAAAACCAAGACCAACCTCAGCCTAGAAACCTCATCCCCCCTAACTGTGAG
CACCTCAGGCGCCCTCACCGTAGCAGCCGCCGCTCCCCTGGCGGTGGCCGGCACCTCCCTCACC
ATGCAATCAGAGGCCCCCCTGACAGTACAGGATGCAAAACTCACCCTGGCCACCAAAGGCCCCC
TGACCGTGTCTGAAGGCAAACTGGCCTTGCAAACATCGGCCCCGCTGACGGCCGCTGACAGCAG
CACCCTCACAGTCAGTGCCACACCACCCCTTAGCACAAGCAATGGCAGCTTGGGTATTGACATG
CAAGCCCCCATTTACACCACCAATGGAAAACTAGGACTTAACTTTGGCGCTCCCCTGCATGTGGT
AGACAGCCTAAATGCACTGACTGTAGTTACTGGCCAAGGTCTTACGATAAACGGAACAGCCCTA
CAAACTAGAGTCTCAGGTGCCCTCAACTATGACACATCAGGAAACCTAGAATTGAGAGCTGCAG
GGGGTATGCGAGTTGATGCAAATGGTCAACTTATCCTTGATGTAGCTTACCCATTTGATGCACAA
AACAATCTCAGCCTTAGGCTTGGACAGGGACCCCTGTTTGTTAACTCTGCCCACAACTTGGATGT
```

DESCRIPTION OF THE SEQUENCES

```
TAACTACAACAGAGGCCTCTACCTGTTCACATCTGGAAATACCAAAAAGCTAGAAGTTAATATC
AAAACAGCCAAGGGTCTCATTTATGATGACACTGCTATAGCAATCAATGCGGGTGATGGGCTAC
AGTTTGACTCAGGCTCAGATACAAATCCATTAAAAACTAAACTTGGATTAGGACTGGATTATGA
CTCCAGCAGAGCCATAATTGCTAAACTGGGAACTGGCCTAAGCTTTGACAACACAGGTGCCATC
ACAGTAGGCAACAAAATGATGACAAGCTTACCTTGTGGACCACACCAGACCCATCCCCTAACT
GTAGAATCTATTCAGAGAAAGATGCTAAATTCACACTTGTTTTGACTAAATGCGGCAGTCAGGT
GTTGGCCAGCGTTTCTGTTTTATCTGTAAAAGGTAGCCTTGCCGCCCATCAGTGGCACAGTAACTA
GTGCTCAGATTGTCCTCAGATTTGATGAAAATGGAGTTCTACTAAGCAATTCTTCCCTTGACCCT
CAATACTGGAACTACAGAAAAGGTGACCTTACAGAGGGCACTGCATATACCAACGCAGTGGGA
TTTATGCCCAACCTCACAGCATACCCAAAAACACAGAGCCAAACTGCTAAAAGCAACATTGTAA
GTCAGGTTTACTTGAATGGGGACAAATCCAAACCCATGACCCTCACCATTACCCTCAATGGAAC
TAATGAAACAGGAGATGCCACAGTAAGCACTTACTCCATGTCATTCTCATGGAACTGGAATGGA
AGTAATTACATTAATGAAACGTTCCAAACCAACTCCTTCACCTTCTCCTACATCGCCCAAGAA

SEQ ID NO: 3-Polypeptide sequence of ChAd155 penton
MRRAAMYQEGPPPSYESVVGAAAAAPSSPFASQLLEPPYVPPRYLRPTGGRNSIRYSELAPLFDTTRV
YLVDNKSADVASLNYQNDHSNFLTTVIQNNDYSPSEASTQTINLDDRSHWGGDLKTILHTNMPNVN
EFMFTNKFKARVMVSRSHTKEDRVELKYEWVEFELPEGNYSETMTIDLMNNAIVEHYLKVGRQNG
VLESDIGVKFDTRNFRLGLDPVTGLVMPGVYTNEAFHPDIILLPGCGVDFTYSRLSNLLGIRKRQPFQE
GFRITYEDLEGGNIPALLDVEAYQDSLKENEAGQEDTAPAASAAAEQGEDAADTAAADGAEADPA
MVVEAPEQEEDMNDSAVRGDTFVTRGEEKQAEAEAAAEEKQLAAAAAAAALAAAEAESEGTKPA
KEPVIKPLFEDSKKRSYNLLKDSTNTAYRSWYLAYNYGDPSTGVRSWTLLCTPDVTCGSEQVYWSL
PDMMQDPVTFRSTRQVSNFPVVGAELLPVHSKSFYNDQAVYSQLIRQFTSLTHVFNRFPENQILARPP
APTITTVSENVPALTDHGTLPLRNSIGGVQRVTVTDARRRTCPYVYKALGIVSPRVLSSRTF SEQ ID NO: 4-Polynucleotide sequence encoding ChAd155 penton
ATGCGGCGCGCGGCGATGTACCAGGAGGGACCTCCTCCCTCTTACGAGAGCGTGGTGGGCGCGG
CGGCGGCGGCGCCCTCTTCTCCCTTTGCGTCGCAGCTGCTGGAGCCGCCGTACGTGCCTCCGCGC
TACCTGCGGCCTACGGGGGGGAGAAACAGCATCCGTTACTCGGAGCTGGCGCCCCTGTTCGACA
CCACCCGGGTGTACCTGGTGGACAACAAGTCGGCGGACGTGGCCTCCCTGAACTACCAGAACGA
CCACAGCAATTTTTTGACCACGGTCATCCAGAACAATGACTACAGCCCGAGCGAGGCCAGCACC
CAGACCATCAATCTGGATGACCGGTCGCACTGGGGCGGCGACCTGAAAACCATCCTGCACACCA
ACATGCCCAACGTGAACGAGTTCATGTTCACCAATAAGTTCAAGGCGCGGGTGATGGTGTCGCG
CTCGCACACCAAGGAAGACCGGGTGGAGCTGAAGTACGAGTGGGTGGAGTTCGAGCTGCCAGA
GGGCAACTACTCCGAGACCATGACCATTGACCTGATGAACAACGCGATCGTGGAGCACTATCTG
AAAGTGGGCAGGCAGAACGGGGTCCTGGAGAGCGACATCGGGGTCAAGTTCGACACCAGGAAC
TTCCGCCTGGGGCTGGACCCCGTGACCGGGCTGGTTATGCCCGGGGTGTACACCAACGAGGCCT
TCCATCCCGACATCATCCTGCTGCCCGGCTGCGGGGTGGACTTCACTTACAGCCGCCTGAGCAAC
CTCCTGGGCATCCGCAAGCGGCAGCCCTTCCAGGAGGGCTTCAGGATCACCTACGAGGACCTGG
AGGGGGGCAACATCCCCGCGCTCCTCGATGTGGAGGCCTACCAGGATAGCTTGAAGGAAAATG
AGGCGGGACAGGAGGATACCGCCCCCGCCGCCTCCGCCGCCGCGAGCAGGGCGAGGATGCTG
CTGACACCGCGGCCGCGGACGGGGCAGAGGCCGACCCCGCTATGGTGGTGGAGGCTCCCGAGC
AGGAGGAGGACATGAATGACAGTGCGGTGCGCGGAGACACCTTCGTCACCCGGGGGGAGGAAA
AGCAAGCGGAGGCCGAGGCCGCGGCCGAGGAAAAGCAACTGGCGGCAGCAGCGGCGGCGGCG
GCGTTGGCCGCGGCGGAGGCTGAGTCTGAGGGGACCAAGCCCGCCAAGGAGCCCGTGATTAAG
CCCCTGACCGAAGATAGCAAGAAGCGCAGTTACAACCTGCTCAAGGACAGCACCAACACCGCG
TACCGCAGCTGGTACCTGGCCTACAACTACGGCGACCCGTCGACGGGGGTGCGCTCCTGGACCC
TGCTGTGCACGCCGGACGTGACCTGCGGCTCGGAGCAGGTGTACTGGTCGCTGCCCGACATGAT
GCAAGACCCCGTGACCTTCCGCTCCACGCGGCAGGTCAGCAACTTCCCGGTGGTGGGCGCCGAG
CTGCTGCCCGTGCACTCCAAGAGCTTCTACAACGACCAGGCCGTCTACTCCCAGCTCATCCGCCA
GTTCACCTCTCTGACCCACGTGTTCAATCGCTTTCCTGAGAACCAGATTCTGGCGCGCCCGCCCG
CCCCCACCATCACCACCGTCAGTGAAAACGTTCCTGCTCTCACAGATCACGGGACGCTACCGCT
GCGCAACAGCATCGGAGGAGTCCAGCGAGTGACCGTTACTGACGCCAGACGCCGCACCTGCCCC
TACGTTTACAAGGCCTTGGGCATAGTCTCGCCGCGCGTCCTTTCCAGCCGCACTTTT SEQ ID NO: 5-Polypeptide sequence of ChAd155 hexon
MATPSMMPQWSYMHISGQDASEYLSPGLVQFARATDSYFSLSNKFRNPTVAPTHDVTTDRSQRLTL
RFIPVDREDTAYSYKARFTLAVGDNRVLDMASTYFDIRGVLDRGPTFKPYSGTAYNSLAPKGAPNSC
EWEWQEETQTAEEAQDEEEDEAEAEEEMPQEEQAPVKKTHVYAQAPLSGEKITKDGLQIGTDATAIL
QKPIYADPTFQPEPQIGESQWNEADASVAGGRVLKKTTPMKPCYGSYARPTNANGGQGVLVEKDGG
KMESQVDMQFFSTSENARNEANNIQPKLVLYSEDVHMETPDTHISYKPAKSDDNSKVMLGQQSMPN
RPNYIGFRDNFIGLMYYNSTGNMGVLAGQASQLNAVVDLQDRNTELSYQLLLDSMGDRTRYFSMW
NQAVDSYDPDVRIIENHGFLDELPNYCFPLGGIGVTDTYQAIKTNGNGNGGGNTTWTKDETFADRN
EIGVGNNFAMEINLSANLWRNFLYSNVALYLPDKLKYNPSNVEISDNPNTYDYMNKRVVAPGLVDC
YINLGARWSLDYMDNVNPFNHHRNAGLRYRSMLLGNGRYVPFHIQVPQKFFAIKNLLLLPGSYTYE
WNFRKDVNMVLQSSLGNDLRVDGASIKFESICLYATFFPMAHNTASTLEAMLRNDTNDQSFNDYLS
AANMLYPIPANATNVPISIPSRNWAAFRGWAFTRLKTKETPSLGSGFDPYYTYSGSIPYLDGTFYLNH
TFKKVSVTFDSSVSWPGNDRLLTPNEFLIKRSVDGEGYNVAQCNMTKDWFLIQMLANYNIGYQGFY
IPESYKDRMYSFFRNFQPMSRQVVDETKYKDYQQVGIIHQHNNSGFVGYLAPTMREGQAYPANFPY
PLIGKTAVDSVTQKKFLCDRTLWRIPFSSNFMSMGALTDLGQNLLYANSAHALDMTFEVDPMDEPT
LLYVLFEVFDVVRVHQPHRGVIETVYLRTPFSAGNATT SEQ ID NO: 6-Polynucleotide sequence encoding ChAd155 hexon
ATGGCGACCCCATCGATGATGCCGCAGTGGTCGTACATGCACATCTCGGGCCAGGACGCCTCGG
AGTACCTGAGCCCCGGGCTGGTGCAGTTCGCCCGCGCCACCGAGAGCTACTTCAGCCTGAGTAA
CAAGTTTAGGAACCCCACGGTGGCGCCCACGCACGATGTGACCACCGACCGGTCTCAGCGCCTG
ACGCTGCGGTTCATTCCCGTGGACCGCGAGGACACCGCGTACTCGTACAAGGCGCGGTTCACCC
```

| DESCRIPTION OF THE SEQUENCES |
|---|
| TGGCCGTGGGCGACAACCGCGTGCTGGACATGGCCTCCACCTACTTTGACATCCGCGGGGTGCT |
| GGACCGGGGTCCCACTTTCAAGCCCTACTCTGGCACCGCCTACAACTCCCTGGCCCCCAAGGGC |
| GCTCCCAACTCCTGCGAGTGGGAGCAAGAGGAAACTCAGGCAGTTGAAGAAGCAGCAGAAGAG |
| GAAGAAGAAGATGCTGACGGTCAAGCTGAGGAAGAGCAAGCAGCTACCAAAAAGACTCATGTA |
| TATGCTCAGGCTCCCCTTTCTGGCGAAAAAATTAGTAAAGATGGTCTGCAAATAGGAACGGACG |
| CTACAGCTACAGAACAAAAACCTATTTATGCAGACCCTACATTCCAGCCCGAACCCCAAATCGG |
| GGAGTCCCAGTGGAATGAGGCAGATGCTACAGTCGCCGGCGGTAGAGTGCTAAAGAAATCTACT |
| CCCATGAAACCATGCTATGGTTCCTATGCAAGACCCACAAATGCTAATGGAGGTCAGGGTGTAC |
| TAACGGCAAATGCCCAGGGACAGCTAGAATCTCAGGTTGAAATGCAATTCTTTTCAACTTCTGA |
| AAACGCCCGTAACGAGGCTAACAACATTCAGCCCAAATTGGTGCTGTATAGTGAGGATGTGCAC |
| ATGGAGACCCCGGATACGCACCTTTCTTACAAGCCCGCAAAAAGCGATGACAATTCAAAAATCA |
| TGCTGGGTCAGCAGTCCATGCCCAACAGACCTAATTACATCGGCTTCAGAGACAACTTTATCGG |
| CCTCATGTATTACAATAGCACTGGCAACATGGGAGTGCTTGCAGGTCAGGCCTCTCAGTTGAAT |
| GCAGTGGTGGACTTGCAAGACAGAAACACAGAACTGTCCTACCAGCTCTTGCTTGATTCCATGG |
| GTGACAGAACCAGATACTTTTCCATGTGGAATCAGGCAGTGGACAGTTATGACCCAGATGTTAG |
| AATTATTGAAAATCATGGAACTGAAGACGAGCTCCCCAACTATTGTTTCCCTCTGGGTGGCATAG |
| GGGTAACTGACACTTACCAGGCTGTTAAAACCAACAATGGCAATAACGGGGGCCAGGTGACTTG |
| GACAAAAGATGAAACTTTTGCAGATCGCAATGAAATAGGGGTGGGAAACAATTTCGCTATGGA |
| GATCAACCTCAGTGCCAACCTGTGGAGAAACTTCCTGTACTCCAACGTGGCGCTGTACCTACCA |
| GACAAGCTTAAGTACAACCCCTCCAATGTGGACATCTCTGACAACCCCAACACTACGATTACA |
| TGAACAAGCGAGTGGTGGCCCCGGGGCTGGTGGACTGCTACATCAACCTGGGCGCGCTGGTC |
| GCTGGACTACATGGACAACGTCAACCCCTTCAACCACCACCGCAATGCGGGCCTGCGCTACCGC |
| TCCATGCTCCTGGGCAACGGGCGCTACGTGCCCTTCCACATCCAGGTGCCCCAGAAGTTCTTTGC |
| CATCAAGAACCTCCTCCTCCTGCCGGGCTCCTACACCTACGAGTGGAACTTCAGGAAGGATGTC |
| AACATGGTCCTCCAGAGCTCTCTGGGTAACGATCTCAGGGTGGACGGGGCCAGCATCAAGTTCG |
| AGAGCATCTGCCTCTACGCCACCTTCTTCCCCATGGCCCACAACACGGCCTCCACGCTCGAGGCC |
| ATGCTCAGGAACGACACCAACGACCAGTCCTTCAATGACTACCTCTCCGCCGCCAACATGCTCT |
| ACCCCATACCCGCCAACGCCACCAACGTCCCCATCTCCATCCCTCGCGCAACTGGGCGGCCTTC |
| CGCGGCTGGGCCTTCACCCGCCTCAAGACCAAGGAGACCCCCTCCCTGGGCTCGGGATTCGACC |
| CCTACTACACCTACTCGGGCTCCATTCCCTACCTGGACGGCACCTTCTACCTCAACCACACTTTC |
| AAGAAGGTCTCGGTCACCTTCGACTCCTCGGTCAGCTGGCCGGGCAACGACCGTCTGCTCACCC |
| CCAACGAGTTCGAGATCAAGCGCTCGGTCGACGGGGAGGGCTACAACGTGGCCCAGTGCAACA |
| TGACCAAGGACTGGTTCCTGGTCCAGATGCTGGCCAACTACAACATCGGCTACCAGGGCTTCTA |
| CATCCCAGAGAGCTACAAGGACAGGATGTACTCCTTCTTCAGGAACTTCCAGCCCATGAGCCGG |
| CAGGTGGTGGACCAGACCAAGTACAAGGACTACCAGGAGGTGGGCATCATCCACCAGCACAAC |
| AACTCGGGCTTCGTGGGCTACCTCGCCCCCACCATGCGCGAGGGACAGGCCTACCCCGCCAACT |
| TCCCCTATCCGCTCATAGGCAAGACCGCGGTCGACAGCATCACCCAGAAAAAGTTCCTCTGCGA |
| CCGCACCCTCTGGCGCATCCCCTTCTCCAGCAACTTCATGTCCATGGGTGCGCTCTCGGACCTGG |
| GCCAGAACTTGCTCTACGCCAACTCCGCCCACGCCCTCGACATGACCTTCGAGGTCGACCCCATG |
| GACGAGCCCACCCTTCTCTATGTTCTGTTCGAAGTCTTTGACGTGGTCCGGGTCCACCAGCCGCA |
| CCGCGGCGTCATCGAGACCGTGTACCTGCGTACGCCCTTCTCGGCCGGCAACGCCACCACC |

SEQ ID NO: 7-Polynucleotide sequence encoding ChAd155#1434 backbone construct
| |
|---|
| CATCATCAATAATATACCTTATTTTGGATTGAAGCCAATATGATAATGAGATGGGCGGCGCGGG |
| GCGGGGCGCGGGCGGGAGGCGGGTTTGGGGGCGGGCCGGCGGGGCGGTGTGGCGGAA |
| GTGGACTTTGTAAGTGTGGCGGATGTGACTTGCTAGTGCCGGGCGCGGTAAAAGTGACGTTTTC |
| CGTGCGCGACAACGCCCCCGGGAAGTGACATTTTTCCCGCGGTTTTTACCGGATGTTGTAGTGAA |
| TTTGGGCGTAACCAAGTAAGATTTGGCCATTTTCGCGGGAAAACTGAAACGGGGAAGTGAAATC |
| TGATTAATTTTGCGTTAGTCATACCGCGTAATATTTGTCTAGGGCCGAGGGACTTTGGCCGATTA |
| CGTGGAGGACTCGCCCAGGTGTTTTTTGAGGTGAATTTCCGCGTTCCGGGTCAAAGTCTGCGTTT |
| TATTATTATAGGGATATCCCATTGCATACGTTGTATCCATATCATAATATGTACATTTATATTGGCT |
| CATGTCCAACATTACCGCCATGTTGACATTGATTATTGACTAGTTATTAATAGTAATCAATTACG |
| GGGTCATTAGTTCATAGCCCATATATGGAGTTCCGCGTTACATAACTTACGGTAAATGGCCCGCC |
| TGGCTGACCGCCCAACGACCCCCGCCCATTGACGTCAATAATGACGTATGTTCCCATAGTAACG |
| CCAATAGGGACTTTCCATTGACGTCAATGGGTGGAGTATTTACGGTAAACTGCCCACTTGGCAGT |
| ACATCAAGTGTATCATATGCCAAGTACGCCCCCTATTGACGTCAATGACGGTAAATGGCCCGCC |
| TGGCATTATGCCCAGTACATGACCTTATGGGACTTTCCTACTTGGCAGTACATCTACGTATTAGT |
| CATCGCTATTACCATGGTGATGCGGTTTTGGCAGTACATCAATGGGCGTGGATAGCGGTTTGACT |
| CACGGGGATTTCCAAGTCTCCACCCCATTGACGTCAATGGGAGTTTGTTTTGGCACCAAAATCAA |
| CGGGACTTTCCAAAATGTCGTAACAACTCCGCCCCATTGACGCAAATGGGCGGTAGGCGTGTAC |
| GGTGGGAGGTCTATATAAGCAGAGCTCTCCCTATCAGTGATAGAGATCTCCCTATCAGTGATAG |
| AGATCGTCGACGAGCTCGTTTAGTGAACCGTCAGATCGCCTGGAGACGCCATCCACGCTGTTTTG |
| ACCTCCATAGAAGACACCGGGACCGATCCAGCCTCCGCGGCCGGGAACGGTGCATTGGAACGC |
| GGATTCCCCGTGCCAAGAGTGAGATCTTCCGTTTATCTAGGTACCGGGCCCCCCTCGAGGTCGA |
| CGGTATCGATAAGCTTCACGCTGCCGCAAGCACTCAGGGCGCAAGGGCTGCTAAAGGAAGCGG |
| AACACGTAGAAAGCCAGTCCGCAGAAACGGTGCTGACCCCGGATGAATGTCAGCTACTGGGCTA |
| TCTGGACAAGGGAAAACGCAAGCGCAAAGAGAAAGCAGGTAGCTTGCAGTGGGCTTACATGGC |
| GATAGCTAGACTGGGCGGTTTTATGGACAGCAAGCGAACCGGAATTGCCAGCTGGGGCGCCCTC |
| TGGTAAGGTTGGGAAGCCCTGCAAAGTAAACTGGATGGCTTTCTTGCCGCCAAGGATCTGATGG |
| CGCAGGGGATCAAGATCTAACCAGGAGCTATTTAATGGCAACAGTTAACCAGCTGGTACGCAAA |
| CCACGTGCTCGCAAAGTTGCGAAAAGCAACGTGCCTGCGCTGGAAGCATGCCCGCAAAAACGTG |
| GCGTATGTACTCGTGTATATACTACCACTCCTAAAAAACCGAACTCCGCGCTGCGTAAAGTATGC |
| CGTGTTCGTCTGACTAACGGTTTCGAAGTGACTTCCTACATCGGTGGTGAAGGTCACAACCTGCA |
| GGAGCACTCCGTGATCCTGATCCGTGGCGGTCGTGTTAAAGACCTCCCGGGTGTTCGTTACCACA |
| CCGTACGTGGTGCGCTTGACTGCTCCGGCGTTAAAGACCGTAAGCAGGCTCGTTCCAAGTATGG |
| CGTGAAGCGTCCTAAGGCTTAATGGTAGATCTGATCAAGAGACAGGATGACGGTCGTTTCGCAT |
| GCTTGAACAAGATGGATTGCACGCAGGTTCTCCGGCCGCTTGGGTGGAGAGGCTATTCGGCTAT |

DESCRIPTION OF THE SEQUENCES

```
GACTGGGCACAACAGACAATCGGCTGCTCTGATGCCGCCGTGTTCCGGCTGTCAGCGCAGGGGC
GCCCGGTTCTTTTTGTCAAGACCGACCTGTCCGGTGCCCTGAATGAACTGCAGGACGAGGCAGC
GCGGCTATCGTGGCTGGCCACGACGGGCGTTCCTTGCGCAGCTGTGCTCGACGTTGTCACTGAA
GCGGGAAGGGACTGGCTGCTATTGGGCGAAGTGCCGGGGCAGGATCTCCTGTCATCTCACCTTG
CTCCTGCCGAGAAAGTATCCATCATGGCTGATGCAATGCGGCGGCTGCATACGCTTGATCCGGC
TACCTGCCCATTCGACCACCAAGCGAAACATCGCATCGAGCGAGCACGTACTCGGATGGAAGCC
GGTCTTGTCGATCAGGATGATCTGGACGAAGAGCATCAGGGGCTCGCGCCAGCCGAACTGTTCG
CCAGGCTCAAGGCGCGCATGCCCGACGGCGAGGATCTCGTCGTGACCCATGGCGATGCCTGCTT
GCCGAATATCATGGTGGAAAATGGCCGCTTTTCTGGATTCATCGACTGTGGCCGGCTGGGTGTG
GCGGACCGCTATCAGGACATAGCGTTGGCTACCCGTGATATTGCTGAAGAGCTTGGCGGCGAAT
GGGCTGACCGCTTCCTCGTGCTTTACGGTATCGCCGCTCCCGATTCGCAGCGCATCGCCTTCTAT
CGCCTTCTTGACGAGTTCTTCTGAGCGGGACTCTGGGGTTCGAAATGACCGACCAAGCGACGCC
CAACCTGCCATCACGAGATTTCGATTCCACCGCCGCCTTCTATGAAAGGTTGGGCTTCGGAATCG
TTTTCCGGGACGCCGGCTGGATGATCCTCCAGCGCGGGGATCTCATGCTGGAGTTCTTCGCCCAC
CCCGGGCTCGATCCCCTCGGGGGAATCAGAATTCAGTCGACAGCGGCCGCGATCTGCTGTGCC
TTCTAGTTGCCAGCCATCTGTTGTTTGCCCCTCCCCCGTGCCTTCCTTGACCCTGGAAGGTGCCAC
TCCCACTGTCCTTTCCTAATAAAATGAGGAAATTGCATCGCATTGTCTGAGTAGGTGTCATTCTA
TTCTGGGGGGTGGGGTGGGGCAGGACAGCAAGGGGGAGGATTGGGAAGACAATAGCAGGCATG
CTGGGGATGCGGTGGGCTCTATGGCCGATCAGCGATCGCTGAGGTGGGTGAGTGGGCGTGGCCT
GGGGTGGTCATGAAAATATATAAGTTGGGGGTCTTAGGGTCTCTTTATTTGTGTTGCAGAGACCG
CCGGAGCCATGAGCGGGAGCAGCAGCAGCAGCAGTAGCAGCAGCGCCTTGGATGGCAGCATCG
TGAGCCCTTATTTGACGACGCGGATGCCCCACTGGGCCGGGGTGCGTCAGAATGTGATGGGCTC
CAGCATCGACGGCCGACCCGTCCTGCCCGCAAATTCCGCCACGCTGACCTATGCGACCGTCGCG
GGGACGCCGTTGGACGCCACCGCCGCCGCCGCCACCGCAGCCGCCTTCGGCCGTGCGCAGCC
TGGCCACGGACTTTGCATTCCTGGGACCACTGGCGACAGGGGCTACTTCTCGGGCCGCTGCTGCC
GCCGTTCGCGATGACAAGCTGACCGCCCTGCTGGCGCAGTTGGATGCGCTTACTCGGGAACTGG
GTGACCTTTCTCAGCAGGTCATGGCCCTGCGCCAGCAGGTCTCCTCCCTGCAAGCTGGCGGGAAT
GCTTCTCCCACAAATGCCGTTTAAGATAAATAAAACCAGACTCTGTTTGGATTAAAGAAAAGTA
GCAAGTGCATTGCTCTCTTTATTTCATAATTTTCCGCGCGCGATAGGCCCTAGACCAGCGTTCTC
GGTCGTTGAGGGTGCGGTGTATCTTCTCCAGGACGTGGTAGAGGTGGCTCTGGACGTTGAGATA
CATGGGCATGAGCCCGTCCCGGGGGTGGAGGTAGCACCACTGCAGAGCTTCATGCTCCGGGGTG
GTGTTGTAGATGATCCAGTCGTAGCAGGAGCGCTGGGCATGGTGCCTAAAAATGTCCTTCAGCA
GCAGGCCGATGGCCAGGGGGAGGCCCTTGGTGTAAGTGTTTACAAAACGGTTAAGTTGGGAAG
GGTGCATTCGGGGAGAGATGATGTGCATCTTGGACTGTATTTTTAGATTGGCGATGTTTCCGCCC
AGATCCCTTCTGGGATTCATGTTGTGCAGGACCACCAGTACAGTGTATCCGGTGCACTTGGGGA
ATTTGTCATGCAGCTTAGAGGGAAAAGCGTGGAAGAACTTGGAGACGCCTTTGTGGCCTCCCAG
ATTTTCCATGCATTCGTCCATGATGATGGCAATGGGCCCGCGGGAGGCAGCTTGGGCAAAGATA
TTTCTGGGGTCGCTGACGTCGTAGTTGTGTTCCAGGGTGAGGTCGTCATAGGCCATTTTTACAAA
GCGCGGGCGGAGGGTGCCCGACTGGGGATGATGGTCCCCTCTGGCCCTGGGGCGTAGTTGCCC
TCGCAGATCTGCATTTCCCAGGCCTTAATCTCGGAGGGGGGAATCATATCCACCTGCGGGGCGA
TGAAGAAAACGGTTTCCGGAGCCGGGGAGATTAACTGGGATGAGAGCAGGTTTCTAAGCAGCT
GTGATTTTCCACAACCGGTGGGCCCATAAATAACACCTATAACCGGTTGCAGCTGGTAGTTTAG
AGAGCTGCAGCTGCCGTCGTCCCGGAGGAGGGGGGCCACCTCGTTGAGCATGTCCCTGACGCGC
ATGTTCTCCCCGACCAGATCCGCCAGAAGGCGCTCGCCGCCCAGGGACAGCAGCTCTTGCAAGG
AAGCAAAGTTTTTCAGCGGCTTGAGGCCGTCCGCCGTGGGCATGTTTTTCAGGGTCTGGCTCAGC
AGCTCCAGGCGGTCCCAGAGCTCGGTGACGTGCTCTACGGCATCTCTATCCAGCATATCTCCTCG
TTTCGCGGGTTGGGGCGACTTTCGCTGTAGGGCACCAAGCGGTGGTCGTCCAGCGGGCAGAG
TCATGTCCTTCCATGGGCGCAGGGTCCTCGTCAGGGTGGTCTGGGTCACGGTGAAGGGGTGCGC
TCCGGGCTGAGCGCTTGCCAAGGTGCGCTTGAGGCTGGTTCTGCTGGTGCTGAAGCGCTGCAGC
TCTTCGCCCTGCGCGTCGGCCAGGTAGCATTTGACCATGGTGTCATAGTCCAGCCCCTCCGCGGC
GTGTCCCTTGGCGCGCAGCTTGCCCTTGGAGGTGGCGCCGCACGAGGGGCAGAGCAGGCTCTTG
AGCGCGTAGAGCTTGGGGGCGAGGAAGACCGATTCGGGGAGTAGGCGTCCGCGCCGCAGACC
CCGCACACGGTCTCGCACTCCACCAGCCAGGTGAGCTCGGGGCGCGCGGGTCAAAAACCAGGT
TTCCCCCATGCTTTTTGATGCGTTTCTTACCTCGGGTCTCCATGAGGTGGTGTCCCCGCTCGGTGA
CGAAGAGGCTGTCCGTGTCTCCGTAGACCGACTTGAGGGGTCTTTTCTCAGGGGGGTCCCTCGG
TCTTCCTCGTAGAGGAACTCGGACCACTCTGAGACGAAGGCCCGCGTCCAGGCCAGGACGAAGG
AGGCTATGTGGGAGGGGTAGCGGTCGTTGTCCACTAGGGGGTCCACCTTCTCCAAGGTGTGAAG
ACACATGTCGCCTTCCTCGGCGTCCAGGAAGGTGATTGGCTTGTAGGGTGTAGGCCACGTGACCG
GGGGTTCCTGACGGGGGGGTATAAAAGGGGGTGGGGGCGCGCTCGTCGTCACTCTCTTCCGCAT
CGCTGTCTGCGAGGGCCAGCTGCTGGGGTGAGTATTCCCTCTCGAAGGCGGGCATGACCTCCGC
GCTGAGGTTGTCAGTTTCCAAAAACGAGGAGGATTTGATGTTCACCTGTCCCGAGGTGATACCTT
TGAGGGTACCCGCGTCCATCTGGTCAGAAAACACGATCTTTTTATTGTCCAGCTTGGTGGCGAAC
GACCCGTAGAGGGCGTTGGAGAGCAGCTTGGCGATGGAGCGCAGGGTCTGGTTCTTGTCCCTGT
CGGCGCGCTCCTTGGCCGCGATGTTGAGCTGCACGTACTCGCGCGCGACGCAGCGCCACTCGGG
GAAGACGGTGGTGCGCTCGTCGGGCACCAGGCGCACGCGCCAGCCGCGGTTGTGCAGGGTGAC
CAGGTCCACGCTGGTGGCGACCTCGCCGCGCAGGCGCTCGTTGGTCCAGCAGAGACGGCCGCCC
TTGCGCGAGCAGAAGGGGGGCAGGGGGTCGAGCTGGGTCTCGTCCGGGGGTCCGCGTCCACG
GTGAAAACCCCGGGGCGCAGGCGCGCGTCGAAGTAGTCTATCTTGCAACCTTGCATGTCCAGCG
CCTGCTGCCAGTCGCGGGCGGCGAGCGCGCGCTCGTAGGGGTTGAGCGGCGGGCCCCAGGGCAT
GGGGTGGGTGAGTGCGGAGGCGTACATGCCGCAGATGTCATAGACGTAGAGGGGCTCCCGCAG
GACCCCGATGTAGGTGGGGTAGCAGCGGCCGCCGCGGATGCTGGCGCGCACGTAGTCATACAGC
TCGTGCGAGGGGGCGAGGAGGTCGGGGCCCAGGTTGGTGCGGCGGGGCGCTCCGCGCGGAAG
ACGATCTGCCTGAAGATGGCATGCGAGTTGGAAGAGATGGTGGGCGCTGGAAGACGTTGAAG
CTGGCGTCCTGCAGGCCGACGCGTCGCGCACGAAGGAGGCGTAGGAGTCGCGCAGCTTGTGTA
CCAGCTCGGCGGTGACCTGCACGTCGAGCGCGCAGTAGTCGAGGGTCTCGCGGATGATGTCATA
TTTAGCCTGCCCCTTCTTTTTCCACAGCTCGCGGTTGAGGACAAACTCTTCGCGGTCTTTCCAGTA
CTCTTGGATCGGGAAACCGTCCGGTTCCGAACGGTAAGAGCCTAGCATGTAGAACTGGTTGACG
```

| DESCRIPTION OF THE SEQUENCES |
|---|
| GCCTGGTAGGCGCAGCAGCCCTTCTCCACGGGGAGGGCGTAGGCCTGCGCGGCCTTGCGGAGCG |
| AGGTGTGGGTCAGGGCGAAGGTGTCCCTGACCATGACTTTGAGGTACTGGTGCTTGAAGTCGGA |
| GTCGTCGCAGCCGCCCCGCTCCCAGAGCGAGAAGTCGGTGCGCTTCTTGGAGCGGGGGTTGGGC |
| AGAGCGAAGGTGACATCGTTGAAGAGGATTTTGCCCGCGCGGGGCATGAAGTTGCGGGTGATGC |
| GGAAGGGCCCCGGCACTTCAGAGCGGTTGTTGATGACCTGGGCGGCGAGCACGATCTCGTCGAA |
| GCCGTTGATGTTGTGGCCCACGATGTAGAGTTCCAGGAAGCGGGGCCGGCCCTTTACGGTGGGC |
| AGCTTCTTTAGCTCTTCGTAGGTGAGCTCCTCGGGCGAGGCGAGGCCGTGCTCGGCCAGGGCCC |
| AGTCCGCGAGGTGCGGGTTGTCTCTGAGGAAGGACTTCCAGAGGTCGCGGGCCAGGAGGGTCTG |
| CAGGCGGTCTCTGAAGGTCCTGAACTGGCGGCCCACGGCCATTTTTTCGGGGGTGATGCAGTAG |
| AAGGTGAGGGGGTCTTGCTGCCAGCGGTCCCAGTCGAGCTGCAGGGCGAGGTCGCGCGCGGCG |
| GTGACCAGGCGCTCGTCGCCCCCGAATTTCATGACCAGCATGAAGGGCACGAGCTGCTTTCCGA |
| AGGCCCCCATCCAAGTGTAGGTCTCTACATCGTAGGTGACAAAGAGGCGCTCCGTGCGAGGATG |
| CGAGCCGATCGGGAAGAACTGGATCTCCCGCCACCAGTTGGAGGAGTGGCTGTTGATGTGGTGG |
| AAGTAGAAGTCCCGTCGCCGGGCCGAACACTCGTGCTGGCTTTTGTAAAAGCGAGCGCAGTACT |
| GGCAGCGCTGCACGGGCTGTACCTCATGCACGAGATGCACCTTTCGCCCGCGCACGAGGAAGCC |
| GAGGGGAAATCTGAGCCCCCCGCCTGGCTCGCGGCATGGCTGGTTCTCTTCGCCCTCGTTCCAG |
| GTCCGTCTCCGTCTGGCTCCTCGAGGGGTGTTACGGTGGAGCGGACCACCACGCCGCGCGAGCC |
| GCAGGTCCAGATATCGGCGCGCGGCGGTCGGAGTTTGATGACGACATCGCGCAGCTGGGAGCTG |
| TCCATGGTCTGGAGCTCCCGCGGCGGCGGCAGGTCAGCCGGGAGTTCTTGCAGGTTCACCTCGC |
| AGAGTCGGGCCAGGGCGCGGGGCAGGTCTAGGTGGTACCTGATCTCTAGGGGCGTGTTGGTGGC |
| GGCGTCGATGGCTTGCAGGAGCCCGCAGCCCCGGGGGCGACGACGGTGCCCCGCGGGGTGGT |
| GGTGGTGGTGGCGGTGCAGCTCAGAAGCGGTGCCGCGGGCGGGCCCCGGAGGTAGGGGGGC |
| TCCGGTCCCGCGGGCAGGGCGGCAGCGGCACGTCGGCGTGGAGCGCGGGCAGGAGTTGGTGC |
| TGTGCCCGGAGGTTGCTGGCGAAGGCGACGACGCGGCGGTTGATCTCCTGGATCTGGCGCCTCT |
| GCGTGAAGACGACGGGCCCGGTGAGCTTGAACCTGAAAGAGAGTTCGACAGAATCAATCTCGG |
| TGTCATTGACCGCGGCCTGGCGCAGGATCTCCTGCACGTCTCCCGAGTTGTCTTGGTAGGCGATC |
| TCGGCCATGAACTGCTCGATCTCTTCCTCCTGGAGGTCTCCGCGTCCGGCGCGTTCCACGGTGGC |
| CGCCAGGTCGTTGGAGATGCGCCCATGAGCTGCGAGAAGGCGTTGAGTCCGCCCTCGTTCCAG |
| ACTCGGCTGTAGACCACGCCCCCCTGGTCATCGCGGGCGCGCATGACCACCTGCGCGAGGTTGA |
| GCTCCACGTGCCGCGCGAAGACGGCGTAGTTGCGCAGACGCTGGAAGAGGTAGTTGAGGGTGG |
| TGGCGGTGTGCTCGGCCACGAAGAAGTTCATGACCCAGCGGCGCAACGTGGATTCGTTGATGTC |
| CCCCAAGGCCTCCAGCCGTTCCATGGCCTCGTAGAAGTCCACGGCGAAGTTGAAAAACTGGGAG |
| TTGCGCGCCGACACGGTCAACTCCTCCTCCAGAAGACGGATGAGCTCGGCGACGGTGTCGCGCA |
| CCTCGCGCTCGAAGGCTATGGGGATCTCTTCCTCCGCTAGCATCACCACCTCCTCCTCTTCCTCCT |
| CTTCTGGCACTTCCATGATGGCTTCCTCCTCTTCGGGGGGTGGCGGCGGCGGCGGTGGGGGAGG |
| GGGCGCTCTGCGCCGGCGGCGGCGCACCGGGAGGCGGTCCACGAAGCGCGCGATCATCTCCCCG |
| CGGCGGCGGCGCATGGTCTCGGTGACGGCGCGGCCGTTCTCCCGGGGGCGCAGTTGGAAGACGC |
| CGCCGGACATCTGGTGCTGGGGCGGGTGGCCGTGAGGCAGCGAGACGGCGCTGACGATGCATCT |
| CAACAATTGCTGCGTAGGTACGCCGCCGAGGGACCTGAGGGAGTCCATATCCACCGGATCCGAA |
| AACCTTTCGAGGAAGGCGTCTAACCAGTCGCAGTCGCAAGGTAGGCTGAGCACCGTGGCGGGCG |
| GCGGGGGGTGGGGGAGTGTCTGGCGGAGGTGCTGCTGATGATGTAATTGAAGTAGGCGGACTT |
| GACACGGCGGATGGTCGACAGGAGCACCATGTCCTTGGGTCCGGCCTGCTGGATGCGGAGGCGG |
| TCGGCTATGCCCCAGGCTTCGTTCTGGCATCGGCGCAGGTCCTTGTAGTAGTCTTGCATGAGCCT |
| TTCCACCGGCACCTCTTCTCCTTCCTCTTCTGCTTCTTCCATGTCTGCTTCGGCCCTGGGGCGGCG |
| CCGCGCCCCCTGCCCCCATGCGCGTGACCCCGAACCCCCTGAGCGGTTGGAGCAGGGCCAGG |
| TCGGCGACGACGCGCTCGGCCAGGATGGCCTGCTGCACCTGCGTGAGGGTGGTTTGGAAGTCAT |
| CCAAGTCCACGAAGCGGTGGTAGGCGCCCGTGTTGATGGTGTAGGTGCAGTTGGCCATGACGGA |
| CCAGTTGACGGTCTGGTGGCCCGGTTGCGACATCTCGGTGTACCTGAGTCGCGAGTAGGCGCGG |
| GAGTCGAAGACGTAGTCGTTGCAAGTCCGCACCAGGTACTGGTAGCCCACCAGGAAGTGCGGCG |
| GCGGCTGGCGGTAGAGGGGCCAGCGCAGGGTGGCGGGGGTCCGGGGGCCAGGTCTTCCAGCA |
| TGAGGCGGTGGTAGGCGTAGATGTACCTGGACATCCAGGTGATACCCGCGGCGGTGGTGGAGGC |
| GCGCGGGAAGTCGCGCACCCGGTTCCAGATGTTGCGCAGGGGCAGAAAGTGCTCCATGGTAGGC |
| GTGCTCTGTCCAGTCAGACGCGCGCAGTCGTTGATACTCTAGACCAGGGAAAACGAAAGCCGGT |
| CAGCGGGCACTCTTCCGTGGTCTGGTGAATAGATCGCAAGGGTATCATGGCGGAGGGCCTCGGT |
| TCGAGCCCCGGGTCCGGGCCGGACGGTCCGCCATGATCCACGCGGTTACCGCCCGCGTGTCGAA |
| CCCAGGTGTGCGACGTCAGACAACGGTGGAGTGTTCCTTTTGGCGTTTTTCTGGCCGGGCGCCGG |
| CGCCGCGTAAGAGACTAAGCCGCGAAAGCGAAAGCAGTAAGTGGCTCGCTCCCCGTAGCCGGA |
| GGGATCCTTGCTAAGGGTTGCGTTGCGGCGAACCCCGGTTCGAATCCCGTACTCGGGCCGGCCG |
| GACCCGCGGCTAAGGTGTTGGATTGGCCTCCCCCTCGTATAAAGACCCCGCTTGCGGATTGACTC |
| CGGACACGGGACGAGCCCCTTTTATTTTTGCTTTCCCCAGATGCATCCGGTGCTGCGGCAGATG |
| CGCCCCCGCCCCAGCAGCAGCAACAACACCAGCAAGAGCGGCAGCAACAGCAGCGGGAGTCA |
| TGCAGGGCCCCTCACCCACCCTCGGCGGGCCGGCCACCTCGGCGTCCGCGGCCGTGTCTGGCG |
| CCTGCGGCGGCGGCGGGGGGCCGGCTGACGACCCCGAGGAGCCCCGCGGCGCAGGGCCAGAC |
| ACTACCTGGACCTGGAGGAGGGCGAGGGCCTGGCGCGGCTGGGGGCGCCGTCTCCCGAGCGCC |
| ACCCGCGGGTGCAGCTGAAGCGCGACTCGCGCGAGGCGTACGTGCCTCGGCAGAACCTGTTCAG |
| GGACCGCGCGGGCGAGGAGCCCGAGGAGATGCGGGACAGGAGGTTCAGCGCAGGGCGGGAGC |
| TGCGGCAGGGGCTGAACCGCGAGCGGCTGCTGCGCGAGGAGGACTTTGAGCCCGACGCGCGGA |
| CGGGGATCAGCCCCGCGCGCGCACGTGGCGGCCGCCGACCTGGTGACGGCGTACGAGCAGA |
| CGGTGAACCAGGAGATCAACTTCCAAAAGAGTTTCAACAACCACGTGCGCACGCTGGTGGCGCG |
| CGAGGAGGTGACCATCGGGCTGATGCACCTGTGGGACTTTGTAAGCGCGCTGGTGCAGAACCCC |
| AACAGCAAGCCTCTGACGGCGCAGCTGTTCCTGATAGTGCAGCACAGCAGGGACAACGAGGCG |
| TTTAGGGACGCGCTGCTGAACATCACCGAGCCCGAGGGTCGGTGGCTGCTGGACCTGATTAACA |
| TCCTGCAGAGCATAGTGGTGCAGGAGCGCAGCCTGAGCCTGGCCGACAAGGTGGCGGCCATCA |
| ACTACTCGATGCTGAGCCTGGGCAAGTTTTACGCGCGCAAGATCTACCAGACGCCGTACGTGCC |
| CATAGACAAGGAGGTGAAGATCGACGGTTTTTACATGCGCATGGCGCTGAAGGTGCTCACCCTG |
| AGCGACGACCTGGGCGTGTACCGCAACGAGCGCATCCACAAGGCCGTGAGCGTGAGCCGGCGG |
| CGCGAGCTGAGCGACCGCGAGCTGATGCACAGCCTGCAGCGGGCGCTGGCGGGCGCCGGCAGC |

DESCRIPTION OF THE SEQUENCES

```
GGCGACAGGGAGGCGGAGTCCTACTTCGATGCGGGGCGGACCTGCGCTGGGCGCCCAGCCGG
CGGGCCCTGGAGGCCGCGGGGGTCCGCGAGGACTATGACGAGGACGGCGAGGAGGATGAGGAG
TACGAGCTAGAGGAGGGCGAGTACCTGGACTAAACCGCGGGTGGTGTTTCCGGTAGATGCAAG
ACCCGAACGTGGTGGACCCGGCGCTGCGGGCGGCTCTGCAGAGCCAGCCGTCCGGCCTTAACTC
CTCAGACGACTGGCGACAGGTCATGGACCGCATCATGTCGCTGACGGCGCGTAACCCGGACGCG
TTCCGGCAGCAGCCGCAGGCCAACAGGCTCTCCGCCATCCTGGAGGCGGTGGTGCCTGCGCGCT
CGAACCCCACGCACGAGAAGGTGCTGGCCATAGTGAACGCGCTGGCCGAGAACAGGGCCATCC
GCCCGGACGAGGCCGGGCTGGTGTACGACGCGCTGCTGCAGCGCGTGGCCCGCTACAACAGCG
GCAACGTGCAGACCAACCTGGACCGGCTGGTGGGGACGTGCGCGAGGCGGTGGCGCAGCGCG
AGCGCGCGGATCGGCAGGGCAACCTGGGCTCCATGGTGGCGCTGAATGCCTTCCTGAGCACGCA
GCCGGCCAACGTGCCGCGGGGGCAGGAAGACTACACCAACTTTGTGAGCGCGCTGCGGCTGATG
GTGACCGAGACCCCCCAGAGCGAGGTGTACCAGTCGGGCCCGGACTACTTCTTCCAGACCAGCA
GACAGGGCCTGCAGACGGTGAACCTGAGCCAGGCTTTCAAGAACCTGCGGGGGCTGTGGGGCG
TGAAGGCGCCCACCGGCGACCGGGCGACGGTGTCCAGCCTGCTGACGCCCAACTCGCGCCTGCT
GCTGCTGCTGATCGCGCCGTTCACGGACAGCGGCAGCGTGTCCGGGACACCTACCTGGGGCAC
CTGCTGACCCTGTACCGCGAGGCCATCGGGCAGGCGCAGGTGGACGAGCACACCTTCCAGGAGA
TCACCAGCGTGAGCCGCGCGCTGGGGCAGGAGGCACGAGCAGCCTGGAGGCGACTCTGAACT
ACCTGCTGACCAACCGGCGGCAGAAGATTCCCTCGCTGCACAGCCTGACCTCCGAGGAGGAGCG
CATCTTGCGCTACGTGCAGCAGAGCGTGAGCCTGAACCTGATGCGCGACGGGGTGACGCCCAGC
GTGGCGCTGGACATGACCGCGCGCAACATGGAACCGGGCATGTACGCGCGCGCACCGGCCTTACA
TCAACCGCCTGATGGACTACCTGCATCGCGCGGCGGCCGTGAACCCCGAGTACTTTACCAACGC
CATCCTGAACCCGCACTGGCTCCCGCCGCCCGGGTTCTACAGCGGGGGCTTCGAGGTCCCGGAG
ACCAACGATGGCTTCCTGTGGGACGACATGGACGACAGCGTGTTCTCCCCGCGGCCGCAGGCGC
TGGCGGAAGCGTCCCTGCTGCGTCCCAAGAAGGAGGAGGAGGAGGAGCGAGTCGCCGCCGCG
GCAGCAGCGGCGTGGCTTCTCTGTCCGAGCTGGGGGCGGCAGCCGCCGCGCGCCCCGGGTCCCT
GGGCGGCAGCCCCTTTCCGAGCCTGGTGGGGTCTCTGCACAGCGAGCGCACCACCCGCCCTCGG
CTGCTGGGCGAGGACGAGTACCTGAATAACTCCCTGCTGCAGCCGGTGCGGGAGAAAAACCTGC
CTCCCGCCTTCCCCAACAACGGGATAGAGAGCCTGGTGGACAAGATGAGCAGATGGAAGACCT
ATGCGCAGGAGCACAGGGACGCGCCTGCGCTCCGGCCGCCCACGCGGCGCCAGCGCCACGACC
GGCAGCGGGGCTGGTGTGGGATGACGAGGACTCCGCGGACGATAGCAGCGTGCTGGACCTGG
GAGGGAGCGGCAACCCGTTCGCGCACCTGCGCCCCCGCCTGGGGAGGATGTTTTAAAAAAAAA
AAAAAAAAGCAAGAAGCATGATGCAAAAATTAAATAAAACTCACCAAGGCCATGGCGACCGAG
CGTTGGTTTCTTGTGTTCCCTTCAGTATGCGGCGCGCGGCGATGTACCAGGAGGGACCTCCTCCC
TCTTACGAGAGCGTGGTGGGCGCGGCGGCGGCGGCGCCCTCTTCTCCCTTTGCGTCGCAGCTGCT
GGAGCCGCCGTACGTGCCTCCGCGCTACCTGCGGCCTACGGGGGGGAGAAACAGCATCCGTTAC
TCGGAGCTGGCGCCCCTGTTCGACACCACCCGGGTGTACCTGGTGGACAACAAGTCGGCGGACG
TGGCCTCCCTGAACTACCAGAACGACCACAGCAATTTTTTGACCACGGTCATCCAGAACAATGA
CTACAGCCCGAGCGAGGCCAGCACCCAGACCATCAATCTGGATGACCGGTCGCACTGGGGCGGC
GACCTGAAAACCATCCTGCACACCAACATGCCCAACGTGAACGAGTTCATGTTCACCAATAAGT
TCAAGGCGCGGGTGATGGTGTCGCGCTCGCACACCAAGGAAGACCGGGTGGAGCTGAAGTACG
AGTGGGTGGAGTTCGAGCTGCCAGAGGGCAACTACTCCGAGACCATGACCATTGACCTGATGAA
CAACGCGATCGTGGAGCACTATCTGAAAGTGGGCAGGCAGAACGGGGTCCTGGAGAGCGACAT
CGGGGTCAAGTTCGACACCAGGAACTTCCGCCTGGGGCTGGACCCCGTGACCGGGCTGGTTATG
CCCGGGGTGTACACCAACGAGGCCTTCCATCCCGACATCATCCTGCTGCCCGGCTGCGGGGTGG
ACTTCACTTACAGCCGCCTGAGCAACCTCCTGGGCATCCGCAAGCGGCAGCCCTTCCAGGAGGG
CTTCAGGATCACCTACGAGGACCTGGAGGGGGGCAACATCCCCGCGCTCCTCGATGTGGAGGCC
TACCAGGATAGCTTGAAGGAAAATGAGGCGGGACAGGAGGATACCGCCCCCGCCGCCTCCGCC
GCCGCCGAGCAGGGCGAGGATGCTGCTGACACCGCGGCCGCGGACGGGGCAGAGGCCGACCCC
GCTATGGTGGTGGAGGCTCCCGAGCAGGAGGAGGACATGAATGACAGTGCGGTGCGCGGAGAC
ACCTTCGTCACCCGGGGGGAGGAAAAGCAAGCGGAGGCCGAGGCCGCGGCCGAGGAAAAGCA
ACTGGCGGCAGCAGCGGCGGCGGCGGCGTTGGCCGCGGCGGAGGCTGAGTCTGAGGGGACCAA
GCCCGCCAAGGAGCCCGTGATTAAGCCCTGACCGAAGATAGCAAGAAGCGCAGTTACAACCT
GCTCAAGGACAGCACCAACACCGCGTACCGCAGCTGGTACCTGGCCTACAACTACGGCGACCCG
TCGACGGGGTGCGCTCCTGGACCCTGCTGTGCACGCCGGACGTGACCTGCGGCTCGGAGCAGG
TGTACTGGTCGCTGCCCGACATGATGCAAGACCCCGTGACCTTCCGCTCCACGCGGCAGGTCAG
CAACTTCCCGGTGGTGGGCGCCGAGCTGCTGCCCGTGCACTCCAAGAGCTTCTACAACGACCAG
GCCGTCTACTCCCAGCTCATCCGCCAGTTCACCTCTCTGACCCACGTGTTCAATCGCTTTCCTGAG
AACCAGATTCTGGCGCGCCCGCCCGCCCCCACCATCACCACCGTCAGTGAAAACGTTCCTGCTCT
CACAGATCACGGGACGCTACCGCTGCGCAACAGCATCGGAGGAGTCCAGCGAGTGACCGTTACT
GACGCCAGACGCCGCACCTGCCCCTACGTTTACAAGGCCTTGGGCATAGTCTCGCCGCGCGTCCT
TTCCAGCGCACTTTTTGAGCAACACCACCATCATGTCCATCCTGATCTCACCCAGCAATAACTC
CGGCTGGGGACTGCTGCGCGCGCCCAGCAAGATGTTCGGAGGGGCGAGGAAGCGTTCCGAGCA
GCACCCCGTGCGCGTGCGCGGGCACTTCCGCGCCCCCTGGGGAGCGCACAAACGCGGCCGCGCG
GGGCGCACCACCGTGGACGACGCCATCGACTCGGTGGTGGAGCAGGCGCGCAACTACAGGCCC
GCGGTCTCTACCGTGGACGCGGCCATCCAGACCGTGGTGCGGGGCGCGCGGCGGTACGCCAAGC
TGAAGAGCCGCCGGAAGCGCGTGGCCCGCCGCCACCGCCGCCGACCCGGGGCGCGCCAAAC
GCGCCGCCGCGGCCCTGCTTCGCCGGGCCAAGCGCACGGCCGCCGCCGCCGCCATGAGGGCCGC
GCGCCGCTTGGCCGCCGGCATCACCGCCGCCACCATGGCCCCCCGTACCCGAAGACGCGCGGCC
GCCGCCGCCGCCGCCGCCATCAGTGACATGGCCAGCAGGCGCCGGGGCAACGTGTACTGGGTGC
GCGACTCGGTGACCGGCACGCGCGTGCCCGTGCGCTTCCGCCCCCCGCGGACTTGAGATGATGT
GAAAAAAACACTGAGTCTCCTGCTGTTGTGTATCCCAGCGGCGGCGGCCGCGCGCAGCGTC
ATGTCCAAGCGCAAAATCAAAGAAGAGATGCTCCAGGTCGTCGCGCCGGAGATCTATGGGCCCC
CGAAGAAGGAAGAGCAGGATTCGAAGCCCCGCAAGATAAAGCGGGTCAAAAAGAAAAAGAAA
GATGATGACGATGCCGATGGGGAGGTGGAGTTCCTGCGCGCCACGGCGCCCAGGCGCCCGGTGC
AGTGGAAGGGCCGGCGCGTAAAGCGCGTCCTGCGCCCCGGCACCGCGGTGGTCTTCACGCCCGG
CGAGCGCTCCACCCGGACTTTCAAGCGCGTCTATGACGAGGTGTACGGCGACGAAGACCTGCTG
GAGCAGGCCAACGAGCGCTTCGGAGAGTTTGCTTACGGGAAGCGTCAGCGGGCGCTGGGGAAG
```

| DESCRIPTION OF THE SEQUENCES |
|---|
| GAGGACCTGCTGGCGCTGCCGCTGGACCAGGGCAACCCCACCCCCAGTCTGAAGCCCGTGACCC |
| TGCAGCAGGTGCTGCCGAGCAGCGCACCCTCCGAGGCGAAGCGGGGTCTGAAGCGCGAGGGCG |
| GCGACCTGGCGCCCACCGTGCAGCTCATGGTGCCCAAGCGGCAGAGGCTGGAGGATGTGCTGGA |
| GAAAATGAAAGTAGACCCCGGTCTGCAGCCGGACATCAGGGTCCGCCCCATCAAGCAGGTGGC |
| GCCGGGCCTCGGCGTGCAGACCGTGGACGTGGTCATCCCCACCGGCAACTCCCCCGCCGCCGCC |
| ACCACTACCGCTGCCTCCACGGACATGGAGACACAGACCGATCCCGCCGCAGCCGCAGCCGCAG |
| CCGCCGCCGCGACCTCCTCGGCGGAGGTGCAGACGGACCCCTGGCTGCCGCCGGCGATGTCAGC |
| TCCCCGCGCGCGTCGCGGGCGCAGGAAGTACGGCGCCGCCAACGCGCTCCTGCCCGAGTACGCC |
| TTGCATCCTTCCATCGCGCCCACCCCCGGCTACCGAGGCTATACCTACCGCCCGCGAAGAGCCA |
| AGGGTTCCACCCGCCGTCCCCGCCGACGCGCCGCCGCCACCACCCGCCGCCGCCGCCGCAGACG |
| CCAGCCCGCACTGGCTCCAGTCTCCGTGAGGAAAGTGGCGCGCGACGGACACACCCTGGTGCTG |
| CCCAGGGCGCGCTACCACCCCAGCATCGTTTAAAAGCCTGTTGTGGTTCTTGCAGATATGGCCCT |
| CACTTGCCGCCTCCGTTTCCCGGTGCCGGGATACCGAGGAGGAAGATCGCGCCGCAGGAGGGGT |
| CTGGCCGGCCGCGGCCTGAGCGGAGGCAGCCGCCGCGCGCACCGGCGGCGACGCGCCACCAGC |
| CGACGCATGCGCGGCGGGGTGCTGCCCCTGTTAATCCCCCTGATCGCCGCGGCGATCGGCGCCG |
| TGCCCGGGATCGCCTCCGTGGCCTTGCAAGCGTCCCAGAGGCATTGACAGACTTGCAAACTTGC |
| AAATATGGAAAAAAAAACCCCAATAAAAAAGTCTAGACTCTCACGCTCGCTTGGTCCTGTGACT |
| ATTTTGTAGAATGGAAGACATCAACTTTGCGTCGCTGGCCCCGCGTCACGGCTCGCGCCCGTTCC |
| TGGGACACTGGAACGATATCGGCACCAGCAACATGAGCGGTGGCGCCTTCAGTTGGGGCTCTCT |
| GTGGAGCGGCATTAAAAGTATCGGGTCTGCCGTTAAAAATTACGGCTCCCGGGCCTGGAACAGC |
| AGCACGGGCCAGATGTTGAGAGACAAGTTGAAAGAGCAGAACTTCCAGCAGAAGGTGGTGGAG |
| GGCCTGGCCTCCGGCATCAACGGGGTGGTGGACCTGGCCAACCAGGCCGTGCAGAATAAGATCA |
| ACAGCAGACTGGACCCCCGGCCGCCGGTGGAGGAGGTGCCGCCGGCGCTGGAGACGGTGTCCC |
| CCGATGGGCGTGGCGAGAAGCGCCCGCGGCCCGATAGGGAAGAGACCACTCTGGTCACGCAGA |
| CCGATGAGCCGCCCCCGTATGAGGAGGCCCTGAAGCAAGGTCTGCCCACCCACGCGGCCCATCGC |
| GCCCATGGCCACCGGGGTGGTGGGCCGCCACACCCCCGCCACGCTGGACTTGCCTCCGCCCGCC |
| GATGTGCCGCAGCAGCAGAAGGCGGCACAGCCGGGCCCGCCCGCGACCGCCTCCCGTTCCTCCG |
| CCGGTCCTCTGCGCCGCGCGGCCAGCGGCCCCCGCGGGGGGGTCGCGAGGCACGGCAACTGGC |
| AGAGCACGCTGAACAGCATCGTGGGTCTGGGGGTGCGGTCCGTGAAGCGCCGCCGATGCTACTG |
| AATAGCTTAGCTAACGTGTTGTATGTGTGTATGCGCCCTATGTCGCCGCCAGAGGAGCTGCTGAG |
| TCGCCGCCGTTCGCGCGCCCACCACCACCGCCACTCCGCCCCTCAAGATGGCGACCCCATCGAT |
| GATGCCGCAGTGGTCGTACATGCACATCTCGGGCCAGGACGCCTCGGAGTACCTGAGCCCCGGG |
| CTGGTGCAGTTCGCCCGCGCCACCGAGAGCTACTTCAGCCTGAGTAACAAGTTTAGGAACCCCA |
| CGGTGGCGCCCACGCACGATGTGACCACCGACCGGTCTCAGCGCCTGACGCTGCGGTTCATTCC |
| CGTGGACCGCGAGGACACCGCGTACTCGTACAAGGCGCGGTTCACCCTGGCCGTGGGCGACAAC |
| CGCGTGCTGGACATGGCCTCCACCTACTTTGACATCCGCGGGGTGCTGGACCGGGGTCCCACTTT |
| CAAGCCCTACTCTGGCACCGCCTACAACTCCCTGGCCCCCAAGGGCGCTCCCAACTCCTGCGAGT |
| GGGAGCAAGAGGAAACTCAGGCAGTTGAAGAAGCAGCAGAAGAGGAAGAAGAAGATGCTGAC |
| GGTCAAGCTGAGGAAGAGCAAGCAGCTACCAAAAAGACTCATGTATATGCTCAGGCTCCCCTTT |
| CTGGCGAAAAAATTAGTAAAGATGGTCTGCAAATAGGAACGGACGCTACAGCTACAGAACAAA |
| AACCTATTTATGCAGACCCTACATTCCAGCCCGAACCCCAAATCGGGGAGTCCCAGTGGAATGA |
| GGCAGATGCTACAGTCGCCGGCGGTAGAGTGCTAAAGAAATCTACTCCCATGAAACCATGCTAT |
| GGTTCCTATGCAAGACCCACAAATGCTAATGGAGGTCAGGGTGTACTAACGGCAAATGCCCAGG |
| GACAGCTAGAATCTCAGGTTGAAATGCAATTCTTTTCAACTTCTGAAAACGCCCGTAACGAGGC |
| TAACAACATTCAGCCCAAATTGGTGCTGTATAGTGAGGATGTGCACATGGAGACCCCGGATACG |
| CACCTTTCTTACAAGCCCGCAAAAAGCGATGACAATTCAAAAATCATGCTGGGTCAGCAGTCCA |
| TGCCCAACAGACCTAATTACATCGGCTTCAGAGACAACTTTATCGGCCTCATGTATTACAATAGC |
| ACTGGCAACATGGGAGTGCTTGCAGGTCAGGCCTCTCAGTTGAATGCAGTGGTGGACTTGCAAG |
| ACAGAAACACAGAACTGTCCTACCAGCTCTTGCTTGATTCCATGGGTGACAGAACCAGATACTT |
| TTCCATGTGGAATCAGGCAGTGGACAGTTATGACCCAGATGTTAGAATTATTGAAAATCATGGA |
| ACTGAAGACGAGCTCCCCAACTATTGTTTCCCTCTGGGTGGCATAGGGGTAACTGACACTTACCA |
| GGCTGTTAAAACCAACAATGGCAATAACGGGGGCCAGGTGACTTGGACAAAAGATGAAACTTTT |
| GCAGATCGCAATGAAATAGGGGTGGGAAACAATTTCGCTATGGAGATCAACCTCAGTGCCAACC |
| TGTGGAGAAACTTCCTGTACTCCAACGTGGCGCTGTACCTACCAGACAAGCTTAAGTACAACCC |
| CTCCAATGTGGACATCTCTGACAACCCCAACACCTACGATTACATGAACAAGCGAGTGGTGGCC |
| CCGGGGCTGGTGGACTGCTACATCAACCTGGGCGCGCGCTGGTCGCTGGACTACATGGACAACG |
| TCAACCCCTTCAACCACCACCGCAATGCGGGCCTGCGCTACCGCTCCATGCTCCTGGGCAACGG |
| GCGCTACGTGCCCTTCCACATCCAGGTGCCCCAGAAGTTCTTTGCCATCAAGAACCTCCTCCTCC |
| TGCCGGGCTCCTACACCTACGAGTGGAACTTCAGGAAGGATGTCAACATGGTCCTCCAGAGCTC |
| TCTGGGTAACGATCTCAGGGTGGACGGGGCCAGCATCAAGTTCGAGAGCATCTGCCTCTACGCC |
| ACCTTCTTCCCCATGGCCCACAACACGGCCTCCACGCTCGAGGCCATGCTCAGGAACGACACCA |
| ACGACCAGTCCTTCAATGACTACCTCTCCGCGCCAACATGCTCTACCCCATACCCGCCAACGCC |
| ACCAACGTCCCCATCTCCATCCCTCGCGCAACTGGGCGGCCTTCCGCGGCTGGGCCTTCACCCG |
| CCTCAAGACCAAGGAGACCCCCTCCCTGGGCTCGGGATTCGACCCCTACTACACCTACTCGGGC |
| TCCATTCCCTACCTGGACGGCACCTTCTACCTCAACCACACTTTCAAGAAGGTCTCGGTCACCTT |
| CGACTCCTCGGTCAGCTGGCCGGGCAACGACCGTCTGCTCACCCCCAACGAGTTCGAGATCAAG |
| CGCTCGGTCGACGGGGAGGGCTACAACGTGGCCCAGTGCAACATGACCAAGGACTGGTTCCTGG |
| TCCAGATGCTGGCCAACTACAACATCGGCTACCAGGGCTTCTACATCCCAGAGAGCTACAAGGA |
| CAGGATGTACTCCTTCTTCAGGAACTTCCAGCCCATGAGCCGGCAGGTGGTGGACCAGACCAAG |
| TACAAGGACTACCAGGAGGTGGGCATCATCCACCAGCACAACAACTCGGGCTTCGTGGGCTACC |
| TCGCCCCCACCATGCGCGAGGGACAGGCCTACCCCGCCAACTTCCCCTATCGCTCATAGGCAA |
| GACCGCGGTCGACAGCATCACCCAGAAAAAGTTCCTCTGCGACCGCACCCTCTGGCGCATCCCC |
| TTCTCCAGCAACTTCATGTCCATGGGTGCGCTCTCGGACCTGGGCCAGAACTTGCTCTACGCCAA |
| CTCCGCCCACGCCCTCGACATGACCTTCGAGGTCGACCCCATGGACGAGCCCACCCTTCTCTATG |
| TTCTGTTCGAAGTCTTTGACGTGGTCCGGGTCCACCAGCCGCACCGCGGCGTCATCGAGACCGTG |
| TACCTGCGTACGCCCTTCTCGGCCGGCAACGCCACCACCTAAAGAAGCAAGCCGCAGTCATCGC |
| CGCCTGCATGCCGTCGGGTTCCACCGAGCAAGAGCTCAGGGCCATCGTCAGAGACCTGGGATGC |

DESCRIPTION OF THE SEQUENCES

```
GGGCCCTATTTTTTGGGCACCTTCGACAAGCGCTTCCCTGGCTTTGTCTCCCCACACAAGCTGGC
CTGCGCCATCGTCAACACGGCCGGCCGCGAGACCGGGGGCGTGCACTGGCTGGCCTTCGCCTGG
AACCCGCGCTCCAAAACATGCTTCCTCTTTGACCCCTTCGGCTTTTCGGACCAGCGGCTCAAGCA
AATCTACGAGTTCGAGTACGAGGGCTTGCTGCGTCGCAGCGCCATCGCCTCCTCGCCCGACCGCT
GCGTCACCCTCGAAAAGTCCACCCAGACCGTGCAGGGGCCCGACTCGGCCGCTGCGGTCTCTT
CTGCTGCATGTTTCTGCACGCCTTTGTGCACTGGCCTCAGAGTCCCATGGACCGCAACCCCACCA
TGAACTTGCTGACGGGGGTGCCCAACTCCATGCTCCAGAGCCCCCAGGTCGAGCCCACCCTGCG
CCGCAACCAGGAGCAGCTCTACAGCTTCCTGGAGCGCCACTCGCCTTACTTCCGCCGCCACAGC
GCACAGATCAGGAGGGCCACCTCCTTCTGCCACTTGCAAGAGATGCAAGAAGGGTAATAACGAT
GTACACACTTTTTTTCTCAATAAATGGCATCTTTTTATTTATACAAGCTCTCTGGGGTATTCATTT
CCCACCACCACCCGCCGTTGTCGCCATCTGGCTCTATTTAGAAATCGAAAGGGTTCTGCCGGGAG
TCGCCGTGCGCCACGGGCAGGGACACGTTGCGATACTGGTAGCGGGTGCCCCACTTGAACTCGG
GCACCACCAGGCGAGGCAGCTCGGGGAAGTTTTCGCTCCACAGGCTGCGGGTCAGCACCAGCGC
GTTCATCAGGTCGGGCGCCGAGATCTTGAAGTCGCAGTTGGGGCCGCCGCCCTGCGCGCGCGAG
TTGCGGTACACCGGGTTGCAGCACTGGAACACCAACAGCGCCGGGTGCTTCACGCTGGCCAGCA
CGCTGCGGTCGGAGATCAGCTCGGCGTCCAGGTCCTCCGCGTTGCTCAGCGCGAACGGGGTCAT
CTTGGGCACTTGCCGCCCCAGGAAGGGCGCGTGCCCCGGTTTCGAGTTGCAGTCGCAGCGCAGC
GGGATCAGCAGGTGCCCGTGCCCGGACTCGGCGTTGGGGTACAGCGCGCGCATGAAGGCCTGCA
TCTGGCGGAAGGCCATCTGGGCCTTGGCGCCCTCCGAGAAGAACATGCCGCAGGACTTGCCCGA
GAACTGGTTTGCGGGGCAGCTGGCGTCGTGCAGGCAGCAGCGCGTCGGTGTTGGCGATCTGC
ACCACGTTGCGCCCCACCGGTTCTTCACGATCTTGGCCTTGGACGATTGCTCCTTCAGCGCGCG
CTGCCCGTTCTCGCTGGTCACATCCATCTCGATCACATGTTCCTTGTTCACCATGCTGCTGCCGTG
CAGACACTTCAGCTCGCCCTCCGTCTCGGTGCAGCGGTGCTGCCACAGCGCGCAGCCCGTGGGC
TCGAAAGACTTGTAGGTCACCTCCGCGAAGGACTGCAGGTACCCCTGCAAAAAGCGGCCCATCA
TGGTCACGAAGGTCTTGTTGCTGCTGAAGGTCAGCTGCAGCCCGCGGTGCTCCTCGTTCAGCCAG
GTCTTGCACACGGCCGCCAGCGCCTCCACCTGGTCGGGCAGCATCTTGAAGTTCACCTTCAGCTC
ATTCTCCACGTGGTACTTGTCCATCAGCGTGCGCGCCGCCTCCATGCCCTTCTCCCAGGCCGACA
CCAGCGGCAGGCTCACGGGGTTCTTCACCATCACCGTGGCCGCCGCCTCCGCCGCGCTTTCGCTT
TCCGCCCCGCTGTTCTCTTCCTCTTCCTCCTCTTCCTCGCCGCCGCCCACTCGCAGCCCCCGCACC
ACGGGGTCGTCTTCCTGCAGGCGCTGCACCTTGCGCTTGCCGTTGCGCCCCTGCTTGATGCGCAC
GGGCGGGTTGCTGAAGCCCACCATCACCAGCGCGGCCTCTTCTTGCTCGTCCTCGCTGTCCAGAA
TGACCTCCGGGGAGGGGGGTTGGTCATCCTCAGTACCGAGGCACGCTTCTTTTTCTTCCTGGGG
GCGTTCGCCAGCTCCGCGGCTGCGGCCGCTGCCGAGGTCGAAGGCCGAGGGCTGGGCGTGCGCG
GCACCAGCGCGTCCTGCGAGCCGTCCTCGTCCTCCTCGGACTCGAGACGGAGGCGGGCCCGCTT
CTTCGGGGGCGCGCGGGGCGGCGGAGGCGGCGGCGGCGACGGAGACGGGGACGAGACATCGTC
CAGGGTGGGTGGACGGCGGGCCGCGCCGCGTCCGCGCTCGGGGGTGGTCTCGCGCTGGTCCTCT
TCCCGACTGGCCATCTCCCACTGCTCCTTCTCCTATAGGCAGAAAGAGATCATGGAGTCTCTCAT
GCGAGTCGAGAAGGAGGAGGACAGCCTAACCGCCCCCTCTGAGCCCTCCACCACCGCCGCCACC
ACCGCCAATGCCGCCGGGACGACGCGCCCACCGAGACCACCGCCAGTACCACCCTCCCCAGCG
ACGCACCCCCGCTCGAGAATGAAGTGCTGATCGAGCAGGACCCGGGTTTTGTGAGCGGAGAGG
AGGATGAGGTGGATGAGAAGGAGAAGGAGGAGGTCGCCGCCTCAGTGCCAAAAGAGGATAAA
AAGCAAGACCAGGACGACGCAGATAAGGATGAGACAGCAGTCGGGCGGGGAACGGAAGCCA
TGATGCTGATGACGGCTACCTAGACGTGGGAGACGACGTGCTGCTTAAGCACCTGCACCGCCAG
TGCGTCATCGTCTGCGACGCGCTGCAGGAGCGCTGCGAAGTGCCCCTGGACGTGGCGGAGGTCA
GCCGCGCCTACGAGCGGCACCTCTTCGCGCCGCACGTGCCCCCCAAGCGCCGGGAGAACGGCAC
CTGCGAGCCCAACCCGCGTCTCAACTTCTACCCGGTCTTCGCGGTACCCGAGGTGCTGGCCACCT
ACCACATCTTTTTCCAAAACTGCAAGATCCCCCTCTCCTGCCGCGCCAACCGCACCCGCGCCGAC
AAAACCCTGACCCTGCGGCAGGGCGCCCACATACCTGATATCGCCTCTCTGGAGGAAGTGCCCA
AGATCTTCGAGGGTCTCGGTCGCGACGAGAAACGGGCGGCGAACGCCTCGGGCAGAACGTCCTGCACT
CCACCCTCAAAGGGGAGGCGCGCCGCGACTACATCCGCGACTGCGCCTACCTCTTCCTCTGCTAC
ACCTGGCAGACGGCCATGGGGGTCTGGCAGCAGTGCCTGGAGGAGCGCAACCTCAAGGAGCTG
GAAAAGCTCCTCAAGCGCACCCTCAGGGACCTCTGGACGGGCTTCAACGAGCGCTCGGTGGCCG
CCGCGCTGGCGGACATCATCTTTCCCGAGCGCCTGCTCAAGCACCTGCAGCAGGGCCTGCCCGA
CTTCACCAGCCAGAGCATGCTGCAGAACTTCAGGACTTTCATCCTGGAGCGCTCGGGCATCCTGC
CGGCCACTTGCTGCGCGCTGCCCAGCGACTTCGTGCCCATCAAGTACAGGGAGTGCCCGCCGCC
GCTCTGGGCCACTGCTACCTCTTCCAGCTGGCCAACTACCTCGCCTACCACTCGGACCTCATGG
AAGACGTGAGCGGCGAGGGCCTGCTCGAGTGCCACTGCCGCTGCAACCTCTGCACGCCCCACCG
CTCTCTAGTCTGCAACCCGCAGCTGCTCAGCGAGAGTCAGATTACGTACCTTCGAGCTGCAGG
GTCCCTCGCCTGACGAGAAGTCCGCGGCTCCAGGGCTGAAACTCACTCCGGGGCGTGTGGACTTC
CGCCTACCTACGCAAATTTGTACCTGAGGACTACCACGCCCACGAGATCAGGTTCTACGAAGAC
CAATCCCGCCCGCCAAGGCGGAGCTCACCGCCTGCGTCATCACCCAGGGGCACATCCTGGGCC
AATTGCAAGCCATCAACAAAGCCCGCCGAGAGTTCTTGCTGAAAAAGGGTCGGGGGGTGTACCT
GGACCCCCAGTCCGGCGAGGAGTCTAAACCCGCTACCCCCGCCGCCGCCCAGCAGCGGGACCTT
GCTTCCCAGGATGGCACCCAGAAAGAAGCAGCAGCCGCCGCCGCCGCAGCCATACATGCTT
CTGGAGGAAGAGGAGGAGGACTGGGACAGTCAGGCAGAGGAGGTTTCGGACGAGGAGCAGGA
GGGAGATGATGGAAGACTGGGAGGAGGACAGCAGCCTAGACGAGGAAGCTTCAGAGGCCGAAG
AGGTGGCAGACGCAACACCATCGCCCTCGGTCGCAGCCCCTCGCCGGGGCCCCTGAAATCCTC
CGAACCCAGCACCAGCGCTATAACCTCCGCTCCTCCGGCGCCGGCGCCACCCGCCCGCAGACCC
AACCGTAGATGGGACACCACAGGAACCGGGGTCGGTAAGTCCAAGTGCCCGCCGCCGCCACCG
```

| DESCRIPTION OF THE SEQUENCES |
|---|
| CAGCAGCAGCAGCAGCAGCGCCAGGGCTACCGCTCGTGGCGCGGGCACAAGAACGCCATAGTC |
| GCCTGCTTGCAAGACTGCGGGGGCAACATCTCTTTCGCCCGCCGCTTCCTGCTATTCCACCACGG |
| GGTCGCCTTTCCCCGCAATGTCCTGCATTACTACCGTCATCTCTACAGCCCCTACTGCAGCGGCG |
| ACCCAGAGGCGGCAGCGGCAGCCACAGCGGCGACCACCACCTAGGAAGATATCCTCCGCGGGC |
| AAGACAGCGGCAGCAGCGGCCAGGAGACCCGCGGCAGCAGCGGCGGGAGCGGTGGGCGCACT |
| GCGCCTCTCGCCCAACGAACCCCTCTCGACCCGGGAGCTCAGACACAGGATCTTCCCCACTTTGT |
| ATGCCATCTTCCAACAGAGCAGAGGCCAGGAGCAGGAGCTGAAAATAAAAAACAGATCTCTGC |
| GCTCCCTCACCCGCAGCTGTCTGTATCACAAAAGCGAAGATCAGCTTCGGCGCACGCTGGAGGA |
| CGCGGAGGCACTCTTCAGCAAATACTGCGCGCTCACTCTTAAAGACTAGCTCCGCGCCCTTCTCG |
| AATTTAGGCGGGAGAAAACTACGTCATCGCCGGCCGCCGCCCAGCCCGCCCAGCCGAGATGAGC |
| AAAGAGATTCCCACGCCATACATGTGGAGCTACCAGCCGCAGATGGGACTCGCGGCGGGAGCG |
| GCCCAGGACTACTCCACCCGCATGAACTACATGAGCGCGGGACCCCACATGATCTCACAGGTCA |
| ACGGGATCCGCGCCCAGCGAAACCAAATACTGCTGGAACAGGCGGCCATCACCGCCACGCCCC |
| GCCATAATCTCAACCCCCGAAATTGGCCCGCCGCCCTCGTGTACCAGGAAACCCCTCCGCCAC |
| CACCGTACTACTTCCGCGTGACGCCCAGGCCGAAGTCCAGATGACTAACTCAGGGGCGCAGCTC |
| GCGGGCGGCTTTCGTCACGGGGCGCGGCCGCTCCGACCAGGTATAAGACACCTGATGATCAGAG |
| GCCGAGGTATCCAGCTCAACGACGAGTCGGTGAGCTCTTCGCTCGGTCTCCGTCCGGACGGAAC |
| TTTCCAGCTCGCCGGATCCGGCCGCTCTTCGTTCACGCCCCGCCAGGCGTACCTGACTCTGCAGA |
| CCTCGTCCTCGGAGCCCCGCTCCGGCGGCATCGGAACCCTCCAGTTCGTGGAGGAGTTCGTGCCC |
| TCGGTCTACTTCAACCCCTTCTCGGGACCTCCCGGACGCTACCCCGACCAGTTCATTCCGAACTT |
| TGACGCGGTGAAGGACTCGGCGGACGGCTACGACTGAATGTCAGGTGTCGAGGCAGAGCAGCT |
| TCGCCTGAGACACCTCGAGCACTGCCGCCGCCACAAGTGCTTCGCCCGCGGTTCTGGTGAGTTCT |
| GCTACTTTCAGCTACCCGAGGAGCATACCGAGGGGCCGGCGCACGGCGTCCGCCTGACCACCCA |
| GGGCGAGGTTACCTGTTCCCTCATCCGGGAGTTTACCCTCCGCTCCCCTGCTAGTGGAGCGGGAGC |
| GGGGTCCCTGTGTCCTAACTATCGCCTGCAACTGCCCTAACCCTGGATTACATCAAGATCTTTGC |
| TGTCATCTCTGTGCTGAGTTTAATAAACGCTGAGATCAGAATCTACTGGGGCTCCTGTCGCCATC |
| CTGTGAACGCCACCGTCTTCACCCACCCCGACCAGGCCCAGGCGAACCTCACCTGCGGTCTGCA |
| TCGGAGGGCCAAGAAGTACCTCACCTGGTACTTCAACGGCACCCCCTTTGTGGTTTACAACAGCT |
| TCGACGGGGACGGAGTCTCCCTGAAAGACCAGCTCTCCGGTCTCAGCTACTCCATCCACAAGAA |
| CACCACCCTCCAACTCTTCCCTCCCTACCTGCCGGGAACCTACGAGTGCGTCACCGGCCGCTGCA |
| CCCACCTCACCCGCCTGATCGTAAACCAGAGCTTTCCGGGAACAGATAACTCCCTCTTCCCCAGA |
| ACAGGAGGTGAGCTCAGGAAACTCCCCGGGGACCAGGGCGGAGCGTACCTTCGACCCTTGTG |
| GGGTTAGGATTTTTTATTACCGGGTTGCTGGCTCTTTTAATCAAAGTTTCCTTGAGATTTGTTCTT |
| TCCTTCTACGTGTATGAACACCTCAACCTCCAATAACTCTACCCTTTCTTCGGAATCAGGTGACTT |
| CTCTGAAATCGGGCTTGGTGTGCTGCTTACTCTGTTGATTTTTTTCCTTATCATACTCAGCCTTCT |
| GTGCCTCAGGCTCGCCGCCTGCTGCGCACACATCTATATCTACTGCTGGTTGCTCAAGTGCAGGG |
| GTCGCCACCCAAGATGAACAGGTACATGGTCCTATCGATCCTAGGCCTGCTGGCCCTGGCGGCC |
| TGCAGCGCCGCCAAAAAAGAGATTACCTTTGAGGAGCCCGCTTGCAATGTAACTTTCAAGCCCG |
| AGGGTGACCAATGCACCACCCTCGTCAAATGCGTTACCAATCATGAGAGGCTGCGCATCGACTA |
| CAAAAACAAAACTGGCCAGTTTGCGGTCTATAGTGTGTTTACGCCCGGAGACCCCTCTAACTACT |
| CTGTCACCGTCTTCCAGGGCGGACAGTCTAAGATATTCAATTACACTTTCCCTTTTTATGAGTTAT |
| GCGATGCGGTCATGTACATGTCAAAACAGTACAACCTGTGGCCTCCCTCTCCCCAGGCGTGTGTG |
| GAAAATACTGGGTCTTACTGCTGTATGGCTTTCGCAATCACTACGCTCGCTCTAATCTGCACGGT |
| GCTATACATAAAATTCAGGCAGAGGCGAATCTTTATCGATGAAAAGAAAATGCCTTGATCGCTA |
| ACACCGGCTTTCTATCTGCAGAATGAATGCAATCACCTCCCTACTAATCACCACCACCCTCCTTG |
| CGATTGCCCATGGGTTGACACGAATCGAAGTGCCAGTGGGGTCCAATGTCACCATGGTGGGCCC |
| CGCCGGCAATTCCACCCTCATGTGGGAAAAATTTGTCCGCAATCAATGGGTTCATTTCTGCTCTA |
| ACCGAATCAGTATCAAGCCCAGAGCCATCTGCGATGGGCAAAATCTAACTCTGATCAATGTGCA |
| AATGATGGATGCTGGGTACTATTACGGGCAGCGGGGAGAAATCATTAATTACTGGCGACCCCAC |
| AAGGACTACATGCTGCATGTAGTCGAGGCACTTCCCACTACCACCCCCACTACCACCTCTCCCAC |
| CACCACCACCACTACTACTACTACTACTACTACTACTACCACTACCGCTGCCCGCCATA |
| CCCGCAAAAGCACCATGATTAGCACAAAGCCCCTCGTGCTCACTCCCACGCCGGCGGGCCCAT |
| CGGTGCGACCTCAGAAACCACCGAGCTTTGCTTCTGCCAATGCACTAACGCCAGCGCTCATGAA |
| CTGTTCGACCTGGAGAATGAGGATGTCCAGCAGAGCTCCGCTTGCCTGACCCAGGAGGCTGTGG |
| AGCCCGTTGCCCTGAAGCAGATCGGTGATTCAATAATTGACTCTTCTTCTTTTGCCACTCCCGAA |
| TACCCTCCCGATTCTACTTTCCACATCACGGGTACCAAAGACCCTAACCTCTCTTTCTACCTGATG |
| CTGCTGCTCTGTATCTCTGTGGTCTCTTCCGCGCTGATGTTACTGGGGATGTTCTGCTGCCTGATC |
| TGCCGCAGAAAGAGAAAAGCTCGCTCTCAGGGCCAACCACTGATGCCCTTCCCCTACCCCCGG |
| ATTTTGCAGATAACAAGATATGAGCTCGCTGCTGACACTAACCGCTTTACTAGCCTGCGCTCTAA |
| CCCTTGTCGCTTGCGACTCGAGATTCCACAATGTCACAGCTGTGGCAGGAGAAAATGTTACTTTC |
| AACTCCACGGCCGATACCCAGTGGTCGTGGAGTGGCTCAGGTAGCTACTTAACTATCTGCAATA |
| GCTCCACTTCCCCCGGCATATCCCCAACCAAGTACCAATGCAATGCCAGCCTGTTCACCCTCATC |
| AACGCTTCCACCCTGGACAATGGACTCTATGTAGGCTATGTACCCTTTGGTGGGCAAGGAAAGA |
| CCCACGCTTACAACCTGGAAGTTCGCCAGCCCAGAACCACTACCCAAGCTTCTCCCACCACCAC |
| CACCACCACCACCATCACCAGCAGCAGCAGCAGCAGCAGCACAGCAGCAGCAGCAGATTATT |
| GACTTTGGTTTTGGCCAGCTCATCTGCCGCTACCCAGGCCATCTACAGCTCTGTGCCCGAAACCA |
| CTCAGATCCACCGCCCAGAAACGACCACCGCCACCACCCTACACACCTCCAGCGATCAGATGCC |
| GACCAACATCACCCCCTTGGCTCTTCAAATGGGACTTACAAGCCCCACTCCAAAACCAGTGGAT |
| GCGGCCGAGGTCTCCGCCCTCGTCAATGACTGGGCGGGCTGGGAATGTGGTGGTTCGCCATAG |
| GCATGATGGCGCTCTGCCTGCTTCTGCTCTGGCTCATCTGCTGCCTCCACCGCAGGCGAGCCAGA |
| CCCCCCATCTATAGACCCATCATTGTCCTGAACCCCGATAATGATGGGATCCATAGATTGGATGG |
| CCTGAAAAACCTACTTTTTTCTTTTACAGTATGATAAATTGAGACATGCCTCGCATTTTCTTGTAC |
| ATGTTCCTTCTCCCACCTTTTCTGGGGTGTTCTACGCTGGCCGCTGTGTCTCACCTGGAGGTAGAC |
| TGCCTCTCACCCTTCACTGTCTACCTGCTTTACGGATTGGTCACCCTCACTCTCATCTGCAGCCTA |
| ATCACAGTAATCATCGCCTTCATCCAGTGCATTGATTACATCTGTGTGCGCCTCGCATACTTCAG |
| ACACCACCCGCAGTACCGAGACAGGAACATTGCCCAACTTCTAAGACTGCTCTAATCATGCATA |
| AGACTGTGATCTGCCTTCTGATCCTCTGCATCCTGCCCACCCTCACCTCCTGCCAGTACACCACA |

DESCRIPTION OF THE SEQUENCES

```
AAATCTCCGCGCAAAAGACATGCCTCCTGCCGCTTCACCCAACTGTGGAATATACCCAAATGCT
ACAACGAAAAGAGCGAGCTCTCCGAAGCTTGGCTGTATGGGGTCATCTGTGTCTTAGTTTTCTGC
AGCACTGTCTTTGCCCTCATAATCTACCCCTACTTTGATTTGGGATGGAACGCGATCGATGCCAT
GAATTACCCCACCTTTCCCGCACCCGAGATAATTCCACTGCGACAAGTTGTACCCGTTGTCGTTA
ATCAACGCCCCCCATCCCCTACGCCCACTGAAATCAGCTACTTTAACCTAACAGGCGGAGATGA
CTGACGCCCTAGATCTAGAAATGGACGGCATCAGTACCGAGCAGCGTCTCCTAGAGAGGCGCAG
GCAGGCGGCTGAGCAAGAGCGCCTCAATCAGGAGCTCCGAGATCTCGTTAACCTGCACCAGTGC
AAAAGAGGCATCTTTTGTCTGGTAAAGCAGGCCAAAGTCACCTACGAGAAGACCGGCAACAGC
CACCGCCTCAGTTACAAATTGCCCACCCAGCGCCAGAAGCTGGTGCTCATGGTGGGTGAGAATC
CCATCACCGTCACCCAGCACTCGGTAGAGACCGAGGGGTGTCTGCACTCCCCCTGTCGGGGTCC
AGAAGACCTCTGCACCCTGGTAAAGACCCTGTGCGGTCTCAGAGATTTAGTCCCCTTTAACTAAT
CAAACACTGGAATCAATAAAAAGAATCACTTACTTAAAATCAGACAGCAGGTCTCTGTCCAGTT
TATTCAGCAGCACCTCCTTCCCCTCCTCCCAACTCTGGTACTCCAAACGCCTTCTGGCGGCAAAC
TTCCTCCACACCCTGAAGGGAATGTCAGATTCTTGCTCCTGTCCCTCCGCACCCACTATCTTCATG
TTGTTGCAGATGAAGCGCACCAAAACGTCTGACGAGAGCTTCAACCCCGTGTACCCCTATGACA
CGGAAAGCGGCCCTCCCTCCGTCCCTTTCCTCACCCCTCCCTTCGTGTCTCCCGATGGATTCCAA
GAAAGTCCCCCCGGGGTCCTGTCTCTGAACCTGGCCGAGCCCCTGGTCACTTCCCACGGCATGCT
CGCCCTGAAAATGGGAAGTGGCCTCTCCCTGGACGACGCTGGCAACCTCACCTCTCAAGATATC
ACCACCGCTAGCCCTCCCCTCAAAAAAACCAAGACCAACCTCAGCCTAGAAACCTCATCCCCCC
TAACTGTGAGCACCTCAGGCGCCCTCACCGTAGCAGCCGCCGCTCCCCTGGCGGTGGCCGGCAC
CTCCCTCACCATGCAATCAGAGGCCCCCCTGACAGTACAGGATGCAAAACTCACCCTGGCCACC
AAAGGCCCCCTGACCGTGTCTGAAGGCAAACTGGCCTTGCAAACATCGGCCCCGCTGACGGCCG
CTGACAGCAGCACCCTCACAGTCAGTGCCACACCACCCCTTAGCACAAGCAATGGCAGCTTGGG
TATTGACATGCAAGCCCCCATTTACACCACCAATGGAAAACTAGGACTTAACTTTGGCGCTCCC
TGCATGTGGTAGACAGCCTAAATGCACTGACTGTAGTTACTGGCCAAGGTCTTACGATAAACGT
AACAGCCCTACAAACTAGAGTCTCAGGTGCCCTCAACTATGACACATCAGGAAACCTAGAATTG
AGAGCTGCAGGGGGTATGCGAGTTGATGCAAATGGTCAACTTATCCTTGATGTAGCTTACCCATT
TGATGCACAAAACAATCTCAGCCTTAGGCTTGGACAGGGACCCCTGTTTGTTAACTCTGCCCACA
ACTTGGATGTTAACTACAACAGAGGCCTCTACCTGTTCACATCTGGAAATACCAAAAAGCTAGA
AGTTAATATCAAAACAGCCAAGGGTCTCATTTATGATGACACTGCTATAGCAATCAATGCGGGT
GATGGGCTACAGTTTGACTCAGGCTCAGATACAAATCCATTAAAAACTAAACTTGGATTAGGAC
TGGATTATGACTCCAGCAGAGCCATAATTGCTAAACTGGGAACTGGCCTAAGCTTTGACAACAC
AGGTGCCATCACAGTAGGCAACAAAAATGATGACAAGCTTACCTTGTGGACCACACCAGACCCA
TCCCCTAACTGTAGAATCTATTCAGAGAAAGATGCTAAATTCACACTTGTTTTGACTAAATGCGG
CAGTCAGGTGTTGGCCAGCGTTTCTGTTTTATCTGTAAAAGGTAGCCTTGCGCCCATCAGTGGCA
CAGTAACTAGTGCTCAGATTGTCCTCAGATTTGATGAAATGGAGTTCTACTAAGCAATTCTTCC
CTTGACCCTCAATACTGGAACTACAGAAAAGGTGACCTTACAGAGGGCACTGCATATACCAACG
CAGTGGGATTTATGCCCAACCTCACAGCATACCCAAAAACACAGAGCCAAACTGCTAAAAGCAA
CATTGTAAGTCAGGTTTACTTGAATGGGGACAAATCCAAACCCATGACCCTCACCATTACCCTCA
ATGGAACTAATGAAACAGGAGATGCCACAGTAAGCACTTACTCCATGTCATTCTTCATGGAACTG
GAATGGAAGTAATTACATTAATGAAACGTTCCAAACCAACTCCTTCACCTTCTCCTACATCGCCC
AAGAATAAAAAGCATGACGCTGTTGATTTGATTCAATGTGTTTCTGTTTTATTTTCAAGCACAAC
AAAATCATTCAAGTCATTCTTCCATCTTAGCTTAATAGACACAGTAGCTTAATAGACCCAGTAGT
GCAAAGCCCCATTCTAGCTTATAACTAGTGGAGAAGTACTCGCCTACATGGGGGTAGAGTCATA
ATCGTGCATCAGGATAGGCGGTGGTGCTGCAGCAGCGCGCGAATAAACTGCTGCCGCCGCCGC
TCCGTCCTGCAGGAATACAACATGGCAGTGGTCTCCTCAGCGATGATTCGCACCGCCCGCAGCA
TAAGGCGCCTTGTCCTCCGGGCACAGCAGCGCACCCTGATCTCACTTAAATCAGCACAGTAACT
GCAGCACAGCACCACAATATTGTTCAAAATCCCACAGTGCAAGGCGCTGTATCCAAAGCTCATG
GCGGGGACCACAGAACCCACGTGGCCATCATACCACAAGCGCAGGTAGATTAAGTGGCGACCC
CTCATAAACACGCTGGACATAAACATTACCTCTTTTGGCATGTTGTAATTCACCACCTCCCGGTA
CCATATAAACCTCTGATTAAACATGGCGCATCCACCACCATCCTAAACCAGCTGGCCAAAACC
TGCCCGCCGGCTATACACTGCAGGGAACCGGGACTGGAACAATGACAGTGGAGAGCCCAGGAC
TCGTAACCATGGATCATCATGCTCGTCATGATATCAATGTTGCACAACACAGGCACACGTGCA
TACACTTCCTCAGGATTACAAGCTCCTCCCGCGTTAGAACCATATCCCAGGGAACAACCCATTCC
TGAATCAGCGTAAATCCCACACTGCAGGGAAGACCTCGCACGTAACTCACGTTGTGCATTGTCA
AAGTGTTACATTCGGGCAGCAGCGGATGATCCTCCAGTATGGTAGCGCGGGTTTCTGTCTCAAA
AGGAGGTAGACGATCCCTACTGTACGGAGTGCGCCGAGACAACCGAGATCGTGTTGGTCGTAGT
GTCATGCCAAATGGAACGCCGGACGTAGTCATATTTCCTGAAGTCTTAGATCTCTCAACGCAGC
ACCAGCACCAACACTTCGCAGTGTAAAAGGCCAAGTGCCGAGAGAGTATATATAGGAATAAAA
AGTGACGTAAACGGGCAAAGTCCAAAAAACGCCCAGAAAAACCGCACGCGAACCTACGCCCCG
AAACGAAAGCCAAAAAACACTAGACACTCCCTTCCGGCGTCAACTTCCGCTTTCCCACGCTACG
TCACTTGCCCCAGTCAAACAAACTACATATCCCGAACTTCCAAGTCGCCACGCCCAAAACACCG
CCTACACCTCCCCGCCCGCCGGCCCGCCCCAAACCGCCTCCCGCCCCGCGCCCCGCCCCGCGC
CGCCCATCTCATTATCATATTGGCTTCAATCAAAATAAGGTATATTATTGATGATGGTTTAAAC
GGATCCAATTCTTGAAGACGAAAGGGCCTCGTGATACGCCTATTTTTATAGGTTAATGTCATGAT
AATAATGGTTTCTTAGACGTCAGGTGGCACTTTTCGGGGAAATGTGCGCGGAACCCCTATTTGTT
TATTTTTCTAAATACATTCAAATATGTATCCGCTCATGAGACAATAACCCTGATAAATGCTTCAA
TAATATTGAAAAAGGAAGAGTATGAGTATTCAACATTTCCGTGTCGCCCTTATTCCCTTTTTTGC
GGCATTTTGCCTTCCTGTTTTTGCTCACCCAGAAACGCTGGTGAAAGTAAAAGATGCTGAAGATC
AGTTGGGTGCACGAGTGGGTTACATCGAACTGGATCTCAACAGCGGTAAGATCCTTGAGAGTTT
TCGCCCCGAAGAACGTTTTCCAATGATGAGCACTTTTAAAGTTCTGCTATGTGGCGCGGTATTAT
CCCGTGTTGACGCCGGGCAAGAGCAACTCGGTCGCCGCATACACTATTCTCAGAATGACTTGGT
TGAGTACTCACCAGTCACAGAAAAGCATCTTACGGATGGCATGACAGTAAGAGAATTATGCAGT
GCTGCCATAACCATGAGTGATAACACTGCGGCCAACTTACTTCTGACAACGATCGGAGGACCGA
AGGAGCTAACCGCTTTTTTGCACAACATGGGGGATCATGTAACTCGCCTTGATCGTTGGGAACC
GGAGCTGAATGAAGCCATACCAAACGACGAGCGTGACACCACGATGCCTGTAGCAATGGCAAC
AACGTTGCGCAAACTATTAACTGGCGAACTACTTACTCTAGCTTCCCGGCAACAATTAATAGACT
```

| DESCRIPTION OF THE SEQUENCES |
|---|
| GGATGGAGGCGGATAAAGTTGCAGGACCACTTCTGCGCTCGGCCCTTCCGGCTGGCTGGTTTATT
GCTGATAAATCTGGAGCCGGTGAGCGTGGGTCTCGCGGTATCATTGCAGCACTGGGGCCAGATG
GTAAGCCCTCCCGTATCGTAGTTATCTACACGACGGGGAGTCAGGCAACTATGGATGAACGAA
TAGACAGATCGCTGAGATAGGTGCCTCACTGATTAAGCATTGGTAACTGTCAGACCAAGTTTAC
TCATATATACTTTAGATTGATTTAAAAGGATCTAGGTGAAGATCCTTTTTGATAATCTCATGACC
AAAATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTACCA
GCGGTGGTTTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAAGAACTCTG
TAGCACCGCCTACATACCTCGCTCTGCTAATCCTGTTACCAGTGGCTGCTGCCAGTGGCGATAAG
TCGTGTCTTACCGGGTTGGACTCAAGACGATAGTTACCGGATAAGGCGCAGCGGTCGGGCTGAA
CGGGGGGTTCGTGCACACAGCCCAGCTTGGAGCGAACGACCTACACCGAACTGAGATACCTACA
GCGTGAGCTATGAGAAAGCGCCACGCTTCCCGAAGGGAGAAAGGCGGACAGGTATCCGGTAAG
CGGCAGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGGGGGC
GGAGCCTATGGAAAAACGCCAGCAACGCGGCCTTTTTACGGTTCCTGGCCTTTTGCTGGCCTTGA
AGCTGTCCCTGATGGTCGTCATCTACCTGCCTGGACAGCATGGCCTGCAACGCGGGCATCCCGAT
GCCGCCGGAAGCGAGAAGAATCATAATGGGGAAGGCCATCCAGCCTCGCGTCGCAGATCCGAA
TTCGTTTAAAC

SEQ ID NO: 8-Polynucleotide sequence encoding ChAd155#1390 backbone construct
CATCATCAATAATATACCTTATTTTGGATTGAAGCCAATATGATAATGAGATGGGCGGCGCGGG
GCGGGGCGCGGGGCGGGAGGCGGGTTTGGGGCGGGCCGGCGGGCGGGGCGGTGTGGCGGAA
GTGGACTTTGTAAGTGTGGCGGATGTGACTTGCTAGTGCCGGGCGCGGTAAAAGTGACGTTTTC
CGTGCGCGACAACGCCCCCGGGAAGTGACATTTTTCCCGCGGTTTTTACCGGATGTTGTAGTGAA
TTTGGGCGTAACCAAGTAAGATTTGGCCATTTTCGCGGGAAAACTGAAACGGGGAAGTGAAATC
TGATTAATTTTGCGTTAGTCATACCGCGTAATATTTGTCTAGGGCCGAGGGACTTTGGCCGATTA
CGTGGAGGACTCGCCCAGGTGTTTTTTGAGGTGAATTTCCGCGTTCCGGGTCAAAGTCTGCGTTT
TATTATTATAGGATATCCCATTGCATACGTTGTATCCATATCATAATATGTACATTTATATTGGCT
CATGTCCAACATTACCGCCATGTTGACATTGATTATTGACTAGTTATTAATAGTAATCAATTACG
GGGTCATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTAACG
CCAATAGGGACTTTCCATTGACGTCAATGGGTGGAGTATTTACGGTAAACTGCCCACTTGGCAGT
ACATCAAGTGTATCATATGCCAAGTACGCCCCCTATTGACGTCAATGACGGTAAATGGCCCGCC
TGGCATTATGCCCAGTACATGACCTTATGGGACTTTCCTACTTGGCAGTACATCTACGTATTAGT
CATCGCTATTACCATGGTGATGCGGTTTTGGCAGTACATCAATGGGCGTGGATAGCGGTTTGACT
CACGGGGATTTCCAAGTCTCCACCCCATTGACGTCAATGGGAGTTTGTTTTGGCACCAAAATCAA
CGGGACTTTCCAAAATGTCGTAACAACTCCGCCCCATTGACGCAAATGGGCGGTAGGCGTGTAC
GGTGGGAGGTCTATATAAGCAGAGCTCTCTCCTATCAGTGATAGAGATCTCCCTATCAGTGATAG
AGATCGTCGACGAGCTCGTTTAGTGAACCGTCAGATCGCCTGGAGACGCCATCCACGCTGTTTTG
ACCTCCATAGAAGACACCGGGACCGATCCAGCCTCCGCGGCCGGGAACGGTGCATTGGAACGC
GGATTCCCCGTGCCAAGAGTGAGATCTTCCGTTTATCTAGGTACCGGGCCCCCCCTCGAGGTCGA
CGGTATCGATAAGCTTCACGCTGCCGCAAGCACTCAGGGCGCAAGGGCTGCTAAAGGAAGCGG
AACACGTAGAAAGCCAGTCCGCAGAAACGGTGCTGACCCCGGATGAATGTCAGCTACTGGGCTA
TCTGGACAAGGGAAAACGCAAGCGCAAAGAGAAAGCAGGTAGCTTGCAGTGGGCTTACATGGC
GATAGCTAGACTGGGCGGTTTTATGGACAGCAAGCGAACCGGAATTGCCAGCTGGGGCGCCCTC
TGGTAAGGTTGGGAAGCCCTGCAAAGTAAACTGGATGGCTTTCTTGCCGCCAAGGATCTGATGG
CGCAGGGGATCAAGATCTAACCAGGAGCTATTTAATGGCAACAGTTAACCAGCTGGTACGCAAA
CCACGTGCTCGCAAAGTTGCGAAAAGCAACGTGCCTGCGCTGGAAGCATGCCCGCAAAAACGTG
GCGTATGTACTCGTGTATATACTACCACTCCTAAAAAACCGAACTCCGCGCTGCGTAAAGTATGC
CGTGTTCGTCTGACTAACGGTTTCGAAGTGACTTCCTACATCGGTGGTGAAGGTCACAACCTGCA
GGAGCACTCCGTGATCCTGATCCGTGGCGGTCGTGTTAAAGACCTCCCGGGTGTTCGTTACCACA
CCGTACGTGGTGCGCTTGACTGCTCCGGCGTTAAAGACCGTAAGCAGGCTCGTTCCAAGTATGG
CGTGAAGCGTCCTAAGGCTTAATGGTAGATCTGATCAAGAGACAGGATGACGGTCGTTTCGCAT
GCTTGAACAAGATGGATTGCACGCAGGTTCTCCGGCCGCTTGGGTGGAGAGGCTATTCGGCTAT
GACTGGGCACAACAGACAATCGGCTGCTCTGATGCCGCCGTGTTCCGGCTGTCAGCGCAGGGGC
GCCCGGTTCTTTTTGTCAAGACCGACCTGTCCGGTGCCCTGAATGAACTGCAGGACGAGGCAGC
GCGGCTATCGTGGCTGGCCACGACGGGCGTTCCTTGCGCAGCTGTGCTCGACGTTGTCACTGAA
GCGGGAAGGGACTGGCTGCTATTGGGCGAAGTGCCGGGGCAGGATCTCCTGTCATCTCACCTTG
CTCCTGCCGAGAAAGTATCCATCATGGCTGATGCAATGCGGCGGCTGCATACGCTTGATCCGGC
TACCTGCCCATTCGACCACCAAGCGAAACATCGCATCGAGCGAGCACGTACTCGGATGGAAGCC
GGTCTTGTCGATCAGGATGATCTGGACGAAGAGCATCAGGGGCTCGCGCCAGCCGAACTGTTCG
CCAGGCTCAAGGCGCGCATGCCCGACGGCGAGGATCTCGTCGTGACCCATGGCGATGCCTGCTT
GCCGAATATCATGGTGGAAAATGGCCGCTTTTCTGGATTCATCGACTGTGGCCGGCTGGGTGTG
GCGGACCGCTATCAGGACATAGCGTTGGCTACCCGTGATATTGCTGAAGAGCTTGGCGGCGAAT
GGGCTGACCGCTTCCTCGTGCTTTACGGTATCGCCGCTCCCGATTCGCAGCGCATCGCCTTCTAT
CGCCTTCTTGACGAGTTCTTCTGAGCGGGACTCTGGGGTTCGAAATGACCGACCAAGCGACGCC
CAACCTGCCATCACGAGATTTCGATTCCACCGCCGCCTTCTATGAAAGGTTGGGCTTCGGAATCG
TTTTCCGGGACGCCGGCTGGATGATCCTCCAGCGCGGGGATCTCATGCTGGAGTTCTTCGCCCAC
CCCGGGCTCGATCCCCTCGGGGGAATCAGAATTCAGTCGACAGCGGCCGCGATCTGCTGTGCC
TTCTAGTTGCCAGCCATCTGTTGTTTGCCCCTCCCCCGTGCCTTCCTTGACCCTGGAAGGTGCCAC
TCCCACTGTCCTTTCCTAATAAAATGAGGAAATTGCATCGCATTGTCTGAGTAGGTGTCATTCTA
TTCTGGGGGGTGGGGTGGGCAGGACAGCAAGGGGGAGGATTGGGAAGACAATAGCAGGCATG
CTGGGGATGCGGTGGGCTCTATGGCCGATCAGCGATCGCTGAGGTGGGTGAGTGGGCGTGGCCT
GGGGTGGTCATGAAAATATATAAGTTGGGGGTCTTAGGGTCTCTTTATTTGTGTTGCAGAGACCG
CCGGAGCCATGAGCGGGAGCAGCAGCAGCAGCAGTAGCAGCAGCGCCTTGGATGGCAGCATCG
TGAGCCCTTATTTGACGACGCGGATGCCCCACTGGGCCGGGGTGCGTCAGAATGTGATGGGCTC |

| DESCRIPTION OF THE SEQUENCES |
|---|
| CAGCATCGACGGCCGACCCGTCCTGCCCGCAAATTCCGCCACGCTGACCTATGCGACCGTCGCG |
| GGGACGCCGTTGGACGCCACCGCCGCCGCCGCCGCCACCGCAGCCGCCTCGGCCGTGCGCAGCC |
| TGGCCACGGACTTTGCATTCCTGGGACCACTGGCGACAGGGGCTACTTCTCGGGCCGCTGCTGCC |
| GCCGTTCGCGATGACAAGCTGACCGCCCTGCTGGCGCAGTTGGATGCGCTTACTCGGGAACTGG |
| GTGACCTTTCTCAGCAGGTCATGGCCCTGCGCCAGCAGGTCTCCTCCCTGCAAGCTGGCGGGAAT |
| GCTTCTCCCACAAATGCCGTTTAAGATAAATAAAACCAGACTCTGTTTGGATTAAAGAAAAGTA |
| GCAAGTGCATTGCTCTCTTTATTTCATAATTTTCCGCGCGCGATAGGCCCTAGACCAGCGTTCTC |
| GGTCGTTGAGGGTGCGGTGTATCTTCTCCAGGACGTGGTAGAGGTGGCTCTGGACGTTGAGATA |
| CATGGGCATGAGCCCGTCCCGGGGGTGGAGGTAGCACCACTGCAGAGCTTCATGCTCCGGGGTG |
| GTGTTGTAGATGATCCAGTCGTAGCAGGAGCGCTGGGCATGGTGCCTAAAAATGTCCTTCAGCA |
| GCAGGCCGATGGCCAGGGGGAGGCCCTTGGTGTAAGTGTTTACAAAACGGTTAAGTTGGGAAG |
| GGTGCATTCGGGGAGAGATGATGTGCATCTTGGACTGTATTTTTAGATTGGCGATGTTTCCGCCC |
| AGATCCCTTCTGGGATTCATGTTGTGCAGGACCACCAGTACAGTGTATCCGGTGCACTTGGGGA |
| ATTTGTCATGCAGCTTAGAGGGAAAAGCGTGGAAGAACTTGGAGACGCCTTTGTGGCCTCCCAG |
| ATTTTCCATGCATTCGTCCATGATGATGGCAATGGGCCCGCGGGAGGCAGCTTGGGCAAAGATA |
| TTTCTGGGGTCGCTGACGTCGTAGTTGTGTTCCAGGGTGAGGTCGTCATAGGCCATTTTTACAAA |
| GCGCGGGCGGAGGGTGCCCGACTGGGGGATGATGGTCCCCTCTGGCCCTGGGGCGTAGTTGCCC |
| TCGCAGATCTGCATTTCCCAGGCCTTAATCTCGGAGGGGGGAATCATATCCACCTGCGGGGCGA |
| TGAAGAAAACGGTTTCCGGAGCCGGGGAGATTAACTGGGATGAGAGCAGGTTTCTAAGCAGCT |
| GTGATTTTCCACAACCGGTGGGCCCATAAATAACACCTATAACCGGTTGCAGCTGGTAGTTTAG |
| AGAGCTGCAGCTGCCGTCGTCCCGGAGGAGGGGGGCCACCTCGTTGAGCATGTCCCTGACGCGC |
| ATGTTCTCCCCGACCAGATCCGCCAGAAGGCGCTCGCCGCCCAGGGACAGCAGCTCTTGCAAGG |
| AAGCAAAGTTTTTCAGCGGCTTGAGGCCGTCCGCCGTGGGCATGTTTTTCAGGGTCTGGCTCAGC |
| AGCTCCAGGCGGTCCCAGAGCTCGGTGACGTGCTCTACGGCATCTCTATCCAGCATATCTCCTCG |
| TTTCGCGGGTTGGGGCGACTTTCGCTGTAGGGCACCAAGCGGTGGTCGTCCAGCGGGGCCAGAG |
| TCATGTCCTTCCATGGGCGCAGGGTCCTCGTCAGGGTGGTCTGGGTCACGGTGAAGGGGTGCGC |
| TCCGGGCTGAGCGCTTGCCAAGGTGCGCTTGAGGCTGGTTCTGCTGGTGCTGAAGCGCTGCCGG |
| TCTTCGCCCTGCGCGTCGGCCAGGTAGCATTTGACCATGGTGTCATAGTCCAGCCCCTCCGCGGC |
| GTGTCCCTTGGCGCGCAGCTTGCCCTTGGAGGTGGCGCCGCACGAGGGGCAGAGCAGGCTCTTG |
| AGCGCGTAGAGCTTGGGGGCGAGGAAGACCGATTCGGGGGAGTAGGCGTCCGCGCCGCAGACC |
| CCGCACACGGTCTCGCACTCCACCAGCCAGGTGAGCTCGGGGCGCGCCGGGTCAAAAACCAGGT |
| TTCCCCCATGCTTTTTGATGCGTTTCTTACCTCGGGTCTCCATGAGGTGGTGTCCCCGCTCGGTGA |
| CGAAGAGGCTGTCCGTGTCTCCGTAGACCGACTTGAGGGGTCTTTTCTCCAGGGGGGTCCCTCGG |
| TCTTCCTCGTAGAGGAACTCGGACCACTCTGAGACGAAGGCCCGCGTCCAGGCCAGGACGAAGG |
| AGGCTATGTGGGAGGGGTAGCGGTCGTTGTCCACTAGGGGGTCCACCTTCTCCAAGGTGTGAAG |
| ACACATGTCGCCTTCCTCGGCGTCCAGGAAGGTGATTGGCTTGTAGGTGTAGGCCACGTGACCG |
| GGGGTTCCTGACGGGGGGGTATAAAAGGGGGTGGGGCGCGCTCGTCGTCACTCTCTTCCGCAT |
| CGCTGTCTGCGAGGGCCAGCTGCTGGGGTGAGTATTCCCTCTCGAAGGCGGGCATGACCTCCGC |
| GCTGAGGTTGTCAGTTTCCAAAAACGAGGAGGATTTGATGTTCACCTGTCCCGAGGTGATACCTT |
| TGAGGGTACCCGCGTCCATCTGGTCAGAAAACACGATCTTTTTATTGTCCAGCTTGGTGGCGAAC |
| GACCCGTAGAGGGCGTTGGAGAGCAGCTTGGCGATGGAGCGCAGGGTCGAGGGTCTCGCGGATGATGTCATA |
| CGGCGCGCTCCTTGGCCGCGATGTTGAGCTGCACGTACTCGCGCGCGACGCAGCGCCACTCGGG |
| GAAGACGGTGGTGCGCTCGTCGGGCACCAGGCGCACGCGCCAGCCGCGGTTGTGCAGGGTGAC |
| CAGGTCCACGCTGGTGGCGACCTCGCCGCGCAGGCGCTCGTTGGTCCAGCAGAGACGGCCGCCC |
| TTGCGCGAGCAGAAGGGGGCAGGGGGTCGAGCTGGGTCTCGTCCGGGGGTCCGCGTCCACG |
| GTGAAAACCCCGGGGCGCAGGCGCGCGTCGAAGTAGTCTATCTTGCAACCTTGCATGTCCAGCG |
| CCTGCTGCCAGTCGCGGGCGGCGAGCGCGCGCTCGTAGGGGTTGAGCGGCGGGCCCCAGGGCAT |
| GGGGTGGGTGAGTGCGGAGGCGTACATGCCGCAGATGTCATAGACGTAGAGGGGCTCCCGCAG |
| GACCCCGATGTAGGTGGGGTAGCAGCGGCCGCCGCGGATGCTGGCGCGCACGTAGTCATACAGC |
| TCGTGCGAGGGGGCGAGGAGGTCGGGGCCCAGGTTGGTGCGGGCGGGGCGCTCCGCGCGGAAG |
| ACGATCTGCCTGAAGATGGCATGCGAGTTGGAAGAGATGGTGGGGCGCTGGAAGACGTTGAAG |
| CTGGCGTCCTGCAGGCCGACGGCGTCGCGCACGAAGGAGGCGTAGGAGTCGCGCAGCTTGTGTA |
| CCAGCTCGGCGGTGACCTGCACGTCGAGCGCGCAGTAGTCGATGGGTCTCGCGGATGATGTCATA |
| TTTAGCCTGCCCCTTCTTTTTCCACAGCTCGCGGTTGAGGACAAACTCTTCGCGGTCTTTCCAGTA |
| CTCTTGGATCGGGAAACCGTCCGGTTCCGAACGGTAAGAGCCTAGCATGTAGAACTGGTTGACG |
| GCCTGGTAGGCGCAGCAGCCCTTCTCCACGGGGAGGGCGTAGGCCTGCGCGGCCTTGCGGAGCG |
| AGGTGTGGGTCAGGGCGAAGGTGTCCCTGACCATGACTTTGAGGTACTGGTGCTTGAAGTCGGA |
| GTCGTCGCAGCCGCCCCGCTCCCAGAGCGAGAAGTCGGTGCGCTTCTTGGAGCGGGGGTTGGGC |
| AGAGCGAAGGTGACATCGTTGAAGAGGATTTTGCCCGCGCGGGGCATGAAGTTGCGGGTGATGC |
| GGAAGGGCCCCGGCACTTCAGAGCGGTTGTTGATGACCTGGGCGGCGAGCACGATCTCGTCGAA |
| GCCGTTGATGTTGTGGCCCACGATGTAGAGTTCCAGGAAGCGGGGCCGGCCCTTTACGGTGGGC |
| AGCTTCTTTAGCTCTTCGTAGGTGAGCTCCTCGGGCGAGGCGAGGCCGTGCTCGGCCAGGGCCC |
| AGTCCGCGAGGTGCGGGTTGTCTCTGAGGAAGGACTTCCAGAGGTCGCGGGCCAGGAGGGTCTG |
| CAGGCGGTCTCTGAAGGTCCTGAACTGGCGGCCCACGGCCATTTTTTCGGGGGTGATGCAGTAG |
| AAGGTGAGGGGGTCTTGCTGCCAGCGGTCCCAGTCGAGCTGCAGGGCGAGGTCGCGCGCGGCG |
| GTGACCAGGCGCTCGTCGCCCCGAATTTCATGACCAGCATGAAGGGCACGAGCTGCTTTCCGA |
| AGGCCCCCATCCAAGTGTAGGTCTCTACATCGTAGGTGACAAAGAGGCGCTCCGTGCGAGGATG |
| CGAGCCGATCGGGAAGAACTGGATCTCCCGCCACCAGTTGGAGGAGTGGCTGTTGATGTGGTGG |
| AAGTAGAAGTCCCGTCGCCGGGCCGAACACTCGTGCTGGCTTTTGTAAAAGCGAGCGCAGTACT |
| GGCAGCGCTGCACGGGCTGTACCTCATGCACGAGATGCACCTTTCGCCCGCGCACGAGGAAGCC |
| GAGGGGAAATCTGAGCCCCCCGCCTGGCTCGCGGCATGGCTGGTTCTCTTCTACTTTGGATGCGT |
| GTCCGTCTCCGTCTGGCTCCTCGAGGGGTGTTACGGTGGAGCGGACCACCACCGCCGCGCGACC |
| GCAGGTCCAGATATCGGCGCGCGGCGGTCGGAGTTTGATGACGACATCGCGCAGCTGGGAGCTG |
| TCCATGGTCTGGAGCTCCCGCGGCGGCGGCAGGTCAGCCGGGAGTTCTTGCAGGTTCACCTCGC |
| AGAGTCGGGCCAGGGCGCGGGCAGGTCTAGGTGGTACCTGATCTCTAGGGGCGTGTTGGTGGC |
| GGCGTCGATGGCTTGCAGGAGCCCGCAGCCCCGGGGGCGACGACGGTGCCCCGCGGGTGGT |
| GGTGGTGGTGGCGGTGCAGCTCAGAAGCGGTGCCGCGGGCGGGCCCCCGGAGGTAGGGGGGC |

| DESCRIPTION OF THE SEQUENCES |
|---|
| TCCGGTCCCGCGGGCAGGGGCGGCAGCGGCACGTCGGCGTGGAGCGCGGGCAGGAGTTGGTGC |
| TGTGCCCGGAGGTTGCTGGCGAAGGCGACGACGCGGCGGTTGATCTCCTGGATCTGGCGCCTCT |
| GCGTGAAGACGACGGGCCCGGTGAGCTTGAACCTGAAAGAGAGTTCGACAGAATCAATCTCGG |
| TGTCATTGACCGCGGCCTGGCGCAGGATCTCCTGCACGTCTCCCGAGTTGTCTTGGTAGGCGATC |
| TCGGCCATGAACTGCTCGATCTCTTCCTCCTGGAGGTCTCCGCGTCCGGCGCGTTCCACGGTGGC |
| CGCCAGGTCGTTGGAGATGCGCCCCATGAGCTGCGAGAAGGCGTTGAGTCCGCCCTCGTTCCAG |
| ACTCGGCTGTAGACCACGCCCCCCTGGTCATCGCGGGCGCGCATGACCACCTGCGCGAGGTTGA |
| GCTCCACGTGCCGCGCGAAGACGGCGTAGTTGCGCAGACGCTGGAAGAGGTAGTTGAGGGTGG |
| TGGCGGTGTGCTCGGCCACGAAGAAGTTCATGACCCAGCGGCGCAACGTGGATTCGTTGATGTC |
| CCCCAAGGCCTCCAGCCGTTCCATGGCCTCGTAGAAGTCCACGGCGAAGTTGAAAAACTGGGAG |
| TTGCGCGCCGACACGGTCAACTCCTCCTCCAGAAGACGGATGAGCTCGGCGACGGTGTCGCGCA |
| CCTCGCGCTCGAAGGCTATGGGGATCTCTTCCTCCGCTAGCATCACCACCTCCTCCTCTTCCTCCT |
| CTTCTGGCACTTCCATGATGGCTTCCTCCTCTTCGGGGGGTGGCGGCGGCGGCGGTGGGGGAGG |
| GGGCGCTCTGCGCCGGCGGCGGCGCACCGGGAGGCGGTCCACGAAGCGCGCGATCATCTCCCCG |
| CGGCGGCGGCGCATGGTCTCGGTGACGGCGCGGCCGTTCTCCCGGGGGCGCAGTTGGAAGACGC |
| CGCCGGACATCTGGTGCTGGGGCGGGTGGCCGTGAGGCAGCGAGACGGCGCTGACGATGCATCT |
| CAACAATTGCTGCGTAGGTACGCCGCCGAGGGACCTGAGGGAGTCCATATCCACCGGATCCGAA |
| AACCTTTCGAGGAAGGCGTCTAACCAGTCGCAGTCGCAAGGTAGGCTGAGCACCGTGGCGGGCG |
| GCGGGGGTGGGGGAGTGTCTGGCGGAGGTGCTGCTGATGATGTAATTGAAGTAGGCGGACTT |
| GACACGGCGGATGGTCGACAGGAGCACCATGTCCTTGGGTCCGGCCTGCTGGATGCGGAGGCGG |
| TCGGCTATGCCCCAGGCTTCGTTCTGGCATCGGCGCAGGTCCTTGTAGTAGTCTTGCATGAGCCT |
| TTCCACCGGCACCTCTTCTCCTTCCTCTTCTGCTTCTTCCATGTCTGCTTCGGCCCTGGGGCGGCG |
| CCGCGCCCCCTGCCCCCATGCGCGTGACCCCGAACCCCCTGAGCGGTTGGAGCAGGGCCAGG |
| TCGGCGACGACGCGCTCGGCCAGGATGGCCTGCTGCACCTGCGTGAGGGTGGTTTGGAAGTCAT |
| CCAAGTCCACGAAGCGGTGGTAGGCGCCCGTGTTGATGGTGTAGGTGCAGTTGGCCATGACGGA |
| CCAGTTGACGGTCTGGTGGCCGGTTGCGACATCTCGGTGTACCTGAGTCGCGAGTAGGCGCGG |
| GAGTCGAAGACGTAGTCGTTGCAAGTCCGCACCAGGTACTGGTAGCCCACCAGGAAGTGCGGCG |
| GCGGCTGGCGGTAGAGGGGCCAGCGCAGGGTGGCGGGGGCTCCGGGGGCCAGGTCTTCCAGCA |
| TGAGGCGGTGGTAGGCGTAGATGTACCTGGACATCCAGGTGATACCCGCGGCGGTGGTGGAGGC |
| GCGCGGGAAGTCGCGCACCCGGTTCCAGATGTTGCGCAGGGGCAGAAAGTGCTCCATGGTAGGC |
| GTGCTCTGTCCAGTCAGACGCGCGCAGTCGTTGATACTCTAGACCAGGGAAAACGAAAGCCGGT |
| CAGCGGGCACTCTTCCGTGGTCTGGTGAATAGATCGCAAGGGTATCATGGCGGAGGGCCTCGGT |
| TCGAGCCCCGGGTCCGGGCCGGACGGTCCGCCATGATCCACGCGGTTACCGCCCGCGTGTCGAA |
| CCCAGGTGTGCGACGTCAGACAACGGTGGAGTGTTCCTTTTGGCGTTTTTCTGGCCGGGCGCCGG |
| CGCCGCGTAAGAGACTAAGCCGCGAAAGCGAAAGCAGTAAGTGGCTCGCTCCCGTAGCCGGA |
| GGGATCTTGCTAAGGGTTGCGTTGCGGCGAACCCCGGTTCGAATCCCGTACTCGGGCCGGCCG |
| GACCCGCGGCTAAGGTGTTGGATTGGCCTCCCCCTCGTATAAAGACCCCGCTTGCGGATTGACTC |
| CGGACACGGGACGAGCCCCTTTTATTTTTGCTTTCCCCAGATGCATCCGGTGCTGCGGCAGATG |
| CGCCCCCCGCCCCAGCAGCAGCAACAACACCAGCAAGAGCGGCAGCAACAGCAGCGGGAGTCA |
| TGCAGGGCCCCCTCACCCACCCTCGGCGGGCGGCCACCTCGGCGTCGCGCGCCGTGTCTGGCG |
| CCTGCGGCGGCGGCGGGGGCCGGCTGACGACCCCGAGGAGCCCCCGCGGCGCAGGGCCAGAC |
| ACTACCTGGACCTGGAGGAGGGCGAGGGCCTGGCGCGGCTGGGGGCGCCGTCTCCCGAGCGCC |
| ACCCGCGGGTGCAGCTGAAGCGCGACTCGCGCGAGGCGTACGTGCCTCGGCAGAACCTGTTCAG |
| GGACCGCGCGGGCGAGGAGCCCGAGGAGATGCGGGACAGGAGGTTCAGCGCAGGGCGGGAGC |
| TGCGGCAGGGGCTGAACGCGAGCGGCTGCTGCGCGAGGAGGACTTTGAGCCCGACGCGCGGA |
| CGGGGATCAGCCCCGCGCGCGCACGTGGCGGCCGCCGACCTGGTGACGGCGTACGAGCAGA |
| CGGTGAACCAGGAGATCAACTTCCAAAAGAGTTTCAACAACCACGTGCGCACGCTGGTGGCGCG |
| CGAGGAGGTGACCATCGGGCTGATGCACCTGTGGGACTTTGTAAGCGCGCTGGTGCAGAACCCC |
| AACAGCAAGCCTCTGACGGCGCAGCTGTTCCTGATAGTGCAGCACAGCAGGGACAACGAGGCG |
| TTTAGGGACGCGCTGCTGAACATCACCGAGCCCGAGGGTCGGTGGCTGCTGGACCTGATTAACA |
| TCCTGCAGAGCATAGTGGTGCAGGAGCGCAGCCTGAGCCTGGCCGACAAGGTGGCGGCCATCA |
| ACTACTCGATGCTGAGCCTGGGCAAGTTTTACGCGCGCAAGATCTACCAGACGCCGTACGTGCC |
| CATAGACAAGGAGGTGAAGATCGACGGTTTTTACATGCGCATGGCGCTGAAGGTGCTCACCCTG |
| AGCGACGACCTGGGCGTGTACCGCAACGAGCGCATCCACAAGGCCGTGAGCGTGAGCCGGCGG |
| CGCGAGCTGAGCGACCGCGAGCTGATGCACAGCCTGCAGCGGGCGCTGGCGGGCGCCGGCAGC |
| GGCGACAGGGAGGCGGAGTCCTACTTCGATGCGGGGCGGACCTGCGCTGGGCGCCCAGCCGG |
| CGGGCCCTGGAGGCGCGGGGGTCCGCGAGGACTATGACGAGGACGGCGAGGAGGATGAGGAG |
| TACGAGCTAGAGGAGGCGGAGTACCTGGACTAAACCGCGGGTGGTGTTTCCGGTAGATGCAAG |
| ACCCGAACGTGGTGGACCCGGCGCTGCGGGCGGCTCTGCAGAGCCAGCCGTCCGGCCTTAACTC |
| CTCAGACGACTGGCGACAGGTCATGGACCGCATCATGTCGCTGACGGCGCGTAACCCGGACGCG |
| TTCCGGCAGCAGCCGCAGGCCAACAGGCTCTCCGCCATCCTGGAGGCGGTGGTGCCTGCGCGCT |
| CGAACCCCACGCACGAGAAGGTGCTGGCCATAGTGAACGCGCTGGCCGAGAACAGGGCCATCC |
| GCCCGGACGAGGCCGGGCTGGTGTACGACGCGCTGCTGCAGCGCGTGGCCCGCTACAACAGCG |
| GCAACGTGCAGACCAACCTGGACCGGCTGGTGGGGGACGTGCGCGAGGCGGTGGCGCAGCGCG |
| AGCGCGCGGATCGGCAGGGCAACCTGGGCTCCATGGTGGCGCTGAATGCCTTCCTGAGCACGCA |
| GCCGGCCAACGTGCCGCGGGGGCAGGAAGACTACACCAACTTTGTGAGCGCTGCGGCGCTGATG |
| GTGACCGAGACCCCCCAGAGCGAGGTGTACCAGTCGGGCCCGGACTACTTCTTCCAGACCAGCA |
| GACAGGGCCTGCAGACGGTGAACCTGAGCCAGGCTTTCAAGAACCTGCGGGGCTGTGGGCG |
| TGAAGGCGCCCACCGGCGACCGGGCGACGGTGTCCAGCCTGCTGACGCCCAACTCGCGCCTGCT |
| GCTGCTGCTGATCGCGCCGTTCACGGACAGCGGCAGCGTGTCCCGGGACACCTACCTGGGGCAC |
| CTGCTGACCCTGTACCGCGAGGCCATCGGGCAGGCGCAGGTGGACGAGCACACCTTCCAGGAGA |
| TCACCAGCGTGAGCCGCGCGCTGGGGCAGGAGGACACGAGCAGCCTGGAGGCGACTCTGAACT |
| ACCTGCTGACCAACCGGCGGCAGAAGATTCCCTCGCTGCACAGCCTGACCTCCGAGGAGGAGCG |
| CATCTTGCGCTACGTGCAGCAGAGCGTGAGCCTGAACCTGATGCGCGACGGGGTGACGCCCAGC |
| GTGGCGCTGGACATGACCGCGCGCAACATGGAACCGGGCATGTACGCCGCGCACCGGCCTTACA |
| TCAACCGCCTGATGGACTACCTGCATCGCGCGGCGGCCGTGAACCCCGAGTACTTTACCAACGC |
| CATCCTGAACCCGCACTGGCTCCCGCCGCCCGGGTTCTACAGCGGGGGCTTCGAGGTCCCGGAG |

| DESCRIPTION OF THE SEQUENCES |
|---|
| ACCAACGATGGCTTCCTGTGGGACGACATGGACGACAGCGTGTTCTCCCCGCGGCCGCAGGCGC |
| TGGCGGAAGCGTCCCTGCTGCGTCCCAAGAAGGAGGAGGAGGAGGAGGCGAGTCGCCGCCGCG |
| GCAGCAGCGGCGTGGCTTCTCTGTCCGAGCTGGGGGCGGCAGCCGCCGCGCGCCCCGGGTCCCT |
| GGGCGGCAGCCCCTTTCCGAGCCTGGTGGGGTCTCTGCACAGCGAGCGCACCACCCGCCCTCGG |
| CTGCTGGGCGAGGACGAGTACCTGAATAACTCCCTGCTGCAGCCGGTGCGGGAGAAAAACCTGC |
| CTCCCGCCTTCCCCAACAACGGGATAGAGAGCCTGGTGGACAAGATGAGCAGATGGAAGACCT |
| ATGCGCAGGAGCACAGGGACGCGCCTGCGCTCCGGCCGCCCACGCGGCGCCAGCGCCACGACC |
| GGCAGCGGGGGCTGGTGTGGGATGACGAGGACTCCGCGGACGATAGCAGCGTGCTGGACCTGG |
| GAGGGAGCGGCAACCCGTTCGCGCACCTGCGCCCCCGCCTGGGGAGGATGTTTTAAAAAAAAA |
| AAAAAAAAGCAAGAAGCATGATGCAAAAATTAAATAAAACTCACCAAGGCCATGGCGACCGAG |
| CGTTGGTTTCTTGTGTTCCCTTCAGTATGCGGCGCGCGGCGATGTACCAGGAGGGACCTCCTCCC |
| TCTTACGAGAGCGTGGTGGGCGCGGCGGCGGCGGCGCCCTCTTCTCCCTTTGCGTCGCAGCTGCT |
| GGAGCCGCCGTACGTGCCTCCGCGCTACCTGCGGCCTACGGGGGGGAGAAACAGCATCCGTTAC |
| TCGGAGCTGGCGCCCCTGTTCGACACCACCCGGGTGTACCTGGTGGACAACAAGTCGGCGGACG |
| TGGCCTCCCTGAACTACCAGAACGACCACAGCAATTTTTTGACCACGGTCATCCAGAACAATGA |
| CTACAGCCCGAGCGAGGCCAGCACCCAGACCATCAATCTGGATGACCGGTCGCACTGGGGCGGC |
| GACCTGAAAACCATCCTGCACACCAACATGCCCAACGTGAACGAGTTCATGTTCACCAATAAGT |
| TCAAGGCGCGGGTGATGGTGTCGCGCTCGCACACCAAGGAAGACCGGGTGGAGCTGAAGTACG |
| AGTGGGTGGAGTTCGAGCTGCCAGAGGGCAACTACTCCGAGACCATGACCATTGACCTGATGAA |
| CAACGCGATCGTGGAGCACTATCTGAAAGTGGGCAGGCAGAACGGGGTCCTGGAGAGCGACAT |
| CGGGGTCAAGTTCGACACCAGGAACTTCCGCCTGGGGCTGGACCCCGTGACCGGGCTGGTTATG |
| CCCGGGGTGTACACCAACGAGGCCTTCCATCCCGACATCATCCTGCTGCCCGGCTGCGGGGTGG |
| ACTTCACTTACAGCCGCCTGAGCAACCTCCTGGGCATCCGCAAGCGGCAGCCCTTCCAGGAGGG |
| CTTCAGGATCACCTACGAGGACCTGGAGGGGGGCAACATCCCCGCGCTCCTCGATGTGGAGGCC |
| TACCAGGATAGCTTGAAGGAAAATGAGGCGGGACAGGAGGATACCGCCCCCGCCGCCTCCGCC |
| GCCGCCGAGCAGGGCGAGGATGCTGCTGACACCGCGGCCGCGGACGGGGCAGAGGCCGACCCC |
| GCTATGGTGGTGGAGGCTCCCGAGCAGGAGGAGGACATGAATGACAGTCGGTGCGCGGAGAC |
| ACCTTCGTCACCCGGGGGGAGGAAAAGCAAGCGGAGGCCGAGGCCGCGGCCGAGGAAAAGCA |
| ACTGGCGGCAGCAGCGGCGGCGGCGGCGTTGGCCGCGGCGGAGGCTGAGTCTGAGGGGACCAA |
| GCCCGCCAAGGAGCCCGTGATTAAGCCCCTGACCGAAGATAGCAAGAAGCGCAGTTACAACCT |
| GCTCAAGGACAGCACCAACACCGCGTACCGCAGCTGGTACCTGGCCTACAACTACGGCGACCCG |
| TCGACGGGGGTGCGCTCCTGGACCCTGCTGTGCACGCCGGACGTGACCTGCGGCTCGGAGCAGG |
| TGTACTGGTCGCTGCCCGACATGATGCAAGACCCCGTGACCTTCCGCTCCACGCGGCAGGTCAG |
| CAACTTCCCGGTGGTGGGCGCCGAGCTGCTGCCCGTGCACTCCAAGAGCTTCTACAACGACCAG |
| GCCGTCTACTCCCAGCTCATCCGCCAGTTCACCTCTCTGACCCACGTGTTCAATCGCTTTCCTGAG |
| AACCAGATTCTGGCGCGCCCGCCCGCCCCCACCATCACCACCGTCAGTGAAAACGTTCCTGCTCT |
| CACAGATCACGGGACGCTACCGCTGCGCAACAGCATCGGAGGAGTCCAGCGAGTGACCGTTACT |
| GACGCCAGACGCCGCACCTGCCCCTACGTTTACAAGGCCTTGGGCATAGTCTCGCCGCGCGTCCT |
| TTCCAGCCGCACTTTTTGAGCAACACCACCATCATGTCCATCCTGATCTCACCCAGCAATAACTC |
| CGGCTGGGACTGCTGCGCGCGCCCAGCAAGATGTTCGGAGGGGCGAGGAAGCGTTCCGAGCA |
| GCACCCCGTGCGCGTGCGCGGGCACTTCCGCGCCCCTGGGGAGCGCACAAACGCGGCCGCGCG |
| GGGCGCACCACCGTGGACGACGCCATCGACTCGGTGGTGGAGCAGGCGCGCAACTACAGGCCC |
| GCGGTCTCTACCGTGGACGCGGCCATCCAGACCGTGGTGCGGGGCGCGCGGCGGTACGCCAAGC |
| TGAAGAGCCGCCGGAAGCGCGTGGCCCGCCGCCACCGCCGCCGACCCGGGGCCGCCGCCAAAC |
| GCGCCGCCGCGCCCTGCTTCGCCGGGCCAAGCGCACGGGCCGCCGCGCGCCGCCGCCATGAGGGCCGC |
| GCGCCGCTTGGCCGCCGGCATCACCGCCGCCACCATGGCCCCCCGTACCCGAAGACGCGCGGCC |
| GCCGCCGCCGCCGCCGCCATCAGTGACATGGCCAGCAGGCGCCGGGGCAACGTGTACTGGGTGC |
| GCGACTCGGTGACCGGCACGCGCGTGCCCGTGCGCTTCCGCCCCCCGCGGACTTGAGATGATGT |
| GAAAAAACAACACTGAGTCTCCTGCTGTTGTGTATCCCAGCGGCGGCGGCGCGCAGCGTC |
| ATGTCCAAGCGCAAAATCAAAGAAGAGATGCTCCAGGTCGTCGCGCCGGAGATCTATGGGCCCC |
| CGAAGAAGGAAGAGCAGGATTCGAAGCCCGCAAGATAAAGCGGGTCAAAAAGAAAAAGAAA |
| GATGATGACGATGCCGATGGGGAGGTGGAGTTCCTGCGCGCCACGGCGCCCAGGCGCCCGGTGC |
| AGTGGAAGGGCCGGCGCGTAAAGCGCGTCCTGCGCCCCGGCACCGCGGTGGTCTTCACGCCCGG |
| CGAGCGCTCCACCCGGACTTTCAAGCGCGTCTATGACGAGGTGTACGGCGACGAAGACCTGCTG |
| GAGCAGGCCAACGAGCGCTTCGGAGAGTTTGCTTACGGGAAGCGTCAGCGGGCGCTGGGGAAG |
| GAGGACCTGCTGGCGCTGCCGCTGGACCAGGGCAACCCCACCCCCAGTCTGAAGCCCGTGACCC |
| TGCAGCAGGTGCTGCCGAGCAGCGCACCCTCCGAGGCGAAGCGGGGTCTGAAGCGCGAGGGCG |
| GCGACCTGGCGCCCACCGTGCAGCTCATGGTGCCCAAGCGGCAGAGGCTGGAGGATGTGCTGGA |
| GAAAATGAAAGTAGACCCCGGTCTGCAGCCGGACATCAGGGTCCGCCCCATCAAGCAGGTGGC |
| GCCGGGCCTCGGCGTGCAGACCGTGGACGTGGTCATCCCCACCGGCAACTCCCCCGCCGCCGCC |
| ACCACTACCGCTGCCTCCACGGACATGGAGACACAGACCGATCCCGCCGCAGCCGCAGCCGCAG |
| CCGCCGCCGCGACCTCCTCGGCGGAGGTGCAGACGGACCCCTGGCTGCCGCCGGCGATGTCAGC |
| TCCCCGCGCGCGTCGCGGGCGCAGGAAGTACGGCGCCGCCAACGCGCTCCTGCCCGAGTACGCC |
| TTGCATCCTTCCATCGCGCCCACCCCCGGCTACCGAGGCTATACCTACCGCCCGCGAAGAGCCA |
| AGGGTTCCACCCGCCGTCCCCGCCGACGCGCCGCCGCCACCACCCGCCGCCGCCGCCGCAGACG |
| CCAGCCCGCACTGGCTCCAGTCTCCGTGAGGAAAGTGGCGCGCGACGGACACACCCTGGTGCTG |
| CCCAGGGCGCGCTACCACCCCAGCATCGTTTAAAAGCCTGTTGTGGTTCTTGCAGATATGCCCT |
| CACTTGCCGCCTCCGTTTCCCGGTGCCGGGATACCGAGGAGGAAGATCGCGCCGCAGGAGGGGT |
| CTGGCCGGCCGCGGCCTGAGCGGAGGCAGCCGCCGCGCGCACCGGCGGCGACGCGCCACCAGC |
| CGACGCATGCGCGGCGGGTGCTGCCCCTGTTAATCCCCCTGATCGCCGCGGCGATCGGCGCCG |
| TGCCCGGGATCGCCTCCGTGGCCTTGCAAGCGTCCCAGAGGCATTGACAGACTTGCAAACTTGC |
| AAATATGGAAAAAAAAACCCCAATAAAAAAAGTCTAGACTCTCACGCTCGCTTGGTCCTGTGACT |
| ATTTTGTAGAATGGAAGACATCAACTTTGCGTCGCTGGCCCCGCGTCACGGCTCGCGCCCGTTCC |
| TGGGACACTGGAACGATATCGGCACCAGCAACATGAGCGGTGCGCCTTCAGTTGGGCTCTCT |
| GTGGAGCGGCATTAAAAGTATCGGGTCTGCCGTTAAAAATTACGGCTCCCGGGCCTGGAACAGC |
| AGCACGGGCCAGATGTTGAGAGACAAGTTGAAAGAGCAGAACTTCCAGCAGAAGGTGGTGGAG |
| GGCCTGGCCTCCGGCATCAACGGGGTGGTGGACCTGGCCAACCAGGCCGTGCAGAATAAGATCA |

| DESCRIPTION OF THE SEQUENCES |
| --- |
| ACAGCAGACTGGACCCCCGGCCGCCGGTGGAGGAGGTGCCGCCGGCGCTGGAGACGGTGTCCC |
| CCGATGGGCGTGGCGAGAAGCGCCCGCGGCCCGATAGGGAAGAGACCACTCTGGTCACGCAGA |
| CCGATGAGCCGCCCCCGTATGAGGAGGCCCTGAAGCAAGGTCTGCCCACCACGCGGCCCATCGC |
| GCCCATGGCCACCGGGGTGGTGGGCCGCCACACCCCCGCCACGCTGGACTTGCCTCCGCCCGCC |
| GATGTGCCGCAGCAGCAGAAGGCGGCACAGCCGGGCCGCCCGCGACCGCCTCCCGTTCCTCCG |
| CCGGTCCTCTGCGCCGCGCGGCCAGCGGCCCCCGCGGGGGGTCGCGAGGCACGGCAACTGGC |
| AGAGCACGCTGAACAGCATCGTGGGTCTGGGGGTGCGGTCCGTGAAGCGCCGCCGATGCTACTG |
| AATAGCTTAGCTAACGTGTTGTATGTGTGTATGCGCCCTATGTCGCCGCCAGAGGAGCTGCTGAG |
| TCGCCGCCGTTCGCGCGCCCACCACCACCGCCACTCCGCCCCTCAAGATGGCGACCCCATCGAT |
| GATGCCGCAGTGGTCGTACATGCACATCTCGGGCCAGGACGCCTCGGAGTACCTGAGCCCCGGG |
| CTGGTGCAGTTCGCCCGCGCCACCGAGAGCTACTTCAGCCTGAGTAACAAGTTTAGGAACCCCA |
| CGGTGGCGCCCACGCACGATGTGACCACCGACCGGTCTCAGCGCCTGACGCTGCGGTTCATTCC |
| CGTGGACCGCGAGGACACCGCGTACTCGTACAAGGCGCGGTTCACCCTGGCCGTGGGCGACAAC |
| CGCGTGCTGGACATGGCCTCCACCTACTTTGACATCGCGGGGTGCTGGACCGGGGTCCCACTTT |
| CAAGCCCTACTCTGGCACCGCCTACAACTCCCTGGCCCCAAGGGCGCTCCCAACTCCTGCGAGT |
| GGGAGCAAGAGGAAACTCAGGCAGTTGAAGAAGCAGCAGAAGAGGAAGAAGAAGATGCTGAC |
| GGTCAAGCTGAGGAAGAGCAAGCAGCTACCAAAAAGACTCATGTATATGCTCAGGCTCCCCTTT |
| CTGGCGAAAAAATTAGTAAAGATGGTCTGCAAATAGGAACGGACGCTACAGCTACAGAACAAA |
| AACCTATTTATGCAGACCCTACATTCCAGCCCGAACCCCAAATCGGGGAGTCCCAGTGGAATGA |
| GGCAGATGCTACAGTCGCCGGCGGTAGAGTGCTAAAGAAATCTACTCCCATGAAACCATGCTAT |
| GGTTCCTATGCAAGACCCCACAAATGCTAATGGAGGTCAGGGTGTACTAACGGCAAATGCCCAGG |
| GACAGCTAGAATCTCAGGTTGAAATGCAATTCTTTTCAACTTCTGAAAACGCCCGTAACGAGGC |
| TAACAACATTCAGCCCAAATTGGTGCTGTATAGTGAGGATGTGCACATGGAGACCCCGGATACG |
| CACCTTTCTTACAAGCCCGCAAAAAGCGATGACAATTCAAAAATCATGCTGGGTCAGCAGTCCA |
| TGCCCAACAGACCTAATTACATCGGCTTCAGAGACAACTTTATCGGCCTCATGTATTACAATAGC |
| ACTGGCAACATGGGAGTGCTTGCAGGTCAGGCCTCTCAGTTGAATGCAGTGGTGGACTTGCAAG |
| ACAGAAACACAGAACTGTCCTACCAGCTCTTGCTTGATTCCATGGGTGACAGAACCAGATACTT |
| TTCCATGTGGAATCAGGCAGTGGACAGTTATGACCCAGATGTTAGAATTATTGAAAATCATGGA |
| ACTGAAGACGAGCTCCCCAACTATTGTTTCCCTCTGGGTGGCATAGGGGTAACTGACACTTACCA |
| GGCTGTTAAAACCAACAATGGCAATAACGGGGGCCAGGTGACTTGGACAAAAGATGAAACTTTT |
| GCAGATCGCAATGAAATAGGGGTGGGAAACAATTTCGCTATGGAGATCAACCTCAGTGCCAACC |
| TGTGGAGAAACTTCCTGTACTCCAACGTGGCGCTGTACCTACCAGACAAGCTTAAGTACAACCC |
| CTCCAATGTGGACATCTCTGACAACCCCAACACCTACGATTACATGAACAAGCGAGTGGTGGCC |
| CCGGGGCTGGTGGACTGCTACATCAACCTGGGCGCGCGCTGGTCGCTGGACTACATGGACAACG |
| TCAACCCCTTCAACCACCACCGCAATGCGGGCCTGCGCTACCGCTCCATGCTCCTGGGCAACGG |
| GCGCTACGTGCCCTTCCACATCCAGGTGCCCCAGAAGTTCTTTGCCATCAAGAACCTCCTCCTCC |
| TGCCGGGCTCCTACACCTACGAGTGGAACTTCAGGAAGGATGTCAACATGGTCCTCCAGAGCTC |
| TCTGGGTAACGATCTCAGGGTGGACGGGGCCAGCATCAAGTTCGAGAGCATCTGCCTCTACGCC |
| ACCTTCTTCCCCATGGCCCACAACACGGCCTCCACGCTCGAGGCCATGCTCAGGAACGACACCA |
| ACGACCAGTCCTTCAATGACTACCTCTCCGCCGCCAACATGCTCTACCCCATACCCGCCAACGCC |
| ACCAACGTCCCCATCTCCATCCCCTCGCGCAACTGGGCGGCCTTCCGCGGCTGGGCCTTCACCCG |
| CCTCAAGACCAAGGAGACCCCCTCCCTGGGCTCGGGATTCGACCCCTACTACACCTACTCGGGC |
| TCCATTCCCTACCTGGACGGCACCTTCTACCTCAACCACACTTTCAAGAAGGTCTCGGTCACCTT |
| CGACTCCTCGGTCAGCTGGCCGGGCAACGACCGTCTGCTCACCCCCAACGAGTTCGAGATCAAG |
| CGCTCGGTCGACGGGGAGGGCTACAACGTGGCCCAGTGCAACATGACCAAGGACTGGTTCCTGG |
| TCCAGATGCTGGCCAACTACAACATCGGCTACCAGGGCTTCTACATCCCAGAGAGCTACAAGGA |
| CAGGATGTACTCCTTCTTCAGGAACTTCCAGCCCATGAGCCGGCAGGTGGTGGACCAGACCAAG |
| TACAAGGACTACCAGGAGGTGGGCATCATCCACCAGCACAACAACTCGGGCTTCGTGGGCTACC |
| TCGCCCCCACCATGCGCGAGGGACAGGCCTACCCCGCCAACTTCCCCTATCCGCTCATAGGCAA |
| GACCGCGGTCGACAGCATCACCCAGAAAAAGTTCCTCTGCGACCGCACCCTCTGGCGCATCCCC |
| TTCTCCAGCAACTTCATGTCCATGGGTGCGCTCTCGGACCTGGGCCAGAACTTGCTCTACGCCAA |
| CTCCGCCCACGCCCTCGACATGACCTTCGAGGTCGACCCCATGGACGAGCCCACCCTTCTCTATG |
| TTCTGTTCGAAGTCTTTGACGTGGTCCGGGTCCACCAGCCGCACCGCGGCGTCATCGAGACCGTG |
| TACCTGCGTACGCCCTTCTCGGCCGGCAACGCCACCACCTAAAGAAGCAAGCCGCAGTCATCGC |
| CGCCTGCATGCCGTCGGGTTCCACCGAGCAAGAGCTCAGGGCCATCGTCAGAGACCTGGATGC |
| GGGCCCTATTTTTTGGGCACCTTCGACAAGCGCTTCCCTGGCTTTGTCTCCCCACACAAGCTGGC |
| CTGCGCCATCGTCAACACGGCCGGCCGCGAGACCGGGGGCGTGCACTGGCTGGCCTTCGCCTGG |
| AACCCGCGCTCCAAAACATGCTTCCTCTTTGACCCCTTCGGCTTTTCGGACCAGCGGCTCAAGCA |
| AATCTACGAGTTCGAGTACGAGGGCTTGCTGCGTCGCAGCGCCATCGCCTCCTCGCCCGACCGCT |
| GCGTCACCCTCGAAAAGTCCACCCAGACCGTGCAGGGGCCCGACTCGGCCGCCTGCGGTCTCTT |
| CTGCTGCATGTTTCTGCACGCCTTTGTGCACTGGCCTCAGATGCCCATGGCCGCCAACCCCACCA |
| TGAACTTGCTGACGGGGGTGCCCAACTCCATGCTCCAGAGCCCCCAGGTCGAGCCCACCCTGCG |
| CCGCAACCAGGAGCAGCTCTACAGCTTCCTGGAGCGCCACTCGCCTTACTTCCGCCGCCACAGC |
| GCACAGATCAGGAGGGCCACCTCCTTCTGCCACTTGCAAGAGATGCAAGAAGGGTAATAACGAT |
| GTACACACTTTTTTTCTCAATAAATGGCATCTTTTTATTTATACAAGCTCTCTGGGGTATTCATTT |
| CCCACCACCACCCGCCGTTGTCGCCATCTGGCTCTATTTAGAAATCGAAAGGGTTCTGCCGGGAG |
| TCGCCGTGCGCCACGGGCAGGGACACGTTGCGATACTGGTAGCGGGTGCCCCACTTGAACTCGG |
| GCACCACCAGGCGAGGCAGCTCGGGGAAGTTTTCGCTCCACAGGCTGCGGGTCAGCACCAGCGC |
| GTTCATCAGGTCGGGCGCCGAGATCTTGAAGTCGCAGTTGGGGCCGCCGCCCTGCGCGCGCGAG |
| TTGCGGTACACCGGGTTGCAGCACTGGAACACCAACAGCGCCGGGTGCTTCACGCTGGCCAGCA |
| CGCTGCGGTCGGAGATCAGCTCGGCGTCCAGGTCCTCCGCGTTGCTCAGCGCGAACGGGGTCAT |
| CTTGGGCACTTGCCGCCCCAGGAAGGGCGCGTGCCCCGGTTTCGAGTTGCAGTCGCAGCGCAGC |
| GGGATCAGCAGGTGCCCGTGCCCGGACTCGGCGTTGGGGTACAGCGCGCGCATGAAGGCCTGCA |
| TCTGGCGGAAGGCCATCTGGGCCTTGGCGCCCTCCGAGAAGAACATGCCGCAGGACTTGCCCGA |
| GAACTGGTTTGCGGGCAGCTGGCGTCGTGCAGGCAGCAGCGCGCGTCGGTGTTGGCGATCTGC |
| ACCACGTTGCGCCCCACCGGTTCTTCACGATCTTGGCCTTGGACGATTGCTCCTTCAGCGCGCG |
| CTGCCCGTTCTCGCTGGTCACATCCATCTCGATCACATGTTCCTTGTTCACCATGCTGCTGCCGTG |

| DESCRIPTION OF THE SEQUENCES |
|---|
| CAGACACTTCAGCTCGCCCTCCGTCTCGGTGCAGCGGTGCTGCCACAGCGCGCAGCCCGTGGGC |
| TCGAAAGACTTGTAGGTCACCTCCGCGAAGGACTGCAGGTACCCCTGCAAAAAGCGGCCCATCA |
| TGGTCACGAAGGTCTTGTTGCTGCTGAAGGTCAGCTGCAGCCCGCGGTGCTCCTCGTTCAGCCAG |
| GTCTTGCACACGGCCGCCAGCGCCTCCACCTGGTCGGGCAGCATCTTGAAGTTCACCTTCAGCTC |
| ATTCTCCACGTGGTACTTGTCCATCAGCGTGCGCGCCGCCTCCATGCCCTTCTCCCAGGCCGACA |
| CCAGCGGCAGGCTCACGGGGTTCTTCACCATCACCGTGGCCGCCGCCTCCGCCGCGCTTTCGCTT |
| TCCGCCCCGCTGTTCTCTTCCTCTTCCTCCTCTTCCTCGCCGCCGCCCACTCGCAGCCCCCGCACC |
| ACGGGGTCGTCTTCCTGCAGGCGCTGCACCTTGCGCTTGCCGTTGCGCCCCTGCTTGATGCGCAC |
| GGGCGGGTTGCTGAAGCCCACCATCACCAGCGCGGCCTCTTCTTGCTCGTCCTCGCTGTCCAGAA |
| TGACCTCCGGGGAGGGGGGTTGGTCATCCTCAGTACCGAGGCACGCTTCTTTTTCTTCCTGGGG |
| GCGTTCGCCAGCTCCGCGGCTGCGGCCGCTGCCGAGGTCGAAGGCCGAGGGCTGGGCGTGCGCG |
| GCACCAGCGCGTCCTGCGAGCCGTCCTCGTCCTCCTCGGACTCGAGACGGAGGCGGGCCCGCTT |
| CTTCGGGGGCGCGCGGGGCGGCGGAGGCGGCGGCGGCGACGGAGACGGGGACGAGACATCGTC |
| CAGGGTGGGTGGACGGCGGGCCGCGCCGCGTCCGCGCTCGGGGGTGGTCTCGCGCTGGTCCTCT |
| TCCCGACTGGCCATCTCCCACTGCTCCTTCTCCTATAGGCAGAAAGAGATCATGGAGTCTCTCAT |
| GCGAGTCGAGAAGGAGGAGGACAGCCTAACCGCCCCCTCTGAGCCCTCCACCACCGCCGCCACC |
| ACCGCCAATGCCGCCGCGGACGACGCGCCCACCGAGACCACCGCCAGTACCACCCTCCCCAGCG |
| ACGCACCCCGCTCGAGAATGAAGTGCTGATCGAGCAGGACCCGGGTTTTGTGAGCGGAGAGG |
| AGGATGAGGTGGATGAGAAGGAGAAGGAGGAGGTCGCCGCCTCAGTGCCAAAAGAGGATAAA |
| AAGCAAGACCAGGACGACGCAGATAAGGATGAGACAGCAGTCGGGCGGGGGAACGGAAGCCA |
| TGATGCTGATGACGGCTACCTAGACGTGGGAGACGACGTGCTGCTTAAGCACCTGCACCGCCAG |
| TGCGTCATCGTCTGCGACGCGCTGCAGGAGCGCTGCGAAGTGCCCCTGGACGTGGCGGAGGTCA |
| GCCGCGCCTACGAGCGGCACCTCTTCGCGCCGCACGTGCCCCCCAAGCGCCGGGAGAACGGCAC |
| CTGCGAGCCCAACCCGCGTCTCAACTTCTACCCGGTCTTCGCGGTACCCGAGGTGCTGGCCACCT |
| ACCACATCTTTTTCCAAAACTGCAAGATCCCCCTCTCCTGCCGCGCCAACCGCACCCGCGCCGAC |
| AAAACCCTGACCCTGCGGCAGGGCGCCCACATACCTGATATCGCCTCTCTGGAGGAAGTGCCCA |
| AGATCTTCGAGGGTCTCGGTCGCGACGAGAAACGGGCGGCGAACGCTCTGCACGGAGACAGCG |
| AAAACGAGAGTCACTCGGGGGTGCTGGTGGAGCTCGAGGGCGACAACGCGCGCCTGGCCGTAC |
| TCAAGCGCAGCATAGAGGTCACCCACTTTGCCTACCCGGCGCTCAACCTGCCCCCCAAGGTCAT |
| GAGTGTGGTCATGGGCGAGCTCATCATGCGCCGCGCCCAGCCCCTGGCCGCGGATGCAAACTTG |
| CAAGAGTCCTCCGAGGAAGGCCTGCCCGCGGTCAGCGACGAGCAGCTGGCGCGCTGGCTGGAG |
| ACCCGCGACCCCGCGCAGCTGGAGGAGCGGCGCAAGCTCATGATGGCCGCGGTGCTGGTCACCG |
| TGGAGCTCGAGTGTCTGCAGCGCTTCTTCGCGGACCCCGAGATGCAGCGCAAGCTCGAGGAGAC |
| CCTGCACTACACCTTCCGCCAGGGCTACGTGCGCCAGGCCTGCAAGATCTCCAACGTGGAGCTC |
| TGCAACCTGGTCTCCTACCTGGGCATCCTGCACGAGAACGCCTCGGGCAGAACGTCCTGCACT |
| CCACCCTCAAAGGGGAGGCGCGCCGCGACTACATCCGCGACTGCGCCTACCTCTTCCTCTGCTAC |
| ACCTGGCAGACGGCCATGGGGGTCTGGCAGCAGTGCCTGGAGGAGCGCAACCTCAAGGAGCTG |
| GAAAAGCTCCTCAAGCGCACCCTCAGGGACCTCTGGACGGGCTTCAACGAGCGCTCGGTGGCCG |
| CCGCGCTGGCGGACATCATCTTTCCCGAGCGCCTGCTCAAGACCCTGCAGCAGGGCCTGCCCGA |
| CTTCACCGCCAGAGCATGCTGCAGAACTTCAGGACTTTCATCCTGGAGCGCTCGGGCATCCTGC |
| CGGCCACTTGCTGCGCGCTGCCCAGCGACTTCGTGCCCATCAAGTACAGGGAGTGCCCGCCGCC |
| GCTCTGGGGCCACTGCTACCTCTTCCAGCTGGCCAACTACCTCGCCTACCACTCGGACCTCATGG |
| AAGACGTGAGCGGCGAGGGCCTGCTCGAGTGCCACTGCCGCTGCAACCTCTGCACGCCCCACCG |
| CTCTCTAGTCTGCAACCCGCAGCTGCTCAGCGAGAGTCAGATTATCGGTACCTTCGAGCTGCAGG |
| GTCCCTCGCCTGACGAGAAGTCCGCGGCTCCAGGGCTGAAACTCACTCCGGGGCTGTGGACTTC |
| CGCCTACCTACGCAAATTTGTACCTGAGGACTACCACGCCCACGAGATCAGGTTCTACGAAGAC |
| CAATCCCGCCCGCCCAAGGCGGAGCTCACCGCCTGCGTCATCACCCAGGGGCACATCCTGGGCC |
| AATTGCAAGCCATCAACAAAGCCCGCCGAGAGTTCTTGCTGAAAAAGGGTCGGGGGGTGTACCT |
| GGACCCCCAGTCCGGCGAGGAGCTAAACCCGCTACCCCCGCCGCCGCCGCCAGCAGCGGGACCTT |
| GCTTCCCAGGATGGCACCCAGAAAGAAGCAGCAGCCGCCGCCGCCGCCGCAGCCATACATGCTT |
| CTGGAGGAAGAGGAGGAGGACTGGGACAGTCAGGCAGAGGAGGTTTCGGACGAGGAGCAGGA |
| GGAGATGATGGAAGACTGGGAGGAGGACAGCAGCCTAGACGAGGAAGCTTCAGAGGCCGAAG |
| AGGTGGCAGACGCAACACCATCGCCCTCGGTCGCAGCCCCCTGCGCGGGGCCCCTGAAATCCTC |
| CGAACCCAGCACCAGCGCTATAACCTCCGCTCCTCCGGCGCCGGCGCCACCCGCCCGCAGACCC |
| AACCGTAGATGGGACACCACAGGAACCGGGGTCGGTAAGTCCAAGTGCCCGCCGCCGCCACCG |
| CAGCAGCAGCAGCAGCGCCAGGGCTACCGCTCGTGGCGCGGGCACAAGAACGCCATAGTC |
| GCCTGCTTGCAAGACTGCGGGGGCAACATCTCTTTCGCCCGCCGCTTCCTGCTATTCCACCACGG |
| GGTCGCCTTTCCCCGCAATGTCCTGCATTACTACCGTCATCTCTACAGCCCCTACTGCAGCGGCG |
| ACCCAGAGGCGGCAGCGGCAGCCACAGCGGCGACCACCACCTAGGAAGATATCCTCCGCGGGC |
| AAGACAGCGGCAGCAGCGGCCAGGAGACCCGCGGCAGCAGCGGCGGGAGCGGTGGGCGCACT |
| GCGCCTCTCGCCCAACGAACCCCTCTCGACCCGGGAGCTCAGACACAGGATCTTCCCCACTTTGT |
| ATGCCATCTTCCAACAGAGCAGAGGCCAGGAGCAGGAGCTGAAAATAAAAAACAGATCTCTGC |
| GCTCCCTCACCCGCAGCTGTCTGTATCACAAAAGCGAAGATCAGCTTCGGCGCACGCTGGAGGA |
| CGCGGAGGCACTCTTCAGCAAATACTGCGCGCTCACTCTTAAAGACTAGCTCCGCGCCCTTCTCG |
| AATTTAGGCGGGAGAAAACTACGTCATCGCCGGCCGCCGCCCAGCCCGCCCAGCCGAGATGAGC |
| AAAGAGATTCCCACGCCATACATGTGGAGCTACCAGCCGCAGATGGGACTCGCGGCGGGAGCG |
| GCCCAGGACTACTCCACCCGCATGAACTACATGAGCGCGGGACCCCACATGATCTCACAGGTCA |
| ACGGGATCCGCGCCCAGCGAAACCAAATACTGCTGGAACAGGCGGCCATCACCGCCACGCCCC |
| GCCATAATCTCAACCCCCGAAATTGGCCCGCCGCCCTCGTGTACCAGGAAACCCCTCCGCCAC |
| CACCGTACTACTTCCGCGTGACGCCCAGGCCGAAGTCCAGATGACTAACTCAGGGGCGCAGCTC |
| GCGGGCGGCTTTCGTCACGGGGCGCGGCCGCTCCGACCAGGTATAAGACACCTGATGATCAGAG |
| GCCGAGGTATCCAGCTCAACGACGAGTCGGTGAGCTCTTCGCTCGGTCTTCCGTCCGGACGGAAC |
| TTTCCAGCTCGCCGGATCCGGCCGCTCTTCGTTCACGCCCCGCCAGGCGTACCTGACTCTGCAGA |
| CCTCGTCCTCGGAGCCCCGCTCCGGCGGCATCGGAACCCTCCAGTTCGTGGAGGAGTTCGTGCCC |
| TCGGTCTACTTCAACCCCTTCTCGGGACCTCCCGGACGCTACCCCGACCAGTTCATTCCGAACTT |
| TGACGCGGTGAAGGACTCGGCGGACGGCTACGACTGAATGTCAGGTGTCGAGGCAGAGCAGCT |
| TCGCCTGAGACACCTCGAGCACTGCCGCCGCCACAAGTGCTTCGCCCGCGGTTCTGGTGAGTTCT |

DESCRIPTION OF THE SEQUENCES

```
GCTACTTTCAGCTACCCGAGGAGCATACCGAGGGGCCGGCGCACGGCGTCCGCCTGACCACCCA
GGGCGAGGTTACCTGTTCCCTCATCCGGGAGTTTACCCTCCGTCCCCTGCTAGTGGAGCGGGAGC
GGGGTCCCTGTGTCCTAACTATCGCCTGCAACTGCCCTAACCCTGGATTACATCAAGATCTTTGC
TGTCATCTCTGTGCTGAGTTTAATAAACGCTGAGATCAGAATCTACTGGGGCTCCTGTCGCCATC
CTGTGAACGCCACCGTCTTCACCCACCCCGACCAGGCCCAGGCGAACCTCACCTGCGGTCTGCA
TCGGAGGGCCAAGAAGTACCTCACCTGGTACTTCAACGGCACCCCCTTTGTGGTTTACAACAGCT
TCGACGGGGACGGAGTCTCCCTGAAAGACCAGCTCTCCGGTCTCAGCTACTCCATCCACAAGAA
CACCACCCTCCAACTCTTCCCTCCCTACCTGCCGGGAACCTACGAGTGCGTCACCGGCCGCTGCA
CCCACCTCACCCGCCTGATCGTAAACCAGAGCTTTCCGGGAACAGATAACTCCCTCTTCCCCAGA
ACAGGAGGTGAGCTCAGGAAACTCCCCGGGGACCAGGGCGGAGACGTACCTTCGACCCTTGTG
GGGTTAGGATTTTTTATTACCGGGTTGCTGGCTCTTTTAATCAAAGTTTCTTGAGATTTGTTCTT
TCCTTCTACGTGTATGAACACCTCAACCTCCAATAACTCTACCCTTTCTTCGGAATCAGGTGACTT
CTCTGAAATCGGGCTTGGTGTGCTGCTTACTCTGTTGATTTTTTTCCTTATCATACTCAGCCTTCT
GTGCCTCAGGCTCGCCGCCTGCTGCGCACACATCTATATCTACTGCTGGTTGCTCAAGTGCAGGG
GTCGCCACCCAAGATGAACAGGTACATGGTCCTATCGATCCTAGGCCTGCTGGCCCTGGCGCC
TGCAGCGCCGCCAAAAAAGAGATTACCTTTGAGGAGCCCGCTTGCAATGTAACTTTCAAGCCCG
AGGGTGACCAATGCACCACCCTCGTCAAATGCGTTACCAATCATGAGAGGCTGCGCATCGACTA
CAAAAACAAAACTGGCCAGTTTGCGGTCTATAGTGTGTTTACGCCCGGAGACCCCTCTAACTACT
CTGTCACCGTCTTCCAGGGCGGACAGTCTAAGATATTCAATTACACTTTCCCTTTTTATGAGTTAT
GCGATGCGGTCATGTACATGTCAAAACAGTACAACCTGTGGCCTCCCTCTCCCCAGGCGTGTGTG
GAAAATACTGGGTCTTACTGCTGTATGGCTTTCGCAATCACTACGCTCGCTCTAATCTGCACGGT
GCTATACATAAAATTCAGGCAGAGGCGAATCTTTATCGATGAAAAGAAAATGCCTTGATCGCTA
ACACCGGCTTTCTATCTGCAGAATGAATGCAATCACCTCCCTACTAATCACCACCACCCTCCTTG
CGATTGCCCATGGGTTGACACGAATCGAAGTGCCAGTGGGGTCCAATGTCACCATGGTGGGCCC
CGCCGGCAATTCCACCCTCATGTGGGAAAAATTTGTCCGCAATCAATGGGTTCATTTCTGCTCTA
ACCGAATCAGTATCAAGCCCAGAGCCATCTGCGATGGGCAAAATCTAACTCTGATCAATGTGCA
AATGATGGATGCTGGGTACTATTACGGGCAGCGGGAGAAATCATTAATTACTGGCGACCCCAC
AAGGACTACATGCTGCATGTAGTCGAGGCACTTCCCACTACCACCCCCACTACCACCTCTCCCAC
CACCACCACCACTACTACTACTACTACTACTACTACTACTACCACTACCGCTGCCCGCCATA
CCCGCAAAAGCACCATGATTAGCACAAAGCCCCCTCGTGCTCACTCCCACGCCGGCGGGCCCAT
CGGTGCGACCTCAGAAACCACCGAGCTTTGCTTCTGCCAATGCACTAACGCCAGCGCTCATGAA
CTGTTCGACCTGGAGAATGAGGATGTCCAGCAGAGCTCCGCTTGCCTGACCCAGGAGGCTGTGG
AGCCCGTTGCCCTGAAGCAGATCGGTGATTCAATAATTGACTCTTCTTCTTTTGCCACTCCCGAA
TACCCTCCCGATTCTACTTTCCACATCACGGGTACCAAAGACCCTAACCTCTCTTTCTACCTGATG
CTGCTGCTCTGTATCTCTGTGGTCTCTTCCGCGCTGATGTTACTGGGGATGTTCTGCTGCCTGATC
TGCCGCAGAAAGAGAAAAGCTCGCTCTCAGGGCCAACCACTGATGCCCTTCCCCTACCCCCCGG
ATTTTGCAGATAACAAGATATGAGCTCGCTGCTGACACTAACCGCTTTACTAGCGTCTGCGCTCTAA
CCCTTGTCGCTTGCGACTCGAGATTCCACAATGTCACAGCTGTGGCAGGAGAAAATGTTACTTTC
AACTCCACGGCCGATACCCAGTGGTCGTGGAGTGGCTCAGGTAGCTACTTAACTATCTGCAATA
GCTCCACTTCCCCCGGCATATCCCCAACCAAGTACCAATGCAATGCCAGCCTGTTCACCCTCATC
AACGCTTCCACCCTGGACAATGGACTCTATGTAGGCTATGTACCCTTTGGTGGGCAAGGAAAGA
CCCACGCTTACAACCTGGAAGTTCGCCAGCCCAGAACCACTACCCAAGCTTCTCCCACCACCAC
CACCACCACCACCATCACCAGCAGCAGCAGCAGCAGCAGCCACAGCAGCAGCAGCAGATTATT
GACTTTGGTTTTGGCCAGCTCATCTGCCGCTACCCAGGCCATCTACAGCTCTGTGCCCGAAACCA
CTCAGATCCACCGCCCAGAAACGACCACCGCCACCACCCTACACACCTCCAGCGATCAGATGCC
GACCAACATCACCCCCTTGGCTCTTCAAATGGGACTTACAAGCCCCACTCCAAAACCAGTGGAT
GCGGCCGAGGTCTCCGCCCTCGTCAATGACTGGGCGGGCTGGGAATGTGGTGGTTCGCCATAG
GCATGATGGCGCTCTGCCTGCTTCTGCTCTGGCTCATCTGCTGCCTCCACCGCAGGCGAGCCAGA
CCCCCCATCTATAGACCCATCATTGTCCTGAACCCCGATAATGATGGGATCCATAGATTGGATGG
CCTGAAAAACCTACTTTTTTCTTTTACAGTATGATAAATTGAGACATGCCTCGCATTTTCTTGTAC
ATGTTCCTTCTCCCACCTTTTCTGGGGTGTTCTACGCTGGCCGCTGTGTCTCACCTGGAGGTAGAC
TGCCTCTCACCCCTTCACTGTCTACCTGCTTTACGGATTGGTCACCCTCACTCTCATCTGCAGCCTA
ATCACAGTAATCATCGCCTTCATCCAGTGCATTGATTACATCTGTGTGCGCCTCGCATACTTCAG
ACACCACCCGCAGTACCGAGACAGGAACATTGCCCAACTTCTAAGACTGCTCTAATCATGCATA
AGACTGTGATCTGCCTTCTGATCCTCTGCATCCTGCCCACCCTCACCTCCTGCCAGTACACCACA
AAATCTCCGCGCAAAAGACATGCCTCCTGCCGCTTCACCCAACTGTGGAATATACCCAAATGCT
ACAACGAAAAGAGCGAGCTCTCCGAAGCTTGGCTGTATGGGGTCATCTGTGTCTTAGTTTTCTGC
AGCACTGTCTTTGCCCTCATAATCTACCCCTACTTTGATTTGGGATGGAACGCGATCGATGCCAT
GAATTACCCCACCTTTCCCGCACCCGAGATAATTCCACTGCGACAAGTTGTACCCGTTGTCGTTA
ATCAACGCCCCCATCCCCTACGCCCACTGAAATCAGCTACTTTAACCTAACAGGCGGAGATGA
CTGACGCCTAGATCTAGAAATGGACGGCATCAGTACCGAGCAGCGTCTCCTAGAGAGGCGCAG
GCAGGCGGCTGAGCAAGAGCGCCTCAATCAGGAGCTCCGAGATCTCGTTAACCTGCACCAGTGC
AAAAGAGGCATCTTTTGTCTGGTAAAGCAGGCCAAAGTCACCTACGAGAAGACCGGCAACAGC
CACCGCCTCAGTTACAAATTGCCCACCCAGCGCCAGAAGCTGGTGCTCATGGTGGGTGAGAATC
CCATCACCGTCACCCAGCACTCGGTAGAGACCGAGGGGTGTCTGCACTCCCCCTGTCGGGGTCC
AGAAGACCTCTGCACCCTGGTAAAGACCCTGTGCGGTCTCAGAGATTTAGTCCCCTTTAACTAAT
CAAACACTGGAATCAATAAAAAGAATCACTTACTTAAAATCAGACAGCAGGTCTCTGTCCAGTT
TATTCAGCAGCACCTCCTTCCCCTCCTCCCAACTCTGGTACTCCAAACGCCTTCTGGCGGCAAAC
TTCCTCCACACCCTGAAGGGAATGTCAGATTCTTGCTCCTGTCCCTCCGCACCCACTATCTTCATG
TTGTTGCAGATGAAGCGCACCAAAACGTCTGACGAGAGCTTCAACCCCGTGTACCCCTATGACA
CGGAAAGCGGCCCTCCCTCCGTCCCTTTCCTCACCCCTCCCTTCGTGTCTCCCGATGGATTCCAA
GAAAGTCCCCCCGGGGTCCTGTCTCTGAACCTGGCCGAGCCCCTGGTCACTTCCCACGGCATGCT
CGCCCTGAAAATGGGAAGTGGCCTCTCCCTGGACGACGCTGGCAACCTCACCTCTCAAGATATC
ACCACCGCTAGCCCTCCCCTCAAAAAAACCAAGACCAACCTCAGCCTAGAAACCTCATCCCCCC
TAACTGTGAGCACCTCAGGCGCCCTCACCGTAGCAGCCGCCGCTCCCCTGGCGGTGGCCGGCAC
CTCCCTCACCATGCAATCAGAGGCCCCCCTGACAGTACAGGATGCAAAACTCACCCTGGCCACC
AAAGGCCCCCTGACCGTGTCTGAAGGCAAACTGGCCTTGCAAACATCGGCCCCGCTGACGGCCG
```

DESCRIPTION OF THE SEQUENCES

```
CTGACAGCAGCACCCTCACAGTCAGTGCCACACCACCCCTTAGCACAAGCAATGGCAGCTTGGG
TATTGACATGCAAGCCCCCATTTACACCACCAATGGAAAACTAGGACTTAACTTTGGCGCTCCCC
TGCATGTGGTAGACAGCCTAAATGCACTGACTGTAGTTACTGGCCAAGGTCTTACGATAAACGG
AACAGCCCTACAAACTAGAGTCTCAGGTGCCCTCAACTATGACACATCAGGAAACCTAGAATTG
AGAGCTGCAGGGGGTATGCGAGTTGATGCAAATGGTCAACTTATCCTTGATGTAGCTTACCCATT
TGATGCACAAAACAATCTCAGCCTTAGGCTTGGACAGGGACCCCTGTTTGTTAACTCTGCCCACA
ACTTGGATGTTAACTACAACAGAGGCCTCTACCTGTTCACATCTGGAAATACCAAAAAGCTAGA
AGTTAATATCAAAACAGCCAAGGGTCTCATTTATGATGACACTGCTATAGCAATCAATGCGGGT
GATGGGCTACAGTTTGACTCAGGCTCAGATACAAATCCATTAAAAACTAAACTTGGATTAGGAC
TGGATTATGACTCCAGCAGAGCCATAATTGCTAAACTGGGAACTGGCCTAAGCTTTGACAACAC
AGGTGCCATCACAGTAGGCAACAAAAATGATGACAAGCTTACCTTGTGGACCACACCAGACCCA
TCCCCTAACTGTAGAATCTATTCAGAGAAAGATGCTAAATTCACACTTGTTTTGACTAAATGCGG
CAGTCAGGTGTTGGCCAGCGTTTCTGTTTTATCTGTAAAAGGTAGCCTTGCGCCCATCAGTGGCA
CAGTAACTAGTGCTCAGATTGTCCTCAGATTTGATGAAAATGGAGTTCTACTAAGCAATTCTTCC
CTTGACCCTCAATACTGGAACTACAGAAAAGGTGACCTTACAGAGGGCACTGCATATACCAACG
CAGTGGGATTTATGCCCAACCTCACAGCATACCCAAAAACACAGAGCCAAACTGCTAAAAGCAA
CATTGTAAGTCAGGTTTACTTGAATGGGGACAAATCCAAACCCATGACCCTCACCATTACCCTCA
ATGGAACTAATGAAACAGGAGATGCCACAGTAAGCACTTACTCCATGTCATTCTCATGGAACTG
GAATGGAAGTAATTACATTAATGAAACGTTCCAAACCAACTCCTTCACCTTCTCCTACATCGCCC
AAGAATAAAAAGCATGACGCTGTTGATTTGATTCAATGTGTTTCTGTTTTATTTTCAAGCACAAC
AAAATCATTCAAGTCATTCTTCCATCTTAGCTTAATAGACACAGTAGCTTAATAGACCCAGTAGT
GCAAAGCCCCATTCTAGCTTATAACTAGTGGAGAAGTACTCGCCTACATGGGGGTAGAGTCATA
ATCGTGCATCAGGATAGGGCGGTGGTGCTGCAGCAGCGCGCGAATAAACTGCTGCCGCCGCCGC
TCCGTCCTGCAGGAATACAACATGGCAGTGGTCTCCTCAGCGATGATTCGCACCGCCCGCAGCA
TAAGGCGCCTTGTCCTCCGGGCACAGCAGCGCACCCTGATCTCACTTAAATCAGCACAGTAACT
GCAGCACAGCACCACAATATTGTTCAAAATCCCACAGTGCAAGGCGCTGTATCCAAAGCTCATG
GCGGGGACCACAGAACCCACGTGGCCATCATACCACAAGCGCAGGTAGATTAAGTGGCGACCC
CTCATAAACACGCTGGACATAAACATTACCTCTTTTGGCATGTTGTAATTCACCACCTCCCGGTA
CCATATAAACCTCTGATTAAACATGGCGCCATCCACCACCATCCTAAACCAGCTGGCCAAAACC
TGCCCGCCGGCTATACACTGCAGGGAACCGGGACTGGAACAATGACAGTGGAGAGCCCAGGAC
TCGTAACCATGGATCATCATGCTCGTCATGATATCAATGTTGGCACAACACAGGCACACGTGCA
TACACTTCCTCAGGATTACAAGCTCCTCCCGCGTTAGAACCATATCCCAGGGAACAACCCATTCC
TGAATCAGCGTAAATCCCACACTGCAGGGAAGACCTCGCACGTAACTCACGTTGTGCATTGTCA
AAGTGTTACATTCGGGCAGCAGCGGATGATCCTCCAGTATGGTAGCGCGGGTTTCTGTCTCAAA
AGGAGGTAGACGATCCCTACTGTACGGAGTGCGCCGAGACAACCGAGATCGTGTTGGTCGTAGT
GTCATGCCAAATGGAACGCCGGACGTAGTCATATTTCCTGAAGTCTTAGATCTCTCAACGCAGC
ACCAGCACCAACACTTCGCAGTGTAAAAGGCCAAGTGCCGAGAGAGTATATATAGGAATAAAA
AGTGACGTAAACGGGCAAAGTCCAAAAAACGCCCAGAAAACCGCACGCGAACCTACGCCCCG
AAACGAAAGCCAAAAAACACTAGACACTCCCTTCCGGCGTCAACTTCCGCTTTCCCACGCTACG
TCACTTGCCCCAGTCAAACAAACTACATATCCCGAACTTCCAAGTCGCCACGCCCAAAACACCG
CCTACACCTCCCCGCCCGCCGGCCCGCCCCCAAACCCGCCTCCCGCCCCGCGCCCCGCCCCGCGC
CGCCCATCTCATTATCATATTGGCTTCAATCCAAAATAAGGTATATTATTGATGATGGTTTAAAC
GGATCCTCTAGAGTCGACCTGCAGGCATGCAAGCTTGAGTATTCTATAGTGTCACCTAAATAGCT
TGGCGTAATCATGGTCATAGCTGTTTCCTGTGTGAAATTGTTATCCGCTCACAATTCCACACAAC
ATACGAGCCGGAAGCATAAAGTGTAAAGCCTGGGGTGCCTAATGAGTGAGCTAACTCACATTAA
TTGCGTTGCGCTCACTGCCCGCTTTCCAGTCGGGAAACCTGTCGTGCCAGCTGCATTAATGAATC
GGCCAACGCGAACCCCTTGCGGCCGCCCGGGCCGTCGACCAATTCTCATGTTTGACAGCTTATCA
TCGAATTTCTGCCATTCATCCGCTTATTATCACTTATTCAGGCGTAGCAACCAGGCGTTTAAGGG
CACCAATAACTGCCTTAAAAAAATTACGCCCCGCCCTGCCACTCATCGCAGTACTGTTGTAATTC
ATTAAGCATTCTGCCGACATGGAAGCCATCACAAACGGCATGATGAACCTGAATCGCCAGCGGC
ATCAGCACCTTGTCGCCTTGCGTATAATATTTGCCCATGGTGAAAACGGGGGCGAAGAAGTTGT
CCATATTGGCCACGTTTAAATCAAAACTGGTGAAACTCACCCAGGGATTGGCTGAGACGAAAAA
CATATTCTCAATAAACCCTTTAGGGAAATAGGCCAGGTTTTCACCGTAACACGCCACATCTTGCG
AATATATGTGTAGAAACTGCCGGAAATCGTCGTGGTATTCACTCCAGAGCGATGAAAACGTTTC
AGTTTGCTCATGGAAAACGGTGTAACAAGGGTGAACACTATCCCATATCACCAGCTCACCGTCT
TTCATTGCCATACGGAATTCCGGATGAGCATTCATCAGGCGGGCAAGAATGTGAATAAAGGCCG
GATAAAACTTGTGCTTATTTTTCTTTACGGTCTTTAAAAAGGCCGTAATATCCAGCTGAACGGTC
TGGTTATAGGTACATTGAGCAACTGACTGAAATGCCTCAAAATGTTCTTTACGATGCCATTGGGA
TATATCAACGGTGGTATATCCAGTGATTTTTTCTCCATTTTAGCTTCCTTAGCTCCTGAAAATCT
CGATAACTCAAAAAATACGCCCGGTAGTGATCTTATTTCATTATGGTGAAAGTTGGAACCTCTTA
CGTGCCGATCAACGTCTCATTTTCGCCAAAGTTGGCCCAGGGCTTCCCGGTATCAACAGGGAC
ACCAGGATTTATTTATTCTGCGAAGTGATCTTCCGTCACAGGTATTTATTCGCGATAAGCTCATG
GAGCGGCGTAACCGTCGCACAGGAAGGACAGAGAAAGCGCGATCTGGGAAGTGACGGACAG
AACGGTCAGGACCTGGATTGGGGAGGCGGTTGCCGCCGCTGCTGCTGACGGTGTGACGTTCTCT
GTTCCGGTCACACCACATACGTTCCGCCATTCCTATGCGATGCACATGCTGTATGCCGGTATACC
GCTGAAAGTTCTGCAAAGCCTGATGGGACATAAGTCCATCAGTTCAACGGAGTCTACACGAAG
GTTTTTGCGCTGGATGTGGCTGCCCGGCACCGGGTGCAGTTTGCGATGCCGGAGTCTGATGCGGT
TGCGATGCTGAAACAATTATCCTGAGAATAAATGCCTTGGCCTTTATATGGAAATGTGGAACTG
AGTGGATATGCTGTTTTTGTCTGTTAAACAGAGAAGCTGGCTGTTATCCACTGAGAAGCGAACG
AAACAGTCGGGAAAATCTCCCATTATCGTAGAGATCCGCATTATTAATCTCAGGAGCCTGTGTA
GCGTTTATAGGAAGTAGTGTTCTGTCATGATGCCTGCAAGCGGTAACGAAAACGATTTGAATAT
GCCTTCAGGAACAATAGAAATCTTCGTGCGGTGTTACGTTGAAGTGGAGCGGATTATGTCAGCA
ATGGACAGAACAACCTAATGAACACAGAACCATGATGTGGTCTGTCCTTTTACAGCCAGTAGTG
CTCGCCGCAGTCGAGCGACAGGGCGAAGCCCTCGAGTGAGCGAGGAAGCACCAGGGAACAGCA
CTTATATATTCTGCTTACACACGATGCCTGAAAAACTTCCCTTGGGGTTATCCACTTATCCACG
GGGATATTTTTATAATTATTTTTTTTATAGTTTTAGATCTTCTTTTTTAGAGCGCTTGTAGGCCT
TTATCCATGCTGGTTCTAGAGAAGGTGTTGTGACAAATTGCCCTTTCAGTGTGACAAATCACCCT
```

DESCRIPTION OF THE SEQUENCES

```
CAAATGACAGTCCTGTCTGTGACAAATTGCCCTTAACCCTGTGACAAATTGCCCTCAGAAGAAG
CTGTTTTTTCACAAAGTTATCCCTGCTTATTGACTCTTTTTTATTTAGTGTGACAATCTAAAAACT
TGTCACACTTCACATGGATCTGTCATGGCGGAAACAGCGGTTATCAATCACAAGAAACGTAAAA
ATAGCCCGCGAATCGTCCAGTCAAACGACCTCACTGAGGCGGCATATAGTCTCTCCCGGGATCA
AAAACGTATGCTGTATCTGTTCGTTGACCAGATCAGAAAATCTGATGGCACCCTACAGGAACAT
GACGGTATCTGCGAGATCCATGTTGCTAAATATGCTGAAATATTCGGATTGACCTCTGCGGAAG
CCAGTAAGGATATACGGCAGGCATTGAAGAGTTTCGCGGGGAAGGAAGTGGTTTTTTATCGCCC
TGAAGAGGATGCCGGCGATGAAAAAGGCTATGAATCTTTTCCTTGGTTTATCAAACGTGCGCAC
AGTCCATCCAGAGGGCTTTACAGTGTACATATCAACCCATATCTCATTCCCTTCTTTATCGGGTT
ACAGAACCGGTTTACGCAGTTTCGGCTTAGTGAAACAAAAGAAATCACCAATCCGTATGCCATG
CGTTTATACGAATCCCTGTGTCAGTATCGTAAGCCGGATGGCTCAGGCATCGTCTCTGAAAAT
CGACTGGATCATAGAGCGTTACCAGCTGCCTCAAAGTTACCAGCGTATGCCTGACTTCCGCCGCC
GCTTCCTGCAGGTCTGTGTTAATGAGATCAACAGCAGAACTCCAATGCGCCTCTCATACATTGAG
AAAAAGAAAGGCCGCCAGACGACTCATATCGTATTTTCCTTCCGCGATATCACTTCCATGACGA
CAGGATAGTCTGAGGGTTATCTGTCACAGATTTGAGGGTGGTTCGTCACATTTGTTCTGACCTAC
TGAGGGTAATTTGTCACAGTTTTGCTGTTTCCTTCAGCCTGCATGGATTTTCTCATACTTTTTGAA
CTGTAATTTTTAAGGAAGCCAAATTTGAGGGCAGTTTGTCACAGTTGATTTCCTTCTCTTTCCCTT
CGTCATGTGACCTGATATCGGGGGTTAGTTCGTCATCATTGATGAGGGTTGATTATCACAGTTTA
TTACTCTGAATTGGCTATCCGCGTGTGTACCTCTACCTGGAGTTTTTCCCACGGTGGATATTTCTT
CTTGCGCTGAGCGTAAGAGCTATCTGACAGAACAGTTCTTCTTTGCTTCCTCGCCAGTTCGCTCG
CTATGCTCGGTTACACGGCTGCGGCGAGCGCTAGTGATAATAAGTGACTGAGGTATGTGCTCTTC
TTATCTCCTTTTGTAGTGTTGCTCTTATTTTAAACAACTTTGCGGTTTTTTGATGACTTTGCGATTT
TGTTGTTGCTTTGCAGTAAATTGCAAGATTTAATAAAAAAACGCAAAGCAATGATTAAAGGATG
TTCAGAATGAAACTCATGGAAACACTTAACCAGTGCATAAACGCTGGTCATGAAATGACGAAGG
CTATCGCCATTGCACAGTTTAATGATGACAGCCCGGAAGCGAGGAAAATAACCCGGCGCTGGAG
AATAGGTGAAGCAGCGGATTTAGTTGGGGTTTCTTCTCAGGCTATCAGAGATGCCGAGAAAGCA
GGGCGACTACCGCACCCGGATATGGAAATTCGAGGACGGGTTGAGCAACGTGTTGGTTATACAA
TTGAACAAATTAATCATATGCGTGATGTGTTTGGTACGCGATTGCGACGTGCTGAAGACGTATTT
CCACCGGTGATCGGGGTTGCTGCCCATAAAGGTGGCGTTTACAAAACCTCAGTTTCTGTTCATCT
TGCTCAGGATCTGGCTCTGAAGGGGCTACGTGTTTTGCTCGTGGAAGGTAACGACCCCCAGGGA
ACAGCCTCAATGTATCACGGATGGGTACCAGATCTTCATATTCATGCAGAAGACACTCTCCTGCC
TTTCTATCTTGGGGAAAAGGACGATGTCACTTATGCAATAAAGCCCACTTGCTGGCCGGGGCTTG
ACATTATTCCTTCCTGTCTGGCTCTGCACCGTATTGAAACTGAGTTAATGGGCAAATTTGATGAA
GGTAAACTGCCCACCGATCCACACCTGATGCTCCGACTGGCCATTGAAACTGTTGCTCATGACTA
TGATGTCATAGTTATTGACAGCGCGCCTAACCTGGGTATCGGCACGATTAATGTCGTATGTGCTG
CTGATGTGCTGATTGTTCCCACGCCTGCTGAGTTGTTTGACTACACCTCCGCACTGCAGTTTTTCG
ATATGCTTCGTGATCTGCTCAAGAACGTTGATCTTAAAGGGTTCGAGCCTGATGTACGTATTTTG
CTTACCAAATACAGCAATAGTAATGGCTCTCAGTCCCGTGGATGGAGGAGCAAATTCGGGATG
CCTGGGGAAGCATGGTTCTAAAAAATGTTGTACGTGAAACGGATGAAGTTGGTAAAGGTCAGAT
CCGGATGAGAACTGTTTTTGAACAGGCCATTGATCAACGCTCTTCAACTGGTGCTCTGGAGAAAT
GCTCTTTCTATTTGGGAACCTGTCTGCAATGAAATTTTCGATCGTCTGATTAAACCACGCTGGGA
GATTAGATAATGAAGCGTGCGCCTGTTATTCCAAAACATACGCTCAATACTCAACCGGTTGAAG
ATACTTCGTTATCGACACCAGCTGCCCCGATGGTGGATTCGTTAATTGCGCGCGTAGGAGTAATG
GCTCGCGGTAATGCCATTACTTTGCCTGTATGTGGTCGGGATGTGAAGTTTACTCTTGAAGTGCT
CCGGGGTGATAGTGTTGAGAAGACCTCTCGGGTATGGTCAGGTAATGAACGTGACCAGGAGCTG
CTTACTGAGGACGCACTGGATGATCTCATCCCTTCTTTTCTACTGACTGGTCAACAGACACCGGC
GTTCGGTCGAAGAGTATCTGGTGTCATAGAAATTGCCGATGGGAGTCGCCGTCGTAAAGCTGCT
GCACTTACCGAAAGTGATTATCGTGTTCTGGTTGGCGAGCTGGATGATGAGCAGATGGCTGCAT
TATCCAGATTGGGTAACGATTATCGCCCAACAAGTGCTTATGAACGTGGTCAGCGTTATGCAAG
CCGATTGCAGAATGAATTTGCTGGAAATATTTCTGCGCTGGCTGATGCGGAAAATATTTCACGTA
AGATTATTACCCGCTGTATCAACACCGCCAAATTGCCTAAATCAGTTGTTGCTCTTTTTTCTCACC
CCGGTGAACTATCTGCCCGGTCAGGTGATGCACTTCAAAAAGCCTTTACAGATAAAGAGGAATT
ACTTAAGCAGCAGGCATCTAACCTTCATGAGCAGAAAAAAGCTGGGGTGATATTTGAAGCTGAA
GAAGTTATCACTCTTTTAACTTCTGTGCTTAAAACGTCATCTGCATCAAGAACTAGTTTAAGCTC
ACGACATCAGTTTGCTCCTGGAGCGACAGTATTGTATAAGGGCGATAAAATGGTGCTTAACCTG
GACAGGTCTCGTGTTCCAACTGAGTGTATAGAGAAAATTGAGGCCATTCTTAAGGAACTTGAAA
AGCCAGCACCCTGATGCGACCACGTTTTAGTCTACGTTTATCTGTCTTTACTTAATGTCCTTTGTT
ACAGGCCAGAAAGCATAACTGGCCTGAATATTCTCTCTGGGCCCACTGTTCCACTTGTATCGTCG
GTCTGATAATCAGACTGGGACCACGGTCCCACTCGTATCGTCGGTCTGATTATTAGTCTGGGACC
ACGGTCCCACTCGTATCGTCGGTCTGATTATTAGTCTGGGACCACGGTCCCACTCGTATCGTCGG
TCTGATAATCAGACTGGGACCACGGTCCCACTCGTATCGTCGGTCTGATTATTAGTCTGGGACCA
TGGTCCCACTCGTATCGTCGGTCTGATTATTAGTCTGGGACCACGGTCCCACTCGTATCGTCGGT
CTGATTATTAGTCTGGAACCACGGTCCCACTCGTATCGTCGGTCTGATTATTAGTCTGGGACCAC
GGTCCCACTCGTATCGTCGGTCTGATTATTAGTCTGGGACCACGATCCCACTCGTGTTGTCGGTC
TGATTATCGGTCTGGGACCACGGTCCCACTTGTATTGTCGATCAGACTATCAGCGTGAGACTACG
ATTCCATCAATGCCTGTCAAGGGCAAGTATTGACATGTCGTCGTAACCTGTAGAACGGAGTAAC
CTCGGTGTGCGGTTGTATGCCTGCTGTGGATTGCTGCTGTGTCCTGCTTATCCACAACATTTTGCG
CACGGTTATGTGGACAAAATACCTGGTTACCCAGGCCGTGCCGGCACGTTAACCGGGCTGCATC
CGATGCAAGTGTGTCGCTGTCGACGAGCTCGCGAGCTCGGACATGAGGTTGCCCCGTATTCAGT
GTCGCTGATTTGTATTGTCTGAAGTTGTTTTTACGTTAAGTTGATGCAGATCAATTAATACGATA
CCTGCGTCATAATTGATTATTTGACGTGGTTTGATGGCCTCCACGCACGTCGTTGTGATATGTAGATG
ATAATCATTATCACTTTACGGGTCCTTTCCGGTGATCCGACAGGTTACGGGCGGCGACCTCGCG
GGTTTTCGCTATTTATGAAAATTTTCCGGTTTAAGGCGTTTCCGTTCTTCTTCGTCATAACTTAAT
GTTTTTATTTAAATACCCTCTGAAAAGAAAGGAAACGACAGGTGCTGAAAGCGAGCTTTTTGG
CCTCTGTCGTTTCCTTTCTCTGTTTTTGTCCGTGGAATGAACAATGGAAGTCCGAGCTCATCGCTA
ATAACTTCGTATAGCATACATTATACGAAGTTATATTCGATGCGGCCGCAAGGGGTTCGCGTCA
GCGGGTGTTGGCGGGTGTCGGGGCTGGCTTAACTATGCGGCATCAGAGCAGATTGTACTGAGAG
```

| DESCRIPTION OF THE SEQUENCES |
|---|
| TGCACCATATGCGGTGTGAAATACCGCACAGATGCGTAAGGAGAAAATACCGCATCAGGCGCC<br>ATTCGCCATTCAGGCTGCGCAACTGTTGGGAAGGGCGATCGGTGCGGGCCTCTTCGCTATTACGC<br>CAGCTGGCGAAAGGGGATGTGCTGCAAGGCGATTAAGTTGGGTAACGCCAGGGTTTTCCCAGT<br>CACGACGTTGTAAAACGACGGCCAGTGAATTGTAATACGACTCACTATAGGGCGAATTCGAGCT<br>CGGTACCCGGGGATCCTCGTTTAAAC<br><br>SEQ ID NO: 9-Polynucleotide sequence encoding ChAd155#1375 backbone construct<br>CATCATCAATAATATACCTTATTTTGGATTGAAGCCAATATGATAATGAGATGGGCGGCGCGGG<br>GCGGGGCGCGGGGCGGGAGGCGGGTTTGGGGGCGGGCCGGCGGGCGGGGCGGTGTGGCGGAA<br>GTGGACTTTGTAAGTGTGGCGGATGTGACTTGCTAGTGCCGGGCGCGGTAAAAGTGACGTTTTC<br>CGTGCGCGACAACGCCCCCGGGAAGTGACATTTTTCCCGCGGTTTTTACCGGATGTTGTAGTGAA<br>TTTGGGCGTAACCAAGTAAGATTTGGCCATTTTCGCGGGAAAACTGAAACGGGGAAGTGAAATC<br>TGATTAATTTTGCGTTAGTCATACCGCGTAATATTTGTCTAGGGCCGAGGGACTTTGGCCGATTA<br>CGTGGAGGACTCGCCCAGGTGTTTTTTGAGGTGAATTTCCGCGTTCCGGGTCAAAGTCTGCGTTT<br>TATTATTATAGGATATCCCATTGCATACGTTGTATCCATATCATAAATATGTACATTTATATTGGCT<br>CATGTCCAACATTACCGCCATGTTGACATTGATTATTGACTAGTTATTAATAGTAATCAATTACG<br>GGGTCATTAGTTCATAGCCCATATATGGAGTTCCGCGTTACATAACTTACGGTAAATGGCCCGCC<br>TGGCTGACCGCCCAACGACCCCCGCCCATTGACGTCAATAATGACGTATGTTCCCATAGTAACG<br>CCAATAGGGACTTTCCATTGACGTCAATGGGTGGAGTATTTACGGTAAACTGCCCACTTGGCAGT<br>ACATCAAGTGTATCATATGCCAAGTACGCCCCCTATTGACGTCAATGACGGTAAATGGCCCGCC<br>TGGCATTATGCCCAGTACATGACCTTATGGGACTTTCCTACTTGGCAGTACATCTACGTATTAGT<br>CATCGCTATTACCATGGTGATGCGGTTTTGGCAGTACATCAATGGGCGTGGATAGCGGTTTGACT<br>CACGGGGATTTCCAAGTCTCCACCCCATTGACGTCAATGGGAGTTTGTTTTGGCACCAAAATCAA<br>CGGGACTTTCCAAAATGTCGTAACAACTCCGCCCCATTGACGCAAATGGGCGGTAGGCGTGTAC<br>GGTGGGAGGTCTATATAAGCAGAGCTCTCCCTATCAGTGATAGAGATCTCCCTATCAGTGATAG<br>AGATCGTCGACGAGCTCGTTTAGTGAACCGTCAGATCGCCTGGAGACGCCATCCACGCTGTTTTG<br>ACCTCCATAGAAGACACCGGGACCGATCCAGCCTCCGCGGCCGGGAACGGTGCATTGGAACGC<br>GGATTCCCCGTGCCAAGAGTGAGATCTTCCGTTTATCTAGGTACCGGGCCCCCCCTCGAGGTCGA<br>CGGTATCGATAAGCTTCACGCTGCCGCAAGCACTCAGGGCGCAAGGGCTGCTAAAGGAAGCGG<br>AACACGTAGAAAGCCAGTCCGCAGAAACGGTGCTGACCCCGGATGAATGTCAGCTACTGGGCTA<br>TCTGGACAAGGGAAAACGCAAGCGCAAAGAGAAAGCAGGTAGCTTGCAGTGGGCTTACATGGC<br>GATAGCTAGACTGGGCGGTTTTATGGACAGCAAGCGAACCGGAATTGCCAGCTGGGGCGCCCTC<br>TGGTAAGGTTGGGAAGCCCTGCAAAGTAAACTGGATGGCTTTCTTGCCGCCAAGGATCTGATGG<br>CGCAGGGGATCAAGATCTAACCAGGAGCTATTTAATGGCAACAGTTAACCAGCTGGTACGCAAA<br>CCACGTGCTCGCAAAGTTGCGAAAAGCAACGTGCCTGCGCTGGAAGCATGCCCGCAAAAACGTG<br>GCGTATGTACTCGTGTATATACTACCACTCCTAAAAAACCGAACTCCGCGCTGCGTAAAGTATGC<br>CGTGTTCGTCTGACTAACGGTTTCGAAGTGACTTCCTACATCGGTGGTGAAGGTCACAACCTGCA<br>GGAGCACTCCGTGATCCTGATCCGTGGCGGTCGTGTTAAAGACCTCCCGGGTGTTCGTTACCACA<br>CCGTACGTGGTGCGCTTGACTGCTCCGGCGTTAAAGACCGTAAGCAGGCTCGTTCCAAGTATGG<br>CGTGAAGCGTCCTAAGGCTTAATGGTAGATCTGATCAAGAGACAGGATGACGGTCGTTTCGCAT<br>GCTTGAACAAGATGGATTGCACGCAGGTTCTCCGGCCGCTTGGGTGGAGAGGCTATTCGGCTAT<br>GACTGGGCACAACAGACAATCGGCTGCTCTGATGCCGCCGTGTTCCGGCTGTCAGCGCAGGGGC<br>GCCCGGTTCTTTTTGTCAAGACCGACCTGTCCGGTGCCCTGAATGAACTGCAGGACGAGGCAGC<br>GCGGCTATCGTGGCTGGCCACGACGGGCGTTCCTTGCGCAGCTGTGCTCGACGTTGTCACTGAA<br>GCGGGAAGGGACTGGCTGCTATTGGGCGAAGTGCCGGGGCAGGATCTCCTGTCATCTCACCTTG<br>CTCCTGCCGAGAAAGTATCCATCATGGCTGATGCAATGCGGCGGCTGCATACGCTTGATCCGGC<br>TACCTGCCCATTCGACCACCAAGCGAAACATCGCATCGAGCGAGCACGTACTCGGATGGAAGCC<br>GGTCTTGTCGATCAGGATGATCTGGACGAAGAGCATCAGGGGCTCGCGCCAGCCGAACTGTTCG<br>CCAGGCTCAAGGCGCGCATGCCCGACGGCGAGGATCTCGTCGTGACCCATGGCGATGCCTGCTT<br>GCCGAATATCATGGTGGAAAATGGCCGCTTTTCTGGATTCATCGACTGTGGCCGGCTGGGTGTG<br>GCGGACCGCTATCAGGACATAGCGTTGGCTACCCGTGATATTGCTGAAGAGCTTGGCGGCGAAT<br>GGGCTGACCGCTTCCTCGTGCTTTACGGTATCGCCGCTCCCGATTCGCAGCGCATCGCCTTCTAT<br>CGCCTTCTTGACGAGTTCTTCTGAGCGGGACTCTGGGGTTCGAAATGACCGACCAAGCGACGCC<br>CAACCTGCCATCACGAGATTTCGATTCCACCGCCGCCTTCTATGAAAGGTTGGGCTTCGGAATCG<br>TTTTCCGGGACGCCGGCTGGATGATCCTCCAGCGCGGGGATCTCATGCTGGAGTTCTTCGCCCAC<br>CCCGGGCTCGATCCCCTCGGGGGAATCAGAATTCAGTCGACAGCGGCCGCGATCTGCTGTGCC<br>TTCTAGTTGCCAGCCATCTGTTGTTTGCCCCTCCCCCGTGCCTTCCTTGACCCTGGAAGGTGCCAC<br>TCCCACTGTCCTTTCCTAATAAAATGAGGAAATTGCATCGCATTGTCTGAGTAGGTGTCATTCTA<br>TTCTGGGGGGTGGGGTGGGCAGGACAGCAAGGGGGAGGATTGGGAAGACAATAGCAGGCATG<br>CTGGGGATGCGGTGGGCTCTATGGCCGATCAGCGATCGCTGAGGTGGGTGAGTGGGCGTGGCCT<br>GGGGTGGTCATGAAAATATATAAGTTGGGGGTCTTAGGGTCTCTTTATTTGTTGTTGCAGAGACCG<br>CCGGAGCCATGAGCGGGAGCAGCAGCAGCAGCAGTAGCAGCAGCGCCTTGGATGGCAGCATCG<br>TGAGCCCTTATTTGACGACGCGGATGCCCCACTGGGCCGGGGTGCGTCAGAATGTGATGGGCTC<br>CAGCATCGACGGCCGACCCGTCCTGCCCGCAAATTCCGCCACGCTGACCTATGCGACCGTCGCG<br>GGGACGCCGTTGGACGCCACCGCCGCCGCCGCCGCCACCGCAGCCGCCTCGGCCGTGCGCAGCC<br>TGGCCACGGACTTTGCATTCCTGGGACCACTGGCGACAGGGGCTACTTCTCGGCTCGTGCTGCC<br>GCCGTTCGCGATGACAAGCTGACCGCCCTGCTGGCGCAGTTGGATGCGCTTACTCGGGAACTGG<br>GTGACCTTTCTCAGCAGGTCATGGCCCTGCGCCAGCAGGTCTCCTCCCTGCAAGCTGCGGGAAT<br>GCTTCTCCCACAAATGCCGTTTAAGATAAATAAAACCAGACTCTGTTTGGATTAAAGAAAAGTA<br>GCAAGTGCATTGCTCTCTTTATTTCATAATTTTCCGCGCGCGATAGGCCCTAGACCAGCGTTCTC<br>GGTCGTTGAGGGTGCGGTGTATCTTCTCCAGGACGTGGTAGAGGTGGCTCTGGACGTTGAGATA<br>CATGGGCATGAGCCCGTCCCGGGGGTGGAGGTAGCACCACTGCAGAGCTTCATGCTCCGGGGTG<br>GTGTTGTAGATGATCCAGTCGTAGCAGGAGCGCTGGGCATGGTGCCTAAAAATGTCCTTCAGCA<br>GCAGGCCGATGCCAGGGGGAGGCCCTTGGTGTAAGTGTTTACAAAACGGTTAAGTTGGGAAG<br>GGTGCATTCGGGAGAGATGATGTGCATCTTGGACTGTATTTTTAGATTGGCGATGTTTCCGCCC<br>AGATCCCTTCTGGGATTCATGTTGTGCAGGACCACCAGTACAGTGTATCCGGTGCACTTGGGGA<br>ATTTGTCATGCAGCTTAGAGGGAAAAGCGTGGAAGAACTTGGAGACGCCTTTGTGGCCTCCCAG |

DESCRIPTION OF THE SEQUENCES

```
ATTTTCCATGCATTCGTCCATGATGATGGCAATGGGCCCGCGGGAGGCAGCTTGGGCAAAGATA
TTTCTGGGGTCGCTGACGTCGTAGTTGTGTTCCAGGGTGAGGTCGTCATAGGCCATTTTTACAAA
GCGCGGGCGGAGGGTGCCCGACTGGGGGATGATGGTCCCCTCTGGCCCTGGGGCGTAGTTGCCC
TCGCAGATCTGCATTTCCCAGGCCTTAATCTCGGAGGGGGGAATCATATCCACCTGCGGGGCGA
TGAAGAAAACGGTTTCCGGAGCCGGGGAGATTAACTGGGATGAGAGCAGGTTTCTAAGCAGCT
GTGATTTTCCACAACCGGTGGGCCCATAAATAACACCTATAACCGGTTGCAGCTGGTAGTTTAG
AGAGCTGCAGCTGCCGTCGTCCCGGAGGAGGGGGGCCACCTCGTTGAGCATGTCCCTGACGCGC
ATGTTCTCCCCGACCAGATCCGCCAGAAGGCGCTCGCCGCCCAGGGACAGCAGCTCTTGCAAGG
AAGCAAAGTTTTTCAGCGGCTTGAGGCCGTCCGCCGTGGGCATGTTTTTCAGGGTCTGGCTCAGC
AGCTCCAGGCGGTCCCAGAGCTCGGTGACGTGCTCTACGGCATCTCTATCCAGCATATCTCCTCG
TTTCGCGGGTTGGGGCGACTTTCGCTGTAGGGCACCAAGCGGTGGTCGTCCAGCGGGGCCAGAG
TCATGTCCTTCCATGGGCGCAGGGTCCTCGTCAGGGTGGTCTGGGTCACGGTGAAGGGGTGCGC
TCCGGGCTGAGCGCTTGCCAAGGTGCGCTTGAGGCTGGTTCTGCTGGTGCTGAAGCGCTGCCGG
TCTTCGCCCTGCGCGTCGGCCAGGTAGCATTTGACCATGGTGTCATAGTCCAGCCCCTCCGCGGC
GTGTCCCTTGGCGCGCAGCTTGCCCTTGGAGGTGGCGCCGCACGAGGGGCAGAGCAGGCTCTTG
AGCGCGTAGAGCTTGGGGGCGAGGAAGACCGATTCGGGGGAGTAGGCGTCCGCGCCGCAGACC
CCGCACACGGTCTCGCACTCCACCAGCCAGGTGAGCTCGGGGCGCGCCGGGTCAAAAACCAGGT
TTCCCCCATGCTTTTTGATGCGTTTCTTACCTCGGGTCTCCATGAGGTGGTGTCCCCGCTCGGTGA
CGAAGAGGCTGTCCGTGTCTCCGTAGACCGACTTGAGGGGTCTTTTCTCCAGGGGGGTCCCTCGG
TCTTCCTCGTAGAGGAACTCGGACCACTCTGAGACGAAGGCCCGCGTCCAGGACGGAGG
AGGCTATGTGGGAGGGGTAGCGGTCGTTGTCCACTAGGGGGTCCACCTTCTCCAAGGTGTGAAG
ACACATGTCGCCTTCCTCGGCGTCCAGGAAGGTGATTGGCTTGTAGGTGTAGGCCACGTGACCG
GGGGTTCCTGACGGGGGGTATAAAAGGGGTGGGGCGCGCTCGTCGTCACTCTCTTCCGCAT
CGCTGTCTGCGAGGGCCAGCTGCTGGGGTGAGTATTCCCTCTCGAAGGCGGGCATGACCTCCGC
GCTGAGGTTGTCAGTTTCCAAAAACGAGGAGGATTTGATGTTCACCTGTCCCGAGGTGATACCTT
TGAGGGTACCCGCGTCCATCTGGTCAGAAAACACGATCTTTTTATTGTCCAGCTTGGTGGCGAAC
GACCCGTAGAGGGCGTTGGAGAGCAGCTTGGCGATGGAGCGCAGGGTCTGGTTCTTGTCCCTGT
CGGCGCGCTCCTTGGCCGCGATGTTGAGCTGCACGTACTCGCGCGCGACGCAGCGCCACTCGGG
GAAGACGGTGGTGCGCTCGTCGGGCACCAGGCGCACGCGCCAGCCGCGGTTGTGCAGGGTGAC
CAGGTCCACGCTGGTGGCGACCTCGCCGCGCAGGCGCTCGTTGGTCCAGCAGAGACGGCCGCCC
TTGCGCGAGCAGAAGGGGGGCAGGGGGTCGAGCTGGGTCTCGTCCGGGGGGTCCGCGTCCACG
GTGAAAACCCGGGGCGCAGGCGCGCGTCGAAGTAGTCTATCTTGCAACCTTGCATGTCCAGCG
CCTGCTGCCAGTCGCGGGCGGCGAGCGCGCGCTCGTAGGGGTTGAGCGGCGGGCCCCAGGGCAT
GGGGTGGGTGAGTGCGGAGGCGTACATGCCGCAGATGTCATAGACGTAGAGGGGCTCCCGCAG
GACCCCGATGTAGGTGGGGTAGCAGCGGCCGCCGGGATGCTGGCGCGCACGTAGTCATACAGC
TCGTGCGAGGGGGCGAGGAGGTCGGGGCCCAGGTTGGTGCGGGCGGGGCGCTCCGCGCGGAAG
ACGATCTGCCTGAAGATGGCATGCGAGTTGGAAGAGATGGTGGGGCGCTGGAAGACGTTGAAG
CTGGCGTCCTGCAGGCCGACGCGTCGCGCACGAAGGAGGCGTAGGAGTCGCGCAGCTTGTGTA
CCAGCTCGGCGGTGACCTGCACGTCGAGCGCGCAGTAGTCGAGGGTCTCGCGGATGATGTCATA
TTTAGCCTGCCCCTTCTTTTTCCACAGCTCGCGGTTGAGGACAAACTCTTCGCGTCTTTTCCAGTA
CTCTTGGATCGGGAAACCGTCCGGTTCCGAACGGTAAGAGCCTAGCATGTAGAACTGGTTGACG
GCCTGGTAGGCGCAGCAGCCCTTCTCCACGGGGAGGGCGTAGGCCTGCGCGGCCTTGCGGAGCG
AGGTGTGGGTCAGGGCGAAGGTGTCCCTGACCATGACTTTGAGGTACTGGTGCTTGAAGTCGGA
GTCGTCGCAGCCGCCCCGCTCCCAGAGCGAGAAGTCGGTGCGCTTCTTGGAGCGGGGGTTGGGC
AGAGCGAAGGTGACATCGTTGAAGAGGATTTTGCCCGCGCGGGGCATGAAGTTGCGGGTGATGC
GGAAGGGCCCCGGCACTTCAGAGCGGTTGTTGATGACCTGGCGGCGAGCACGATCTCGTCGAA
GCCGTTGATGTTGTGGCCCACGATGTAGAGTTCCAGGAAGCGGGGCCGGCCCTTTACGGTGGGC
AGCTTCTTTAGCTCTTCGTAGGTGAGCTCCTCGGGCGAGGCGAGGCCGTGCTCGGCCAGGGCCC
AGTCCGCGAGGTGCGGGTTGTCTCTGAGGAAGGACTTCCAGAGGTCGCGGGCGCAGGAGGGTCTG
CAGGCGGTCTCTGAAGGTCCTGAACTGGCGGCCCACGGCCATTTTTTCGGGGGTGATGCAGTAG
AAGGTGAGGGGTCTTGCTGCCAGCGGTCCCAGTCGAGCTGCAGGGCGAGGTCGCGCGCGGCG
GTGACCAGGCGCTCGTCGCCCCGAATTTCATGACCAGCATGAAGGGCACGAGCTGCTTTCCGA
AGGCCCCCATCCAAGTGTAGGTCTCTACATCGTAGGTGACAAAGAGGCGCTCCGTGCGAGGATG
CGAGCCGATCGGGAAGAACTGGATCTCCCGCCACCAGTTGGAGGAGTGGCTGTTGATGTGGTGG
AAGTAGAAGTCCCGTCGCCGGGCCGAACACTCGTGCTGGCTTTTGTAAAAGCGAGCGCAGTACT
GGCAGCGCTGCACGGGCTGTACCTCATGCACGAGATGCACCTTTCGCCCGCGCACGAGGAAGCC
GAGGGGAAATCTGAGCCCCCCGCCTGGCTCGCGGCATGGCTGGTTCTTCTTCTACTTTGGATGCGT
GTCCGTCTCCGTCTGGCTCCTCGAGGGGTGTTACGGTGGAGCGGACCACCACGCCGCGCGAGCC
GCAGGTCCAGATATCGGCGCGCGGCGGTCGGAGTTTGATGACGACATCGCGCAGCTGGGAGCTG
TCCATGGTCTGGAGCTCCCGCGGCGGCGGCAGGTCAGCCGGGAGTTCTTGCAGGTTCACCTCGC
AGAGTCGGGCCAGGGCGCGGGGCAGGTCTAGGTGGTACCTGATCTCTAGGGGCGTGTTGGTGGC
GGCGTCGATGGCTTGCAGGAGCCCGCAGCCCCGGGGGGCGACGACGGTGCCCCGCGGGGTGGT
GGTGGTGGTGGCGGTGCAGCTCAGAAGCGGTGCCGCGGGCGGGCCCCCGGAGGTAGGGGGGGC
TCCGGTCCCGCGGGCAGGGCGGCAGCGGCACGTCGGCGTGGAGCGCGGGCAGGAGTTGGTGC
TGTGCCCGGAGGTTGCTGGCGAAGGCGACGACGCGGCGGTTGATCTCCTGGATCTGGCGCCTCT
GCGTGAAGACGACGGGCCCGGTGAGCTTGAACCTGAAAGAGAGTTTGACAGAATCAATCTCGG
TGTCATTGACCGCGGCCTGGCGCAGGATCTCCTGCACGTCTCCCGAGTTGTCTTGGTAGGCGATC
TCGGCCATGAACTGCTCGATCTCTTCCTCCTGGAGGTCTCCGCGTCGGCGCGTTCCACGGTGGC
CGCCAGGTCGTTGGAGATGCGCCCCATGAGCTGCGAGAAGGCGTTGAGTCCGCCCTCGTTCCAG
ACTCGGCTGTAGACCACGCCCCCTGGTCATCGCGGGCGCGCATGACCACCTGCGCGAGGTTGA
GCTCCACGTGCCGCGCGAAGACGGCGTAGTTGCGCAGACGCTGGAAGAGGTAGTTGAGGGTGG
TGGCGGTGTGCTCGGCCACGAAGAAGTTCATGACCCAGCGGCCAACGTGGATTCGTTGATGTC
CCCCAAGGCCTCCAGCCGTTCCATGGCCTCGTAGAAGTCCACGGCGAAGTTGAAAAACTGGGAG
TTGCGCGCCGACACGGTCAACTCCTCCTCAGAAGACGGATGAGCTCGGCGACGGTGTCGCGCA
CCTCGCGCTCGAAGGCTATGGGGATCTCTTCCTCCGCTAGCATCACCACCTCCTCCTCTTCCTCCT
CTTCTGGCACTTCCATGATGGCTTCCTCCTCTTCGGGGGTGGCGGCGGCGGCGGTGGGGAGG
GGGCGCTCTGCGCCGGCGGCGGCGCACCGGGAGGCGGTCCACGAAGCGCGCGATCATCTCCCCG
```

| DESCRIPTION OF THE SEQUENCES |
|---|
| CGGCGGCGGCGCATGGTCTCGGTGACGGCGCGGCCGTTCTCCCGGGGCGCAGTTGGAAGACGC |
| CGCCGGACATCTGGTGCTGGGGCGGGTGGCCGTGAGGCAGCGAGACGGCGCTGACGATGCATCT |
| CAACAATTGCTGCGTAGGTACGCCGCCGAGGGACCTGAGGGAGTCCATATCCACCGGATCCGAA |
| AACCTTTCGAGGAAGGCGTCTAACCAGTCGCAGTCGCAAGGTAGGCTGAGCACCGTGGCGGGCG |
| GCGGGGGGTGGGGGAGTGTCTGGCGGAGGTGCTGCTGATGATGTAATTGAAGTAGGCGGACTT |
| GACACGGCGGATGGTCGACAGGAGCACCATGTCCTTGGGTCCGGCCTGCTGGATGCGGAGGCGG |
| TCGGCTATGCCCCAGGCTTCGTTCTGGCATCGGCGCAGGTCCTTGTAGTAGTCTTGCATGAGCCT |
| TTCCACCGGCACCTCTTCTCCTTCCTCTTCTGCTTCTTCCATGTCTGCTTCGGCCCTGGGGCGGCG |
| CCGCGCCCCCTGCCCCCATGCGCGTGACCCCGAACCCCCTGAGCGGTTGGAGCAGGGCCAGG |
| TCGGCGACGACGCGCTCGGCCAGGATGGCCTGCTGCACCTGCGTGAGGGTGGTTTGGAAGTCAT |
| CCAAGTCCACGAAGCGGTGGTAGGCGCCCGTGTTGATGGTGTAGGTGCAGTTGGCCATGACGGA |
| CCAGTTGACGGTCTGGTGGCCCGGTTGCGACATCTCGGTGTACCTGAGTCGCGAGTAGGCGCGG |
| GAGTCGAAGACGTAGTCGTTGCAAGTCCGCACCAGGTACTGGTAGCCCACCAGGAAGTGCGGCG |
| GCGGCTGGCGGTAGAGGGGCCAGCGCAGGGTGGCGGGGGCTCCGGGGGCCAGGTCTTCCAGCA |
| TGAGGCGGTGGTAGGCGTAGATGTACCTGGACATCCAGGTGATACCCGCGGCGGTGGTGGAGGC |
| GCGCGGGAAGTCGCGCACCCGGTTCCAGATGTTGCGCAGGGGCAGAAAGTGCTCCATGGTAGGC |
| GTGCTCTGTCCAGTCAGACGCGCGCAGTCGTTGATACTCTAGACCAGGGAAAACGAAAGCCGGT |
| CAGCGGGCACTCTTCCGTGGTCTGGTGAATAGATCGCAAGGGTATCATGGCGGAGGGCCTCGGT |
| TCGAGCCCCGGGTCCGGGCCGGACGGTCCGCCATGATCCACGCGGTTACCGCCCGCGTGTCGAA |
| CCCAGGTGTGCGACGTCAGACAACGGTGGAGTGTTCCTTTTGGCGTTTTTCTGGCCGGGCGCGG |
| CGCCGCGTAAGAGACTAAGCCGCGAAAGCGAAAGCAGTAAGTGGCTCGCTCCCCGTAGCCGGA |
| GGGATCCTTGCTAAGGGTTGCGTTGCGGCGAACCCCGGTTCGAATCCCGTACTCGGGCCGGCCG |
| GACCCGCGGCTAAGGTGTTGGATTGGCCTCCCCCTCGTATAAAGACCCCGCTTGCGGATTGACTC |
| CGGACACGGGGACGAGCCCCTTTTATTTTTGCTTTCCCCAGATGCATCCGGTGCTGCGGCAGATG |
| CGCCCCCCGCCCCAGCAGCAGCAACAACACCAGCAAGAGCGGCAGCAACAGCAGCGGGAGTCA |
| TGCAGGGCCCCCTCACCCACCCTCGGCGGGCCGGCCACCTCGGCGTCCGCGGCCGTGTCTGGCG |
| CCTGCGGCGGCGGCGGGGGGCCGGCTGACGACCCCGAGGAGCCCCGCGGCGCAGGGCCAGAC |
| ACTACCTGGACCTGGAGGAGGGCGAGGGCCTGGCGCGGCTGGGGGCGCCGTCTCCCGAGCGCC |
| ACCCGCGGGTGCAGCTGAAGCGCGACTCGCGCGAGGCGTACGTGCCTCGGCAGAACCTGTTCAG |
| GGACCGCGCGGGCGAGGAGCCCGAGGAGATGCGGGACAGGAGGTTCAGCGCAGGGCGGGAGC |
| TGCGGCAGGGGCTGAACCGCGAGCGGCTGCTGCGCGAGGAGGACTTTGAGCCCGACGCGCGGA |
| CGGGGATCAGCCCCGCGCGCGCGCACGTGGCGGCCGCCGACCTGGTGACGGCGTACGAGCAGA |
| CGGTGAACCAGGAGATCAACTTCCAAAAGAGTTTCAACAACCACGTGCGCACGCTGGTGGCGCG |
| CGAGGAGGTGACCATCGGGCTGATGCACCTGTGGGACTTTGTAAGCGCGCTGGTGCAGAACCCC |
| AACAGCAAGCCTCTGACGGCGCAGCTGTTCCTGATAGTGCAGCACAGCAGGGACAACGAGGCG |
| TTTAGGGACGCGCTGCTGAACATCACCGAGCCCGAGGGTCGGTGGCTGCTGGACCTGATTAACA |
| TCCTGCAGAGCATAGTGGTGCAGGAGCGCAGCCTGAGCCTGGCCGACAAGGTGGCGGCCATCA |
| ACTACTCGATGCTGAGCCTGGGCAAGTTTTACGCGCGCAAGATCTACCAGACGCCGTACGTGCC |
| CATAGACAAGGAGGTGAAGATCGACGGTTTTTACATGCGCATGGCGCTGAAGGTGCTCACCCTG |
| AGCGACGACCTGGGCGTGTACCGCAACGAGCGCATCCACAAGGCCGTGAGCGTGAGCCGGCGG |
| CGCGAGCTGAGCGACCGCGAGCTGATGCACAGCCTGCAGCGGGCGCTGGCGGGCGCCGGCAGC |
| GGCGACAGGGAGGCGGAGTCCTACTTCGATGCGGGGCGGACCTGCGCTGGGCGCCCAGCCGG |
| CGGGCCCTGGAGGCCGCGGGGGTCCGCGAGGACTATGACGAGGACGGCGAGGAGGATGAGGAG |
| TACGAGCTAGAGGAGGGCGAGTACCTGGACTAAACCGCGGGTGGTGTTTCCGGTAGATGCAAG |
| ACCCGAACGTGGTGGACCCGGCGCTGCGGGCGGCTCTGCAGAGCCAGCCGTCCGGCCTTAACTC |
| CTCAGACGACTGGCGACAGGTCATGGACCGCATCATGTCGCTGACGGCGCGTAACCCGGACGCG |
| TTCCGGCAGCAGCCGCAGGCCAACAGGCTCTCCGCCATCCTGGAGGCGGTGGTGCCTGCGCGCT |
| CGAACCCCACGCACGAGAAGGTGCTGGCCATAGTGAACGCGCTGGCCGAGAACAGGGCCATCC |
| GCCCGGACGAGGCCGGGCTGGTGTACGACGCGCTGCTGCAGCGCGTGGCCCGCTACAACAGCG |
| GCAACGTGCAGACCAACCTGGACCGGCTGGTGGGGGACGTGCGCGAGGCGGTGGCGCAGCGCG |
| AGCGCGCGGATCGGCAGGGCAACCTGGGCTCCATGGTGGCGCTGAATGCCTTCCTGAGCACGCA |
| GCCGGCCAACGTGCCGCGGGGCAGGAAGACTACACCAACTTTGTGAGCGCGCTGCGGCTGATG |
| GTGACCGAGACCCCCCAGAGCGAGGTGTACCAGTCGGGCCCGGACTACTTCTTCCAGACCAGCA |
| GACAGGGCCTGCAGACGGTGAACCTGAGCCAGGCTTTCAAGAACCTGCGGGGCTGTGGGGCG |
| TGAAGGCGCCCACCGGCGACCGGGCGACGGTGTCCAGCCTGCTGACGCCCAACTCGCGCCTGCT |
| GCTGCTGCTGATCGCGCCGTTCACGGACAGCGGCAGCGTGTCCCGGGACACCTACCTGGGGCAC |
| CTGCTGACCCTGTACCGCGAGGCCATCGGGCAGGCGCAGGTGGACGAGCACACCTTCCAGGAGA |
| TCACCAGCGTGAGCCGCGCGCTGGGGCAGGAGGACACGAGCAGCCTGGAGGCGACTCTGAACT |
| ACCTGCTGACCAACCGGCGGCAGAAGATTCCCTCGCTGCACAGCCTGACCTCCGAGGAGGAGCG |
| CATCTTGCGCTACGTGCAGCAGAGCGTGAGCCTGAACCTGATGCGCGACGGGGTGACGCCCAGC |
| GTGGCGCTGGACATGACCGCGCGCAACATGGAACCGGGCATGTACGCCGCGCACCGGCCTTACA |
| TCAACCGCCTGATGGACTACCTGCATCGCGCGGCGGCCGTGAACCCCGAGTACTTTACCAACGC |
| CATCCTGAACCCGCACTGGCTCCCGCCGCCCGGGTTCTACAGCGGGGCTTCGAGGTCCCGGAG |
| ACCAACGATGGCTTCCTGTGGGACGACATGGACGACAGCGTGTTCTCCCCGCGGCCGCAGGCGC |
| TGGCGGAAGCGTCCCTGCTGCGTCCCAAGAAGGAGGAGGAGGAGGAGGCGAGTCGCCGCCGCG |
| GCAGCAGCGGCGTGGCTTCTCTGTCCGAGCTGGGGGCGGCAGCCGCCGCGCGCCCCGGGTCCCT |
| GGGCGGCAGCCCCTTTCCGAGCCTGGTGGGGTCTCTGCACAGCGAGCGCACCACCCGCCCTCGG |
| CTGCTGGGCGAGGACGAGTACCTGAATAACTCCCTGCTGCAGCCGGTGCGGGAGAAAAACCTGC |
| CTCCCGCCTTCCCCAACAACGGGATAGAGAGCCTGGTGGACAAGATGAGCAGATGGAAGACCT |
| ATGCGCAGGAGCACAGGGACGCGCCTGCGCTCCGGCCGCCCACGCGGCGCCAGCGCCACGACC |
| GGCAGCGGGGCTGGTGTGGGATGACGAGGACTCCGCGGACGATAGCAGCGTGCTGGACCTGG |
| GAGGGAGCGGCAACCCGTTCGCGCACCTGCGCCCCCGCCTGGGGAGGATGTTTTAAAAAAAAAA |
| AAAAAAAAGCAAGAAGCATGATGCAAAAATTAAATAAAACTCACCAAGGCCATGGCGACCGAG |
| CGTTGGTTTCTTGTGTTCCCTTCAGTATGCGGCGCGCGGCGATGTACCAGGAGGGACCTCCTCCC |
| TCTTACGAGAGCGTGGTGGGCGCGGCGGCGGCGGCGCCCTCTTCTCCCTTTGCGTCGCAGCTGCT |
| GGAGCCGCCGTACGTGCCTCCGCGCTACCTGCGGCCTACGGGGGGGAGAAACAGCATCCGTTAC |
| TCGGAGCTGGCGCCCCTGTTCGACACCACCCGGGTGTACCTGGTGGACAACAAGTCGGCGGACG |

DESCRIPTION OF THE SEQUENCES

```
TGGCCTCCCTGAACTACCAGAACGACCACAGCAATTTTTTGACCACGGTCATCCAGAACAATGA
CTACAGCCCGAGCGAGGCCAGCACCCAGACCATCAATCTGGATGACCGGTCGCACTGGGGCGGC
GACCTGAAAACCATCCTGCACACCAACATGCCCAACGTGAACGAGTTCATGTTCACCAATAAGT
TCAAGGCGCGGGTGATGGTGTCGCGCTCGCACACCAAGGAAGACCGGGTGGAGCTGAAGTACG
AGTGGGTGGAGTTCGAGCTGCCAGAGGGCAACTACTCCGAGACCATGACCATTGACCTGATGAA
CAACGCGATCGTGGAGCACTATCTGAAAGTGGGCAGGCAGAACGGGGTCCTGGAGAGCGACAT
CGGGGTCAAGTTCGACACCAGGAACTTCCGCCTGGGGCTGGACCCCGTGACCGGGCTGGTTATG
CCCGGGGTGTACACCAACGAGGCCTTCCATCCCGACATCATCCTGCTGCCCGGCTGCGGGGTGG
ACTTCACTTACAGCCGCCTGAGCAACCTCCTGGGCATCCGCAAGCGGCAGCCCTTCCAGGAGGG
CTTCAGGATCACCTACGAGGACCTGGAGGGGGGCAACATCCCCGCGCTCCTCGATGTGGAGGCC
TACCAGGATAGCTTGAAGGAAAATGAGGCGGGACAGGAGGATACCGCCCCCGCCGCCTCCGCC
GCCGCCGAGCAGGGCGAGGATGCTGCTGACACCGCGGCCGCGGACGGGGCAGAGGCCGACCCC
GCTATGGTGGTGGAGGCTCCCGAGCAGGAGGAGGACATGAATGACAGTGCGGTGCGCGGAGAC
ACCTTCGTCACCCGGGGGGAGGAAAAGCAAGCGGAGGCCGAGGCCGCGGCCGAGGAAAAGCA
ACTGGCGGCAGCAGCGGCGGCGGCGGCGTTGGCCGCGGCGGAGGCTGAGTCTGAGGGGACCAA
GCCCGCCAAGGAGCCCGTGATTAAGCCCCTGACCGAAGATAGCAAGAAGCGCAGTTACAACCT
GCTCAAGGACAGCACCAACACCGCGTACCGCAGCTGGTACCTGGCCTACAACTACGGCGACCCG
TCGACGGGGTGCGCTCCTGGACCCTGCTGTGCACGCCGGACGTGACCTGCGGCTCGGAGCAGG
TGTACTGGTCGCTGCCCGACATGATGCAAGACCCCGTGACCTTCCGCTCCACGCGGCAGGTCAG
CAACTTCCCGGTGGTGGGCGCCGAGCTGCTGCCCGTGCACTCCAAGAGCTTCTACAACGACCAG
GCCGTCTACTCCCAGCTCATCCGCCAGTTCACCTCTCTGACCCACGTGTTCAATCGCTTTCCTGAG
AACCAGATTCTGGCGCGCCCGCCCGCCCCCACCATCACCACCGTCAGTGAAAACGTTCCTGCTCT
CACAGATCACGGGACGCTACCGCTGCGCAACAGCATCGGAGGAGTCCAGCGAGTGACCGTTACT
GACGCCAGACGCCGCACCTGCCCCTACGTTTACAAGGCCTTGGGCATAGTCTCGCCGCGCGTCCT
TTCCAGCCGCACTTTTTGAGCAACACCACCATCATGTCCATCCTGATCTCACCCAGCAATAACTC
CGGCTGGGGACTGCTGCGCGCGCCCAGCAAGATGTTCGGAGGGGCGAGGAAGCGTTCCGAGCA
GCACCCCGTGCGCGTGCGCGGGCACTTCCGCGCCCCCTGGGGAGCGCACAAACGCGGCCGCGCG
GGGCGCACCACCGTGGACGACGCCATCGACTCGGTGGTGGAGCAGGCGCGCAACTACAGGCCG
GCGGTCTCTACCGTGGACGCGGCCATCCAGACCGTGGTGCGGGGCGCGCGGCGGTACGCCAAGC
TGAAGAGCCGCCGGAAGCGCGTGGCCCGCCGCCACCGCCGCCGACCCGGGGCCGCCGCCAAAC
GCGCCGCCGCGGCCCTGCTTCGCCGGGCCAAGCGCACGGGCCGCCGCGCCGCCATGAGGGCCGC
GCGCCGCTTGGCCGCCGGCATCACCGCCGCCACCATGGCCCCCCGTACCCGAAGCAGCGCGGCC
GCCGCCGCCGCCGCCATCAGTGACATGGCCAGCAGGCGCCGGGGCAACGTGTACTGGGTGC
GCGACTCGGTGACCGGCACGCGCGTGCCCGTGCGCTTCCGCCCCCCGCGGACTTGAGATGATGT
GAAAAAACAACACTGAGTCTCCTGCTGTTGTGTGTATCCCAGCGGCGGCGGCGCGCGCAGCGTC
ATGTCCAAGCGCAAAATCAAAGAAGAGATGCTTCCAGGTCGTCGCGCCGGAGATCTATGGGCCCC
CGAAGAAGGAAGAGCAGGATTCGAAGCCCCGCAAGATAAAGCGGGTCAAAAAGAAAAAGAAA
GATGATGACGATGCCGATGGGGAGGTGGAGTTCCTGCGCGCCACGGCGCCCAGGCGCCCGGTGC
AGTGGAAGGGCCGGCGCGTAAAGCGCGTCCTGCGCCCCGGCACCGCGGTGGTCTTCACGCCCGG
CGAGCGCTCCACCCGGACTTTCAAGCGCGTCTATGACGAGGTGTACGGCGACGAAGACCTGCTG
GAGCAGGCCAACGAGCGCTTCGGAGAGTTTGCTTACGGGAAGCGTCAGCGGGCGCTGGGGAAG
GAGGACCTGCTGGCGCTGCCGCTGGACCAGGGCAACCCCACCCCCAGTCTGAAGCCCGTGACCC
TGCAGCAGGTGCTGCCGAGCAGCGCCACCCTCCGAGGCGAAGCGGGGTCTGAAGCGCGAGGGCG
GCGACCTGGCGCCCACCGTGCAGCTCATGGTGCCCAAGCGGCAGAGGCTGGAGGATGTGCTGGA
GAAAATGAAAGTAGACCCCGGTCTGCAGCCGGACATCAGGGTCCGCCCCATCAAGCAGGTGGC
GCCGGGCCTCGGCGTGCAGACCGTGGACGTGGTCATCCCCACCGGCAACTCCCCCGCCGCCGCC
ACCACTACCGCTGCCTCCACGGACATGGAGACACAGACCGATCCCGCCGCAGCCGCAGCCGCAG
CCGCCGCCGCGACCTCCTCGGCGGAGGTGCAGACGGACCCCTGGCTGCCGCCGGCGATGTCAGC
TCCCCGCGCGTCGCGGGCGCAGGAAGTACGGCGCCGCCAACGCGCTCCTGCCCGAGTACGCC
TTGCATCCTTCCATCGCGCCCACCCCCGGCTACCGAGGCTATACCTACCGCCCGCGAAGAGCCA
AGGGTTCCACCCGCCGTCCCCGCCGACGCGCCGCCGCCACCACCCGCCGCCGCCGCAGACG
CCAGCCCGCACTGGCTCCAGTCTCCGTGAGGAAAGTGGCGCGCGACGGACACACCCTGGTGCTG
CCCAGGGCGCGCTACCACCCCAGCATCGTTTAAAAGCCTGTTGTGGTTCTTGCAGATATGGCCCT
CACTTGCCGCCTCCGTTTCCCGGTGCCGGGATACCGAGGAGGAAGATCGCGCCGCAGGAGGGGT
CTGGCCGGCCGCGGCCTGAGCGGAGGCAGCCGCCGCGCGCACCGGCGGCGACGCGCCACCAGC
CGACGCATGCGCGGCGGGGTGCTGCCCCTGTTAATCCCCCTGATCGCCGCGGCGATCGGCGCCG
TGCCCGGGATCGCCTCCGTGGCCTTGCAAGCGTCCCAGAGGCATTGACAGACTTGCAAACTTGC
AAATATGGAAAAAAAAACCCCAATAAAAAAGTCTAGACTCTCACGCTCGCTTGGTCCTGTGACT
ATTTTGTAGAATGGAAGACATCAACTTTTGCGTCGCTGGCCCCGCGTCACGGCTCGCGCCCGTTCC
TGGGACACTGGAACGATATCGGCACCAGCAACATGAGCGGTGGCGCCTTCAGTTGGGGCTCTCT
GTGGAGCGGCATTAAAAGTATCGGGTCTGCCGTTAAAAATTACGGCTCCCGGGCCTGGAACAGC
AGCACGGGCCAGATGTTGAGAGACAAGTTGAAAGAGCAGAACTTCCAGCAGAAGGTGGTGGAG
GGCCTGGCCTCCGGCATCAACGGGGTGGTGGACCTGGCCAACCAGGCCGTGCAGAATAAGATCA
ACAGCAGACTGGACCCCCGGCCGCCGGTGGAGGAGGTGCCGCCGGCGCTGGAGACGGTGTCCC
CCGATGGGCGTGGCGAGAAGCGCCCGCGGCCCGATAGGGAAGAGACCACTCTGGTCACGCAGA
CCGATGAGCCGCCCCCGTATGAGGAGGCCCTGAAGCAAGGTCTGCCCACCACGCGGCCCATCGC
GCCCATGGCCACCGGGGTGGTGGGCGCCACACCCCCGCCACGCTGGACTTGCCTCCGCCCGCC
GATGTGCCGCAGCAGCAGAAGGCGGCACAGCCGGGCCCGCCCGCGACCGCCTCCCGTTCCTCCG
CCGGTCCTCTGCGCCGCGCGGCCAGCGGCCCCGCGGGGGGTCGCGAGGCACGGCAACTGGC
AGAGCACGCTGAACAGCATCGTGGGTCTGGGGGTGCGGTCCGTGAAGCGCCGCCGATGCTACTG
AATAGCTTAGCTAACGTGTTGTATGTGTGTATGCGCCCTATGTCGCCGCCAGAGGAGCTGCTGAG
TCGCCGCGTTCGCGCGCCCACCACCACCGCCACTCCGCCCCTCAAGATGGCGACCCCATCGAT
GATGCCGCAGTGGTCGTACATGCACATCTCGGGCCAGGACGCCTCGGAGTACCTGAGCCCCGGG
CTGGTGCAGTTCGCCCGCGCCACCGAGAGCTACTTCAGCCTGAGTAACAAGTTTAGGAACCCCA
CGGTGGCGCCCACGCACGATGTGACCACCGACCGGTCTCAGCGCCCTGACGCTGCGGTTCATTCC
CGTGGACCGCGAGGACACCGCGTACTCGTACAAGGCGCGGTTCACCCTGGCCGTGGGCGACAAC
CGCGTGCTGGACATGGCCTCCACCTACTTTGACATCCGCGGGGTGCTGGACCGGGGTCCCACTTT
```

| DESCRIPTION OF THE SEQUENCES |
|---|
| CAAGCCCTACTCTGGCACCGCCTACAACTCCCTGGCCCCCAAGGGCGCTCCCAACTCCTGCGAGT |
| GGGAGCAAGAGGAAACTCAGGCAGTTGAAGAAGCAGCAGAAGAGGAAGAAGAAGATGCTGAC |
| GGTCAAGCTGAGGAAGAGCAAGCAGCTACCAAAAAGACTCATGTATATGCTCAGGCTCCCCTTT |
| CTGGCGAAAAAATTAGTAAAGATGGTCTGCAAATAGGAACGGACGCTACAGCTACAGAACAAA |
| AACCTATTTATGCAGACCCTACATTCCAGCCCGAACCCCAAATCGGGGAGTCCCAGTGGAATGA |
| GGCAGATGCTACAGTCGCCGGCGGTAGAGTGCTAAAGAAATCTACTCCCATGAAACCATGCTAT |
| GGTTCCTATGCAAGACCCACAAATGCTAATGGAGGTCAGGGTGTACTAACGGCAAATGCCCAGG |
| GACAGCTAGAATCTCAGGTTGAAATGCAATTCTTTTCAACTTCTGAAAACGCCCGTAACGAGGC |
| TAACAACATTCAGCCCAAATTGGTGCTGTATAGTGAGGATGTGCACATGGAGACCCCGGATACG |
| CACCTTTCTTACAAGCCCGCAAAAAGCGATGACAATTCAAAAATCATGCTGGGTCAGCAGTCCA |
| TGCCCAACAGACCTAATTACATCGGCTTCAGAGACAACTTTATCGGCCTCATGTATTACAATAGC |
| ACTGGCAACATGGGAGTGCTTGCAGGTCAGGCCTCTCAGTTGAATGCAGTGGTGGACTTGCAAG |
| ACAGAAACACAGAACTGTCCTACCAGCTCTTGCTTGATTCCATGGGTGACAGAACCAGATACTT |
| TTCCATGTGGAATCAGGCAGTGGACAGTTATGACCCAGATGTTAGAATTATTGAAAATCATGGA |
| ACTGAAGACGAGCTCCCCAACTATTGTTTCCCTCTGGGTGGCATAGGGGTAACTGACACTTACCA |
| GGCTGTTAAAACCAACAATGGCAATAACGGGGGCCAGGTGACTTGGACAAAAGATGAAACTTTT |
| GCAGATCGCAATGAAATAGGGGTGGGAAACAATTTCGCTATGGAGATCAACCTCAGTGCCAACC |
| TGTGGAGAAACTTCCTGTACTCCAACGTGGCGCTGTACCTACCAGACAAGCTTAAGTACAACCC |
| CTCCAATGTGGACATCTCTGACAACCCCAACACCTACGATTACATGAACAAGCGAGTGGTGGCC |
| CCGGGGCTGGTGGACTGCTACATCAACCTGGGCGCGCGCTGGTCGCTGGACTACATGGACAACG |
| TCAACCCCTTCAACCACCACCGCAATGCGGGCCTGCGCTACCGCTCCATGCTCCTGGGCAACGG |
| GCGCTACGTGCCCTTCCACATCCAGGTGCCCCAGAAGTTCTTTGCCATCAAGAACCTCCTCCTCC |
| TGCCGGGCTCCTACACCTACGAGTGGAACTTCAGGAAGGATGTCAACATGGTCCTCCAGAGCTC |
| TCTGGGTAACGATCTCAGGGTGGACGGGGCCAGCATCAAGTTCGGACATGCATCTGCCTCTACGCC |
| ACCTTCTTCCCCATGGCCCACAACACGGCCTCCACGCTCGAGGCCATGCTCAGGAACGACACCA |
| ACGACCAGTCCTTCAATGACTACCTCTCCGCCGCCAACATGCTCTACCCCATACCCGCCAACGCC |
| ACCAACGTCCCCATCTCCATCCCCTCGCGCAACTGGGCGGCCTTCCGCGGCTGGGCCTTCACCCG |
| CCTCAAGACCAAGGAGACCCCCTCCCTGGGCTCGGGATTCGACCCCCTACTACACCTACTCGGGC |
| TCCATTCCCTACCTGGACGGCACCTTCTACCTCAACCACACTTTCAAGAAGGTCTCGGTCACCTT |
| CGACTCCTCGGTCAGCTGGCCGGGCAACGACCGTCTGCTCACCCCCAACGAGTTCGAGATCAAG |
| CGCTCGGTCGACGGGGAGGGCTACAACGTGGCCCAGTGCAACATGACCAAGGACTGGTTCCTGG |
| TCCAGATGCTGGCCAACTACAACATCGGCTACCAGGGCTTCTACATCCCAGAGAGCTACAAGGA |
| CAGGATGTACTCCTTCTTCAGGAACTTCCAGCCCATGAGCCGGCAGGTGGTGGACCAGACCAAG |
| TACAAGGACTACCAGGAGGTGGGCATCATCCACCAGCACAACAACTCGGGCTTCGTGGGCTACC |
| TCGCCCCCACCATGCGCGAGGGACAGGCCTACCCCGCCAACTTCCCCTATCGCTCATAGGCAA |
| GACCGCGGTCGACAGCATCACCCAGAAAAAGTTCCTCTGCGACGCACCCTCTGGCGCATCCCC |
| TTCTCCAGCAACTTCATGTCCATGGGTGCGCTCTCGGACCTGGGCCAGAACTTGCTCTACGCCAA |
| CTCCGCCCACGCCCTCGACATGACCTTCGAGGTCGACCCCATGGACGAGCCCACCCTTCTCTATG |
| TTCTGTTCGAAGTCTTTGACGTGGTCCGGGTCCACCAGCCGCACCGCGGCGTCATCGAGACCGTG |
| TACCTGCGTACGCCCTTCTCGGCCGGCAACGCCACCACCTAAAGAAGCAAGCCGCAGTCATCGC |
| CGCCTGCATGCCGTCGGGTTCCACCGAGCAAGAGCTCAGGGCCATCGTCAGAGACCTGGGATGC |
| GGGCCCTATTTTTTGGGCACCTTCGACAAGCGCTTCCCTGGCTTTGTCTCCCCACACAAGCTGGC |
| CTGCGCCATCGTCAACACGGCCGGCCGCGAGACCGGGGGCGTGCACTGGCTGGCCTTCGCCTGG |
| AACCCGCGCTCCAAAACATGCTTCCTCTTTGACCCCTTCGGCTTTTCGGACCAGCGGCTCAAGCA |
| AATCTACGAGTTCGAGTACGAGGGCTTGCTGCGTCGCAGCGCCATCGCCTCCTCGCCCGACCGCT |
| GCGTCACCCTCGAAAAGTCCACCCAGACCGTGCAGGGGCCCGACTCGGCCGCCTGCGGTCTCTT |
| CTGCTGCATGTTTCTGCACGCCTTTGTGCACTGGCCTCAGAGTCCCATGGACCGCAACCCCACCA |
| TGAACTTGCTGACGGGGGTGCCCAACTCCATGCTCCAGAGCCCCCAGGTCGAGCCCACCCTGCG |
| CCGCAACCAGGAGCAGCTCTACAGCTTCCTGGAGCGCCACTCGCCTTACTTCCGCCGCCACAGC |
| GCACAGATCAGGAGGGCCACCTCCTTCTGCCACTTGCAAGAGATGCAAGAAGGGTAATAACGAT |
| GTACACACTTTTTTTCTCAATAAATGGCATCTTTTTATTTATACAAGCTCTCTGGGGTATTCATTT |
| CCCACCACCACCCGCCGTTGTCGCCATCTGGCTCTATTTAGAAATCGAAAGGGTTCTGCCGGGAG |
| TCGCCGTGCGCCACGGGCAGGGACACGTTGCGATACTGGTAGCGGGTGCCCCACTTGAACTCGG |
| GCACCACCAGGCGAGGCAGCTCGGGGAAGTTTTCGCTCCACAGGCTGCGGGTCAGCACCAGCGC |
| GTTCATCAGGTCGGGCGCCGAGATCTTGAAGTCGCAGTTGGGGCCGCCGCCCTGCGCGCGCGAG |
| TTGCGGTACACCGGGTTGCAGCACTGGAACACCAACAGCGCCGGGTGCTTCACGCTGGCCAGCA |
| CGCTGCGGTCGGAGATCAGCTCGGCGTCCAGGTCCTCCGCGTTGCTCAGCGCGGAACGGGGTCAT |
| CTTGGGCACTTGCCGCCCAGGAAGGGCGCGTGCCCCGGTTTCGAGTTGCAGTCGCAGCGCAGC |
| GGGATCAGCAGGTGCCCGTGCCCGGACTCGGCGTTGGGGTACAGCGCGCGCATGAAGGCCTGCA |
| TCTGGCGGAAGGCCATCTGGGCCTTGGCGCCCTCCGAGAAGAACATGCCGCAGGACTTGCCCGA |
| GAACTGGTTTGCGGGGCAGCTGGCGTCGTGCAGGCAGCAGCGCGCGTCGGTGTTGGCGATCTGC |
| ACCACGTTGCGCCCCACCGGTTCTTCACGATCTTGGCCTTGGACGATTGCTCCTTCAGCGCGCG |
| CTGCCCGTTCTCGCTGGTCACATCCATCTCGATCACATGTTCCTTGTTCACCATGCTGCTGCCGTG |
| CAGACACTTCAGCTCGCCCTCCGTCTCGGTGCAGCGGTGCTGCCACAGCGCGCAGCCCGTGGGC |
| TCGAAAGACTTGTAGGTCACCTCCGCGAAGGACTGCAGGTACCCCTGCAAAAAGCGGCCCATCA |
| TGGTCACGAAGGTCTTGTTGCTGCTGAAGGTCAGCTGCAGCCCGCGGTGCTCCTCGTTCAGCCAG |
| GTCTTGCACACGGCCGCCAGCGCCTCCACCTGGTCGGGCAGCATCTTGAAGTTCACCTTCAGCTC |
| ATTCTCCACGTGGTACTTGTCCATCAGCGTGCGCGCCGCCTCCATGCCCTTCTCCCAGGCCGACA |
| CCAGCGGCAGGCTCACGGGGTTCTTCACCATCACCGTGGCCGCCGCCTCCGCCGCGCTTTCGCTT |
| TCCGCCCCGCTGTTCTCTTCCTCTTCCTCCTCTTCCTCGCCGCCGCCCACTCGCAGCCCCCGCACC |
| ACGGGGTCGTCTTCCTGCAGGCGCTGCACCTTGCGTTGCGTTGCGCCCCTGCTTGATGCGCAC |
| GGGCGGGTTGCTGAAGCCCACCATCACCAGCGCGGCCTCTTCTTGCTCGTCCTCGCTGTCCAGAA |
| TGACCTCCGGGAGGGGGGTTGGTCATCCTCAGTACCGAGGCACGCTTCTTTTTCTTCCTGGGG |
| GCGTTCGCCAGCTCCGCGGCTGCGGCCGCTGCCGAGGTCGAAGGCCGAGGGCTGGGCGTGCGCG |
| GCACCAGCGCGTCCTGCGAGCCGTCCTCGTCCTCCTCGGACTCGAGACGGAGGCGGGCCCGCTT |
| CTTCGGGGGCGCGCGGGGCGGCGGAGGCGGCGGCGGCGACGAGACGGGGACGAGACATCGTC |
| CAGGGTGGGTGGACGGCGGGCCGCGCCGCGTCCGCGCTCGGGGGTGGTCTCGCGCTGGTCCTCT |

DESCRIPTION OF THE SEQUENCES

```
TCCCGACTGGCCATCTCCCACTGCTCCTTCTCCTATAGGCAGAAAGAGATCATGGAGTCTCTCAT
GCGAGTCGAGAAGGAGGAGGACAGCCTAACCGCCCCCTCTGAGCCCTCCACCACCGCCGCCACC
ACCGCCAATGCCGCCGGACGACGCGCCCACCGAGACCACCGCAGTACCACCCTCCCCAGCG
ACGCACCCCCGCTCGAGAATGAAGTGCTGATCGAGCAGGACCCGGGTTTTGTGAGCGGAGAGG
AGGATGAGGTGGATGAGAAGGAGAAGGAGGAGGTCGCCGCCTCAGTGCCAAAAGAGGATAAA
AAGCAAGACCAGGACGACGCAGATAAGGATGAGACAGCAGTCGGGCGGGGGAACGGAAGCCA
TGATGCTGATGACGGCTACCTAGACGTGGGAGACGACGTGCTGCTTAAGCACCTGCACCGCCAG
TGCGTCATCGTCTGCGACGCGCTGCAGGAGCGCTGCGAAGTGCCCCTGGACGTGGCGGAGGTCA
GCCGCGCCTACGAGCGGCACCTCTTCGCCGCGCACGTGCCCCCCAAGCGCCGGGAGAACGGCAC
CTGCGAGCCCAACCCGCGTCTCAACTTCTACCCGGTCTTCGCGGTACCCGAGGTGCTGGCCACCT
ACCACATCTTTTTCCAAAACTGCAAGATCCCCCTCTCCTGCCGCGCCAACCGCACCCGCGCCGAC
AAAACCCTGACCCTGCGGCAGGGCGCCCACATACCTGATATCGCCTCTCTGGAGGAAGTGCCCA
AGATCTTCGAGGGTCTCGGTCGCGACGAGAAACGGGCGGCGAACGCTCTGCACGGAGACAGCG
AAAACGAGAGTCACTCGGGGGTGCTGGTGGAGCTCGAGGGCGACAACGCGCGCCTGGCCGTAC
TCAAGCGCAGCATAGAGGTCACCCACTTTGCCTACCCGGCGCTCAACCTGCCCCCCAAGGTCAT
GAGTGTGGTCATGGGCGAGCTCATCATGCGCGCGCCCAGCCCCTGGCCGCGGATGCAAACTTG
CAAGAGTCCTCCGAGGAAGGCCTGCCCGCGGTCAGCGACGAGCAGCTGGCGCGCTGGCTGGAG
ACCCGCGACCCCGCGCAGCTGGAGGAGCGGCGCAAGCTCATGATGGCCGCGGTGCTGGTCACCG
TGGAGCTCGAGTGTCTGCAGCGCTTCTTCGCGGACCCCGAGATGCAGCGCAAGCTCGAGGAGAC
CCTGCACTACACCTTCCGCCAGGGCTACGTGCGCCAGGCCTGCAAGATCTCCAACGTGGAGCTC
TGCAACCTGGTCTCCTACCTGGGCATCCTGCACGAGAACCGCCTCGGGCAGAACGTCCTGCACT
CCACCCTCAAAGGGGAGGCGCGCCGCGACTACATCCGCGACTGCGCCTACCTCTTCCTCTGCTAC
ACCTGGCAGACGGCCATGGGGGTCTGGCAGCAGTGCCTGGAGGAGCGCAACCTCAAGGAGCTG
GAAAAGCTCCTCAAGCGCACCCTCAGGGACCTCTGGACGGGCTTCAACGAGCGCTCGGTGGCCG
CCGCGCTGGCGGACATCATCTTTCCCGAGCGCCTGCTCAAGACCCTGCAGCAGGGCCTGCCCGA
CTTCACCAGCCAGAGCATGCTGCAGAACTTCAGGACTTTCATCCTGGAGCGCTCGGGCATCCTGC
CGGCCACTTGCTGCGCGCTGCCCAGCGACTTCGTGCCCATCAAGTACAGGGAGTGCCCGCCGCC
GCTCTGGGGCCACTGCTACCTCTTCCAGCTGGCCAACTACCTCGCCTACCACTCGGACCTCATGG
AAGACGTGAGCGGCGAGGGCCTGCTCGAGTGCCACTGCCGCTGCAACCTCTGCACGCCCCACCG
CTCTCTAGTCTGCAACCCGCAGCTGCTCAGCGAGAGTCAGATTATCGGTACCTTCGAGCTGCAGG
GTCCCTCGCCTGACGAGAAGTCCGCGGCTCCAGGGCTGAAACTCACTCCGGGGCTGTGGACTTC
CGCCTACCTACGCAAATTTGTACCTGAGGACTACCACGCCCACGAGATCAGGTTCTACGAAGAC
CAATCCCGCCCGCCCAAGGCGGAGCTCACCGCCTGCGTCATCACCCAGGGGCACATCCTGGGCC
AATTGCAAGCCATCAACAAAGCCCGCCGAGAGTTCTTGCTGAAAAAGGGTCGGGGGGTGTACCT
GGACCCCCAGTCCGGCGAGGAGCTAAACCCGCTACCCCCGCCGCCGCCCAGCAGCGGGACCTT
GCTTCCCAGGATGGCACCCAGAAAGAAGCAGCAGCCGCCGCCGCCGCCGCAGCCATACATGCTT
CTGGAGGAAGAGGAGGAGGACTGGGACAGTCAGGCAGAGGAGGTTTCGGACGAGGAGCAGGA
GGAGATGATGGAAGACTGGGAGGAGGACAGCAGCCTAGACGAGGAAGCTTCAGAGGCCGAAG
AGGTGGCAGACGCAACACCATCGCCCTCGGTCGCAGCCCCTCGCCGGGGCCCTGAAATCCTC
CGAACCCAGCACCAGCGCTATAACCTCCGCTCCTCCGGCGCCGGCGCCACCCGCCCGCAGACCC
AACCGTAGATGGGACACCACAGGAACCGGGGTCGGTAAGTCCAAGTGCCCGCCGCCGCCACCG
CAGCAGCAGCAGCAGCAGCGCCAGGGCTACCGCTCGTGGCGGGCACAAGAACGCCATAGTC
GCCTGCTTGCAAGACTGCGGGGGCAACATCTCTTTCGCCCGCCGCTTCCTGCTATTCCACCACGG
GGTCGCCTTTCCCCGCAATGTCCTGCATTACTACCGTCATCTCTACAGCCCCTACTGCAGCGGCG
ACCCAGAGGCGGCAGCGGCAGCCACAGCGGCGACCACCACCTAGGAAGATATCCTCCGCGGGC
AAGACAGCGGCAGCAGCGGCCAGGAGACCCGCGGCAGCAGCGGCGGGAGCGGTGGGCGCACT
GCGCCTCTCGCCCAACGAACCCCTCTCGACCCGGGAGCTCAGACACAGGATCTTCCCCACTTTGT
ATGCCATCTTCCAACAGAGCAGAGGCCAGGAGCAGGAGCTGAAAATAAAAAACAGATCTCTGC
GCTCCCTCACCCGCAGCTGTCTGTATCACAAAAGCGAAGATCAGCTTCGGCGCACGCTGGAGGA
CGCGGAGGCACTCTTCAGCAAATACTGCGCGCTCACTCTTAAAGACTAGTCCGCGCCCTTCTCG
AATTTAGGCGGGAGAAAACTACGTCATCGCCGGCCGCCGCCCAGCCCGCCCAGCCGAGATGAGC
AAAGAGATTCCCACGCCATACATGTGGAGCTACCAGCCGCAGATGGGACTCGCGGCGGGAGCG
GCCCAGGACTACTCCACCCGCATGAACTACATGAGCGCGGGACCCCACATGATCTCACAGGTCA
ACGGGATCCGCGCCCAGCGAAACCAAATACTGCTGGAACAGGCGGCCATCACCGCCACGCCCC
GCCATAATCTCAACCCCCGAAATTGGCCCGCCGCCCTCGTGTACCAGGAAACCCCCTCCGCCAC
CACCGTACTACTTCCGCGTGACGCCCAGGCCGAAGTCCAGATGACTAACTCAGGGGCGCAGCTC
GCGGGCGGCTTTCGTCACGGGGCGCGGCCGCTCCGACCAGGTATAAGACACCTGATGATCAGAG
GCCGAGGTATCCAGCTCAACGACGAGTCGGTGAGCTCTTCGCTCGGTCTCCGTCCGGACGGAAC
TTTCCAGCTCGCCGGATCCGGCCGCTCTTCGTTCACGCCCCGCCAGGCGTACCTGACTCTGCAGA
CCTCGTCCTCGGAGCCCGCTCCGGCGGCATCGGAACCCTCCAGTTCGTGGAGGAGTTCGTGCCC
TCGGTCTACTTCAACCCCTTCTCGGGACCTCCCGGACGCTACCCCGACCAGTTCATTCCGAACTT
TGACGCGGTGAAGGACTCGGCGGACGGCTACGACTGAATGTCAGGTGTCGAGGCAGAGCAGCT
TCGCCTGAGACACCTCGAGCACTGCCGCCGCCACAAGTGCTTCGCCCGCGGTTCTGGTGAGTTCT
GCTACTTTCAGCTACCCGAGGAGCATACCGAGGGGCCGGCGCACGGCGTCCGCCTGACCACCCA
GGGCGAGGTTACCTGTTCCCTCATCCGGGAGTTTACCCTCCGTCCCCTGCTAGTGGAGCGGGAGC
GGGGTCCCTGTGTCCTAACTATCGCCTGCAACTGCCCTAACCCTGGATTACATCAAGATCTTTGC
TGTCATCTCTGTGCTGAGTTTAATAAACGCTGAGATCAGAATCTACTGGGGCTCCTGTCGCCATC
CTGTGAACGCCACCGTCTTCACCCACCCCGACCAGGCCCAGGCGAACCTCACCTGCGGTCTGCA
TCGGAGGGCCAAGAAGTACCTCACCTGGTACTTCAACGGCACCCCCTTTGTGGTTTACAACAGCT
TCGACGGGGACGGAGTCTCCCTGAAAGACCAGCTCTCCGGTCTCAGCTACTCCATCCACAAGAA
CACCACCCTCCAACTCTTCCCTCCCTACCTGCCGGGAACCTACGAGTGCGTCACCGGCCGCTGCA
CCCACCTCACCCGCCTGATCGTAAACCAGAGCTTTCGGGAACAGATAACTCCCTCTTCCCCAGA
ACAGGAGGTGAGCTCAGGAAACTCCCCGGGGACCAGGGCGGAGACGTACCTTCGACCCTTGTG
GGGTTAGGATTTTTTATTACCGGGTTGCTGGCTCTTTTAATCAAAGTTTCCTTGAGATTTGTTCTT
TCCTTCTACGTGTATGAACACCTCAACCTCCAATAACTCTACCCTTTCTTCGGAATCAGGTGACTT
CTCTGAAATCGGGCTTGGTGTGCTGCTTACTCTGTTGATTTTTTTCCTTATCATACTCAGCCTTCT
GTGCCTCAGGCTCGCCGCCTGCTGCGCACACATCTATATCTACTGCTGGTTGCTCAAGTGCAGGG
```

-continued

DESCRIPTION OF THE SEQUENCES

```
GTCGCCACCCAAGATGAACAGGTACATGGTCCTATCGATCCTAGGCCTGCTGGCCCTGGCGGCC
TGCAGCGCCGCCAAAAAAGAGATTACCTTTGAGGAGCCCGCTTGCAATGTAACTTTCAAGCCCG
AGGGTGACCAATGCACCACCCTCGTCAAATGCGTTACCAATCATGAGAGGCTGCGCATCGACTA
CAAAAACAAAACTGGCCAGTTTGCGGTCTATAGTGTGTTTACGCCCGGAGACCCCTCTAACTACT
CTGTCACCGTCTTCCAGGGCGGACAGTCTAAGATATTCAATTACACTTTCCCTTTTTATGAGTTAT
GCGATGCGGTCATGTACATGTCAAAACAGTACAACCTGTGGCCTCCCTCTCCCAGGCGTGTGTG
GAAAATACTGGGTCTTACTGCTGTATGGCTTTCGCAATCACTACGCTCGCTCTAATCTGCACGGT
GCTATACATAAAATTCAGGCAGAGGCGAATCTTTATCGATGAAAAGAAAATGCCTTGATCGCTA
ACACCGGCTTTCTATCTGCAGAATGAATGCAATCACCTCCCTACTAATCACCACCACCCTCTTG
CGATTGCCCATGGGTTGACACGAATCGAAGTGCCAGTGGGGTCCAATGTCACCATGGTGGGCCC
CGCCGGCAATTCCACCCTCATGTGGGAAAAATTTGTCCGCAATCAATGGGTTCATTTCTGCTCTA
ACCGAATCAGTATCAAGCCCAGAGCCATCTGCGATGGGCAAAATCTAACTCTGATCAATGTGCA
AATGATGGATGCTGGGTACTATTACGGGCAGCGGGGAGAAATCATTAATTACTGGCGACCCCAC
AAGGACTACATGCTGCATGTAGTCGAGGCACTTCCCACTACCACCCCACTACCACCTCTCCCAC
CACCACCACCACTACTACTACTACTACTACTACTACTACTACGCTGCCCGCCATA
CCCGCAAAAGCACCATGATTAGCACAAAGCCCCCTCGTGCTCACTCCCACGCCGGCGGGCCCAT
CGGTGCGACCTCAGAAACCACCGAGCTTTGCTTCTGCCAATGCACTAACGCCAGCGCTCATGAA
CTGTTCGACCTGGAGAATGAGGATGTCCAGCAGAGCTCCGCTTGCCTGACCCAGGAGGCTGTGG
AGCCCGTTGCCCTGAAGCAGATCGGTGATTCAATAATTGACTCTTCTTCTTTTGCCACTCCCGAA
TACCCTCCCGATTCTACTTTCCACATCACGGGTACCAAAGACCCTAACCTCTCTTTCTACCTGATG
CTGCTGCTCTGTATCTCTGTGGTCTCTTCCGCGCTGATGTTACTGGGGATGTTCTGCTGCCTGATC
TGCCGCAGAAAGAGAAAAGCTCGCTCTCAGGGCCAACCACTGATGCCCTTCCCCTACCCCCCGG
ATTTTGCAGATAACAAGATATGAGCTCGCTGCTGACACTAACCGCTTTACTAGCCTGCGCTCTAA
CCCTTGTCGCTTGCGACTCGAGATTCCACAATGTCACAGCTGTGGCAGGAGAAATGTTACTTTC
AACTCCACGGCCGATACCCAGTGGTCGTGGAGTGGCTCAGGTAGCTACTTAACTATCTGCAATA
GCTCCACTTCCCCCGGCATATCCCCAACCAAGTACCAATGCAATGCCAGCCTGTTCACCCTCATC
AACGCTTCCACCCTGGACAATGGACTCTATGTAGGCTATGTACCCTTTGGTGGGCAAGGAAAGA
CCCACGCTTACAACCTGGAAGTTCGCCAGCCCAGAACCACTACCCAAGCTTCTCCCACCACCAC
CACCACCACCACCATCACCAGCAGCAGCAGCAGCAGCAGCCACAGCAGCAGCAGCAGATTATT
GACTTTGGTTTTGGCCAGCTCATCTGCCGCTACCCAGGCCATCTACAGCTCTGTGCCCGAAACCA
CTCAGATCCACCGCCCAGAAACGACCACCGCCACCACCCTACACACCTCCAGCGATCAGATGCC
GACCAACATCACCCCCTTGGCTCTTCAAATGGGACTTACAAGCCCCACTCCAAAACCAGTGGAT
GCGGCCGAGGTCTCCGCCCTCGTCAATGACTGGGCGGGGCTGGGAATGTGGTGGTTCGCCATAG
GCATGATGGCGCTCTGCCTGCTTCTGCTCTGGCTCATCTGCTGCCTCCACCGCAGGCGAGCCAGA
CCCCCCATCTATAGACCCATCATTGTCCTGAACCCCGATAATGATGGGATCCATAGATTGGATGG
CCTGAAAAACCTACTTTTTTCTTTTACAGTATGATAAATTGAGACATGCCTCGCATTTTCTTGTAC
ATGTTCCTTCTCCCACCTTTTCTGGGGTGTTCTACGCTGGCCGCTGTGTCTCACCTGGAGGTAGAC
TGCCTCTCACCCTTCACTGTCTACCTGCTTTACGGATTGGTCACCCTCACTCTCATCTGCAGCCTA
ATCACAGTAATCATCGCCTTCATCCAGTGCATTGATTACATCTGTGTGCGCCTCGCATACTTCAG
ACACCACCCGCAGTACCGAGACAGGAACATTGCCCAACTTCTAAGACTGCTCTAATCATGCATA
AGACTGTGATCTGCCTTCTGATCCTCTGCATCCTGCCCACCCTCACCTCCTGCCAGTACACCACA
AAATCTCCGCGCAAAAGACATGCCTCCTGCCGCTTCACCCAACTGTGGAATATACCCAAATGCT
ACAACGAAAAGAGCGAGCTCTCCGAAGCTTGGCTGTATGGGGTCATCTGTGTCTTAGTTTTCTGC
AGCACTGTCTTTGCCCTCATAATCTACCCCTACTTTGATTTGGGATGGAACGCGATCGATGCCAT
GAATTACCCCACCTTTCCCGCACCCGAGATAATTCCACTGCGACAAGTTGTACCCGTTGTCGTTA
ATCAACGCCCCCCATCCCCTACGCCCACTGAAATCAGCTACTTTAACCTAACAGGCGGAGATGA
CTGACGCCCTAGATCTAGAAATGGACGGCATCAGTACCGAGCAGCGTCTCCTAGAGAGGCGCAG
GCAGGCGGCTGAGCAAGAGCGCCTCAATCAGGAGCTCCGAGATCTCGTTAACCTGCACCAGTGC
AAAAGAGGGCATCTTTTGTCTGGTAAAGCAGGCCAAAGTCACCTACGAGAAGACCGGCAACAGC
CACCGCCTCAGTTACAAATTGCCCACCCAGCGCCAGAAGCTGGTGCTCATGGTGGGTGAGAATC
CCATCACCGTCACCCAGCACTCGGTAGAGACCGAGGGGTGTCTGCACTCCCCTGTCGGGGTCC
AGAAGACCTCTGCACCCTGGTAAAGACCCTGTGCGGTCTCAGAGATTTAGTCCCCTTTAACTAAT
CAAACACTGGAATCAATAAAAAGAATCACTTACTTAAAATCAGACAGCAGGTCTCTGTCCAGTT
TATTCAGCAGCACCTCCTTCCCCTCCTCCCAACTCTGGTACTCCAAACGCCTTCTGGCGGCAAAC
TTCCTCCACACCCTGAAGGGAATGTCAGATTCTTGCTCCTGTCCCTCCGCACCCACTATCTTCATG
TTGTTGCAGATGAAGCGCACCAAAACGTCTGACGAGAGCTTCAACCCCGTGTACCCCTATGACA
CGGAAAGCGGCCCTCCCTCCGTCCCTTTCCTCACCCCTCCCTTCGTGTCTCCCGATGGATTCCAA
GAAAGTCCCCCCGGGGTCCTGTCTCTGAACCTGGCCGAGCCCCTGGTCACTTCCCACGGCATGCT
CGCCCTGAAAATGGGAAGTGGCCTCTCCCTGGACGACGCTGGCAACCTCACCTCTCAAGATATC
ACCACCGCTAGCCCTCCCCTCAAAAAAACCAAGACCAACCTCAGCCTAGAAACCTCATCCCCCC
TAACTGTGAGCACCTCAGGCGCCCTCACCGTAGCAGCCGCCGCTCCCCTGGCGGTGGCCGGCAC
CTCCCTCACCATGCAATCAGAGGCCCCCCTGACAGTACAGGATGCAAAACTCACCCTGGCCACC
AAAGGCCCCCTGACCGTGTCTGAAGGCAAACTGGCCTTGCAAACATCGGCCCCGCTGACGGCCG
CTGACAGCAGCACCCTCACAGTCAGTGCCACACCACCCCTTAGCACAAGCAATGGCAGCTTGGG
TATTGACATGCAAGCCCCCATTTACACCACCAATGGAAAACTAGGACTTAACTTTGGCGCTCCCC
TGCATGTGGTAGACAGCCTAAATGCACTGACTGTAGTTACTGGCCAAGGTCTTACGATAAACGG
AACAGCCCTACAAACTAGAGTCTCAGGTGCCCTCAACTATGACACATCAGGAAACCTAGAATTG
AGAGCTGCAGGGGGTATGCGAGTTGATGCAAATGGTCAACTTATCCTTGATGTAGCTTACCCATT
TGATGCACAAAACAATCTCAGCCTTAGGCTTGGACAGGGACCCCTGTTTGTTAACTCTGCCCACA
ACTTGGATGTTAACTACAACAGAGGCCTCTACCTGTTCACATCTGGAAATACCAAAAAGCTAGA
AGTTAATATCAAAACAGCCAAGGGTCTCATTTATGATGACACTGCTATAGCAATCAATGCGGGT
GATGGGCTACAGTTTGACTCAGGCTCAGATACAAATCCATTAAAAACTAAACTTGGATTAGGAC
TGGATTATGACTCCAGCAGAGCCATAATTGCTAAACTGGGAACTGGCCTAAGCTTTGACAACAC
AGGTGCCATCACAGTAGGCAACAAAATGATGACAAGCTTACCTTGTGGACCACACCAGACCCA
TCCCCTAACTGTAGAATCTATTCAGAGAAAGATGCTAAATTCACACTTGTTTTGACTAAATGCGG
CAGTCAGGTGTTGGCCAGCGTTTCTGTTTTATCTGTAAAAGGTAGCCTTGCGCCCATCAGTGGCA
CAGTAACTAGTGCTCAGATTGTCCTCAGATTTGATGAAAATGGAGTTCTACTAAGCAATTCTTCC
```

DESCRIPTION OF THE SEQUENCES

```
CTTGACCCTCAATACTGGAACTACAGAAAAGGTGACCTTACAGAGGGCACTGCATATACCAACG
CAGTGGGATTTATGCCCAACCTCACAGCATACCCAAAAACACAGAGCCAAACTGCTAAAAGCAA
CATTGTAAGTCAGGTTTACTTGAATGGGGACAAATCCAAACCCATGACCCTCACCATTACCCTCA
ATGGAACTAATGAAACAGGAGATGCCACAGTAAGCACTTACTCCATGTCATTCTCATGGAACTG
GAATGGAAGTAATTACATTAATGAAACGTTCCAAACCAACTCCTTCACCTTCTCCTACATCGCCC
AAGAATAAAAAGCATGACGCTGTTGATTTGATTCAATGTGTTTCTGTTTTATTTTCAAGCACAAC
AAAATCATTCAAGTCATTCTTCCATCTTAGCTTAATAGACACAGTAGCTTAATAGACCCAGTAGT
GCAAAGCCCCATTCTAGCTTATAGATCAGACAGTGATAATTAACCACCACCACCACCATACCTTT
TGATTCAGGAAATCATGATCATCACAGGATCCTAGTCTTCAGGCCGCCCCTCCCTCCCAAGACA
CAGAATACACAGTCCTCTCCCCCCGACTGGCTTTAAATAACACCATCTGGTTGGTCACAGACATG
TTCTTAGGGGTTATATTCCACACGGTCTCCTGCCGCGCCAGGCGCTCGTCGGTGATGTTGATAAA
CTCTCCCGGCAGCTCGCTCAAGTTCACGTCGCTGTCCAGCGGCTGAACCTCCGGCTGACGCGATA
ACTGTGCGACCGGCTGCTGGACGAACGGAGGCCGCGCCTACAAGGGGGTAGAGTCATAATCCTC
GGTCAGGATAGGGCGGTGATGCAGCAGCAGCGAGCGAAACATCTGCTGCCGCCGCCGCTCCGTC
CGGCAGGAAAACAACACGCCGGTGGTCTCCTCCGCGATAATCCGCACCGCCCGCAGCATCAGCT
TCCTCGTTCTCCGCGCGCAGCACCTCACCCTTATCTCGCTCAAATCGGCGCAGTAGGTACAGCAC
AGCACCACGATGTTATTCATGATCCCACAGTGCAGGGCGCTGTATCCAAAGCTCATGCCGGGAA
CCACCGCCCCACGTGGCCATCGTACCACAAGCGCACGTAAATCAAGTGTCGACCCCTCATGAA
CGCGCTGGACACAAACATTACTTCCTTGGGCATGTTGTAATTCACCACCTCCCGGTACCAGATAA
ACCTCTGGTTGAACAGGGCACCTTCCACCACCATCCTGAACCAAGAGGCCAGAACCTGCCCACC
GGCTATGCACTGCAGGGAACCCGGGTTGGAACAATGACAATGCAGACTCCAAGGCTCGTAACCG
TGGATCATCCGGCTGCTGAAGGCATCGATGTTGGCACAACACAGACACACGTGCATGCACTTTC
TCATGATTAGCAGCTCTTCCCTCGTCAGGATCATATCCCAAGGAATAACCCATTCTTGAATCAAC
GTAAAACCCACACAGCAGGGAAGGCCTCGCACATAACTCACGTTGTGCATGGTCAGCGTGTTGC
ATTCCGGAAACAGCGGATGATCCTCCAGTATCGAGGCGCGGGTCTCCTTCTCACAGGGAGGTAA
AGGGTCCCTGCTGTACGGACTGCGCCGGGACGACCGAGATCGTGTTGAGCGTAGTGTCATGGAA
AAGGGAACGCCGGACGTGGTCATACTTCTTGAAGCAGAACCAGGTTCGCGCGTGGCAGGCCTCC
TTGCGTCTGCGGTCTCGCCGTCTAGCTCGCTCCGTGTGATAGTTGTAGTACAGCCACTCCCGCAG
AGCGTCGAGGCGCACCCTGGCTTCCGGATCTATGTAGACTCCGTCTTGCACCGCGGCCCTGATAA
TATCCACCACCGTAGAATAAGCAACACCCAGCCAAGCAATACACTCGCTCTGCGAGCGGCAGAC
AGGAGGAGCGGGCAGAGATGGGAGAACCATGATAAAAAACTTTTTTTAAAGAATATTTTCCAAT
TCTTCGAAAGTAAGATCTATCAAGTGGCAGCGCTCCCCTCCACTGGCGCGGTCAAACTCTACGG
CCAAAGCACAGACAACGGCATTTCTAAGATGTTCCTTAATGGCGTCCAAAAGACACACCGCTCT
CAAGTTGCAGTAAACTATGAATGAAAACCCATCCGGCTGATTTTCCAATATAGACGCGCCGGCA
GCGTCCACCAAACCCAGATAATTTTCTTCTCTCCAGCGGTTTACGATCTGTCTAAGCAAATCCCT
TATATCAAGTCCGACCATGCCAAAAATCTGCTCAAGAGCGCCCTCCACCTTCATGTACAAGCAG
CGCATCATGATTGCAAAAATTCAGGTTCTTCAGAGACCTGTATAAGATTCAAAATGGGAACATT
AACAAAAATTCCTCTGTCGCGCAGATCCCTTCGCAGGGCAAGCTGAACATAATCAGACAGGTCC
GAACGGACCAGTGAGGCCAAATCCCCACCAGGAACCAGATCCAGAGACCCTATACTGATTATGA
CGCGCATACTCGGGGCTATGCTGACCAGCGTAGCGCCGATGTAGGCGTGCTGCATGGGCGGCGA
GATAAAATGCAAAGTGCTGGTTAAAAAATCAGGCAAAGCCTCGCGCAAAAAAGCTAACACATC
ATAATCATGCTCATGCAGGTAGTTGCAGGTAAGCTCAGGAACCAAAACGGAATAACACACGATT
TTCCTCTCAAACATGACTTCGCGGATACTGCGTAAAACAAAAAATTATAAATAAAAAATTAATT
AAATAACTTAAACATTGGAAGCCTGTCTCACAACAGGAAAAACCACTTTAATCAACATAAGACG
GGCCACGGGCATGCCGGCATAGCCGTAAAAAAATTGGTCCCCGTGATTAACAAGTACCACAGAC
AGCTCCCCGGTCATGTCGGGGGTCATCATGTGAGACTCTGTATACACGTCTGGATTGTGAACATC
AGACAAACAAAGAAATCGAGCCACGTAGCCCGGAGGTATAATCACCCGCAGGCGGAGGTACAG
CAAAACGACCCCCATAGGAGGAATCACAAAATTAGTAGGAGAAAAAAATACATAAACACCAGA
AAAACCCTGTTGCTGAGGCAAAATAGCGCCCTCCCGATCCAAAACAACATAAAGCGCTTCCACA
GGAGCAGCCATAACAAAGACCCGAGTCTTACCAGTAAAAGAAAAAAGATCTCTCAACGCAGCA
CCAGCACCAACACTTCGCAGTGTAAAAGGCCAAGTGCCGAGAGAGTATATATAGGAATAAAAA
GTGACGTAAACGGGCAAAGTCCAAAAAACGCCCAGAAAAACCGCACGCGAACCTACGCCCCGA
AACGAAAGCCAAAAAACACTAGACACTCCCTTCCGGCGTCAACTTCCGCTTTCCCACGCTACGT
CACTTGCCCCAGTCAAACAAACTACATATCCCGAACTTCCAAGTCGCCACGCCCAAAACACCGC
CTACACCTCCCCGCCCGCCGGCCCGCCCCAAACCCGCCTCCCGCCCCGCGCCCCGCCCCGCGCC
GCCCATCTCATTATCATATTGGCTTCAATCCAAAATAAGGTATATTATTGATGATGGTTTAAACG
GATCCTCTAGAGTCGACCTGCAGGCATGCAAGCTTGAGTATTCTATAGTGTCACCTAAATAGCTT
GGCGTAATCATGGTCATAGCTGTTTCCTGTGTGAAATTGTTATCCGCTCACAATTCCACACAACA
TACGAGCCGGAAGCATAAAGTGTAAAGCCTGGGGTGCCTAATGAGTGAGCTAACTCACATTAAT
TGCGTTGCGCTCACTGCCCGCTTTCCAGTCGGGAAACCTGTCGTGCCAGCTGCATTAATGAATCG
GCCAACGCGAACCCCTTGCGGCCGCCGGGCCGTCGACCAATTCTCATGTTTGACAGCTTATCAT
CGAATTTCTGCCATTCATCCGCTTATTATCACTTATTCAGGCGTAGCAACCAGGCGTTTAAGGGC
ACCAATAACTGCCTTAAAAAAATTACGCCCCGCCCTGCCACTCATCGCAGTACTGTTGTAATTCA
TTAAGCATTCTGCCGACATGGAAGCCATCACAAACGGCATGATGAACCTGAATCGCCAGCGGCA
TCAGCACCTTGTCGCCTTGCGTATAATATTTGCCCATGGTGAAAACGGGGGCGAAGAAGTTGTC
CATATTGGCCACGTTTAAATCAAAACTGGTGAAACTCACCCAGGGATTGGCTGAGACGAAAAAC
ATATTCTCAATAAACCCTTTAGGGAAATAGGCCAGGTTTTCACCGTAACACGCCACATCTTGCGA
ATATATGTGTAGAAACTGCCGGAAATCGTCGTGGTATTCACTCCAGAGCGATGAAAACGTTTCA
GTTTGCTCATGGAAAACGGTGTAACAAGGGTGAACACTATCCCATATCACCAGCTCACCGTCTTT
CATTGCCATACGGAATTCCGGATGAGCATTCATCAGGCGGGCAAGAATGTGAATAAAGGCCGGA
TAAAACTTGTGCTTATTTTTCTTTACGGTCTTTAAAAAGGCCGTAATATCCAGCTGAACGGTCTG
GTTATAGGTACATTGAGCAACTGACTGAAATGCCTCAAAATGTTCTTTACGATGCCATTGGGATA
TATCAACGGTGGTATATCCAGTGATTTTTTTCTCCATTTTAGCTTCCTTAGCTCCTGAAAATCTCG
ATAACTCAAAAAATACGCCCGGTAGTGATCTTATTTCATTATGGTGAAAGTTGGAACCTCTTACG
TGCCGATCAACGTCTCATTTTCGCCAAAAGTTGGCCCAGGGCTTCCCGGTATCAACAGGGACAC
CAGGATTTATTTATTCTGCGAAGTGATCTTCCGTCACAGGTATTTATTCGCGATAAGCTCATGGA
GCGGCGTAACCGTCGCACAGGAAGGACAGAGAAAGCGCGGATCTGGGAAGTGACGGACAGAAC
```

DESCRIPTION OF THE SEQUENCES

```
GGTCAGGACCTGGATTGGGGAGGCGGTTGCCGCCGCTGCTGCTGACGGTGTGACGTTCTCTGTTC
CGGTCACACCACATACGTTCCGCCATTCCTATGCGATGCACATGCTGTATGCCGGTATACCGCTG
AAAGTTCTGCAAAGCCTGATGGGACATAAGTCCATCAGTTCAACGGAAGTCTACACGAAGGTTT
TTGCGCTGGATGTGGCTGCCCGGCACCGGGTGCAGTTTGCGATGCCGGAGTCTGATGCGGTTGC
GATGCTGAAACAATTATCCTGAGAATAAATGCCTTGGCCTTTATATGGAAATGTGGAACTGAGT
GGATATGCTGTTTTTGTCTGTTAAACAGAGAAGCTGGCTGTTATCCACTGAGAAGCGAACGAAA
CAGTCGGGAAAATCTCCCATTATCGTAGAGATCCGCATTATTAATCTCAGGAGCCTGTGTAGCGT
TTATAGGAAGTAGTGTTCTGTCATGATGCCTGCAAGCGGTAACGAAAACGATTTGAATATGCCTT
CAGGAACAATAGAAATCTTCGTGCGGTGTTACGTTGAAGTGGAGCGGATTATGTCAGCAATGGA
CAGAACAACCTAATGAACACAGAACCATGATGTGGTCTGTCCTTTTACAGCCAGTAGTGCTCGC
CGCAGTCGAGCGACAGGGCGAAGCCCTCGAGTGAGCGAGGAAGCACCAGGGAACAGCACTTAT
ATATTCTGCTTACACACGATGCCTGAAAAAACTTCCCTTGGGGTTATCCACTTATCCACGGGGAT
ATTTTTATAATTATTTTTTTATAGTTTTTAGATCTTCTTTTTTAGAGCGCCTTGTAGGCCTTTATC
CATGCTGGTTCTAGAGAAGGTGTTGTGACAAATTGCCCTTTCAGTGTGACAAATCACCCTCAAAT
GACAGTCCTGTCTGTGACAAATTGCCCTTAACCCTGTGACAAATTGCCCTCAGAAGAAGCTGTTT
TTTCACAAAGTTATCCCTGCTTATTGACTCTTTTTTATTTAGTGTGACAATCTAAAAACTTGTCAC
ACTTCACATGGATCTGTCATGGCGGAAACAGCGGTTATCAATCACAAGAAACGTAAAAATAGCC
CGCGAATCGTCCAGTCAAACGACCTCACTGAGGCGGCATATAGTCTCTCCCGGGATCAAAAACG
TATGCTGTATCTGTTCGTTGACCAGATCAGAAAATCTGATGGCACCCTACAGGAACATGACGGT
ATCTGCGAGATCCATGTTGCTAAATATGCTGAAATATTCGGATTGACCTCTGCGGAAGCCAGTA
AGGATATACGGCAGGCATTGAAGAGTTTCGCGGGGAAGGAAGTGGTTTTTTATCGCCCTGAAGA
GGATGCCGGCGATGAAAAAGGCTATGAATCTTTTCCTTGGTTTATCAAACGTGCGCACAGTCCAT
CCAGAGGGCTTTACAGTGTACATATCAACCCATATCTCATTCCCTTCTTTATCGGGTTACAGAAC
CGGTTTACGCAGTTTCGGCTTAGTGAAACAAAAGAAATCACCAATCCGTATGCCATGCGTTTATA
CGAATCCCTGTGTCAGTATCGTAAGCCGGATGGCTCAGGCATCGTCTCTCTGAAAATCGACTGG
ATCATAGAGCGTTACCAGCTGCCTCAAAGTTACCAGCGTATGCCTGACTTCCGCCGCCGCTTCCT
GCAGGTCTGTGTTAATGAGATCAACAGCAGAACTCCAATGCGCCTCTCATACATTGAGAAAAAG
AAAGGCCGCCAGACGACTCATATCGTATTTTCCTTCCGCGATATCACTTCCATGACGACAGGATA
GTCTGAGGGTTATCTGTCACAGATTTGAGGGTGGTTCGTCACATTTGTTCTGACCTACTGAGGGT
AATTTGTCACAGTTTTGCTGTTTCCTTCAGCCTGCATGGATTTTCTCATACTTTTTGAACTGTAAT
TTTTAAGGAAGCCAAATTTGAGGGCAGTTTGTCACAGTTGATTTCCTTCTCTTTCCCTTCGTCATG
TGACCTGATATCGGGGGTTAGTTCGTCATCATTGATGAGGGTTGATTATCACAGTTTATTACTCT
GAATTGGCTATCCGCGTGTGTACCTCTACCTGGAGTTTTTCCCACGGTGGATATTTCTTCTTGCGC
TGAGCGTAAGAGCTATCTGACAGAACAGTTCTTCTTTGCTTCCTCGCCAGTTCGCTCGCTATGCT
CGGTTACACGGCTGCGGCGAGCGCTAGTGATAATAAGTGACTGAGGTATGTGCTCTTCTTATCTC
CTTTTGTAGTGTTGCTCTTATTTTAAACAACTTTGCGGTTTTTTGATGACTTTGCGATTTTGTTGTT
GCTTTGCAGTAAATTGCAAGATTTAATAAAAAAACGCAAAGCAATGATTAAAGGATGTTCAGAA
TGAAACTCATGGAAACACTTAACCAGTGCATAAACGCTGGTCATGAAATGACGAAGGCTATCGC
CATTGCACAGTTTAATGATGACAGCCCGGAAGCGAGGAAAATAACCCGGCGCTGGAGAATAGG
TGAAGCAGCGGATTTAGTTGGGGTTCTTCTCAGGCTATCAGAGATGCCGAGAAAGCAGGGCGA
CTACCGCACCCGGATATGGAAATTCGAGGACGGGTTGAGCAACGTGTTGGTTATACAATTGAAC
AAATTAATCATATGCGTGATGTGTTTGGTACGCGATTGCGACGTGCTGAAGACGTATTTCCACCG
GTGATCGGGGTTGCTGCCCATAAAGGTGGCGTTTACAAAACCTCAGTTTCTGTTCATCTTGCTCA
GGATCTGGCTCTGAAGGGGCTACGTGTTTTGCTCGTGGAAGGTAACGACCCCCAGGGAACAGCC
TCAATGTATCACGGATGGGTACCAGATCTTCATATTCATGCAGAAGACACTCTCCTGCCTTTCTA
TCTTGGGGAAAAGGACGATGTCACTTATGCAATAAAGCCCACTTGCTGGCCGGGGCTTGACATT
ATTCCTTCCTGTCTGGCTCTGCACCGTATTGAAACTGAGTTAATGGGCAAATTTGATGAAGGTAA
ACTGCCCACCGATCCACACCTGATGCTCCGACTGGCCATTGAAACTGTTGCTCATGACTATGATG
TCATAGTTATTGACAGCGCGCCTAACCTGGGTATCGGCACGATTAATGTCGTATGTGCTGCTGAT
GTGCTGATTGTTCCCACGCCTGCTGAGTTGTTTGACTACACCTCCGCACTGCAGTTTTTCGATATG
CTTCGTGATCTGCTCAAGAACGTTGATCTTAAAGGGTTCGAGCCTGATTACGTATTTTGCTTAC
CAAATACAGCAATAGTAATGGCTCTCAGTCCCCGTGGATGGAGGAGCAAATTCGGGATGCCTGG
GGAAGCATGGTTCTAAAAAATGTTGTACGTGAAACGGATGAAGTTGGTAAAGGTCAGATCCGGA
TGAGAACTGTTTTTGAACAGGCCATTGATCAACGCTCTTCAACTGGTGCCTGGAGAAATGCTCTT
TCTATTTGGGAACCTGTCTGCAATGAAATTTTCGATCGTCTGATTAAACCACGCTGGGAGATTAG
ATAATGAAGCGTGCGCCTGTTATTCCAAAACATACGCTCAATACTCAACCGGTTGAAGATACTTC
GTTATCGACACCAGCTGCCCCGATGGTGGATTCGTTAATTGCGCGCGTAGGAGTAATGGCTCGC
GGTAATGCCATTACTTTGCCTGTATGTGGTCGGGATGTGAAGTTTACTCTTGAAGTGCTCCGGGG
TGATAGTGTTGAGAAGACCTCTCGGGTATGGTCAGGTAATGAACGTGACCAGGAGCTGCTTACT
GAGGACGCACTGGATGATCTCATCCCTTCTTTTCTACTGACTGGTCAACAGACACCGGCGTTCGG
TCGAAGAGTATCTGGTGTCATAGAAATTGCCGATGGGAGTCGCCGTCGTAAAGCTGCTGCACTT
ACCGAAAGTGATTATCGTGTTCTGGTTGGCGAGCTGGATGATGAGCAGATGGCTGCATTATCCA
GATTGGGTAACGATTATCGCCCAACAAGTGCTTATGAACGTGGTCAGCGTTATGCAAGCCGATT
GCAGAATGAATTTGCTGGAAATATTTCTGCGCTGGCTGATGCGGAAAATATTTCACGTAAGATT
ATTACCCGCTGTATCAACACCGCCAAATTGCCTAAATCAGTTGTTGCTCTTTTTTCTCACCCCGGT
GAACTATCTGCCCGGTCAGGTGATGCACTTCAAAAAGCCTTTACAGATAAAGAGGAATTACTTA
AGCAGCAGGCATCTAACCTTCATGAGCAGAAAAAAGCTGGGGTGATATTTGAAGCTGAAGAAG
TTATCACTCTTTTAACTTCTGTGCTTAAAACGTCATCTGCATCAAGAACTAGTTTAAGCTCACGA
CATCAGTTTGCTCCTGGAGCGACAGTATTGTATAAGGGCGATAAAATGGTGCTTAACCTGGACA
GGTCTCGTGTTCCAACTGAGTGTATAGAGAAAATTGAGGCCATTCTTAAGGAACTTGAAAAGCC
AGCACCCTGATGCGACCACGTTTTAGTCTACGTTTATCTGTCTTTTACTTAATGTCCTTTGTTACAG
GCCAGAAAGCATAACTGGCCTGAATATTCTCTCTGGGCCCACTGTTCCACTTGTATCGTCGGTCT
GATAATCAGACTGGGACCACGGTCCCACTCGTATCGTCGGTCTGATTATTAGTCTGGGACCACG
GTCCCACTCGTATCGTCGGTCTGATTATTAGTCTGGGACCACGGTCCCACTCGTATCGTCGGTCT
GATAATCAGACTGGGACCACGGTCCCACTCGTATCGTCGGTCTGATTATTAGTCTGGGACCATGG
TCCCACTCGTATCGTCGGTCTGATTATTAGTCTGGGACCACGGTCCCACTCGTATCGTCGGTCTG
ATTATTAGTCTGGAACCACGGTCCCACTCGTATCGTCGGTCTGATTATTAGTCTGGGACCACGGT
```

DESCRIPTION OF THE SEQUENCES

CCCACTCGTATCGTCGGTCTGATTATTAGTCTGGGACCACGATCCCACTCGTGTTGTCGGTCTGA
TTATCGGTCTGGGACCACGGTCCCACTTGTATTGTCGATCAGACTATCAGCGTGAGACTACGATT
CCATCAATGCCTGTCAAGGGCAAGTATTGACATGTCGTCGTAACCTGTAGAACGGAGTAACCTC
GGTGTGCGGTTGTATGCCTGCTGTGGATTGCTGCTGTGTCCTGCTTATCCACAACATTTTGCGCA
CGGTTATGTGGACAAAATACCTGGTTACCCAGGCCGTGCCGGCACGTTAACCGGGCTGCATCCG
ATGCAAGTGTGTCGCTGTCGACGAGCTCGCGAGCTCGGACATGAGGTTGCCCCGTATTCAGTGT
CGCTGATTTGTATTGTCTGAAGTTGTTTTTACGTTAAGTTGATGCAGATCAATTAATACGATACCT
GCGTCATAATTGATTATTTGACGTGGTTTGATGGCCTCCACGCACGTTGTGATATGTAGATGATA
ATCATTATCACTTTACGGGTCCTTTCCGGTGATCCGACAGGTTACGGGGCGGCGACCTCGCGGGT
TTTCGCTATTTATGAAAATTTTCCGGTTTAAGGCGTTTCCGTTCTTCTTCGTCATAACTTAATGTTT
TTATTTAAAATACCCTCTGAAAAGAAAGGAAACGACAGGTGCTGAAAGCGAGCTTTTTGGCCTC
TGTCGTTTCCTTTCTCTGTTTTTGTCCGTGGAATGAACAATGGAAGTCCGAGCTCATCGCTAATA
ACTTCGTATAGCATACATTATACGAAGTTATATTCGATGCGGCCGCAAGGGGTTCGCGTCAGCG
GGTGTTGGCGGGTGTCGGGGCTGGCTTAACTATGCGGCATCAGAGCAGATTGTACTGAGAGTGC
ACCATATGCGGTGTGAAATACCGCACAGATGCGTAAGGAGAAAATACCGCATCAGGCGCCATTC
GCCATTCAGGCTGCGCAACTGTTGGGAAGGGCGATCGGTGCGGGCCTCTTCGCTATTACGCCAG
CTGGCGAAAGGGGGATGTGCTGCAAGGCGATTAAGTTGGGTAACGCCAGGGTTTTCCCAGTCAC
GACGTTGTAAAACGACGGCCAGTGAATTGTAATACGACTCACTATAGGGCGAATTCGAGCTCGG
TACCCGGGGATCCTCGTTTAAAC

SEQ ID NO: 10-Polynucleotide sequence encoding wild type ChAd155
CATCATCAATAATATACCTTATTTTGGATTGAAGCCAATATGATAATGAGATGGGCGGCGCGGG
GCGGGAGGCGGGTCCGGGGCGGGCCGGCGGGCGGGGCGGTGTGGCGGAAGTGGACTTTGTAA
GTGTGGCGGATGTGACTTGCTAGTGCCGGGCGCGGTAAAAGTGACGTTTTCCGTGCGCGACAAC
GCCCACGGGAAGTGACATTTTTCCCGCGGTTTTTACCGGATGTTGTAGTGAATTTGGGCGTAACC
AAGTAAGATTTGGCCATTTTCGCGGGAAAACTGAAACGGGGAAGTGAAATCTGATTAATTTCGC
GTTAGTCATACCGCGTAATATTTGTCGAGGGCCGAGGGACTTTGGCCGATTACGTGGAGGACTC
GCCCAGGTGTTTTTGAGGTGAATTTCCGCGTTCCGGGTCAAAGTCTCCGTTTTTATTATTATAGTC
AGCTGACGCGGAGTGTATTTATACCCTCTGATCTCGTCAAGTGGCCACTCTTGAGTGCCAGCGAG
TAGAGTTTTCTCCTCTGCCGCTCTCCGCTCCGCTCCGCTCGGCTCTGACACCGGGGAAAAAATGA
GACATTTCACCTACGATGGCGGTGTGCTCACCGGCCAGCTGGCTGCTGAAGTCCTGGACACCCT
GATCGAGGAGGTATTGGCCGATAATTATCCTCCCTCGACTCCTTTTGAGCCACCTACACTTCACG
AACTCTACGATCTGGATGTGGTGGGGCCCAGCGATCCGAACGAGCAGGCGGTTCCAGTTTTTTT
CCAGAGTCCATGTTGTTGGCCAGCCAGGAGGGGTCGAACTTGAGACCCCTCCTCCGATCGTGG
ATTCCCCCGATCCGCCGCAGCTGACTAGGCAGCCCGAGCGCTGTGCGGGACCTGAGACTATGCC
CCAGCTGCTACCTGAGGTGATCGATCTCACCTGTAATGAGTCTGGTTTTCCACCCAGCGAGGATG
AGGACGAAGAGGGTGAGCAGTTTGTGTTAGATTCTGTGGAACAACCCGGGCGAGGATGCAGGT
CTTGTCAATATCACCGGAAAAACACAGGAGACTCCCAGATTATGTGTTCTCTGTGTTATATGAAG
ATGACCTGTATGTTTATTTACAGTAAGTTTATCATCTGTGGGCAGGTGGGCTATAGTGTGGGTGG
TGGTCTTTGGGGGGTTTTTAATATATGTCAGGGGTTATGCTGAAGACTTTTTTATTGTGATTTTT
AAAGGTCCAGTGTCTGAGCCCGAGCAAGAACCTGAACCGGAGCCTGAGCCTTCTCGCCCCAGGA
GAAAGCCTGTAATCTTAACTAGACCCAGCGCACCGGTAGCGAGAGGCCTCAGCAGCGCGGAGA
CCACCGACTCCGGTGCTTCCTCATCACCCCCGGAGATTCACCCCTGGTGCCCCTGTGTCCCGTT
AAGCCCGTTGCCGTGAGAGTCAGTGGGCGGCGGTCTGCTGTGGAGTGCATTGAGGACTTGCTTT
TTGATTCACAGGAACCTTTGGACTTGAGCTTGAAACGCCCCAGGCATTAAACCTGGTCACCTGG
ACTGAATGAGTTGACGCCTATGTTTGCTTTTGAATGACTTAATGTGTATAGATAATAAAGAGTGA
GATAATGTTTTAATTGCATGGTGTGTTTAACTTGGGCGGAGTCTGCTGGGTATATAAGCTTCCCT
GGGCTAAACTTGGTTACACTTGACCTCATGGAGGCCTGGGAGTGTTTGGAGAACTTTGCCGGAG
TTCGTGCCTTGCTGGACGAGAGCTCTAACAATACCTCTTGGTGGTGGAGGTATTTGTGGGGCTCT
CCCCAGGGCAAGTTAGTTTGTAGAATCAAGGAGGATTACAAGTGGGAATTTGAAGAGCTTTTGA
AATCCTGTGGTGAGCTATTGGATTCTTTGAATCTAGGCCACCAGGCTCTCTTCCAGGAGAAGGTC
ATCAGGACTTTGGATTTTTCCACACCGGGGCGCATTGCAGCCGCGGTTGCTTTTCTAGCTTTTTTG
AAGGATAGATGGAGCGAAGAGACCCACTTGAGTTCGGGCTACGTCCTGGATTTTCTGGCCATGC
AACTGTGGAGAGCATGGATCAGACACAAGAACAGGCTGCAACTGTTGTCTTCCGTCCGCCCGTT
GCTGATTCCGGCGGAGGAGCAACAGGCCGGGTCAGAGGACCGGGCCGTCGGGATCCGGAGGA
GAGGGCACCGAGGCCGGGCGAGAGGAGCGCGCTGAACCTGGGAACCGGGCTGAGCGGCCATCC
ACATCGGGAGTGAATGTCGGGCAGGTGGTGGATCTTTTTCCAGAACTGCGGCGGATTTTGACTA
TTAGGGAGGATGGGCAATTTGTTAAGGGTCTTAAGAGGGAGAGGGGGCTTCTGAGCATAACG
AGGAGGCCAGTAATTTAGCTTTTAGCTTGATGACCAGACACCGTCCAGAGTGCATCACTTTTCAG
CAGATTAAGGACAATTGTGCCAATGAGTTGGATCTGTTGGGTCAGAAGTATAGCATAGAGCAGC
TGACCACTTACTGGCTGCAGCCGGGTGATGATCTGGAGGAAGCTATTAGGGTGTATGCTAAGGT
GGCCCTGCGGCCCGATTGCAAGTACAAGCTCAAGGGGCTGGTGAATATCAGGAATTGTTGCTAC
ATTTCTGGCAACGGGCGGAGGTGGAGATAGAGACCGAAGACAGGGTGGCTTTCAGATGCAGC
ATGATGAATATGTGGCCGGGGGTGCTGGGCATGGACGGGGTGGTGATTATGAATGTGAGGTTCA
CGGGGCCCAACTTTAACGGCACGGTGTTTTGGGGAACACCAACCTGGTCCTGCACGGGGTGAG
CTTCTATGGGTTTAACAACACCTGTGTGGAGGCCTGGACCGATGTCGATTGAAGGTCCGCGGTTGCGCCT
TTTATGGATGTTGGAAGGCCATAGTGAGCCGCCCTAAGAGCAGGAGTTCCATTAAGAAATGCTT
GTTTGAGAGGTGCACCTTGGGGATCCTGGCCGAGGGCAACTGCAGGGTGCGCCACAATGTGGCC
TCCGAGTGCGGTTGCTTCATGCTAGTCAAGAGCGTGGCGGTAATCAAGCATAATATGGTGTGCG
GCAACAGCGAGGACAAGGCCTCACAGATGCTGACCTGCACGGATGCAACTGCCACTTGCTGAA
GACCATCCATGTAACCAGCCACAGCCGGAAGGCCTGGCCCGTGTTCGAGCACAACTTGCTGACC
CGCTGCTCCTTGCATCTGGGCAACAGGCGGGGGGTGTTCCTGCCCTATCAATGCAACTTTAGTCA
CACCAAGATCTTGCTAGAGCCCGAGAGCATGTCCAAGGTGAACTTGAACGGGGTGTTTGACATG
ACCATGAAGATCTGGAAGGTGCTGAGGTACGACGAGACCAGGTCCCGGTGCAGACCCTGCGAG
TGCGGGGGCAAGCATATGAGGAACCAGCCCGTGATGCTGGATGTGACCGAGGAGCTGAGGACA
GACCACTTGGTTCTGGCCTGCACCAGGGCCGAGTTTGGTTCTAGCGATGAAGACACAGATTGAG
GTGGGTGAGTGGGCGTGGCCTGGGGTGGTCATGAAAATATATAAGTTGGGGGTCTTAGGGTCTC -continued

| DESCRIPTION OF THE SEQUENCES |
|---|
| TTTATTTGTGTTGCAGAGACCGCCGGAGCCATGAGCGGGAGCAGCAGCAGCAGCAGTAGCAGCA |
| GCGCCTTGGATGGCAGCATCGTGAGCCCTTATTTGACGACGCGGATGCCCCACTGGGCCGGGGT |
| GCGTCAGAATGTGATGGGCTCCAGCATCGACGGCCGACCCGTCCTGCCCGCAAATTCCGCCACG |
| CTGACCTATGCGACCGTCGCGGGGACGCCGTTGGACGCCACCGCCGCGCCGCCGCCACCGCAG |
| CCGCCTCGGCCGTGCGCAGCCTGGCCACGGACTTTGCATTCCTGGGACCACTGGCGACAGGGGC |
| TACTTCTCGGGCCGCTGCTGCCGCCGTTCGCGATGACAAGCTGACCGCCCTGCTGGCGCAGTTGG |
| ATGCGCTTACTCGGGAACTGGGTGACCTTTCTCAGCAGGTCATGGCCCTGCGCCAGCAGGTCTCC |
| TCCCTGCAAGCTGGCGGGAATGCTTCTCCCACAAATGCCGTTTAAGATAAATAAAACCAGACTC |
| TGTTTGGATTAAAGAAAAGTAGCAAGTGCATTGCTCTCTTTATTTCATAATTTTCCGCGCGCGAT |
| AGGCCCTAGACCAGCGTTCTCGGTCGTTGAGGGTGCGGTGTATCTTCTCCAGGACGTGGTAGAG |
| GTGGCTCTGGACGTTGAGATACATGGGCATGAGCCCGTCCCGGGGGTGGAGGTAGCACCACTGC |
| AGAGCTTCATGCTCCGGGGTGGTGTTGTAGATGATCCAGTCGTAGCAGGAGCGCTGGGCATGGT |
| GCCTAAAAATGTCCTTCAGCAGCAGGCCGATGGCCAGGGGGAGGCCCTTGGTGTAAGTGTTTAC |
| AAAACGGTTAAGTTGGGAAGGGTGCATTCGGGGAGAGATGATGTGCATCTTGGACTGTATTTTT |
| AGATTGGCGATGTTTCCGCCCAGATCCCTTCTGGGATTCATGTTGTGCAGGACCACCAGTACAGT |
| GTATCCGGTGCACTTGGGGAATTTGTCATGCAGCTTAGAGGGAAAAGCGTGGAAGAACTTGGAG |
| ACGCCTTTGTGGCCTCCCAGATTTTCCATGCATTCGTCCATGATGATGGCAATGGGCCCGCGGA |
| GGCAGCTTGGGCAAAGATATTTCTGGGGTCGCTGACGTCGTAGTTGTGTTCCAGGGTGAGGTCG |
| TCATAGGCCATTTTTACAAAGCGCGGGCGGAGGGTGCCCGACTGGGGGATGATGGTCCCCTCTG |
| GCCCTGGGGCGTAGTTGCCCTCGCAGATCTGCATTTCCCAGGCCTTAATCTCGGAGGGGGGAAT |
| CATATCCACCTGCGGGGCGATGAAGAAAACGGTTTCCGGAGCCGGGGAGATTAACTGGGATGA |
| GAGCAGGTTTCTAAGCAGCTGTGATTTTCCACAACCGGTGGGCCCATAAATAACACCTATAACC |
| GGTTGCAGCTGGTAGTTTAGAGAGCTGCAGCTGCCGTCGTCCCGAGGAGGGGGCCACCTCGT |
| TGAGCATGTCCCTGACGCGCATGTTCTCCCCGACCAGATCCGCCAGAAGGCGCTCGCCGCCCAG |
| GGACAGCAGCTCTTGCAAGGAAGCAAAGTTTTTCAGCGGCTTGAGGCCGTCCGCCGTGGGCATG |
| TTTTTCAGGGTCTGGCTCAGCAGCTCCAGGCGGTCCCAGAGCTCGGTGACGTGCTCTACGGCATC |
| TCTATCCAGCATATCTCCTCGTTTCGCGGGTTGGGGCGACTTTCGCTGTAGGGCACCAAGCGGTG |
| GTCGTCCAGCGGGGCCAGAGTCATGTCCTTCCATGGGCGCAGGTCCTCGTCAGGGTGGTCTGG |
| GTCACGGTGAAGGGGTGCGCTCCGGGCTGAGCGCTTGCCAAGGTGCGCTTGAGGCTGGTTCTGC |
| TGGTGCTGAAGCGCTGCCGGTCTTCGCCCTGCGCGTCGGCCAGGTAGCATTTGACCATGGTGTCA |
| TAGTCCAGCCCCTCCGCGGCGTGTCCCTTGGCGCGCAGCTTGCCCTTGGAGGTGGCGCCGCACG |
| AGGGGCAGAGCAGGCTCTTGAGCGCGTAGAGCTTGGGGGCGAGGAAGACCGATTCGGGGGAGT |
| AGGCGTCCGCGCCGCAGACCCCGCACACGGTCTCGCACTCCACCAGCCAGGTGAGCTCGGGGCG |
| CGCCGGGTCAAAAACCAGGTTTCCCCCATGCTTTTTGATGCGTTTCTTACCTCGGGTCTCCATGA |
| GGTGGTGTCCCCGCTCGGTGACGAAGAGGCTGTCCGTGTCTCCGTAGACCGACTTGAGGGGTCT |
| TTTCTCCAGGGGGGTCCCTCGGTCTTCCTCGTAGAGGAACTCGGACCACTCTGAGACGAAGGCC |
| CGCGTCCAGGCCAGGACGAAGGAGGCTATGTGGAGGGGTAGCGGTCGTTGTCCACTAGGGGG |
| TCCACCTTCTCCAAGGTGTGAAGACACATGTCGCCTTCCTCGGCGTCCAGGAAGGTGATTGGCTT |
| GTAGGTGTAGGCCACGTGACCGGGGGTTCCTGACGGGGGGGTATAAAAGGGGGTGGGGCGCG |
| CTCGTCGTCACTCTCTTCCGCATCGCTGTCTGCGAGGGCCAGCTGCTGGGGTGAGTATTCCCTCT |
| CGAAGGCGGGCATGACCTCCGCGCTGAGGTTGTCAGTTTCCAAAAACGAGGAGGATTTGATGTT |
| CACCTGTCCCGAGGTGATACCTTTGAGGGTACCCGCGTCCATCTGGTCAGAAAACACGATCTTTT |
| TATTGTCCAGCTTGGTGGCGAACGACCCGTAGAGGGCGTTGGAGAGCAGCTTGGCGATGGAGCG |
| CAGGGTCTGGTTCTTGTCCCTGTCGGCGCGCTCCTTGGCCGCGATGTTGAGCTGCACGTACTCGC |
| GCGCGACGCAGCGCCACTCGGGGAAGACGGTGGTGCGCTCGTCGGGCACCAGGCGCACGCGCC |
| AGCCGCGGTTGTGCAGGGTGACCAGGTCCACGCTGGTGGCGACCTCGCCGCGCAGGCGCTCGTT |
| GGTCCAGCAGAGACGGCCGCCCTTGCGCGAGCAGAAGGGGGGCAGGGGGTCGAGCTGGGTCTC |
| GTCCGGGGGGTCCGCGTCCACGGTGAAAACCCCGGGGCGCAGGCGCGCGTCGAAGTAGTCTATC |
| TTGCAACCTTGCATGTCCAGCGCCTGCTGCCAGTCGCGGGCGGCGAGCGCGCGCTCGTAGGGGT |
| TGAGCGGCGGGCCCCAGGGCATGGGGTGGGTGAGTGCGGAGGCGTACATGCCGCAGATGTCAT |
| AGACGTAGAGGGGCTCCCGCAGGACCCCGATGTAGGTGGGGTAGCAGCGGCCGCCGCGGATGC |
| TGGCGCGCACGTAGTCATACAGCTCGTGCGAGGGGGCGAGGAGGTCGGGGCCCAGGTTGGTGC |
| GGGCGGGGCGCTCCGCGCGGAAGACGATCTGCCTGAAGATGGCATGCGAGTTGGAAGAGATGG |
| TGGGGCGCTGGAAGACGTTGAAGCTGGCGTCCTGCAGGCCGACGGCGTCGCGCACGAAGGAGG |
| CGTAGGAGTCGCGCAGCTTGTGTACCAGCTCGGCGGTGACCTGCACGTCGAGCGCGCAGTAGTC |
| GAGGGTCTCGCGGATGATGTCATATTTAGCCTGCCCCTTCTTTTTCCACAGCTCGCGGTTGAGGA |
| CAAACTCTTCGCGGTCTTTCCAGTACTCTTGGATCGGGAAACCGTCCGGTTCCGAACGGTAAGAG |
| CCTAGCATGTAGAACTGGTTGACGGCCTGGTAGGCGCAGCAGCCCTTCTCCACGGGGAGGGCGT |
| AGGCCTGCGCGGCCTTGCGGAGCGAGGTGTGGGTCAGGGCGAAGGTGTCCCTGACCATGACTTT |
| GAGGTACTGGTGCTTGAAGTCGGAGTCGTCGCAGCCGCCCCGCTCCCAGAGCGAGAAGTCGGTG |
| CGCTTCTTGGAGCGGGGGTTGGGCAGAGCGAAGGTGACATCGTTGAAGAGGATTTTGCCCGCGC |
| GGGGCATGAAGTTGCGGGTGATGCGGAAGGGCCCCGGCACTTCAGAGCGGTTGTTGATGACCTG |
| GGCGGCGAGCACGATCTCGTCGAAGCCGTTGATGTTGTGGCCCACGATGTAGAGTTCCAGGAAG |
| CGGGGCCGGCCCTTTACGGTGGGCAGCTTCTTTAGCTCTTCGTAGGTGAGCTCCTCGGGCGAGGC |
| GAGGCCGTGCTCGGCCAGGGCCCAGTCCGCGAGGTGCGGGTTGTCTCTGAGGAAGGACTTCCAG |
| AGGTCGCGGGCCAGGAGGGTCTGCAGGCGGTCTCTGAAGGTCCTGAACTGGCGGCCCACGGCCA |
| TTTTTTCGGGGGTGATGCAGTAGAAGGTGAGGGGGTCTTGCTGCCAGCGGTCCCAGTCGAGCTG |
| CAGGGCGAGGTCGCGCGCGGCCGGTGACCAGGCGCTCGTCGCCCCCGAATTTCATGACCAGCATG |
| AAGGGCACGAGCTGCTTTCCGAAGGCCCCCATCCAAGTGTAGGTCTCTACATCGTAGGTGACAA |
| AGAGGCGCTCCGTGCGAGGATGCGAGCCGATCGGGAAGAACTGGATCTCCCGCCACCAGTTGG |
| AGGAGTGGCTGTTGATGTGGTGGAAGTAGAAGTCCCGTCGCCGGGCCGAACACTCGTGCTGGCT |
| TTTGTAAAAGCGAGCGCAGTACTGGCAGCGCTGCACGGGCTGTACCTCATGCACAGAGATGCACC |
| TTTCGCCCGCGCACGAGGAAGCCGAGGGGAAATCTGAGCCCCCCGCCTGGCTCGCGGCATGGCT |
| GGTTCTCTTCTACTTTGGATGCGTGTCCGTCTCCGTCTGGCTCCTGAGGGGTGTTACGGTGGAG |
| CGGACCACCACGCCGCGCGAGCCGCAGGTCCAGATATCGGCGCGGCGGTCGGAGTTTGATGA |
| CGACATCGCGCAGCTGGGAGCTGTCCATGGTCTGGAGCTCCCGCGGCGGCGGCAGGTCAGCCGG |
| GAGTTCTTGCAGGTTCACCTCGCAGAGTCGGGCCAGGGCGCGGGGCAGGTCTAGGTGGTACCTG |

| DESCRIPTION OF THE SEQUENCES |
|---|
| ATCTCTAGGGGCGTGTTGGTGGCGGCGTCGATGGCTTGCAGGAGCCCGCAGCCCGGGGGGCGA |
| CGACGGTGCCCCGCGGGGTGGTGGTGGTGGCGGTGCAGCTCAGAAGCGGTGCCGCGGGCG |
| GGCCCCCGGAGGTAGGGGGGGCTCCGGTCCCGCGGGCAGGGGCGGCAGCGGCACGTCGGCGTG |
| GAGCGCGGGCAGGAGTTGGTGCTGTGCCCGGAGGTTGCTGGCGAAGGCGACGACGCGGCGGTT |
| GATCTCCTGGATCTGGCGCCTCTGCGTGAAGACGACGGGCCCGGTGAGCTTGAACCTGAAAGAG |
| AGTTCGACAGAATCAATCTCGGTGTCATTGACCGCGGCCTGGCGCAGGATCTCCTGCACGTCTCC |
| CGAGTTGTCTTGGTAGGCGATCTCGGCCATGAACTGCTCGATCTCTTCCTCCTGGAGGTCTCCGC |
| GTCCGGCGCGTTCCACGGTGGCCGCCAGGTCGTTGGAGATGCGCCCCATGAGCTGCGAGAAGGC |
| GTTGAGTCCGCCCTCGTTCCAGACTCGGCTGTAGACCACGCCCCCTGGTCATCGCGGGCGCGCA |
| TGACCACCTGCGCGAGGTTGAGCTCCACGTGCCGCGCGAAGACGGCGTAGTTGCGCAGACGCTG |
| GAAGAGGTAGTTGAGGGTGGTGGCGGTGTGCTCGGCCACGAAGAAGTTCATGACCCAGCGGCG |
| CAACGTGGATTCGTTGATGTCCCCCAAGGCCTCCAGCCGTTCCATGGCCTCGTAGAAGTCCACGG |
| CGAAGTTGAAAAACTGGGAGTTGCGCGCCGACACGGTCAACTCCTCCTCCAGAAGACGGATGAG |
| CTCGGCGACGGTGTCGCGCACCTCGCGCTCGAAGGCTATGGGGATCTCTTCCTCCGCTAGCATCA |
| CCACCTCCTCCTCTTCCTCCTCTTCTGGCACTTCCATGATGGCTTCCTCCTCTTCGGGGGTGGCG |
| GCGGCGGCGGTGGGGGAGGGGGCGCTCTGCGCCGGCGGCGGCGCACCGGGAGGCGGTCCACGA |
| AGCGCGCGATCATCTCCCCGCGGCGGCGGCGCATGGTCTCGGTGACGGCGCGGCCGTTCTCCCG |
| GGGGCGCAGTTGGAAGACGCCGCCGGACATCTGGTGCTGGGGCGGGTGGCCGTGAGGCAGCGA |
| GACGGCGCTGACGATGCATCTCAACAATTGCTGCGTAGGTACGCCGCCGAGGGACCTGAGGGAG |
| TCCATATCCACCGGATCCGAAAACCTTTCGAGGAAGGCGTCTAACCAGTCGCAGTCGCAAGGTA |
| GGCTGAGCACCGTGGCGGGCGGCGGGGGGTGGGGGGAGTGTCTGGCGGAGGTGCTGCTGATGA |
| TGTAATTGAAGTAGGCGGACTTGACACGGCGGATGGTCGACAGGAGCACCATGTCCTTGGGTCC |
| GGCCTGCTGGATGCGGAGGCGGTCGGCTATGCCCCAGGCTTCGTTCTGGCATCGGCGCAGGTCC |
| TTGTAGTAGTCTTGCATGAGCCTTTCCACCGGCACCTCTTCTCCTTCCTCTTCTGCTTCTTCCATGT |
| CTGCTTCGGCCCTGGGGCGGCGCCGCGCCCCCTGCCCCCATGCGCGTGACCCCGAACCCCTG |
| AGCGGTTGGAGCAGGGCCAGGTCGGCGACGACGCGCTCGGCCAGGATGGCCTGCTGCACCTGC |
| GTGAGGGTGGTTTGGAAGTCATCCAAGTCCACGAAGCGGTGGTAGGCGCCCGTGTTGATGGTGT |
| AGGTGCAGTTGGCCATGACGGACCAGTTGACGGTCTGGTGGCCCGGTTGCGACATCTCGGTGTA |
| CCTGAGTCGCGAGTAGGCGCGGGAGTCGAAGACGTAGTCGTTGCAAGTCCGCACCAGGTACTGG |
| TAGCCCACCAGGAAGTGCGGCGGCGGCTGGCGGTAGAGGGGCCAGCGCAGGGTGGCGGGGGCT |
| CCGGGGGCCAGGTCTTCCAGCATGAGGCGGTGGTAGGCGTAGATGTACCTGGACATCCAGGTGA |
| TACCCGCGGCGGTGGTGGAGGCGCGCGGGAAGTCGCGCACCCGGTTCCAGATGTTGCGCAGGG |
| GCAGAAAGTGCTCCATGGTAGGCGTGCTCTGTCCAGTCAGACGCGCGCAGTCGTTGATACTCTA |
| GACCAGGGAAAACGAAAGCCGGTCAGCGGGCACTCTTCCGTGGTCTGGTGAATAGATCGCAAG |
| GGTATCATGGCGGAGGGCCTCGGTTCGAGCCCCGGGTCCGGGCCGGACGGTCCGCCATGATCCA |
| CGCGGTTACCGCCCGCGTGTCGAACCCAGGTGTGCGACGTCAGACAACGGTGGAGTGTTCCTTT |
| TGGCGTTTTTCTGGCCGGGCGCCGGCGCCGCGTAAGAGACTAAGCCGCGAAAGCGAAAGCAGTA |
| AGTGGCTCGCTCCCCGTAGCCGGAGGGATCCTTGCTAAGGGTTGCGTTGCGGCGAACCCCGGTT |
| CGAATCCCGTACTCGGGCCGGCCGGACCCGCGGCTAAGGTGTTGGATTGGCCTCCCCCTCGTAT |
| AAAGACCCCGCTTGCGGATTGACTCCGGACACGGGGACGAGCCCCTTTTATTTTTGCTTTCCCCA |
| GATGCATCCGGTGCTGCGGCAGATGCGCCCCCCGCCCCAGCAGCAGCAACAACACCAGCAAGA |
| GCGGCAGCAACAGCAGCGGGAGTCATGCAGGGCCCCCTCACCCACCCTCGGCGGGCCGGCCAC |
| CTCGGCGTCCGCGGCCGTGTCTGGCGCCTGCGGCGGCGGCGGGGGGCCGGCTGACGACCCCGAG |
| GAGCCCCCGCGCGCAGGGCCAGACACTACCTGGACCTGGAGGAGGGCGAGGGCCTGGCGCGG |
| CTGGGGGCGCCGTCTCCCGAGCGCCACCCGCGGGTGCAGCTGAAGCGCGACTCGCGCGAGGCGT |
| ACGTGCCTCGGCAGAACCTGTTCAGGGACCGCGCGGGCGAGGAGCCCGAGGAGATGCGGGACA |
| GGAGGTTCAGCGCAGGGCGGGAGCTGCGGCAGGGGCTGAACCGCGAGCGGCTGCTGCGCGAGG |
| AGGACTTTGAGCCCGACGCGCGGACGGGGATCAGCCCCGCGCGCGCACGTGGCGGCCGCCG |
| ACCTGGTGACGGCGTACGAGCAGACGGTGAACCAGGAGATCAACTTCCAAAAGAGTTTCAACA |
| ACCACGTGCGCACGCTGGTGGCGCGCGAGGAGGTGACCATCGGGCTGATGCACCTGTGGGACTT |
| TGTAAGCGCGCTGGTGCAGAACCCCAACAGCAAGCCTCTGACGGCGCAGCTGTTCCTGATAGTG |
| CAGCACAGCAGGGACAACGAGGCGTTTAGGGACGCGCTGCTGAACATCACCGAGCCCGAGGGT |
| CGGTGGCTGCTGGACCTGATTAACATCCTGCAGAGCATAGTGGTGCAGGAGCGCAGCCTGGACC |
| TGGCCGACAAGGTGGCGGCCATCAACTACTCGATGCTGAGCCTGGGCAAGTTTTACGCGCGCAA |
| GATCTACCAGACGCCGTACGTGCCCATAGACAAGGAGGTGAAGATCGACGGTTTTTACATGCGC |
| ATGGCGCTGAAGGTGCTCACCCTGAGCGACGACCTGGGCGTGTACCGCAACGAGCGCATCCACA |
| AGGCCGTGAGCGTGAGCCGGCGGCGCGAGCTGAGCGACCGCGAGCTGATGCACAGCCTGCAGC |
| GGGCGCTGGCGGGCGCCGGCAGCGGCGACAGGGAGGCGGAGTCCTACTTCGATGCGGGGCGG |
| ACCTGCGCTGGGCGCCCAGCCGGCGGGCCCTGGAGGCCGCGGGGTCCGCGAGGACTATGACG |
| AGGACGGCGAGGAGGATGAGGAGTACGAGCTAGAGGAGGGCGAGTACCTGGACTAAACCGCG |
| GGTGGTGTTTCCGGTAGATGCAAGACCCGAACGTGGTGGACCCGGCGTGCGGCGGCTCTGCA |
| GAGCCAGCCGTCCGGCCTTAACTCCTCAGACGACTGGCGACAGGTCATGGACCGCATCATGTCG |
| CTGACGGCGCGTAACCCGGACGCGTTCCGGCAGCAGCCGCAGGCCAACAGGCTCTCCGCCATCC |
| TGGAGGCGGTGGTGCCTGCGCGCTCGAACCCCACGCACGAGAAGGTGCTGGCCATAGTGAACGC |
| GCTGGCCGAGAACAGGGCCATCCGCCCGGACGAGGCCGGGCTGGTGTACGACGCGCTGCTGCA |
| GCGCGTGGCCCGCTACAACAGCGGCAACGTGCAGACCAACCTGGACCGGCTGGTGGGGGACGT |
| GCGCGAGGCGGTGGCGCAGCGCGAGCGCGCGGATCGGCAGGGCAACCTGGGCTCCATGGTGGC |
| GCTGAATGCCTTCCTGAGCACGCAGCCGGCCAACGTGCCGCGGGGGCAGGAAGACTACACCAA |
| CTTTGTGAGCGCGCTGCGGCTGATGGTGACCGAGACCCCCAGAGCGAGGTGTACCAGTCGGGC |
| CCGGACTACTTCTTCCAGACCAGCAGACAGGGCCTGCAGACGGTGAACCTGAGCCAGGCTTTCA |
| AGAACCTGCGGGGCTGTGGGGCGTGAAGGCGCCCACCGGCGACCGGGCGACGGTGTCCAGCC |
| TGCTGACGCCCAACTCGCGCCTGCTGCTGCTGCTGATCGCGCCGTTCACGGACAGCGGCAGCGT |
| GTCCCGGGACACCTACCTGGGGCACCTGCTGACCCTGTACCGCGAGGCCATCGGCAGGCGCAG |
| GTGGACGAGCACACCTTCCAGGAGATCACCAGCGTGAGCCGCGCTGGGGCAGGAGGACACG |
| AGCAGCTGGAGGCGACTCTGAACTACCTGCTGACCAACCGGCGGCAGAAGATTCCCTCGCTGC |
| ACAGCCTGACCTCCGAGGAGGAGCGCATCTTGCGCTACGTGCAGCAGAGCGTGAGCCTGAACCT |
| GATGCGCGACGGGGTGACGCCCAGCGTGGCGCTGGACATGACCGCGCGCAACATGGAACCGGG |

DESCRIPTION OF THE SEQUENCES

```
CATGTACGCCGCGCACCGGCCTTACATCAACCGCCTGATGGACTACCTGCATCGCGCGGCGGCC
GTGAACCCCGAGTACTTTACCAACGCCATCCTGAACCCGCACTGGCTCCCGCCGCCCGGGTTCTA
CAGCGGGGGCTTCGAGGTCCCGGAGACCAACGATGGCTTCCTGTGGGACGACATGGACGACAG
CGTGTTCTCCCCGCGGCCGCAGGCGCTGGCGGAAGCGTCCCTGCTGCGTCCCAAGAAGGAGGAG
GAGGAGGAGGCGAGTCGCCGCCGCGGCAGCAGCGGCGTGGCTTCTCTGTCCGAGCTGGGGGCG
GCAGCCGCCGCGCGCCCCGGGTCCCTGGGCGGCAGCCCCTTTCCGAGCCTGGTGGGGTCTCTGC
ACAGCGAGCGCACCACCCGCCCTCGGCTGCTGGGCGAGGACGAGTACCTGAATAACTCCCTGCT
GCAGCCGGTGCGGGAGAAAAACCTGCCTCCCGCCTTCCCCAACAACGGGATAGAGAGCCTGGTG
GACAAGATGAGCAGATGGAAGACCTATGCGCAGGAGCACAGGGACGCGCCTGCGCTCCGGCCG
CCCACGCGGCGCCAGCGCCACGACCGGCAGCGGGGCTGGTGTGGGATGACGAGGACTCCGCG
GACGATAGCAGCGTGCTGGACCTGGGAGGGAGCGGCAACCCGTTCGCGCACCTGCGCCCCGCC
TGGGGAGGATGTTTTAAAAAAAAAAAAAAAAAGCAAGAAGCATGATGCAAAAATTAAATAAAA
CTCACCAAGGCCATGGCGACCGAGCGTTGGTTTCTTGTGTTCCCTTCAGTATGCGGCGCGCGGCG
ATGTACCAGGAGGGACCTCCTCCCTCTTACGAGAGCGTGGTGGGCGCGGCGGCGGCGGCGCCCT
CTTCTCCCTTTGCGTCGCAGCTGCTGGAGCCGCCGTACGTGCCTCCCGCGCTACCTGCGGCCTACG
GGGGGGAGAAACAGCATCCGTTACTCGGAGCTGGCGCCCCTGTTCGACACCACCCGGGTGTACC
TGGTGGACAACAAGTCGGCGGACGTGGCCTCCCTGAACTACCAGAACGACCACAGCAATTTTTT
GACCACGGTCATCCAGAACAATGACTACAGCCCGAGCGAGGCCAGCACCCAGACCATCAATCTG
GATGACCGGTCGCACTGGGGCGGCGACCTGAAAACCATCCTGCACACCAACATGCCCAACGTGA
ACGAGTTCATGTTCACCAATAAGTTCAAGGCGCGGGTGATGGTGTCGCGCTCGCACACCAAGGA
AGACCGGGTGGAGCTGAAGTACGAGTGGGTGGAGTTCGAGCTGCCAGAGGGCAACTACTCCGA
GACCATGACCATTGACCTGATGAACAACGCGATCGTGGAGCACTATCTGAAAGTGGGCAGGCAG
AACGGGGTCCTGGAGAGCGACATCGGGGTCAAGTTCGACACCAGGAACTTCCGCCTGGGGCTGG
ACCCCGTGACCGGGCTGGTTATGCCCGGGGTGTACACCAACGAGGCCTTCCATCCCGACATCAT
CCTGCTGCCCGGCTGCGGGGTGGACTTCACTTACAGCCGCCTGAGCAACCTCCTGGGCATCCGC
AAGCGGCAGCCCTTCCAGGAGGGCTTCAGGATCACCTACGAGGACCTGGAGGGGGGCAACATC
CCCGCGCTCCTCGATGTGGAGGCCTACCAGGATAGCTTGAAGGAAAATGAGGCGGGACAGGAG
GATACCGCCCCCGCCGCCTCCGCCGCCGCCGAGCAGGGCGAGGATGCTGCTGACACCGCGGCCG
CGGACGGGGCAGAGGCCGACCCCGCTATGGTGGTGGAGGCTCCCGAGCAGGAGGAGGACATGA
ATGACAGTGCGGTGCGCGGAGACACCTTCGTCACCCGGGGGGAGGAAAAGCAAGCGGAGGCCG
AGGCCGCGGCCGAGGAAAAGCAACTGGCGGCAGCAGCGGCGGCGGCGGCGTTGGCCGCGGCGG
AGGCTGAGTCTGAGGGGACCAAGCCCGCCAAGGAGCCCGTGATTAAGCCCCTGACCGAAGATA
GCAAGAAGCGCAGTTACAACCTGCTCAAGGACAGCACCAACACCGCGTACCGCAGCTGGTACCT
GGCCTACAACTACGGCGACCCGTCGACGGGGTGCGCTCCTGGACCCTGCTGTGCACGCCGGAC
GTGACCTGCGGCTCGGAGCAGGTGTACTGGTCGCTGCCCGACATGATGCAAGACCCCGTGACCT
TCCGCTCCACGCGGCAGGTCAGCAACTTCCCGGTGGTGGGCGCCGAGCTGCTGCCCGTGCACTC
CAAGAGCTTCTACAACGACCAGGCCGTCTACTCCCAGCTCATCCGCCAGTTCACCTCTCTGACCC
ACGTGTTCAATCGCTTTCCTGAGAACCAGATTCTGGCGCGCCCGCCCGCCCCCACCATCACCACC
GTCAGTGAAAACGTTCCTGCTCTCACAGATCACGGGACGCTACCGCTGCGCAACAGCATCGGAG
GAGTCCAGCGAGTGACCGTTACTGACGCCAGACGCCGCACCTGCCCCTACGTTTACAAGGCCTT
GGGCATAGTCTCGCCGCGCGTCCTTTCCAGCCGCACTTTTTGAGCAACACCACCATCATGTCCAT
CCTGATCTCACCCAGCAATAACTCCGGCTGGGGACTGCTGCGCGCGCCCAGCAAGATGTTCGGA
GGGGCGAGGAAGCGTTCCGAGCAGCACCCCGTGCGCGTGCGCGGGCACTTCCGCGCCCCCTGGG
GAGCGCACAAACGCGGCCGCGCGGGGCGCACCACCGTGGACGACGCCATCGACTCGGTGGTGG
AGCAGGCGCGCAACTACAGGCCCGCGGTCTCTACCGTGGACGCGGCCATCCAGACCGTGGTGCG
GGGCGCGCGGCGGTACGCCAAGCTGAAGAGCCGCCGGAAGCGCGTGGCCCGCCGCCACCGCCG
CCGACCCGGGGCCGCCGCCAAACGCGCCGCCGCGGCCCTGCTTCGCGGGCCAAGCGCACGGGC
CGCCGCGCCGCCATGAGGGCCGCGCGCCGCTTGGCCGCCGGCATCACCGCCGCCACCATGGCCC
CCCGTACCCGAAGACGCGGCCGCCGCCGCCGCCGCCGCCATCAGTGACATGGCCAGCAGGCG
CCGGGGCAACGTGTACTGGGTGCGCGACTCGGTGACCGGCACGCGCGTGCCCGTGCGCTTCCGC
CCCCCGCGGACTTGAGATGATGTGAAAAAACAACACTGAGTCTCCTGCTGTTGTGTATCCCA
GCGGCGGCGGCGCGCAGCGTCATGTCCAAGCGCAAATCAAAGAAGAGATGCTCCAGGTCG
TCGCGCCGGAGATCTATGGGCCCCGAAGAAGGAAGAGCAGGATTCGAAGCCCCGCAAGATAA
AGCGGGTCAAAAAGAAAAAGAAAGATGATGACGATGCCGATGGGGAGGTGGAGTTCCTGCGCG
CCACGGCGCCCAGGCGCCCGGTGCAGTGGAAGGGCCGGCGCGTAAAGCGCGTCCTGCGCCCCG
GCACCGCGGTGGTCTTCACGCCCGGCGAGCGCTCCACCCGGACTTTCAAGCGCGTCTATGACGA
GGTGTACGGCGACGAAGACCTGCTGGAGCAGGCCAACGAGCGCTTCGGAGAGTTTGCTTACGGG
AAGCGTCAGCGGGCGCTGGGGAAGGAGGACCTGCTGGCGCTGCCGCTGGACCAGGGCAACCCC
ACCCCCAGTCTGAAGCCCGTGACCCTGCAGCAGGTGCTGCCGAGCAGCGCACCCTCCGAGGCGA
AGCGGGGTCTGAAGCGCGAGGGCGGCGACCTGGCGCCCACCGTGCAGCTCATGGTGCCCAAGC
GGCAGAGGCTGGAGGATGTGCTGGAGAAAATGAAAGTAGACCCCGGTCTGCAGCGGGACATCA
GGGTCCGCCCCATCAAGCAGGTGGCGCCGGGCCTCGGCGTGCAGACCGTGGACGTGGTCATCCC
CACCGGCAACTCCCCGCCGCCGCCACCACTACCGCTGCCTCCACGGACATGGAGACACAGACC
GATCCCGCCGCAGCCGCAGCCGCAGCCGCCGCCGCGACCTCCTCGGCGGAGGTGCAGACGGACC
CCTGGCTGCCGCCGGCGATGTCAGCTCCCCGCGCGCGTCGCGGGCGCAGGAAGTACGGCGCCGC
CAACGCGCTCCTGCCCGAGTACGCCTTGCATCCTTCCATCGCGCCCACCCCCGGCTACCGAGGCT
ATACCTACCGCCCGCGAAGAGCCAAGGGTTCCACCCGCCGTCCCCGCCGACGCGCCGCCGCCAC
CACCCGCCGCCGCCGCCGCAGACGCCAGCCCGCACTGGCTCCAGTCTCCGTGAGGAAAGTGGCG
CGCGACGGACACACCCTGGTGCTGCCCAGGGCGCGCTACCACCCCAGCATCGTTTAAAAGCCTG
TTGTGGTTCTTGCAGATATGGCCCTCACTTGCCGCCTCCGTTTCCCGGTGCCGGGATACCGAGGA
GGAAGATCGCGCCGCAGGAGGGTCTGGCCGGCCGCGGCCTGAGCGGAGGCAGCCGCCGCGCG
CACCGGCGGCGACGCGCCACCAGCCGACGCATGCGCGGCGGGGTGCTGCCCCTGTTAATCCCCC
TGATCGCCGCGGCGATCGGCGCCGTGCCCGGGATCGCCTCCGTGGCCTTGCAAGCGTCCCAGAG
GCATTGACAGACTTGCAAACTTGCAAATATGGAAAAAAAAACCCCAATAAAAAAGTCTAGACTC
TCACGCTCGCTTGGTCCTGTGACTATTTTGTAGAATGGAAGACATCAACTTTGCGTCGCTGGCCC
CGCGTCACGGCTCGCGCCCGTTCCTGGGACACTGGAACGATATCGGCACCAGCAACATGAGCGG
TGGCGCCTTCAGTTGGGGCTCTCTGTGGAGCGGCATTAAAAGTATCGGGTCTGCCGTTAAAAATT
```

| DESCRIPTION OF THE SEQUENCES |
|---|
| ACGGCTCCCGGGCCTGGAACAGCAGCACGGGCCAGATGTTGAGAGACAAGTTGAAAGAGCAGA |
| ACTTCCAGCAGAAGGTGGTGGAGGGCCTGGCCTCCGGCATCAACGGGGTGGTGGACCTGGCCAA |
| CCAGGCCGTGCAGAATAAGATCAACAGCAGACTGGACCCCCGGCCGCCGGTGGAGGAGGTGCC |
| GCCGGCGCTGGAGACGGTGTCCCCCGATGGGCGTGGCGAGAAGCGCCCGCGGCCCGATAGGGA |
| AGAGACCACTCTGGTCACGCAGACCGATGAGCCGCCCCCGTATGAGGAGGCCCTGAAGCAAGG |
| TCTGCCCACCACGCGGCCCATCGCGCCCATGGCCACCGGGGTGGTGGGCCGCCACACCCCCGCC |
| ACGCTGGACTTGCCTCCGCCCGCCGATGTGCCGCAGCAGCAGAAGGCGGCACAGCCGGGCCCGC |
| CCGCGACCGCCTCCCGTTCCTCCGCCGGTCCTCTGCGCCGCGCGGCCAGCGGCCCCCGCGGGGG |
| GGTCGCGAGGCACGGCAACTGGCAGAGCACGCTGAACAGCATCGTGGGTCTGGGGGTGCGGTC |
| CGTGAAGCGCCGCCGATGCTACTGAATAGCTTAGCTAACGTGTTGTATGTGTGTATGCGCCCTAT |
| GTCGCCGCCAGAGGAGCTGCTGAGTCGCCGCCGTTCGCGCGCCCACCACCACCGCCACTCCGCC |
| CCTCAAGATGGCGACCCCATCGATGATGCCGCAGTGGTCGTACATGCACATCTCGGGCCAGGAC |
| GCCTCGGAGTACCTGAGCCCCGGGCTGGTGCAGTTCGCCCGCGCCACCGAGAGCTACTTCAGCC |
| TGAGTAACAAGTTTAGGAACCCCACGGTGGCGCCCACGCACGATGTGACCACCGACCGGTCTCA |
| GCGCCTGACGCTGCGGTTCATTCCCGTGGACCGCGAGGACACCGCGTACTCGTACAAGGCGCGG |
| TTCACCCTGGCCGTGGGCGACAACCGCGTGCTGGACATGGCCTCCACCTACTTTGACATCCGCG |
| GGTGCTGGACCGGGGTCCCACTTTCAAGCCCTACTCTGGCACCGCCTACAACTCCCTGGCCCCCA |
| AGGGCGCTCCCAACTCCTGCGAGTGGGAGCAAGAGGAAACTCAGGCAGTTGAAGAAGCAGCAG |
| AAGAGGAAGAAGAAGATGCTGACGGTCAAGCTGAGGAAGAGCAAGCAGCTACCAAAAAGACT |
| CATGTATATGCTCAGGCTCCCCTTTCTGGCGAAAAAATTAGTAAAGATGGTCTGCAAATAGGAA |
| CGGACGCTACAGCTACAGAACAAAAACCTATTTATGCAGACCCTACATTCCAGCCCGAACCCCA |
| AATCGGGGAGTCCCAGTGGAATGAGGCAGATGCTACAGTCGCCGGCGGTAGAGTGCTAAAGAA |
| ATCTACTCCCATGAAACCATGCTATGGTTCCTATGCAAGACCCACAAATGCTAATGGAGGTCAG |
| GGTGTACTAACGGCAAATGCCCAGGGACAGCTAGAATCTCAGGTTGAAATGCAATTCTTTTCAA |
| CTTCTGAAAACGCCCGTAACGAGGCTAACAACATTCAGCCCAAATTGGTGCTGTATAGTGAGGA |
| TGTGCACATGGAGACCCCGGATACGCACCTTTCTTACAAGCCCGCAAAAAGCGATGACAATTCA |
| AAAATCATGCTGGGTCAGCAGTCCATGCCCAACAGACCTAATTACATCGGCTTCAGAGACAACT |
| TTATCGGCCTCATGTATTACAATAGCACTGGCAACATGGGAGTGCTTGCAGGTCAGGCCTCTCAG |
| TTGAATGCAGTGGTGGACTTGCAAGACAGAAACACAGAACTGTCCTACCAGCTCTTGCTTGATT |
| CCATGGGTGACAGAACCAGATACTTTTCCATGTGGAATCAGGCAGTGGACAGTTATGACCCAGA |
| TGTTAGAATTATTGAAAATCATGGAACTGAAGACGAGCTCCCCAACTATTGTTTCCCTCTGGGTG |
| GCATAGGGGTAACTGACACTTACCAGGCTGTTAAAACCAACAATGGCAATAACGGGGGCCAGG |
| TGACTTGGACAAAAGATGAAACTTTTGCAGATCGCAATGAAATAGGGGTGGGAAACAATTTCGC |
| TATGGAGATCAACCTCAGTGCCAACCTGTGGAGAAACTTCCTGTACTCCAACGTGGCGCTGTAC |
| CTACCAGACAAGCTTAAGTACAACCCCTCCAATGTGGACATCTCTGACAACCCCAACACCTACG |
| ATTACATGAACAAGCGAGTGGTGGCCCCGGGGCTGGTGGACTGCTACATCAACCTGGGCGCGCG |
| CTGGTCGCTGGACTACATGGACAACGTCAACCCCTTCAACCACCACCGCAATGCGGGCCTGCGC |
| TACCGCTCCATGCTCCTGGGCAACGGGCGCTACGTGCCCTTCCACATCCAGGTGCCCCAGAAGTT |
| CTTTGCCATCAAGAACCTCCTCCTCCTGCCGGGCTCCTACACCTACGAGTGGAACTTCAGGAAGG |
| ATGTCAACATGGTCCTCCAGAGCTCTCTGGGTAACGATCTCAGGGTGGACGGGGCCAGCATCAA |
| GTTCGAGAGCATCTGCCTCTACGCCACCTTCTTCCCCATGGCCCACAACACGGCCTCCACGCTCG |
| AGGCCATGCTCAGGAACGACACCAACGACCAGTCCTTCAATGACTACCTCTCCGCCGCCAACAT |
| GCTCTACCCCATACCCGCCAACGCCACCAACGTCCCCATCTCCATCCCCTCGCGCAACTGGGCGG |
| CCTTCCGCGGCTGGGCCTTCACCCGCCTCAAGACCAAGGAGACCCCCTCCCTGGGCTCGGGATTC |
| GACCCCTACTACACCTACTCGGGCTCCATTCCCTACCTGGACGGCACCTTCTACCTCAACCACAC |
| TTTCAAGAAGGTCTCGGTCACCTTCGACTCCTCGGTCAGCTGGCCGGGCAACGACCGTCTGCTCA |
| CCCCCAACGAGTTCGAGATCAAGCGCTCGGTCGACGGGGAGGGCTACAACGTGGCCCAGTGCA |
| ACATGACCAAGGACTGGTTCCTGGTCCAGATGCTGGCCAACTACAACATCGGCTACCAGGGCTT |
| CTACATCCCAGAGAGCTACAAGGACAGGATGTACTCCTTCTTCAGGAACTTCCAGCCCATGAGC |
| CGGCAGGTGGTGGACCAGACCAAGTACAAGGACTACCAGGAGGTGGGCATCATCCACCAGCAC |
| AACAACTCGGGCTTCGTGGGCTACCTCGCCCCCACCATGCGCGAGGGACAGGCCTACCCCGCCA |
| ACTTCCCCTATCCGCTCATAGGCAAGACCGCGGTCGACAGCATCACCCAGAAAAAGTTCCTCTG |
| CGACCGCACCCTCTGGCGCATCCCCTTCTCCAGCAACTTCATGTCCATGGGTGCGCTCTCGGACC |
| TGGGCCAGAACTTGCTCTACGCCAACTCCGCCCACGCCCTCGACATGACCTTCGAGGTCGACCCC |
| ATGGACGAGCCCACCCTTCTCTATGTTCTGTTCGAAGTCTTTGACGTGGTCCGGGTCCACCAGCC |
| GCACCGCGGCGTCATCGAGACCGTGTACCTGCGTACGCCCTTCTCGGCCGGCAACGCCACCACC |
| TAAAGAAGCAAGCCGCAGTCATCGCCGCTGCATGCCGTCGGGTTCCACCGAGCAAGAGCTCAG |
| GGCCATCGTCAGAGACCTGGGATGCGGGCCCTATTTTTTGGGCACCTTCGACAAGCGCTTCCCTG |
| GCTTTGTCTCCCCACACAAGCTGGCCTGCGCCATCGTCAACACGGCCGGCCGCGAGACCGGGGG |
| CGTGCACTGGCTGGCCTTCGCCTGGAACCCGCGCTCCAAAACATGCTTCCTCTTTGACCCCTTCG |
| GCTTTTCGGACCAGCGGCTCAAGCAAATCTACGAGTTCGAGTACGAGGGCTTGCTGCGTCGCAG |
| CGCCATCGCCTCCTCGCCCGACCGCTGCGTCACCCTCGAAAAGTCCACCCAGACCGTGCAGGGG |
| CCCGACTCGGCCGCCTGCGGTCTCTTCTGCTGCATGTTTCTGCACGCCTTTGTGCACTGGCCTCAG |
| AGTCCCATGGACCGCAACCCCACCATGAACTTGCTGACGGGGTGCCCAACTCCATGCTCCAGA |
| GCCCCCAGGTCGAGCCCACCCTGCGCCGCAACCAGGAGCAGCTCTACAGCTTCCTGGAGCGCCA |
| CTCGCCTTACTTCCGCCGCCACAGCGCACAGATCAGGAGGGCCACCTCCTTCTGCCACTTGCAAG |
| AGATGCAAGAAGGGTAATAACGATGTACACACTTTTTTTCTCAATAAATGGCATCTTTTTATTTA |
| TACAAGCTCTCTGGGGTATTCATTTCCCACCACCACCCGCCGTTGTCGCCATCTGGCTCTATTTAG |
| AAATCGAAAGGGTTCTGCCGGGAGTCGCCGTGCGCCACGGGCAGGGACACGTTGCGATACTGGT |
| AGCGGGTGCCCCACTTGAACTCGGGCACCACCAGGCGAGGCAGCTCGGGGAAGTTTTCGCTCCA |
| CAGGCTGCGGGTCAGCACCAGCGCGTTCATCAGGTCGGCGCCGAGATCTTGAAGTCGCAGTTG |
| GGGCCGCCGCCCTGCGCGCGCGAGTTGCGGTACACCGGGTTGCAGCACTGGAACACCAACAGCC |
| CCGGGTGCTTCACGCTGGCCAGCACGCTGCGGTCGGAGATCAGCTCGGCGTCCAGGTCCTCCGC |
| GTTGCTCAGCGCGAACGGGGTCATCTTGGGCACTTGCCGCCCCAGGAAGGGCGCGTGCCCCGGT |
| TTCGAGTTGCAGTCGCAGCGCAGCGGGATCAGCAGGTGCCCGTGCCCGGACTCGGCGTTGGGGT |
| ACAGCGCGCGCATGAAGGCCTGCATCTGGCGGAAGGCCATCTGGGCCTTGGCGCCCTCCGAGAA |
| GAACATGCCGCAGGACTTGCCCGAGAACTGGTTTGCGGGGCAGCTGGCGTCGTGCAGGCAGCAG |

| DESCRIPTION OF THE SEQUENCES |
|---|
| CGCGCGTCGGTGTTGGCGATCTGCACCACGTTGCGCCCCACCGGTTCTTCACGATCTTGGCCTT |
| GGACGATTGCTCCTTCAGCGCGCGCTGCCCGTTCTCGCTGGTCACATCCATCTCGATCACATGTT |
| CCTTGTTCACCATGCTGCTGCCGTGCAGACACTTCAGCTCGCCCTCCGTCTCGGTGCAGCGGTGC |
| TGCCACAGCGCGCAGCCCGTGGGCTCGAAAGACTTGTAGGTCACCTCCGCGAAGGACTGCAGGT |
| ACCCCTGCAAAAAGCGGCCCATCATGGTCACGAAGGTCTTGTTGCTGCTGAAGGTCAGCTGCAG |
| CCCGCGGTGCTCCTCGTTCAGCCAGGTCTTGCACACGGCCGCCAGCGCCTCCACCTGGTCGGGCA |
| GCATCTTGAAGTTCACCTTCAGCTCATTCTCCACGTGGTACTTGTCCATCAGCGTGCGCGCCGCC |
| TCCATGCCCTTCTCCCAGGCCGACACCAGCGGCAGGCTCACGGGGTTCTTCACCATCACCGTGGC |
| CGCCGCCTCCGCCGCGCTTTCGCTTTCCGCCCCGCTGTTCTCTTCCTCTTCCTCCTCTTCCTCGCCG |
| CCGCCCACTCGCAGCCCCGCACCACGGGGTCGTCTTCCTGCAGGCGCTGCACCTTGCGCTTGCC |
| GTTGCGCCCCTGCTTGATGCGCACGGGCGGGTTGCTGAAGCCCACCATCACCAGCGCGGCCTCTT |
| CTTGCTCGTCCTCGCTGTCCAGAATGACCTCCGGGGAGGGGGGGTTGGTCATCCTCAGTACCGA |
| GGCACGCTTCTTTTTCTTCCTGGGGGCGTTCGCCAGCTCCGCGGCTGCGGCCGCTGCCGAGGTCG |
| AAGGCCGAGGGCTGGGCGTGCGCGGCACCAGCGCGTCCTGCGAGCCGTCCTCGTCCTCCTCGGA |
| CTCGAGACGGAGGCGGGCCCGCTTCTTCGGGGGCGCGCGGGGCGGCGGAGGCGGCGGCGGCGA |
| CGGAGACGGGGACGAGACATCGTCCAGGGTGGGTGGACGGCGGGCCGCGCCGGCGTCCGCGCTC |
| GGGGGTGGTCTCGCGCTGGTCCTCTTCCCGACTGGCCATCTCCCACTGCTCCTTCTCCTATAGGC |
| AGAAAGAGATCATGGAGTCTCTCATGCGAGTCGAGAAGGAGGAGGACAGCCTAACCGCCCCCT |
| CTGAGCCCTCCACCACCGCCGCCACCACCGCCAATGCCGCCGCGGACGACGCGCCCACCGAGAC |
| CACCGCCAGTACCACCCTCCCCAGCGACGCCACCCCCGCTCGAGAATGAAGTGCTGATCGAGCAG |
| GACCCGGGTTTTGTGAGCGGAGAGGAGGATGAGGTGGATGAGAAGGAGAAGGAGGAGGTCGCC |
| GCCTCAGTGCCAAAAGAGGATAAAAAGCAAGACCAGGACGACGCAGATAAGGATGAGACAGC |
| AGTCGGGCGGGGGAACGGAAGCCATGATGCTGATGACGGCTACCTAGACGTGGGAGACGACGT |
| GCTGCTTAAGCACCTGCACCGCCAGTGCGTCATCGTCTGCGACGCGCTGCAGGAGCGCTGCGAA |
| GTGCCCCTGGACGTGGCGGAGGTCAGCCGCGCCTACGAGCGGCACCTCTTCGCGCCGCACGTGC |
| CCCCCAAGCGCCGGGAGAACGGCACCTGCGAGCCCAACCCGCGTCTCAACTTCTACCCGGTCTT |
| CGCGGTACCCGAGGTGCTGGCCACCTACCACATCTTTTTCCAAAACTGCAAGATCCCCCTCTCCT |
| GCCGCGCCAACCGCACCCGCGCCGACAAAACCCTGACCCTGCGGCAGGGCGCCCACATACCTGA |
| TATCGCCTCTCTGGAGGAAGTGCCCAAGATCTTCGAGGGTCTCGGTCGCGACGAGAAACGGGCG |
| GCGAACGCTCTGCACGGAGACAGCGAAAACGAGAGTCACTCGGGGGTGCTGGTGGAGCTCGAG |
| GGCGACAACGCGCGCCTGGCCGTACTCAAGCGCAGCATAGAGGTCACCCACTTTGCCTACCCGG |
| CGCTCAACCTGCCCCCCAAGGTCATGAGTGTGGTCATGGGCGAGCTCATCATGCGCCGCGCCCA |
| GCCCCTGGCCGCGGATGCAAACTTGCAAGAGTCCTCCGAGGAAGGCCTGCCCGCGGTCAGCGAC |
| GAGCAGCTGGCGCGCTGGCTGGAGACCCGCGACCCCGCGCAGCTGGAGGAGCGGCGCAAGCTC |
| ATGATGGCCGCGGTGCTGGTCACCGTGGAGCTCGAGTGTCTGCAGCGCTTCTTCGCGGACCCCG |
| AGATGCAGCGCAAGCTCGAGGAGACCCTGCACTACACCTTCCGCCAGGGCTACGTGCGCCAGGC |
| CTGCAAGATCTCCAACGTGGAGCTCTGCAACCTGGTCTCCTACCTGGGCATCCTGCACGAGAAC |
| CGCCTCGGGCAGAACGTCCTGCACTCCACCCTCAAAGGGGAGGCGCGCCGCGACTACATCCGCG |
| ACTGCGCCTACCTCTTCCTCTGCTACACCTGGCAGACGGCCATGGGGGTCTGGCAGCAGTGCCTG |
| GAGGAGCGCAACCTCAAGGAGCTGGAAAAGCTCCTCAAGCGCCACCCTCAGGGACCTCTGGACG |
| GGCTTCAACGAGCGCTCGGTGGCCGCCGCGCTGGCGGACATCATCTTTCCCGAGCGCCTGCTCA |
| AGACCCTGCAGCAGGGCCTGCCCGACTTCACCAGCCAGAGCATGCTGCAGAACTTCAGGACTTT |
| CATCCTGGAGCGCTCGGGCATCCTGCCGGCCACTTGCTGCGCGCTGCCCAGCGACTTCGTGCCCA |
| TCAAGTACAGGGAGTGCCCGCCGCCGCTCTGGGGCCACTGCTACCTCTTCCAGCTGGCCAACTA |
| CCTCGCCTACCACTCGGACCTCATGGAAGACGTGAGCGGCGAGGGCCTGCTCGAGTGCCACTGC |
| CGCTGCAACCTCTGCACGCCCCACCGCTCTCTAGTCTGCAACCCGCAGCTGCTCAGCGAGAGTCA |
| GATTATCGGTACCTTCGAGCTGCAGGGTCCCTCGCCTGACGAGAAGTCCGCGGCTCCAGGGCTG |
| AAACTCACTCCGGGGCTGTGGACTTCCGCCTACCTACGCAAATTTGTACCTGAGGACTACCACGC |
| CCACGAGATCAGGTTCTACGAAGACCAATCCCGCCCGCCCAAGGCGGAGCTCACCGCCTGCGTC |
| ATCACCCAGGGGCACATCCTGGGCAATTGCAAGCCATCAACAAAGCCCGCCGAGAGTTCTTGC |
| TGAAAAAGGGTCGGGGGGTGTACCTGGACCCCCAGTCCGGCGAGGAGCTAAACCCGCTACCCCC |
| GCCGCCGCCCAGCAGCGGGACCTTGCTTCCCAGGATGGCACCCAGAAAGAAGCAGCAGCCGC |
| CGCCGCCGCCGCAGCCATACATGCTTCTGGAGGAAGAGGAGGAGGACTGGGACAGTCAGGCAG |
| AGGAGGTTTCGGACGAGGAGCAGGAGGAGATGATGGAAGACTGGGAGGAGGACAGCAGCCTA |
| GACGAGGAAGCTTCAGAGGCCGAAGAGGTGGCAGACGCAACACCATCGCCCTCGGTCGCAGCC |
| CCCTCGCCGGGGCCCCTGAAATCCTCCGAACCCAGCACCAGCGCTATAACCTCCGCTCCTCCGGC |
| GCCGGCGCCACCCGCCCGCAGACCCAACCGTAGATGGGACACCACAGGAACCGGGGTCGGTAA |
| GTCCAAGTGCCCGCCGCCGCCACCGCAGCAGCAGCAGCAGCAGCGCCAGGGCTACCGCTCGTGG |
| CGCGGGCACAAGAACGCCATAGTCGCCTGCTTGCAAGACTGCGGGGGCAACATCTCTTTCGCCC |
| GCCGCTTCCTGCTATTCCACCACGGGGTCGCCTTTCCCCGCAATGTCCTGCATTACTACCGTCATC |
| TCTACAGCCCCTACTGCAGCGGCGACCCAGAGGCGGCAGCGGCAGCCACAGCGGCGACCACCA |
| CCTAGGAAGATATCCTCCGCGGGCAAGACAGCGGCAGCAGCGGCCAGGAGACCCGCGGCAGCA |
| GCGGCGGGAGCGGTGGGCGCACTGCGCCTCTCGCCCAACGAACCCCTCTCGACCCGGGAGCTCA |
| GACACAGGATCTTCCCCACTTTGTATGCCATCTTCCAACAGAGCAGAGGCCAGGAGCAGGAGCT |
| GAAAATAAAAAACAGATCTCTGCGCTCCCTCACCCGCAGCTGTCTGTATCACAAAAGCGAAGAT |
| CAGCTTCGGCGCCACGCTGGAGGACGCGGAGGCACTCTTCAGCAAATACTGCGCGCTCACTCTTA |
| AAGACTAGCTCCGCGCCCTTCTCGAATTTAGGCGGGAGAAAACTACGTCATCGCCGGCCGCCGC |
| CCAGCCCGCCCAGCCGAGATGAGCAAAGAGATTCCCACGCCATACATGTGGAGCTACCAGCCGC |
| AGATGGGACTCGCGGCGGGAGCGGCCCAGGACTACTCCACCCGCATGAACTACATGAGCGCGG |
| GACCCCACATGATCTCACAGGTCAACGGGATCCGCGCCCAGCGAAACCAAATACTGCTGGAACA |
| GGCGGCCATCACCGCCACGCCCCGCCATAATCTCAACCCCGAAATTGGCCCGCCGCCCTCGTG |
| TACCAGGAAACCCCCTCCGCCACCACCGTACTACTTCCGCGTGACGCCCAGGCCGAAGTCCAGA |
| TGACTAACTCAGGGGCGCAGCTCGCGGGCGGCTTTCGTCACGGGGCGCGGCCGCTCCGACCAGG |
| TATAAGACACCTGATGATCAGAGGCCGAGGTATCCAGCTCAACGACGAGTCGGTGAGCTCTTCG |
| CTCGGTCTCCGTCCGGACGGAACTTTCCAGCTCGCCGGATCCGGCCGCTCTTCGTTCACGCCCCG |
| CCAGGCGTACCTGACTCTGCAGACCTCGTCCTCGGAGCCCCGCTCCGGCGGCATCGGAACCCTC |
| CAGTTCGTGGAGGAGTTCGTGCCCTCGGTCTACTTCAACCCCTTCTCGGGACCTCCCGGACGCTA |

DESCRIPTION OF THE SEQUENCES

```
CCCCGACCAGTTCATTCCGAACTTTGACGCGGTGAAGGACTCGGCGGACGGCTACGACTGAATG
TCAGGTGTCGAGGCAGAGCAGCTTCGCCTGAGACACCTCGAGCACTGCCGCCGCCACAAGTGCT
TCGCCCGCGGTTCTGGTGAGTTCTGCTACTTTCAGCTACCCGAGGAGCATACCGAGGGGCCGGC
GCACGGCGTCCGCCTGACCACCCAGGGCGAGGTTACCTGTTCCCTCATCCGGGAGTTTACCCTCC
GTCCCCTGCTAGTGGAGCGGGAGCGGGGTCCCTGTGTCCTAACTATCGCCTGCAACTGCCCTAAC
CCTGGATTACATCAAGATCTTTGCTGTCATCTCTGTGCTGAGTTTAATAAACGCTGAGATCAGAA
TCTACTGGGGCTCCTGTCGCCATCCTGTGAACGCCACCGTCTTCACCCACCCCGACCAGGCCCAG
GCGAACCTCACCTGCGGTCTGCATCGGAGGGCCAAGAAGTACCTCACCTGGTACTTCAACGGCA
CCCCCTTTGTGGTTTACAACAGCTTCGACGGGGACGGAGTCTCCCTGAAAGACCAGCTCTCCGGT
CTCAGCTACTCCATCCACAAGAACACCACCCTCCAACTCTTCCCTCCCTACCTGCCGGGAACCTA
CGAGTGCGTCACCGGCCGCTGCACCCACCTCACCCGCCTGATCGTAAACCAGAGCTTTCCGGGA
ACAGATAACTCCCTCTTCCCCAGAACAGGAGGTGAGCTCAGGAAACTCCCCGGGGACCAGGGCG
GAGACGTACCTTCGACCCTTGTGGGGTTAGGATTTTTTATTACCGGGTTGCTGGCTCTTTTAATCA
AAGTTTCCTTGAGATTTGTTCTTTCCTTCTACGTGTATGAACACCTCAACCTCCAATAACTCTACC
CTTTCTTCGGAATCAGGTGACTTCTCTGAAATCGGGCTTGGTGTGCTGCTTACTCTGTTGATTTTT
TTCCTTATCATACTCAGCCTTCTGTGCCTCAGGCTCGCCGCCTGCTGCGCACACATCTATATCTAC
TGCTGGTTGCTCAAGTGCAGGGGTCGCCACCCAAGATGAACAGGTACATGGTCCTATCGATCCT
AGGCCTGCTGGCCCTGGCGGCCTGCAGCGCCGCCAAAAAAGAGATTACCTTTGAGGAGCCCGCT
TGCAATGTAACTTTCAAGCCCGAGGGTGACCAATGCACCACCCTCGTCAAATGCGTTACCAATC
ATGAGAGGCTGCGCATCGACTACAAAAACAAAACTGGCCAGTTTGCGGTCTATAGTGTGTTTAC
GCCCGGAGACCCCTCTAACTACTCTGTCACCGTCTTCCAGGGCGGACAGTCTAAGATATTCAATT
ACACTTTCCCTTTTTATGAGTTATGCGATGCGGTCATGTACATGTCAAAACAGTACAACCTGTGG
CCTCCCTCTCCCCAGGCGTGTGTGGAAAATACTGGGTCTTACTGCTGTATGGCTTTCGCAATCAC
TACGCTCGCTCTAATCTGCACGGTGCTATACATAAAATTCAGGCAGAGGCGAATCTTTATCGATG
AAAAGAAAATGCCTTGATCGCTAACACCGGCTTTCTATCTGCAGAATGAATGCAATCACCTCCCT
ACTAATCACCACCACCCTCCTTGCGATTGCCCATGGGTTGACACGAATCGAAGTGCCAGTGGGG
TCCAATGTCACCATGGTGGGCCCCGCCGGCAATTCCACCCTCATGTGGGAAAAATTTGTCCGCA
ATCAATGGGTTCATTTCTGCTCTAACCGAATCAGTATCAAGCCCAGAGCCATCTGCGATGGGCA
AAATCTAACTCTGATCAATGTGCAAATGATGGATGCTGGGTACTATTACGGGCAGCGGGGAGAA
ATCATTAATTACTGGCGACCCCACAAGGACTACATGCTGCATGTAGTCGAGGCACTTCCCACTAC
CACCCCCACTACCACCTCTCCCACCACCACCACCACTACTACTACTACTACTACTACTACTACTA
CTACCACTACCGCTGCCGCCATACCCGCAAAAGCACCATGATTAGCACAAAGCCCCCTCGTGC
TCACTCCCACGCCGGCGGGCCCATCGGTGCGACCTCAGAAACCACCGAGCTTTGCTTCTGCCAAT
GCACTAACGCCAGCGCTCATGAACTGTTCGACCTGGAGAATGAGGATGTCCAGCAGAGCTCCGC
TTGCCTGACCCAGGAGGCTGTGGAGCCCGTTGCCCTGAAGCAGATCGGTGATTCAATAATTGAC
TCTTCTTCTTTTGCCACTCCCGAATACCCTCCCGATTCTACTTTCCACATCACGGGTACCAAAGAC
CCTAACCTCTCTTTCTACCTGATGCTGCTGCTCTGTATCTCTGTGGTCTCTTCCGCGCTGATGTTA
CTGGGGATGTTCTGCTGCCTGATCTGCCGCAGAAAGAGAAAAGCTCGCTCTCAGGGCCAACCAC
TGATGCCCTTCCCCTACCCCCCGGATTTTGCAGATAACAAGATATGAGCTCGCTGCTGACACTAA
CCGCTTTACTAGCCTGCGCTCTAACCCTTGTCGCTTGCGACTCGAGATTCCACAATGTCACAGCT
GTGGCAGGAGAAAATGTTACTTTCAACTCCACGGCCGATACCCAGTGGTCGTGGAGTGGCTCAG
GTAGCTACTTAACTATCTGCAATAGCTCCACTTCCCCCGGCATATCCCCAACCAAGTACCAATGC
AATGCCAGCCTGTTCACCCTCATCAACGCTTCCACCCTGGACAATGGACTCTATGTAGGCTATGT
ACCCTTTGGTGGGCAAGGAAAGACCCACGCTTACAACCTGGAAGTTCGCCAGCCCAGAACCACT
ACCCAAGCTTCTCCCACCACCACCACCACCACCATCACCAGCAGCAGCAGCAGCAGCAGCAGCC
ACAGCAGCAGCAGCAGATTATTGACTTTGGTTTTGGCCAGCTCATCTGCCGCTACCCAGGCCATC
TACAGCTCTGTGCCCGAAACCACTCAGATCCACCGCCCAGAAACGACCACCGCCACCACCCTAC
ACACCTCCAGCGATCAGATGCCGACCAACATCACCCCCTTGGCTCTTCAAATGGGACTTACAAG
CCCCACTCCAAAACCAGTGGATGCGGCCGAGGTCTCCGCCCTCGTCAATGACTGGGCGGGGCTG
GGAATGTGGTGGTTCGCCATAGGCATGATGGCGCTCTGCCTGCTTCTGCTCTGGCTCATCTGCTG
CCTCCACCGCAGGCGAGCCAGACCCCCCATCTATAGACCCCATCATTGTCCTGAACCCCGATAAT
GATGGGATCCATAGATTGGATGGCCTGAAAAACCTACTTTTTTCTTTTACAGTATGATAAATTGA
GACATGCCTCGCATTTTCTTGTACATGTTCCTTCTCCCACCTTTTCTGGGGTGTTCTACGCTGGCC
GCTGTGTCTCACCTGGAGGTAGACTGCCTCTCACCCTTCACTGTCTACCTGCTTTACGGATTGGTC
ACCCTCACTCTCATCTGCAGCCTAATCACAGTAATCATCGCCTTCATCCAGTGCATTGATTACAT
CTGTGTGCGCCTCGCATACTTCAGACACCACCCGCAGTACCGAGACAGGAACATTGCCCAACTT
CTAAGACTGCTCTAATCATGCATAAGACTGTGATCTGCCTTCTGATCCTCTGCATCCTGCCCACC
CTCACCTCCTGCCAGTACACCACAAAATCTCCGCGCAAAAGACATGCCTCCTGCCGCTTCACCCA
ACTGTGGAATATACCCAAATGCTACAACGAAAAGAGCGAGCTCTCCGAAGCTTGGCTGTATGGG
GTCATCTGTGTCTTAGTTTTCTGCAGCACTGTCTTTGCCCTCATAATCTACCCCTACTTTGATTTG
GGATGGAACGCGATCGATGCCATGAATTACCCCACCTTTCCCGCACCCGAGATAATTCCACTGC
GACAAGTTGTACCCGTTGTCGTTAATCAACGCCCCCCATCCCCTACGCCCACTGAAATCAGCTAC
TTTAACCTAACAGGCGGAGATGACTGACGCCCTAGATCTAGAAATGGACGGCATCAGTACCGAG
CAGCGTCTCCTAGAGAGGCGCAGGCAGGCGGCTGAGCAAGAGCGCCTCAATCAGGAGCTCCGA
GATCTCGTTAACCTGCACCAGTGCAAAAGAGGCATCTTTTGTCTGGTAAAGCAGGCCAAAGTCA
CCTACGAGAAGACCGGCAACAGCCACCGCCTCAGTTACAAATTGCCCACCCAGCGCCAGAAGCT
GGTGCTCATGGTGGGTGAGAATCCCATCACCGTCACCCAGCACTCGGTAGAGACCGAGGGGTGT
CTGCACTCCCCCTGTCGGGGTCCAGAAGACCTCTGCACCCTGGTAAAGACCCTGTGCGGTCTCAG
AGATTTAGTCCCCTTTAACTAATCAAACACTGGAATCAATAAAAAGAATCACTTACTTAAAATC
AGACAGCAGGTCTCTGTCCAGTTTATTCAGCAGCACCTCCTTCCCCTCCTCCCAACTCTGGTACT
CCAAACGCCTTCTGGCGGCAAACTTCCTCCACACCCTGAAGGGAATGTCAGATTCTTGCTCCTGT
CCCTCCGCACCCACTATCTTCATGTTGTTGCAGATGAAGCGCACCAAAACGTCTGACGAGAGCTT
CAACCCCGTGTACCCCTATGACACGGAAAGCGGCCCTCCCTCCGTCCCTTTCCTCACCCCTCCCT
TCGTGTCTCCCGATGGATTCCAAGAAAGTCCCCCCGGGGTCCTGTCTCTGAACCTGGCCGAGCCC
CTGGTCACTTCCCACGGCATGCTCGCCCTGAAAATGGGAAGTGGCCTCTCCCTGGACGACGCTG
GCAACCTCACCTCTCAAGATATCACCACCGCTAGCCCCTCCCCTCAAAAAAACCAAGACCAACCT
CAGCCTAGAAACCTCATCCCCCCTAACTGTGAGCACCTCAGGCGCCCTCACCGTAGCAGCCGCC
```

| DESCRIPTION OF THE SEQUENCES |
|---|
| GCTCCCCTGGCGGTGGCCGGCACCTCCCTCACCATGCAATCAGAGGCCCCCCTGACAGTACAGG |
| ATGCAAAACTCACCCTGGCCACCAAAGGCCCCCTGACCGTGTCTGAAGGCAAACTGGCCTTGCA |
| AACATCGGCCCCGCTGACGGCCGCTGACAGCAGCACCCTCACAGTCAGTGCCACACCACCCCTT |
| AGCACAAGCAATGGCAGCTTGGGTATTGACATGCAAGCCCCCATTTACACCACCAATGGAAAAC |
| TAGGACTTAACTTTGGCGCTCCCCTGCATGTGGTAGACAGCCTAAATGCACTGACTGTAGTTACT |
| GGCCAAGGTCTTACGATAAACGGAACAGCCCTACAAACTAGAGTCTCAGGTGCCCTCAACTATG |
| ACACATCAGGAAACCTAGAATTGAGAGCTGCAGGGGGTATGCGAGTTGATGCAAATGGTCAACT |
| TATCCTTGATGTAGCTTACCCATTTGATGCACAAAACAATCTCAGCCTTAGGCTTGGACAGGGAC |
| CCCTGTTTGTTAACTCTGCCCACAACTTGGATGTTAACTACAACAGAGGCCTCTACCTGTTCACA |
| TCTGGAAATACCAAAAAGCTAGAAGTTAATATCAAAACAGCCAAGGGTCTCATTTATGATGACA |
| CTGCTATAGCAATCAATGCGGGTGATGGGCTACAGTTTGACTCAGGCTCAGATACAAATCCATT |
| AAAAACTAAACTTGGATTAGGACTGGATTATGACTCCAGCAGAGCCATAATTGCTAAACTGGGA |
| ACTGGCCTAAGCTTTGACAACACAGGTGCCATCACAGTAGGCAACAAAAATGATGACAAGCTTA |
| CCTTGTGGACCACACCAGACCCATCCCCTAACTGTAGAATCTATTCAGAGAAAGATGCTAAATT |
| CACACTTGTTTTGACTAAATGCGGCAGTCAGGTGTTGGCCAGCGTTTCTGTTTTATCTGTAAAAG |
| GTAGCCTTGCGCCCATCAGTGGCACAGTAACTAGTGCTCAGATTGTCCTCAGATTTGATGAAAAT |
| GGGAGTTCTACTAAGCAATTCTTCCCTTGACCCTCAATACTGGAACTACAGAAAAGGTGACCTTAC |
| AGAGGGCACTGCATATACCAACGCAGTGGGATTTATGCCCAACCTCACAGCATACCCAAAAACA |
| CAGAGCCAAACTGCTAAAAGCAACATTGTAAGTCAGGTTTACTTGAATGGGGACAAATCCAAAC |
| CCATGACCCTCACCATTACCCTCAATGGAACTAATGAAACAGGAGATGCCACAGTAAGCACTTA |
| CTCCATGTCATTCTCATGGAACTGGAATGGAAGTAATTACATTAATGAAACGTTCCAAACCAACT |
| CCTTCACCTTCTCCTACATCGCCCAAGAATAAAAAGCATGACGCTGTTGATTTGATTCAATGTGT |
| TTCTGTTTTATTTTCAAGCACAACAAAATCATTCAAGTCATTCTTCCATCTTAGCTTAATAGACAC |
| AGTAGCTTAATAGACCCAGTAGTGCAAAGCCCCATTCTAGCTTATAGATCAGACAGTGATAATT |
| AACCACCACCACCACCATACCTTTTGATTCAGGAAATCATGATCATCACAGGATCCTAGTCTTCA |
| GGCCGCCCCTCCCTCCCAAGACACAGAATACACAGTCCTCTCCCCCGACTGGCTTTAAATAAC |
| ACCATCTGGTTGGTCACAGACATGTTCTTAGGGGTTATATTCCACACGGTCTCCTGCCGCGCCAG |
| GCGCTCGTCGGTGATGTTGATAAACTCTCCCGGCAGCTCGCTCAAGTTCACGTCGCTGTCCAGCG |
| GCTGAACCTCCGGCTGACGCGATAACTGTGCGACCGGCTGCTGGACGAACGGAGGCCGCGCCTA |
| CAAGGGGGTAGAGTCATAATCCTCGGTCAGGATAGGGCGGTGATGCAGCAGCAGCGAGCGAAA |
| CATCTGCTGCCGCCGCCGCTCCGTCCGGCAGGAAAACAACACGCCGGTGGTCTCCTCCGCGATA |
| ATCCGCACCGCCCGCCAGCATCAGCTTCCTCGTTCTCCGCGCGCAGCACCTCACCCTTATCTGCT |
| CAAATCGGCGCAGTAGGTACAGCACAGCACCACGATGTTATTCATGATCCCACAGTGCAGGGCG |
| CTGTATCCAAAGCTCATGCCGGGAACCACCGCCCCACGTGGCCATCGTACCACAAGCGCACGT |
| AAATCAAGTGTCGACCCCTCATGAACGCGCTGGACACAAACATTACTTCCTTGGGCATGTTGTA |
| ATTCACCACCTCCCGGTACCAGATAAACCTCTGGTTGAACAGGGCACCTTCCACCACCATCCTGA |
| ACCAAGAGGCCAGAACCTGCCCACCGGCTATGCACTGCAGGGAACCCGGGTTGGAACAATGAC |
| AATGCAGACTCCAAGGCTCGTAACCGTGGATCATCCGGCTGCTGAAGGCATCGATGTTGGCACA |
| ACACAGACACGTGCATGCACTTTCTCATGATTAGCAGCTCTTCCCTCGTCAGGATCATATCCC |
| AAGGAATAACCCATTCTTGAATCAACGTAAAACCCACACAGCAGGGAAGGCCTCGCACATAACT |
| CACGTTGTGCATGGTCAGCGTGTTGCATTCCGGAAACAGCGGATGATCCTCCAGTATCGAGGCG |
| CGGGTCTCCTTCTCACAGGGAGGTAAAGGGTCCCTGCTGTACGGACTGCGCCGGGACGACCGAG |
| ATCGTGTTGAGCGTAGTGTCATGGAAAAGGGAACGCCGGACGTGGTCATACTTCTTGAAGCAGA |
| ACCAGGTTCGCGCGTGGCAGGCCTCCTTGCGTCTGCGGTCTCGCCGTCTAGCTCGCTCCGTGTGA |
| TAGTTGTAGTACAGCCACTCCCGCAGAGCGTCGAGGCGCACCTTGCTTCCGGATCTATGTAGA |
| CTCCGTCTTGCACCGCGGCCCTGATAATATCCACCACCGTAGAATAAGCAACACCCAGCCAAGC |
| AATACACTCGCTCTGCGAGCGGCAGACAGGAGGAGCGGGCAGAGATGGGAGAACCATGATAAA |
| AAACTTTTTTTAAAGAATATTTTCCAATTCTTCGAAAGTAAGATCTATCAAGTGGCAGCGCTCCC |
| CTCCACTGGCGCGGTCAAACTCTACGGCCAAAGCACAGACAACGGCATTTCTAAGATGTTCCTT |
| AATGGCGTCCAAAAGACACACCGCTCTCAAGTTGCAGTAAACTATGAATGAAAACCCATCCGGC |
| TGATTTTCCAATATAGACGCGCCGGCAGCGTCCACCAAACCCAGATAATTTTCTTCTCTCCAGCG |
| GTTTACGATCTGTCTAAGCAAATCCCTTATATCAAGTCCGACCATGCCAAAAATCTGCTCAAGAG |
| CGCCCTCCACCTTCATGTACAAGCAGCGCATCATGATTGCAAAAATTCAGGTTCTTCAGAGACCT |
| GTATAAGATTCAAAATGGGAACATTAACAAAAATTCCTCTGTCGCGCAGATCCCTTCGCAGGGC |
| AAGCTGAACATAATCAGACAGGTCCGAACGGACCAGTGAGGCCAAATCCCCACCAGGAACCAG |
| ATCCAGAGACCCTATACTGATTATGACGCGCATACTCGGGGCTATGCTGACCAGCGTAGCGCCG |
| ATGTAGGCGTGCTGCATGGGCGGCGAGATAAAATGCAAAGTGCTGGTTAAAAAATCAGGCAAA |
| GCCTCGCGCAAAAAAGCTAACACATCATAATCATGCTCATGCAGGTAGTTGCAGGTAAGCTCAG |
| GAACCAAAACGGAATAACACACGATTTTCCTCTCAAACATGACTTCGCGGATACTGCGTAAAAC |
| AAAAAATTATAAATAAAAAATTAATTAAATAACTTAAACATTGGAAGCCTGTCTCACAACAGGA |
| AAAACCACTTTAATCAACATAAGACGGGCCACGGGCATGCCGGCATAGCCGTAAAAAAATTGGT |
| CCCCGTGATTAACAAGTACCACAGACAGCTCCCCGGTCATGTCGGGGGTCATCATGTGAGACTC |
| TGTATACACGTCTGGATTGTGAACATCAGACAAACAAAGAAATCGAGCCACGTAGCCCGGAGGT |
| ATAATCACCCGCAGGCGGAGGTACAGCAAAACGACCCCCATAGGAGGAATCACAAAATTAGTA |
| GGAGAAAAAATACATAAACACCAGAAAAACCCTGTTGCTGAGGCAAAATAGCGCCCTCCCGA |
| TCCAAAACAACATAAAGCGCTTCCACAGGAGCAGCCATAACAAGACCCGAGTCTTACCAGTAA |
| AAGAAAAAAGATCTCTCAACGCAGCACCCAGCACCAACACTTCGCAGTGTAAAAGGCCAAGTGC |
| CGAGAGAGTATATATAGGAATAAAAAGTGACGTAAACGGGCAAAGTCCAAAAAACGCCCAGAA |
| AAACCGCACGCGAACCTACGCCCCGAAACGAAAGCCAAAAAACACTAGACACTCCCTTCCGGC |
| GTCAACTTCCGCTTTCCCACGCTACGTCACTTCCCCCGGTCAAACAAACTACATATCCCGAACTT |
| CCAAGTCGCCACGCCCAAAACACCGCCTACACCTCCCCGCCCGCCGGCCCGCCCCGGACCCGC |
| CTCCCGCCCCGCGCCGCCCATCTCATTATCATATTGGCTTCAATCCAAAATAAGGTATATTATTG |
| ATGATG |

SEQ ID NO: 11-Polynucleotide sequence encoding ChAd155/RSV
CATCATCAATAATATACCTTATTTTGGATTGAAGCCAATATGATAATGAGATGGGCGGCGCGGG
GCGGGGCGCGGGGCGGGAGGCGGGTTTGGGGGCGGGCCGGCGGGCGGGGCGGTGTGGCGGAA

DESCRIPTION OF THE SEQUENCES

```
GTGGACTTTGTAAGTGTGGCGGATGTGACTTGCTAGTGCCGGGCGCGGTAAAAGTGACGTTTTC
CGTGCGCGACAACGCCCCCGGGAAGTGACATTTTTCCCGCGGTTTTTACCGGATGTTGTAGTGAA
TTTGGGCGTAACCAAGTAAGATTTGGCCATTTTCGCGGGAAAACTGAAACGGGGAAGTGAAATC
TGATTAATTTTGCGTTAGTCATACCGCGTAATATTTGTCTAGGGCCGAGGGACTTTGGCCGATTA
CGTGGAGGACTCGCCCAGGTGTTTTTTGAGGTGAATTTCCGCGTTCCGGGTCAAAGTCTGCGTTT
TATTATTATAGGATATCCCATTGCATACGTTGTATCCATATCATAATATGTACATTTATATTGGCT
CATGTCCAACATTACCGCCATGTTGACATTGATTATTGACTAGTTATTAATAGTAATCAATTACG
GGGTCATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTAACG
CCAATAGGGACTTTCCATTGACGTCAATGGGTGGAGTATTTACGGTAAACTGCCCACTTGGCAGT
ACATCAAGTGTATCATATGCCAAGTACGCCCCCTATTGACGTCAATGACGGTAAATGGCCCGCC
TGGCATTATGCCCAGTACATGACCTTATGGGACTTTCCTACTTGGCAGTACATCTACGTATTAGT
CATCGCTATTACCATGGTGATGCGGTTTTGGCAGTACATCAATGGGCGTGGATAGCGGTTTGACT
CACGGGGATTTCCAAGTCTCCACCCCATTGACGTCAATGGGAGTTTGTTTTGGCACCAAAATCAA
CGGGACTTTCCAAAATGTCGTAACAACTCCGCCCCATTGACGCAAATGGGCGGTAGGCGTGTAC
GGTGGGAGGTCTATATAAGCAGAGCTCTCCCTATCAGTGATAGAGATCTCCCTATCAGTGATAG
AGATCGTCGACGAGCTCGTTTAGTGAACCGTCAGATCGCCTGGAGACGCCATCCACGCTGTTTTG
ACCTCCATAGAAGACACCGGGACCGATCCAGCCTCCGCGGCCGGGAACGGTGCATTGGAACGC
GGATTCCCCGTGCCAAGAGTGAGATCTTCCGTTTATCTAGGTACCAGATATCGCCACCATGGAAC
TGCTGATCCTGAAGGCCAACGCCATCACCACCATCCTGACCGCCGTGACCTTCTGCTTCGCCAGC
GGCCAGAACATCACCGAGGAATTCTACCAGAGCACCTGTAGCGCCGTGAGCAAGGGCTACCTGA
GCGCCCTGAGAACCGGCTGGTACACCAGCGTGATCACCATCGAGCTGAGCAACATCAAAGAAA
ACAAGTGCAACGGCACCGACGCCAAAGTGAAGCTGATCAAGCAGGAACTGGACAAGTACAAGA
ACGCCGTGACCGAGCTGCAGCTGCTGATGCAGAGCACCCCCGCCACCAACAACCGGGCCAGAC
GGGAGCTGCCCCGGTTCATGAACTACACCCTGAACAACGCCAAAAAGACCAACGTGACCCTGAG
CAAGAAGCGGAAGCGGCGGTTCCTGGGCTTTCTGCTGGGCGTGGGCAGCGCCATTGCCAGCGGC
GTGGCCGTGTCTAAGGTGCTGCACCTGGAAGGCGAAGTGAACAAGATCAAGAGCGCCCTGCTGA
GCACCAACAAGGCCGTGGTGTCCCTGAGCAACGGCGTGAGCGTGCTGACCAGCAAGGTGCTGG
ATCTGAAGAACTACATCGACAAGCAGCTGCTGCCCATCGTGAACAAGCAGAGCTGCAGCATCAG
CAACATCGAGACAGTGATCGAGTTCCAGCAGAAGAACAACCGGCTGCTGGAAATCACCCGGGA
GTTCAGCGTGAACGCCGGCGTGACCACCCCTGTGTCCACCTACATGCTGACCAACAGCGAGCTG
CTGAGCCTGATCAACGACATGCCCATCACCAACGACCAGAAAAAGCTGATGAGCAACAACGTG
CAGATCGTGCGGCAGCAGAGCTACTCCATCATGTCCATCATCAAAGAAGAGGTGCTGGCCTACG
TGGTGCAGCTGCCCCTGTACGGCGTGATCGACACCCCTGCTGGAAGCTGCACACCAGCCCCT
GTGCACCACCAACACCAAAGAGGGCAGCAACATCTGCCTGACCCGGACCGACAGAGGCTGGTA
CTGCGACAACGCCGGCAGCGTGTCATTCTTTCCACAGGCCGAGACATGCAAGGTGCAGAGCAAC
CGGGTGTTCTGCGACACCATGAACAGCCTGACCCTGCCCTCCGAAGTGAACCTGTGCAACGTGG
ACATCTTCAACCCCAAGTACGACTGCAAGATCATGACCTCCAAGACCGACGTGTCCAGCTCCGT
GATCACCTCCCTGGGCGCCATCGTGTCCTGCTACGGCAAGACCAAGTGCACCGCCAGCAACAAG
AACCGGGGCATCATCAAGACCTTCAGCAACGGCTGCGACTACGTGTCCAACAAGGGGGTGGAC
ACCGTGTCCGTGGGCAACACCCTGTACTACGTGAACAAACAGGAAGGCAAGAGCCTGTACGTGA
AGGGCGAGCCCATCATCAACTTCTACGACCCCCTGGTGTTCCCCAGCGACGAGTTCGACGCCAG
CATCAGCCAGGTGAACGAGAAGATCAACCAGAGCCTGGCCTTCATCCGGAAGTCCGACGAGCTG
CTGCACAATGTGAATGCCGGCAAGTCCACCACCAACCGGAAGCGGAGAGCCCCTGTGAAGCAG
ACCCTGAACTTCGACCTGCTGAAGCTGGCCGGCGACGTGGAGAGCAATCCCGGCCCTATGGCCC
TGAGCAAAGTGAAACTGAACGATACACTGAACAAGGACCAGCTGCTGTCCAGCAGCAAGTACA
CCATCCAGCGGAGCACCGGCGACAGCATCGATACCCCCAACTACGACGTGCAGAAGCACATCA
ACAAGCTGTGCGGCATGCTGCTGATCACAGAGGACGCCAACCACAAGTTCACCGGCCTGATCGG
CATGCTGTACGCCATGAGCCGGCTGGGCCGGGAGGACACCATCAAGATCCTGCGGGACGCCGGC
TACCACGTGAAGGCCAATGGCGTGGACGTGACCACACACCGGCAGGACATCAACGGCAAAGA
ATGAAGTTCGAGGTGCTGACCCTGGCCAGCCTGACCACCGAGATCCAGATCAATATCGAGATCG
AGAGCCGGAAGTCCTACAAGAAAATGCTGAAAGAAATGGGCGAGGTGGCCCCCGAGTACAGAC
ACGACAGCCCCGACTGCGGCATGATCATCCTGTGTATCGCCGCCCTGGTGATCACAAAGCTGGC
CGCTGGCGACAGATCTGGCCTGACAGCCGTGATCAGACGGGCCAACAATGTGCTGAAGAACGA
GATGAAGCGGTACAAGGGCCTGCTGCCCAAGGACATTGCCAACAGCTTCTACGAGGTGTTCGAG
AAGTACCCCCACTTCATCGACGTGTTCGTGCACTTCGGCATTGCCCAGAGCAGCACCAGAGGCG
GCTCCAGAGTGGAGGGCATCTTCGCCGGCCTGTTCATGAACGCCTACGGCGCTGGCCAGGTGAT
GCTGAGATGGGCGTGCTGGCCAAGAGCGTGAAGAACATCATGCTGGGCCACGCCAGCGTGCA
GGCCGAGATGGAACAGGTGGTGGAGGTGTACGAGTACGCCCAGAAGCTGGGCGGAGAGGCCGG
CTTCTACCACATCCTGAACAACCCTAAGGCCTCCCTGCTGTCCCTGACCCAGTTCCCCCACTTCTC
CAGCGTGGTGCTGGGGAAATGCCGCCGGACTGGGCATCATGGGCGAGTACCGGGGCACCCCAG
AAACCAGGACCTGTACGACGCCGCCAAGGCCTACGCCGAGCAGCTGAAAGAAAACGGCGTGAT
CAACTACAGCGTGCTGGACCTGACCGCTGAGGAACTGGAAGCCATCAAGCACCAGCTGAACCCC
AAGGACAACGACGTGGAGCTGGGAGGCGGAGGATCTGGCGGCGGAGGCATGAGCAGACGGAA
CCCCTGCAAGTTCGAGATCCGGGGCCACTGCCTGAACGGCAAGCGGTGCCACTTCAGCCACAAC
TACTTCGAGTGGCCCCCTCATGCTCTGCTGGTGCGGCAGAACTTCATGCTGAACCGGATCCTGAA
GTCCATGGACAAGAGCATCGACACCCTGAGCGAGATCAGCGGAGCCGCCGAGCTGGACAGAAC
CGAGGAATATGCCCTGGGCGTGGTGGGAGTGCTGGAAAGCTACATCGGCTCCATCAACAACATC
ACAAAGCAGAGCGCCTGCGTGGCCATGAGCAAGCTGCTGACAGAGCTGAACAGCGACGACATC
AAGAAGCTGAGGGACAACGAGGAACTGAACAGCCCCAAGATCCGGGTGTACAACACCGTGATC
AGCTACATTGAGAGCAACCGCAAGAACAACAAGCAGACCATCCATCTGCTGAAGCGGCTGCCC
GCCGACGTGCTGAAAAAGACCATCAAGAACACCCTGGACATCCACAAGTCCATCACCATCAACA
ATCCCAAAGAAAGCACCGTGTCTGACACCAACGATCACGCCAAGAACAACGACACCACCTGAT
GAGCGGCCGCGATCTGCTGTGCCTTCTAGTTGCCAGCCATCTGTTGTTTGCCCCTCCCCCGTGCCT
TCCTTGACCCTGGAAGGTGCCACTCCCACTGTCCTTTCCTAATAAAATGAGGAAATTGCATCGCA
TTGTCTGAGTAGGTGTCATTCTATTCTGGGGGGTGGGTGGGCAGGACAGCAAGGGGGAGGAT
TGGGAAGACAATAGCAGGCATGCTGGGGATGCGGTGGGCTCTATGGCCGATCAGCGATCGCTGA
```

| DESCRIPTION OF THE SEQUENCES |
|---|
| GGTGGGTGAGTGGGCGTGGCCTGGGGTGGTCATGAAAATATATAAGTTGGGGGTCTTAGGGTCT |
| CTTTATTTGTGTTGCAGAGACCGCCGGAGCCATGAGCGGGAGCAGCAGCAGCAGCAGTAGCAGC |
| AGCGCCTTGGATGGCAGCATCGTGAGCCCTTATTTGACGACGCGGATGCCCCACTGGGCCGGGG |
| TGCGTCAGAATGTGATGGGCTCCAGCATCGACGGCCGACCCGTCCTGCCCGCAAATTCCGCCAC |
| GCTGACCTATGCGACCGTCGCGGGGACGCCGTTGGACGCCACCGCCGCCGCCGCCGCCACCGCA |
| GCCGCCTCGGCCGTGCGCAGCCTGGCCACGGACTTTGCATTCCTGGGACCACTGGCGACAGGGG |
| CTACTTCTCGGGCCGCTGCTGCCGCCGTTCGCGATGACAAGCTGACCGCCCTGCTGGCGCAGTTG |
| GATGCGCTTACTCGGGAACTGGGTGACCTTTCTCAGCAGGTCATGGCCCTGCGCCAGCAGGTCTC |
| CTCCCTGCAAGCTGGCGGGAATGCTTCTCCCACAAATGCCGTTTAAGATAAATAAAACCAGACT |
| CTGTTTGGATTAAAGAAAAGTAGCAAGTGCATTGCTCTCTTTATTTCATAATTTTCCGCGCGCGA |
| TAGGCCCTAGACCAGCGTTCTCGGTCGTTGAGGGTGCGGTGTATCTTCTCCAGGACGTGGTAGA |
| GGTGGCTCTGGACGTTGAGATACATGGGCATGAGCCCGTCCCGGGGGTGGAGGTAGCACCACTG |
| CAGAGCTTCATGCTCCGGGGTGGTGTTGTAGATGATCCAGTCGTAGCAGGAGCGCTGGGCATGG |
| TGCCTAAAAATGTCCTTCAGCAGCAGGCCGATGGCCAGGGGGAGGCCCTTGGTGTAAGTGTTTA |
| CAAAACGGTTAAGTTGGGAAGGGTGCATTCGGGGAGAGATGATGTGCATCTTGGACTGTATTTT |
| TAGATTGGCGATGTTTCCGCCCAGATCCCTTCTGGGATTCATGTTGTGCAGGACCACCAGTACAG |
| TGTATCCGGTGCACTTGGGGAATTTGTCATGCAGCTTAGAGGGAAAAGCGTGGAAGAACTTGGA |
| GACGCCTTTGTGGCCTCCCAGATTTTCCATGCATTCGTCCATGATGATGGCAATGGGCCCGCGGG |
| AGGCAGCTTGGGCAAAGATATTTCTGGGGTCGCTGACGTCGTAGTTGTGTTCCAGGGTGAGGTC |
| GTCATAGGCCATTTTTACAAAGCGCGGGCGGAGGGTGCCCGACTGGGGGATGGTCCCCTCT |
| GGCCCTGGGGCGTAGTTGCCCTCGCAGATCTGCATTTCCCAGGCCTTAATCTCGGAGGGGGGAA |
| TCATATCCACCTGCGGGCGATGAAGAAAACGGTTTCCGGAGCCGGGGAGATTAACTGGGATGA |
| GAGCAGGTTTCTAAGCAGCTGTGATTTTCCACAACCGGTGGGCCCATAAATAACACCTATAACC |
| GGTTGCAGCTGGTAGTTTAGAGAGCTGCAGCTGCCGTCGTCCCGGAGGAGGGGGCCACCTCGT |
| TGAGCATGTCCCTGACGCGCATGTTCTCCCCGACCAGATCCGCCAGAAGGCGCTCGCCGCCCAG |
| GGACAGCAGCTCTTGCAAGGAAGCAAAGTTTTTCAGCGGCTTGAGGCCGTCCGCCGTGGGCATG |
| TTTTTCAGGGTCTGGCTCAGCAGCTCCAGGCGGTCCCAGAGCTCGGTGACGTGCTCTACGGCATC |
| TCTATCCAGCATATCTCCTCGTTTCGCGGGTTGGGGCGACTTTCGCTGTAGGGCACCAAGCGGTG |
| GTCGTCCAGCGGGGCCAGAGTCATGTCCTTCCATGGGCGCAGGGTCCTCGTCAGGGTGGTCTGG |
| GTCACGGTGAAGGGGTGCGCTCCGGGCTGAGCGCTTGCCAAGGTGCGCTTGAGGCTGGTTCTGC |
| TGGTGCTGAAGCGCTGCCGGTCTTCGCCCTGCGCGTCGGCCAGGTAGCATTTGACCATGGTGTCA |
| TAGTCCAGCCCCTCCGCGGCGTGTCCCTTGGCGCGCAGCTTGCCCTTGGAGGTGGCGCCGCACG |
| AGGGGCAGAGCAGGCTCTTGAGCGCGTAGAGCTTGGGGGCGAGGAAGACCGATTCGGGGGAGT |
| AGGCGTCCGCGCCGCAGACCCCGCACACGGTCTCGCACTCCACCAGCCAGGTGAGCTCGGGGCG |
| CGCCGGGTCAAAAACCAGGTTTCCCCCATGCTTTTTGATGCGTTTCTTACCTCGGGTCTCCATGA |
| GGTGGTGTCCCCGCTCGGTGACGAAGAGGCTGTCCGTGTCTCCGTAGACCGACTTGAGGGGTCT |
| TTTCTCCAGGGGGGTCCCTCGGTCTTCCTCGTAGAGGAACTCGGACCACTCTGAGACGAAGGCC |
| CGCGTCCAGGCCAGGACGGAAGGAGGCTATGTGGGAGGGGTAGCGGTCGTTGTCCACTAGGGGG |
| TCCACCTTCTCCAAGGTGTGAAGACACATGTCGCCTTCCTCGGCGTCCAGGAAGGTGATTGGCTT |
| GTAGGTGTAGGCCACGTGACCGGGGGTTCCTGACGGGGGGTATAAAAGGGGTGGGGCGCG |
| CTCGTCGTCACTCTCTTCCGCATCGCTGTCTGCGAGGGCCAGCTGCTGGGGGTGAGTATTCCCTCT |
| CGAAGGCGGGCATGACCTCCGCGCTGAGGTTGTCAGTTTCCAAAAACGAGGAGGATTTGATGTT |
| CACCTGTCCCGAGGTGATACCTTTGAGGGTACCCGCGTCCATCTGGTCAGAAAACACGATCTTTT |
| TATTGTCCAGCTTGGTGGCGAACGACCCGTAGAGGGCGTTGGAGAGCAGCTTGGCGATGGAGCG |
| CAGGGTCTGGTTCTTGTCCCTGTCGGCGCGCTCCTTGGCCGCGATGTTGAGCTGCACGTACTCGC |
| GCGCGACGCAGCGCCACTCGGGGAAGACGGTGGTGCGCTCGTCGGGCACCAGGCGCACGCGCC |
| AGCCGCGGTTGTGCAGGGTGACCAGGTCCACGCTGGTGGCGACCTCGCCGCGCAGGCGCTCGTT |
| GGTCCAGCAGAGACGGCCGCCCTTGCGCGAGCAGAAGGGGGGCAGGGGGTCGAGCTGGGTCTC |
| GTCCGGGGGTCCGCGTCCACGGTGAAAACCCCGGGGCGCAGGCGCGCGTCGAAGTAGTCTATC |
| TTGCAACCTTGCATGTCCAGCGCCTGCTGCCAGTCGCGGGCGGCGAGCGCGCGCTCGTAGGGGT |
| TGAGCGGCGGGCCCCAGGGCATGGGGTGGTGAGTGCGGAGGCGTACATGCCGCAGATGTCAT |
| AGACGTAGAGGGGCTCCCGCAGGACCCCGATGTAGGTGGGGTAGCAGCGGCCGCCGCGGATGC |
| TGGCGCGCACGTAGTCATACAGCTCGTGCGAGGGGGCGAGGAGGTCGGGGCCCAGGTTGGTGC |
| GGGCGGGGCGCTCCGCGCGGAAGACGATCTGCCTGAAGATGGCATGCGAGTTGGAAGAGATGG |
| TGGGGCGCTGGAAGACGTTGAAGCTGGCGTCCTGCAGGCCGACGGCGTCGCGCACGAAGGAGG |
| CGTAGGAGTCGCGCAGCTTGTGTACCAGCTCGGCGGTGACCTGCACGTCGAGCGCGCAGTAGTC |
| GAGGGTCTCGCGGATGATGTCATATTTAGCCTGCCCCTTCTTTTTCCACAGCTCGCGGTTGAGGA |
| CAAACTCTTCGCGGTCTTTCCAGTACTCTTGGATCGGGAAACCGTCCGGTTCCGAACGGTAAGAG |
| CCTAGCATGTAGAACTGGTTGACGGCCTGGTAGGCGCAGCAGCCCTTCTCCACGGGGAGGGCGT |
| AGGCCTGCGCGGCCTTGCGGAGCGAGGTGTGGGTCAGGGCGAAGGTGTCCCTGACCATGACTTT |
| GAGGTACTGGTGCTTGAAGTCGGAGTCGTCGCAGCCGCCCCGCTCCCAGAGCGAGAAGTCGGTG |
| CGCTTCTTGGAGCGGGGGTTGGGCAGAGCGAAGGTGACATCGTTGAAGAGGATTTTGCCCGCGC |
| GGGGCATGAAGTTGCGGGTGATGCGGAAGGGCCCCGGCACTTCAGAGCGGTTGTTGATGACCTG |
| GGCGGCGAGCACGATCTCGTCGAAGCCGTTGATGTTGTGGCCCACGATGTAGAGTTCCAGGAAG |
| CGGGGCCGGCCCTTTACGGTGGGCAGCTTCTTTAGCTCTTCGTAGGTGAGCTCCTCGGGCGAGGC |
| GAGGCCGTGCTCGGCCAGGGCCCAGTCCGCGAGGTGCGGGTTGTCTCTGAGGAAGGACTTCCAG |
| AGGTCGCGGGCCAGGAGGGTCTGCAGGCGGTCTCTGAAGGTCCTGAACTGGCGGCCCACGGCCA |
| TTTTTTCGGGGGTGATGCAGTAGAAGGTGAGGGGGTCTTGCTGCCAGCGGTCCCAGTCGAGCTG |
| CAGGGCGAGGTCGCGCGCGGCGGTGACCAGGCGCTCGTCGCCCCCGAATTTCATGACCAGCATG |
| AAGGGCACGAGCTGCTTTCCGAAGGCCCCCATCCAAGTGTAGGTCTCTACATCGTAGGTGACAA |
| AGAGGCGCTCCGTGCGAGGATGCGAGCCGATCGGGAAGAACTGGATCTCCGCCACCAGTTGG |
| AGGAGTGGCTGTTGATGTGGTGGAAGTAGAAGTCCCGTCGCCGGGCCGAACACTCGTGCTGGCT |
| TTTGTAAAAGCGAGCGCAGTACTGGCAGCGCTGCACGGGCTGTACCTCATGCACGAGATGCACC |
| TTTCGCCCGCGCACGAGGAAGCCGAGGGGAAATCTGAGCCCCCCGCCTGGCTCGCGGCATGCT |
| GGTTCTCTTCTACTTTGGATGCGTGTCCGTCTCCGTCTGGCTCCTCGAGGGGTGTTACGGTGGAG |
| CGGACCACCACGCCGCGCGAGCCGCAGGTCCAGATATCGGCGCGCGCGGTCGGAGTTTGATGA |
| CGACATCGCGCAGCTGGGAGCTGTCCATGGTCTGGAGCTCCCGCGGCGGCGGCAGGTCAGCCGG |

DESCRIPTION OF THE SEQUENCES

```
GAGTTCTTGCAGGTTCACCTCGCAGAGTCGGGCCAGGGCGCGGGGCAGGTCTAGGTGGTACCTG
ATCTCTAGGGGCGTGTTGGTGGCGGCGTCGATGGCTTGCAGGAGCCCGCAGCCCGGGGGGCGA
CGACGGTGCCCGCGGGGTGGTGGTGGTGGTGGCGGTGCAGCTCAGAAGCGGTGCCGCGGGCG
GGCCCCCGGAGGTAGGGGGGGCTCCGGTCCCGCGGGCAGGGGCGGCAGCGGCACGTCGGCGTG
GAGCGCGGGCAGGAGTTGGTGCTGTGCCCGGAGGTTGCTGGCGAAGGCGACGACGCGGCGGTT
GATCTCCTGGATCTGGCGCCTCTGCGTGAAGACGACGGGCCCGGTGAGCTTGAACCTGAAAGAG
AGTTCGACAGAATCAATCTCGGTGTCATTGACCGCGGCCTGGCGCAGGATCTCCTGCACGTCTCC
CGAGTTGTCTTGGTAGGCGATCTCGGCCATGAACTGCTCGATCTCTTCCTCCTGGAGGTCTCCGC
GTCCGGCGCGTTCCACGGTGGCCGCCAGGTCGTTGGAGATGCGCCCCATGAGCTGCGAGAAGGC
GTTGAGTCCGCCCTCGTTCCAGACTCGGCTGTAGACCACGCCCCCTGGTCATCGCGGGCGCGCA
TGACCACCTGCGCGAGGTTGAGCTCCACGTGCCGCGCGAAGACGGCGTAGTTGCGCAGACGCTG
GAAGAGGTAGTTGAGGGTGGTGGCGGTGTGCTCGGCCACGAAGAAGTTCATGACCCAGCGGCG
CAACGTGGATTCGTTGATGTCCCCAAGGCCTCCAGCCGTTCCATGGCCTCGTAGAAGTCCACGG
CGAAGTTGAAAAACTGGGAGTTGCGCGCCGACACGGTCAACTCCTCCTCCAGAAGACGGATGAG
CTCGGCGACGGTGTCGCGCACCTCGCGCTCGAAGGCTATGGGGATCTCTTCCTCCGCTAGCATCA
CCACCTCCTCCTCTTCCTCCTCTTCTGGCACTTCCATGATGGCTTCCTCCTCTTCGGGGGGTGGCG
GCGGCGGCGGTGGGGAGGGGGCGCTCTGCGCCGGCGGCGGCGCACCGGGAGGCGGTCCACGA
AGCGCGCGATCATCTCCCCGCGGCGGCGGCGCATGGTCTCGGTGACGGCGCGGCCGTTCTCCCG
GGGGCGCAGTTGGAAGACGCCGCCGGACATCTGGTGCTGGGGCGGGTGGCCGTGAGGCAGCGA
GACGGCGCTGACGATGCATCTCAACAATTGCTGCGTAGGTACGCCGCCGAGGGACCTGAGGGAG
TCCATATCCACCGGATCCGAAAACCTTTCGAGGAAGGCGTCTAACCAGTCGCAGTCGCAAGGTA
GGCTGAGCACCGTGGCGGGCGGCGGGGGGTGGGGGAGTGTCTGGCGGAGGTGCTGCTGATGA
TGTAATTGAAGTAGGCGGACTTGACACGGCGGATGGTCGACAGGAGCACCATGTCCTTGGGTCC
GGCCTGCTGGATGCGGAGGCGGTCGGCTATGCCCCAGGCTTCGTTCTGGCATCGGCGCAGGTCC
TTGTAGTAGTCTTGCATGAGCCTTTCCACCGGCACCTCTTCTCCTTCCTCTTCTGCTTCTTCCATGT
CTGCTTCGGCCCTGGGGCGGCGCCGCGCCCCCTGCCCCCATGCGCGTGACCCCGAACCCCCTG
AGCGGTTGGAGCAGGGCCAGGTCGGCGACGACGCGCTCGGCCAGGATGGCCTGCTGCACCTGC
GTGAGGGTGGTTTGGAAGTCATCCAAGTCCACGAAGCGGTGGTAGGCGCCCGTGTTGATGGTGT
AGGTGCAGTTGGCCATGACGGACCAGTTGACGGTCTGGTGGCCCGGTTGCGACATCTCGGTGTA
CCTGAGTCGCGAGTAGGCGCGGGAGTCGAAGACGTAGTCGTTGCAAGTCCGCCACCAGGTACTGG
TAGCCCACCAGGAAGTGCGGCGGCGGCTGGCGGTAGAGGGGCCAGCGCAGGGTGGCGGGGGCT
CCGGGGGCCAGGTCTTCCAGCATGAGGCGGTGGTAGGCGTAGATGTACCTGGACATCCAGGTGA
TACCCGCGGCGGTGGTGGAGGCGCGCGGGAAGTCGCGCACCCGGTTCCAGATGTTGCGCAGGG
GCAGAAAGTGCTCCATGGTAGGCGTGCTCTGTCCAGTCAGACGCGCGCAGTCGTTGATACTCTA
GACCAGGGAAAACGAAAGCCGGTCAGCGGGCACTCTTCCGTGGTCTGGTGAATAGATCGCAAG
GGTATCATGGCGGAGGGCCTCGGTTCGAGCCCCGGGTCCGGGCCGGACGGTCCGCCATGATCCA
CGCGGTTACCGCCCGCGTGTCGAACCCAGGTGTGCGACGTCAGACAACGGTGGAGTGTTCCTTT
TGGCGTTTTTCTGGCGGGCGCCGGCGCCGCGTAAGAGACTAAGCGCGAAAGCGAAAGCAGTA
AGTGGCTCGCTCCCCGTAGCCGGAGGGGATCCTTGCTAAGGGTTGCGTTGCGGCGAACCCCGGTT
CGAATCCCGTACTCGGGCCGGCCGGACCCGCGGCTAAGGTGTTGGATTGGCCTCCCCCTCGTAT
AAAGACCCCGCTTGCGGATTGACTCCGGACACGGGGACGAGCCCCTTTTATTTTTGCTTTCCCCA
GATGCATCCGGTGCTGCGGCAGATGCGCCCCCGCCCCAGCAGCAGCAACAACACCAGCAAGA
GCGGCAGCAACAGCAGCGGGAGTCATGCAGGGCCCCCTCACCCACCCTCGGCGGGCCGGCCAC
CTCGGCGTCCGCGGCCGTGTCTGGCGCCTGCGGCGGCGGCGGGGGGCCGGCTGACGACCCCGAG
GAGCCCCCGCGGCGCAGGGCCAGACACTACCTGGACCTGGAGGAGGGGCGAGGGCCTGGCGCGG
CTGGGGGCGCCGTCTCCCGAGCGCCACCCGCGGGTGCAGCTGAAGCGCGACTCGCGCGAGGCGT
ACGTGCCTCGGCAGAACCTGTTCAGGGACCGCGCGGGCGAGGAGCCCGAGGAGATGCGGGACA
GGAGGTTCAGCGCAGGGCGGGAGCTGCGGCAGGGGCTGAACCGCGAGCGGCTGCTGCGCGAGG
AGGACTTTGAGCCCGACGCGCGGACGGGGATCAGCCCCGCGGCGGCACGTGGCGGCCGCCG
ACCTGGTGACGGCGTACGAGCAGACGGTGAACCAGGAGATCAACTTCCAAAAGAGTTTCAACA
ACCACGTGCGCACGCTGGTGGCGCGCGAGGAGGTGACCATCGGGCTGATGCACCTGTGGGACTT
TGTAAGCGCGCTGGTGCAGAACCCCAACAGCAAGCCTCTGACGGCGCAGCTGTTCCTGATAGTG
CAGCACAGCAGGGACAACGAGGCGTTTAGGGACGCGCTGCTGAACATCACCGAGCCCGAGGGT
CGGTGGCTGCTGGACCTGATTAACATCCTGCAGAGCATAGTGGTGCAGGAGCGCAGCCTGAGCC
TGGCCGACAAGGTGGCGGCCATCAACTACTCGATGCTGAGCCTGGGCAAGTTTTACGCGCGCAA
GATCTACCAGACGCCGTACGTGCCCATAGACAAGGAGGTGAAGATCGACGGTTTTTACATGCGC
ATGGCGCTGAAGGTGCTCACCCTGAGCGACGACCTGGGCGTGTACCGCAAGAGCGCATCCACA
AGGCCGTGAGCGTGAGCCGGCGGCGCGAGCTGAGCGACCGCGAGCTGATGCACAGCCTGCAGC
GGGCGCTGGGGCGCCGGCAGCGGCGACAGGGAGGCGGAGTCCTACTTCGATGCGGGGCGG
ACCTGCGCTGGGCGCCCAGCCGGCGGGCCCTGGAGGCCGCGGGGGTCCGCGAGGACTATGACG
AGGACGGCGAGGAGGATGAGGAGTACGAGCTAGAGGAGGGCGAGTACCTGGACTAAACCGCG
GGTGGTGTTTCCGGTAGATGCAAGACCCGAACGTGGTGGACCCGGCGCTGCGGGCGGCTCTGCA
GAGCCAGCCGTCCGGCCTTAACTCCTCAGACGACTGGCGACAGGTCATGGACCGCATCATGTCG
CTGACGGCGCGTAACCCGGACGCGTTCCGGCAGCAGCCGCAGGCCAACAGGCTCTCGCCATCC
TGGAGGCGGTGGTGCCTGCGCGCTCGAACCCCACGCACGAGAAGGTGCTGGCCATAGTGAACGC
GCTGGCCGAGAACAGGGCCATCCGCCCGGACGAGGCCGGGCTGGTGTACGACGCGCTGCTGCA
GCGCGTGGCCCGCTACAACAGCGGCAACGTGCAGACCAACCTGGACCGGCTGGTGGGGGACGT
GCGCGAGGCGGTGGCGCAGCGCGAGCGCGGATCGGCAGGGCAACCTGGGCTCCATGGTGGC
GCTGAATGCCTTCCTGAGCACGCAGCCGGCCAACGTGCCGCGGGGCAGGAAGACTACACCAA
CTTTGTGAGCGCGCTGCGGCTGATGGTGACCGAGACCCCCAGAGCGAGGTGTACCAGTCGGGC
CCGGACTACTTCTTCCAGACCAGCAGACAGGGCCTGCAGACGGTGAACCTGAGCCAGGCTTTCA
AGAACCTGCGGGGGCTGTGGGGCGTGAAGGCGCCCACCGGCGACCGGGCGACGGTGTCCAGCC
TGCTGACGCCCAACTCGCGCCTGCTGCTGCTGCTGATCGCGCCGTTCACGGACAGCGGCAGCGT
GTCCGGGACACCTACCTGGGGCACCTGCTGACCCTGTACCGCGAGGCCATCGGCAGGCGCAG
GTGGACGAGCACACCTTCCAGGAGATCACCAGCGTGAGCCGCGCGCTGGGGCAGGAGGACACG
AGCAGCCTGGAGGCGACTCTGAACTACCTGCTGACCAACCGGCGCAGAAGATTCCCTCGCTGC
ACAGCCTGACCTCCGAGGAGGAGCGCATCTTGCGCTACGTGCAGCAGAGCGTGAGCCTGAACCT
```

| DESCRIPTION OF THE SEQUENCES |
|---|
| GATGCGCGACGGGGTGACGCCCAGCGTGGCGCTGGACATGACCGCGCGCAACATGGAACCGGG |
| CATGTACGCCGCGCACCGGCCTTACATCAACCGCCTGATGGACTACCTGCATCGCGCGGCGCC |
| GTGAACCCCGAGTACTTTACCAACGCCATCCTGAACCCGCACTGGCTCCCGCCGCCCGGGTTCTA |
| CAGCGGGGGCTTCGAGGTCCCGGAGACCAACGATGGCTTCCTGTGGGACGACATGGACGACAG |
| CGTGTTCTCCCCGCGGCCGCAGGCGCTGGCGGAAGCGTCCCTGCTGCGTCCCAAGAAGGAGGAG |
| GAGGAGGAGGCGAGTCGCCGCCGCGGCAGCAGCGGCGTGGCTTCTCTGTCCGAGCTGGGGGCG |
| GCAGCCGCCGCGCGCCCGGGTCCCTGGGCGGCAGCCCCTTTCCGAGCCTGGTGGGGTCTCTGC |
| ACAGCGAGCGCACCACCCGCCCTCGGCTGCTGGGCGAGGACGAGTACCTGAATAACTCCCTGCT |
| GCAGCCGGTGCGGGAGAAAAACCTGCCTCCCGCCTTCCCAACAACGGGATAGAGAGCCTGGTG |
| GACAAGATGAGCAGATGGAAGACCTATGCGCAGGAGCACAGGGACGCGCCTGCGCTCCGGCCG |
| CCCACGCGGCGCCAGCGCCACGACCGGCAGCGGGGGCTGGTGTGGGATGACGAGGACTCCGCG |
| GACGATAGCAGCGTGCTGGACCTGGGAGGGAGCGGCAACCCGTTCGCGCACCTGCGCCCCGCC |
| TGGGGAGGATGTTTTAAAAAAAAAAAAAAAAAGCAAGAAGCATGATGCAAAAATTAAATAAAA |
| CTCACCAAGGCCATGGCGACCGAGCGTTGGTTTCTTGTGTTCCCTTCAGTATGCGGCGCGCGGCG |
| ATGTACCAGGAGGGACCTCCTCCCTCTTACGAGAGCGTGGTGGGCGCGGCGGCGGCGGCGCCT |
| CTTCTCCCTTTGCGTCCAGCTGCTGGAGCCGCCGTACGTGCCTCCCGCGCTACCTGCGGCCTACG |
| GGGGGGAGAAACAGCATCCGTTACTCGGAGCTGGCGCCCCTGTTCGACACCACCCGGGTGTACC |
| TGGTGGACAACAAGTCGGCGGACGTGGCCTCCCTGAACTACCAGAACGACCACAGCAATTTTTT |
| GACCACGGTCATCCAGAACAATGACTACAGCCCGAGCGAGGCCAGCACCCAGACCATCAATCTG |
| GATGACCGGTCGCACTGGGGCGGCGACCTGAAAACCATCCTGCACACCAACATGCCCAACGTGA |
| ACGAGTTCATGTTCACCAATAAGTTCAAGGCGCGGGTGATGGTGTCGCGCTCGCACACCAAGGA |
| AGACCGGGTGGAGCTGAAGTACGAGTGGGTGGAGTTCGAGCTGCCAGAGGGCAACTACTCCGA |
| GACCATGACCATTGACCTGATGAACAACGCGATCGTGGAGCACTATCTGAAAGTGGGCAGGCAG |
| AACGGGGTCCTGGAGAGCGACATCGGGGTCAAGTTCGACACCAGGAACTTCCGCCTGGGGCTGG |
| ACCCCGTGACCGGGCTGGTTATGCCCGGGGTGTACACCAACGAGGCCTTCCATCCCGACATCAT |
| CCTGCTGCCCGGCTGCGGGGTGGACTTCACTTACAGCCGCCTGAGCAACCTCCTGGGCATCCGC |
| AAGCGGCAGCCCTTCCAGGAGGGCTTCAGGATCACCTACGAGGACCTGGAGGGGGGCAACATC |
| CCCGCGCTCCTCGATGTGGAGGCCTACCAGGATAGCTTGAAGGAAAATGAGGCGGGACAGGAG |
| GATACCGCCCCCGCCGCCTCCGCCGCCGCCGAGCAGGGCGAGGATGCTGCTGACACCGCGGCCG |
| CGGACGGGGCAGAGGCCGACCCCGCTATGGTGGTGGAGGCTCCCGAGCAGGAGGAGGACATGA |
| ATGACAGTGCGGTGCGCGGAGACACCTTCGTCACCCGGGGGGAGGAAAAGCAAGCGGAGGCCG |
| AGGCCGCGGCCGAGGAAAAGCAACTGGCGGCAGCAGCGGCGGCGGCGGTTGGCCGCGGCGG |
| AGGCTGAGTCTGAGGGGACCAAGCCCGCCAAGGAGCCCGTGATTAAGCCCCTGACCGAAGATA |
| GCAAGAAGCGCAGTTACAACCTGCTCAAGGACAGCACCAACACCGCGTACCGCAGCTGGTACCT |
| GGCCTACAACTACGGCGACCCGTCGACGGGGGTGCGCTCCTGGACCCTGCTGTGCACGCCGGAC |
| GTGACCTGCGGCTCGGAGCAGGTGTACTGGTCGCTGCCCGACATGATGCAAGACCCCGTGACCT |
| TCCGCTCCACGCGGCAGGTCAGCAACTTCCCGGTGGTGGGCGCCGAGCTGCTGCCCGTGCACTC |
| CAAGAGCTTCTACAACGACCAGGCCGTCTACTCCCAGCTCATCCGCCAGTTCACCTCTCTGACCC |
| ACGTGTTCAATCGCTTTCCTGAGAACCAGATTCTGGCGCGCCCGCCCGCCCCCACCATCACCACC |
| GTCAGTGAAAACGTTCCTGCTCTCACAGATCACGGGACGCTACCGCTGCGCAACAGCATCGGAG |
| GAGTCCAGCGAGTGACCGTTACTGACGCCAGACGCCGCACCTGCCCCTACGTTTACAAGGCCTT |
| GGGCATAGTCTCGCCGCGCGTCCTTTCCAGCCGCACTTTTTGAGCAACACCACCATCATGTCCAT |
| CCTGATCTCACCCAGCAATAACTCCGGCTGGGACTGCTGCGCGCGCCCAGCAAGATGTTCGGA |
| GGGGCGAGGAAGCGTTCCGAGCAGCACCCCGTGCGCGTGCGCGGGCACTTCCGCGCCCCCTGGG |
| GAGCGCACAAACGCGGCCGCGGGGGCGCACCACCGTGGACGACGCCATCGACTCGGTGGTGG |
| AGCAGGCGCGCAACTACAGGCCCGCGGTCTCTACCGTGGACGCGGCCATCCAGACCGTGGTGCG |
| GGGCGCGCGGCGGTACGCCAAGCTGAAGAGCCGCCGGAAGCGCGTGGCCCGCCGCCACCGCCG |
| CCGACCCGGGGCCGCCGCCAAACGCGCCGCCGCGGCCCTGCTTCGCCGGGCCAAGCGCACGGGC |
| CGCCGCGCCGCCATGAGGGCCGCGCGCCGCTTGGCCGCCGGCATCACCGCCGCCACCATGGCCC |
| CCCGTACCCGAAGACGCGCGGCCGCCGCCGCCGCCGCCGCCATCAGTGACATGGCCGCAGCAGGCG |
| CCGGGGCAACGTGTACTGGGTGCGCGACTCGGTGACCGGCACGCGCGTGCCCGTGCGCTTCCGC |
| CCCCCGCGGACTTGAGATGATGTGAAAAAACAACACTGAGTCTCCTGCTGTTGTGTGTATCCCA |
| GCGGCGGCGGCGCGCGCAGCGTCATGTCCAAGCGCAAAATCAAAGAAGAGATGCTCCAGGTCG |
| TCGCGCCGGAGATCTATGGGCCCCGAAGAAGGAAGAGCAGGATTCGAAGCCCCGCAAGATAA |
| AGCGGGTCAAAAAGAAAAGAAAGATGATGACGATGCCGATGGGGAGGTGGAGTTCCTGCGCG |
| CCACGGCGCCCAGGCGCCCGGTGCAGTGGAAGGGCCGGCGCGTAAAGCGCGTCCTGCGCCCCG |
| GCACCGCGGTGGTCTTCACGCCCGGCGAGCGCTCCACCCGGACTTTCAAGCGCGTCTATGACGA |
| GGTGTACGGCGACGAAGACCTGCTGGAGCAGGCCAACGAGCGCTTCGGAGAGTTTGCTTACGGG |
| AAGCGTCAGCGGGCGCTGGGGAAGGAGGACCTGCTGGCGCTGCCGCTGGACCAGGGCAACCCC |
| ACCCCCAGTCTGAAGCCCGTGACCCTGCAGCAGGTGCTGCCGAGCAGCGCACCCTCCGAGGCGA |
| AGCGGGGTCTGAAGCGCGAGGGCGGCGACCTGGCGCCCACCGTGCAGCTCATGGTGCCCAAGC |
| GGCAGAGGCTGGAGGATGTGCTGGAGAAAATGAAAGTAGACCCCGGTCTGCAGCCGGACATCA |
| GGGTCCGCCCCATCAAGCAGGTGGCGCCGGGCCTCGGCGTGCAGACCGTGGACGTGGTCATCCC |
| CACCGGCAACTCCCCGCCGCCGCCACCACTACCGCTGCCTCCACGGACATGGAGACACAGACC |
| GATCCCGCCGCAGCCGCAGCCGCAGCCGCCGCCGCGACCTCCTCGGCGGAGGTGCAGACGGACC |
| CCTGGCTGCCGCCGGCGATGTCAGCTCCCCGCGCGCGTCGCGGGCGCAGGAAGTACGGCCGCGC |
| CAACGCGCTCCTGCCCGAGTACGCCTTGCATCCTTCCATCGCGCCCACCCCCGGCTACCGAGGCT |
| ATACCTACCGCCCGCGAAGAGCCAAGGGTTCCACCCGCCGTCCCCGCCGACGCGCCGCCGCCAC |
| CACCCGCCGCCGCCGCCGCAGACGCCAGCCCGCACTGGCTCCAGTCTCCGTGAGGAAAGTGGCG |
| CGCGACGGACACACCCTGGTGCTGCCCAGGGCGCGCTACCACCCCAGCATCGTTTAAAAGCCTG |
| TTGTGGTTCTTGCAGATATGGCCCTCACTTGCCGCCTCCGTTTCCCGGTGCCGGATACCGAGGA |
| GGAAGATCGCGCCGCAGGAGGGGGTCTGGCCGGCCGCGGCCTCGAGCGGAGGCAGCCGCCGCGCG |
| CACCGGCGGCGACGCGCCACCAGCCGACGCATGCGCGGCGGGGTGCTGCCCCTGTTAATCCCCC |
| TGATCGCCGCGGCGATCGGCGCCGTGCCCGGGATCGCCTCCGTGGCCTTGCAAGCGTCCCAGAG |
| GCATTGACAGACTTGCAAACTTGCAAATATGGAAAAAAAAACCCCAATAAAAAAGTCTAGACTC |
| TCACGCTCGCTTGGTCCTGTGACTATTTTGTAGAATGGAAGACATCAACTTTGCGTCGCTGGCCC |
| CGCGTCACGGCTCGCGCCCGTTCCTGGGACACTGGAACGATATCGGCACCAGCAACATGAGCGG |

DESCRIPTION OF THE SEQUENCES

```
TGGCGCCTTCAGTTGGGGCTCTCTGTGGAGCGGCATTAAAAGTATCGGGTCTGCCGTTAAAAATT
ACGGCTCCCGGGCCTGGAACAGCAGCACGGGCCAGATGTTGAGAGACAAGTTGAAAGAGCAGA
ACTTCCAGCAGAAGGTGGTGGAGGGCCTGGCCTCCGGCATCAACGGGGTGGTGGACCTGGCCAA
CCAGGCCGTGCAGAATAAGATCAACAGCAGACTGGACCCCCGGCCGCCGGTGGAGGAGGTGCC
GCCGGCGCTGGAGACGGTGTCCCCCGATGGGCGTGGCGAGAAGCGCCCGCGGCCCGATAGGGA
AGAGACCACTCTGGTCACGCAGACCGATGAGCCGCCCCCGTATGAGGAGGCCCTGAAGCAAGG
TCTGCCCACCACGCGGCCCATCGCGCCCATGGCCACCGGGGTGGTGGGCCGCCACACCCCGCC
ACGCTGGACTTGCCTCCGCCCGCCGATGTGCCGCAGCAGCAGAAGGCGGCACAGCCGGGCCCGC
CCGCGACCGCCTCCCGTTCCTCCGCCGGTCCTCTGCGCCGCGCGGCCAGCGGCCCCGCGGGGG
GGTCGCGAGGCACGGCAACTGGCAGAGCACGCTGAACAGCATCGTGGGTCTGGGGGTGCGGTC
CGTGAAGCGCCGCCGATGCTACTGAATAGCTTAGCTAACGTGTTGTATGTGTGTATGCGCCTAT
GTCGCCGCCAGAGGAGCTGCTGAGTCGCCGCCGTTCGCGCGCCCACCACCACCGCCACTCCGCC
CCTCAAGATGGCGACCCCATCGATGATGCCGCAGTGGTCGTACATGCACATCTCGGGCCAGGAC
GCCTCGGAGTACCTGAGCCCCGGGCTGGTGCAGTTCGCCCGCGCCACCGAGAGCTACTTCAGCC
TGAGTAACAAGTTTAGGAACCCCACGGTGGCGCCCACGCACGATGTGACCACCGACCGGTCTCA
GCGCCTGACGCTGCGGTTCATTCCCGTGGACCGCGAGGACACCGCGTACTCGTACAAGGCGCGG
TTCACCCTGGCCGTGGGCGACAACCGCGTGCTGGACATGGCCTCCACCTACTTTGACATCCGCGG
GGTGCTGGACCGGGGTCCCACTTTCAAGCCCTACTCTGGCACCGCCTACAACTCCCTGGCCCCCA
AGGGCGCTCCCAACTCCTGCGAGTGGGAGCAAGAGGAAACTCAGGCAGTTGAAGAAGCAGCAG
AAGAGGAAGAAGAAGATGCTGACGGTCAAGCTGAGGAAGAGCAAGCAGCTACCAAAAAGACT
CATGTATATGCTCAGGCTCCCCTTTCTGGCGAAAAAATTAGTAAAGATGGTCTGCAAATAGGAA
CGGACGCTACAGCTACAGAACAAAAACCTATTTATGCAGACCCTACATTCCAGCCCGAACCCCA
AATCGGGGAGTCCCAGTGGAATGAGGCAGATGCTACAGTCGCCGGCGGTAGAGTGCTAAAGAA
ATCTACTCCCATGAAACCATGCTATGTTCCTATGCAAGACCCCACAAATGCTAATGGAGGTCAG
GGTGTACTAACGGCAAATGCCCAGGGACAGCTAGAATCTCAGGTTGAAATGCAATTCTTTTCAA
CTTCTGAAAACGCCCGTAACGAGGCTAACAACATTCAGCCCAAATTGGTGCTGTATAGTGAGGA
TGTGCACATGGAGACCCCGGATACGCACCTTTCTTACAAGCCCGCAAAAAGCGATGACAATTCA
AAAATCATGCTGGGTCAGCAGTCCATGCCCAACAGACCTAATTACATCGGCTTCAGAGACAACT
TTATCGGCCTCATGTATTACAATAGCACTGGCAACATGGGAGTGCTTGCAGGTCAGGCCTCTCAG
TTGAATGCAGTGGTGGACTTGCAAGACAGAAACACAGAACTGTCCTACCAGCTCTTGCTTGATT
CCATGGGTGACAGAACCAGATACTTTTCCATGTGGAATCAGGCAGTGGACAGTTATGACCCAGA
TGTTAGAATTATTGAAAATCATGGAACTGAAGACGAGCTCCCCAACTATTGTTTCCCTCTGGGTG
GCATAGGGGTAACTGACACTTACCAGGCTGTTAAAACCAACAATGGCAATAACGGGGGCCAGG
TGACTTGGACAAAAGATGAAACTTTTGCAGATCGCAATGAAATAGGGGTGGGAAACAATTTCGC
TATGGAGATCAACCTCAGTGCCAACCTGTGGAGAAACTTCCTGTACTCCAACGTGGCGCTGTAC
CTACCAGACAAGCTTAAGTACAACCCCTCCAATGTGGACATCTCTGACAACCCCAACACCTACG
ATTACATGAACAAGCGAGTGGTGGCCCCGGGGCTGGTGGACTGCTACATCAACCTGGGCGCGCG
CTGGTCGCTGGACTACATGGACAACGTCAACCCCTTCAACCACCACCGCAATGCGGGCCTGCGC
TACCGCTCCATGCTCCTGGGCAACGGGCGCTACGTGCCCTTCCACATCCAGGTGCCCCAGAAGTT
CTTTGCCATCAAGAACCTCCTCCTCCTGCCGGGCTCCTACACCTACGAGTGGAACTTCAGGAAGG
ATGTCAACATGGTCCTCCAGAGCTCTCTGGGTAACGATCTCAGGGTGGACGGGGCCAGCATCAA
GTTCGAGAGCATCTGCCTCTACGCCACCTTCTTCCCCATGGCCCACAACACGGCCTCCACGCTCG
AGGCCATGCTCAGGAACGACACCAACGACCAGTCCTTCAATGACTACCTCTCCGCCGCCAACAT
GCTCTACCCCATACCCGCCAACGCCACCAACGTCCCCATCTCCATCCCCTCGCGCAACTGGGCGG
CCTTCCGCGGCTGGGCCTTCACCCGCCTCAAGACCAAGGAGACCCCCTCCCTGGGCTCGGGATTC
GACCCCTACTACACCTACTCGGGCTCCATTCCCTACCTGGACGGACACCTTCTACCTCAACCACAC
TTTCAAGAAGGTCTCGGTCACCTTCGACTCCTCGGTCAGCTGGCCGGGCAACGACCGTCTGCTCA
CCCCCAACGAGTTCGAGATCAAGCGCTCGGTCGACGGGGAGGGCTACAACGTGGCCCAGTGCA
ACATGACCAAGGACTGGTTCCTGGTCCAGATGCTGGCCAACTACAACATCGGCTACCAGGGCTT
CTACATCCCAGAGAGCTACAAGGACAGGATGTACTCCTTCTTCAGGAACTTCCAGCCCATGAGC
CGGCAGGTGGTGGACCAGACCAAGTACAAGGACTACCAGGAGGTGGGCATCATCCACCAGCAC
AACAACTCGGGCTTCGTGGGCTACCTCGCCCCACCATGCGCGAGGGACAGGCCTACCCCGCCA
ACTTCCCCTATCCGCTCATAGGCAAGACCGCGGTCGACAGCATCACCCAGAAAAAGTTCCTCTG
CGACCGCACCCTCTGGCGCATCCCCTTCTCCAGCAACTTCATGTCCATGGGTGCGCTCTCGGACC
TGGGCCAGAACTTGCTCTACGCCAACTCCGCCCACGCCCTCGACATGACCTTCGAGGTCGACCCC
ATGGACGAGCCCACCCTTCTCTATGTTCTGTTCGAAGTCTTTGACGTGGTCCGGGTCCACCAGCC
GCACCGCGGCGTCATCGAGACCGTGTACCTGCGTACGCCCTTCTCGGCCGGCAACGCCACCACC
TAAAGAAGCAAGCCGCAGTCATCGCCGCCTGCATGCCGTCGGGTTCCACCGAGCAAGAGCTCAG
GGCCATCGTCAGAGACCTGGGATGCGGGCCCTATTTTTTGGGCACCTTCGACAAGCGCTTCCCTG
GCTTTGTCTCCCCACACAAGCTGGCCTGCGCCATCGTCAACACGGCCGGCCGCGAGACCGGGGG
CGTGCACTGGCTGGCCTTCGCCTGGAACCCGCGCTCCAAAACATGCTTCCTCTTTGACCCCTTCG
GCTTTTCGGACCAGCGGCTCAAGCAAATCTACGAGTTCGAGTACGAGGGCTTGCTGCGTCGCAG
CGCCATCGCCTCCTCGCCCGACCGCTGCGTCACCCTCGAAAAGTCCACCCAGACCGTGCAGGGG
CCCGACTCGGCCGCCTGCGGTCTCTTCTGCTGCATGTTTCTGCACGCCTTTGTGCACTGGCCTCAG
AGTCCCATGGACCGCAACCCCCACCATGAACTTGCTGACGGGGTGCCCAACTCCATGCTCCAGA
GCCCCCAGGTCGAGCCCACCCTGCGCCGCAACCAGGAGCAGCTCTACAGCTTCCTGGAGCGCCA
CTCGCCTTACTTCCGCGCCACAGCGCACAGATCAGGAGGGCCACCTCCTTCTGCCACTTGCAAG
AGATGCAAGAAGGGTAATAACGATGTACACACTTTTTTTTCTCAATAAATGGCATCTTTTTATTTA
TACAAGCTCTCTGGGGTATTCATTTCCCACCACCACCCGCCGTTGTCGCCATCTGGCTCTATTTAG
AAATCGAAAGGGTTCTGCCGGGAGTCGCCGTGCGCCACGGGCAGGGACACGTTGCGATACTGGT
AGCGGGTGCCCCACTTGAACTCGGGCACCACCAGGCGAGGCAGCTCGGGGAAGTTTTCGCTCCA
CAGGCTGCGGGTCAGCACCAGCGCGTTCATCAGGTCGGGCGCCGAGATCTTGAAGTCGCAGTTG
GGGCCGCCGCCCTGCGCGCGCGAGTTGCGGTACACCGGGTTGCAGCACTGGAACACCAACAGCG
CCGGGTGCTTCACGCTGGCCAGCACGCTGCGGTCGGAGATCAGCTCGGCGTCCAGGTCCTCCGC
GTTGCTCAGCGCGAACGGGGTCATCTTGGGCACTTGCCGCCCCAGGAAGGGCGCGTGCCCCGGT
TTCGAGTTGCAGTCGCAGCGCAGCGGGATCAGCAGGTGCCCGTGCCCGGACTCGGCGTTGGGT
ACAGCGCGCGCATGAAGGCCTGCATCTGGCGGAAGGCCATCTGGGCCTTGGCGCCCTCCGAGAA
```

-continued

| DESCRIPTION OF THE SEQUENCES |
|---|
| GAACATGCCGCAGGACTTGCCCGAGAACTGGTTTGCGGGGCAGCTGGCGTCGTGCAGGCAGCAG |
| CGCGCGTCGGTGTTGGCGATCTGCACCACGTTGCGCCCCACCGGTTCTTCACGATCTTGGCCTT |
| GGACGATTGCTCCTTCAGCGCGCGCTGCCCGTTCTCGCTGGTCACATCCATCTCGATCACATGTT |
| CCTTGTTCACCATGCTGCTGCCGTGCAGACACTTCAGCTCGCCCTCCGTCTCGGTGCAGCGGTGC |
| TGCCACAGCGCGCAGCCCGTGGGCTCGAAAGACTTGTAGGTCACCTCCGCGAAGGACTGCAGGT |
| ACCCCTGCAAAAAGCGGCCCATCATGGTCACGAAGGTCTTGTTGCTGCTGAAGGTCAGCTGCAG |
| CCCGCGGTGCTCCTCGTTCAGCCAGGTCTTGCACACGGCCGCCAGCGCCTCCACCTGGTCGGGCA |
| GCATCTTGAAGTTCACCTTCAGCTCATTCTCCACGTGGTACTTGTCCATCAGCGTGCGCGCCGCC |
| TCCATGCCCTTCTCCCAGGCCGACACCAGCGGCAGGCTCACGGGGTTCTTCACCATCACCGTGGC |
| CGCCGCCTCCGCCGCGCTTTCGCTTTCCGCCCCGCTGTTCTCTTCCTCTTCCTCCTCTTCCTCGCCG |
| CCGCCCACTCGCAGCCCCCGCACCACGGGGTCGTCTTCCTGCAGGCGCTGCACCTTGCGCTTGCC |
| GTTGCGCCCCTGCTTGATGCGCACGGGCGGGTTGCTGAAGCCCACCATCACCAGCGCGGCCTCTT |
| CTTGCTCGTCCTCGCTGTCCAGAATGACCTCCGGGGAGGGGGGTTGGTCATCCTCAGTACCGA |
| GGCACGCTTCTTTTTCTTCCTGGGGGCGTTCGCCAGCTCCGCGGCTGCGGCCGCTGCCGAGGTCG |
| AAGGCCGAGGGCTGGGCGTGCGCGGCACCAGCGCGTCCTGCGAGCCGTCCTCGTCCTCCTCGGA |
| CTCGAGACGGAGGCGGGCCCGCTTCTTCGGGGGGCGCGCGGGGCGGCGGAGGCGGCGGCGGCGA |
| CGGAGACGGGGACGAGACATCGTCCAGGGTGGGTGGACGGCGGGCCGCGCCGCGTCCGCGCTC |
| GGGGGTGGTCTCGCGCTGGTCCTCTTCCCGACTGGCCATCTCCCACTGCTCCTTCTCCTATAGGC |
| AGAAAGAGATCATGGAGTCTCTCATGCGAGTCGAGAAGGAGGAGGACAGCCTAACCGCCCCCT |
| CTGAGCCCTCCACCACCGCCGCCACCACCGCCAATGCCGCCGCGGACGACGCGCCCACCGAGAC |
| CACCGCCAGTACCACCCTCCCCAGCGACGCACCCCCGCTCGAGAATGAAGTGCTGATCGAGCAG |
| GACCCGGGTTTTGTGAGCGGAGAGGAGGATGAGGTGGATGAGAAGGAGAAGGAGGAGGTCGCC |
| GCCTCAGTGCCAAAAGAGGATAAAAAGCAAGACCAGGACGACGCAGATAAGGATGAGACAGC |
| AGTCGGGCGGGGGAACGGAAGCCATGATGCTGATGACGGCTACCTAGACGTGGGAGACGACGT |
| GCTGCTTAAGCACCTGCACCGCCAGTGCGTCATCGTCTGCGACGCGCTGCAGGAGCGCTGCGAA |
| GTGCCCCTGGACGTGGCGGAGGTCAGCCGCGCCTACGAGCGGCACCTCTTCGCGCCGCACGTGC |
| CCCCCAAGCGCCGGGAGAACGGCACCTGCGAGCCCAACCCGCGTCTCAACTTCTACCCGGTCTT |
| CGCGGTACCCGAGGTGCTGGCCACCTACCACATCTTTTTCCAAAACTGCAAGATCCCCCCTCCT |
| GCCGCGCCAACCGCACCCGCGCCGACAAAACCCTGACCCTGCGGCAGGGCGCCCACATACCTGA |
| TATCGCCTCTCTGGAGGAAGTGCCCAAGATCTTCGAGGGTCTCGGTCGCGACGAGAACGGGCG |
| GCGAACGCTCTGCACGGAGACAGCGAAAACGAGAGTCACTCGGGGGTGCTGGTGGAGCTCGAG |
| GGCGACAACGCGCGCCTGGCCGTACTCAAGCGCAGCATAGAGGTCACCCACTTTGCCTACCCGG |
| CGCTCAACCTGCCCCCCAAGGTCATGAGTGTGGTCATGGGCGAGCTCATCATGCGCCGCGCCCA |
| GCCCCTGGCCGCGGATGCAAACTTGCAAGAGTCCTCCGAGGAAGGCCTGCCCGCGGTCAGCGAC |
| GAGCAGCTGGCGCGCTGGCTGGAGACCCGCGACCCCGCGCAGCTGGAGGAGCGGCGCAAGCTC |
| ATGATGGCCGCGGTGCTGGTCACCGTGGAGCTCGAGTGTCTGCAGCGCTTCTTCGCGGACCCCG |
| AGATGCAGCGCAAGCTCGAGGAGACCCTGCACTACACCTTCCGCCAGGGCTACGTGCGCCAGGC |
| CTGCAAGATCTCCAACGTGGAGCTCTGCAACCTGGTCTCCTACCTGGGCATCCTGCACGAGAAC |
| CGCCTCGGGCAGAACGTCCTGCACTCCACCCTCAAAGGGGAGGCGCGCCGCGACTACATCCGCG |
| ACTGCGCCTACCTCTTCCTCTGCTACACCTGGCAGACGGCCATGGGGGTCTGGCAGCAGTGCCTG |
| GAGGAGCGCAACCTCAAGGAGCTGGAAAAGCTCCTCAAGCGCACCCTCAGGGACCTCTGGACG |
| GGCTTCAACGAGCGCTCGGTGGCCGCCGCGCTGGCGGACATCATCTTTCCCGAGCGCCTGCTCA |
| AGACCCTGCAGCAGGGCCTGCCCGACTTCACCAGCCAGAGCATGCTGCAGAACTTCAGGACTTT |
| CATCCTGGAGCGCTCGGGCATCCTGCCGGCCACTTGCTGCGCGCTGCCCAGCGACTTCGTGCCCA |
| TCAAGTACAGGGAGTGCCCGCCGCCGCTCTGGGGCCACTGCTACCTCTTCCAGCTGGCCAACTA |
| CCTCGCCTACCACTCGGACCTCATGGAAGACGTGAGCGGCGAGGGCCTGCTCGAGTGCCACTGC |
| CGCTGCAACCTCTGCACGCCCCACCGCTCTCTAGTCTGCAACCCGCAGCTGCTCAGCGAGAGTCA |
| GATTATCGGTACCTTCGAGCTGCAGGGTCCCTCGCCTGACGAGAAGTCCGCGGCTCCAGGGCTG |
| AAACTCACTCCGGGGCTGTGGACTTCCGCCTACCTACGCAAATTTGTACCTGAGGACTACCACGC |
| CCACGAGATCAGGTTCTACGAAGACCAATCCCGCCCGCCCAAGGCGGAGCTCACCGCCTGCGTC |
| ATCACCCAGGGGCACATCCTGGGCCAATTGCAAGCCATCAACAAAGCCCGCCGAGAGTTCTTGC |
| TGAAAAAGGGTCGGGGGTGTACCTGGACCCCCAGTCCGGCGAGGAGCTAAACCCGCTACCCCCC |
| GCCGCCGCCCCAGCAGCGGGACCTTGCTTCCCAGGATGGCACCCAGAAAGAAGCAGCAGCCGC |
| CGCCGCCGCCGCAGCCATACATGCTTCTGGAGGAAGAGGAGGAGGACTGGGACAGTCAGGCAG |
| AGGAGGTTTCGGACGAGGAGCAGGAGGAGATGATGGAAGACTGGGAGGAGGACAGCAGCCTA |
| GACGAGGAAGCTTCAGAGGCCGAAGAGGTGGCAGACGCAACACCATCGCCCTCGGTCGCAGCC |
| CCCTCGCCGGGGCCCCTGAAATCTCCGAACCCAGCACCAGCGCTATAACCTCCGCTCCTCCGGC |
| GCCGGCGCCACCCGCCCGCAGACCCAACCGTAGATGGGACACCACAGGAACCGGGGTCGGTAA |
| GTCCAAGTGCCCGCCGCCGCCACCGCAGCAGCAGCAGCAGCAGCGCCAGGGCTACCGCTCGTGG |
| CGCGGGCACAAGAACGCCATAGTCGCCTGCTTGCAAGACTGCGGGGGCAACATCTCTTTCGCCC |
| GCCGCTTCCTGCTATTCCACCACGGGGTCGCCTTTCCCCGCAATGCTCATTACTACCGTCATC |
| TCTACAGCCCCTACTGCAGCGGCGACCCAGAGGCGGCAGCGGCAGCCACAGCGGCGACCACCA |
| CCTAGGAAGATATCCTCCGCGGGCAAGACAGCGGCAGCAGCGGCCAGGAGACCCGCGGCAGCA |
| GCGGCGGGAGCGGTGGGCGCACTGCGCCTCTCGCCCAACGAACCCCTCTCGACCCGGGAGCTCA |
| GACACAGGATCTTCCCCACTTTGTATGCCATCTTCCAACAGAGCAGAGGCCAGGAGCAGGAGCT |
| GAAAATAAAAAACAGATCTCTGCGCTCCCTCACCCGCAGCTGTCTGTATCACAAAAGCGAAGAT |
| CAGCTTCGGCGCACGCTGGAGGACGCGGAGGCACTCTTCAGCAAATACTGCGCGCTCACTCTTA |
| AAGACTAGCTCCGCGCCCTTCTCGAATTTAGGCGGGAGAAAACTACGTCATCGCCGGCCGCCGC |
| CCAGCCCGCCCAGCCGAGATGAGCAAAGAGATTCCCACGCCATACATGTGGAGCTACCAGCCGC |
| AGATGGGACTCGCGGCGGGAGCGGCCCAGGACTACTCCACCCGCATGAACTACATGAGCGCGG |
| GACCCCACATGATCTCACAGGTCAACGGGATCGCGCCCAGCGAAACCAAATACTGCTGGAACA |
| GGCGGCCATCACCGCCACGCCCCGCCATAATCTCAACCCCCGAAATTGGCCCGCCGCCCTCGTG |
| TACCAGGAAACCCCCTCCGCCACCACCGTACTACTTCCGCGTGACGCCCAGGCCGAAGTCCAGA |
| TGACTAACTCAGGGGCGCAGCTCGCGGGCGCTTTCGTCACGGGGCGCGGCCGCTCCGACCAGG |
| TATAAGACACCTGATGATCAGAGGCCGAGGTATCCAGCTCAACGACGAGTCGGTGAGCTCTTCG |
| CTCGGTCTCCGTCCGGACGGAACTTTCCAGCTCGCCGGATCCGGCCGCTCTTCGTTCACGCCCCG |
| CCAGGCGTACCTGACTCTGCAGACCTCGTCCTCGGAGCCCCGCTCCGGCGGCATCGGAACCCTC |

| DESCRIPTION OF THE SEQUENCES |
|---|
| CAGTTCGTGGAGGAGTTCGTGCCCTCGGTCTACTTCAACCCCTTCTCGGGACCTCCCGGACGCTA |
| CCCCGACCAGTTCATTCCGAACTTTGACGCGGTGAAGGACTCGGCGGACGGCTACGACTGAATG |
| TCAGGTGTCGAGGCAGAGCAGCTTCGCCTGAGACACCTCGAGCACTGCCGCCGCCACAAGTGCT |
| TCGCCCGCGGTTCTGGTGAGTTCTGCTACTTTCAGCTACCCGAGGAGCATACCGAGGGGCCGGC |
| GCACGGCGTCCGCCTGACCACCCAGGGCGAGGTTACCTGTTCCCTCATCCGGGAGTTTACCCTCC |
| GTCCCCTGCTAGTGGAGCGGGAGCGGGGTCCCTGTGTCCTAACTATCGCCTGCAACTGCCCTAAC |
| CCTGGATTACATCAAGATCTTTGCTGTCATCTCTGTGCTGAGTTTAATAAACGCTGAGATCAGAA |
| TCTACTGGGGCTCCTGTCGCCATCCTGTGAACGCCACCGTCTTCACCCACCCCGACCAGGCCCAG |
| GCGAACCTCACCTGCGGTCTGCATCGGAGGGCCAAGAAGTACCTCACCTGGTACTTCAACGGCA |
| CCCCCTTTGTGGTTTACAACAGCTTCGACGGGGACGGAGTCTCCCTGAAAGACCAGCTCTCCGGT |
| CTCAGCTACTCCATCCACAAGAACACCACCCTCCAACTCTTCCCTCCCTACCTGCCGGGAACCTA |
| CGAGTGCGTCACCGGCCGCTGCACCCACCTCACCCGCCTGATCGTAAACCAGAGCTTTCCGGGA |
| ACAGATAACTCCCTCTTCCCCAGAACAGGAGGTGAGCTCAGGAAACTCCCCGGGGACCAGGGCG |
| GAGACGTACCTTCGACCCTTGTGGGGTTAGGATTTTTTATTACCGGGTTGCTGGCTCTTTTAATCA |
| AAGTTTCCTTGAGATTTGTTCTTTCCTTCTACGTGTATGAACACCTCAACCTCCAATAACTCTACC |
| CTTTCTTCGGAATCAGGTGACTTCTCTGAAATCGGGCTTGGTGTGCTGCTTACTCTGTTGATTTTT |
| TTCCTTATCATACTCAGCCTTCTGTGCCTCAGGCTCGCCGCCTGCTGCGCACACATCTATATCTAC |
| TGCTGGTTGCTCAAGTGCAGGGGTCGCCACCCAAGATGAACAGGTACATGGTCCTATCGATCCT |
| AGGCCTGCTGGCCCTGGCGGCCTGCAGCGCCGCCAAAAAGAGATTACCTTTGAGGAGCCCGCT |
| TGCAATGTAACTTTCAAGCCCGAGGGTGACCAATGCACCACCCTCGTCAAATGCGTTACCAATC |
| ATGAGAGGCTGCGCATCGACTACAAAAACAAAACTGGCCAGTTTGCGGTCTATAGTGTGTTTAC |
| GCCCGGAGACCCCTCTAACTACTCTGTCACCGTCTTCCAGGGCGGACAGTCTAAGATATTCAATT |
| ACACTTTCCCTTTTTATGAGTTATGCGATGCGGTCATGTACATGTCAAAACAGTACAACCTGTGG |
| CCTCCCTCTCCCCAGGCGTGTGTGGAAAATACTGGGTCTTACTGCTGTATGGCTTTCGCAATCAC |
| TACGCTCGCTCTAATCTGCACGGTGCTATACATAAAATTCAGGCAGAGGCGAATCTTTATCGATG |
| AAAAGAAATGCCTTGATCGCTAACACCGGCTTTCTATCTGCAGAATGAATGCAATCACCTCCCT |
| ACTAATCACCACCACCCTCCTTGCGATTGCCCATGGGTTGACACGAATCGAAGTGCCAGTGGGG |
| TCCAATGTCACCATGGTGGGCCCCGCCGGCAATTCCACCCTCATGTGGGAAAAATTTGTCCGCA |
| ATCAATGGGTTCATTTCTGCTCTAACCGAATCAGTATCAAGCCCAGAGCCATCTGCGATGGGCA |
| AAATCTAACTCTGATCAATGTGCAAATGGATGCTGGGTACTATTACGGGCAGCGGGGAGAA |
| ATCATTAATTACTGGCGACCCCACAAGGACTACATGCTGCATGTAGTCGAGGCACTTCCCACTAC |
| CACCCCCACTACCACCTCTCCCACCACCACCACCACTACTACTACTACTACTACTACTACTACTA |
| CTACCACTACCGCTGCCCGCCATACCCGCAAAAGCACCATGATTAGCACAAAGCCCCCTCGTGC |
| TCACTCCCACGCCGGCGGGCCCATCGGTGCGACCTCAGAAACCACCGAGCTTTGCTTCTGCCAAT |
| GCACTAACGCCAGCGCTCATGAACTGTTCGACCTGGAGAATGAGGATGTCCAGCAGAGCTCCGC |
| TTGCCTGACCCAGGAGGCTGTGGAGCCCGTTGCCCTGAAGCAGATCGGTGATTCAATAATTGAC |
| TCTTCTTCTTTTGCCACTCCCGAATACCCTCCCGATTCTACTTTCCACATCACGGGTACCAAAGAC |
| CCTAACCTCTCTTTCTACCTGATGCTGCTGCTCTGTATCTCTGTGGTCTCTTCCGCGCTGATGTTA |
| CTGGGGATGTTCTGCTGCCTGATCTGCCGCAGAAAGAGAAAAGCTCGCTCTCAGGGCCAACCAC |
| TGATGCCCTTCCCCTACCCCCCGGATTTTGCAGATAACAAGATATGAGCTCGCTGCTGACACTAA |
| CCGCTTTACTAGCCTGCGCTCTAACCCTTGTCGCTTGCGACTCGAGATTCCACAATGTCACAGCT |
| GTGGCAGGAGAAAATGTTACTTTCAACTCCACGGCCGATACCCAGTGGTCGTGGAGTGGCTCAG |
| GTAGCTACTTAACTATCTGCAATAGCTCCACTTCCCCCGGCATATCCCCAACCAAGTACCAATGC |
| AATGCCAGCCTGTTCACCCTCATCAACGCTTCCACCCTGGACAATGGACTCTATGTAGGCTATGT |
| ACCCTTTGGTGGGCAAGGAAAGACCCACGCTTACAACCTGGAAGTTCGCCAGCCCAGAACCACT |
| ACCCAAGCTTCTCCCACCACCACCACCACCACCATCACCAGCAGCAGCAGCAGCAGCAGCAGCC |
| ACAGCAGCAGCAGCAGATTATTGACTTTGGTTTTGGCCAGCTCATCTGCCGCTACCCAGGCCATC |
| TACAGCTCTGTGCCCGAAACCACTCAGATCCACCGCCCAGAAACGACCACCGCCACCACCCTAC |
| ACACCTCCAGCGATCAGATGCCGACCAACATCACCCCCTTGGCTCTTCAAATGGGACTTACAAG |
| CCCCACTCCAAAACCAGTGGATGCGGCCGAGGTCTCCGCCCTCGTCAATGACTGGGCGGGGCTG |
| GGAATGTGGTGGTTCGCCATAGGCATGATGGCGCTCTGCCTGCTTCTGCTCTGGCTCATCTGCTG |
| CCTCCACCGCAGGCGAGCCAGACCCCCCATCTATAGACCCATCATTGTCCTGAACCCCGATAAT |
| GATGGGATCCATAGATTGGATGGCCTGAAAAACCTACTTTTTTCTTTTACAGTATGATAAATTGA |
| GACATGCCTCGCATTTTCTTGTACATGTTCCTTCTCCCACCTTTTCTGGGGTGTTCTACGCTGGCC |
| GCTGTGTCTCACCTGGAGGTAGACTGCCTCTCACCCTTCACTGTCTACCTGCTTTACGGATTGGTC |
| ACCCTCACTCTCATCTGCAGCCTAATCACAGTAATCATCGCCTTCATCCAGTGCATTGATTACAT |
| CTGTGTGCGCCTCGCATACTTCAGACACCACCCGCAGTACCGGACAGGAACATTGCCCAACTT |
| CTAAGACTGCTCTAATCATGCATAAGACTGTGATCTGCCTTCTGATCCTCTGCATCCTGCCCACC |
| CTCACCTCCTGCCAGTACACCACAAAATCTCCGCGCAAAAGACATGCCTCCTGCCGCTTCACCCA |
| ACTGTGGAATATACCCAAATGCTACAACGAAAAGAGCGAGCTCTCCGAAGCTTGGCTGTATGGG |
| GTCATCTGTGTCTTAGTTTTCTGCAGCACTGTCTTTGCCCTCATAATCTACCCCTACTTTGATTTG |
| GGATGGAACGCGATCGATGCCATGAATTACCCCACCTTTCCCGCACCCGAGATAATTCCACTGC |
| GACAAGTTGTACCCGTTGTCGTTAATCAACGCCCCCATCCCCTACGCCCACTGAAATCAGCTAC |
| TTTAACCTAACAGGCGGAGATGACTGACGCCCTAGATCTAGAAATGGACGGCATCAGTACCGAG |
| CAGCGTCTCCTAGAGAGGCGCAGGCAGGCGGCTGAGCAAGAGCGCCTCAATCAGGAGCTCCGA |
| GATCTCGTTAACCTGCACCAGTGCAAAAGAGGCATCTTTTGTCTGGTAAAGCAGGCCAAAGTCA |
| CCTACGAGAAGACCGGCAACAGCCACCGCCTCAGTTACAAATTGCCCACCCAGCGCCAGAAGCT |
| GGTGCTCATGGTGGGTGAGAATCCCATCACCGTCACCCAGCACTCGGTAGAGACCGAGGGGTGT |
| CTGCACTCCCCCTGTCGGGGTCCAGAAGACCTCTGCACCCTGGTAAAGACCCTGTGCGGTCTCAG |
| AGATTTAGTCCCCTTTAACTAATCAAACACTGGAATCAATAAAAAGAATCACTTACTTAAAATC |
| AGACAGCAGGTCTCTGTCCAGTTTATTCAGCAGCACCTCCTTCCCCTCCTCCCAACTCTGGTACT |
| CCAAACGCCTTCTGGCGGCAAACTTCCTCCACACCCTGAAGGGAATGTCAGATTCTTGCTCCTGT |
| CCCTCCGCACCCACTATCTTCATGTTGTTGCAGATGAAGCGCACCAAAACGTCTGACGAGAGCTT |
| CAACCCCGTGTACCCCTATGACACGGAAAGCGGCCCTCCCTCCGTCCCTTTCCTCACCCCTCCCT |
| TCGTGTCTCCCGATGGATTCCAAGAAAGTCCCCCCGGGGTCCTGTCTCTGAACCTGGCCGAGCCC |
| CTGGTCACTTCCCACGGCATGCTCGCCCTGAAAATGGAAGTGGCCTCTCCCTGGACGACGCTG |
| GCAACCTCACCTCTCAAGATATCACCACCGCTAGCCCTCCCCTCAAAAAAACCAAGACCAACCT |

| DESCRIPTION OF THE SEQUENCES |
|---|
| CAGCCTAGAAACCTCATCCCCCCTAACTGTGAGCACCTCAGGCGCCCTCACCGTAGCAGCCGCC<br>GCTCCCCTGGCGGTGGCCGGCACCTCCCTCACCATGCAATCAGAGGCCCCCCTGACAGTACAGG<br>ATGCAAAACTCACCCTGGCCACCAAAGGCCCCCTGACCGTGTCTGAAGGCAAACTGGCCTTGCA<br>AACATCGGCCCCGCTGACGGCCGCTGACAGCAGCACCCTCACAGTCAGTGCCACACCACCCCTT<br>AGCACAAGCAATGGCAGCTTGGGTATTGACATGCAAGCCCCCATTTACACCACCAATGGAAAAC<br>TAGGACTTAACTTTGGCGCTCCCCTGCATGTGGTAGACAGCCTAAATGCACTGACTGTAGTTACT<br>GGCCAAGGTCTTACGATAAACGGAACAGCCCTACAAACTAGAGTCTCAGGTGCCCTCAACTATG<br>ACACATCAGGAAACCTAGAATTGAGAGCTGCAGGGGGTATGCGAGTTGATGCAAATGGTCAACT<br>TATCCTTGATGTAGCTTACCCATTTGATGCACAAAACAATCTCAGCCTTAGGCTTGGACAGGGAC<br>CCCTGTTTGTTAACTCTGCCCACAACTTGGATGTTAACTACAACAGAGGCCTCTACCTGTTCACA<br>TCTGGAAATACCAAAAAGCTAGAAGTTAATATCAAAACAGCCAAGGGTCTCATTTATGATGACA<br>CTGCTATAGCAATCAATGCGGGTGATGGGCTACAGTTTGACTCAGGCTCAGATACAAATCCATT<br>AAAAACTAAACTTGGATTAGGACTGGATTATGACTCCAGCAGAGCCATAATTGCTAAACTGGGA<br>ACTGGCCTAAGCTTTGACAACACAGGTGCCATCACAGTAGGCAACAAAAATGATGACAAGCTTA<br>CCTTGTGGACCACACCAGACCCATCCCCTAACTGTAGAATCTATTCAGAGAAAGATGCTAAATT<br>CACACTTGTTTTGACTAAATGCGGCAGTCAGGTGTTGGCCAGCGTTTCTGTTTTATCTGTAAAAG<br>GTAGCCTTGCGCCCATCAGTGGCACAGTAACTAGTGCTCAGATTGTCCTCAGATTTGATGAAAAT<br>GGAGTTCTACTAAGCAATTCTTCCCTTGACCCTCAATACTGGAACTACAGAAAAGGTGACCTTAC<br>AGAGGGCACTGCATATACCAACGCAGTGGGATTTATGCCCAACCTCACAGCATACCCAAAAACA<br>CAGAGCCAAACTGCTAAAAGCAACATTGTAAGTCAGGTTTACTTGAATGGGGACAAATCCAAAC<br>CCATGACCCTCACCATTACCCTCAATGGAACTAATGAAACAGGAGATGCCACAGTAAGCACTTA<br>CTCCATGTCATTCTCATGGAACTGGAATGGAAGTAATTACATTAATGAAACGTTCCAAACCAACT<br>CCTTCACCTTCTCCTACATCGCCCAAGAATAAAAAGCATGACGCTGTTGATTTGATTCAATGTGT<br>TTCTGTTTTATTTTCAAGCACAACAAAATCATTCAAGTCATTCTTCCATCTTAGCTTAATAGACAC<br>AGTAGCTTAATAGACCCAGTAGTGCAAAGCCCCATTCTAGCTTATAACTAGTGGAGAAGTACTC<br>GCCTACATGGGGGTAGAGTCATAATCGTGCATCAGGATAGGGCGGTGGTGCTGCAGCAGCGCGC<br>GAATAAACTGCTGCCGCCGCCGCTCCGTCCTGCAGGAATACAACATGGCAGTGGTCTCCTCAGC<br>GATGATTCGCACCGCCCGCAGCATAAGGCGCCTTGTCCTCCGGGCACAGCAGCGCACCCTGATC<br>TCACTTAAATCAGCACAGTAACTGCAGCACAGCACCCACAATATTGTTCAAAATCCCACAGTGCA<br>AGGCGCTGTATCCAAAGCTCATGGCGGGGACCACAGAACCCACGTGGCCATCATACCACAAGCG<br>CAGGTAGATTAAGTGGCGACCCCTCATAAACACGCTGGACATAAACATTACCTCTTTTGGCATGT<br>TGTAATTCACCACCTCCCGGTACCATATAAACCTCTGATTAAACATGGCGCCATCCACCACCATC<br>CTAAACCAGCTGGCCAAAACCTGCCCGCCGGCTATACACTGCAGGGAACCGGGACTGGAACAAT<br>GACAGTGGAGAGCCCAGGACTCGTAACCATGGATCATCATGCTCGTCATGATATCAATGTTGGC<br>ACAACACAGGCACACGTGCATACACTTCCTCAGGATTACAAGCTCCTCCCCGCGTTAGAACCATA<br>TCCCAGGGAACAACCCATTCCTGAATCAGCGTAAATCCCACACTGCAGGGAAGACCTCGCACGT<br>AACTCACGTTGTGCATTGTCAAAGTGTTACATTCGGGCAGCAGCGGATGATCCTCCAGTATGGTA<br>GCGCGGGTTTCTGTCTCAAAAGGAGGTAGACGATCCCTACTGTACGGAGTGCGCCGAGACAACC<br>GAGATCGTGTTGGTCGTAGTGTCATGCCAAATGGAACGCCGGACGTAGTCATATTTCCTGAAGT<br>CTTAGATCTCTCAACGCAGCACCAGCACCAACACTTCGCAGTGTAAAAGGCCAAGTGCCGAGAG<br>AGTATATATAGGAATAAAAAGTGACGTAAACGGGCAAAGTCCAAAAAACGCCCAGAAAAACCG<br>CACGCGAACCTACGCCCCGAAACGAAAGCCAAAAAACACTAGACACTCCCTTCCGGCGTCAACT<br>TCCGCTTTCCCACGCTACGTCACTTGCCCCAGTCAAACAAACTACATATCCCGAACTTCCAAGTC<br>GCCACGCCCAAAACACCGCCTACACCTCCCCGCCCGCCGCCCGCCCCCAAACCCGCCTCCCGC<br>CCCGCGCCCCGCCCCGCGCCGCCCATCTCATTATCATATTGGCTTCAATCCAAAATAAGGTATAT<br>TATTGATGATG<br><br>SEQ ID NO: 12-Polynucleotide sequence encoding the CASI promoter<br>GGAGTTCCGCGTTACATAACTTACGGTAAATGGCCCGCCTGGCTGACCGCCCAACGACCCCCGC<br>CCATTGACGTCAATAATGACGTATGTTCCCATAGTAACGCCAATAGGGACTTTCCATTGACGTCA<br>ATGGGTGGAGTATTTACGGTAAACTGCCCACTTGGCAGTACATCAAGTGTATCATATGCCAAGT<br>ACGCCCCCTATTGACGTCAATGACGGTAAATGGCCCGCCTGGCATTATGCCCAGTACATGACCTT<br>ATGGGACTTTCCTACTTGGCAGTACATCTACGTATTAGTCATCGCTATTACCATGGTCGAGGTGA<br>GCCCCACGTTCTGCTTCACTCTCCCCATCTCCCCCCCCTCCCCACCCCCAATTTTGTATTTATTTAT<br>TTTTTAATTATTTTTGTGCAGCGATGGGGGCGGGGGGGGGGGGGGCGCGCGCCAGGCGGGGCG<br>GGGCGGGGCGAGGGGCGGGGCGGGGCGAGGCGGAGAGGTGCGGCGGCAGCCAATCAGAGCGG<br>CGCGCTCCGAAAGTTTCCTTTTATGGCGAGGCGGCGGCGGCGGCGGCCCTATAAAAAGCGAAGC<br>GCTCCCTATCAGTGATAGAGATCTCCCTATCAGTGATAGAGATCGTCGACGAGCTCGCGGCGGG<br>CGGGAGTCGCTGCGCGCTGCCTTCGCCCCGTGCCCCGCTCCGCCGCCGCCTCGCGCCGCCCGCCC<br>CGGCTCTGACTGACCGCGTTACTAAAACAGGTAAGTCCGGCCTCCGCGCGGGTTTGGCGCCTC<br>CCGCGGGCGCCCCCTCCTCACGGCGAGCGCTGCCACGTCAGACGAAGGGCGCAGCGAGCGTCC<br>TGATCCTTCCGCCCGGACGCTCAGGACAGCGGCCCGCTGCTCATAAGACTCGGCCTTAGAACCC<br>CAGTATCAGCAGAAGGACATTTTAGGACGGGACTTGGGTGACTCTAGGGCACTGGTTTTCTTTCC<br>AGAGAGCGGAACAGGCGAGGAAAAGTAGTCCCTTCTCGGCGATTCTGCGGAGGGATCTCCGTG<br>GGGCGGTGAACGCCGATGATGCCTCTACTAACCATGTTCATGTTTTCTTTTTTTTCTACAGGTCC<br>TGGGTGACGAACAG<br><br>SEQ ID NO: 13-Ad5orf6 primer 1 polynucleotide sequence<br>ATACGGACTAGTGGAGAAGTACTCGCCTACATG<br><br>SEQ ID NO: 14-Ad5orf6 primer 2 polynucleotide sequence<br>ATACGGAAGATCTAAGACTTCAGGAAATATGACTAC<br><br>SEQ ID NO: 15-BAC/CHAd155 ΔE1_TetO hCMV RpsL-Kana primer 1 polynucleotide sequence<br>ATTCAGTGTACAGGCGCGCCAAAGCATGACGCTGTTGATTTGATTC |

| DESCRIPTION OF THE SEQUENCES |
|---|

SEQ ID NO: 16-BAC/CHAd155 ΔE1_TetO hCMV RpsL-Kana (#1375) primer 2 polynucleotide sequence
ACTAGGACTAGTTATAAGCTAGAATGGGGCTTTGC SEQ ID NO: 17-1021-FW E4 Del Step1 primer polynucleotide sequence
TTAATAGACACAGTAGCTTAATAGACCCAGTAGTGCAAAGCCCCATTCTAGCTTATAACCCCTAT
TTGTTTATTTTTCT SEQ ID NO: 18-1022-RW E4 Del Step1 primer polynucleotide sequence
ATATATACTCTCTCGGCACTTGGCCTTTTACACTGCGAAGTGTTGGTGCTGGTGCTGCGTTGAGA
GATCTTTATTTGTTAACTGTTAATTGTC SEQ ID NO: 19-1025-FW E4 Del 5tep2 primer polynucleotide sequence
TTAATAGACACAGTAGCTTAATA SEQ ID NO: 20-1026-RW E4 Del 5tep2 primer polynucleotide sequence
GGAAGGGAGTGTCTAGTGTT SEQ ID NO: 21-91-SubMonte FW primer polynucleotide sequence
CAATGGGCGTGGATAGCGGTTTGAC SEQ ID NO: 22-90-BghPolyA RW primer polynucleotide sequence
CAGCATGCCTGCTATTGTC SEQ ID NO: 23-CMVfor primer polynucleotide sequence
CATCTACGTATTAGTCATCGCTATTACCA SEQ ID NO: 24-CMVrev primer polynucleotide sequence
GACTTGGAAATCCCCGTGAGT SEQ ID NO: 25-CMVFAM-TAMRA qPCR probe polynucleotide sequence
ACATCAATGGGCGTGGATAGCGGTT SEQ ID NO: 26-Woodchuck Hepatitis Virus Posttranscriptional Regulatory Element (WPRE) polynucleotide sequence
TAATCAACCTCTGGATTACAAAATTTGTGAAAGATTGACTGGTATTCTTAACTATGTTGCTCCTTT
TACGCTATGTGGATACGCTGCTTTAATGCCTTTGTATCATGCTATTGCTTCCCGTATGGCTTTCAT
TTTCTCCTCCTTGTATAAATCCTGGTTGCTGTCTCTTTATGAGGAGTTGTGGCCCGTTGTCAGGCA
ACGTGGCGTGGTGTGCACTGTGTTTGCTGACGCAACCCCCACTGGTTGGGGCATTGCCACCACCT
GTCAGCTCCTTTCCGGGACTTTCGCTTTCCCCCTCCCTATTGCCACGGCGGAACTCATCGCCGCCT
GCCTTGCCCGCTGCTGGACAGGGGCTCGGCTGTTGGGCACTGACAATTCCGTGGTGTTGTCGGG
GAAATCATCGTCCTTTCCTTGGCTGCTCGCCTGTGTTGCCACCTGGATTCTGCGCGGGACGTCCTT
CTGCTACGTCCCTTCGGCCCTCAATCCAGCGGACCTTCCTTCCCGCGGCCTGCTGCCGGCTCTGC
GGCCTCTTCCGCGTCTTCGCCTTCGCCCTCAGACGAGTCGGATCTCCCTTTGGGCCGCCTCCCCG
CCT SEQ ID NO: 27-ChAd3 fiber amino acid sequence
MKRTKTSDESFNPVYPYDTESGPPSVPFLTPPFVSPDGFQESPPGVLSLNLAEPLVTSHGMLALKMGS
GLSLDDAGNLTSQDITTASPPLKKTKTNLSLETSSPLTVSTSGALTVAAAAPLAVAGTSLTMQSEAPL
TVQDAKLTLATKGPLTVSEGKLALQTSAPLTAADSSTLTVSATPPINVSSGSLGLDMEDPMYTHDGK
LGIRIGGPLRVVDSLHTLTVVTGNGLTVDNNALQTRVTGALGYDTSGNLQLRAAGGMRIDANGQLI
LNVAYPFDAQNNLSLRLGQGPLYINTDHNLDLNCNRGLTTTTNTKKLETKISSGLDYDTNGAVIIK
LGTGLSFDNTGALTVGNTGDDKLTLWTTPDPSPNCRIHSDKDCKFTLVLTKCGSQILASVAALAVSG
NLASITGTVASVTIFLRFDQNGVLMENSSLDRQYWNFRNGNSTNAAPYTNAVGFMPNLAAYPKTQS
QTAKNNIVSQVYLNGDKSKPMTLTITLNGTNESSETSQVSHYSMSFTWAWESGQYATETFATNSFTF
SYIAEQ SEQ ID NO: 28- PanAd3 fiber amino acid sequence
MKRAKTSDETFNPVYPYDTENGPPSVPFLTPPFVSPDGFQESPPGVLSLRLSEPLVTSHGMLALKMGN
GLSLDDAGNLTSQDVTTVTPPLKKTKTNLSLQTSAPLTVSSGSLTVAAAAPLAVAGTSLTMQSQAPL
TVQDAKLGLATQGPLTVSEGKLTLQTSAPLTAADSSTLTVGTTPPISVSSGSLGLDMEDPMYTHDGK
LGIRIGGPLQVVDSLHTLTVVTGNGITVANNALQTKVAGALGYDSSGNLELRAAGGMRINTGQLIL
DVAYPFDAQNNLSLRLGQGPLYVNTNHNLDLNCNRGLTTTTSSNTTKLETKIDSGLDYNANGAIIAK
LGTGLTFDNTGAITVGNTGDDKLTLWTTPDPSPNCRIHADKDKFTLVLTKCGSQILASVAALAVSGN
LSSMTGTVSSVTIFLRFDQNGVLMENSSLDKEYWNFRNGNSTNATPYTNAVGFMPNLSAYPKTQSQ
TAKNNIVSEVYLHGDKSKPMILTITLNGTNESSETSQVSHYSMSFTWSWDSGKYATETFATNSFTFSY
IAEQ SEQ ID NO: 29-ChAd17 fiber amino acid sequence
MKRTKTSDESFNPVYPYDTESGPPSVPFLTPPFVSPDGFQESPPGVLSLNLAEPLVTSHGMLALKMGS
GLSLDDAGNLTSQDITSTTPPLKKTKTNLSLETSSPLTVSTSGALTVAAAAPLAVAGTSLTMQSEAPL
AVQDAKLTLATKGPLTVSEGKLALQTSAPLTAADSSTLTVSSTPPISVSSGSLGLDMEDPMYTHDGK
LGIRIGGPLRVVDSLHTLTVVTGNGLTVDNNALQTRVTGALGYDTSGNLQLRAAGGMRIDANGQLI
LDVAYPFDAQNNLSLRLGQGPLYVNTDHNLDLNCNRGLTTTTTNNTKKLETKISSGLDYDTNGAVII
KLGTGLSFDNTGALTVGNTGDDKLTLWTTPDPSPNCRIHSDKDCKFTLVLTKCGSQILASVAALAVS
GNLASITGTVASVTIFLRFDQNGVLMENSSLDKQYWNFRNGNSTNAAPYTNAVGFMPNLAAYPKTQ

| DESCRIPTION OF THE SEQUENCES |
|---|

SQTAKNNIVSQVYLNGDKSKPMTLTITLNGTNESSETSQVSHYSMSFTWAWESGQYA1'ETFATNSFT
FSYIAEQ

SEQ ID NO: 30-ChAd19 fiber amino acid sequence
MKRTKTSDKSFNPVYPYDTENGPPSVPFLTPPFVSPDGFQESPPGVLSLNLAEPLVTSHGMLALKMGS
GLSLDDAGNLTSQDVTTTTPPLKKTKTNLSLETSAPLTVSTSGALTLAAAAPLAVAGTSLTMQSEAPL
TVQDAKLTLATKGPLTVSEGKLALQTSAPLTAADSSTLTVSATPPISVSSGSLGLDMEDPMYTHDGK
LGIRIGGPLRVVDSLHTLTVVTGNGIAVDNNALQTRVTGALGYDTSGNLQLRAAGGMRIDANGQLIL
DVAYPFDAQNNLSLRLGQGPLYVNTDHNLDLNCNRGLTTTTTNNTKKLETKIGSGLDYDTNGAVIIK
LGTGVSFDSTGALSVGNTGDDKLTLWTTPDPSPNCRIHSDKDCKFTLVLTKCGSQILASVAALAVSG
NLASITGTVSSVTIFLRFDQNGVLMENSSLDKQYWNFRNGNSTNATPYTNAVGFMPNLAAYPKTQS
QTAKNNIVSQVYLNGDKSKPMTLTITLNGTNESSETSQVSHYSMSFTWAWESGQYATETFATNSFTF
SYIAEQ SEQ ID NO: 31-ChAd24 fiber amino acid sequence
MKRTKTSDESFNPVYPYDTENGPPSVPFLTPPFVSPDGFQESPPGVLSLNLAEPLVTSHGMLALKMGS
GLSLDDAGNLTSQDVTTTTPPLKKTKTNLSLETSAPLTVSTSGALTLAAAAPLAVAGTSLTMQSEAPL
TVQDAKLTLATKGPLTVSEGKLALQTSAPLTAADSSTLTVSATPPINVSSGSLGLDMENPMYTHDGK
LGIRIGGPLRVVDSLHTLTVVTGNGIAVDNNALQTRVTGALGYDTSGNLQLRAAGGMRIDANGQLIL
DVAYPFDAQNNLSLRLGQGPLYVNTDHNLDLNCNRGLTTTTTNNTKKLETKIGSGLDYDTNGAVIIK
LGTGVSFDSTGALSVGNTGDDKLTLWTTPDPSPNCRIHSDKDCKFTLVLTKCGSQILASVAALAVSG
NLASITGTVSSVTIFLRFDQNGVLMENSSLDKQYWNFRNGNSTNATPYTNAVGFMPNLAAYPKTQS
QTAKNNIVSQVYLNGDKSKPMILTITLNGTNESSETSQVSHYSMSFTWAWESGQYATETFATNSFTFS
YIAEQ SEQ ID NO: 32-ChAd11 fiber amino acid sequence
MKRTKTSDESFNPVYPYDTENGPPSVPFLTPPFVSPDGFQESPPGVLSLNLAEPLVTSHGMLALKMGS
GLSLDDAGNLTSQDVTTTTPPLKKTKTNLSLETSAPLTVSTSGALTLAAAAVPLAVAGTSLTMQSEAPL
TVQDAKLTLATKGPLTVSEGKLALQTSAPLTAADSSTLTISATPPLSTSNGSLGIDMQAPIYTTNGKLG
LNFGAPLHVVDSLNALTVVTGQGLTINGTALQTRVSGALNYDSSGNLELRAAGGMRVDANGKLILD
VAYPFDAQNNLSLRLGQGPLFVNSAHNLDVNYNRGLYLFTSGNTKKLEVNIKTAKGLIYDDTAIAIN
PGDGLEFGSGSDTNPLKTKLGLGLEYDSSRAIIAKLGTGLSFDNTGAITVGNKNDDKLTLWTTPDPSP
NCRIYSEKDAKFTLVLTKCGSQVLASVSVLSVKGSLAPISGTVTSAQIILRFDENGVLLSNSSLDPQYW
NYRKGDLTEGTAYTNAVGFMPNLTAYPKTQSQTAKSNIVSQVYLNGDKSKPMILTITLNGTNETGD
ATVSTYSMSFSWNWNGSNYINETFQTNSFTFSYIAQE SEQ ID NO: 33-ChAd20 fiber amino acid sequence
MKRTKTSDESFNPVYPYDTESGPPSVPFLTPPFVSPDGFQESPPGVLSLNLAEPLVTSHGMLALKMGS
GLSLDDAGNLTSQDITTASPPLKKTKTNLSLETSSPLTVSTSGALTVAAAAPLAVAGTSLTMQSEAPL
TVQDAKLTLATKGPLTVSEGKLALQTSAPLTAADSSTLTVSATPPLSTSNGSLGIDMQAPIYTTNGKL
GLNFGAPLHVVDSLNALTVVTGQGLTINGTALQTRVSGALNYDTSGNLELRAAGGMRVDANGQLIL
DVAYPFDAQNNLSLRLGQGPLFVNSAHNLDVNYNRGLYLFTSGNTKKLEVNIKTAKGLIYDDTAIAI
NAGDGLQFDSGSDTNPLKTKLGLGLDYDSSRAIIAKLGTGLSFDNTGAITVGNKNDDKLTLWTTPDP
SPNCRIYSEKDAKFTLVLTKCGSQVLASVSVLSVKGSLAPISGTVTSAQIVLRFDENGVLLSNSSLDPQ
YWNYRKGDLTEGTAYTNAVGFMPNLTAYPKTQSQTAKSNIVSQVYLNGDKSKPMTLTITLNGTNET
GDATVSTYSMSFSWNWNGSNYINETFQTNSFTFSYIAQE SEQ ID NO: 34-ChAd31 fiber amino acid sequence
MKRTKTSDESFNPVYPYDTESGPPSVPFLTPPFVSPDGFQESPPGVLSLNLAEPLVTSHGMLALKMGS
GLSLDDAGNLTSQDITTASPPLKKTKTNLSLETSSPLTVSTSGALTVAAAAPLAVAGTSLTMQSEAPL
TVQDAKLTLATKGPLTVSEGKLALQTSAPLTAADSSTLTVSATPPLSTSNGSLGIDMQAPIYTTNGKL
GLNFGAPLHVVDSLNALTVVTGQGLTINGTALQTRVSGALNYDTSGNLELRAAGGMRVDANGQLIL
DVAYPFDAQNNLSLRLGQGPLFVNSAHNLDVNYNRGLYLFTSGNTKKLEVNIKTAKGLIYDDTAIAI
NAGDGLQFDSGSDTNPLKTKLGLGLDYDSSRAIIAKLGTGLSFDNTGAITVGNKNDDKLTLWTTPDP
SPNCRIYSEKDAKFTLVLTKCGSQVLASVSVLSVKGSLAPISGTVTSAQIVLRFDENGVLLSNSSLDPQ
YWNYRKGDLTEGTAYTNAVGFMPNLTAYPKTQSQTAKSNIVSQVYLNGDKSKPMTLTITLNGTNET
GDATVSTYSMSFSWNWNGSNYINETFQTNSFTFSYIAQE SEQ ID NO: 35-PanAd1 fiber amino acid sequence
MKRAKTSDETFNPVYPYDTENGPPSVPFLTPPFVSPDGFQESPPGVLSLRLSEPLVTSHGMLALKMGN
GLSLDDAGNLTSQDVTTVTPPLKKTKTNLSLQTSAPLTVSSGSLTVAAAAPLAVAGTSLTMQSQAPL
TVQDAKLGLATQGPLTVSEGKLTQTSAPLTAADSSTLTVSATPPLSTSNGSLSIDMQAPIYTTNGKL
ALNIGAPLHVVDTLNALTVVTGQGLTINGRALQTRVTGALSYDTEGNIQLQAGGGMRIDNNGQLILN
VAYPFDAQNNLSLRLGQGPLIVNSAHNLDLNLNRGLYLFTSGNTKKLEVNIKTAKGLFYDGTAIAIN
AGDGLQFGSGSDTNPLQTKLGLGLEYDSNKAIITKLGTGLSFDNTGAITVGNKNDDKLTLWTTPDPS
PNCRINSEKDAKLTLVLTKCGSQVLASVSVLSVKGSLAPISGTVTSAQIVLRFDENGVLLSNSSLDPQY
WNYRKGDS1'EGTAYTNAVGFMPNLTAYPKTQSQTAKSNIVSQVYLNGDKTKPMTLTITLNGTNETG
DATVSTYSMSFSWNWNGSNYINDTFQTNSFTFSYIAQE SEQ ID NO: 36-PanAd2 fiber amino acid sequence
MKRAKTSDETFNPVYPYDTENGPPSVPFLTPPFVSPDGFQESPPGVLSLRLSEPLVTSHGMLALKMGN
GLSLDDAGNLTSQDVTTVTPPLKKTKTNLSLQTSAPLTVSSGSLTVAAAAPLAVAGTSLTMQSQAPL
TVQDAKLGLATQGPLTVSEGKLTQTSAPLTAADSSTLTVSATPPLSTSNGSLSIDMQAPIYTTNGKL
ALNIGAPLHVVDTLNALTVVTGQGLTINGRALQTRVTGALSYDTEGNIQLQAGGGMRIDNNGQLILN
VAYPFDAQNNLSLRLGQGPLIVNSAHNLDLNLNRGLYLFTSGNTKKLEVNIKTAKGLFYDGTAIAIN
AGDGLQFGSGSDTNPLQTKLGLGLEYDSNKAIITKLGTGLSFDNTGAITVGNKNDDKLTLWTTPDPS
PNCRINSEKDAKLTLVLTKCGSQVLASVSVLSVKGSLAPISGTVTSAQIVLRFDENGVLLSNSSLDPQY

| DESCRIPTION OF THE SEQUENCES |
|---|
| WNYRKGDS1'EGTAYTNAVGFMPNLTAYPKTQSQTAKSNIVSQVYLNGDKTKPMTLTITLNGTNETG<br>DATVSTYSMSFSWNWNGSNYINDTFQTNSFTFSYIAQE<br><br>SEQ ID NO: 37-RSV FΔTM amino acid sequence<br>MELLILKANAITTILTAVTFCFASGQNITEEFYQSTCSAVSKGYLSALRTGWYTSVITIELSNIKENKCN<br>GTDAKVKLIKQELDKYKNAVTELQLLMQSTPATNNRARRELPRFMNYTLNNAKKTNVTLSKKRKR<br>RFLGFLLGVGSAIASGVAVSKVLHLEGEVNKIKSALLSTNKAVVSLSNGVSVLTSKVLDLKNYIDKQ<br>LLPIVNKQSCSISNIETVIEFQQKNNRLLEITREFSVNAGVTTPVSTYMLTNSELLSLNDMPITNDQKKL<br>MSNNVQIVRQQSYSIMSIIKEEVLAYVVQLPLYGVIDTPCWKLHTSPLCTTNTKEGSNICLTRTDRGW<br>YCDNAGSVSFFPQAETCKVQSNRVFCDTMNSLTLPSEVNLCNVDIFNPKYDCKIMTSKTDVSSSVITS<br>LGAIVSCYGKTKCTASNKNRGIIKTFSNGCDYVSNKGVDTVSVGNTLYYVNKQEGKSLYVKGEPIIN<br>FYDPLVFPSDEFDASISQVNEKINQSLAFIRKSDELLHNVNAGKSTTNRKRRAPVKQTLNFDLLKLAG<br>DVESNPGPMALSKVKLNDTLNKDQLLSSSKYTIQRSTGDSIDTPNYDVQKHINKLCGMLLITEDANH<br>KFTGLIGMLYAMSRLGREDTIKILRDAGYHVKANGVDVTTHRQDINGKEMKFEVLTLASLTTEIQINI<br>EIESRKSYKKMLKEMGEVAPEYRHDSPDCGMIILCIAALVITKLAAGDRSGLTAVIRRANNVLKNEM<br>KRYKGLLPKDIANS<br>FYEVIAEKYPHFIDVFVHFGIAQSSTRGGSRVEGIFAGLFMNAYGAGQVMLRWGVLAKSVKNIMLGH<br>ASVQAEMEQVVEVYEYAQKLGGEAGFYHILNNPKASLLSLTQFPHFSSVVLGNAAGLGIMGEYRGT<br>PRNQDLYDAAKAYAEQLKENGVINYSVLDLTAEELEAIKHQLNPKDNDVELGGGGSGGGGMSRRN<br>PCKIALIRGHCLNGKRCHFSHNYFEWPPHALLVRQNFMLNRILKSMDKSIDTLSEISGAAELDRILEYA<br>LGVVGVLESYIGSINNITKQSACVAMSKLLTELNSDDIKKLRDNEELNSPKIRVYNTVISYIESNRKNN<br>KQTIHLLKRLPADVLKKTIKNTLDIHKSITINNPKESTVSDTNDHAKNNDTT<br><br>SEQ ID NO: 38-HIV Gag polynucleotide sequence<br>ATGGGTGCTAGGGCTTCTGTGCTGTCTGGTGGTGAGCTGGACAAGTGGGAGAAGATCAGGCTGA<br>GGCCTGGTGGCAAGAAGAAGTACAAGCTAAAGCACATTGTGTGGGCCTCCAGGGAGCTGGAGA<br>GGTTTGCTGTGAACCCTGGCCTGCTGGAGACCTCTGAGGGGTGCAGGCAGATCCTGGGCCAGCT<br>CCAGCCCTCCCTGCAAACAGGCTCTGAGGAGCTGAGGTCCCTGTACAACACAGTGGCTACCCTG<br>TACTGTGTGCACCAGAAGATTGATGTGAAGGACACCAAGGAGGCCCTGGAGAAGATTGAGGAG<br>GAGCAGAACAAGTCCAAGAAGAAGGCCCAGCAGGCTGCTGCTGGCACAGGCAACTCCAGCCAG<br>GTGTCCCAGAACTACCCCATTGTGCAGAACCTCCAGGGCCAGATGGTGCACCAGGCCATCTCCC<br>CCCGGACCCTGAATGCCTGGGTGAAGGTGGTGGAGGAGAGGCCTTTCTCCCCTGAGGTGATCCC<br>ATGTTCTCTGCCCTGTCTGAGGGTGCCACCCCCCAGGACCTGAACACCATGCTGAACACAGTGG<br>GGGGCCATCAGGCTGCCATGCAGATGCTGAAGGAGACCATCAATGAGGAGGCTGCTGAGTGGG<br>ACAGGCTGCATCCTGTGCACGCTGGCCCCATTGCCCCCGGCCAGATGAGGGAGCCCAGGGGCTC<br>TGACATTGCTGGCACCACCTCCACCCTCCAGGAGCAGATTGGCTGGATGACCAACAACCCCCC<br>ATCCCTGTGGGGGAAATCTACAAGAGGTGGATCATCCTGGGCCTGAACAAGATTGTGAGGATGT<br>ACTCCCCCACCTCCATCCTGGACATCAGGCAGGGCCCCAAGGAGCCCTTCAGGGACTATGTGGA<br>CAGGTTCTACAAGACCCTGAGGGCTGAGCAGGCCTCCCAGGAGGTGAAGAACTGGATGACAGA<br>GACCCTGCTGGTGCAGAATGCCAACCCTGACTGCAAGACCATCCTGAAGGCCCTGGGCCCTGCT<br>GCCACCCTGGAGGAGATGATGACAGCCTGCCAGGGGGTGGGGGGCCCTGGTCACAAGGCCAGG<br>GTGCTGGCTGAGGCCATGTCCCAGGTGACCAACTCCGCCACCATCATGATGCAGAGGGGCAACT<br>TCAGGAACCAGAGGAAGACAGTGAAGTGCTTCAACTGTGGCAAGGTGGGCCACATTGCCAAGA<br>ACTGTAGGGCCCCCAGGAAGAAGGGCTGCTGGAAGTGTGGCAAGGAGGGCCACCAGATGAAGG<br>ACTGCAATGAGAGGCAGGCCAACTTCCTGGGCAAAATCTGGCCCTCCCACAAGGGCAGGCCTGG<br>CAACTTCCTCCAGTCCAGGCCTGAGCCCACAGCCCCTCCCGAGGAGTCCTTCAGGTTTGGGGAG<br>GAGAAGACCACCCCCAGCCAGAAGCAGGAGCCCATTGACAAGGAGCTGTACCCCCTGGCCTCCC<br>TGAGGTCCCTGTTTGGCAACGACCCCTCCTCCCAGTAA |

What is claimed is:

1. An isolated recombinant adenoviral polynucleotide encoding:
   (a) an adenovirus penton polypeptide having the amino acid sequence according to SEQ ID NO: 3;
   (b) an adenovirus hexon polypeptide having the amino acid sequence according to SEQ ID NO: 5;
   (c) an adenovirus fiber polypeptide having the amino acid sequence according to SEQ ID NO: 1; and
   (d) an antigenic protein that is not isolated from or present in a naturally occurring adenovirus;
wherein the isolated recombinant adenoviral polynucleotide comprises a mutation or deletion recombinantly introduced into the backbone of the adenoviral polynucleotide which renders non-functional at least one gene of an adenoviral genomic region selected from the group consisting of E1A, E1B, E2A, E2B, E3 and E4.

2. A composition comprising the isolated recombinant adenoviral polynucleotide of claim 1 and a pharmaceutically acceptable excipient.

3. An isolated host cell comprising the isolated recombinant adenoviral polynucleotide of claim 1.

4. The cell according to claim 3 wherein the isolated host cell is able to grow in suspension.

5. The polynucleotide according to claim 1, wherein the polynucleotide further comprises at least one of the following:
   (a) an adenoviral 5' inverted terminal repeat;
   (b) an adenoviral E1A region, or a fragment thereof selected from among the E1A_280R and E1A_243R regions;
   (c) an adenoviral E1B or IX region, or a fragment thereof, selected from the group consisting of the E1B_19K, E1B_55K and IX regions;
   (d) an adenoviral E2b region; or a fragment thereof, selected from the group consisting of the E2B pTP, E2B Polymerase and E2B_IVa2 regions;
   (e) an adenoviral L1 region, or a fragment thereof, said fragment encoding an adenoviral protein selected from the group consisting of the L1_13.6k protein, L1_52k and L1_Ia protein;
   (f) an adenoviral L2 region, or a fragment thereof, said fragment encoding an adenoviral protein selected from the group consisting of the L2_penton protein, L2_pVIIL, L2_V, and L2_pX protein;
   (g) an adenoviral L3 region, or a fragment thereof, said fragment encoding an adenoviral protein selected from the group consisting of the L3_pVI protein, L3_hexon protein and L3_protease;
   (h) an adenoviral E2A region;
   (i) ara adenoviral L4 region, or a fragment thereof, said fragment encoding an adenoviral protein selected from the group consisting of the L4_100k protein, the L4_33k protein and protein L4_VIII;
   (j) an adenoviral E3 region, or a fragment thereof, selected from the group consisting of E3 ORR1, E3 ORF2, E3 ORF3, E3 ORF4, E3 ORFS, E3 ORF6, E3 ORF7, E3 ORF8, and E3 ORF9;
   (k) an adenoviral LS region, or a fragment thereof, said fragment encoding the L5_fiber fiber protein;
   (l) an adenoviral E4 region, or a fragment thereof selected from the group consisting of E4 ORF7, E4 ORF6, E4 ORF4, E4 d ORF3, E4 ORF2, and E4 ORF1; and
   (m) an adenoviral 3'-end, or an adenoviral 3' inverted terminal repeat.

6. The polynucleotide according to claim 5, further comprising an adenoviral VAI or VAII RNA region.

7. The polynucleotide according to claim 6, wherein the VAI or VAII RNA region is from Ad5.

8. The polynucleotide according to claim 1, wherein the genomic regions are E1A, E1B or a combination thereof.

9. The recombinant adenoviral polynucleotide according to claim 1, wherein the recombinant adenoviral polynucleotide is replication-incompetent when infected into a host cell.

10. A method of inducing an immune response in a subject comprising administering the composition of claim 2 to a mammalian subject.

11. The isolated recombinant adenoviral polynucleotide of claim 1, wherein said polynucleotide produces higher expression of the encoded antigenic protein when infected into a host cell than a PanAd3 adenovirus vector encoding the same antigenic protein.

12. The isolated recombinant adenoviral polynucleotide of claim 1, wherein said polynucleotide produces more viral particles per cell when infected into a host cell than a PanAd3 adenovirus vector encoding the same antigenic protein.

* * * * *

```
                        SEQUENCE LISTING

<160> NUMBER OF SEQ ID NOS: 38

<210> SEQ ID NO 1
<211> LENGTH: 578
<212> TYPE: PRT
<213> ORGANISM: Simian adenovirus

<400> SEQUENCE: 1

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
                20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
        50                  55                  60

Lys Met Gly Ser Gly Leu Ser Leu Asp Asp Ala Gly Asn Leu Thr Ser
```

```
                65                  70                  75                  80
Gln Asp Ile Thr Thr Ala Ser Pro Pro Leu Lys Lys Thr Lys Thr Asn
                    85                  90                  95
Leu Ser Leu Glu Thr Ser Ser Pro Leu Thr Val Ser Thr Ser Gly Ala
                    100                 105                 110
Leu Thr Val Ala Ala Ala Ala Pro Leu Ala Val Ala Gly Thr Ser Leu
                    115                 120                 125
Thr Met Gln Ser Glu Ala Pro Leu Thr Val Gln Asp Ala Lys Leu Thr
                    130                 135                 140
Leu Ala Thr Lys Gly Pro Leu Thr Val Ser Glu Gly Lys Leu Ala Leu
145                 150                 155                 160
Gln Thr Ser Ala Pro Leu Thr Ala Ala Asp Ser Ser Thr Leu Thr Val
                    165                 170                 175
Ser Ala Thr Pro Pro Leu Ser Thr Ser Asn Gly Ser Leu Gly Ile Asp
                    180                 185                 190
Met Gln Ala Pro Ile Tyr Thr Thr Asn Gly Lys Leu Gly Leu Asn Phe
                    195                 200                 205
Gly Ala Pro Leu His Val Val Asp Ser Leu Asn Ala Leu Thr Val Val
                    210                 215                 220
Thr Gly Gln Gly Leu Thr Ile Asn Gly Thr Ala Leu Gln Thr Arg Val
225                 230                 235                 240
Ser Gly Ala Leu Asn Tyr Asp Thr Ser Gly Asn Leu Glu Leu Arg Ala
                    245                 250                 255
Ala Gly Gly Met Arg Val Asp Ala Asn Gly Gln Leu Ile Leu Asp Val
                    260                 265                 270
Ala Tyr Pro Phe Asp Ala Gln Asn Asn Leu Ser Leu Arg Leu Gly Gln
                    275                 280                 285
Gly Pro Leu Phe Val Asn Ser Ala His Asn Leu Asp Val Asn Tyr Asn
                    290                 295                 300
Arg Gly Leu Tyr Leu Phe Thr Ser Gly Asn Thr Lys Lys Leu Glu Val
305                 310                 315                 320
Asn Ile Lys Thr Ala Lys Gly Leu Ile Tyr Asp Asp Thr Ala Ile Ala
                    325                 330                 335
Ile Asn Ala Gly Asp Gly Leu Gln Phe Asp Ser Gly Ser Asp Thr Asn
                    340                 345                 350
Pro Leu Lys Thr Lys Leu Gly Leu Gly Leu Asp Tyr Asp Ser Ser Arg
                    355                 360                 365
Ala Ile Ile Ala Lys Leu Gly Thr Gly Leu Ser Phe Asp Asn Thr Gly
                    370                 375                 380
Ala Ile Thr Val Gly Asn Lys Asn Asp Asp Lys Leu Thr Leu Trp Thr
385                 390                 395                 400
Thr Pro Asp Pro Ser Pro Asn Cys Arg Ile Tyr Ser Glu Lys Asp Ala
                    405                 410                 415
Lys Phe Thr Leu Val Leu Thr Lys Cys Gly Ser Gln Val Leu Ala Ser
                    420                 425                 430
Val Ser Val Leu Ser Val Lys Gly Ser Leu Ala Pro Ile Ser Gly Thr
                    435                 440                 445
Val Thr Ser Ala Gln Ile Val Leu Arg Phe Asp Glu Asn Gly Val Leu
                    450                 455                 460
Leu Ser Asn Ser Ser Leu Asp Pro Gln Tyr Trp Asn Tyr Arg Lys Gly
465                 470                 475                 480
Asp Leu Thr Glu Gly Thr Ala Tyr Thr Asn Ala Val Gly Phe Met Pro
                    485                 490                 495
```

```
Asn Leu Thr Ala Tyr Pro Lys Thr Gln Ser Gln Thr Ala Lys Ser Asn
                500                 505                 510

Ile Val Ser Gln Val Tyr Leu Asn Gly Asp Lys Ser Lys Pro Met Thr
            515                 520                 525

Leu Thr Ile Thr Leu Asn Gly Thr Asn Glu Thr Gly Asp Ala Thr Val
        530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 2
<211> LENGTH: 1734
<212> TYPE: DNA
<213> ORGANISM: Simian adenovirus

<400> SEQUENCE: 2
```

| | | | | | |
|---|---|---|---|---|---|
| atgaagcgca | ccaaaacgtc | tgacgagagc | ttcaaccccg | tgtacccta | tgacacggaa | 60 |
| agcggccctc | cctccgtccc | tttcctcacc | cctcccttcg | tgtctcccga | tggattccaa | 120 |
| gaaagtcccc | ccggggtcct | gtctctgaac | ctggccgagc | cctggtcac | ttcccacggc | 180 |
| atgctcgccc | tgaaaatggg | aagtggcctc | tccctggacg | acgctggcaa | cctcacctct | 240 |
| caagatatca | ccaccgctag | ccctcccctc | aaaaaaacca | agaccaacct | cagcctagaa | 300 |
| acctcatccc | cctaactgt | gagcacctca | ggcgccctca | ccgtagcagc | cgccgctccc | 360 |
| ctggcggtgg | ccggcaccct | cctcaccatg | caatcagagg | ccccctgac | agtacaggat | 420 |
| gcaaaactca | ccctggccac | caaaggcccc | ctgaccgtgt | ctgaaggcaa | actggccttg | 480 |
| caaacatcgg | ccccgctgac | ggccgctgac | agcagcaccc | tcacagtcag | tgccacacca | 540 |
| ccccttagca | caagcaatgg | cagcttgggt | attgacatgc | aagcccccat | ttacaccacc | 600 |
| aatggaaaac | taggacttaa | ctttggcgct | ccctgcatg | tggtagacag | cctaaatgca | 660 |
| ctgactgtag | ttactggcca | aggtcttacg | ataaacggaa | cagccctaca | aactagagtc | 720 |
| tcaggtgccc | tcaactatga | cacatcagga | acctagaat | tgagagctgc | aggggtatg | 780 |
| cgagttgatg | caaatggtca | acttatcctt | gatgtagctt | acccatttga | tgcacaaaac | 840 |
| aatctcagcc | ttaggcttgg | acagggaccc | ctgtttgtta | actctgccca | caacttggat | 900 |
| gttaactaca | cagaggcct | ctacctgttc | acatctggaa | ataccaaaaa | gctagaagtt | 960 |
| aatatcaaaa | cagccaaggg | tctcatttat | gatgacactg | ctatagcaat | caatgcgggt | 1020 |
| gatgggctac | agtttgactc | aggctcagat | acaaatccat | taaaaactaa | acttggatta | 1080 |
| ggactggatt | atgactccag | cagagccata | attgctaaac | tgggaactgg | cctaagcttt | 1140 |
| gacaacacag | gtgccatcac | agtaggcaac | aaaaatgatg | acaagcttac | cttgtggacc | 1200 |
| acaccagacc | catcccctaa | ctgtagaatc | tattcagaga | aagatgctaa | attcacactt | 1260 |
| gttttgacta | aatgcggcag | tcaggtgttg | gccagcgttt | ctgtttttatc | tgtaaaaggt | 1320 |
| agccttgcgc | ccatcagtgg | cacagtaact | agtgctcaga | ttgtcctcag | atttgatgaa | 1380 |
| aatggagttc | tactaagcaa | ttcttccctt | gaccctcaat | actggaacta | cagaaaaggt | 1440 |
| gaccttacag | agggcactgc | atataccaac | gcagtgggat | ttatgcccaa | cctcacagca | 1500 |
| tacccaaaaa | cacagagcca | aactgctaaa | agcaacattg | taagtcaggt | ttacttgaat | 1560 |
| ggggacaaat | ccaaacccat | gaccctcacc | attaccctca | atggaactaa | tgaaacagga | 1620 |

```
gatgccacag taagcactta ctccatgtca ttctcatgga actggaatgg aagtaattac   1680
attaatgaaa cgttccaaac caactccttc accttctcct acatcgccca agaa        1734
```

<210> SEQ ID NO 3
<211> LENGTH: 593
<212> TYPE: PRT
<213> ORGANISM: Simian adenovirus

<400> SEQUENCE: 3

```
Met Arg Arg Ala Ala Met Tyr Gln Glu Gly Pro Pro Pro Ser Tyr Glu
1               5                   10                  15

Ser Val Val Gly Ala Ala Ala Ala Pro Ser Ser Pro Phe Ala Ser
            20                  25                  30

Gln Leu Leu Glu Pro Pro Tyr Val Pro Pro Arg Tyr Leu Arg Pro Thr
            35                  40                  45

Gly Gly Arg Asn Ser Ile Arg Tyr Ser Glu Leu Ala Pro Leu Phe Asp
    50                  55                  60

Thr Thr Arg Val Tyr Leu Val Asp Asn Lys Ser Ala Asp Val Ala Ser
65                  70                  75                  80

Leu Asn Tyr Gln Asn Asp His Ser Asn Phe Leu Thr Thr Val Ile Gln
                85                  90                  95

Asn Asn Asp Tyr Ser Pro Ser Glu Ala Ser Thr Gln Thr Ile Asn Leu
            100                 105                 110

Asp Asp Arg Ser His Trp Gly Gly Asp Leu Lys Thr Ile Leu His Thr
        115                 120                 125

Asn Met Pro Asn Val Asn Glu Phe Met Phe Thr Asn Lys Phe Lys Ala
    130                 135                 140

Arg Val Met Val Ser Arg Ser His Thr Lys Glu Asp Arg Val Glu Leu
145                 150                 155                 160

Lys Tyr Glu Trp Val Glu Phe Glu Leu Pro Glu Gly Asn Tyr Ser Glu
                165                 170                 175

Thr Met Thr Ile Asp Leu Met Asn Asn Ala Ile Val Glu His Tyr Leu
            180                 185                 190

Lys Val Gly Arg Gln Asn Gly Val Leu Glu Ser Asp Ile Gly Val Lys
        195                 200                 205

Phe Asp Thr Arg Asn Phe Arg Leu Gly Leu Asp Pro Val Thr Gly Leu
    210                 215                 220

Val Met Pro Gly Val Tyr Thr Asn Glu Ala Phe His Pro Asp Ile Ile
225                 230                 235                 240

Leu Leu Pro Gly Cys Gly Val Asp Phe Thr Tyr Ser Arg Leu Ser Asn
                245                 250                 255

Leu Leu Gly Ile Arg Lys Arg Gln Pro Phe Gln Glu Gly Phe Arg Ile
            260                 265                 270

Thr Tyr Glu Asp Leu Glu Gly Gly Asn Ile Pro Ala Leu Leu Asp Val
        275                 280                 285

Glu Ala Tyr Gln Asp Ser Leu Lys Glu Asn Glu Ala Gly Gln Glu Asp
    290                 295                 300

Thr Ala Pro Ala Ala Ser Ala Ala Ala Glu Gln Gly Glu Asp Ala Ala
305                 310                 315                 320

Asp Thr Ala Ala Ala Asp Gly Ala Glu Ala Asp Pro Ala Met Val Val
                325                 330                 335

Glu Ala Pro Glu Gln Glu Glu Asp Met Asn Asp Ser Ala Val Arg Gly
            340                 345                 350
```

```
Asp Thr Phe Val Thr Arg Gly Glu Glu Lys Gln Ala Glu Ala
            355                 360                 365
Ala Ala Glu Glu Lys Gln Leu Ala Ala Ala Ala Ala Ala Leu
    370                 375                 380
Ala Ala Ala Glu Ala Glu Ser Glu Gly Thr Lys Pro Ala Lys Glu Pro
385                 390                 395                 400
Val Ile Lys Pro Leu Thr Glu Asp Ser Lys Lys Arg Ser Tyr Asn Leu
                405                 410                 415
Leu Lys Asp Ser Thr Asn Thr Ala Tyr Arg Ser Trp Tyr Leu Ala Tyr
            420                 425                 430
Asn Tyr Gly Asp Pro Ser Thr Gly Val Arg Ser Trp Thr Leu Leu Cys
            435                 440                 445
Thr Pro Asp Val Thr Cys Gly Ser Glu Gln Val Tyr Trp Ser Leu Pro
            450                 455                 460
Asp Met Met Gln Asp Pro Val Thr Phe Arg Ser Thr Arg Gln Val Ser
465                 470                 475                 480
Asn Phe Pro Val Val Gly Ala Glu Leu Leu Pro Val His Ser Lys Ser
                485                 490                 495
Phe Tyr Asn Asp Gln Ala Val Tyr Ser Gln Leu Ile Arg Gln Phe Thr
            500                 505                 510
Ser Leu Thr His Val Phe Asn Arg Phe Pro Glu Asn Gln Ile Leu Ala
            515                 520                 525
Arg Pro Pro Ala Pro Thr Ile Thr Thr Val Ser Glu Asn Val Pro Ala
            530                 535                 540
Leu Thr Asp His Gly Thr Leu Pro Leu Arg Asn Ser Ile Gly Gly Val
545                 550                 555                 560
Gln Arg Val Thr Val Thr Asp Ala Arg Arg Arg Thr Cys Pro Tyr Val
                565                 570                 575
Tyr Lys Ala Leu Gly Ile Val Ser Pro Arg Val Leu Ser Ser Arg Thr
            580                 585                 590
Phe

<210> SEQ ID NO 4
<211> LENGTH: 1779
<212> TYPE: DNA
<213> ORGANISM: Simian adenovirus

<400> SEQUENCE: 4
atgcggcgcg cggcgatgta ccaggaggga cctcctccct cttacgagag cgtggtgggc      60
gcggcggcgg cggcgccctc ttctcccttt gcgtcgcagc tgctggagcc gccgtacgtg     120
cctccgcgct acctgcggcc tacgggggga agaaacagca tccgttactc ggagctggcg     180
cccctgttcg acaccacccg ggtgtacctg gtggacaaca gtcggcgga cgtggcctcc     240
ctgaactacc agaacgacca cagcaatttt ttgaccacgg tcatccagaa caatgactac     300
agcccgagcg aggccagcac ccagaccatc aatctggatg accggtcgca ctggggcggc     360
gacctgaaaa ccatcctgca caccaacatg cccaacgtga acgagttcat gttcaccaat     420
aagttcaagg cgcgggtgat ggtgtcgcgc tcgcacacca aggaagaccg ggtggagctg     480
aagtacgagt gggtggagtt cgagctgcca gagggcaact actccgagac catgaccatt     540
gacctgatga caacgcgat cgtggagcac tatctgaaag tgggcaggca gaacggggtc     600
ctggagagcg acatcggggt caagttcgac accaggaact tccgcctggg gctgacccc      660
gtgaccgggc tggttatgcc cggggtgtac accaacgagg ccttccatcc cgacatcatc     720
```

```
ctgctgcccg gctgcggggt ggacttcact tacagccgcc tgagcaacct cctgggcatc    780
cgcaagcggc agcccttcca ggagggcttc aggatcacct acgaggacct ggagggggc    840 aacatccccg cgctcctcga tgtggaggcc taccaggata gcttgaagga aaatgaggcg    900
ggacaggagg ataccgcccc cgccgcctcc gccgccgccg agcagggcga ggatgctgct    960
gacaccgcgg ccgcggacgg ggcagaggcc gaccccgcta tggtggtgga ggctcccgag   1020
caggaggagg acatgaatga cagtgcggtg cgcggagaca ccttcgtcac ccggggggag   1080
gaaaagcaag cggaggccga ggccgcggcc gaggaaaagc aactggcggc agcagcggcg   1140
gcggcggcgt tggccgcggc ggaggctgag tctgagggga ccaagcccgc caaggagccc   1200
gtgattaagc ccctgaccga agatagcaag aagcgcagtt acaacctgct caaggacagc   1260
accaacaccg cgtaccgcag ctggtacctg gcctacaact acggcgaccc gtcgacgggg   1320
gtgcgctcct ggaccctgct gtgcacgccg gacgtgacct gcggctcgga gcaggtgtac   1380
tggtcgctgc ccgacatgat gcaagacccc gtgaccttcc gctccacgcg gcaggtcagc   1440
aacttcccgg tggtgggcgc cgagctgctg cccgtgcact ccaagagctt ctacaacgac   1500
caggccgtct actcccagct catccgccag ttcacctctc tgacccacgt gttcaatcgc   1560
tttcctgaga accagattct ggcgcgcccg cccgccccca ccatcaccac cgtcagtgaa   1620
aacgttcctg ctctcacaga tcacgggacg ctaccgctgc gcaacagcat cggaggagtc   1680
cagcgagtga ccgttactga cgccagacgc cgcacctgcc cctacgttta caaggccttg   1740
ggcatagtct cgccgcgcgt cctttccagc cgcactttt                           1779

<210> SEQ ID NO 5
<211> LENGTH: 964
<212> TYPE: PRT
<213> ORGANISM: Simian adenovirus

<400> SEQUENCE: 5

Met Ala Thr Pro Ser Met Met Pro Gln Trp Ser Tyr Met His Ile Ser
1               5                   10                  15

Gly Gln Asp Ala Ser Glu Tyr Leu Ser Pro Gly Leu Val Gln Phe Ala
            20                  25                  30

Arg Ala Thr Asp Ser Tyr Phe Ser Leu Ser Asn Lys Phe Arg Asn Pro
        35                  40                  45

Thr Val Ala Pro Thr His Asp Val Thr Thr Asp Arg Ser Gln Arg Leu
    50                  55                  60

Thr Leu Arg Phe Ile Pro Val Asp Arg Glu Asp Thr Ala Tyr Ser Tyr
65                  70                  75                  80

Lys Ala Arg Phe Thr Leu Ala Val Gly Asp Asn Arg Val Leu Asp Met
                85                  90                  95

Ala Ser Thr Tyr Phe Asp Ile Arg Gly Val Leu Asp Arg Gly Pro Thr
            100                 105                 110

Phe Lys Pro Tyr Ser Gly Thr Ala Tyr Asn Ser Leu Ala Pro Lys Gly
        115                 120                 125

Ala Pro Asn Ser Cys Glu Trp Glu Gln Glu Glu Thr Gln Thr Ala Glu
    130                 135                 140

Glu Ala Gln Asp Glu Glu Glu Asp Glu Ala Glu Glu Glu Glu Glu Met
145                 150                 155                 160

Pro Gln Glu Glu Gln Ala Pro Val Lys Lys Thr His Val Tyr Ala Gln
                165                 170                 175

Ala Pro Leu Ser Gly Glu Lys Ile Thr Lys Asp Gly Leu Gln Ile Gly
            180                 185                 190
```

-continued

```
Thr Asp Ala Thr Ala Thr Glu Gln Lys Pro Ile Tyr Ala Asp Pro Thr
        195                 200                 205
Phe Gln Pro Glu Pro Gln Ile Gly Glu Ser Gln Trp Asn Glu Ala Asp
        210                 215                 220
Ala Ser Val Ala Gly Gly Arg Val Leu Lys Lys Thr Thr Pro Met Lys
225                 230                 235                 240
Pro Cys Tyr Gly Ser Tyr Ala Arg Pro Thr Asn Ala Asn Gly Gly Gln
                    245                 250                 255
Gly Val Leu Val Glu Lys Asp Gly Gly Lys Met Glu Ser Gln Val Asp
                260                 265                 270
Met Gln Phe Phe Ser Thr Ser Glu Asn Ala Arg Asn Glu Ala Asn Asn
            275                 280                 285
Ile Gln Pro Lys Leu Val Leu Tyr Ser Glu Asp Val His Met Glu Thr
        290                 295                 300
Pro Asp Thr His Ile Ser Tyr Lys Pro Ala Lys Ser Asp Asp Asn Ser
305                 310                 315                 320
Lys Val Met Leu Gly Gln Gln Ser Met Pro Asn Arg Pro Asn Tyr Ile
                    325                 330                 335
Gly Phe Arg Asp Asn Phe Ile Gly Leu Met Tyr Tyr Asn Ser Thr Gly
                340                 345                 350
Asn Met Gly Val Leu Ala Gly Gln Ala Ser Gln Leu Asn Ala Val Val
            355                 360                 365
Asp Leu Gln Asp Arg Asn Thr Glu Leu Ser Tyr Gln Leu Leu Leu Asp
        370                 375                 380
Ser Met Gly Asp Arg Thr Arg Tyr Phe Ser Met Trp Asn Gln Ala Val
385                 390                 395                 400
Asp Ser Tyr Asp Pro Asp Val Arg Ile Ile Glu Asn His Gly Thr Glu
                    405                 410                 415
Asp Glu Leu Pro Asn Tyr Cys Phe Pro Leu Gly Gly Ile Gly Val Thr
                420                 425                 430
Asp Thr Tyr Gln Ala Ile Lys Thr Asn Gly Asn Gly Asn Gly Gly Gly
            435                 440                 445
Asn Thr Thr Trp Thr Lys Asp Glu Thr Phe Ala Asp Arg Asn Glu Ile
        450                 455                 460
Gly Val Gly Asn Asn Phe Ala Met Glu Ile Asn Leu Ser Ala Asn Leu
465                 470                 475                 480
Trp Arg Asn Phe Leu Tyr Ser Asn Val Ala Leu Tyr Leu Pro Asp Lys
                    485                 490                 495
Leu Lys Tyr Asn Pro Ser Asn Val Glu Ile Ser Asp Asn Pro Asn Thr
                500                 505                 510
Tyr Asp Tyr Met Asn Lys Arg Val Val Ala Pro Gly Leu Val Asp Cys
            515                 520                 525
Tyr Ile Asn Leu Gly Ala Arg Trp Ser Leu Asp Tyr Met Asp Asn Val
        530                 535                 540
Asn Pro Phe Asn His His Arg Asn Ala Gly Leu Arg Tyr Arg Ser Met
545                 550                 555                 560
Leu Leu Gly Asn Gly Arg Tyr Val Pro Phe His Ile Gln Val Pro Gln
                    565                 570                 575
Lys Phe Phe Ala Ile Lys Asn Leu Leu Leu Leu Pro Gly Ser Tyr Thr
                580                 585                 590
Tyr Glu Trp Asn Phe Arg Lys Asp Val Asn Met Val Leu Gln Ser Ser
            595                 600                 605
```

```
Leu Gly Asn Asp Leu Arg Val Asp Gly Ala Ser Ile Lys Phe Glu Ser
610                 615                 620
Ile Cys Leu Tyr Ala Thr Phe Phe Pro Met Ala His Asn Thr Ala Ser
625                 630                 635                 640
Thr Leu Glu Ala Met Leu Arg Asn Asp Thr Asn Asp Gln Ser Phe Asn
            645                 650                 655
Asp Tyr Leu Ser Ala Ala Asn Met Leu Tyr Pro Ile Pro Ala Asn Ala
        660                 665                 670
Thr Asn Val Pro Ile Ser Ile Pro Ser Arg Asn Trp Ala Ala Phe Arg
    675                 680                 685
Gly Trp Ala Phe Thr Arg Leu Lys Thr Lys Glu Thr Pro Ser Leu Gly
690                 695                 700
Ser Gly Phe Asp Pro Tyr Tyr Thr Tyr Ser Gly Ser Ile Pro Tyr Leu
705                 710                 715                 720
Asp Gly Thr Phe Tyr Leu Asn His Thr Phe Lys Lys Val Ser Val Thr
                725                 730                 735
Phe Asp Ser Ser Val Ser Trp Pro Gly Asn Asp Arg Leu Leu Thr Pro
            740                 745                 750
Asn Glu Phe Glu Ile Lys Arg Ser Val Asp Gly Glu Gly Tyr Asn Val
        755                 760                 765
Ala Gln Cys Asn Met Thr Lys Asp Trp Phe Leu Ile Gln Met Leu Ala
    770                 775                 780
Asn Tyr Asn Ile Gly Tyr Gln Gly Phe Tyr Ile Pro Glu Ser Tyr Lys
785                 790                 795                 800
Asp Arg Met Tyr Ser Phe Phe Arg Asn Phe Gln Pro Met Ser Arg Gln
                805                 810                 815
Val Val Asp Glu Thr Lys Tyr Lys Asp Tyr Gln Gln Val Gly Ile Ile
            820                 825                 830
His Gln His Asn Asn Ser Gly Phe Val Gly Tyr Leu Ala Pro Thr Met
        835                 840                 845
Arg Glu Gly Gln Ala Tyr Pro Ala Asn Phe Pro Tyr Pro Leu Ile Gly
    850                 855                 860
Lys Thr Ala Val Asp Ser Val Thr Gln Lys Lys Phe Leu Cys Asp Arg
865                 870                 875                 880
Thr Leu Trp Arg Ile Pro Phe Ser Ser Asn Phe Met Ser Met Gly Ala
                885                 890                 895
Leu Thr Asp Leu Gly Gln Asn Leu Leu Tyr Ala Asn Ser Ala His Ala
            900                 905                 910
Leu Asp Met Thr Phe Glu Val Asp Pro Met Asp Glu Pro Thr Leu Leu
        915                 920                 925
Tyr Val Leu Phe Glu Val Phe Asp Val Val Arg Val His Gln Pro His
    930                 935                 940
Arg Gly Val Ile Glu Thr Val Tyr Leu Arg Thr Pro Phe Ser Ala Gly
945                 950                 955                 960
Asn Ala Thr Thr

<210> SEQ ID NO 6
<211> LENGTH: 2880
<212> TYPE: DNA
<213> ORGANISM: Simian adenovirus

<400> SEQUENCE: 6
atggcgaccc catcgatgat gccgcagtgg tcgtacatgc acatctcggg ccaggacgcc    60
tcggagtacc tgagccccgg gctggtgcag ttcgcccgcg ccaccgagag ctacttcagc   120
```

```
ctgagtaaca agtttaggaa ccccacggtg gcgcccacgc acgatgtgac caccgaccgg    180
tctcagcgcc tgacgctgcg gttcattccc gtggaccgcg aggacaccgc gtactcgtac    240
aaggcgcggt tcaccctggc cgtgggcgac aaccgcgtgc tggacatggc ctccacctac    300
tttgacatcc gcggggtgct ggaccggggt cccactttca gccctactc tggcaccgcc     360 tacaactccc tggcccccaa gggcgctccc aactcctgcg agtgggagca agaggaaact    420
caggcagttg aagaagcagc agaagaggaa gaagaagatg ctgacggtca agctgaggaa    480
gagcaagcag ctaccaaaaa gactcatgta tatgctcagg ctccccttc tggcgaaaaa     540 attagtaaag atggtctgca aataggaacg acgctacag ctacagaaca aaaacctatt     600
tatgcagacc ctacattcca gcccgaaccc caaatcgggg agtcccagtg aatgaggca    660 gatgctacag tcgccggcgg tagagtgcta aagaaatcta ctcccatgaa accatgctat    720
ggttcctatg caagacccac aaatgctaat ggaggtcagg gtgtactaac ggcaaatgcc    780
cagggacagc tagaatctca ggttgaaatg caattctttt caacttctga aaacgcccgt    840
aacgaggcta acaacattca gcccaaattg gtgctgtata gtgaggatgt gcacatggag    900
accccggata cgcacctttc ttacaagccc gcaaaaagcg atgacaattc aaaaatcatg    960
ctgggtcagc agtccatgcc aacagacct aattacatcg gcttcagaga aactttatc   1020 ggcctcatgt attacaatag cactggcaac atgggagtgc ttgcaggtca ggcctctcag   1080
ttgaatgcag tggtggactt gcaagacaga aacacagaac tgtcctacca gctcttgctt   1140
gattccatgg gtgacagaac cagatacttt tccatgtgga atcaggcagt ggacagttat   1200
gacccagatg ttagaattat tgaaaatcat ggaactgaag acgagctccc caactattgt   1260
ttccctctgg gtggcatagg ggtaactgac acttaccagg ctgttaaaac caacaatggc   1320
aataacgggg gccaggtgac ttggacaaaa gatgaaactt ttgcagatcg caatgaaata   1380
gggtggggaa acaatttcgc tatggagatc aacctcagtg ccaacctgtg gagaaacttc   1440
ctgtactcca acgtggcgct gtacctacca gacaagctta agtacaaccc ctccaatgtg   1500
gacatctctg acaaccccaa cacctacgat tacatgaaca agcgagtggt ggccccgggg   1560
ctggtggact gctacatcaa cctgggcgcg cgctggtcgc tggactacat ggacaacgtc   1620
aaccccttca ccaccaccg caatgcgggc ctgcgctacc gctccatgct cctgggcaac   1680
gggcgctacg tgcccttcca catccaggtg ccccagaagt tctttgccat caagaacctc   1740
ctcctcctgc ggggctccta cacctacgag tggaacttca ggaaggatgt caacatggtc   1800
ctccagagct ctctgggtaa cgatctcagg gtggacgggg ccagcatcaa gttcgagagc   1860
atctgcctct acgccacctt cttccccatg gcccacaaca cggcctccac gctcgaggcc   1920
atgctcagga acgacaccaa cgaccagtcc ttcaatgact acctctccgc cgccaacatg   1980
ctctacccca tacccgccaa cgccaccaac gtccccatct ccatcccctc gcgcaactgg   2040
gcggccttcc gcggctgggc cttcacccgc tcaagacca aggagacccc ctccctgggc   2100
tcgggattcg acccctacta cacctactcg ggctccattc cctacctgga cggcaccttc   2160
tacctcaacc acactttcaa gaaggtctcg gtcaccttcg actcctcggt cagctggccg   2220
ggcaacgacc gtctgctcac ccccaacgag ttcgagatca agcgctcggt cgacggggag   2280
ggctacaacg tggcccagtg caacatgacc aaggactggt tcctggtcca gatgctggcc   2340
aactacaaca tcggctacca gggcttctac atcccagaga gctacaagga caggatgtac   2400
tccttcttca ggaacttcca gcccatgagc cggcaggtgg tggaccagac caagtacaag   2460
```

```
gactaccagg aggtgggcat catccaccag cacaacaact cgggcttcgt gggctacctc    2520
gcccccacca tgcgcgaggg acaggcctac cccgccaact tcccctatcc gctcataggc    2580
aagaccgcgg tcgacagcat cacccagaaa aagttcctct gcgaccgcac cctctggcgc    2640
atccccttct ccagcaactt catgtccatg ggtgcgctct cggacctggg ccagaacttg    2700
ctctacgcca actccgccca cgccctcgac atgaccttcg aggtcgaccc catggacgag    2760
cccacccttc tctatgttct gttcgaagtc tttgacgtgg tccgggtcca ccagccgcac    2820
cgcggcgtca tcgagaccgt gtacctgcgt acgcccttct cggccggcaa cgccaccacc    2880

<210> SEQ ID NO 7
<211> LENGTH: 37912
<212> TYPE: DNA
<213> ORGANISM: Simian adenovirus

<400> SEQUENCE: 7
catcatcaat aatataccTt attttggatt gaagccaata tgataatgag atgggcggcg      60
cggggcgggg cgcggggcgg gaggcgggtt tgggggcggg ccggcgggcg gggcggtgtg     120
gcggaagtgg actttgtaag tgtggcggat gtgacttgct agtgccgggc gcggtaaaag     180
tgacgttttc cgtgcgcgac aacgcccccg ggaagtgaca ttttttcccgc ggttttttacc    240 ggatgttgta gtgaatttgg gcgtaaccaa gtaagatttg gccattttcg cgggaaaact     300
gaaacgggga agtgaaatct gattaatttt gcgttagtca taccgcgtaa tatttgtcta     360
gggccgaggg actttggccg attacgtgga ggactcgccc aggtgttttt tgaggtgaat     420
ttccgcgttc cgggtcaaag tctgcgtttt attattatag gatatcccat tgcatacgtt     480
gtatccatat cataatatgt acatttatat tggctcatgt ccaacattac cgccatgttg     540
acattgatta ttgactagtt attaatagta atcaattacg gggtcattag ttcatagccc     600
atatatggag ttccgcgtta cataacttac ggtaaatggc ccgcctggct gaccgcccaa     660
cgacccccgc ccattgacgt caataatgac gtatgttccc atagtaacgc caatagggac     720
tttccattga cgtcaatggg tggagtattt acggtaaact gcccacttgg cagtacatca     780
agtgtatcat atgccaagta cgccccctat tgacgtcaat gacggtaaat ggcccgcctg     840
gcattatgcc cagtacatga ccttatggga ctttcctact tggcagtaca tctacgtatt     900
agtcatcgct attaccatgg tgatgcggtt ttggcagtac atcaatgggc gtggatagcg     960
gtttgactca cggggatttc caagtctcca ccccattgac gtcaatggga gtttgttttg    1020
gcaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
agatctccct atcagtgata gagatcgtcg acgagtcgt ttagtgaacc gtcagatcgc    1200
ctggagacgc catccacgct gttttgacct ccatagaaga caccgggacc gatccagcct    1260
ccgcggccgg gaacggtgca ttggaacgcg gattccccgt gccaagagtg agatcttccg    1320
tttatctagg taccgggccc cccctcgagg tcgacggtat cgataagctt cacgctgccg    1380
caagcactca gggcgcaagg gctgctaaag gaagcggaac acgtagaaag ccagtccgca    1440
gaaacggtgc tgaccccgga tgaatgtcag ctactgggct atctggacaa gggaaaacgc    1500
aagcgcaaag agaaagcagg tagcttgcag tgggcttaca tggcgatagc tagactgggc    1560
ggttttatgg acagcaagcg aaccggaatt gccagctggg gcgccctctg gtaaggttgg    1620
gaagccctgc aaagtaaact ggatggcttt cttgccgcca aggatctgat ggcgcagggg    1680
atcaagatct aaccaggagc tatttaatgg caacagttaa ccagctggta cgcaaaccac    1740
```

```
gtgctcgcaa agttgcgaaa agcaacgtgc ctgcgctgga agcatgcccg caaaaacgtg    1800
gcgtatgtac tcgtgtatat actaccactc ctaaaaaacc gaactccgcg ctgcgtaaag    1860
tatgccgtgt tcgtctgact aacggtttcg aagtgacttc ctacatcggt ggtgaaggtc    1920
acaacctgca ggagcactcc gtgatcctga tccgtggcgg tcgtgttaaa gacctcccgg    1980
gtgttcgtta ccacaccgta cgtggtgcgc ttgactgctc cggcgttaaa gaccgtaagc    2040
aggctcgttc caagtatggc gtgaagcgtc ctaaggctta atggtagatc tgatcaagag    2100
acaggatgac ggtcgtttcg catgcttgaa caagatggat tgcacgcagg ttctccggcc    2160
gcttgggtgg agaggctatt cggctatgac tgggcacaac agacaatcgg ctgctctgat    2220
gccgccgtgt tccggctgtc agcgcagggg cgcccggttc tttttgtcaa gaccgacctg    2280
tccggtgccc tgaatgaact gcaggacgag gcagcgcggc tatcgtggct ggccacgacg    2340
ggcgttcctt gcgcagctgt gctcgacgtt gtcactgaag cgggaaggga ctggctgcta    2400
ttgggcgaag tgccggggca ggatctcctg tcatctcacc ttgctcctgc cgagaaagta    2460
tccatcatgg ctgatgcaat gcggcggctg catacgcttg atccggctac ctgcccattc    2520
gaccaccaag cgaaacatcg catcgagcga gcacgtactc ggatggaagc cggtcttgtc    2580
gatcaggatg atctggacga agagcatcag gggctcgcgc cagccgaact gttcgccagg    2640
ctcaaggcgc gcatgcccga cggcgaggat ctcgtcgtga cccatggcga tgcctgcttg    2700
ccgaatatca tggtggaaaa tggccgcttt tctggattca tcgactgtgg ccggctgggt    2760
gtggcggacc gctatcagga catagcgttg gctacccgtg atattgctga agagcttggc    2820
ggcgaatggg ctgaccgctt cctcgtgctt tacggtatcg ccgctcccga ttcgcagcgc    2880
atcgccttct atcgccttct tgacgagttc ttctgagcgg gactctgggg ttcgaaatga    2940
ccgaccaagc gacgcccaac ctgccatcac gagatttcga ttccaccgcc gccttctatg    3000
aaaggttggg cttcggaatc gttttccggg acgccggctg gatgatcctc cagcgcgggg    3060
atctcatgct ggagttcttc gcccaccccg ggctcgatcc cctcgggggg aatcagaatt    3120
cagtcgacag cggccgcgat ctgctgtgcc ttctagttgc cagccatctg ttgtttgccc    3180
ctcccccgtg ccttccttga ccctggaagg tgccactccc actgtccttt cctaataaaa    3240
tgaggaaatt gcatcgcatt gtctgagtag gtgtcattct attctggggg gtggggtggg    3300
gcaggacagc aagggggagg attgggaaga caatagcagg catgctgggg atgcggtggg    3360
ctctatggcc gatcagcgat cgctgaggtg ggtgagtggg cgtggcctgg ggtggtcatg    3420
aaaatatata agttgggggt cttagggtct ctttatttgt gttgcagaga ccgccggagc    3480
catgagcggg agcagcagca gcagcagtag cagcagcgcc ttggatggca gcatcgtgag    3540
cccttatttg acgacgcgga tgccccactg gccggggtg cgtcagaatg tgatgggctc    3600
cagcatcgac ggccgacccg tcctgcccgc aaattccgcc acgctgacct atgcgaccgt    3660
cgcggggacg ccgttggacg ccaccgccgc cgccgccgcc accgcagccg cctcggccgt    3720
gcgcagcctg gccacggact ttgcattcct gggaccactg gcgacagggg ctacttctcg    3780
ggccgctgct gccgccgttc gcgatgacaa gctgaccgcc ctgctggcgc agttggatgc    3840
gcttactcgg gaactgggtg acctttctca gcaggtcatg gccctgcgcc agcaggtctc    3900
ctccctgcaa gctggcggga atgcttctcc cacaaatgcc gtttaagata aataaaacca    3960
gactctgttt ggattaaaga aaagtagcaa gtgcattgct ctctttatt cataattttc    4020 cgcgcgcgat aggccctaga ccagcgttct cggtcgttga gggtgcggtg tatcttctcc    4080
```

| | |
|---|---|
| aggacgtggt agaggtggct ctggacgttg agatacatgg gcatgagccc gtcccggggg | 4140 |
| tggaggtagc accactgcag agcttcatgc tccggggtgg tgttgtagat gatccagtcg | 4200 |
| tagcaggagc gctgggcatg gtgcctaaaa atgtccttca gcagcaggcc gatggccagg | 4260 |
| gggaggccct tggtgtaagt gtttacaaaa cggttaagtt gggaagggtg cattcgggga | 4320 |
| gagatgatgt gcatcttgga ctgtattttt agattggcga tgtttccgcc cagatccctt | 4380 |
| ctgggattca tgttgtgcag gaccaccagt acagtgtatc cggtgcactt ggggaatttg | 4440 |
| tcatgcagct tagagggaaa agcgtggaag aacttggaga cgcctttgtg gcctcccaga | 4500 |
| ttttccatgc attcgtccat gatgatggca atgggcccgc gggaggcagc ttgggcaaag | 4560 |
| atatttctgg ggtcgctgac gtcgtagttg tgttccaggg tgaggtcgtc ataggccatt | 4620 |
| tttacaaagc gcgggcggag ggtgcccgac tgggggatga tggtcccctc tggccctggg | 4680 |
| gcgtagttgc cctcgcagat ctgcatttcc caggccttaa tctcggaggg gggaatcata | 4740 |
| tccacctgcg gggcgatgaa gaaaacggtt ccggagccg gggagattaa ctgggatgag | 4800 |
| agcaggtttc taagcagctg tgattttcca caaccggtgg gcccataaat aacacctata | 4860 |
| accggttgca gctggtagtt tagagagctg cagctgccgt cgtcccggag gagggggcc | 4920 |
| acctcgttga gcatgtccct gacgcgcatg ttctccccga ccagatccgc cagaaggcgc | 4980 |
| tcgccgccca gggacagcag ctcttgcaag gaagcaaagt ttttcagcgg cttgaggccg | 5040 |
| tccgccgtgg gcatgttttt cagggtctgg ctcagcagct ccaggcggtc ccagagctcg | 5100 |
| gtgacgtgct ctacggcatc tctatccagc atatctcctc gtttcgcggg ttggggcgac | 5160 |
| tttcgctgta gggcaccaag cggtggtcgt ccagcgggc cagagtcatg tccttccatg | 5220 |
| ggcgcagggt cctcgtcagg gtggtctggg tcacggtgaa ggggtgcgct ccgggctgag | 5280 |
| cgcttgccaa ggtgcgcttg aggctggttc tgctggtgct gaagcgctgc cggtcttcgc | 5340 |
| cctgcgcgtc ggccaggtag catttgacca tggtgtcata gtccagcccc tccgcggcgt | 5400 |
| gtcccttggc gcgcagcttg cccttggagg tggcgccgca cgaggggcag agcaggctct | 5460 |
| tgagcgcgta gagcttgggg gcgaggaaga ccgattcggg ggagtaggcg tccgcgccgc | 5520 |
| agaccccgca cacggtctcg cactccacca gccaggtgag ctcggggcgc gccgggtcaa | 5580 |
| aaaccaggtt tcccccatgc ttttgatgc gtttcttacc tcgggtctcc atgaggtggt | 5640 |
| gtccccgctc ggtgacgaag aggctgtccg tgtctccgta gaccgacttg aggggtcttt | 5700 |
| tctccagggg ggtccctcgg tcttcctcgt agaggaactc ggaccactct gagacgaagg | 5760 |
| cccgcgtcca ggccaggacg aaggaggcta tgtgggaggg gtagcggtcg ttgtccacta | 5820 |
| gggggtccac cttctccaag gtgtgaagac acatgtcgcc ttcctcggcg tccaggaagg | 5880 |
| tgattggctt gtaggtgtag gccacgtgac cgggggttcc tgacgggggg gtataaaagg | 5940 |
| gggtgggggc gcgctcgtcg tcactctctt ccgcatcgct gtctgcgagg ccagctgct | 6000 |
| ggggtgagta ttccctctcg aaggcgggca tgacctccgc gctgaggttg tcagtttcca | 6060 |
| aaaacgagga ggatttgatg ttcacctgtc ccgaggtgat acctttgagg gtacccgcgt | 6120 |
| ccatctggtc agaaaacacg atcttttat tgtccagctt ggtggcgaac gacccgtaga | 6180 |
| gggcgttgga gagcagcttg gcgatggagc gcagggtctg gttcttgtcc ctgtcggcgc | 6240 |
| gctccttggc cgcgatgttg agctgcacgt actcgcgcgc gacgcagcgc cactcgggga | 6300 |
| agacggtggt gcgctcgtcg ggcaccaggc gcacgcgcca gccgcggttg tgcagggtga | 6360 |
| ccaggtccac gctggtggcg acctcgccgc gcaggcgctc gttggtccag cagagacggc | 6420 |
| cgcccttgcg cgagcagaag gggggcaggg ggtcgagctg ggtctcgtcc gggggggtccg | 6480 |

```
cgtccacggt gaaaacccog gggcgcaggc gcgcgtcgaa gtagtctatc ttgcaacctt    6540
gcatgtccag cgcctgctgc cagtcgcggg cggcgagcgc gcgctcgtag gggttgagcg    6600
gcgggcccca gggcatgggg tgggtgagtg cggaggcgta catgccgcag atgtcatgga    6660
cgtagagggg ctcccgcagg accccgatgt aggtggggta gcagcggccg ccgcggatgc    6720
tggcgcgcac gtagtcatac agctcgtgcg aggggggcgag gaggtcgggg cccaggttgg    6780
tgcgggcggg gcgctccgcg cggaagacga tctgcctgaa gatggcatgc gagttggaag    6840
agatggtggg gcgctggaag acgttgaagc tggcgtcctg caggccgacg cgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttcttttttcc    7020
acagctcgcg gttgaggaca aactcttcgc ggtctttcca gtactcttgg atcgggaaac    7080
cgtccggttc cgaacggtaa gagcctagca gtagaactg gttgacggcc tggtaggcgc    7140
agcagccctt ctccacgggg aggcgtagg cctgcgcgc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg gggttgggca    7320
gagcgaaggt gacatcgttg aagaggattt tgcccgcgcg gggcatgaag ttgcgggtga    7380
tgcggaaggg ccccggcact tcagagcggt tgttgatgac ctgggcggcg agcacgatct    7440
cgtcgaagcc gttgatgttg tggcccacga tgtagagttc caggaagcgg ggccggccct    7500
ttacggtggg cagcttcttt agctcttcgt aggtgagctc ctcgggcgag gcgaggccgt    7560
gctcggccag ggcccagtcc gcgaggtgcg ggttgtctct gaggaaggac ttccagaggt    7620
cgcgggccag gagggtctgc aggcggtctc tgaaggtcct gaactggcgg cccacggcca    7680
ttttttcggg ggtgatgcag tagaaggtga ggggtcttg ctgccagcgg tcccagtcga    7740
gctgcagggc gaggtcgcgc gcggcggtga ccaggcgctc gtcgccccg aatttcatga    7800
ccagcatgaa gggcacgagc tgcttttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc accttttcgcc cgcgcacgag gaagccgagg ggaaatctga    8100
gcccccgcc tggctcgcgg catggctggt tctcttctac tttggatgcg tgtccgtctc    8160
cgtctggctc ctcgaggggt gttacggtgg agcggaccac cacgccgcgc gagccgcagg    8220
tccagatatc ggcgcgcggc ggtcggagtt tgatgacgac atcgcgcagc tgggagctgt    8280
ccatggtctg gagctcccgc ggcggcggca ggtcagccgg gagttcttgc aggttcacct    8340
cgcagagtcg ggccagggcg cggggcaggt ctaggtggta cctgatctct aggggcgtgt    8400
tggtggcggc gtcgatggct tgcaggagcc cgcagcccg gggggcgacg acggtgcccc    8460
gcggggtggt ggtggtggtg gcggtgcagc tcagaagcgg tgccgcgggc gggcccccgg    8520
aggtaggggg ggctccggtc ccgcgggcag gggcggcagc ggcacgtcgg cgtggagcgc    8580
gggcaggagt tggtgctgtg cccggaggtt gctggcgaag gcgacgacgc ggcggttgat    8640
ctcctggatc tggcgcctct gcgtgaagac gacgggcccg gtgagcttga acctgaaaga    8700
gagttcgaca gaatcaatct cggtgtcatt gaccgcggcc tggcgcagga tctcctgcac    8760
gtctcccgag ttgtcttggt aggcgatctc ggccatgaac tgctcgatct cttcctcctg    8820
```

-continued

```
gaggtctccg cgtccggcgc gttccacggt ggccgccagg tcgttggaga tgcgccccat    8880
gagctgcgag aaggcgttga gtccgccctc gttccagact cggctgtaga ccacgccccc    8940
ctggtcatcg cgggcgcgca tgaccacctg cgcgaggttg agctccacgt gccgcgcgaa    9000
gacggcgtag ttgcgcagac gctggaagag gtagttgagg gtggtggcgg tgtgctcggc    9060
cacgaagaag ttcatgaccc agcggcgcaa cgtggattcg ttgatgtccc ccaaggcctc    9120
cagccgttcc atggcctcgt agaagtccac ggcgaagttg aaaaactggg agttgcgcgc    9180
cgacacggtc aactcctcct ccagaagacg gatgagctcg gcgacggtgt cgcgcacctc    9240
gcgctcgaag gctatgggga tctcttcctc cgctagcatc accacctcct cctcttcctc    9300
ctcttctggc acttccatga tggcttcctc ctcttcgggg ggtggcggcg gcggcggtgg    9360 gggaggggc gctctgcgcc ggcggcggc caccggagg cggtccacga agcgcgcgat      9420
catctccccg cggcggcggc gcatggtctc ggtgacggcg cggccgttct cccggggggcg    9480 cagttggaag acgccgccgg acatctggtg ctggggcggg tggccgtgag gcagcgagac    9540
ggcgctgacg atgcatctca acaattgctg cgtaggtacg ccgccgaggg acctgaggga    9600
gtccatatcc accggatccg aaaacctttc gaggaaggcg tctaaccagt cgcagtcgca    9660
aggtaggctg agcaccgtgg cgggcggcgg ggggtggggg gagtgtctgg cggaggtgct    9720
gctgatgatg taattgaagt aggcggactt gacacggcgg atggtcgaca ggagcaccat    9780
gtccttgggt ccggcctgct ggatgcgag gcggtcggct atgccccagg cttcgttctg    9840
gcatcggcgc aggtccttgt agtagtcttg catgagcctt ccaccggca cctcttctcc     9900 ttcctcttct gcttcttcca tgtctgcttc ggccctgggg cggcgccgcg ccccctgcc    9960 ccccatgcgc gtgaccccga accccctgag cggttggagc agggccaggt cggcgacgac    10020
gcgctcggcc aggatggcct gctgcacctg cgtgagggtg gtttggaagt catccaagtc    10080
cacgaagcgg tggtaggcgc ccgtgttgat ggtgtaggtg cagttggcca tgacggacca    10140
gttgacggtc tggtggcccg gttgcgacat ctccggtgtac ctgagtcgcg agtaggcgcg    10200
ggagtcgaag acgtagtcgt tgcaagtccg caccaggtac tggtagccca ccaggaagtg    10260
cggcggcggc tggcggtaga ggggccagcc caggtggcg ggggctccgg gggccaggtc     10320
ttccagcatg aggcggtggt aggcgtagat gtacctggac atccaggtga tacccgcggc    10380
ggtggtggag gcgcgcggga agtcgcgcac ccggttccag atgttgcgca ggggcagaaa    10440
gtgctccatg gtaggcgtgc tctgtccagt cagacgcgcg cagtcgttga tactctagac    10500
cagggaaaac gaaagccggt cagcgggcac tcttccgtgg tctggtgaat agatcgcaag    10560
ggtatcatgg cggagggcct cggttcgagc cccgggtccg ggccggacgg tccgccatga    10620
tccacgcggt taccgcccgc gtgtcgaacc caggtgtgcg acgtcagaca acggtggagt    10680
gttccttttg gcgttttct ggccgggcgc cggcgccgcg taagagacta agccgcgaaa    10740
gcgaaagcag taagtggctc gctccccgta gccggaggga tccttgctaa gggttgcgtt    10800
gcggcgaacc ccgttcgaa tcccgtactc gggccggccg acccgcggc taaggtgttg     10860 gattggcctc cccctcgtat aaagaccccg cttgcggatt gactccggac acggggacga    10920 gccccttta ttttttgcttt ccccagatgc atccggtgct gcggcagatg cgccccccgc    10980
cccagcagca gcaacaacac cagcaagagc ggcagcaaca gcagcgggag tcatgcaggg    11040 cccccctcacc caccctcggc gggcggccca cctcggcgtc cgcggccgtg tctggcgcct    11100
gcggcggcgc cgggggccg gctgacgacc ccgaggagcc ccgcggcgc agggccgac      11160 actacctgga cctggaggag ggcgagggcc tggcgcggct gggggcgccg tctcccgagc    11220
```

```
gccacccgcg ggtgcagctg aagcgcgact cgcgcgaggc gtacgtgcct cggcagaacc    11280
tgttcaggga ccgcgcgggc gaggagcccg aggagatgcg ggacaggagg ttcagcgcag    11340
ggcgggagct gcggcagggg ctgaaccgcg agcggctgct gcgcgaggag gactttgagc    11400
ccgacgcgcg gacggggatc agccccgcgc gcgcgcacgt ggcggccgcc gacctggtga    11460
cggcgtacga gcagacggtg aaccaggaga tcaacttcca aaagagtttc aacaaccacg    11520
tgcgcacgct ggtggcgcgc gaggaggtga ccatcgggct gatgcacctg tgggactttg    11580
taagcgcgct ggtgcagaac cccaacagca agcctctgac ggcgcagctg ttcctgatag    11640
tgcagcacag cagggacaac gaggcgttta gggacgcgct gctgaacatc accgagcccg    11700
agggtcggtg gctgctggac ctgattaaca tcctgcagag catagtggtg caggagcgca    11760
gcctgagcct ggccgacaag gtggcggcca tcaactactc gatgctgagc ctgggcaagt    11820
tttacgcgcg caagatctac cagacgccgt acgtgcccat agacaaggag gtgaagatcg    11880
acggttttta catgcgcatg gcgctgaagg tgctcaccct gagcgacgac ctgggcgtgt    11940
accgcaacga gcgcatccac aaggccgtga gcgtgagccg gcggcgcgag ctgagcgacc    12000
gcgagctgat gcagagcctg cagcgggcgc tggcgggcgc cggcagcggc gacagggagg    12060
cggagtccta cttcgatgcg ggggcggacc tgcgctgggc gcccagccgg cgggccctgg    12120
aggccgcggg ggtccgcgag gactatgacg aggacggcga ggaggatgag gagtacgagc    12180
tagaggaggg cgagtacctg gactaaaccg cgggtggtgt ttccggtaga tgcaagaccc    12240
gaacgtggtg gacccggcgc tgcgggcggc tctgcagagc cagccgtccg gccttaactc    12300
ctcagacgac tggcgacagg tcatggaccg catcatgtcg ctgacggcgc gtaacccgga    12360
cgcgttccgg cagcagccgc aggccaacag gctctccgcc atcctggagg cggtggtgcc    12420
tgcgcgctcg aaccccacgc acgagaaggt gctggccata gtgaacgcgc tggccgagaa    12480
cagggccatc cgcccggacg aggccgggct ggtgtacgac gcgctgctgc agcgcgtggc    12540
ccgctacaac agcggcaacg tgcagaccaa cctggaccgg ctggtggggg acgtgcgcga    12600
ggcggtggcg cagcgcgagc gcgcggatcg gcagggcaac ctgggctcca tggtggcgct    12660
gaatgccttc ctgagcacgc agccggccaa cgtgccgcgg gggcaggaag actacaccaa    12720
ctttgtgagc gcgctgcggc tgatggtgac cgagaccccc cagagcgagg tgtaccagtc    12780
gggcccggac tacttcttcc agaccagcag acagggcctg cagacggtga acctgagcca    12840
ggctttcaag aacctgcggg ggctgtgggg cgtgaaggcg cccaccggcg accgggcgac    12900
ggtgtccagc ctgctgacgc ccaactcgcg cctgctgctg ctgctgatcg cgccgttcac    12960
ggacagcggc agcgtgtccc gggacaccta cctgggcac ctgctgaccc tgtaccgcga    13020
ggccatcggg caggcgcagg tggacgagca caccttccag gagatcacca gcgtgagccg    13080
cgcgctgggg caggaggaca cgagcagcct ggaggcgact ctgaactacc tgctgaccaa    13140
ccggcggcag aagattccct cgctgcacag cctgacctcc gaggaggagc gcatcttgcg    13200
ctacgtgcag cagagcgtga gcctgaacct gatgcgcgac ggggtgacgc ccagcgtggc    13260
gctggacatg accgcgcgca acatggaacc gggcatgtac gccgcgcacc ggccttacat    13320
caaccgcctg atggactacc tgcatcgcgc ggcggccgtg aaccccgagt actttaccaa    13380
cgccatcctg aacccgcact ggctcccgcc gcccgggttc tacagcgggg gcttcgaggt    13440
cccggagacc aacgatggct tcctgtggga cgacatggac gacagcgtgt tctccccgcg    13500
gccgcaggcg ctggcggaag cgtccctgct gcgtcccaag aaggaggagg aggaggaggc    13560
```

```
gagtcgccgc cgcggcagca gcggcgtggc ttctctgtcc gagctggggg cggcagccgc   13620
cgcgcgcccc gggtccctgg gcggcagccc ctttccgagc ctggtggggt ctctgcacag   13680
cgagcgcacc acccgccctc ggctgctggg cgaggacgag tacctgaata actccctgct   13740
gcagccggtg cgggagaaaa acctgcctcc cgccttcccc aacaacggga tagagagcct   13800
ggtggacaag atgagcagat ggaagaccta tgcgcaggag cacagggacg cgcctgcgct   13860
ccggccgccc acgcggcgcc agcgccacga ccggcagcgg gggctggtgt gggatgacga   13920
ggactccgcg gacgatagca gcgtgctgga cctgggaggg agcggcaacc cgttcgcgca   13980
cctgcgcccc cgcctgggga ggatgtttta aaaaaaaaaa aaaaaagcaa gaagcatgat   14040
gcaaaaatta aataaaactc accaaggcca tggcgaccga gcgttggttt cttgtgttcc   14100
cttcagtatg cggcgcgcgg cgatgtacca ggagggacct cctccctctt acgagagcgt   14160
ggtgggcgcg gcggcggcgg cgccctcttc tccctttgcg tcgcagctgc tggagccgcc   14220
gtacgtgcct ccgcgctacc tgcggcctac gggggggaga aacagcatcc gttactcgga   14280
gctggcgccc ctgttcgaca ccacccgggt gtacctggtg gacaacaagt cggcggacgt   14340
ggcctccctg aactaccaga acgaccacag caattttttg accacggtca tccagaacaa   14400
tgactacagc ccgagcgagg ccagcaccca gaccatcaat ctggatgacc ggtcgcactg   14460
gggcggcgac ctgaaaacca tcctgcacac caacatgccc aacgtgaacg agttcatgtt   14520
caccaataag ttcaaggcgc gggtgatggt gtcgcgctcg cacaccaagg aagacccggt   14580
ggagctgaag tacgagtggg tggagttcga gctgccagag ggcaactact ccgagaccat   14640
gaccattgac ctgatgaaca acgcgatcgt ggagcactat ctgaaagtgg gcaggcagaa   14700
cggggtcctg gagagcgaca tcggggtcaa gttcgacacc aggaacttcc gcctggggct   14760
ggaccccgtg accgggctgg ttatgcccgg ggtgtacacc aacgaggcct tccatcccga   14820
catcatcctg ctgcccggct gcggggtgga cttcacttac agccgcctga gcaacctcct   14880
gggcatccgc aagcggcagc ccttccagga gggcttcagg atcacctacg aggacctgga   14940 gggggggcaac atccccgcgc tcctcgatgt ggaggcctac caggatagct tgaaggaaaa   15000
tgaggcggga caggaggata ccgccccgc cgcctccgcc gccgcgagc agggcgagga   15060 tgctgctgac accgcggccg cggacggggc agaggccgac cccgctatgg tggtggaggc   15120
tcccgagcag gaggaggaca tgaatgacag tgcggtgcgc ggagacacct tcgtcacccg   15180
gggggaggaa aagcaagcgg aggccgaggc cgcggccgag gaaaagcaac tggcggcagc   15240
agcggcggcg gcgcgttgg ccgcggcgga ggctgagtct gagggaccca gcccgccaa    15300 ggagcccgtg attaagcccc tgaccgaaga tagcaagaag cgcagttaca acctgctcaa   15360
ggacagcacc aacaccgcgt accgcagctg gtacctggcc tacaactacg cgacccgtc    15420 gacgggggtg cgctcctgga ccctgctgtg cacgccggac gtgacctgcg gctcggagca   15480
ggtgtactgg tcgctgcccg acatgatgca agacccgtg accttccgct ccacgcggca   15540
ggtcagcaac ttcccggtgg tgggcgccga gctgctgccc gtgcactcca agagcttcta   15600
caacgaccag gccgtctact cccagctcat ccgccagttc acctctctga cccacgtgtt   15660
caatcgcttt cctgagaacc agattctggc gcgcccgccc gcccccacca tcaccaccgt   15720
cagtgaaaac gttcctgctc tcacagatca cgggacgcta ccgctgcgca acagcatcgg   15780
aggagtccag cgagtgaccg ttactgacgc cagacgccgc acctgcccct acgtttacaa   15840
ggccttgggc atagtctcgc cgcgcgtcct ttccagccgc actttttgag caacaccacc   15900
atcatgtcca tcctgatctc acccagcaat aactccggct ggggactgct gcgcgcgccc   15960
```

```
agcaagatgt tcggaggggc gaggaagcgt tccgagcagc accccgtgcg cgtgcgcggg   16020
cacttccgcg cccctgggg agcgcacaaa cgcggccgcg cggggcgcac caccgtggac    16080
gacgccatcg actcggtggt ggagcaggcg cgcaactaca ggcccgcggt ctctaccgtg   16140
gacgcggcca tccagaccgt ggtgcggggc gcgcggcggt acgccaagct gaagagccgc   16200
cggaagcgcg tggcccgccg ccaccgccgc cgacccgggg ccgccgccaa acgcgccgcc   16260
gcggccctgc ttcgccgggc caagcgcacg ggccgccgcg ccgccatgag ggccgcgcgc   16320
cgcttggccg ccggcatcac cgccgccacc atggcccccc gtacccgaag acgcgcggcc   16380
gccgccgccg ccgccgccat cagtgacatg gccagcaggc gccggggcaa cgtgtactgg   16440
gtgcgcgact cggtgaccgg cacgcgcgtg cccgtgcgct tccgccccc gcggacttga    16500 gatgatgtga aaaacaaca ctgagtctcc tgctgttgtg tgtatcccag cggcggcggc    16560
gcgcgcagcg tcatgtccaa gcgcaaaatc aaagaagaga tgctccaggt cgtcgcgccg   16620
gagatctatg gccccgaa gaaggaagag caggattcga agcccgcaa gataaagcgg      16680 gtcaaaaaga aaagaaaga tgatgacgat gccgatgggg aggtggagtt cctgcgcgcc    16740
acggcgccca ggcgccggt gcagtggaag ggccggcgcg taaagcgcgt cctgcgcccc    16800
ggcaccgcgg tggtcttcac gcccggcgag cgctccaccc ggactttcaa gcgcgtctat   16860
gacgaggtgt acggcgacga agacctgctg gagcaggcca acgagcgctt cggagagttt   16920
gcttacggga agcgtcagcg ggcgctgggg aaggaggacc tgctggcgct gccgctggac   16980
cagggcaacc ccaccccag tctgaagccc gtgaccctgc agcaggtgct gccgagcagc    17040
gcaccctccg aggcgaagcg gggtctgaag cgcgagggcg gcgacctggc gcccaccgtg   17100
cagctcatgg tgcccaagcg gcagaggctg gaggatgtgc tggagaaaat gaaagtagac   17160
cccggtctgc agccggacat cagggtccgc cccatcaagc aggtggcgcc gggcctcggc   17220
gtgcagaccg tggacgtggt catccccacc ggcaactccc ccgccgccgc caccactacc   17280
gctgcctcca cggacatgga gacacagacc gatcccgccg cagccgcagc cgcagccgcc   17340
gccgcgacct cctcggcgga ggtgcagacg gaccccctggc tgccgccggc gatgtcagct   17400 cccgcgcgc gtcgcgggcg caggaagtac ggcgccgcca acgcgctcct gcccgagtac   17460
gccttgcatc cttccatcgc gcccaccccc ggctaccgag gctataccta ccgcccgcga   17520
agagccaagg gttccacccg ccgtcccgc cgacgcgccg ccgccaccac ccgccgccgc     17580
cgccgcagac gccagcccgc actggctcca gtctccgtga ggaaagtggc gcgcgacgga   17640 cacccctgg tgctgcccag ggcgcgctac caccccagca tcgtttaaaa gcctgttgtg    17700
gttcttgcag atatggcct cacttgccgc ctccgtttcc cggtgccggg ataccgagga    17760
ggaagatcgc gccgcaggag gggtctggcc ggccgcggcc tgagcggagg cagccgccgc   17820
gcgcaccggc ggcgacgcgc caccagccga cgcatgcgcg cggggtgct gcccctgtta    17880 atccccctga tcgccgcggc gatcggcgcc gtgcccggga tcgcctccgt ggccttgcaa   17940
gcgtcccaga ggcattgaca gacttgcaaa cttgcaaata tggaaaaaaa acccccaata   18000
aaaaagtcta gactctcacg ctcgcttggt cctgtgacta ttttgtagaa tggaagacat    18060
caactttgcg tcgctggccc cgcgtcacgg ctcgcgcccg ttcctgggac actgaaacga   18120
tatcggcacc agcaacatga gcggtggcgc cttcagttgg ggctctctgt ggagcggcat   18180
taaaagtatc gggtctgccg ttaaaaatta cggctcccgg gcctgaaaca gcagcacggg   18240
ccagatgttg agagacaagt tgaaagagca gaacttccag cagaaggtgg tggagggcct   18300
```

```
ggcctccggc atcaacgggg tggtggacct ggccaaccag gccgtgcaga ataagatcaa    18360
cagcagactg gaccccggc cgccggtgga ggaggtgccg ccggcgctgg agacggtgtc     18420
ccccgatggg cgtggcgaga agcgcccgcg gcccgatagg gaagagacca ctctggtcac    18480
gcagaccgat gagccgcccc cgtatgagga ggccctgaag caaggtctgc ccaccacgcg    18540
gcccatcgcg cccatggcca ccggggtggt gggccgccac acccccgcca cgctggactt    18600
gcctccgccc gccgatgtgc cgcagcagca gaaggcggca cagccgggcc cgcccgcgac    18660
cgcctcccgt tcctccgccg gtcctctgcg ccgcgcggcc agcggccccc gcggggggt     18720
cgcgaggcac ggcaactggc agagcacgct gaacagcatc gtgggtctgg gggtgcggtc    18780
cgtgaagcgc cgccgatgct actgaatagc ttagctaacg tgttgtatgt gtgtatgcgc    18840
cctatgtcgc cgccagagga gctgctgagt cgccgccgtt cgcgcgccca ccaccaccgc    18900
cactccgccc ctcaagatgg cgaccccatc gatgatgccg cagtggtcgt acatgcacat    18960
ctcgggccag gacgcctcgg agtacctgag ccccgggctg gtgcagttcg cccgcgccac    19020
cgagagctac ttcagcctga gtaacaagtt taggaacccc acggtggcgc ccacgcacga    19080
tgtgaccacc gaccggtctc agcgcctgac gctgcggttc attcccgtgg accgcgagga    19140
caccgcgtac tcgtacaagg cgcggttcac cctggccgtg ggcgacaacc gcgtgctgga    19200
catggcctcc acctactttg acatccgcgg ggtgctggac cggggtccca ctttcaagcc    19260
ctactctggc accgcctaca actccctggc ccccaagggc gctcccaact cctgcgagtg    19320
ggagcaagag gaaactcagg cagttgaaga agcagcagaa gaggaagaag aagatgctga    19380
cggtcaagct gaggaagagc aagcagctac caaaaagact catgtatatg ctcaggctcc    19440
cctttctggc gaaaaaatta gtaaagatgg tctgcaaata ggaacggacg ctacagctac    19500
agaacaaaaa cctatttatg cagaccctac attccagccc gaaccccaaa tcggggagtc    19560
ccagtggaat gaggcagatg ctacagtcgc cggcggtaga gtgctaaaga aatctactcc    19620
catgaaacca tgctatggtt cctatgcaag acccacaaat gctaatggag gtcagggtgt    19680
actaacggca aatgcccagg gacagctaga atctcaggtt gaaatgcaat tcttttcaac    19740
ttctgaaaac gcccgtaacg aggctaacaa cattcagccc aaattggtgc tgtatagtga    19800
ggatgtgcac atggagaccc cggatacgca ccttttcttac aagcccgcaa aaagcgatga    19860
caattcaaaa atcatgctgg gtcagcagtc catgcccaac agacctaatt acatcggctt    19920
cagagacaac tttatcggcc tcatgtatta caatagcact ggcaacatgg gagtgcttgc    19980
aggtcaggcc tctcagttga atgcagtggt ggacttgcaa gacagaaaca cagaactgtc    20040
ctaccagctc ttgcttgatt ccatgggtga cagaaccaga tactttttcca tgtggaatca    20100
ggcagtggac agttatgacc cagatgttag aattattgaa aatcatggaa ctgaagacga    20160
gctccccaac tattgtttcc ctctgggtgg catagggta actgacactt accaggctgt     20220
taaaaccaac aatggcaata acgggggcca ggtgacttgg acaaaagatg aaacttttgc    20280
agatcgcaat gaaatagggg tgggaaacaa tttcgctatg gagatcaacc tcagtgccaa    20340
cctgtggaga aacttcctgt actccaacgt ggcgctgtac ctaccagaca agcttaagta    20400
caaccctcc aatgtggaca tctctgacaa ccccaacacc tacgattaca tgaacaagcg     20460
agtggtggcc ccggggctgg tggactgcta catcaacctg ggcgcgcgct ggtcgctgga    20520
ctacatggac aacgtcaacc ccttcaacca ccaccgcaat gcgggcctgc gctaccgctc    20580
catgctcctg ggcaacgggc gctacgtgcc cttccacatc caggtgcccc agaagttctt    20640
tgccatcaag aacctcctcc tcctgccggg ctcctacacc tacgagtgga acttcaggaa    20700
```

```
ggatgtcaac atggtcctcc agagctctct gggtaacgat ctcagggtgg acggggccag   20760
catcaagttc gagagcatct gcctctacgc caccttcttc cccatggccc acaacacggc   20820
ctccacgctc gaggccatgc tcaggaacga caccaacgac cagtccttca atgactacct   20880
ctccgccgcc aacatgctct acccccatac cgccaacgcc accaacgtcc ccatctccat   20940
cccctcgcgc aactgggcgg ccttccgcgg ctgggccttc acccgcctca agaccaagga   21000
gaccccctcc ctgggctcgg gattcgaccc ctactacacc tactcgggct ccattcccta   21060
cctggacggc accttctacc tcaaccacac tttcaagaag gtctcggtca ccttcgactc   21120
ctcggtcagc tggccgggca acgaccgtct gctcaccccc aacgagttcg agatcaagcg   21180
ctcggtcgac ggggagggct acaacgtggc ccagtgcaac atgaccaagg actggttcct   21240
ggtccagatg ctggccaact acaacatcgg ctaccagggc ttctacatcc cagagagcta   21300
caaggacagg atgtactcct tcttcaggaa cttccagccc atgagccggc aggtggtgga   21360
ccagaccaag tacaaggact accaggaggt gggcatcatc caccagcaca caactcggg    21420
cttcgtgggc tacctcgccc ccaccatgcg cgagggacag gcctaccccg ccaacttccc   21480
ctatccgctc ataggcaaga ccgcggtcga cagcatcacc cagaaaaagt tcctctgcga   21540
ccgcacccctc tggcgcatcc ccttctccag caacttcatg tccatgggtg cgctctcgga   21600
cctgggccag aacttgctct acgccaactc cgcccacgcc ctcgacatga ccttcgaggt   21660
cgaccccatg gacgagccca cccttctcta tgttctgttc gaagtctttg acgtggtccg   21720
ggtccaccag ccgcaccgcg gcgtcatcga accgtgtac ctgcgtacgc ccttctcggc    21780
cggcaacgcc accacctaaa gaagcaagcc gcagtcatcg ccgcctgcat gccgtcgggt   21840
tccaccgagc aagagctcag ggccatcgtc agagacctgg gatgcgggcc ctattttttg   21900
ggcaccttcg acaagcgctt ccctggcttt gtctccccac acaagctggc ctgcgccatc   21960
gtcaacacgg ccggccgcga ccgggggc gtgcactggc tggccttcgc ctggaacccg     22020
cgctccaaaa catgcttcct cttttgaccccc ttcggctttt cggaccagcg gctcaagcaa  22080
atctacgagt tcgagtacga gggcttgctg cgtcgcagcg ccatcgcctc ctcgcccgac   22140
cgctgcgtca ccctcgaaaa gtccacccag accgtgcagg ggcccgactc ggccgcctgc   22200
ggtctcttct gctgcatgtt tctgcacgcc tttgtgcact ggcctcagag tcccatggac   22260
cgcaacccca ccatgaactt gctgacgggg gtgcccaact ccatgctcca gagccccag    22320
gtcgagccca ccctgcgccg caaccaggag cagctctaca gcttcctgga gcgccactcg   22380
ccttacttcc gccgccacag cgcacagatc aggagggcca cctccttctg ccacttgcaa   22440
gagatgcaag aagggtaata acgatgtaca cactttttttc tcaataaat ggcatctttt    22500
tatttataca agctctctgg ggtattcatt tccaccacc acccgccgtt gtcgccatct    22560
ggctctattt agaaatcgaa agggttctgc cgggagtcgc cgtgcgccac gggcagggac   22620
acgttgcgat actggtagcg ggtgccccac ttgaactcgg gcaccaccag gcgaggcagc   22680
tcggggaagt tttcgctcca caggctgcgg gtcagcacca gcgcgttcat caggtcgggc   22740
gccgagatct tgaagtcgca gttggggccg ccgccctgcg cgcgcgagtt gcggtacacc   22800
gggttgcagc actggaacac caacagcgcc gggtgcttca cgctggccag cacgctgcgg   22860
tcggagatca gctcggcgtc caggtcctcc gcgttgctca gcgcgaacgg gtcatcttg    22920
ggcacttgcc gccccaggaa gggcgcgtgc ccggtttcg agttcagtc gcagcgcagc     22980
gggatcagca ggtgcccgtg cccggactcg gcgttggggt acagcgcgcg catgaaggcc   23040
```

```
tgcatctggc ggaaggccat ctgggccttg gcgccctccg agaagaacat gccgcaggac   23100
ttgcccgaga actggtttgc ggggcagctg cgtcgtgca ggcagcagcg cgcgtcggtg    23160
ttggcgatct gcaccacgtt gcgccccac cggttcttca cgatcttggc cttggacgat    23220
tgctccttca gcgcgcgctg cccgttctcg ctggtcacat ccatctcgat cacatgttcc   23280
ttgttcacca tgctgctgcc gtgcagacac ttcagctcgc cctccgtctc ggtgcagcgg   23340
tgctgccaca gcgcgcagcc cgtgggctcg aaagacttgt aggtcacctc cgcgaaggac   23400
tgcaggtacc cctgcaaaaa gcggcccatc atggtcacga aggtcttgtt gctgctgaag   23460
gtcagctgca gcccgcggtg ctcctcgttc agccaggtct tgcacacggc cgccagcgcc   23520
tccacctggt cgggcagcat cttgaagttc accttcagct cattctccac gtggtacttg   23580
tccatcagcg tgcgcgccgc ctccatgccc ttctcccagg ccgacaccag cggcaggctc   23640
acggggttct tcaccatcac cgtggccgcc gcctccgccg cgctttcgct ttccgccccg   23700
ctgttctctt cctcttcctc ctcttcctcg ccgccgccca ctcgcagccc ccgcaccacg   23760
gggtcgtctt cctgcaggcg ctgcaccttg cgcttgccgt tgcgccctg cttgatgcgc    23820 acgggcgggt tgctgaagcc caccatcacc agcgcggcct cttcttgctc gtcctcgctg   23880
tccagaatga cctccgggga gggggggttg gtcatcctca gtaccgaggc acgcttcttt   23940
ttcttcctgg gggcgttcgc cagctccgcg gctgcggccg ctgccgaggt cgaaggccga   24000
gggctgggcg tgcgcggcac cagcgcgtcc tgcgagccgt cctcgtcctc ctcggactcg   24060
agacggaggc gggcccgctt cttcgggggc gcgcggggcg gcggaggcgg cggcggcgac   24120
ggagacgggg acgagacatc gtccagggtg ggtggacggc gggccgcgcc gcgtccgcgc   24180 tcggggggtgg tctcgcgctg gtcctcttcc cgactggcca tctcccactg ctccttctcc   24240
tataggcaga aagagatcat ggagtctctc atgcgagtcg agaaggagga ggacagccta   24300 accgcccct ctgagccctc caccaccgcc gccaccaccg ccaatgccgc cgcggacgac    24360
gcgcccaccg agaccaccgc cagtaccacc ctccccagcg acgcaccccc gctcgagaat   24420
gaagtgctga tcgagcagga cccgggtttt gtgagcggag aggaggatga ggtggatgag   24480
aaggagaagg aggaggtcgc cgcctcagtg ccaaaagagg ataaaaagca agaccaggac   24540
gacgcagata aggatgagac agcagtcggg cgggggaacg gaagccatga tgctgatgac   24600
ggctacctag acgtgggaga cgacgtgctg cttaagcacc tgcaccgcca gtgcgtcatc   24660
gtctgcgacg cgctgcagga gcgctgcgaa gtgcccctgg acgtggcgga ggtcagccgc   24720
gcctacgagc ggcacctctt cgcgccgcac gtgcccccca agcgccggga gaacggcacc   24780
tgcgagccca cccgcgtctc aacttctac ccggtcttcg cggtacccga ggtgctggcc    24840
acctaccaca tctttttcca aaactgcaag atcccctct cctgccgcgc caaccgcacc    24900
cgcgccgaca aaaccctgac cctgcggcag ggcgcccaca tacctgatat cgcctctctg   24960
gaggaagtgc ccaagatctt cgagggtctc ggtcgcgacg agaaacgggc ggcgaacgct   25020
ctgcacgagg acagcgaaaa cgagagtcac tcggggggtgc tggtgagct cgaggcgac    25080 aacgcgcgcc tggccgtact caagcgcagc atagaggtca cccactttgc ctacccggcg   25140
ctcaacctgc cccccaaggt catgagtgtg gtcatgggcg agctcatcat gcgccgcgcc   25200
cagcccctgg ccgcggatgc aaacttgcaa gagtcctccg aggaaggcct gcccgcggtc   25260
agcgacgagc agctggcgcg ctggctggag acccgcgacc ccgcgcagct ggaggagcgg   25320
cgcaagctca tgatgccgc ggtgctggtc accgtgagc tcgagtgtct gcagcgcttc    25380
ttcgcggacc ccgagatgca gcgcaagctc gaggagaccc tgcactacac cttccgccag   25440
```

```
ggctacgtgc gccaggcctg caagatctcc aacgtggagc tctgcaacct ggtctcctac   25500
ctgggcatcc tgcacgagaa ccgcctcggg cagaacgtcc tgcactccac cctcaaaggg   25560
gaggcgcgcc gcgactacat ccgcgactgc gcctacctct tcctctgcta cacctggcag   25620
acggccatgg gggtctggca gcagtgcctg gaggagcgca acctcaagga gctggaaaag   25680
ctcctcaagc gcaccctcag ggacctctgg acgggcttca acgagcgctc ggtggccgcc   25740
gcgctggcgg acatcatctt tcccgagcgc ctgctcaaga ccctgcagca gggcctgccc   25800
gacttcacca gccagagcat gctgcagaac ttcaggactt tcatcctgga gcgctcgggc   25860
atcctgccgg ccacttgctg cgcgctgccc agcgacttcg tgcccatcaa gtacagggag   25920
tgcccgccgc cgctctgggg ccactgctac ctcttccagc tggccaacta cctcgcctac   25980
cactcggacc tcatggaaga cgtgagcggc gagggcctgc tcgagtgcca ctgccgctgc   26040
aacctctgca cgccccaccg ctctctagtc tgcaacccgc agctgctcag cgagagtcag   26100
attatcggta ccttcgagct gcagggtccc tcgcctgacg agaagtccgc ggctccaggg   26160
ctgaaactca ctccggggct gtggacttcc gcctacctac gcaaatttgt acctgaggac   26220
taccacgccc acgagatcag gttctacgaa gaccaatccc gccgcccaa ggcggagctc   26280 accgcctgcg tcatcaccca ggggcacatc ctgggccaat gcaagccat caacaaagcc   26340 cgccgagagt tcttgctgaa aaagggtcgg ggggtgtacc tggaccccca gtccggcgag   26400
gagctaaacc cgctaccccc gccgccgccc cagcagcggg accttgcttc ccaggatggc   26460
acccagaaag aagcagcagc cgccgccgcc gccgcagcca tacatgcttc tggaggaaga   26520
ggaggaggac tgggacagtc aggcagagga ggtttcggac gaggagcagg aggagatgat   26580
ggaagactgg gaggaggaca gcagcctaga cgaggaagct tcagaggccg aagaggtggc   26640
agacgcaaca ccatcgccct cggtcgcagc ccctcgccg gggcccctga atcctccga   26700 acccagcacc agcgctataa cctccgctcc tccggcgccg cgccacccg cccgcagacc   26760 caaccgtaga tgggacacca caggaaccgg ggtcggtaag tccaagtgcc cgccgccgcc   26820
accgcagcag cagcagcagc agcgccaggg ctaccgctcg tggcgcgggc acaagaacgc   26880
catagtcgcc tgcttgcaag actgcggggg caacatctct ttcgcccgcc gcttcctgct   26940
attccaccac ggggtcgcct ttccccgcaa tgtcctgcat tactaccgtc atctctacag   27000 ccctactgc agcggcgacc cagaggcgg agcggcagcc acagcggcga ccaccaccta   27060
ggaagatatc ctccgcgggc aagacagcgg cagcagcggc caggagaccc gcggcagcag   27120 cggcggggagc ggtgggcgca ctgcgcctct cgcccaacga accctctcg acccgggagc   27180 tcagacacag gatcttcccc actttgtatg ccatcttcca acagagcaga ggccaggagc   27240
aggagctgaa aataaaaaac agatctctgc gctccctcac ccgcagctgt ctgtatcaca   27300
aaagcgaaga tcagcttcgg cgcacgctgg aggacgcgga ggcactcttc agcaaatact   27360
gcgcgctcac tcttaaagac tagctccgcg cccttctcga atttaggcgg gagaaaacta   27420
cgtcatcgcc ggccgccgcc cagcccgccc agccgagatg agcaaagaga ttcccacgcc   27480
atacatgtgg agctaccagc cgcagatggg actcgcggcg ggagcggccc aggactactc   27540
cacccgcatg aactacatga gcgcgggacc ccacatgatc tcacaggtca acgggatccg   27600
cgcccagcga aaccaaatac tgctggaaca ggcggccatc accgccacgc cccgccataa   27660
tctcaacccc cgaaattggc ccgccgccct cgtgtaccag gaaaccccct ccgccaccac   27720
cgtactactt ccgcgtgacg cccaggccga agtccagatg actaactcag gggcgcagct   27780
```

```
cgcgggcggc tttcgtcacg gggcgcggcc gctccgacca ggtataagac acctgatgat   27840
cagaggccga ggtatccagc tcaacgacga gtcggtgagc tcttcgctcg gtctccgtcc   27900
ggacggaact ttccagctcg ccggatccgg ccgctcttcg ttcacgcccc gccaggcgta   27960
cctgactctg cagacctcgt cctcggagcc ccgctccggc ggcatcggaa ccctccagtt   28020
cgtggaggag ttcgtgccct cggtctactt caacccttc tcgggacctc ccggacgcta   28080
ccccgaccag ttcattccga actttgacgc ggtgaaggac tcggcggacg gctacgactg   28140
aatgtcaggt gtcgaggcag agcagcttcg cctgagacac ctcgagcact gccgccgcca   28200
caagtgcttc gcccgcggtt ctggtgagtt ctgctacttt cagctacccg aggagcatac   28260
cgaggggccg gcgcacggcg tccgcctgac cacccagggc gaggttacct gttccctcat   28320
ccggagtttt accctccgtc ccctgctagt ggagcgggag cggggtccct gtgtcctaac   28380
tatcgcctgc aactgcccta accctggatt acatcaagat ctttgctgtc atctctgtgc   28440
tgagtttaat aaacgctgag atcagaatct actgggctc ctgtcgccat cctgtgaacg   28500
ccaccgtctt cacccacccc gaccaggccc aggcgaacct cacctgcggt ctgcatcgga   28560
gggccaagaa gtacctcacc tggtacttca acggcacccc ctttgtggtt tacaacagct   28620
tcgacgggga cggagtctcc ctgaaagacc agctctccgg tctcagctac tccatccaca   28680
agaacaccac cctccaactc ttccctccct acctgccggg aacctacgag tgcgtcaccg   28740
gccgctgcac ccacctcacc cgcctgatcg taaaccagag ctttccggga acagataact   28800
ccctcttccc cagaacagga ggtgagctca ggaaactccc cggggaccag ggcggagacg   28860
taccttcgac ccttgtgggg ttaggatttt ttattaccgg gttgctggct cttttaatca   28920
aagtttcctt gagatttgtt ctttccttct acgtgtatga acacctcaac ctccaataac   28980
tctacccttt cttcggaatc aggtgacttc tctgaaatcg ggcttggtgt gctgcttact   29040
ctgttgattt ttttccttat catactcagc cttctgtgcc tcaggctcgc cgcctgctgc   29100
gcacacatct atatctactg ctggttgctc aagtgcaggg gtcgccaccc aagatgaaca   29160
ggtacatggt cctatcgatc ctaggcctgc tggccctggc ggcctgcagc gccgccaaaa   29220
aagagattac ctttgaggag cccgcttgca atgtaacttt caagcccgag ggtgaccaat   29280
gcaccaccct cgtcaaatgc gttaccaatc atgagaggct gcgcatcgac tacaaaaaca   29340
aaactggcca gtttgcggtc tatagtgtgt ttacgcccgg agacccctct aactactctg   29400
tcaccgtctt ccagggcgga cagtctaaga tattcaatta cactttccct ttttatgagt   29460
tatgcgatgc ggtcatgtac atgtcaaaac agtacaacct gtggcctccc tctccccagg   29520
cgtgtgtgga aaatactggg tcttactgct gtatggcttt cgcaatcact acgctcgctc   29580
taatctgcac ggtgctatac ataaaattca ggcagaggcg aatctttatc gatgaaaaga   29640
aaatgccttg atcgctaaca ccggctttct atctgcagaa tgaatgcaat cacctcccta   29700
ctaatcacca ccaccctcct tgcgattgcc catgggttga cacgaatcga agtgccagtg   29760
gggtccaatg tcaccatggt gggccccgcc ggcaattcca ccctcatgtg ggaaaaattt   29820
gtccgcaatc aatgggttca tttctgctct aaccgaatca gtatcaagcc cagagccatc   29880
tgcgatgggc aaaatctaac tctgatcaat gtgcaaatga tggatgctgg gtactattac   29940
gggcagcggg gagaaatcat taattactgg cgaccccaca aggactacat gctgcatgta   30000
gtcgaggcac ttcccactac caccccact accacctctc ccaccaccac caccactact   30060
actactacta ctactactac tactactacc actaccgctg cccgccatac ccgcaaaagc   30120
accatgatta gcacaaagcc ccctcgtgct cactcccacg ccggcgggcc catcggtgcg   30180
```

| | | | | | |
|---|---|---|---|---|---|
| acctcagaaa | ccaccgagct | ttgcttctgc | caatgcacta | acgccagcgc | tcatgaactg 30240 |
| ttcgacctgg | agaatgagga | tgtccagcag | agctccgctt | gcctgaccca | ggaggctgtg 30300 |
| gagcccgttg | ccctgaagca | gatcggtgat | tcaataattg | actcttcttc | ttttgccact 30360 |
| cccgaatacc | ctcccgattc | tactttccac | atcacgggta | ccaaagaccc | taacctctct 30420 |
| ttctacctga | tgctgctgct | ctgtatctct | gtggtctctt | ccgcgctgat | gttactgggg 30480 |
| atgttctgct | gcctgatctg | ccgcagaaag | agaaaagctc | gctctcaggg | ccaaccactg 30540 |
| atgcccttcc | cctaccccc | ggattttgca | gataacaaga | tatgagctcg | ctgctgacac 30600 |
| taaccgcttt | actagcctgc | gctctaaccc | ttgtcgcttg | cgactcgaga | ttccacaatg 30660 |
| tcacagctgt | ggcaggagaa | aatgttactt | tcaactccac | ggccgatacc | cagtggtcgt 30720 |
| ggagtggctc | aggtagctac | ttaactatct | gcaatagctc | cacttccccc | ggcatatccc 30780 |
| caaccaagta | ccaatgcaat | gccagcctgt | tcaccctcat | caacgcttcc | accctggaca 30840 |
| atggactcta | tgtaggctat | gtacccttg | gtgggcaagg | aaagaccccac | gcttacaacc 30900 |
| tggaagttcg | ccagcccaga | accactaccc | aagcttctcc | caccaccacc | accaccacca 30960 |
| ccatcaccag | cagcagcagc | agcagcagcc | acagcagcag | cagcagatta | ttgactttgg 31020 |
| ttttggccag | ctcatctgcc | gctacccagg | ccatctacag | ctctgtgccc | gaaaccactc 31080 |
| agatccaccg | cccagaaacg | accaccgcca | ccacccctaca | cacctccagc | gatcagatgc 31140 |
| cgaccaacat | caccccttg | gctcttcaaa | tgggacttac | aagccccact | ccaaaaccag 31200 |
| tggatgcggc | cgaggtctcc | gccctcgtca | atgactgggc | ggggctggga | atgtggtggt 31260 |
| tcgccatagg | catgatggcg | ctctgcctgc | ttctgctctg | gctcatctgc | tgcctccacc 31320 |
| gcaggcgagc | cagaccccc | atctatagac | ccatcattgt | cctgaacccc | gataatgatg 31380 |
| ggatccatag | attggatggc | ctgaaaaacc | tactttttc | ttttacagta | tgataaattg 31440 |
| agacatgcct | cgcattttct | tgtacatgtt | ccttctccca | cctttctgg | ggtgttctac 31500 |
| gctggccgct | gtgtctcacc | tggaggtaga | ctgcctctca | cccttcactg | tctacctgct 31560 |
| ttacggattg | tcaccctca | ctctcatctg | cagcctaatc | acagtaatca | tcgccttcat 31620 |
| ccagtgcatt | gattacatct | gtgtgcgcct | cgcatacttc | agacaccacc | cgcagtaccg 31680 |
| agacaggaac | attgcccaac | ttctaagact | gctctaatca | tgcataagac | tgtgatctgc 31740 |
| cttctgatcc | tctgcatcct | gcccaccctc | acctcctgcc | agtacaccac | aaaatctccg 31800 |
| cgcaaaagac | atgcctcctg | ccgcttcacc | caactgtgga | atatacccaa | atgctacaac 31860 |
| gaaaagagcg | agctctccga | agcttggctg | tatggggtca | tctgtgtctt | agttttctgc 31920 |
| agcactgtct | ttgccctcat | aatctacccc | tactttgatt | tgggatggaa | cgcgatcgat 31980 |
| gccatgaatt | accccacctt | tcccgcaccc | gagataattc | cactgcgaca | agttgtaccc 32040 |
| gttgtcgtta | atcaacgccc | cccatcccct | acgcccactg | aaatcagcta | ctttaaccta 32100 |
| acaggcggag | atgactgacg | ccctagatct | agaaatggac | ggcatcagta | ccgagcagcg 32160 |
| tctcctagag | aggcgcaggc | aggcggctga | gcaagagcgc | ctcaatcagg | agctccgaga 32220 |
| tctcgttaac | ctgcaccagt | gcaaaagagg | catcttttgt | ctggtaaagc | aggccaaagt 32280 |
| cacctacgag | aagaccggca | acagccaccg | cctcagttac | aaattgccca | cccagcgcca 32340 |
| gaagctggtg | ctcatggtgg | gtgagaatcc | catcaccgtc | acccagcact | cggtagagac 32400 |
| cgaggggtgt | ctgcactccc | cctgtcgggg | tccagaagac | ctctgcaccc | tggtaaagac 32460 |
| cctgtgcggt | ctcagagatt | tagtccccctt | taactaatca | aacactggaa | tcaataaaaa 32520 |

```
gaatcactta cttaaaatca gacagcaggt ctctgtccag tttattcagc agcacctcct    32580 tccctcctc ccaactctgg tactccaaac gccttctggc ggcaaacttc ctccacaccc    32640
tgaagggaat gtcagattct tgctcctgtc cctccgcacc cactatcttc atgttgttgc    32700
agatgaagcg caccaaaacg tctgacgaga gcttcaaccc cgtgtacccc tatgacacgg    32760
aaagcggccc tccctccgtc cctttcctca cccctccctt cgtgtctccc gatggattcc    32820
aagaaagtcc ccccgggtc ctgtctctga acctggccga gccctggtc acttcccacg    32880 gcatgctcgc cctgaaaatg ggaagtggcc tctccctgga cgacgctggc aacctcacct    32940
ctcaagatat caccaccgct agccctcccc tcaaaaaaac caagaccaac ctcagcctag    33000
aaacctcatc cccctaact gtgagcacct caggcgccct caccgtagca gccgccgctc    33060
ccctggcggt ggccggcacc tccctcacca tgcaatcaga ggccccctg acagtacagg    33120 atgcaaaact caccctggcc accaaaggcc ccctgaccgt gtctgaaggc aaactggcct    33180
tgcaaacatc ggccccgctg acggccgctg acagcagcac cctcacagtc agtgccacac    33240
caccccttag cacaagcaat ggcagcttgg gtattgacat gcaagccccc atttacacca    33300
ccaatggaaa actaggactt aactttggcg ctccctgca tgtggtagac agcctaaatg    33360
cactgactgt agttactggc caaggtctta cgataaacgg aacagccta caaactagag    33420 tctcaggtgc cctcaactat gacacatcag gaaacctaga attgagagct gcaggggta    33480 tgcgagttga tgcaaatggt caacttatcc ttgatgtagc ttacccattt gatgcacaaa    33540
acaatctcag ccttaggctt ggacagggac ccctgtttgt taactctgcc cacaacttgg    33600
atgttaacta caacagagc ctctacctgt tcacatctgg aaataccaaa aagctagaag    33660
ttaatatcaa aacagccaag ggtctcattt atgatgacac tgctatagca atcaatgcgg    33720
gtgatgggct acagtttgac tcaggctcag atacaaatcc attaaaaact aaacttggat    33780
taggactgga ttatgactcc agcagagcca taattgctaa actgggaact ggcctaagct    33840
ttgacaacac aggtgccatc acagtaggca acaaaaatga tgacaagctt accttgtgga    33900
ccacaccaga cccatcccct aactgtagaa tctattcaga gaaagatgct aaattcacac    33960
ttgttttgac taaatgcggc agtcaggtgt tggccagctt ttctgttta tctgtaaaag    34020 gtagccttgc gcccatcagt ggcacagtaa ctagtgctca gattgtcctc agatttgatg    34080
aaaatggagt tctactaagc aattcttccc ttgaccctca atactggaac tacagaaaag    34140
gtgaccttac agagggcact gcatatacca acgcagtggg atttatgccc aacctcacag    34200
cataccccaa aacacagagc caaactgcta aaagcaacat tgtaagtcag gtttacttga    34260
atggggacaa atccaaaccc atgaccctca ccattaccct caatggaact aatgaaacag    34320
gagatgccac agtaagcact tactccatgt cattctcatg gaactggaat ggaagtaatt    34380
acattaatga aacgttccaa accaactcct tcaccttctc ctacatcgcc caagaataaa    34440
aagcatgacg ctgttgattt gattcaatgt gtttctgttt tattttcaag cacaacaaaa    34500
tcattcaagt cattcttcca tcttagctta atagacacag tagcttaata gacccagtag    34560
tgcaaagccc cattctagct tataactagt ggagaagtac tcgcctacat ggggggtagag   34620 tcataatcgt gcatcaggat agggcggtgg tgctgcagca gcgcgcgaat aaactgctgc    34680
cgccgccgct ccgtcctgca ggaatacaac atggcagtgg tctcctcagc gatgattcgc    34740 accgccgca gcataaggcg ccttgtcctc cgggcacagc agcgcaccct gatctcactt    34800
aaatcagcac agtaactgca gcacagcacc acaatattgt tcaaaatccc acagtgcaag    34860
gcgctgtatc caaagctcat ggcggggacc acagaaccca cgtggccatc ataccacaag    34920
```

```
cgcaggtaga ttaagtggcg acccctcata aacacgctgg acataaacat tacctctttt   34980
ggcatgttgt aattcaccac ctcccggtac catataaacc tctgattaaa catggcgcca   35040
tccaccacca tcctaaacca gctggccaaa acctgcccgc cggctataca ctgcagggaa   35100
ccgggactgg aacaatgaca gtggagagcc caggactcgt aaccatggat catcatgctc   35160
gtcatgatat caatgttggc acaacacagg cacacgtgca tacacttcct caggattaca   35220
agctcctccc gcgttagaac catatcccag ggaacaaccc attcctgaat cagcgtaaat   35280
cccacactgc agggaagacc tcgcacgtaa ctcacgttgt gcattgtcaa agtgttacat   35340
tcgggcagca gcgatgatc ctccagtatg gtagcgcggg tttctgtctc aaaaggaggt   35400
agacgatccc tactgtacgg agtgcgccga gacaaccgag atcgtgttgg tcgtagtgtc   35460
atgccaaatg gaacgccgga cgtagtcata tttcctgaag tcttagatct ctcaacgcag   35520
caccagcacc aacacttcgc agtgtaaaag gccaagtgcc gagagagtat atataggaat   35580
aaaaagtgac gtaaacgggc aaagtccaaa aaacgcccag aaaaaccgca cgcgaaccta   35640
cgccccgaaa cgaaagccaa aaaacactag acactcccctt ccggcgtcaa cttccgcttt   35700
cccacgctac gtcacttgcc ccagtcaaac aaactacata tcccgaactt ccaagtcgcc   35760
acgcccaaaa caccgcctac acctccccgc ccgccggccc gccccaaac ccgcctcccg   35820 ccccgcgccc cgccccgcgc cgcccatctc attatcatat tggcttcaat ccaaaataag   35880
gtatattatt gatgatggtt taaacggatc caattcttga agacgaaagg gcctcgtgat   35940
acgcctattt ttataggtta atgtcatgat aataatggtt tcttagacgt caggtggcac   36000
ttttcgggga aatgtgcgcg gaacccctat ttgtttattt ttctaaatac attcaaatat   36060
gtatccgctc atgagacaat aaccctgata aatgcttcaa taatattgaa aaaggaagag   36120
tatgagtatt caacatttcc gtgtcgccct tattcccttt tttgcggcat tttgccttcc   36180
tgtttttgct cacccagaaa cgctggtgaa agtaaaagat gctgaagatc agttgggtgc   36240
acgagtgggt tacatcgaac tggatctcaa cagcggtaag atccttgaga gttttcgccc   36300
cgaagaacgt tttccaatga tgagcacttt taaagttctg ctatgtggcg cggtattatc   36360
ccgtgttgac gccgggcaag agcaactcgg tcgccgcata cactattctc agaatgactt   36420
ggttgagtac tcaccagtca cagaaaagca tcttacggat ggcatgacag taagagaatt   36480
atgcagtgct gccataacca tgagtgataa cactgcggcc aacttacttc tgacaacgat   36540
cggaggaccg aaggagctaa ccgcttttt gcacaacatg ggggatcatg taactcgcct   36600
tgatcgttgg gaaccggagc tgaatgaagc cataccaaac gacgagcgtg acaccacgat   36660
gcctgtagca atggcaacaa cgttgcgcaa actattaact ggcgaactac ttactctagc   36720
ttcccggcaa caattaatag actggatgga ggcggataaa gttgcaggac cacttctgcg   36780
ctcggccctt ccggctggct ggtttattgc tgataaatct ggagccggtg agcgtgggtc   36840
tcgcggtatc attgcagcac tggggccaga tggtaagccc tcccgtatcg tagttatcta   36900
cacgacgggg agtcaggcaa ctatggatga acgaaataga cagatcgctg agataggtgc   36960
ctcactgatt aagcattggt aactgtcaga ccaagtttac tcatatatac tttagattga   37020
tttaaaagga tctaggtgaa gatcctttt tgataatctca tgaccaaaat cccttaacgt   37080
gagttttcgt tccactgagc gtcagacccc gtagaaaaga tcaaaggatc ttcttgagat   37140 ccttttttc tgcgcgtaat ctgctgcttg caaacaaaaa aaccaccgct accagcggtg   37200
gtttgtttgc cggatcaaga gctaccaact ctttttccga aggtaactgg cttcagcaga   37260
```

```
gcgcagatac caaatactgt ccttctagtg tagccgtagt taggccacca cttcaagaac    37320
tctgtagcac cgcctacata cctcgctctg ctaatcctgt taccagtggc tgctgccagt    37380
ggcgataagt cgtgtcttac cgggttggac tcaagacgat agttaccgga taaggcgcag    37440
cggtcgggct gaacgggggg ttcgtgcaca cagcccagct tggagcgaac gacctacacc    37500
gaactgagat acctacagcg tgagctatga aaagcgcca cgcttcccga agggagaaag    37560
gcggacaggt atccggtaag cggcagggtc ggaacaggag agcgcacgag ggagcttcca    37620
gggggaaacg cctggtatct ttatagtcct gtcgggtttc gccacctctg acttgagcgt    37680 cgattttgt gatgctcgtc agggggggcgg agcctatgga aaaacgccag caacgcggcc    37740
tttttacggt tcctggcctt ttgctggcct tgaagctgtc cctgatggtc gtcatctacc    37800
tgcctggaca gcatggcctg caacgcgggc atcccgatgc cgccggaagc gagaagaatc    37860
ataatgggga aggccatcca gcctcgcgtc gcagatccga attcgtttaa ac            37912

<210> SEQ ID NO 8
<211> LENGTH: 43428
<212> TYPE: DNA
<213> ORGANISM: Simian adenovirus

<400> SEQUENCE: 8
catcatcaat aatataccttt attttggatt gaagccaata tgataatgag atgggcggcg      60
cggggcgggg cgcggggcgg gaggcgggtt tgggggcggg ccggcgggcg gggcggtgtg     120
gcggaagtgg actttgtaag tgtggcggat gtgacttgct agtgccgggc gcggtaaaag     180
tgacgttttc cgtgcgcgac aacgcccccg ggaagtgaca tttttcccgc ggttttttacc    240 ggatgttgta gtgaatttgg gcgtaaccaa gtaagatttg gccattttcg cgggaaaact     300
gaaacgggga agtgaaatct gattaatttt gcgttagtca taccgcgtaa tatttgtcta     360
gggccgaggg actttggccg attacgtgga ggactcgccc aggtgttttt tgaggtgaat     420
ttccgcgttc cgggtcaaag tctgcgtttt attattatag gatatcccat tgcatacgtt     480
gtatccatat cataatatgt acatttatat tggctcatgt ccaacattac cgccatgttg     540
acattgatta ttgactagtt attaatagta atcaattacg gggtcattag ttcatagccc     600
atatatggag ttccgcgtta cataacttac ggtaaatggc ccgcctggct gaccgcccaa     660
cgacccccgc ccattgacgt caataatgac gtatgttccc atagtaacgc caatagggac     720
tttccattga cgtcaatggg tggagtattt acggtaaact gcccacttgg cagtacatca     780
agtgtatcat atgccaagta cgccccctat tgacgtcaat gacggtaaat ggcccgcctg     840
gcattatgcc cagtacatga ccttatggga ctttcctact tggcagtaca tctacgtatt     900
agtcatcgct attaccatgg tgatgcggtt ttggcagtac atcaatgggc gtggatagcg     960
gtttgactca cggggatttc caagtctcca ccccattgac gtcaatggga gtttgttttg    1020
gcaccaaaat caacgggact ttccaaaatg tcgtaacaac tccgccccat tgacgcaaat    1080
gggcggtagg cgtgtacggt gggaggtcta tataagcaga gctctcccta tcagtgatag    1140
agatctccct atcagtgata gagatcgtcg acgagctcgt ttagtgaacc gtcagatcgc    1200
ctggagacgc catccacgct gttttgacct ccatagaaga caccgggacc gatccagcct    1260
ccgcggccgg gaacggtgca ttggaacgcg gattcccgt gccaagagtg agatcttccg    1320
tttatctagg taccgggccc cccctcgagg tcgacggtat cgataagctt cacgctgccg    1380
caagcactca gggcgcaagg gctgctaaag gaagcggaac acgtagaaag ccagtccgca    1440
gaaacggtgc tgaccccgga tgaatgtcag ctactgggct atctggacaa gggaaaacgc    1500
```

```
aagcgcaaag agaaagcagg tagcttgcag tgggcttaca tggcgatagc tagactgggc   1560
ggttttatgg acagcaagcg aaccggaatt gccagctggg gcgccctctg gtaaggttgg   1620
gaagccctgc aaagtaaact ggatggcttt cttgccgcca aggatctgat ggcgcagggg   1680
atcaagatct aaccaggagc tatttaatgg caacagttaa ccagctggta cgcaaaccac   1740
gtgctcgcaa agttgcgaaa agcaacgtgc ctgcgctgga agcatgcccg caaaaacgtg   1800
gcgtatgtac tcgtgtatat actaccactc ctaaaaaacc gaactccgcg ctgcgtaaag   1860
tatgccgtgt tcgtctgact aacggtttcg aagtgacttc ctacatcggt ggtgaaggtc   1920
acaacctgca ggagcactcc gtgatcctga tccgtggcgg tcgtgttaaa gacctcccgg   1980
gtgttcgtta ccacaccgta cgtggtgcgc ttgactgctc cggcgttaaa gaccgtaagc   2040
aggctcgttc caagtatggc gtgaagcgtc ctaaggctta atggtagatc tgatcaagag   2100
acaggatgac ggtcgtttcg catgcttgaa caagatggat tgcacgcagg ttctccggcc   2160
gcttgggtgg agaggctatt cggctatgac tgggcacaac agacaatcgg ctgctctgat   2220
gccgccgtgt tccggctgtc agcgcagggg cgcccggttc tttttgtcaa gaccgacctg   2280
tccggtgccc tgaatgaact gcaggacgag gcagcgcggc tatcgtggct ggccacgacg   2340
ggcgttcctt gcgcagctgt gctcgacgtt gtcactgaag cgggaaggga ctggctgcta   2400
ttgggcgaag tgccggggca ggatctcctg tcatctcacc ttgctcctgc cgagaaagta   2460
tccatcatgg ctgatgcaat gcggcggctg catacgcttg atccggctac ctgcccattc   2520
gaccaccaag cgaaacatcg catcgagcga gcacgtactc ggatggaagc cggtcttgtc   2580
gatcaggatg atctggacga agagcatcag gggctcgcgc cagccgaact gttcgccagg   2640
ctcaaggcgc gcatgcccga cggcgaggat ctcgtcgtga cccatggcga tgcctgcttg   2700
ccgaatatca tggtggaaaa tggccgcttt tctggattca tcgactgtgg ccggctgggt   2760
gtggcggacc gctatcagga catagcgttg gctacccgtg atattgctga agagcttggc   2820
ggcgaatggg ctgaccgctt cctcgtgctt tacggtatcg ccgctcccga ttcgcagcgc   2880
atcgccttct atcgccttct tgacgagttc ttctgagcgg gactctgggg ttcgaaatga   2940
ccgaccaagc gacgcccaac ctgccatcac gagatttcga ttccaccgcc gccttctatg   3000
aaaggttggg cttcggaatc gttttccggg acgccggctg gatgatcctc cagcgcgggg   3060
atctcatgct ggagttcttc gcccaccccg gctcgatcc cctcgggggg aatcagaatt   3120
cagtcgacag cggccgcgat ctgctgtgcc ttctagttgc cagccatctg ttgtttgccc   3180
ctccccgtg ccttccttga ccctggaagg tgccactccc actgtccttt cctaataaaa   3240
tgaggaaatt gcatcgcatt gtctgagtag gtgtcattct attctggggg gtggggtggg   3300
gcaggacagc aagggggagg attgggaaga caatagcagg catgctgggg atgcggtggg   3360
ctctatggcc gatcagcgat cgctgaggtg ggtgagtggg cgtggcctgg ggtggtcatg   3420
aaaatatata agtgggggt cttagggtct ctttatttgt gttgcagaga ccgccggagc   3480
catgagcggg agcagcagca gcagcagtag cagcagcgcc ttggatggca gcatcgtgag   3540
cccttatttg acgacgcgga tgccccactg ggccggggtg cgtcagaatg tgatgggctc   3600
cagcatcgac ggccgacccg tcctgccgc aaattccgcc acgctgacct atgcgaccgt   3660
cgcggggacg ccgttggacg ccaccgccgc cgccgccgcc accgcagccg cctcggccgt   3720
gcgcagcctg ccacggact ttgcattcct gggaccactg gcgacagggg ctacttctcg   3780
ggccgctgct gccgccgttc gcgatgacaa gctgaccgcc ctgctggcgc agttggatgc   3840
```

```
gcttactcgg gaactgggtg acctttctca gcaggtcatg gccctgcgcc agcaggtctc    3900
ctccctgcaa gctggcggga atgcttctcc cacaaatgcc gtttaagata aataaaacca    3960
gactctgttt ggattaaaga aaagtagcaa gtgcattgct ctctttattt cataattttc    4020
cgcgcgcgat aggccctaga ccagcgttct cggtcgttga gggtgcggtg tatcttctcc    4080
aggacgtggt agaggtggct ctggacgttg agatacatgg gcatgagccc gtcccggggg    4140
tggaggtagc accactgcag agcttcatgc tccggggtgg tgttgtagat gatccagtcg    4200
tagcaggagc gctgggcatg gtgcctaaaa atgtccttca gcagcaggcc gatggccagg    4260
gggaggccct tggtgtaagt gtttacaaaa cggttaagtt gggaaggggtg cattcggggga    4320
gagatgatgt gcatcttgga ctgtattttt agattggcga tgtttccgcc cagatccctt    4380
ctgggattca tgttgtgcag gaccaccagt acagtgtatc cggtgcactt ggggaatttg    4440
tcatgcagct tagagggaaa agcgtggaag aacttggaga cgcctttgtg gcctcccaga    4500
ttttccatgc attcgtccat gatgatggca atgggcccgc gggaggcagc ttgggcaaag    4560
atatttctgg ggtcgctgac gtcgtagttg tgttccaggg tgaggtcgtc ataggccatt    4620
tttacaaagc gcgggcggag ggtgcccgac tggggatga tggtcccctc tggccctggg    4680
gcgtagttgc cctcgcagat ctgcatttcc caggccttaa tctcggaggg gggaatcata    4740
tccacctgcg gggcgatgaa gaaaacggtt ccggagccg gggagattaa ctgggatgag    4800
agcaggtttc taagcagctg tgattttcca caaccggtgg gccctaaaat aacacctata    4860
accggttgca gctggtagtt tagagagctg cagctgccgt cgtcccggag gagggggcc    4920
acctcgttga gcatgtccct gacgcgcatg ttctccccga ccagatccgc cagaaggcgc    4980
tcgccgccca gggacagcag ctcttgcaag gaagcaaagt ttttcagcgg cttgaggccg    5040
tccgccgtgg gcatgttttt cagggtctgg ctcagcagct ccaggcggtc ccagagctcg    5100
gtgacgtgct ctacggcatc tctatccagc atatctcctc gtttcgcggg ttggggcgac    5160
tttcgctgta gggcaccaag cggtggtcgt ccagcggggc cagagtcatg tccttccatg    5220
ggcgcagggt cctcgtcagg gtggtctggg tcacggtgaa ggggtgcgct ccgggctgag    5280
cgcttgccaa ggtgcgcttg aggctggttc tgctggtgct gaagcgctgc cggtcttcgc    5340
cctgcgcgtc ggccaggtag catttgacca tggtgtcata gtccagcccc tccgcggcgt    5400
gtcccttggc gcgcagcttg cccttggagg tggcgccgca cgaggggcag agcaggctct    5460
tgagcgcgta gagcttgggg gcgaggaaga ccgattcggg ggagtaggcg tccgcgccgc    5520
agaccccgca cacggtctcg cactccacca gccaggtgag ctcggggcgc gccgggtcaa    5580
aaaccaggtt tccccccatgc ttttttgatgc gtttcttacc tcgggtctcc atgaggtggt    5640
gtccccgctc ggtgacgaag aggctgtccg tgtctccgta gaccgacttg aggggtctt    5700
tctccagggg ggtccctcgg tcttcctcgt agaggaactc ggaccactct gagacgaagg    5760
cccgcgtcca ggccaggacg aaggaggcta tgtgggaggg gtagcggtcg ttgtccacta    5820
gggggtccac cttctccaag gtgtgaagac acatgtcgcc ttcctcggcg tccaggaagg    5880
tgattggctt gtaggtgtag gccacgtgac cgggggttcc tgacggggggg gtataaaagg    5940
gggtgggggc gcgctcgtcg tcactctctt ccgcatcgct gtctgcgagg ccagctgct    6000
ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atcttttat tgtccagctt ggtggcgaac gacccgtaga    6180
gggcgttgga gagcagcttg gcgatggagc gcagggtctg gttcttgtcc ctgtcggcgc    6240
```

```
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
ccaggtccac gctggtggcg acctcgccgc gcaggcgctc gttggtccag cagagacggc    6420
cgcccttgcg cgagcagaag ggggggcaggg ggtcgagctg ggtctcgtcc gggggggtccg    6480 cgtccacggt gaaaaccccg gggcgcaggc gcgcgtcgaa gtagtctatc ttgcaacctt    6540
gcatgtccag cgcctgctgc cagtcgcggg cggcgagcgc gcgctcgtag ggttgagcg    6600 gcgggcccca gggcatgggg tgggtgagtg cggaggcgta catgccgcag atgtcataga    6660
cgtagagggg ctcccgcagg accccgatgt aggtggggta gcagcggccg ccgcggatgc    6720
tggcgcgcac gtagtcatac agctcgtgcg aggggcgag gaggtcgggg cccaggttgg    6780
tgcgggcggg gcgctccgcg cggaagacga tctgcctgaa gatggcatgc gagttggaag    6840
agatggtggg gcgctggaag acgttgaagc tggcgtcctg caggccgacg cgtcgcgca    6900 cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttcttttttcc    7020 acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg gggttgggca    7320
gagcgaaggt gacatcgttg aagaggattt tgcccgcgcg gggcatgaag ttgcgggtga    7380
tgcggaaggg ccccggcact tcagagcggt tgttgatgac ctgggcgcg agcacgatct    7440 cgtcgaagcc gttgatgttg tggcccacga tgtagagttc caggaagcgg ggccggccct    7500
ttacggtggg cagcttcttt agctcttcgt aggtgagctc ctcggcgag gcgaggccgt    7560 gctcggccag ggcccagtcc gcgaggtgcg ggttgtctct gaggaaggac ttccagaggt    7620
cgcgggccag gagggtctgc aggcggtctc tgaaggtcct gaactggcgg cccacggcca    7680 tttttttcggg ggtgatgcag tagaaggtga ggggggtcttg ctgccagcgg tcccagtcga    7740
gctgcagggc gaggtcgcgc gcggcggtga ccaggcgctc gtcgcccccg aatttcatga    7800
ccagcatgaa gggcacgagc tgcttttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc accttttcgcc cgcgcacgag gaagccgagg gaaatctga    8100 gccccccgcc tggctcgcgg catggctggt tctcttctac tttggatgcg tgtccgtctc    8160
cgtctggctc ctcgaggggt gttacggtgg agcggaccac cacgccgcgc gagccgcagg    8220
tccagatatc ggcgcgcggc ggtcggagtt tgatgacgac atcgcgcagc tgggagctgt    8280
ccatggtctg gagctcccgc ggcggcggca ggtcagccgg gagttcttgc aggttcacct    8340
cgcagagtcg ggccagggcg cggggcaggt ctaggtggta cctgatctct aggggcgtgt    8400
tggtggcggc gtcgatggct tgcaggagcc cgcagccccg gggggcgacg acggtgcccc    8460
gcggggtggt ggtggtggtg gcggtgcagc tcagaagcgg tgccgcgggc gggccccgg    8520 aggtaggggg ggctccggtc ccgcgggcag gggcggcagc ggcacgtcgg cgtggagcgc    8580
```

-continued

```
gggcaggagt tggtgctgtg cccggaggtt gctggcgaag gcgacgacgc ggcggttgat    8640
ctcctggatc tggcgcctct gcgtgaagac gacgggcccg gtgagcttga acctgaaaga    8700
gagttcgaca gaatcaatct cggtgtcatt gaccgcggcc tggcgcagga tctcctgcac    8760
gtctcccgag ttgtcttggt aggcgatctc ggccatgaac tgctcgatct cttcctcctg    8820
gaggtctccg cgtccggcgc gttccacggt ggccgccagg tcgttggaga tgcgcccat    8880
gagctgcgag aaggcgttga gtccgccctc gttccagact cggctgtaga ccacgcccc    8940
ctggtcatcg cgggcgcgca tgaccacctg cgcgaggttg agctccacgt gccgcgcgaa    9000
gacggcgtag ttgcgcagac gctggaagag gtagttgagg gtggtggcgg tgtgctcggc    9060
cacgaagaag ttcatgaccc agcggcgcaa cgtggattcg ttgatgtccc ccaaggcctc    9120
cagccgttcc atggcctcgt agaagtccac ggcgaagttg aaaaactggg agttgcgcgc    9180
cgacacggtc aactcctcct ccagaagacg gatgagctcg gcgacggtgt cgcgcacctc    9240
gcgctcgaag gctatgggga tctcttcctc cgctagcatc accacctcct cctcttcctc    9300
ctcttctggc acttccatga tggcttcctc ctcttcgggg ggtggcggcg gcggcggtgg    9360
ggaggggggc gctctgcgcc ggcggcggcg caccgggagg cggtccacga agcgcgcgat    9420
catctccccg cggcggcggc gcatggtctc ggtgacggcg cggccgttct cccggggcg    9480
cagttggaag acgccgccgg acatctggtg ctggggcggg tggccgtgag gcagcgagac    9540
ggcgctgacg atgcatctca acaattgctg cgtaggtacg ccgccgaggg acctgaggga    9600
gtccatatcc accggatccg aaaacctttc gaggaaggcg tctaaccagt cgcagtcgca    9660
aggtaggctg agcaccgtgg cgggcggcgg ggggtggggg gagtgtctgg cggaggtgct    9720
gctgatgatg taattgaagt aggcggactt gacacggcgg atggtcgaca ggagcaccat    9780
gtccttgggt ccggcctgct ggatgcgag gcggtcggct atgccccagg cttcgttctg    9840
gcatcggcgc aggtccttgt agtagtcttg catgagcctt tccaccggca cctcttctcc    9900
ttcctcttct gcttcttcca tgtctgcttc ggccctgggg cggcgccgcg cccccctgcc    9960
ccccatgcgc gtgaccccga acccctgag cggttggagc agggccaggt cggcgacgac    10020
gcgctcggcc aggatggcct gctgcacctg cgtgagggtg gtttggaagt catccaagtc    10080
cacgaagcgg tggtaggcgc ccgtgttgat ggtgtaggtg cagttggcca tgacggacca    10140
gttgacggtc tggtggcccg gttgcgacat ctcggtgtac ctgagtcgcg agtaggcgcg    10200
ggagtcgaag acgtagtcgt tgcaagtccg caccaggtac tggtagccca ccaggaagtg    10260
cggcggcggc tggcggtaga ggggccagcg cagggtggcg ggggctccgg gggccaggtc    10320
ttccagcatg aggcggtggt aggcgtagat gtacctggac atccaggtga tacccgcggc    10380
ggtggtggag gcgcgcggga agtcgcgcac ccggttccag atgttgcgca ggggcagaaa    10440
gtgctccatg gtaggcgtgc tctgtccagt cagacgcgcg cagtcgttga tactctagac    10500
cagggaaaac gaaagccggt cagcgggcac tcttccgtgg tctggtgaat agatcgcaag    10560
ggtatcatgg cggagggcct cggttcgagc ccgggtccg ggccgacgg tccgccatga    10620
tccacgcggt taccgcccgc gtgtcgaacc caggtgtgcg acgtcagaca acggtggagt    10680
gttcctttg gcgttttcct ggccgggcgc cggcgccgcg taagagacta agccgcgaaa    10740
gcgaaagcag taagtggctc gctccccgta gccggaggga tccttgctaa gggttgcgtt    10800
gcggcgaacc ccggttcgaa tcccgtactc gggccggccg gacccgcggc taaggtgttg    10860
gattggcctc cccctcgtat aaagacccg cttgcggatt gactccggac acggggacga    10920
gccccttta ttttgcttt cccagatgc atccggtgct gcggcagatg cgccccccgc    10980
```

```
cccagcagca gcaacaacac cagcaagagc ggcagcaaca gcagcgggag tcatgcaggg    11040 cccccctcacc caccctcggc gggccggcca cctcggcgtc cgcggccgtg tctggcgcct    11100
gcggcggcgg cgggggggccg gctgacgacc ccgaggagcc cccgcggcgc agggccagac    11160
actacctgga cctggaggag ggcgagggcc tggcgcggct gggggcgccg tctcccgagc    11220
gccacccgcg ggtgcagctg aagcgcgact cgcgcgaggc gtacgtgcct cggcagaacc    11280
tgttcaggga ccgcgcgggc gaggagcccg aggagatgcg ggacaggagg ttcagcgcag    11340
ggcgggagct gcggcagggg ctgaaccgcg agcggctgct gcgcgaggag gactttgagc    11400
ccgacgcgcg gacggggatc agcccgcgc gcgcgcacgt ggcggccgcc gacctggtga    11460
cggcgtacga gcagacggtg aaccaggaga tcaacttcca aaagagtttc aacaaccacg    11520
tgcgcacgct ggtggcgcgc gaggaggtga ccatcgggct gatgcacctg tgggactttg    11580
taagcgcgct ggtgcagaac cccaacagca agcctctgac ggcgcagctg ttcctgatag    11640
tgcagcacag cagggacaac gaggcgttta gggacgcgct gctgaacatc accgagcccg    11700
agggtcggtg gctgctggac ctgattaaca tcctgcagag catagtggtg caggagcgca    11760
gcctgagcct ggccgacaag gtggcggcca tcaactactc gatgctgagc ctgggcaagt    11820
tttacgcgcg caagatctac cagacgccgt acgtgcccat agacaaggag gtgaagatcg    11880
acggttttta catgcgcatg gcgctgaagg tgctcaccct gagcgacgac ctgggcgtgt    11940
accgcaacga gcgcatccac aaggccgtga gcgtgagccg gcggcgcgag ctgagcgacc    12000
gcgagctgat gcacagcctg cagcgggcgc tggcgggcgc cggcagcggc gacagggagg    12060
cggagtccta cttcgatgcg ggggcggacc tgcgctgggc gcccagccgg cgggccctgg    12120
aggccgcggg ggtccgcgag gactatgacg aggacggcga ggaggatgag gagtacgagc    12180
tagaggaggg cgagtacctg gactaaaccg cgggtggtgt ttccggtaga tgcaagaccc    12240
gaacgtggtg gacccggcgc tgcgggcggc tctgcagagc cagccgtccg gccttaactc    12300
ctcagacgac tggcgacagg tcatggaccg catcatgtcg ctgacggcgc gtaacccgga    12360
cgcgttccgg cagcagccgc aggccaacag gctctccgcc atcctggagg cggtggtgcc    12420
tgcgcgctcg aaccccacgc acgagaaggt gctggccata gtgaacgcgc tggccgagaa    12480
cagggccatc cgcccggacg aggccgggct ggtgtacgac gcgctgctgc agcgcgtggc    12540
ccgctacaac agcggcaacg tgcagaccaa cctggaccgg ctggtggggg acgtgcgcga    12600
ggcggtggcg cagcgcgagc gcgcggatcg gcagggcaac ctgggctcca tggtggcgct    12660
gaatgccttc ctgagcacgc agccggccaa cgtgccgcgg gggcaggaag actacaccaa    12720
ctttgtgagc gcgctgcggc tgatggtgac cgagaccccc cagagcgagg tgtaccagtc    12780
gggcccggac tacttcttcc agaccagcag acagggcctg cagacggtga acctgagcca    12840
ggctttcaag aacctgcggg ggctgtgggg cgtgaaggcg cccaccggcg accgggcgac    12900
ggtgtccagc ctgctgacgc ccaactcgcg cctgctgctg ctgctgatcg cgccgttcac    12960
ggacagcggc agcgtgtccc gggacaccta cctggggcac ctgctgaccc tgtaccgcga    13020
ggccatcggg caggcgcagg tggacagcgca caccttccag gagatcacca gcgtgagccg    13080
cgcgctgggg caggaggaca cgagcagcct ggaggcgact ctgaactacc tgctgaccaa    13140
ccggcggcag aagattccct cgctgcacag cctgacctcc gaggaggagc gcatcttgcg    13200
ctacgtgcag cagagcgtga gcctgaacct gatgcgcgac ggggtgacgc ccagcgtggc    13260
gctggacatg accgcgcgca acatggaacc gggcatgtac gccgcgcacc ggccttacat    13320
```

-continued

```
caaccgcctg atggactacc tgcatcgcgc ggcggccgtg aaccccgagt actttaccaa   13380
cgccatcctg aacccgcact ggctcccgcc gcccgggttc tacagcgggg gcttcgaggt   13440
cccggagacc aacgatggct tcctgtggga cgacatggac gacagcgtgt tctccccgcg   13500
gccgcaggcg ctggcggaag cgtccctgct gcgtcccaag aaggaggagg aggaggaggc   13560
gagtcgccgc cgcggcagca gcggcgtggc ttctctgtcc gagctggggg cggcagccgc   13620
cgcgcgcccc gggtccctgg gcggcagccc ctttccgagc ctggtggggt ctctgcacag   13680
cgagcgcacc acccgccctc ggctgctggg cgaggacgag tacctgaata actccctgct   13740
gcagccggtg cgggagaaaa acctgcctcc cgccttcccc aacaacggga tagagagcct   13800
ggtggacaag atgagcagat ggaagaccta tgcgcaggag cacagggacg cgcctgcgct   13860
ccggccgccc acgcggcgcc agcgccacga ccggcagcgg gggctggtgt gggatgacga   13920
ggactccgcg gacgatagca gcgtgctgga cctgggaggg agcggcaacc cgttcgcgca   13980
cctgcgcccc cgcctgggga ggatgtttta aaaaaaaaa aaaaaagcaa gaagcatgat   14040
gcaaaaatta aataaaactc accaaggcca tggcgaccga gcgttggttt cttgtgttcc   14100
cttcagtatg cggcgcgcgg cgatgtacca ggagggacct cctccctctt acgagagcgt   14160
ggtgggcgcg gcgcggcgg cgccctcttc tccctttgcg tcgcagctgc tggagccgcc   14220
gtacgtgcct ccgcgctacc tgcggcctac ggggggaga aacagcatcc gttactcgga   14280
gctggcgccc ctgttcgaca ccacccgggt gtacctggtg acaacaagt cggcggacgt   14340
ggcctccctg aactaccaga acgaccacag caatttttg accacggtca tccagaacaa   14400
tgactacagc ccgagcgagg ccagcaccca gaccatcaat ctggatgacc ggtcgcactg   14460
gggcggcgac ctgaaaacca tcctgcacac caacatgccc aacgtgaacg agttcatgtt   14520
caccaataag ttcaaggcgc gggtgatggt gtcgcgctcg cacaccaagg aagaccgggt   14580
ggagctgaag tacgagtggg tggagttcga gctgccagag ggcaactact ccgagaccat   14640
gaccattgac ctgatgaaca cgcgatcgt ggagcactat ctgaaagtgg gcaggcagaa   14700
cggggtcctg gagagcgaca tcggggtcaa gttcgacacc aggaacttcc gcctggggct   14760
ggaccccgtg accgggctgg ttatgcccgg ggtgtacacc aacgaggcct tccatcccga   14820
catcatcctg ctgcccggct gcggggtgga cttcacttac agccgcctga gcaacctcct   14880
gggcatccgc aagcggcagc ccttccagga gggcttcagg atcacctacg aggacctgga   14940
ggggggcaac atccccgcgc tcctcgatgt ggaggcctac caggatagct tgaaggaaaa   15000
tgaggcggga caggaggata ccgccccgc cgcctccgcc gccgcgagc agggcgagga   15060
tgctgctgac accgcggccg cggacggggc agaggccgac cccgctatgg tggtggaggc   15120
tcccgagcag gaggaggaca tgaatgacag tgccgtgcgc ggagacacct tcgtcacccg   15180
ggggggaggaa aagcaagcgg aggccgaggc cgcggccgag gaaaagcaac tggcggcagc   15240
agcggcggcg gcggcgttgg ccggcggcga ggctgagtct gaggggacca agcccgccaa   15300
ggagcccgtg attaagcccc tgaccgaaga tagcaagaag cgcagttaca acctgctcaa   15360
ggacagcacc aacaccgcgt accgcagctg gtacctggcc tacaactacg cgacccgtc   15420
gacggggtg cgctcctgga ccctgctgtg cacgccggac gtgacctgcg gctcggagca   15480
ggtgtactgg tcgctgcccg acatgatgca agaccccgtg accttccgct ccacgcggca   15540
ggtcagcaac ttcccggtgg tgggcgccga gctgctgccc gtgcactcca agagcttcta   15600
caacgaccag gccgtctact cccagctcat ccgccagttc acctctctga ccacgtgtt   15660
caatcgcttt cctgagaacc agattctggc gcgcccgccc gccccacca tcaccaccgt   15720
```

```
cagtgaaaac gttcctgctc tcacagatca cgggacgcta ccgctgcgca acagcatcgg   15780
aggagtccag cgagtgaccg ttactgacgc cagacgccgc acctgcccct acgtttacaa   15840
ggccttgggc atagtctcgc cgcgcgtcct ttccagccgc acttttgag caacaccacc    15900 atcatgtcca tcctgatctc acccagcaat aactccggct ggggactgct gcgcgcgccc   15960
agcaagatgt tcggaggggc gaggaagcgt tccgagcagc accccgtgcg cgtgcgcggg   16020
cacttccgcg cccctgggg agcgcacaaa cgcggccgcg cggggcgcac caccgtggac     16080
gacgccatcg actcggtggt ggagcaggcg cgcaactaca ggcccgcggt ctctaccgtg   16140
gacgcggcca tccagaccgt ggtgcggggc gcgcggcggt acgccaagct gaagagccgc   16200
cggaagcgcg tggcccgccg ccaccgccgc cgacccgggg ccgccgccaa acgcgccgcc   16260
gcggccctgc ttcgccgggc caagcgcacg ggccgccgcg ccgccatgag ggccgcgcgc    16320
cgcttggccg ccggcatcac cgccgccacc atggccccc gtacccgaag acgcgcggcc    16380
gccgccgccg ccgccgccat cagtgacatg ccagcaggc gccggggcaa cgtgtactgg    16440
gtgcgcgact cggtgaccgg cacgcgcgtg cccgtgcgct tccgccccc gcggacttga    16500 gatgatgtga aaaacaaca ctgagtctcc tgctgttgtg tgtatcccag cggcggcggc    16560
gcgcgcagcg tcatgtccaa gcgcaaaatc aaagaagaga tgctccaggt cgtcgcgccg   16620
gagatctatg gccccccgaa gaaggaagag caggattcga agcccccgcaa gataaagcgg  16680 gtcaaaaaga aaagaaaga tgatgacgat gccgatgggg aggtggagtt cctgcgcgcc   16740
acggcgccca ggcgcccggt gcagtggaag ggccggcgcg taaagcgcgt cctgcgcccc   16800
ggcaccgcgg tggtcttcac gcccggcgag cgctccaccc ggactttcaa gcgcgtctat   16860
gacgaggtgt acggcgacga agacctgctg gagcaggcca acgagcgctt cggagagttt   16920
gcttacggga agcgtcagcg ggcgctgggg aaggaggacc tgctggcgct gccgctggac   16980
cagggcaacc ccaccccag tctgaagccc gtgaccctgc agcaggtgct gccgagcagc    17040
gcaccctccg aggcgaagcg gggtctgaag cgcgagggcg gcgacctggc gcccaccgtg   17100
cagctcatgg tgcccaagcg gcagaggctg gaggatgtgc tggagaaaat gaaagtagac   17160
cccggtctgc agccggacat cagggtccgc cccatcaagc aggtggcgcc gggcctcggc   17220
gtgcagaccg tggacgtggt catccccacc ggcaactccc ccgccgccgc caccactacc   17280
gctgcctcca cggacatgga gacacagacc gatcccgccg cagccgcagc cgcagccgcc   17340
gccgcgacct cctcggcgga ggtgcagacg gaccctggc tgccgccggc gatgtcagct   17400 ccccgcgcg gtcgcgggcg caggaagtac ggcgccgcca acgcgctcct gcccgagtac    17460
gccttgcatc cttccatcgc gcccacccc ggctaccgag gctataccta ccgcccgcga    17520
agagccaagg gttccacccg ccgtcccgc gacgcgccg ccgccaccac ccgccgccgc     17580
cgccgcagac gccagcccgc actggctcca gtctccgtga ggaaagtggc gcgcgacgga   17640
cacaccctgg tgctgcccag ggcgcgctac cacccccagca tcgtttaaaa gcctgttgtg   17700
gttcttgcag atatggccct cacttgccgc ctccgtttcc cggtgccggg ataccgagga   17760
ggaagatcgc gccgcaggag gggtctggcg ggccgcggcc tgagcggagg cagccgccgc   17820
gcgcaccggc ggcgacgcgc caccagccga cgcatgcgcg gcggggtgct gccccctgtta  17880 atcccctga tcgccgcggc gatcggcgcc gtgcccggga tcgcctccgt ggccttgcaa    17940
gcgtcccaga ggcattgaca gacttgcaaa cttgcaaata tggaaaaaaa aacccccaata  18000 aaaaagtcta gactctcacg ctcgcttggt cctgtgacta ttttgtagaa tggaagacat    18060
```

```
caactttgcg tcgctggccc cgcgtcacgg ctcgcgcccg ttcctgggac actggaacga   18120
tatcggcacc agcaacatga gcggtggcgc cttcagttgg ggctctctgt ggagcggcat   18180
taaaagtatc gggtctgccg ttaaaaatta cggctcccgg gcctggaaca gcagcacggg   18240
ccagatgttg agagacaagt tgaaagagca gaacttccag cagaaggtgg tggagggcct   18300
ggcctccggc atcaacgggg tggtggacct ggccaaccag gccgtgcaga ataagatcaa   18360
cagcagactg gaccccggc cgccggtgga ggaggtgccg ccggcgctgg agacggtgtc   18420
ccccgatggg cgtggcgaga agcgcccgcg gcccgatagg aagagaccca ctctggtcac   18480
gcagaccgat gagccgcccc cgtatgagga ggccctgaag caaggtctgc ccaccacgcg   18540
gcccatcgcg cccatggcca ccggggtggt gggccgccac accccgcca cgctggactt   18600
gcctccgccc gccgatgtgc cgcagcagca gaaggcggca cagccgggcc cgcccgcgac   18660
cgcctcccgt tcctccgccg gtcctctgcg ccgcgcggcc agcggccccc gcgggggggt   18720
cgcgaggcac ggcaactggc agagcacgct gaacagcatc gtgggtctgg gggtgcggtc   18780
cgtgaagcgc cgccgatgct actgaatagc ttagctaacg tgttgtatgt gtgtatgcgc   18840
cctatgtcgc cgccagagga gctgctgagt cgccgccgtt cgcgcgccca ccaccaccgc   18900
cactccgccc ctcaagatgg cgaccccatc gatgatgccg cagtggtcgt acatgcacat   18960
ctcgggccag gacgcctcgg agtacctgag ccccgggctg gtgcagttcg cccgcgccac   19020
cgagagctac ttcagcctga gtaacaagtt taggaacccc acggtggcgc ccacgcacga   19080
tgtgaccacc gaccggtctc agcgcctgac gctgcggttc attcccgtgg accgcgagga   19140
caccgcgtac tcgtacaagg cgcggttcac cctggccgtg ggcgacaacc gcgtgctgga   19200
catggcctcc acctactttg acatccgcgg ggtgctggac cggggtccca ctttcaagcc   19260
ctactctggc accgcctaca actccctggc ccccaagggc gctcccaact cctgcgagtg   19320
ggagcaagag gaaactcagg cagttgaaga agcagcagaa gaggaagaag aagatgctga   19380
cggtcaagct gaggaagagc aagcagctac caaaaagact catgtatatg ctcaggctcc   19440
cctttctggc gaaaaaatta gtaaagatgg tctgcaaata ggaacggacg ctacagctac   19500
agaacaaaaa cctatttatg cagaccctac attccagccc gaaccccaaa tcggggagtc   19560
ccagtggaat gaggcagatg ctacagtcgc cggcggtaga gtgctaaaga aatctactcc   19620
catgaaacca tgctatggtt cctatgcaag acccacaaat gctaatggag gtcagggtgt   19680
actaacggca aatgcccagg acagctaga atctcaggtt gaaatgcaat tcttttcaac   19740
ttctgaaaac gcccgtaacg aggctaacaa cattcagccc aaattggtgc tgtatagtga   19800
ggatgtgcac atggagaccc cggatacgca cctttcttac aagcccgcaa aaagcgatga   19860
caattcaaaa atcatgctgg gtcagcagtc catgcccaac agacctaatt acatcggctt   19920
cagagacaac tttatcggcc tcatgtatta caatagcact ggcaacatgg gagtgcttgc   19980
aggtcaggcc tctcagttga atgcagtggt ggacttgcaa gacagaaaca cagaactgtc   20040
ctaccagctc ttgcttgatt ccatgggtga cagaaccaga tacttttcca tgtggaatca   20100
ggcagtggac agttatgacc cagatgttag aattattgaa atcatggaa ctgaagacga   20160
gctccccaac tattgtttcc ctctgggtgg catagggta actgacactt accaggctgt   20220
taaaaccaac aatggcaata cgggggcca ggtgacttgg acaaagatg aaacttttgc   20280
agatcgcaat gaaataggg tgggaaacaa tttcgctatg gagatcaacc tcagtgccaa   20340
cctgtgggaga aacttcctgt actccaacgt ggcgctgtac ctaccagaca agcttaagta   20400
caaccctcc aatgtggaca tctctgacaa ccccaacacc tacgattaca tgaacaagcg   20460
```

```
agtggtggcc ccggggctgg tggactgcta catcaacctg ggcgcgcgct ggtcgctgga   20520
ctacatggac aacgtcaacc ccttcaacca ccaccgcaat gcgggcctgc gctaccgctc   20580
catgctcctg ggcaacgggc gctacgtgcc cttccacatc caggtgcccc agaagttctt   20640
tgccatcaag aacctcctcc tcctgccggg ctcctacacc tacgagtgga acttcaggaa   20700
ggatgtcaac atggtcctcc agagctctct gggtaacgat ctcagggtgg acggggccag   20760
catcaagttc gagagcatct gcctctacgc caccttcttc cccatggccc acaacacggc   20820
ctccacgctc gaggccatgc tcaggaacga caccaacgac cagtccttca atgactacct   20880
ctccgccgcc aacatgctct accccatacc cgccaacgcc accaacgtcc ccatctccat   20940
cccctcgcgc aactgggcgg ccttccgcgg ctgggccttc acccgcctca agaccaagga   21000 gacccctcc ctgggctcgg gattcgaccc ctactacacc tactcgggct ccattcccta   21060
cctggacggc accttctacc tcaaccacac tttcaagaag gtctcggtca ccttcgactc   21120
ctcggtcagc tggccgggca acgaccgtct gctcaccccc aacgagttcg agatcaagcg   21180
ctcggtcgac ggggagggct acaacgtggc ccagtgcaac atgaccaagg actggttcct   21240
ggtccagatg ctggccaact acaacatcgg ctaccagggc ttctacatcc cagagagcta   21300
caaggacagg atgtactcct tcttcaggaa cttccagccc atgagccggc aggtggtgga   21360
ccagaccaag tacaaggact accaggaggt gggcatcatc caccagcaca caactcggg   21420 cttcgtgggc tacctcgccc ccaccatgcg cgagggacag gcctacccg ccaacttccc   21480 ctatccgctc ataggcaaga ccgcggtcga cagcatcacc cagaaaaagt tcctctgcga   21540 ccgcacctc tggcgcatcc ccttctccag caacttcatg tccatgggtg cgctctcgga   21600
cctgggccag aacttgctct acgccaactc cgcccacgcc ctcgacatga ccttcgaggt   21660
cgaccccatg gacgagccca cccttctcta tgttctgttc gaagtctttg acgtggtccg   21720
ggtccaccag ccgcaccgcg gcgtcatcga gaccgtgtac ctgcgtacgc ccttctcggc   21780
cggcaacgcc accacctaaa gaagcaagcc gcagtcatcg ccgcctgcat gccgtcgggt   21840
tccaccgagc aagagctcag ggccatcgtc agagacctgg gatgcgggcc ctattttttg   21900
ggcaccttcg acaagcgctt ccctggcttt gtctccccac acaagctggc ctgcgccatc   21960
gtcaacacgg ccggccgcga gaccgggggc gtgcactggc tggccttcgc ctggaacccg   22020
cgctccaaaa catgcttcct cttttgacccc ttcggcttt cggaccagcg gctcaagcaa   22080
atctacgagt cgagtacga gggcttgctg cgtcgcagcg ccatcgcctc ctcgcccgac   22140
cgctgcgtca cccttcgaaaa gtccacccag accgtgcagg ggcccgactc ggccgcctgc   22200
ggtctcttct gctgcatgtt tctgcacgcc tttgtgcact ggcctcagag tcccatggac   22260 cgcaaccca ccatgaactt gctgacgggg gtgcccaact ccatgctcca gagccccag    22320 gtcgagccca ccctgcgccg caaccaggag cagctctaca gcttcctgga gcgccactcg   22380
ccttacttcc gccgccacag cgcacagatc aggagggcca cctccttctg ccacttgcaa   22440
gagatgcaag aagggtaata acgatgtaca cacttttttt ctcaataaat ggcatctttt   22500
tatttataca agctctctgg ggtattcatt tcccaccacc acccgccgtt gtcgccatct   22560 ggctctatt agaaatcgaa agggttctgc cgggagtcgc cgtgcgccac gggcagggac   22620
acgttgcgat actggtagcg ggtgccccac ttgaactcgg gcaccaccag gcgaggcagc   22680
tcggggaagt tttcgctcca caggctgcgg gtcagcacca gcgcgttcat caggtcgggc   22740
gccgagatct tgaagtcgca gttggggccg ccgccctgcg cgcgcgagtt gcggtacacc   22800
```

```
gggttgcagc actggaacac caacagcgcc gggtgcttca cgctggccag cacgctgcgg   22860
tcggagatca gctcggcgtc caggtcctcc gcgttgctca gcgcgaacgg ggtcatcttg   22920
ggcacttgcc gccccaggaa gggcgcgtgc cccggtttcg agttgcagtc gcagcgcagc   22980
gggatcagca ggtgcccgtg cccggactcg gcgttggggt acagcgcgcg catgaaggcc   23040
tgcatctggc ggaaggccat ctgggccttg gcgccctccg agaagaacat gccgcaggac   23100
ttgcccgaga actggtttgc ggggcagctg gcgtcgtgca ggcagcagcg cgcgtcggtg   23160
ttggcgatct gcaccacgtt gcgccccac cggttcttca cgatcttggc cttggacgat   23220
tgctccttca gcgcgcgctg cccgttctcg ctggtcacat ccatctcgat cacatgttcc   23280
ttgttcacca tgctgctgcc gtgcagacac ttcagctcgc cctccgtctc ggtgcagcgg   23340
tgctgccaca gcgcgcagcc cgtgggctcg aaagacttgt aggtcacctc cgcgaaggac   23400
tgcaggtacc cctgcaaaaa gcggcccatc atggtcacga aggtcttgtt gctgctgaag   23460
gtcagctgca gcccgcggtg ctcctcgttc agccaggtct tgcacacggc cgccagcgcc   23520
tccacctggt cgggcagcat cttgaagttc accttcagct cattctccac gtggtacttg   23580
tccatcagcg tgcgcgccgc ctccatgccc ttctcccagg ccgacaccag cggcaggctc   23640
acggggttct tcaccatcac cgtggccgcc gcctccgccg cgctttcgct ttccgccccg   23700
ctgttctctt cctcttcctc ctcttcctcg ccgccgccca ctcgcagccc ccgcaccacg   23760
gggtcgtctt cctgcaggcg ctgcaccttg cgcttgccgt tgcgccctg cttgatgcgc   23820 acgggcgggt tgctgaagcc caccatcacc agcgcggcct cttcttgctc gtcctcgctg   23880
tccagaatga cctccgggga gggggggttg gtcatcctca gtaccgaggc acgcttcttt   23940
ttcttcctgg gggcgttcgc cagctccgcg gctgcggccg ctgccgaggt cgaaggccga   24000
gggctgggcg tgcgcggcac cagcgcgtcc tgcgagccgt cctcgtcctc ctcggactcg   24060
agacggaggc gggcccgctt cttcgggggc gcgcggggcg gcggaggcgg cggcggcgac   24120
ggagacgggg acgagacatc gtccaggggtg ggtggacggc gggccgcgcc gcgtccgcgc   24180
tcgggggtgg tctcgcgctg gtcctcttcc cgactggcca tctcccactg ctccttctcc   24240
tataggcaga aagagatcat ggagtctctc atgcgagtcg agaaggagga ggacagccta   24300 accgcccct ctgagccctc caccaccgcc gccaccaccg ccaatgccgc cgcggacgac   24360
gcgcccaccg agaccaccgc cagtaccacc ctccccagcg acgcaccccc gctcgagaat   24420
gaagtgctga tcgagcagga cccgggtttt gtgagcggag aggaggatga ggtggatgag   24480
aaggagaagg aggaggtcgc cgcctcagtg ccaaaagagg ataaaaagca agaccaggac   24540
gacgcagata aggatgagac agcagtcggg cggggaacg gaagccatga tgctgatgac   24600
ggctacctag acgtgggaga cgacgtgctg cttaagcacc tgcaccgcca gtgcgtcatc   24660
gtctgcgacg cgctgcagga gcgctgcgaa gtgcccctgg acgtggcgga ggtcagccgc   24720
gcctacgagc ggcacctctt cgccgcgcac gtgcccccca gcgccgggga aacggcacc   24780 tgcgagccca cccgcgtct caacttctac ccggtcttcg cggtacccga ggtgctggcc   24840
acctaccaca tcttttttcca aaactgcaag atccccctct cctgccgcgc caaccgcacc   24900
cgcgccgaca aaaccctgac cctgcggcag ggcgcccaca tacctgatat cgcctctctg   24960
gaggaagtgc ccaagatctt cgagggtctc ggtcgcgacg agaaacgggc ggcgaacgct   25020
ctgcacggag acagcgaaaa cgagagtcac tcggggggtgc tggtggagct cgagggcgac   25080
aacgcgcgcc tggccgtact caagcgcagc atagaggtca cccactttgc ctacccggcg   25140
ctcaacctgc cccccaaggt catgagtgtg gtcatgggcg agctcatcat gcgccgcgcc   25200
```

```
cagcccctgg ccgcggatgc aaacttgcaa gagtcctccg aggaaggcct gcccgcggtc   25260
agcgacgagc agctggcgcg ctggctggag acccgcgacc ccgcgcagct ggaggagcgg   25320
cgcaagctca tgatggccgc ggtgctggtc accgtggagc tcgagtgtct gcagcgcttc   25380
ttcgcggacc ccgagatgca gcgcaagctc gaggagaccc tgcactacac cttccgccag   25440
ggctacgtgc gccaggcctg caagatctcc aacgtggagc tctgcaacct ggtctcctac   25500
ctgggcatcc tgcacgagaa ccgcctcggg cagaacgtcc tgcactccac cctcaaaggg   25560
gaggcgcgcc gcgactacat ccgcgactgc gcctacctct tcctctgcta cacctggcag   25620
acggccatgg gggtctggca gcagtgcctg gaggagcgca acctcaagga gctggaaaag   25680
ctcctcaagc gcaccctcag ggacctctgg acgggcttca acgagcgctc ggtggccgcc   25740
gcgctggcgg acatcatctt tcccgagcgc ctgctcaaga ccctgcagca gggcctgccc   25800
gacttcacca gccagagcat gctgcagaac ttcaggactt tcatcctgga gcgctcgggc   25860
atcctgccgg ccacttgctg cgcgctgccc agcgacttcg tgcccatcaa gtacaggag   25920
tgcccgccgc cgctctgggg ccactgctac ctcttccagc tggccaacta cctcgcctac   25980
cactcggacc tcatggaaga cgtgagcggc gagggcctgc tcgagtgcca ctgccgctgc   26040
aacctctgca cgccccaccg ctctctagtc tgcaacccgc agctgctcag cgagagtcag   26100
attatcggta ccttcgagct gcagggtccc tcgcctgacg agaagtccgc ggctccaggg   26160
ctgaaactca ctccggggct gtggacttcc gcctacctac gcaaatttgt acctgaggac   26220
taccacgccc acgagatcag gttctacgaa gaccaatccc gccgcccaa ggcggagctc   26280
accgcctgcg tcatcaccca ggggcacatc ctgggccaat gcaagccat caacaaagcc   26340
cgccgagagt tcttgctgaa aaagggtcgg ggggtgtacc tggacccca gtccggcgag   26400
gagctaaacc cgctaccccc gccgccgccc cagcagcggg accttgcttc ccaggatggc   26460
acccagaaag aagcagcagc cgccgccgcc gccgcagcca tacatgcttc tggaggaaga   26520
ggaggaggac tgggacagtc aggcagagga ggtttcggac gaggagcagg aggagatgat   26580
ggaagactgg gaggaggaca gcagcctaga cgaggaagct tcagaggccg aagaggtggc   26640
agacgcaaca ccatcgccct cggtcgcagc ccctcgccg gggcccctga atcctccga   26700
acccagcacc agcgctataa cctccgctcc tccggcgccg cgccacccg cccgcagacc   26760
caaccgtaga tgggacacca caggaaccgg ggtcggtaag tccaagtgcc cgccgccgcc   26820
accgcagcag cagcagcagc agcgccaggg ctaccgctcg tggcgcgggc acaagaacgc   26880
catagtcgcc tgcttgcaag actgcggggg caacatctct ttcgcccgcc gcttcctgct   26940
attccaccac ggggtcgcct ttccccgcaa tgtcctgcat tactaccgtc atctctacag   27000
cccctactgc agcggcgacc cagaggcgg agcggcagcc acagcggcga ccaccaccta   27060
ggaagatatc ctccgcgggc aagacagcgg cagcagcggc caggagaccc gcggcagcag   27120
cggcgggagc ggtgggcgca ctgcgcctct cgcccaacga accctctcg acccgggagc   27180
tcagacacag gatcttcccc actttgtatg ccatcttcca acagagcaga ggccaggagc   27240
aggagctgaa aataaaaaac agatctctgc gctccctcac ccgcagctgt ctgtatcaca   27300
aaagcgaaga tcagcttcgg cgcacgctgg aggacgcgga ggcactcttc agcaaatact   27360
gcgcgctcac tcttaaagac tagctccgcg cccttctcga atttaggcgg gagaaaacta   27420
cgtcatcgcc ggccgccgcc cagcccgccc agcgagatg agcaaagaga ttcccacgcc   27480
atacatgtgg agctaccagc cgcagatggg actcgcggcg ggagcggccc aggactactc   27540
```

```
cacccgcatg aactacatga gcgcgggacc ccacatgatc tcacaggtca acgggatccg   27600
cgcccagcga aaccaaatac tgctggaaca ggcggccatc accgccacgc cccgccataa   27660
tctcaacccc cgaaattggc ccgccgccct cgtgtaccag gaaacccct ccgccaccac    27720 cgtactactt ccgcgtgacg cccaggccga agtccagatg actaactcag gggcgcagct   27780
cgcgggcggc tttcgtcacg gggcgcggcc gctccgacca ggtataagac acctgatgat   27840
cagaggccga ggtatccagc tcaacgacga gtcggtgagc tcttcgctcg gtctccgtcc   27900
ggacggaact ttccagctcg ccggatccgg ccgctcttcg ttcacgcccc gccaggcgta   27960
cctgactctg cagacctcgt cctcggagcc ccgctccggc ggcatcggaa ccctccagtt   28020
cgtggaggag ttcgtgccct cggtctactt caacccttc tcgggacctc ccggacgcta    28080
ccccgaccag ttcattccga actttgacgc ggtgaaggac tcggcggacg gctacgactg   28140
aatgtcaggt gtcgaggcag agcagcttcg cctgagacac ctcgagcact gccgccgcca   28200
caagtgcttc gcccgcggtt ctggtgagtt ctgctacttt cagctacccg aggagcatac   28260
cgaggggccg gcgcacggcg tccgcctgac cacccagggc gaggttacct gttccctcat   28320
ccggagtttt accctccgtc ccctgctagt ggagcgggag cggggtccct gtgtcctaac   28380
tatcgcctgc aactgcccta accctggatt acatcaagat ctttgctgtc atctctgtgc   28440
tgagtttaat aaacgctgag atcagaatct actgggctc ctgtcgccat cctgtgaacg     28500
ccaccgtctt cacccacccc gaccaggccc aggcgaacct cacctgcggt ctgcatcgga   28560
gggccaagaa gtacctcacc tggtacttca acggcacccc ctttgtggtt tacaacagct   28620
tcgacgggga cggagtctcc ctgaaagacc agctctccgg tctcagctac tccatccaca   28680
agaacaccac cctccaactc ttccctcct acctgccggg aacctacgag tgcgtcaccg    28740
gccgctgcac ccacctcacc cgcctgatcg taaaccagag cttccgggga acagataact   28800
ccctcttccc cagaacagga ggtgagctca ggaaactccc cggggaccag ggcggagacg   28860
taccttcgac ccttgtgggg ttaggatttt ttattaccgg gttgctggct cttttaatca   28920
aagtttcctt gagatttgtt ctttccttct acgtgtatga acacctcaac ctccaataac   28980
tctacccttt cttcggaatc aggtgacttc tctgaaatcg gcttggtgt gctgcttact    29040 ctgttgattt ttttccttat catactcagc ctttctgtgcc tcaggctcgc cgcctgctgc   29100
gcacacatct atatctactg ctggttgctc aagtgcaggg gtcgccaccc aagatgaaca   29160
ggtacatggt cctatcgatc ctaggcctgc tggccctggc ggcctgcagc gccgccaaaa   29220
aagagattac ctttgaggag cccgcttgca atgtaacttt caagcccgag ggtgaccaat   29280
gcaccaccct cgtcaaatgc gttaccaatc atgagaggct gcgcatcgac tacaaaaaca   29340
aaactggcca gtttgcggtc tatagtgtgt ttacgcccgg agacccctct aactactctg   29400
tcaccgtctt ccagggcgga cagtctaaga tattcaatta cactttccct ttttatgagt   29460
tatgcgatgc ggtcatgtac atgtcaaaac agtacaacct gtggcctccc tctcccagg    29520 cgtgtgtgga aaatactggg tcttactgct gtatggcttt cgcaatcact acgctcgctc   29580
taatctgcac ggtgctatac ataaaattca ggcagaggcg aatctttatc gatgaaaaga   29640
aaatgccttg atcgctaaca ccggctttct atctgcagaa tgaatgcaat cacctcccta   29700
ctaatcacca ccaccctcct tgcgattgcc catgggttga cacgaatcga agtgccagtg   29760
gggtccaatg tcaccatggt gggccccgcc ggcaattcca ccctcatgtg ggaaaaattt   29820
gtccgcaatc aatgggttca tttctgctct aaccgaatca gtatcaagcc cagagccatc   29880
tgcgatgggc aaaatctaac tctgatcaat gtgcaaatga tggatgctgg gtactattac   29940
```

```
gggcagcggg gagaaatcat taattactgg cgaccccaca aggactacat gctgcatgta   30000
gtcgaggcac ttcccactac cacccccact accacctctc ccaccaccac caccactact   30060
actactacta ctactactac tactactacc actaccgctg cccgccatac ccgcaaaagc   30120
accatgatta gcacaaagcc ccctcgtgct cactcccacg ccggcgggcc catcggtgcg   30180
acctcagaaa ccaccgagct ttgcttctgc caatgcacta acgccagcgc tcatgaactg   30240
ttcgacctgg agaatgagga tgtccagcag agctccgctt gcctgaccca ggaggctgtg   30300
gagcccgttg ccctgaagca gatcggtgat tcaataattg actcttcttc ttttgccact   30360
cccgaatacc ctcccgattc tactttccac atcacgggta ccaaagaccc taacctctct   30420
ttctacctga tgctgctgct ctgtatctct gtggtctctt ccgcgctgat gttactgggg   30480
atgttctgct gcctgatctg ccgcagaaag agaaaagctc gctctcaggg ccaaccactg   30540
atgcccttcc cctacccccc ggattttgca gataacaaga tatgagctcg ctgctgacac   30600
taaccgcttt actagcctgc gctctaaccc ttgtcgcttg cgactcgaga ttccacaatg   30660
tcacagctgt ggcaggagaa aatgttactt tcaactccac ggccgatacc cagtggtcgt   30720
ggagtggctc aggtagctac ttaactatct gcaatagctc cacttccccc ggcatatccc   30780
caaccaagta ccaatgcaat gccagcctgt tcaccctcat caacgcttcc accctggaca   30840
atggactcta tgtaggctat gtacccttg gtgggcaagg aaagacccac gcttacaacc   30900
tggaagttcg ccagcccaga accactaccc aagcttctcc caccaccacc accaccacca   30960
ccatcaccag cagcagcagc agcagcagcc acagcagcag cagcagatta ttgactttgg   31020
ttttggccag ctcatctgcc gctacccagg ccatctacag ctctgtgccc gaaaccactc   31080
agatccaccg cccagaaacg accacgcca ccacccta ca cacctccagc gatcagatgc   31140
cgaccaacat caccccttg gctcttcaaa tgggacttac aagccccact ccaaaaccag   31200
tggatgcggc cgaggtctcc gccctcgtca atgactgggc ggggctggga atgtggtggt   31260
tcgccatagg catgatggcg ctctgcctgc ttctgctctg gctcatctgc tgcctccacc   31320
gcaggcgagc cagaccccc atctatagac ccatcattgt cctgaacccc gataatgatg   31380
ggatccatag attggatggc ctgaaaaacc tactttttc tttacagta tgataaattg   31440 agacatgcct cgcattttct tgtacatgtt ccttctccca cctttctgg ggtgttctac   31500 gctggccgct gtgtctcacc tggaggtaga ctgcctctca cccttcactg tctacctgct   31560
ttacggattg gtcaccctca ctctcatctg cagcctaatc acagtaatca tcgccttcat   31620
ccagtgcatt gattacatct gtgtgcgcct cgcatacttc agacaccacc gcagtaccg   31680 agacaggaac attgcccaac ttctaagact gctctaatca tgcataagac tgtgatctgc   31740
cttctgatcc tctgcatcct gcccaccctc acctcctgcc agtacaccac aaaatctccg   31800
cgcaaaagac atgcctcctg ccgcttcacc caactgtgga atatacccaa atgctacaac   31860
gaaaagagcg agctctccga agcttggctg tatgggtca tctgtgtctt agttttctgc   31920
agcactgtct ttgccctcat aatctacccc tactttgatt tgggatggaa cgcgatcgat   31980
gccatgaatt acccccactt tcccgcaccc gagataattc cactgcgaca agttgtaccc   32040
gttgtcgtta atcaacgccc cccatcccct acgcccactg aaatcagcta ctttaaccta   32100
acaggcggag atgactgacg ccctagatct agaaatggac ggcatcagta ccgagcagcg   32160
tctcctagag aggcgcaggc aggcggctga gcaagagcgc tcaatcagg agctccgaga   32220 tctcgttaac ctgcaccagt gcaaaagagg catcttttgt ctggtaaagc aggccaaagt   32280
```

-continued

```
cacctacgag aagaccggca acagccaccg cctcagttac aaattgccca cccagcgcca   32340
gaagctggtg ctcatggtgg gtgagaatcc catcaccgtc acccagcact cggtagagac   32400
cgaggggtgt ctgcactccc cctgtcgggg tccagaagac ctctgcaccc tggtaaagac   32460
cctgtgcggt ctcagagatt tagtccccct taactaatca aacactggaa tcaataaaaa   32520
gaatcactta cttaaaatca gacagcaggt ctctgtccag tttattcagc agcacctcct   32580
tccctcctc ccaactctgg tactccaaac gccttctggc ggcaaacttc ctccacaccc   32640
tgaagggaat gtcagattct tgctcctgtc cctccgcacc cactatcttc atgttgttgc   32700
agatgaagcg caccaaaacg tctgacgaga gcttcaaccc cgtgtacccc tatgacacgg   32760
aaagcggccc tccctccgtc cctttcctca cccctccctt cgtgtctccc gatggattcc   32820
aagaaagtcc ccccggggtc ctgtctctga acctggccga gccctggtc acttcccacg    32880
gcatgctcgc cctgaaaatg ggaagtggcc tctccctgga cgacgctggc aacctcacct   32940
ctcaagatat caccaccgct agccctcccc tcaaaaaaac caagaccaac ctcagcctag   33000
aaacctcatc cccctaact gtgagcacct caggcgccct caccgtagca gccgccgctc    33060
ccctggcggt ggccggcacc tccctcacca tgcaatcaga ggcccccctg acagtacagg   33120
atgcaaaact caccctggcc accaaaggcc ccctgaccgt gtctgaaggc aaactggcct   33180
tgcaaacatc ggccccgctg acggccgctg acagcagcac cctcacagtc agtgccacac   33240
caccccttag cacaagcaat ggcagcttgg gtattgacat gcaagccccc atttacacca   33300
ccaatggaaa actaggactt aactttggcg ctcccctgca tgtggtagac agcctaaatg   33360
cactgactgt agttactggc caaggtctta cgataaacgg aacagcccta caaactagag   33420
tctcaggtgc cctcaactat gacacatcag gaaacctaga attgagagct gcaggggta    33480
tgcgagttga tgcaaatggt caacttatcc ttgatgtagc ttacccatt gatgcacaaa    33540
acaatctcag ccttaggctt ggacagggac ccctgtttgt taactctgcc cacaacttgg   33600
atgttaacta caacagagge ctctacctgt tcacatctgg aaataccaaa aagctagaag   33660
ttaatatcaa aacagccaag ggtctcattt atgatgacac tgctatagca atcaatgcgg   33720
gtgatgggct acagtttgac tcaggctcag atacaaatcc attaaaaact aaacttggat   33780
taggactgga ttatgactcc agcagagcca taattgctaa actgggaact ggcctaagct   33840
ttgacaacac aggtgccatc acagtaggca acaaaaatga tgacaagctt accttgtgga   33900
ccacaccaga cccatcccct aactgtagaa tctattcaga gaaagatgct aaattcacac   33960
ttgttttgac taaatgcggc agtcaggtgt tggccagcgt ttctgtttta tctgtaaaag   34020
gtagccttgc gcccatcagt ggcacagtaa ctagtgctca gattgtcctc agatttgatg   34080
aaaatggagt tctactaagc aattcttccc ttgaccctca atactggaac tacagaaaag   34140
gtgaccttac agagggcact gcatatacca acgcagtggg atttatgccc aacctcacag   34200
cataccccaa aacacagagc caaactgcta aaagcaacat tgtaagtcag gtttacttga   34260
atgggacaa atccaaaccc atgaccctca ccattaccct caatggaact aatgaaacag   34320
gagatgccac agtaagcact actccatgt cattctcatg gaactggaat ggaagtaatt   34380
acattaatga aacgttccaa accaactcct tcaccttctc ctacatcgcc caagaataaa   34440
aagcatgacg ctgttgattt gattcaatgt gtttctgttt tattttcaag cacaacaaaa   34500
tcattcaagt cattcttcca tcttagctta atagacacag tagcttaata gacccagtag   34560
tgcaaagccc cattctagct tataactagt ggagaagtac tcgcctacat gggggtgag    34620
tcataatcgt gcatcaggat agggcggtgg tgctgcagca gcgcgcgaat aaactgctgc   34680
```

```
cgccgccgct ccgtcctgca ggaatacaac atggcagtgg tctcctcagc gatgattcgc  34740
accgcccgca gcataaggcg ccttgtcctc cgggcacagc agcgcaccct gatctcactt  34800
aaatcagcac agtaactgca gcacagcacc acaatattgt tcaaaatccc acagtgcaag  34860
gcgctgtatc caaagctcat ggcggggacc acagaaccca cgtggccatc ataccacaag  34920
cgcaggtaga ttaagtggcg acccctcata aacacgctgg acataaacat tacctctttt  34980
ggcatgttgt aattcaccac ctcccggtac catataaacc tctgattaaa catggcgcca  35040
tccaccacca tcctaaacca gctggccaaa acctgcccgc cggctataca ctgcagggaa  35100
ccgggactgg aacaatgaca gtggagagcc caggactcgt aaccatggat catcatgctc  35160
gtcatgatat caatgttggc acaacacagg cacacgtgca tacacttcct caggattaca  35220
agctcctccc gcgttagaac catatcccag ggaacaaccc attcctgaat cagcgtaaat  35280
cccacactgc agggaagacc tcgcacgtaa ctcacgttgt gcattgtcaa agtgttacat  35340
tcgggcagca gcggatgatc ctccagtatg gtagcgcggg tttctgtctc aaaaggaggt  35400
agacgatccc tactgtacgg agtgcgccga gacaaccgag atcgtgttgg tcgtagtgtc  35460
atgccaaatg gaacgccgga cgtagtcata tttcctgaag tcttagatct ctcaacgcag  35520
caccagcacc aacacttcgc agtgtaaaag gccaagtgcc gagagagtat atataggaat  35580
aaaaagtgac gtaaacgggc aaagtccaaa aaacgccag aaaaaccgca cgcgaaccta  35640
cgccccgaaa cgaaagccaa aaaacactag acactcccctt ccggcgtcaa cttccgcttt  35700
cccacgctac gtcacttgcc ccagtcaaac aaactacata tcccgaactt ccaagtcgcc  35760
acgcccaaaa caccgcctac acctcccgc ccgccggccc gccccaaac ccgcctcccg  35820
ccccgcgccc cgccccgcgc cgcccatctc attatcatat tggcttcaat ccaaaataag  35880
gtatattatt gatgatggtt taaacggatc ctctagagtc gacctgcagg catgcaagct  35940
tgagtattct atagtgtcac ctaaatagct tggcgtaatc atggtcatag ctgtttcctg  36000
tgtgaaattg ttatccgctc acaattccac acaacatacg agccggaagc ataaagtgta  36060
aagcctgggg tgcctaatga gtgagctaac tcacattaat tgcgttgcgc tcactgcccg  36120
ctttccagtc gggaaacctg tcgtgccagc tgcattaatg aatcggccaa cgcgaacccc  36180
ttgcggccgc ccgggccgtc gaccaattct catgtttgac agcttatcat cgaatttctg  36240
ccattcatcc gcttattatc acttattcag gcgtagcaac caggcgttta agggcaccaa  36300
taactgcctt aaaaaaatta cgccccgccc tgccactcat cgcagtactg ttgtaattca  36360
ttaagcattc tgccgacatg gaagccatca caaacggcat gatgaacctg aatcgccagc  36420
ggcatcagca ccttgtcgcc ttgcgtataa tatttgccca tggtgaaaac ggggggcgaag  36480
aagttgtcca tattggccac gtttaaatca aaactggtga actcacccca gggattggct  36540
gagacgaaaa acatattctc aataaaccct ttagggaaat aggccaggtt ttcaccgtaa  36600
cacgccacat cttgcgaata tatgtgtaga aactgccgga atcgtcgtg gtattcactc  36660
cagagcgatg aaaacgtttc agtttgctca tggaaaacgg tgtaacaagg gtgaacacta  36720
tcccatatca ccagctcacc gtctttcatt gccatacgga attccggatg agcattcatc  36780
aggcgggcaa gaatgtgaat aaaggccgga taaaacttgt gcttattttt ctttacggtc  36840
tttaaaaagg ccgtaatatc cagctgaacg gtctggttat aggtacattg agcaactgac  36900
tgaaatgcct caaaatgttc tttacgatgc cattgggata tatcaacggt ggtatatcca  36960
gtgattttt tctccatttt agcttcctta gctcctgaaa atctcgataa ctcaaaaaat  37020
```

```
acgcccggta gtgatcttat ttcattatgg tgaaagttgg aacctcttac gtgccgatca    37080
acgtctcatt ttcgccaaaa gttggcccag ggcttcccgg tatcaacagg gacaccagga    37140
tttatttatt ctgcgaagtg atcttccgtc acaggtattt attcgcgata agctcatgga    37200
gcggcgtaac cgtcgcacag gaaggacaga gaaagcgcgg atctgggaag tgacggacag    37260
aacggtcagg acctggattg gggaggcggt tgccgccgct gctgctgacg gtgtgacgtt    37320
ctctgttccg gtcacaccac atacgttccg ccattcctat gcgatgcaca tgctgtatgc    37380
cggtataccg ctgaaagttc tgcaaagcct gatgggacat aagtccatca gttcaacgga    37440
agtctacacg aaggttttg cgctggatgt ggctgcccgg caccgggtgc agtttgcgat     37500
gccggagtct gatgcggttg cgatgctgaa acaattatcc tgagaataaa tgccttggcc    37560
tttatatgga aatgtggaac tgagtggata tgctgttttt gtctgttaaa cagagaagct    37620
ggctgttatc cactgagaag cgaacgaaac agtcgggaaa atctcccatt atcgtagaga    37680
tccgcattat taatctcagg agcctgtgta gcgtttatag gaagtagtgt tctgtcatga    37740
tgcctgcaag cggtaacgaa aacgatttga atatgccttc aggaacaata gaaatcttcg    37800
tgcggtgtta cgttgaagtg gagcggatta tgtcagcaat ggacagaaca acctaatgaa    37860
cacagaacca tgatgtggtc tgtccttta cagccagtag tgctcgccgc agtcgagcga    37920
cagggcgaag ccctcgagtg agcgaggaag caccagggaa cagcacttat atattctgct    37980
tacacacgat gcctgaaaaa acttcccttg gggttatcca cttatccacg gggatatttt    38040
tataattatt ttttttatag tttttagatc ttctttttta gagcgccttg taggcccttta   38100
tccatgctgg ttctagagaa ggtgttgtga caaattgccc tttcagtgtg acaaatcacc    38160
ctcaaatgac agtcctgtct gtgacaaatt gcccttaacc ctgtgacaaa ttgccctcag    38220
aagaagctgt tttttcacaa agttatccct gcttattgac tcttttttat ttagtgtgac    38280
aatctaaaaa cttgtcacac ttcacatgga tctgtcatgg cggaaacagc ggttatcaat    38340
cacaagaaac gtaaaaatag cccgcgaatc gtccagtcaa acgacctcac tgaggcggca    38400
tatagtctct cccgggatca aaaacgtatg ctgtatctgt tcgttgacca gatcagaaaa    38460
tctgatggca ccctacagga acatgacggt atctgcgaga tccatgttgc taaatatgct    38520
gaaatattcg gattgacctc tgcggaagcc agtaaggata tacggcaggc attgaagagt    38580
ttcgcgggga aggaagtggt tttttatcgc cctgaagagg atgccggcga tgaaaaaggc    38640
tatgaatctt ttccttggtt tatcaaacgt gcgcacagtc catccagagg gctttacagt    38700
gtacatatca acccatatct cattcccttc tttatcgggt tacagaaccg gtttacgcag    38760
tttcggctta gtgaaacaaa agaaatcacc aatccgtatg ccatgcgttt atacgaatcc    38820
ctgtgtcagt atcgtaagcc ggatggctca ggcatcgtct ctctgaaaat cgactggatc    38880
atagagcgtt accagctgcc tcaaagttac cagcgtatgc ctgacttccg ccgccgcttc    38940
ctgcaggtct gtgttaatga gatcaacagc agaactccaa tgcgcctctc atacattgag    39000
aaaaagaaag gccgccagac gactcatatc gtatttcct tccgcgatat cacttccatg    39060
acgacaggat agtctgaggg ttatctgtca cagatttgag ggtggttcgt cacatttgtt    39120
ctgacctact gagggtaatt tgtcacagtt ttgctgtttc cttcagcctg catggatttt    39180
ctcatacttt ttgaactgta atttttaagg aagccaaatt tgagggcagt tgtcacagt     39240
tgatttcctt ctctttccct tcgtcatgtg acctgatatc ggggttagt tcgtcatcat     39300
tgatgagggt tgattatcac agtttattac tctgaattgg ctatccgcgt gtgtacctct    39360
acctggagtt tttcccacgg tggatatttc ttcttgcgct gagcgtaaga gctatctgac    39420
```

```
agaacagttc ttctttgctt cctcgccagt tcgctcgcta tgctcggtta cacggctgcg   39480
gcgagcgcta gtgataataa gtgactgagg tatgtgctct tcttatctcc ttttgtagtg   39540
ttgctcttat tttaaacaac tttgcggttt tttgatgact ttgcgatttt gttgttgctt   39600
tgcagtaaat tgcaagattt aataaaaaaa cgcaaagcaa tgattaaagg atgttcagaa   39660
tgaaactcat ggaaacactt aaccagtgca taaacgctgg tcatgaaatg acgaaggcta   39720
tcgccattgc acagtttaat gatgacagcc cggaagcgag gaaaataacc cggcgctgga   39780
gaataggtga agcagcggat ttagttgggg tttcttctca ggctatcaga gatgccgaga   39840
aagcagggcg actaccgcac ccggatatgg aaattcgagg acgggttgag caacgtgttg   39900
gttatacaat tgaacaaatt aatcatatgc gtgatgtgtt tggtacgcga ttgcgacgtg   39960
ctgaagacgt atttccaccg gtgatcgggg ttgctgccca taaggtggc gtttacaaaa   40020 cctcagtttc tgttcatctt gctcaggatc tggctctgaa ggggctacgt gttttgctcg   40080
tggaaggtaa cgaccccag ggaacagcct caatgtatca cggatgggta ccagatcttc   40140
atattcatgc agaagacact ctcctgcctt tctatcttgg ggaaaaggac gatgtcactt   40200
atgcaataaa gcccacttgc tggccggggc ttgacattat tccttcctgt ctggctctgc   40260
accgtattga aactgagtta atgggcaaat ttgatgaagg taaactgccc accgatccac   40320
acctgatgct ccgactggcc attgaaactg ttgctcatga ctatgatgtc atagttattg   40380
acagcgcgcc taacctgggt atcggcacga ttaatgtcgt atgtgctgct gatgtgctga   40440
ttgttcccac gcctgctgag ttgtttgact acacctccgc actgcagttt ttcgatatgc   40500
ttcgtgatct gctcaagaac gttgatctta agggttcga gcctgatgta cgtattttgc   40560
ttaccaaata cagcaatagt aatggctctc agtcccgtg gatggaggag caaattcggg   40620
atgcctgggg aagcatggtt ctaaaaaatg ttgtacgtga acggatgaa gttggtaaag   40680 gtcagatccg gatgagaact gttttttgaac aggccattga tcaacgctct tcaactggtg   40740
cctggagaaa tgctctttct atttgggaac ctgtctgcaa tgaaattttc gatcgtctga   40800
ttaaaccacg ctgggagatt agataatgaa gcgtgcgcct gttattccaa aacatacgct   40860
caatactcaa ccggttgaag atacttcgtt atcgacacca gctgccccga tggtggattc   40920
gttaattgcg cgcgtaggag taatggctcg cggtaatgcc attactttgc ctgtatgtgg   40980
tcgggatgtg aagtttactc ttgaagtgct ccggggtgat agtgttgaga agacctctcg   41040
ggtatggtca ggtaatgaac gtgaccagga gctgcttact gaggacgcac tggatgatct   41100
catcccttct tttctactga ctggtcaaca gacaccggcg ttcggtcgaa gagtatctgg   41160
tgtcatagaa attgccgatg ggagtcgccg tcgtaaagct gctgcactta ccgaaagtga   41220
ttatcgtgtt ctggttggcg agctggatga tgagcagatg gctgcattat ccagattggg   41280
taacgattat cgcccaacaa gtgcttatga acgtggtcag cgttatgcaa gccgattgca   41340
gaatgaattt gctggaaata tttctgcgct ggctgatgcg gaaaatattt cacgtaagat   41400
tattacccgc tgtatcaaca ccgccaaatt gcctaaatca gttgttgctc ttttttctca   41460
ccccggtgaa ctatctgccc ggtcaggtga tgcacttcaa aaagccttta cagataaaga   41520
ggaattactt aagcagcagg catctaacct tcatgagcag aaaaaagctg gggtgatatt   41580
tgaagctgaa gaagttatca ctcttttaac ttctgtgctt aaaacgtcat ctgcatcaag   41640
aactagttta agctcacgac atcagtttgc tcctggagcg acagtattgt ataagggcga   41700
taaaatggtg cttaacctgg acaggtctcg tgttccaact gagtgtatag agaaaattga   41760
```

```
ggccattctt aaggaacttg aaaagccagc accctgatgc gaccacgttt tagtctacgt    41820
ttatctgtct ttacttaatg tcctttgtta caggccagaa agcataactg gcctgaatat    41880
tctctctggg cccactgttc cacttgtatc gtcggtctga taatcagact gggaccacgg    41940
tcccactcgt atcgtcggtc tgattattag tctgggacca cggtcccact cgtatcgtcg    42000
gtctgattat tagtctggga ccacggtccc actcgtatcg tcggtctgat aatcagactg    42060
ggaccacggt cccactcgta tcgtcggtct gattattagt ctgggaccat ggtcccactc    42120
gtatcgtcgg tctgattatt agtctgggac cacggtccca ctcgtatcgt cggtctgatt    42180
attagtctgg aaccacgtc ccactcgtat cgtcggtctg attattagtc tgggaccacg    42240
gtcccactcg tatcgtcggt ctgattatta gtctgggacc acgatcccac tcgtgttgtc    42300
ggtctgatta tcggtctggg accacggtcc cacttgtatt gtcgatcaga ctatcagcgt    42360
gagactacga ttccatcaat gcctgtcaag gcaagtatt gacatgtcgt cgtaacctgt    42420
agaacggagt aacctcggtg tgcggttgta tgcctgctgt ggattgctgc tgtgtcctgc    42480
ttatccacaa cattttgcgc acggttatgt ggacaaaata cctggttacc caggccgtgc    42540
cggcacgtta accgggctgc atccgatgca agtgtgtcgc tgtcgacgag ctcgcgagct    42600
cggacatgag gttgccccgt attcagtgtc gctgatttgt attgtctgaa gttgttttta    42660
cgttaagttg atgcagatca attaatacga tacctgcgtc ataattgatt atttgacgtg    42720
gtttgatggc ctccacgcac gttgtgtatat gtagatgata atcattatca ctttacgggt    42780
cctttccggt gatccgacag gttacggggc ggcgacctcg cgggttttcg ctatttatga    42840 aaatttccg gtttaaggcg tttccgttct tcttcgtcat aacttaatgt ttttatttaa    42900 aatacccctct gaaaagaaag gaaacgacag gtgctgaaag cgagcttttt ggcctctgtc    42960
gtttcctttc tctgttttg tccgtggaat gaacaatgga agtccgagct catcgctaat    43020
aacttcgtat agcatacatt atacgaagtt atattcgatg cggccgcaag gggttcgcgt    43080
cagcgggtgt tggcgggtgt cggggctggc ttaactatgc ggcatcagag cagattgtac    43140
tgagagtgca ccatatgcgg tgtgaaatac cgcacagatg cgtaaggaga aataccgca    43200 tcaggcgcca ttcgccattc aggctgcgca actgttggga agggcgatcg gtgcgggcct    43260
cttcgctatt acgccagctg gcgaaagggg gatgtgctgc aaggcgatta agttgggtaa    43320
cgccagggtt ttcccagtca cgacgttgta aaacgacggc cagtgaattg taatacgact    43380
cactataggg cgaattcgag ctcggtaccc ggggatcctc gtttaaac              43428

<210> SEQ ID NO 9
<211> LENGTH: 45227
<212> TYPE: DNA
<213> ORGANISM: Simian adenovirus

<400> SEQUENCE: 9
catcatcaat aatataccct attttggatt gaagccaata tgataatgag atgggcggcg      60
cggggcgggg cgcggggcgg gaggcgggtt tgggggcggg ccggcgggcg gggcggtgtg     120
gcggaagtgg actttgtaag tgtggcggat gtgacttgct agtgccgggc gcggtaaaag     180
tgacgttttc cgtgcgcgac aacgcccccg ggaagtgaca ttttttcccgc ggttttttacc    240 ggatgttgta gtgaatttgg gcgtaaccaa gtaagatttg gccattttcg cgggaaaact     300
gaaacgggga agtgaaatct gattaatttt gcgttagtca taccgcgtaa tatttgtcta     360
gggccgaggg actttggccg attacgtgga ggactcgccc agtgtttttt tgaggtgaat     420
ttccgcgttc cgggtcaaag tctgcgtttt attattatag gatatcccat tgcatacgtt     480
```

```
gtatccatat cataatatgt acatttatat tggctcatgt ccaacattac cgccatgttg    540
acattgatta ttgactagtt attaatagta atcaattacg gggtcattag ttcatagccc    600
atatatggag ttccgcgtta cataacttac ggtaaatggc ccgcctggct gaccgcccaa    660
cgacccccgc ccattgacgt caataatgac gtatgttccc atagtaacgc caatagggac    720
tttccattga cgtcaatggg tggagtattt acggtaaact gcccacttgg cagtacatca    780
agtgtatcat atgccaagta cgccccctat tgacgtcaat gacggtaaat ggcccgcctg    840
gcattatgcc cagtacatga ccttatggga ctttcctact tggcagtaca tctacgtatt    900
agtcatcgct attaccatgg tgatgcggtt ttggcagtac atcaatgggc gtggatagcg    960
gtttgactca cggggatttc caagtctcca ccccattgac gtcaatggga gtttgttttg   1020
gcaccaaaat caacgggact ttccaaaatg tcgtaacaac tccgccccat tgacgcaaat   1080
gggcggtagg cgtgtacggt gggaggtcta tataagcaga gctctcccta tcagtgatag   1140
agatctccct atcagtgata gagatcgcg acgagctcgt ttagtgaacc gtcagatcgc   1200
ctggagacgc catccacgct gttttgacct ccatagaaga caccgggacc gatccagcct   1260
ccgcggccgg gaacggtgca ttggaacgcg gattccccgt gccaagagtg agatcttccg   1320
tttatctagg taccgggccc cccctcgagg tcgacggtat cgataagctt cacgctgccg   1380
caagcactca gggcgcaagg gctgctaaag gaagcggaac acgtagaaag ccagtccgca   1440
gaaacggtgc tgaccccgga tgaatgtcag ctactgggct atctggacaa gggaaaacgc   1500
aagcgcaaag agaaagcagg tagcttgcag tgggcttaca tggcgatagc tagactgggc   1560
ggttttatgg acagcaagcg aaccggaatt gccagctggg gcgccctctg gtaaggttgg   1620
gaagccctgc aaagtaaact ggatggcttt cttgccgcca aggatctgat ggcgcagggg   1680
atcaagatct aaccaggagc tatttaatgg caacagttaa ccagctggta cgcaaaccac   1740
gtgctcgcaa agttgcgaaa agcaacgtgc ctgcgctgga agcatgcccg caaaaacgtg   1800
gcgtatgtac tcgtgtatat actaccactc ctaaaaaacc gaactccgcg ctgcgtaaag   1860
tatgccgtgt tcgtctgact aacggtttcg aagtgacttc ctacatcggt ggtgaaggtc   1920
acaacctgca ggagcactcc gtgatcctga tccgtggcgg tcgtgttaaa gacctcccgg   1980
gtgttcgtta ccacaccgta cgtggtgcgc ttgactgctc cggcgttaaa gaccgtaagc   2040
aggctcgttc caagtatggc gtgaagcgtc taaggcttaa tggtagatc tgatcaagag   2100 acaggatgac ggtcgtttcg catgcttgaa caagatggat tgcacgcagg ttctccggcc   2160
gcttgggtgg agaggctatt cggctatgac tgggcacaac agacaatcgg ctgctctgat   2220
gccgccgtgt tccggctgtc agcgcagggg cgcccggttc tttttgtcaa gaccgacctg   2280
tccggtgccc tgaatgaact gcaggacgag gcagcgcggc tatcgtggct ggccacgacg   2340
ggcgttcctt gcgcagctgt gctcgacgtt gtcactgaag cgggaaggga ctggctgcta   2400
ttgggcgaag tgccggggca ggatctcctg tcatctcacc ttgctcctgc cgagaaagta   2460
tccatcatgg ctgatgcaat gcggcggctg catacgcttg atccggctac ctgcccattc   2520
gaccaccaag cgaaacatcg catcgagcga gcacgtactc ggatggaagc cggtcttgtc   2580
gatcaggatg atctggacga agagcatcag gggctcgcgc cagccgaact gttcgccagg   2640
ctcaaggcgc gcatgcccga cggcgaggat ctcgtcgtga cccatggcga tgcctgcttg   2700
ccgaatatca tggtggaaaa tggccgcttt tctggattca tcgactgtgg ccggctgggt   2760
gtggcggacc gctatcagga catagcgttg gctacccgtg atattgctga agagcttggc   2820
```

```
ggcgaatggg ctgaccgctt cctcgtgctt tacggtatcg ccgctcccga ttcgcagcgc    2880
atcgccttct atcgccttct tgacgagttc ttctgagcgg gactctgggg ttcgaaatga    2940
ccgaccaagc gacgcccaac ctgccatcac gagatttcga ttccaccgcc gccttctatg    3000
aaaggttggg cttcggaatc gttttccggg acgccggctg gatgatcctc cagcgcgggg    3060
atctcatgct ggagttcttc gcccaccccg ggctcgatcc cctcgggggg aatcagaatt    3120
cagtcgacag cggccgcgat ctgctgtgcc ttctagttgc cagccatctg ttgtttgccc    3180
ctcccccgtg ccttccttga ccctggaagg tgccactccc actgtccttt cctaataaaa    3240
tgaggaaatt gcatcgcatt gtctgagtag gtgtcattct attctggggg gtggggtggg    3300
gcaggacagc aagggggagg attgggaaga caatagcagg catgctgggg atgcggtggg    3360
ctctatggcc gatcagcgat cgctgaggtg ggtgagtggg cgtggcctgg ggtggtcatg    3420
aaaatatata agttgggggt cttagggtct ctttatttgt gttgcagaga ccgccggagc    3480
catgagcggg agcagcagca gcagcagtag cagcagcgcc ttggatggca gcatcgtgag    3540
cccttatttg acgacgcgga tgccccactg gccggggtg cgtcagaatg tgatgggctc    3600
cagcatcgac ggccgacccg tcctgcccgc aaattccgcc acgctgacct atgcgaccgt    3660
cgcggggacg ccgttggacg ccaccgccgc cgccgccgcc accgcagccg cctcggccgt    3720
gcgcagcctg gccacggact ttgcattcct gggaccactg gcgacagggg ctacttctcg    3780
ggccgctgct gccgccgttc gcgatgacaa gctgaccgcc ctgctggcgc agttggatgc    3840
gcttactcgg gaactgggtg acctttctca gcaggtcatg gccctgcgcc agcaggtctc    3900
ctccctgcaa gctggcggga atgcttctcc cacaaatgcc gtttaagata aataaaacca    3960
gactctgttt ggattaaaga aaagtagcaa gtgcattgct ctctttattt cataattttc    4020
cgcgcgcgat aggccctaga ccagcgttct cggtcgttga gggtgcggtg tatcttctcc    4080
aggacgtggt agaggtggct ctggacgttg agatacatgg gcatgagccc gtcccgggg    4140 tggaggtagc accactgcag agcttcatgc tccggggtgg tgttgtagat gatccagtcg    4200
tagcaggagc gctgggcatg gtgcctaaaa atgtccttca gcagcaggcc gatggccagg    4260 gggaggcccct tggtgtaagt gtttacaaaa cggttaagtt gggaagggtg cattcgggga    4320
gagatgatgt gcatcttgga ctgtattttt agattggcga tgtttccgcc cagatccctt    4380
ctgggattca tgttgtgcag gaccaccagt acagtgtatc cggtgcactt ggggaatttg    4440
tcatgcagct tagagggaaa agcgtggaag aacttggaga cgcctttgtg gcctcccaga    4500
ttttccatgc attcgtccat gatgatggca atgggcccgc ggaggcagc ttgggcaaag    4560 atatttctgg ggtcgctgac gtcgtagttg tgttccaggg tgaggtcgtc ataggccatt    4620
tttacaaagc gcgggcggag ggtgcccgac tgggggatga tggtcccctc tggccctggg    4680
gcgtagttgc cctcgcagat ctgcatttcc caggccttaa tctcggaggg gggaatcata    4740
tccacctgcg gggcgatgaa gaaaacggtt tccggagccg gggagattaa ctgggatgag    4800
agcaggtttc taagcagctg tgattttcca caaccggtgg gcccataaat aacacctata    4860
accggttgca gctggtagtt tagagagctg cagctgccgt cgtcccggag gagggggcc    4920 acctcgttga gcatgtccct gacgcgcatg ttctccccga ccagatccgc cagaaggcgc    4980
tcgccgccca gggacagcag ctcttgcaag gaagcaaagt ttttcagcgg cttgaggccg    5040
tccgccgtgg gcatgttttt cagggtctgg ctcagcagct ccaggcggtc ccagagctcg    5100
gtgacgtgct ctacggcatc tctatccagc atatctcctc gtttcgcggg ttggggcgac    5160
tttcgctgta gggcaccaag cggtggtcgt ccagcggggc cagagtcatg tccttccatg    5220
```

```
ggcgcagggt cctcgtcagg gtggtctggg tcacggtgaa ggggtgcgct ccgggctgag    5280
cgcttgccaa ggtgcgcttg aggctggttc tgctggtgct gaagcgctgc cggtcttcgc    5340
cctgcgcgtc ggccaggtag catttgacca tggtgtcata gtccagcccc tccgcggcgt    5400
gtcccttggc gcgcagcttg cccttggagg tggcgccgca cgaggggcag agcaggctct    5460
tgagcgcgta gagcttgggg gcgaggaaga ccgattcggg ggagtaggcg tccgcgccgc    5520 agacccgca cacggtctcg cactccacca gccaggtgag ctcggggcgc gccgggtcaa    5580
aaaccaggtt tcccccatgc tttttgatgc gtttcttacc tcgggtctcc atgaggtggt    5640
gtccccgctc ggtgacgaag aggctgtccg tgtctccgta daccgacttg aggggtcttt    5700
tctccagggg ggtccctcgg tcttcctcgt agaggaactc ggaccactct gagacgaagg    5760
cccgcgtcca ggccaggacg aaggaggcta tgtgggaggg gtagcggtcg ttgtccacta    5820
gggggtccac cttctccaag gtgtgaagac acatgtcgcc ttcctcggcg tccaggaagg    5880
tgattggctt gtaggtgtag gccacgtgac cgggggttcc tgacgggggg gtataaaagg    5940 gggtggggc gcgctcgtcg tcactctctt ccgcatcgct gtctgcgagg gccagctgct    6000
ggggtgagta ttccctctcg aaggcgggca tgacctccgc gctgaggttg tcagtttcca    6060
aaaacgagga ggatttgatg ttcacctgtc ccgaggtgat acctttgagg gtacccgcgt    6120
ccatctggtc agaaaacacg atcttttat tgtccagctt ggtggcgaac gacccgtaga    6180
gggcgttgga gagcagcttg gcgatggagc gcagggtctg gttcttgtcc ctgtcggcgc    6240
gctccttggc cgcgatgttg agctgcacgt actcgcgcgc gacgcagcgc cactcgggga    6300
agacggtggt gcgctcgtcg ggcaccaggc gcacgcgcca gccgcggttg tgcagggtga    6360
ccaggtccac gctggtggcg acctcgccgc gcaggcgctc gttggtccag cagagacggc    6420
cgcccttgcg cgagcagaag gggggcaggg ggtcgagctg ggtctcgtcc ggggggtccg    6480
cgtccacggt gaaaaccccg gggcgcaggc gcgcgtcgaa gtagtctatc ttgcaacctt    6540
gcatgtccag cgcctgctgc cagtcgcggg cggcgagcgc gcgctcgtag gggttgagcg    6600
gcgggcccca gggcatgggg tgggtgagtg cggaggcgta catgccgcag atgtcataga    6660
cgtagagggg ctcccgcagg accccgatgt aggtggggta gcagcggccg ccgcggatgc    6720
tggcgcgcac gtagtcatac agtcgtgcg aggggggcgag gaggtcgggg cccaggttgg    6780
tgcgggcggg gcgctccgcg cggaagacga tctgcctgaa gatggcatgc gagttggaag    6840
agatggtggg gcgctggaag acgttgaagc tggcgtcctg caggccgacg gcgtcgcgca    6900
cgaaggaggc gtaggagtcg cgcagcttgt gtaccagctc ggcggtgacc tgcacgtcga    6960
gcgcgcagta gtcgagggtc tcgcggatga tgtcatattt agcctgcccc ttctttttcc    7020
acagctcgcg gttgaggaca aactcttcgc ggtctttcca gtactcttgg atcgggaaac    7080
cgtccggttc cgaacggtaa gagcctagca tgtagaactg gttgacggcc tggtaggcgc    7140
agcagccctt ctccacgggg agggcgtagg cctgcgcggc cttgcggagc gaggtgtggg    7200
tcagggcgaa ggtgtccctg accatgactt tgaggtactg gtgcttgaag tcggagtcgt    7260
cgcagccgcc ccgctcccag agcgagaagt cggtgcgctt cttggagcgg gggttgggca    7320
gagcgaaggt gacatcgttg aagaggattt tgcccgcgcg gggcatgaag ttgcgggtga    7380
tgcggaaggg ccccggcact tcagagcggt tgttgatgac ctgggcggcg agcacgatct    7440
cgtcgaagcc gttgatgttg tggcccacga tgtagagttc caggaagcgg ggccggccct    7500
ttacggtggg cagcttcttt agctcttcgt aggtgagctc ctcgggcgag gcgaggccgt    7560
```

```
gctcggccag ggcccagtcc gcgaggtgcg ggttgtctct gaggaaggac ttccagaggt    7620
cgcgggccag gagggtctgc aggcggtctc tgaaggtcct gaactggcgg cccacggcca    7680
ttttttcggg ggtgatgcag tagaaggtga gggggtcttg ctgccagcgg tcccagtcga    7740
gctgcagggc gaggtcgcgc gcggcggtga ccaggcgctc gtcgccccg aatttcatga    7800 ccagcatgaa gggcacgagc tgctttccga aggcccccat ccaagtgtag gtctctacat    7860
cgtaggtgac aaagaggcgc tccgtgcgag gatgcgagcc gatcgggaag aactggatct    7920
cccgccacca gttggaggag tggctgttga tgtggtggaa gtagaagtcc cgtcgccggg    7980
ccgaacactc gtgctggctt ttgtaaaagc gagcgcagta ctggcagcgc tgcacgggct    8040
gtacctcatg cacgagatgc acctttcgcc cgcgcacgag aagccgagg ggaaatctga    8100 gcccccgcc tggctcgcgg catggctggt tctcttctac tttggatgcg tgtccgtctc    8160
cgtctggctc ctcgaggggt gttacggtgg agcggaccac cacgccgcgc gagccgcagg    8220
tccagatatc ggcgcgcggc ggtcggagtt tgatgacgac atcgcgcagc tgggagctgt    8280
ccatggtctg gagctcccgc ggcggcggca ggtcagccgg gagttcttgc aggttcacct    8340
cgcagagtcg ggccagggcg cggggcaggt ctaggtggta cctgatctct aggggcgtgt    8400
tggtggcggc gtcgatggct tgcaggagcc cgcagccccg ggggcgacg acggtgcccc    8460 gcggggtggt ggtggtggtg gcggtgcagc tcagaagcgg tgccgcgggc gggccccgg    8520 aggtaggggg ggctccggtc ccgcgggcag gggcggcagc ggcacgtcgg cgtggagcgc    8580
gggcaggagt tggtgctgtg cccggaggtt gctggcgaag gcgacgacgc ggcggttgat    8640
ctcctggatc tggcgcctct gcgtgaagac gacgggcccg gtgagcttga acctgaaaga    8700
gagttcgaca gaatcaatct cggtgtcatt gaccgcggcc tggcgcagga tctcctgcac    8760
gtctcccgag ttgtcttggt aggcgatctc ggccatgaac tgctcgatct cttcctcctg    8820
gaggtctccg cgtccggcgc gttccacggt ggccgccagg tcgttggaga tgcgccccat    8880
gagctgcgag aaggcgttga gtccgccctc gttccagact cggctgtaga ccacgccccc    8940
ctggtcatcg cgggcgcgca tgaccacctg cgcgaggttg agctccacgt gccgcgcgaa    9000
gacggcgtag ttgcgcagac gctggaagag gtagttgagg gtggtggcgg tgtgctcggc    9060
cacgaagaag ttcatgaccc agcggcgcaa cgtggattcg ttgatgtccc ccaaggcctc    9120
cagccgttcc atggcctcgt agaagtccac ggcgaagttg aaaaactggg agttgcgcgc    9180
cgacacggtc aactcctcct ccagaagacg gatgagctcg gcgacggtgt cgcgcacctc    9240
gcgctcgaag gctatgggga tctcttcctc cgctagcatc accacctcct cctcttcctc    9300
ctcttctggc acttccatga tggcttcctc ctcttcgggg ggtggcggcg gcggcggtgg    9360
gggagggggc gctctgcgcc ggcggcggcg caccgggagg cggtccacga agcgcgcgat    9420
catctccccg cggcggcggc gcatggtctc ggtgacggcg cggccgttct cccggggcg    9480 cagttggaag acgccgccgg acatctggtc ctggggcggg tggccgtgag gcagcgagac    9540
ggcgctgacg atgcatctca acaattgctg cgtaggtacg ccgccgaggg acctgaggga    9600
gtccatatcc accggatccg aaaacctttc gaggaaggcg tctaaccagt cgcagtcgca    9660
aggtaggctg agcaccgtgg cgggcggcgg ggggtggggg gagtgtctgg cggaggtgct    9720
gctgatgatg taattgaagt aggcggactt gacacggcgg atggtcgaca ggagcaccat    9780
gtccttgggt ccggcctgct ggatgcggag gcggtcggct atgccccagg cttcgttctg    9840
gcatcggcgc aggtccttgt agtagtcttg catgagcctt tccaccggca cctcttctcc    9900
ttcctcttct gcttcttcca tgtctgcttc ggccctgggg cggcgccgcg ccccccctgcc    9960
```

```
ccccatgcgc gtgaccccga accccctgag cggttggagc agggccaggt cggcgacgac    10020
gcgctcggcc aggatggcct gctgcacctg cgtgagggtg gtttggaagt catccaagtc    10080
cacgaagcgg tggtaggcgc ccgtgttgat ggtgtaggtg cagttggcca tgacggacca    10140
gttgacggtc tggtggcccg gttgcgacat ctcggtgtac ctgagtcgcg agtaggcgcg    10200
ggagtcgaag acgtagtcgt tgcaagtccg caccaggtac tggtagccca ccaggaagtg    10260
cggcggcggc tggcggtaga ggggccagcg cagggtggcg ggggctccgg gggccaggtc    10320
ttccagcatg aggcggtggt aggcgtagat gtacctggac atccaggtga tacccgcggc    10380
ggtggtggag gcgcgcggga agtcgcgcac ccggttccag atgttgcgca ggggcagaaa    10440
gtgctccatg gtaggcgtgc tctgtccagt cagacgcgcg cagtcgttga tactctagac    10500
cagggaaaac gaaagccggt cagcgggcac tcttccgtgg tctggtgaat agatcgcaag    10560
ggtatcatgg cggagggcct cggttcgagc cccgggtccg ggccggacgg tccgccatga    10620
tccacgcggt taccgcccgc gtgtcgaacc caggtgtgcg acgtcagaca acggtggagt    10680
gttccttttg gcgttttttct ggccgggcgc cggcgccgcg taagagacta agccgcgaaa    10740
gcgaaagcag taagtggctc gctccccgta gccggaggga tccttgctaa gggttgcgtt    10800
gcggcgaacc ccggttcgaa tcccgtactc gggccggccg gacccgcggc taaggtgttg    10860
gattggcctc cccctcgtat aaagaccccg cttgcggatt gactccggac acggggacga    10920
gcccctttta ttttgctttt cccagatgc atccggtgct gcggcagatg cgccccccgc     10980
cccagcagca gcaacaacac cagcaagagc ggcagcaaca gcagcgggag tcatgcaggg    11040 cccccctcacc caccctcggc gggccggcca cctcggcgtc cgcggccgtg tctggcgcct    11100
gcggcggcgg cggggggccg gctgacgacc ccgaggagcc cccgcggcgc agggccagac    11160
actacctgga cctggaggag ggcgagggcc tggcgcggct ggggcgccg tctcccgagc    11220 gccacccgcg ggtgcagctg aagcgcgact cgcgcgaggc gtacgtgcct cggcagaacc    11280
tgttcaggga ccgcgcgggc gaggagcccg aggagatgcg ggacaggagg ttcagcgcag    11340
ggcgggagct gcggcagggg ctgaaccgcg agcggctgct gcgcgaggag gactttgagc    11400
ccgacgcgcg gacgggatc agccccgcgc gcgcgcacgt ggcggccgcc gacctggtga    11460
cggcgtacga gcagacggtg aaccaggaga tcaacttcca aaagagtttc aacaaccacg    11520
tgcgcacgct ggtggcgcgc gaggaggtga ccatcgggct gatgcacctg tgggactttg    11580
taagcgcgct ggtgcagaac cccaacagca agcctctgac ggcgcagctg ttcctgatag    11640
tgcagcacag cagggacaac gaggcgttta gggacgcgct gctgaacatc accgagcccg    11700
agggtcggtg gctgctggac ctgattaaca tcctgcagag catagtggtg caggagcgca    11760
gcctgagcct ggccgacaag gtggcggcca tcaactactc gatgctgagc ctgggcaagt    11820
tttacgcgcg caagatctac cagacgccgt acgtgcccat agacaaggag gtgaagatcg    11880
acggttttta catgcgcatg gcgctgaagg tgctcaccct gagcgacgac ctgggcgtgt    11940
accgcaacga gcgcatccac aaggccgtga gcgtgagccg gcggcgcgag ctgagcgacc    12000
gcgagctgat gcacagcctg cagcgggcgc tggcgggcgc cggcagcggc gacagggagg    12060
cggagtccta cttcgatgcg ggggcggacc tgcgctgggc gccagccgg cgggccctgg    12120 aggccgcggg ggtccgcgag gactatgacg aggacggcga ggaggatgag gagtacgagc    12180
tagaggaggg cgagtacctg gactaaaccg cgggtggtgt ttccggtaga tgcaagaccc    12240
gaacgtggtg gacccggcgc tgcgggcggc tctgcagagc cagccgtccg gccttaactc    12300
```

-continued

```
ctcagacgac tggcgacagg tcatggaccg catcatgtcg ctgacggcgc gtaacccgga    12360
cgcgttccgg cagcagccgc aggccaacag gctctccgcc atcctggagg cggtggtgcc    12420
tgcgcgctcg aaccccacgc acgagaaggt gctggccata gtgaacgcgc tggccgagaa    12480
cagggccatc cgcccggacg aggccgggct ggtgtacgac gcgctgctgc agcgcgtggc    12540
ccgctacaac agcggcaacg tgcagaccaa cctggaccgg ctggtggggg acgtgcgcga    12600
ggcggtggcg cagcgcgagc gcgcggatcg gcagggcaac ctgggctcca tggtggcgct    12660
gaatgccttc ctgagcacgc agccggccaa cgtgccgcgg gggcaggaag actacaccaa    12720
ctttgtgagc gcgctgcggc tgatggtgac cgagaccccc cagagcgagg tgtaccagtc    12780
gggcccggac tacttcttcc agaccagcag acagggcctg cagacggtga acctgagcca    12840
ggctttcaag aacctgcggg ggctgtgggg cgtgaaggcg cccaccggcg accgggcgac    12900
ggtgtccagc ctgctgacgc ccaactcgcg cctgctgctg ctgctgatcg cgccgttcac    12960
ggacagcggc agcgtgtccc gggacaccta cctgggcac ctgctgaccc tgtaccgcga    13020
ggccatcggg caggcgcagg tggacgagca caccttccag gagatcacca gcgtgagccg    13080
cgcgctgggg caggaggaca cgagcagcct ggaggcgact ctgaactacc tgctgaccaa    13140
ccggcggcag aagattccct cgctgcacag cctgacctcc gaggaggagc gcatcttgcg    13200
ctacgtgcag cagagcgtga gcctgaacct gatgcgcgac ggggtgacgc ccagcgtggc    13260
gctggacatg accgcgcgca acatggaacc gggcatgtac gccgcgcacc ggccttacat    13320
caaccgcctg atggactacc tgcatcgcgc ggcggccgtg aaccccgagt actttaccaa    13380
cgccatcctg aacccgcact ggctcccgcc gcccgggttc tacagcgggg gcttcgaggt    13440
cccggagacc aacgatggct tcctgtggga cgacatggac gacagcgtgt tctccccgcg    13500
gccgcaggcg ctggcggaag cgtccctgct gcgtcccaag aaggaggagg aggaggaggc    13560
gagtcgccgc cgcggcagca gcggcgtggc ttctctgtcc gagctggggg cggcagccgc    13620
cgcgcgcccc gggtccctgg gcggcagccc ctttccgagc ctggtggggt ctctgcacag    13680
cgagcgcacc acccgccctc ggctgctggg cgaggacgag tacctgaata actccctgct    13740
gcagccggtg cgggagaaaa acctgcctcc cgccttcccc aacaacggga tagagagcct    13800
ggtggacaag atgagcagat ggaagaccta tgcgcaggag cacagggacg cgcctgcgct    13860
ccggccgccc acgcggcgcc agcgccacga ccggcagcgg gggctggtgt gggatgacga    13920
ggactccgcg gacgatagca gcgtgctgga cctgggaggg agcggcaacc cgttcgcgca    13980
cctgcgcccc cgcctgggga ggatgtttta aaaaaaaaa aaaaagcaa gaagcatgat    14040 gcaaaaatta aataaaactc accaaggcca tggcgaccga gcgttggttt cttgtgttcc    14100
cttcagtatg cggcgcgcgg cgatgtacca ggagggacct cctccctctt acgagagcgt    14160
ggtgggcgcg gcggcggcgg cgccctcttc tcccttgcg tcgcagctgc tggagccgcc    14220
gtacgtgcct ccgcgctacc tgcggcctac gggggggaga acagcatcc gttactcgga    14280 gctggcgccc ctgttcgaca ccaccgggt gtacctggtg acaacaagt cggcggacgt    14340 ggcctccctg aactaccaga acgaccacag caatttttg accacggtca tccagaacaa    14400
tgactacagc ccgagcgagg ccagcaccca gaccatcaat ctggatgacc ggtcgcactg    14460
gggcggcgac ctgaaaaacca tcctgcacac caacatgccc aacgtgaacg agttcatgtt    14520
caccaataag ttcaaggcgc gggtgatggt gtcgcgctcg cacaccaagg aagaccgggt    14580
ggagctgaag tacgagtggg tggagttcga gctgccagag ggcaactact ccgagaccat    14640
gaccattgac ctgatgaaca cgcgatcgt ggagcactat ctgaaagtgg gcaggcagaa    14700
```

```
cggggtcctg gagagcgaca tcggggtcaa gttcgacacc aggaacttcc gcctggggct   14760
ggaccccgtg accgggctgg ttatgcccgg ggtgtacacc aacgaggcct tccatcccga   14820
catcatcctg ctgcccggct gcggggtgga cttcacttac agccgcctga gcaacctcct   14880
gggcatccgc aagcggcagc ccttccagga gggcttcagg atcacctacg aggacctgga   14940
gggggcaac atccccgcgc tcctcgatgt ggaggcctac caggatagct tgaaggaaaa   15000
tgaggcggga caggaggata ccgccccgc cgcctccgcc gccgccgagc agggcgagga   15060
tgctgctgac accgcggccg cggacggggc agaggccgac cccgctatgg tggtggaggc   15120
tcccgagcag gaggaggaca tgaatgacag tgccgtgcgc ggagacacct tcgtcacccg   15180
ggggaggaa aagcaagcgg aggccgaggc cgcggccgag gaaaagcaac tggcggcagc   15240
agcggcggcg gcgcgttgg ccgcggcgga ggctgagtct gaggggacca agcccgccaa   15300
ggagcccgtg attaagcccc tgaccgaaga tagcaagaag cgcagttaca acctgctcaa   15360
ggacagcacc aacaccgcgt accgcagctg gtacctggcc tacaactacg cgacccgtc   15420
gacggggtg cgctcctgga ccctgctgtg cacgccggac gtgacctgcg gctcggagca   15480
ggtgtactgg tcgctgcccg acatgatgca agaccccgtg accttccgct ccacgcggca   15540
ggtcagcaac ttcccggtgg tgggcgccga gctgctgccc gtgcactcca agagcttcta   15600
caacgaccag gccgtctact cccagctcat ccgccagttc acctctctga cccacgtgtt   15660
caatcgcttt cctgagaacc agattctggc gcgcccgccc gccccacca tcaccaccgt   15720
cagtgaaaac gttcctgctc tcacagatca cgggacgcta ccgctgcgca acagcatcgg   15780
aggagtccag cgagtgaccg ttactgacgc cagacgccgc acctgcccct acgtttacaa   15840
ggccttgggc atagtctcgc cgcgcgtcct ttccagccgc actttttgag caacaccacc   15900
atcatgtcca tcctgatctc acccagcaat aactccggct ggggactgct gcgcgcgccc   15960
agcaagatgt tcggaggggc gaggaagcgt tccgagcagc accccgtgcg cgtgcgcggg   16020
cacttccgcg cccctgggg agcgcacaaa cgcggccgcg cggggcgcac caccgtggac   16080
gacgccatcg actcggtggt ggagcaggcg cgcaactaca ggcccgcggt ctctaccgtg   16140
gacgcggcca tccagaccgt ggtgcggggc gcgcggcggt acgccaagct gaagagccgc   16200
cggaagcgcg tggcccgccg ccaccgccgc cgacccgggg ccgccgccaa acgcgccgcc   16260
gcggccctgc ttcgccgggc caagcgcacg ggccgccgcg ccgccatgag ggccgcgcgc   16320
cgcttggccg ccggcatcac cgccgccacc atggccccc gtacccgaag acgcgcggcc   16380
gccgccgccg ccgccgccat cagtgacatg ccagcaggc gccggggcaa cgtgtactgg   16440
gtgcgcgact cggtgaccgg cacgcgcgtg cccgtgcgct tccgcccccc gcggacttga   16500
gatgatgtga aaaacaaca ctgagtctcc tgctgttgtg tgtatcccag cggcggcggc   16560
gcgcgcagcg tcatgtccaa gcgcaaaatc aaagaagaga tgctccaggt cgtcgcgccg   16620
gagatctatg gccccccgaa gaaggaagag caggattcga agccccgcaa gataaagcgg   16680
gtcaaaaaga aaagaaaga tgatgacgat gccgatgggg aggtggagtt cctgcgcgcc   16740
acggcgccca ggcgcccggt gcagtggaag ggccggcgcg taaagcgcgt cctgcgcccc   16800
ggcaccgcgg tggtcttcac gcccggcgag cgctccaccc ggactttcaa gcgcgtctat   16860
gacgaggtgt acggcgacga agacctgctg gagcaggcca acgagcgctt cggagagttt   16920
gcttacggga agcgtcagcg ggcgctgggg aaggaggacc tgctggcgct gccgctggac   16980
cagggcaacc ccaccccag tctgaagccc gtgaccctgc agcaggtgct gccgagcagc   17040
```

```
gcaccctccg aggcgaagcg gggtctgaag cgcgagggcg gcgacctggc gcccaccgtg   17100
cagctcatgg tgcccaagcg gcagaggctg gaggatgtgc tggagaaaat gaaagtagac   17160
cccggtctgc agccggacat cagggtccgc cccatcaagc aggtggcgcc gggcctcggc   17220
gtgcagaccg tggacgtggt catccccacc ggcaactccc ccgccgccgc caccactacc   17280
gctgcctcca cggacatgga gacacagacc gatcccgccg cagccgcagc cgcagccgcc   17340
gccgcgacct cctcggcgga ggtgcagacg gaccccctggc tgccgccggc gatgtcagct   17400
ccccgcgcgc gtcgcgggcg caggaagtac ggcgccgcca acgcgctcct gcccgagtac   17460
gccttgcatc cttccatcgc gcccaccccc ggctaccgag gctataccta ccgcccgcga   17520
agagccaagg gttccacccg ccgtccccgc cgacgcgccg ccgccaccac ccgccgccgc   17580
cgccgcagac gccagcccgc actggctcca gtctccgtga ggaaagtggc gcgcgacgga   17640
cacaccctgg tgctgcccag ggcgcgctac caccccagca tcgtttaaaa gcctgttgtg   17700
gttcttgcag atatggccct cacttgccgc ctccgtttcc cggtgccggg ataccgagga   17760
ggaagatcgc gccgcaggag gggtctggcc ggccgcggcc tgagcggagg cagccgccgc   17820
gcgcaccggc ggcgacgcgc caccagccga cgcatgcgcg gcggggtgct gcccctgtta   17880
atccccctga tcgccgcggc gatcggcgcc gtgcccggga tcgcctccgt ggccttgcaa   17940
gcgtcccaga ggcattgaca gacttgcaaa cttgcaaata tggaaaaaaa aaccccaata   18000
aaaaagtcta gactctcacg ctcgcttggt cctgtgacta ttttgtagaa tggaagacat   18060
caactttgcg tcgctggccc cgcgtcacgg ctcgcgcccg ttcctgggac actggaacga   18120
tatcggcacc agcaacatga gcggtggcgc cttcagttgg ggctctctgt ggagcggcat   18180
taaaagtatc gggtctgccg ttaaaaatta cggctcccgg gcctggaaca gcagcacggg   18240
ccagatgttg agagacaagt tgaaagagca gaacttccag cagaaggtgg tggagggcct   18300
ggcctccggc atcaacgggg tggtggacct ggccaaccag gccgtgcaga ataagatcaa   18360
cagcagactg gaccccccggc cgccggtgga ggaggtgccg ccggcgctgg agacggtgtc   18420
ccccgatggg cgtggcgaga agcgcccgcg gcccgatagg aagagaccca ctctggtcac   18480
gcagaccgat gagccgcccc cgtatgagga ggccctgaag caaggtctgc ccaccacgcg   18540
gcccatcgcg cccatggcca ccggggtggt gggccgccac accccgccca cgctggactt   18600
gcctccgccc gccgatgtgc cgcagcagca gaaggcggca cagccgggcc cgcccgcgac   18660
cgcctcccgt tcctccgccg gtcctctgcg ccgcgcggcc agcggccccc gcgggggggt   18720
cgcgaggcac ggcaactggc agagcacgct gaacagcatc gtgggtctgg gggtgcggtc   18780
cgtgaagcgc cgccgatgct actgaatagc ttagctaacg tgttgtatgt gtgtatgcgc   18840
cctatgtcgc cgccagagga gctgctgagt cgccgccgtt cgcgcgccca ccaccaccgc   18900
cactccgccc ctcaagatgg cgaccccatc gatgatgccg cagtggtcgt acatgcacat   18960
ctcgggccag gacgcctcgg agtacctgag ccccggggctg gtgcagttcg cccgcgccac   19020
cgagagctac ttcagcctga gtaacaagtt taggaacccc acggtggcgc ccacgcacga   19080
tgtgaccacc gaccggtctc agcgcctgac gctgcggttc attcccgtgg accgcgagga   19140
caccgcgtac tcgtacaagg cgcggttcac cctggccgtg ggcgacaacc gcgtgctgga   19200
catggcctcc acctactttg acatccgcgg ggtgctggac cggggtccca ctttcaagcc   19260
ctactctggc accgcctaca actccctggc cccaaggggc gctcccaact cctgcgagtg   19320
ggagcaagag gaaactcagg cagttgaaga agcagcagaa gaggaagaag aagatgctga   19380
cggtcaagct gaggaagagc aagcagctac caaaaagact catgtatatg ctcaggctcc   19440
```

```
cctttctggc gaaaaaatta gtaaagatgg tctgcaaata ggaacggacg ctacagctac   19500
agaacaaaaa cctatttatg cagaccctac attccagccc gaaccccaaa tcggggagtc   19560
ccagtggaat gaggcagatg ctacagtcgc cggcggtaga gtgctaaaga aatctactcc   19620
catgaaacca tgctatggtt cctatgcaag acccacaaat gctaatggag gtcagggtgt   19680
actaacggca aatgcccagg gacagctaga atctcaggtt gaaatgcaat tcttttcaac   19740
ttctgaaaac gcccgtaacg aggctaacaa cattcagccc aaattggtgc tgtatagtga   19800
ggatgtgcac atggagaccc cggatacgca ccttcttac aagcccgcaa aaagcgatga   19860
caattcaaaa atcatgctgg gtcagcagtc catgcccaac agacctaatt acatcggctt   19920
cagagacaac tttatcggcc tcatgtatta caatagcact ggcaacatgg gagtgcttgc   19980
aggtcaggcc tctcagttga atgcagtggt ggacttgcaa gacagaaaca cagaactgtc   20040
ctaccagctc ttgcttgatt ccatgggtga cagaaccaga tacttttcca tgtggaatca   20100
ggcagtggac agttatgacc cagatgttag aattattgaa aatcatgaaa ctgaagacga   20160
gctccccaac tattgtttcc ctctgggtgg cataggggta actgacactt accaggctgt   20220
taaaaccaac aatggcaata acgggggcca ggtgacttgg acaaaagatg aaacttttgc   20280
agatcgcaat gaaatagggg tgggaaacaa tttcgctatg gagatcaacc tcagtgccaa   20340
cctgtggaga aacttcctgt actccaacgt ggcgctgtac ctaccagaca agcttaagta   20400
caacccctcc aatgtggaca tctctgacaa ccccaacacc tacgattaca tgaacaagcg   20460
agtggtggcc ccggggctgg tggactgcta catcaacctg ggcgcgcgct ggtcgctgga   20520
ctacatggac aacgtcaacc ccttcaacca ccaccgcaat gcgggcctgc gctaccgctc   20580
catgctcctg ggcaacgggc gctacgtgcc cttccacatc caggtgcccc agaagttctt   20640
tgccatcaag aacctcctcc tcctgccggg ctcctacacc tacgagtgga cttcaggaa   20700 ggatgtcaac atggtcctcc agagctctct gggtaacgat ctcagggtgg acggggccag   20760
catcaagttc gagagcatct gcctctacgc caccttcttc cccatggccc acaacacggc   20820
ctccacgctc gaggccatgc tcaggaacga caccaacgac cagtccttca atgactacct   20880
ctccgccgcc aacatgctct accccatacc cgccaacgcc accaacgtcc ccatctccat   20940
cccctcgcgc aactgggcgg ccttccgcgg ctgggccttc accgcctca gaccaagga   21000 gaccccctcc ctgggctcgg gattcgaccc ctactacacc tactcgggct ccattcccta   21060
cctggacggc accttctacc tcaaccacac tttcaagaag gtctcggtca ccttcgactc   21120
ctcggtcagc tggccgggca acgaccgtct gctcaccccc aacgagttcg agatcaagcg   21180
ctcggtcgac ggggagggct acaacgtggc ccagtgcaac atgaccaagg actggttcct   21240
ggtccagatg ctggccaact acaacatcgg ctaccagggc ttctacatcc cagagagcta   21300
caaggacagg atgtactcct tcttcaggaa cttccagccc atgagccggc aggtggtgga   21360
ccagaccaag tacaaggact accaggaggt gggcatcatc accagcacaa caactcggg   21420 cttcgtgggc tacctcgccc ccaccatgcg cgagggacag gcctacccc caacttccc   21480 ctatccgctc ataggcaaga ccgcggtcga cagcatcacc cagaaaaagt tcctctgcga   21540
ccgcacccct ggcgcatcc ccttctccag caacttcatg tccatgggtg cgctctcgga   21600
cctgggccag aacttgctct acgccaactc cgcccacgcc ctcgacatga ccttcgaggt   21660
cgaccccatg gacgagccca cccttctcta tgttctgttc gaagtctttg acgtggtccg   21720
ggtccaccag ccgcaccgcg gcgtcatcga gaccgtgtac ctgcgtacgc ccttctcggc   21780
```

```
cggcaacgcc accacctaaa gaagcaagcc gcagtcatcg ccgcctgcat gccgtcgggt   21840
tccaccgagc aagagctcag ggccatcgtc agagacctgg gatgcgggcc ctattttttg   21900
ggcaccttcg acaagcgctt ccctggcttt gtctccccac acaagctggc ctgcgccatc   21960
gtcaacacgg ccgccgcga gaccggggc gtgcactggc tggccttcgc ctggaacccg    22020
cgctccaaaa catgcttcct cttttgacccc ttcggcttt cggaccagcg gctcaagcaa   22080
atctacgagt tcgagtacga gggcttgctg cgtcgcagcg ccatcgcctc ctcgcccgac   22140
cgctgcgtca ccctcgaaaa gtccacccag accgtgcagg ggcccgactc ggccgcctgc   22200
ggtctcttct gctgcatgtt tctgcacgcc tttgtgcact ggcctcagag tcccatggac   22260 cgcaaccccca ccatgaactt gctgacgggg gtgcccaact ccatgctcca gagcccccag   22320
gtcgagccca ccctgcgccg caaccaggag cagctctaca gcttcctgga gcgccactcg   22380
ccttacttcc gccgccacag cgcacagatc aggagggcca cctccttctg ccacttgcaa   22440
gagatgcaag aagggtaata acgatgtaca cactttttt ctcaataaat ggcatctttt    22500
tatttataca agctctctgg ggtattcatt tcccaccacc accgccgtt gtcgccatct    22560 ggctctattt agaaatcgaa agggttctgc cgggagtcgc cgtgcgccac gggcagggac   22620
acgttgcgat actggtagcg ggtgccccac ttgaactcgg gcaccaccag gcgaggcagc   22680
tcggggaagt tttcgctcca caggctgcgg gtcagcacca gcgcgttcat caggtcgggc   22740
gccgagatct tgaagtcgca gttggggccg ccgcctgcg cgcgcgagtt gcggtacacc    22800
gggttgcagc actggaacac caacagcgcc gggtgcttca cgctggccag cacgctgcgg   22860
tcggagatca gctcggcgtc caggtcctcc gcgttgctca gcgcgaacgg ggtcatcttg   22920
ggcacttgcc gccccaggaa gggcgcgtgc cccggtttcg agttgcagtc gcagcgcagc   22980
gggatcagca ggtgcccgtg cccggactcg gcgttgggt acagcgcgcg catgaaggcc    23040
tgcatctggc ggaaggccat ctgggccttg gcgccctccg agaagaacat gccgcaggac   23100
ttgcccgaga actggtttgc ggggcagctg gcgtcgtgca ggcagcagcg cgcgtcggtg   23160
ttggcgatct gcaccacgtt gcgcccccac cggttcttca cgatcttggc cttggacgat   23220
tgctccttca gcgcgcgctg cccgttctcg ctggtcacat ccatctcgat cacatgttcc   23280
ttgttcacca tgctgctgcc gtgcagacac ttcagctcgc cctccgtctc ggtgcagcgg   23340
tgctgccaca gcgcgcagcc cgtgggctcg aaagacttgt aggtcacctc cgcgaaggac   23400
tgcaggtacc cctgcaaaaa gcggcccatc atggtcacga aggtcttgtt gctgctgaag   23460
gtcagctgca gcccgcggtg ctcctcgttc agccaggtct tgcacacggc cgccagcgcc   23520
tccacctggt cgggcagcat cttgaagttc accttcagct cattctccac gtggtacttg   23580
tccatcagcg tgcgcgccgc ctccatgccc ttctcccagg ccgacaccag cggcaggctc   23640
acggggttct tcaccatcac cgtggccgcc gcctccgccg cgctttcgct ttccgccccg   23700
ctgttctctt cctcttcctc ctcttcctcg ccgccgccca ctcgcagccc ccgcaccacg   23760
gggtcgtctt cctgcaggcg ctgcaccttg cgcttgccgt tgcgcccctg cttgatgcgc   23820
acgggcgggt tgctgaagcc caccatcacc agcgcggcct cttcttgctc gtcctcgctg   23880
tccagaatga cctccgggga ggggggttg gtcatcctca gtaccgaggc acgcttcttt    23940
ttcttcctgg gggcgttcgc cagctccgcg gctgcggccg ctgccgaggt cgaaggccga   24000
gggctgggcg tgcgcggcac cagcgcgtcc tgcgagccgt cctcgtcctc ctcggactcg   24060
agacggaggc gggcccgctt cttcgggggc gcgggggcg gcgaggcgg cggcggcgac    24120 ggagacgggg acgagacatc gtccaggtg ggtggacggc gggccgcgcc gcgtccgcgc    24180
```

| | | | | |
|---|---|---|---|---|
| tcggggtgg | tctcgcgctg | gtcctcttcc | cgactggcca | tctcccactg ctccttctcc | 24240 |
| tataggcaga | aagagatcat | ggagtctctc | atgcgagtcg | agaaggagga ggacagccta | 24300 |
| accgccccct | ctgagccctc | caccaccgcc | gccaccaccg | ccaatgccgc cgcggacgac | 24360 |
| gcgcccaccg | agaccaccgc | cagtaccacc | ctccccagcg | acgcaccccc gctcgagaat | 24420 |
| gaagtgctga | tcgagcagga | cccgggtttt | gtgagcggag | aggaggatga ggtggatgag | 24480 |
| aaggagaagg | aggaggtcgc | cgcctcagtg | ccaaaagagg | ataaaaagca agaccaggac | 24540 |
| gacgcagata | aggatgagac | agcagtcggg | cgggggaacg | gaagccatga tgctgatgac | 24600 |
| ggctacctag | acgtgggaga | cgacgtgctg | cttaagcacc | tgcaccgcca gtgcgtcatc | 24660 |
| gtctgcgacg | cgctgcagga | gcgctgcgaa | gtgcccctgg | acgtggcgga ggtcagccgc | 24720 |
| gcctacgagc | ggcacctctt | cgcgccgcac | gtgcccccca | agcgccggga gaacggcacc | 24780 |
| tgcgagccca | acccgcgtct | caacttctac | ccggtcttcg | cggtacccga ggtgctggcc | 24840 |
| acctaccaca | tcttttttcca | aaactgcaag | atcccctct | cctgccgcgc caaccgcacc | 24900 |
| cgcgccgaca | aaaccctgac | cctgcgcag | ggcgcccaca | tacctgatat cgcctctctg | 24960 |
| gaggaagtgc | ccaagatctt | cgagggtctc | ggtcgcgacg | agaaacgggc ggcgaacgct | 25020 |
| ctgcacggag | acagcgaaaa | cgagagtcac | tcggggtgc | tggtggagct cgagggcgac | 25080 |
| aacgcgcgcc | tggccgtact | caagcgcagc | atagaggtca | cccactttgc ctacccggcg | 25140 |
| ctcaacctgc | cccccaaggt | catgagtgtg | gtcatgggcg | agctcatcat gcgccgcgcc | 25200 |
| cagcccctgg | ccgcggatgc | aaacttgcaa | gagtcctccg | aggaaggcct gcccgcggtc | 25260 |
| agcgacgagc | agctggcgcg | ctggctggag | accgcgacc | ccgcgcagct ggaggagcgg | 25320 |
| cgcaagctca | tgatggccgc | ggtgctggtc | accgtggagc | tcgagtgtct gcagcgcttc | 25380 |
| ttcgcggacc | ccgagatgca | gcgcaagctc | gaggagaccc | tgcactacac cttccgccag | 25440 |
| ggctacgtgc | gccaggcctg | caagatctcc | aacgtggagc | tctgcaacct ggtctcctac | 25500 |
| ctgggcatcc | tgcacgagaa | ccgcctcggg | cagaacgtcc | tgcactccac cctcaaaggg | 25560 |
| gaggcgcgcc | gcgactacat | ccgcgactgc | gcctacctct | tcctctgcta cacctggcag | 25620 |
| acggccatgg | gggtctggca | gcagtgcctg | gaggagcgca | acctcaagga gctggaaaag | 25680 |
| ctcctcaagc | gcaccctcag | ggacctctgg | acgggcttca | acgagcgctc ggtggccgcc | 25740 |
| gcgctggcgg | acatcatctt | tcccgagcgc | ctgctcaaga | ccctgcagca gggcctgccc | 25800 |
| gacttcacca | gccagagcat | gctgcagaac | ttcaggactt | tcatcctgga gcgctcgggc | 25860 |
| atcctgccgg | ccacttgctg | cgcgctgccc | agcgacttcg | tgcccatcaa gtacagggag | 25920 |
| tgcccgccgc | cgctctgggg | ccactgctac | ctcttccagc | tggccaacta cctcgcctac | 25980 |
| cactcggacc | tcatggaaga | cgtgagcggc | gagggcctgc | tcgagtgcca ctgccgctgc | 26040 |
| aacctctgca | cgccccaccg | ctctctagtc | tgcaacccgc | agctgctcag cgagagtcag | 26100 |
| attatcggta | ccttcgagct | gcagggtccc | tcgcctgacg | agaagtccgc ggctccaggg | 26160 |
| ctgaaactca | ctccggggct | gtggacttcc | gcctacctac | gcaaatttgt acctgaggac | 26220 |
| taccacgccc | acgagatcag | gttctacgaa | gaccaatccc | gccgcccaa ggcggagctc | 26280 |
| accgcctgcg | tcatcaccca | ggggcacatc | ctggccaat | tgcaagccat caacaaagcc | 26340 |
| cgccgagagt | tcttgctgaa | aaagggtcgg | ggggtgtacc | tggaccccca gtccggcgag | 26400 |
| gagctaaacc | cgctacccc | gccgccgcc | cagcagcggg | accttgcttc ccaggatggc | 26460 |
| acccagaaag | aagcagcagc | cgccgccgcc | gccgcagcca | tacatgcttc tggaggaaga | 26520 |

```
ggaggaggac tgggacagtc aggcagagga ggtttcggac gaggagcagg aggagatgat    26580
ggaagactgg gaggaggaca gcagcctaga cgaggaagct tcagaggccg aagaggtggc    26640
agacgcaaca ccatcgccct cggtcgcagc cccctcgccg gggcccctga aatcctccga    26700
acccagcacc agcgctataa cctccgctcc tccggcgccg cgccacccg cccgcagacc     26760 caaccgtaga tgggacacca caggaaccgg ggtcggtaag tccaagtgcc cgccgccgcc    26820
accgcagcag cagcagcagc agcgccaggg ctaccgctcg tggcgcgggc acaagaacgc    26880
catagtcgcc tgcttgcaag actgcggggg caacatctct ttcgcccgcc gcttcctgct    26940
attccaccac ggggtcgcct ttccccgcaa tgtcctgcat tactaccgtc atctctacag    27000
cccctactgc agcggcgacc cagaggcggc agcggcagcc acagcggcga ccaccaccta   27060
ggaagatatc ctccgcgggc aagacagcgg cagcagcggc caggagaccc gcggcagcag   27120
cggcgggagc ggtgggcgca ctgcgcctct cgcccaacga acccctctcg acccgggagc   27180
tcagacacag gatcttcccc actttgtatg ccatcttcca acagagcaga ggccaggagc    27240
aggagctgaa aataaaaaac agatctctgc gctccctcac ccgcagctgt ctgtatcaca    27300
aaagcgaaga tcagcttcgg cgcacgctgg aggacgcgga ggcactcttc agcaaatact    27360
gcgcgctcac tcttaaagac tagctccgcg cccttctcga atttaggcgg gagaaaacta    27420
cgtcatcgcc ggccgccgcc cagcccgccc agccgagatg agcaaagaga ttcccacgcc    27480
atacatgtgg agctaccagc cgcagatggg actcgcggcg ggagcggccc aggactactc    27540
cacccgcatg aactacatga gcgcgggacc ccacatgatc tcacaggtca cgggatccg    27600 cgcccagcga aaccaaatac tgctggaaca ggcggccatc accgccacgc cccgccataa    27660
tctcaacccc cgaaattggc ccgccgccct cgtgtaccag gaaaccccct ccgccaccac    27720
cgtactactt ccgcgtgacg cccaggccga agtccagatg actaactcag gggcgcagct    27780
cgcgggcggc tttcgtcacg gggcgcggcc gctccgacca ggtataagac acctgatgat    27840
cagaggccga ggtatccagc tcaacgacga gtcggtgagc tcttcgctcg gtctccgtcc    27900
ggacggaact ttccagctcg ccggatccgg ccgctcttcg ttcacgcccc gccaggcgta    27960
cctgactctg cagacctcgt cctcggagcc ccgctccggc ggcatcggaa ccctccagtt    28020
cgtggaggag ttcgtgccct cggtctactt caacccttc tcgggacctc ccggacgcta    28080
ccccgaccag ttcattccga actttgacgc ggtgaaggac tcggcggacg gctacgactg    28140
aatgtcaggt gtcgaggcag agcagcttcg cctgagacac ctcgagcact gccgccgcca    28200
caagtgcttc gcccgcggtt ctggtgagtt ctgctacttt cagctacccg aggagcatac    28260
cgaggggccg gcgcacggcg tccgcctgac cacccagggc gaggttacct gttccctcat    28320
ccgggagttt accctccgtc ccctgctagt ggagcgggag cggggtcccct gtgtcctaac    28380 tatcgcctgc aactgcccta accctggatt acatcaagat ctttgctgtc atctctgtgc    28440
tgagtttaat aaacgctgag atcagaatct actggggctc ctgtcgccat cctgtgaacg    28500
ccaccgtctt cacccacccc gaccaggccc aggcgaacct cacctgcggt ctgcatcgga    28560
gggccaagaa gtacctcacc tggtacttca acggcacccc ctttgtggtt tacaacagct    28620
tcgacgggga cggagtctcc ctgaaagacc agctctccgg tctcagctac tccatccaca    28680
agaacaccac cctccaactc ttccctccct acctgccggg aacctacgag tgcgtcaccg    28740
gccgctgcac ccacctcacc cgcctgatcg taaaccagag cttttccggga acagataact    28800 ccctcttccc cagaacagga ggtgagctca ggaaactccc cggggaccag gcggagacg     28860 taccttcgac ccttgtgggg ttaggatttt ttattaccgg gttgctggct cttttaatca    28920
```

```
aagtttcctt gagatttgtt ctttccttct acgtgtatga acacctcaac ctccaataac    28980
tctacccttt cttcggaatc aggtgacttc tctgaaatcg ggcttggtgt gctgcttact    29040
ctgttgattt ttttccttat catactcagc cttctgtgcc tcaggctcgc cgcctgctgc    29100
gcacacatct atatctactg ctggttgctc aagtgcaggg gtcgccaccc aagatgaaca    29160
ggtacatggt cctatcgatc ctaggcctgc tggccctggc ggcctgcagc gccgccaaaa    29220
aagagattac ctttgaggag cccgcttgca atgtaacttt caagcccgag ggtgaccaat    29280
gcaccaccct cgtcaaatgc gttaccaatc atgagaggct gcgcatcgac tacaaaaaca    29340
aaactggcca gtttgcggtc tatagtgtgt ttacgcccgg agaccctct aactactctg     29400
tcaccgtctt ccagggcgga cagtctaaga tattcaatta cactttccct ttttatgagt    29460
tatgcgatgc ggtcatgtac atgtcaaaac agtacaacct gtggcctccc tctccccagg    29520
cgtgtgtgga aaatactggg tcttactgct gtatggcttt cgcaatcact acgctcgctc    29580
taatctgcac ggtgctatac ataaaattca ggcagaggcg aatctttatc gatgaaaaga    29640
aaatgccttg atcgctaaca ccggctttct atctgcagaa tgaatgcaat cacctcccta    29700
ctaatcacca ccaccctcct tgcgattgcc catgggttga cacgaatcga agtgccagtg    29760
gggtccaatg tcaccatggt gggccccgcc ggcaattcca ccctcatgtg ggaaaaattt    29820
gtccgcaatc aatgggttca tttctgctct aaccgaatca gtatcaagcc cagagccatc    29880
tgcgatgggc aaaatctaac tctgatcaat gtgcaaatga tggatgctgg gtactattac    29940
gggcagcggg gagaaatcat taattactgg cgaccccaca aggactacat gctgcatgta    30000
gtcgaggcac ttcccactac cacccccact accacctctc ccaccaccac caccactact    30060
actactacta ctactactac tactactacc actaccgctg cccgccatac ccgcaaaagc    30120
accatgatta gcacaaagcc ccctcgtgct cactcccacg ccggcgggcc catcggtgcg    30180
acctcagaaa ccaccgagct ttgcttctgc caatgcacta acgccagcgc tcatgaactg    30240
ttcgacctgg agaatgagga tgtccagcag agctccgctt gcctgaccca ggaggctgtg    30300
gagcccgttg ccctgaagca gatcggtgat tcaataattg actcttcttc ttttgccact    30360
cccgaatacc ctcccgattc tactttccac atcacgggta ccaaagaccc taacctctct    30420
ttctacctga tgctgctgct ctgtatctct gtggtctctt ccgcgctgat gttactgggg    30480
atgttctgct gcctgatctg ccgcagaaag agaaaagctc gctctcaggg ccaaccactg    30540
atgcccttcc cctaccccc ggattttgca gataacaaga tatgagctcg ctgctgacac     30600
taaccgcttt actagcctgc gctctaaccc ttgtcgcttg cgactcgaga ttccacaatg    30660
tcacagctgt ggcaggagaa aatgttactt tcaactccac ggccgatacc cagtggtcgt    30720
ggagtggctc aggtagctac ttaactatct gcaatagctc cacttcccc ggcatatccc     30780
caaccaagta ccaatgcaat gccagcctgt tcaccctcat caacgcttcc accctggaca    30840
atggactcta tgtaggctat gtaccctttg gtgggcaagg aaagacccac gcttacaacc    30900
tggaagttcg ccagcccaga accactaccc aagcttctcc caccaccacc accaccacca    30960
ccatcaccag cagcagcagc agcagcagcc acagcagcag cagcagatta ttgactttgg    31020
ttttggccag ctcatctgcc gctacccagg ccatctacag ctctgtgccc gaaccactc     31080
agatccaccg cccagaaacg accaccgcca ccaccctaca cacctccagc gatcagatgc    31140
cgaccaacat caccccttg gctcttcaaa tgggacttac aagcccccact ccaaaaccag     31200
tggatgcggc cgaggtctcc gccctcgtca atgactgggc ggggctggga atgtggtggt    31260
```

```
tcgccatagg catgatggcg ctctgcctgc ttctgctctg gctcatctgc tgcctccacc   31320
gcaggcgagc cagaccccc atctatagac ccatcattgt cctgaacccc gataatgatg    31380
ggatccatag attggatggc ctgaaaaacc tactttttc ttttacagta tgataaattg    31440
agacatgcct cgcattttct tgtacatgtt ccttctccca ccttttctgg ggtgttctac    31500
gctggccgct gtgtctcacc tggaggtaga ctgcctctca cccttcactg tctacctgct    31560
ttacggattg gtcaccctca ctctcatctg cagcctaatc acagtaatca tcgccttcat    31620
ccagtgcatt gattacatct gtgtgcgcct cgcatacttc agacaccacc cgcagtaccg    31680
agacaggaac attgcccaac ttctaagact gctctaatca tgcataagac tgtgatctgc    31740
cttctgatcc tctgcatcct gcccacccct acctcctgcc agtacaccac aaaatctccg    31800
cgcaaaagac atgcctcctg ccgcttcacc caactgtgga atatacccaa atgctacaac    31860
gaaaagagcg agctctccga agcttggctg tatggggtca tctgtgtctt agttttctgc    31920
agcactgtct ttgccctcat aatctacccc tactttgatt tgggatggaa cgcgatcgat    31980
gccatgaatt ccccaccctt tcccgcaccc gagataattc cactgcgaca agttgtaccc    32040
gttgtcgtta atcaacgccc cccatccct acgcccactg aaatcagcta ctttaaccta     32100
acaggcggag atgactgacg ccctagatct agaaatggac ggcatcagta ccgagcagcg    32160
tctcctagag aggcgcaggc aggcggctga gcaagagcgc ctcaatcagg agctccgaga    32220
tctcgttaac ctgcaccagt gcaaaagagg catcttttgt ctggtaaagc aggccaaagt    32280
cacctacgag aagaccggca acagccaccg cctcagttac aaattgccca cccagcgcca    32340
gaagctggtg ctcatggtgg gtgagaatcc catcaccgtc acccagcact cggtagagac    32400
cgaggggtgt ctgcactccc cctgtcgggg tccagaagac ctctgcaccc tggtaaagac    32460
cctgtgcggt ctcagagatt tagtcccctt taactaatca aacactggaa tcaataaaaa    32520
gaatcactta cttaaaatca gacagcaggt ctctgtccag tttattcagc agcacctcct    32580 tccctcctc ccaactctgg tactccaaac gccttctggc ggcaaacttc ctccacaccc     32640
tgaagggaat gtcagattct tgctcctgtc cctccgcacc cactatcttc atgttgttgc    32700
agatgaagcg caccaaaacg tctgacgaga gcttcaaccc cgtgtacccc tatgacacgg    32760
aaagcggccc tccctccgtc ccttttcctca cccctccctt cgtgtctccc gatggattcc    32820
aagaaagtcc cccgggggtc ctgtctctga acctggccga gcccctggtc acttcccacg    32880
gcatgctcgc cctgaaaatg ggaagtggcc tctccctgga cgacgctggc aacctcacct    32940
ctcaagatat caccaccgct agccctcccc tcaaaaaaac caagaccaac ctcagcctag    33000
aaacctcatc ccccctaact gtgagcacct caggcgccct caccgtagca gccgccgctc    33060
ccctggcggt ggccggcacc tccctcacca tgcaatcaga ggccccctg acagtacagg     33120 atgcaaaact caccctggcc accaaaggcc cctgaccgt gtctgaaggc aaactggcct     33180
tgcaaacatc ggccccgctg acggccgctg acagcagcac cctcacagtc agtgccacac    33240 cacccttag cacaagcaat ggcagcttgg gtattgacat gcaagccccc atttacacca     33300
ccaatggaaa actaggactt aactttggcg ctcccctgca tgtggtagac agcctaaatg    33360
cactgactgt agttactggc caaggtctta cgataaacgg aacagcccta caaactagag    33420
tctcaggtgc cctcaactat gacacatcag gaaacctaga attgagagct gcaggggta    33480 tgcgagttga tgcaaatggt caacttatcc ttgatgtagc ttacccattt gatgcacaaa    33540
acaatctcag ccttaggctt ggacagggac ccctgttgt taactctgcc cacaacttgg     33600
atgttaacta caacagaggc ctctacctgt tcacatctgg aaataccaaa aagctagaag    33660
```

```
ttaatatcaa acagccaag ggtctcattt atgatgacac tgctatagca atcaatgcgg    33720
gtgatgggct acagtttgac tcaggctcag atacaaatcc attaaaaact aaacttggat    33780
taggactgga ttatgactcc agcagagcca taattgctaa actgggaact ggcctaagct    33840
ttgacaacac aggtgccatc acagtaggca acaaaaatga tgacaagctt accttgtgga    33900
ccacaccaga cccatcccct aactgtagaa tctattcaga gaaagatgct aaattcacac    33960
ttgttttgac taaatgcggc agtcaggtgt tggccagcgt ttctgtttta tctgtaaaag    34020
gtagccttgc gcccatcagt ggcacagtaa ctagtgctca gattgtcctc agatttgatg    34080
aaaatggagt tctactaagc aattcttccc ttgaccctca atactggaac tacagaaaag    34140
gtgaccttac agagggcact gcatatacca acgcagtggg atttatgccc aacctcacag    34200
catacccaaa aacacagagc caaactgcta aaagcaacat tgtaagtcag gtttacttga    34260
atggggacaa atccaaaccc atgaccctca ccattaccct caatggaact aatgaaacag    34320
gagatgccac agtaagcact tactccatgt cattctcatg gaactggaat ggaagtaatt    34380
acattaatga acgttccaa accaactcct tcaccttctc ctacatcgcc caagaataaa    34440
aagcatgacg ctgttgattt gattcaatgt gtttctgttt tattttcaag cacaacaaaa    34500
tcattcaagt cattcttcca tcttagctta atagacacag tagcttaata gacccagtag    34560
tgcaaagccc cattctagct tatagatcag acagtgataa ttaaccacca ccaccaccat    34620
accttttgat tcaggaaatc atgatcatca caggatccta gtcttcaggc cgcccccctcc   34680
ctcccaagac acagaataca cagtcctctc ccccgactg gctttaaata caccatctg     34740
gttggtcaca gacatgttct tagggttat attccacacg gtctcctgcc gcgccaggcg    34800
ctcgtcggtg atgttgataa actctcccgg cagctcgctc aagttcacgt cgctgtccag    34860
cggctgaacc tccggctgac gcgataactg tgcgaccggc tgctggacga acggaggccg    34920
cgcctacaag ggggtagagt cataatcctc ggtcaggata gggcggtgat gcagcagcag   34980
cgagcgaaac atctgctgcc gccgccgctc cgtccggcag gaaaacaaca cgccggtggt   35040
ctcctccgcg ataatccgca ccgcccgcag catcagcttc ctcgttctcc gcgcgcagca   35100
cctcacccctt atctcgctca aatcggcgca gtaggtacag cacagcacca cgatgttatt    35160
catgatccca cagtgcaggg cgctgtatcc aaagctcatg ccgggaacca ccgcccccac   35220
gtggccatcg taccacaagc gcacgtaaat caagtgtcga cccctcatga acgcgctgga   35280
cacaaacatt acttccttgg gcatgttgta attcaccacc tcccggtacc agataaacct    35340
ctggttgaac agggcacctt ccaccaccat cctgaaccaa gaggccagaa cctgccccacc   35400
ggctatgcac tgcagggaac ccgggttgga acaatgacaa tgcagactcc aaggctcgta   35460
accgtggatc atccggctgc tgaaggcatc gatgttggca caacacagac acacgtgcat   35520
gcactttctc atgattagca gctcttccct cgtcaggatc atatcccaag gaataaccca   35580
ttcttgaatc aacgtaaaac ccacacagca gggaaggcct cgcacataac tcacgttgtg   35640
catggtcagc gtgttgcatt ccggaaacag cggatgatcc tccagtatcg aggcgcgggt   35700
ctccttctca cagggaggta aagggtccct gctgtacgga ctgcgccggg acgaccgaga   35760
tcgtgttgag cgtagtgtca tggaaaaggg aacgccggac gtggtcatac ttcttgaagc   35820
agaaccaggt tcgcgcgtgg caggcctcct tgcgtctgcg gtctcgccgt ctagctcgct    35880
ccgtgtgata gttgtagtac agccactccc gcagagcgtc gaggcgcacc ctggcttccg   35940
gatctatgta gactccgtct tgcaccgcgg ccctgataat atccaccacc gtagaataag   36000
```

```
caacacccag ccaagcaata cactcgctct gcgagcggca gacaggagga gcgggcagag   36060
atgggagaac catgataaaa aacttttttt aaagaatatt ttccaattct tcgaaagtaa   36120
gatctatcaa gtggcagcgc tcccctccac tggcgcggtc aaactctacg gccaaagcac   36180
agacaacggc atttctaaga tgttccttaa tggcgtccaa aagacacacc gctctcaagt   36240
tgcagtaaac tatgaatgaa aacccatccg gctgattttc aatatagac gcgccggcag    36300 cgtccaccaa acccagataa ttttcttctc tccagcggtt tacgatctgt ctaagcaaat   36360
cccttatatc aagtccgacc atgccaaaaa tctgctcaag agcgccctcc accttcatgt   36420
acaagcagcg catcatgatt gcaaaaattc aggttcttca gagacctgta taagattcaa   36480
aatgggaaca ttaacaaaaa ttcctctgtc gcgcagatcc cttcgcaggg caagctgaac   36540
ataatcagac aggtccgaac ggaccagtga ggccaaatcc ccaccaggaa ccagatccag   36600
agaccctata ctgattatga cgcgcatact cggggctatg ctgaccagcg tagcgccgat   36660
gtaggcgtgc tgcatgggcg gcgagataaa atgcaaagtg ctggttaaaa aatcaggcaa   36720
agcctcgcgc aaaaaagcta acacatcata atcatgctca tgcaggtagt tgcaggtaag   36780
ctcaggaacc aaaacggaat aacacacgat tttcctctca aacatgactt cgcggatact   36840
gcgtaaaaca aaaaattata aataaaaaat taattaaata acttaaacat tggaagcctg   36900
tctcacaaca ggaaaaacca ctttaatcaa cataagacgg ccacgggca tgccggcata    36960 gccgtaaaaa aattggtccc cgtgattaac aagtaccaca gacagctccc cggtcatgtc   37020
gggggtcatc atgtgagact ctgtatacac gtctggattg tgaacatcag acaaacaaag   37080
aaatcgagcc acgtagcccg gaggtataat cacccgcagg cggaggtaca gcaaaacgac   37140
ccccatagga ggaatcacaa aattagtagg agaaaaaaat acataaacac cagaaaaacc   37200
ctgttgctga ggcaaaatag cgccctcccg atccaaaaca acataaagcg cttccacagg   37260
agcagccata acaaagaccc gagtcttacc agtaaaagaa aaagatctc tcaacgcagc     37320 accagcacca acacttcgca gtgtaaaagg ccaagtgccg agagagtata tataggaata   37380
aaaagtgacg taaacgggca aagtccaaaa aacgcccaga aaaccgcac gcgaacctac     37440 gccccgaaac gaaagccaaa aaacactaga cactcccttc cggcgtcaac ttccgctttc   37500
ccacgctacg tcacttgccc cagtcaaaca aactacatat cccgaacttc caagtcgcca   37560
cgcccaaaac accgcctaca cctcccccgcc cgccggcccg cccccaaacc cgcctcccgc   37620
cccgcgcccc gccccgcgcc gcccatctca ttatcatatt ggcttcaatc caaaataagg   37680
tatattattg atgatggttt aaacggatcc tctagagtcg acctgcaggc atgcaagctt   37740
gagtattcta tagtgtcacc taaatagctt ggcgtaatca tggtcatagc tgtttcctgt   37800
gtgaaattgt tatccgctca caattccaca acacatacga gccggaagca taagtgtaa   37860 agcctggggt gcctaatgag tgagctaact cacattaatt gcgttgcgct cactgcccgc   37920
tttccagtcg ggaaacctgt cgtgccagct gcattaatga atcggccaac gcgaacccct   37980
tgcggccgcc cgggccgtcg accaattctc atgtttgaca gcttatcatc gaatttctgc   38040
cattcatccg cttattatca cttattcagg cgtagcaacc aggcgtttaa gggcaccaat   38100
aactgcctta aaaaaattac gccccgccct gccactcatc gcagtactgt tgtaattcat   38160
taagcattct gccgacatgg aagccatcac aaacggcatg atgaacctga atcgccagcg   38220
gcatcagcac cttgtcgcct tgcgtataat atttgcccat ggtgaaaacg ggggcgaaga   38280
agttgtccat attggccacg tttaaatcaa aactggtgaa actcacccag ggattggctg   38340
agacgaaaaa catattctca ataaacccct tagggaaata ggccaggttt tcaccgtaac   38400
```

```
acgccacatc ttgcgaatat atgtgtagaa actgccggaa atcgtcgtgg tattcactcc   38460
agagcgatga aaacgtttca gtttgctcat ggaaaacggt gtaacaaggg tgaacactat   38520
cccatatcac cagctcaccg tcttttcattg ccatacggaa ttccggatga gcattcatca   38580
ggcgggcaag aatgtgaata aaggccggat aaaacttgtg cttatttttc tttacggtct   38640
ttaaaaaggc cgtaatatcc agctgaacgg tctggttata ggtacattga gcaactgact   38700
gaaatgcctc aaaatgttct ttacgatgcc attgggatat atcaacggtg gtatatccag   38760
tgattttttt ctccatttta gcttccttag ctcctgaaaa tctcgataac tcaaaaaata   38820
cgcccggtag tgatcttatt tcattatggt gaaagttgga acctcttacg tgccgatcaa   38880
cgtctcattt tcgccaaaag ttggcccagg gcttcccggt atcaacaggg acaccaggat   38940
ttatttattc tgcgaagtga tcttccgtca caggtattta ttcgcgataa gctcatggag   39000
cggcgtaacc gtcgcacagg aaggacagag aaagcgcgga tctgggaagt gacggacaga   39060
acggtcagga cctggattgg ggaggcggtt gccgccgctg ctgctgacgg tgtgacgttc   39120
tctgttccgg tcacaccaca tacgttccgc cattcctatg cgatgcacat gctgtatgcc   39180
ggtataccgc tgaaagttct gcaaagcctg atgggacata agtccatcag ttcaacggaa   39240
gtctacacga aggttttttgc gctggatgtg gctgcccggc accgggtgca gtttgcgatg   39300
ccggagtctg atgcggttgc gatgctgaaa caattatcct gagaataaat gccttggcct   39360
ttatatggaa atgtggaact gagtggatat gctgtttttg tctgttaaac agagaagctg   39420
gctgttatcc actgagaagc gaacgaaaca gtcgggaaaa tctcccatta tcgtagagat   39480
ccgcattatt aatctcagga gcctgtgtag cgtttatagg aagtagtgtt ctgtcatgat   39540
gcctgcaagc ggtaacgaaa acgatttgaa tatgccttca ggaacaatag aaatcttcgt   39600
gcggtgttac gttgaagtgg agcggattat gtcagcaatg gacagaacaa cctaatgaac   39660
acagaaccat gatgtggtct gtccttttac agccagtagt gctcgccgca gtcgagcgac   39720
agggcgaagc cctcgagtga gcgaggaagc accagggaac agcacttata tattctgctt   39780
acacacgatg cctgaaaaaa cttcccttgg ggttatccac ttatccacgg ggatattttt   39840
ataattattt ttttttatagt ttttagatct tcttttttag agcgccttgt aggcctttat   39900
ccatgctggt tctagagaag gtgttgtgac aaattgccct ttcagtgtga caaatcaccc   39960
tcaaatgaca gtcctgtctg tgacaaattg cccttaaccc tgtgacaaat tgccctcaga   40020
agaagctgtt ttttcacaaa gttatccctg cttattgact ctttttttatt tagtgtgaca   40080 atctaaaaac ttgtcacact tcacatggat ctgtcatggc ggaaacagcg gttatcaatc   40140
acaagaaacg taaaaatagc ccgcgaatcg tccagtcaaa cgacctcact gaggcggcat   40200
atagtctctc ccgggatcaa aaacgtatgc tgtatctgtt cgttgaccag atcagaaaat   40260
ctgatggcac cctacaggaa catgacggta tctgcgagat ccatgttgct aaatatgctg   40320
aaatattcgg attgacctct gcggaagcca gtaaggatat acggcaggca ttgaagagtt   40380
tcgcggggaa ggaagtggtt ttttatcgcc ctgaagagga tgccggcgat gaaaaaggct   40440
atgaatcttt tccttggttt atcaaacgtg cgcacagtcc atccagaggg ctttacagtg   40500
tacatatcaa cccatatctc attcccttct ttatcgggtt acagaaccgg tttacgcagt   40560
ttcggcttag tgaaacaaaa gaaatcacca atccgtatgc catgcgttta cgaatccc   40620 tgtgtcagta tcgtaagccg gatggctcag gcatcgtctc tctgaaaatc gactggatca   40680
tagagcgtta ccagctgcct caaagttacc agcgtatgcc tgacttccgc cgccgcttcc   40740
```

```
tgcaggtctg tgttaatgag atcaacagca gaactccaat gcgcctctca tacattgaga   40800
aaaagaaagg ccgccagacg actcatatcg tattttcctt ccgcgatatc acttccatga   40860
cgacaggata gtctgagggt tatctgtcac agatttgagg gtggttcgtc acatttgttc   40920
tgacctactg agggtaattt gtcacagttt tgctgtttcc ttcagcctgc atggattttc   40980
tcatactttt tgaactgtaa ttttttaagga agccaaattt gagggcagtt tgtcacagtt   41040
gatttccttc tctttcccott cgtcatgtga cctgatatcg ggggttagtt cgtcatcatt   41100
gatgagggtt gattatcaca gtttattact ctgaattggc tatccgcgtg tgtacctcta   41160
cctggagttt ttcccacggt ggatatttct tcttgcgctg agcgtaagag ctatctgaca   41220
gaacagttct tctttgcttc ctcgccagtt cgctcgctat gctcggttac acggctgcgg   41280
cgagcgctag tgataataag tgactgaggt atgtgctctt cttatctcct tttgtagtgt   41340
tgctcttatt ttaaacaact ttgcggtttt ttgatgactt tgcgattttg ttgttgcttt   41400
gcagtaaatt gcaagattta ataaaaaaac gcaaagcaat gattaaagga tgttcagaat   41460
gaaactcatg gaaacactta accagtgcat aaacgctggt catgaaatga cgaaggctat   41520
cgccattgca cagtttaatg atgacagccc ggaagcgagg aaaataaccc ggcgctggag   41580
aataggtgaa gcagcggatt tagttggggt ttcttctcag gctatcagag atgccgaaaa   41640
agcagggcga ctaccgcacc cggatatgga aattcgagga cgggttgagc aacgtgttgg   41700
ttatacaatt gaacaaatta atcatatgcg tgatgtgttt ggtacgcgat gcgacgtgc   41760
tgaagacgta tttccaccgg tgatcggggt tgctgcccat aaaggtggcg tttacaaaac   41820
ctcagtttct gttcatcttg ctcaggatct ggctctgaag gggctacgtg ttttgctcgt   41880
ggaaggtaac gaccccccagg gaacagcctc aatgtatcac ggatgggtac cagatcttca   41940
tattcatgca gaagacactc tcctgccttt ctatcttggg gaaaaggacg atgtcactta   42000
tgcaataaag cccacttgct ggccggggct tgacattatt ccttcctgtc tggctctgca   42060
ccgtattgaa actgagttaa tgggcaaatt tgatgaaggt aaactgccca ccgatccaca   42120
cctgatgctc cgactggcca ttgaaactgt tgctcatgac tatgatgtca tagttattga   42180
cagcgcgcct aacctgggta tcggcacgat taatgtcgta tgtgctgctg atgtgctgat   42240
tgttcccacg cctgctgagt tgtttgacta cacctccgca ctgcagttttt tcgatatgct   42300
tcgtgatctg ctcaagaacg ttgatcttaa agggttcgag cctgatgtac gtattttgct   42360
taccaaatac agcaatagta atggctctca gtccccgtgg atggaggagc aaattcggga   42420
tgcctgggga agcatggttc taaaaaatgt tgtacgtgaa acggatgaag ttggtaaagg   42480
tcagatccgg atgagaactg ttttttgaaca ggccattgat caacgctctt caactggtgc   42540
ctggagaaat gctctttcta tttgggaacc tgtctgcaat gaaattttcg atcgtctgat   42600
taaaccacgc tgggagatta gataatgaag cgtgcgcctg ttattccaaa acatacgctc   42660
aatactcaac cggttgaaga tacttcgtta tcgacaccag ctgccccgat ggtggattcg   42720
ttaattgcgc gcgtaggagt aatggctcgc ggtaatgcca ttactttgcc tgtatgtggt   42780
cgggatgtga agtttactct tgaagtgctc cggggtgata tgttgagaa gacctctcgg   42840
gtatggtcag gtaatgaacg tgaccaggag ctgcttactg aggacgcact ggatgatctc   42900
atcccttctt ttctactgac tggtcaacag acaccggcgt tcggtcgaag agtatctggt   42960
gtcatagaaa ttgccgatgg gagtcgccgt cgtaaagctg ctgcacttac cgaaagtgat   43020
tatcgtgttc tggttggcga gctggatgat gagcagatgg ctgcattatc cagattgggt   43080
aacgattatc gcccaacaag tgcttatgaa cgtggtcagc gttatgcaag ccgattgcag   43140
```

```
aatgaatttg ctggaaatat ttctgcgctg gctgatgcgg aaaatatttc acgtaagatt   43200
attacccgct gtatcaacac cgccaaattg cctaaatcag ttgttgctct tttttctcac   43260
cccggtgaac tatctgcccg gtcaggtgat gcacttcaaa aagcctttac agataaagag   43320
gaattactta agcagcaggc atctaacctt catgagcaga aaaaagctgg ggtgatattt   43380
gaagctgaag aagttatcac tcttttaact tctgtgctta aaacgtcatc tgcatcaaga   43440
actagtttaa gctcacgaca tcagtttgct cctggagcga cagtattgta taagggcgat   43500
aaaatggtgc ttaacctgga caggtctcgt gttccaactg agtgtataga gaaaattgag   43560
gccattctta aggaacttga aaagccagca ccctgatgcg accacgtttt agtctacgtt   43620
tatctgtctt tacttaatgt cctttgttac aggccagaaa gcataactgg cctgaatatt   43680
ctctctgggc ccactgttcc acttgtatcg tcggtctgat aatcagactg gaccacggt   43740 cccactcgta tcgtcggtct gattattagt ctgggaccac ggtcccactc gtatcgtcgg   43800
tctgattatt agtctgggac cacggtccca ctcgtatcgt cggtctgata atcagactgg   43860
gaccacggtc ccactcgtat cgtcggtctg attattagtc tgggaccatg gtcccactcg   43920 tatcgtcgg ctgattatta gtctgggacc acgtcccac tcgtatcgtc ggtctgatta   43980
ttagtctgga accacggtcc cactcgtatc gtcggtctga ttattagtct gggaccacgg   44040
tcccactcgt atcgtcggtc tgattattag tctgggacca cgatcccact cgtgttgtcg   44100
gtctgattat cggtctggga ccacggtccc acttgtattg tcgatcagac tatcagcgtg   44160
agactacgat tccatcaatg cctgtcaagg gcaagtattg acatgtcgtc gtaacctgta   44220
gaacggagta acctcggtgt gcggttgtat gcctgctgtg gattgctgct gtgtcctgct   44280
tatccacaac attttgcgca cggttatgtg gacaaaatac ctggttaccc aggccgtgcc   44340
ggcacgttaa ccgggctgca tccgatgcaa gtgtgtcgct gtcgacgagc tcgcgagctc   44400
ggacatgagg ttgccccgta ttcagtgtcg ctgatttgta ttgtctgaag ttgttttac   44460 gttaagttga tgcagatcaa ttaatacgat acctgcgtca taattgatta tttgacgtgg   44520
tttgatggcc tccacgcacg ttgtgatatg tagatgataa tcattatcac tttacgggtc   44580 cttttccggtg atccgacagg ttacggggcg gcgacctcgc gggttttcgc tatttatgaa   44640
aattttccgg tttaaggcgt ttccgttctt cttcgtcata acttaatgtt tttatttaaa   44700 atacccctctg aaaagaaagg aaacgacagg tgctgaaagc gagcttttg gcctctgtcg   44760 tttcctttct ctgtttttgt ccgtggaatg aacaatggaa gtccgagctc atcgctaata   44820
acttcgtata gcatacatta tacgaagtta tattcgatgc ggccgcaagg ggttcgcgtc   44880
agcgggtgtt ggcgggtgtc ggggctggct taactatgcg gcatcagagc agattgtact   44940
gagagtgcac catatgcgt gtgaaatacc gcacagatgc gtaaggagaa ataccgcat   45000 caggcgccat cgccattca ggctgcgcaa ctgttgggaa gggcgatcgg tgcgggcctc   45060
ttcgctatta cgccagctgg cgaaaggggg atgtgctgca aggcgattaa gttgggtaac   45120
gccagggttt tcccagtcac gacgttgtaa aacgacggcc agtgaattgt aatacgactc   45180
actatagggc gaattcgagc tcggtacccg gggatcctcg tttaaac              45227
```

<210> SEQ ID NO 10
<211> LENGTH: 37830
<212> TYPE: DNA
<213> ORGANISM: Simian adenovirus

<400> SEQUENCE: 10

```
catcatcaat aatatacctt attttggatt gaagccaata tgataatgag atgggcggcg      60
cggggcggga ggcgggtccg ggggcgggcc ggcgggcggg gcggtgtggc ggaagtggac     120
tttgtaagtg tggcggatgt gacttgctag tgccgggcgc ggtaaaagtg acgttttccg     180
tgcgcgacaa cgcccacggg aagtgacatt tttcccgcgg tttttaccgg atgttgtagt     240
gaatttgggc gtaaccaagt aagatttggc cattttcgcg ggaaaactga aacggggaag     300
tgaaatctga ttaatttcgc gttagtcata ccgcgtaata tttgtcgagg ccgagggac      360
tttggccgat tacgtggagg actcgcccag gtgttttttg aggtgaattt ccgcgttccg     420
ggtcaaagtc tccgttttat tattatagtc agctgacgcg gagtgtattt ataccctctg     480
atctcgtcaa gtggccactc ttgagtgcca gcgagtagag ttttctcctc tgccgctctc     540
cgctccgctc cgctcggctc tgacaccggg gaaaaaatga cacatttcac ctacgatggc     600
ggtgtgctca ccggccagct ggctgctgaa gtcctggaca ccctgatcga ggaggtattg     660
gccgataatt atcctccctc gactcctttt gagccaccta cacttcacga actctacgat     720
ctggatgtgg tggggcccag cgatccgaac gagcaggcgg tttccagttt ttttccagag     780
tccatgttgt tggccagcca ggagggggtc gaacttgaga cccctcctcc gatcgtggat     840
tcccccgatc cgccgcagct gactaggcag cccgagcgct gtgcgggacc tgagactatg     900
ccccagctgc tacctgaggt gatcgatctc acctgtaatg agtctggttt tccacccagc     960
gaggatgagg acgaagaggg tgagcagttt gtgttagatt ctgtgaaaca acccgggcga    1020
ggatgcaggt cttgtcaata tcaccggaaa aacacaggag actcccagat tatgtgttct    1080
ctgtgttata tgaagatgac ctgtatgttt atttacagta agtttatcat ctgtgggcag    1140
gtgggctata gtgtgggtgg tggtctttgg ggggtttttt aatatatgtc aggggttatg    1200
ctgaagactt ttttattgtg atttttaaag gtccagtgtc tgagcccgag caagaacctg    1260
aaccggagcc tgagccttct cgccccagga gaaagcctgt aatcttaact agacccagcg    1320
caccggtagc gagaggcctc agcagcgcgg agaccaccga ctccggtgct tcctcatcac    1380
ccccggagat tcacccccctg gtgcccctgt gtcccgttaa gcccgttgcc gtgagagtca    1440
gtgggcggcg gtctgctgtg gagtgcattg aggacttgct ttttgattca caggaacctt    1500
tggacttgag cttgaaacgc cccaggcatt aaacctggtc acctggactg aatgagttga    1560
cgcctatgtt tgcttttgaa tgacttaatg tgtatagata taaagagtg agataatgtt     1620
ttaattgcat ggtgtgttta acttgggcgg agtctgctgg gtatataagc ttccctgggc    1680
taaacttggt tacacttgac ctcatggagg cctgggagtg tttggagaac tttgccggag    1740
ttcgtgcctt gctggacgag agctctaaca ataccctctg gtggtggagg tatttgtggg    1800
gctctcccca gggcaagtta gtttgtagaa tcaaggagga ttacaagtgg gaatttgaag    1860
agcttttgaa atcctgtggt gagctattgg attctttgaa tctaggccac caggctctct    1920
tccaggagaa ggtcatcagg actttggatt ttttccacacc ggggcgcatt gcagccgcgg   1980
ttgcttttct agctttttg aaggatagat ggagcgaaga gacccacttg agttcgggct     2040
acgtcctgga ttttctggcc atgcaactgt ggagagcatg gatcagacac aagaacaggc    2100
tgcaactgtt gtcttccgtc cgcccgttgc tgattccggc ggaggagcaa caggccgggt    2160
cagaggaccg ggcccgtcgg gatccggagg agagggcacc gaggccgggc gagaggagcg    2220
cgctgaacct gggaaccggg ctgagcggcc atccacatcg ggagtgaatg tcgggcaggt    2280
ggtggatctt tttccagaac tgcggcggat tttgactatt agggaggatg ggcaatttgt    2340
taagggtctt aagagggaga gggggggcttc tgagcataac gaggaggcca gtaatttagc   2400
```

|  |  |  |  |  |
|---|---|---|---|---|
| ttttagcttg | atgaccagac | accgtccaga | gtgcatcact | tttcagcaga ttaaggacaa | 2460 |
| ttgtgccaat | gagttggatc | tgttgggtca | gaagtatagc | atagagcagc tgaccactta | 2520 |
| ctggctgcag | ccgggtgatg | atctggagga | agctattagg | gtgtatgcta aggtggccct | 2580 |
| gcggcccgat | tgcaagtaca | agctcaaggg | gctggtgaat | atcaggaatt gttgctacat | 2640 |
| ttctggcaac | ggggcggagg | tggagataga | gaccgaagac | agggtggctt tcagatgcag | 2700 |
| catgatgaat | atgtggccgg | gggtgctggg | catggacggg | gtggtgatta tgaatgtgag | 2760 |
| gttcacgggg | cccaacttta | acggcacggt | gttttggggg | aacaccaacc tggtcctgca | 2820 |
| cggggtgagc | ttctatgggt | ttaacaacac | ctgtgtggag | gcctggaccg atgtgaaggt | 2880 |
| ccgcggttgc | gccttttatg | gatgttggaa | ggccatagtg | agccgcccta agagcaggag | 2940 |
| ttccattaag | aaatgcttgt | ttgagaggtg | caccttgggg | atcctggccg agggcaactg | 3000 |
| cagggtgcgc | cacaatgtgg | cctccgagtg | cggttgcttc | atgctagtca gagcgtggc | 3060 |
| ggtaatcaag | cataatatgg | tgtgcggcaa | cagcgaggac | aaggcctcac agatgctgac | 3120 |
| ctgcacggat | ggcaactgcc | acttgctgaa | gaccatccat | gtaaccagcc acagccggaa | 3180 |
| ggcctggccc | gtgttcgagc | acaacttgct | gacccgctgc | tccttgcatc tgggcaacag | 3240 |
| gcgggggggtg | ttcctgcccct | atcaatgcaa | ctttagtcac | accaagatct tgctagagcc | 3300 |
| cgagagcatg | tccaaggtga | acttgaacgg | ggtgtttgac | atgaccatga agatctggaa | 3360 |
| ggtgctgagg | tacgacgaga | ccaggtcccg | gtgcagaccc | tgcgagtgcg ggggcaagca | 3420 |
| tatgaggaac | cagcccgtga | tgctggatgt | gaccgaggag | ctgaggacag accacttggt | 3480 |
| tctggcctgc | accagggccg | agtttggttc | tagcgatgaa | gacacagatt gaggtgggtg | 3540 |
| agtgggcgtg | gcctgggtg | gtcatgaaaa | tatataagtt | gggggtctta gggtctcttt | 3600 |
| atttgtgttg | cagagaccgc | cggagccatg | agcgggagca | gcagcagcag cagtagcagc | 3660 |
| agcgccttgg | atggcagcat | cgtgagccct | tatttgacga | cgcggatgcc ccactgggcc | 3720 |
| ggggtgcgtc | agaatgtgat | gggctccagc | atcgacggcc | gacccgtcct gcccgcaaat | 3780 |
| tccgccacgc | tgacctatgc | gaccgtcgcg | gggacgccgt | tggacgccac cgccgccgcc | 3840 |
| gccgccaccg | cagccgcctc | ggccgtgcgc | agcctggcca | cggactttgc attcctggga | 3900 |
| ccactggcga | cagggctac | ttctcgggcc | gctgctgccg | ccgttcgcga tgacaagctg | 3960 |
| accgccctgc | tggcgcagtt | ggatgcgctt | actcggaac | tgggtgacct ttctcagcag | 4020 |
| gtcatggccc | tgcgccagca | ggtctcctcc | ctgcaagctg | gcgggaatgc ttctcccaca | 4080 |
| aatgccgttt | aagataaata | aaaccagact | ctgtttggat | taaagaaag tagcaagtgc | 4140 |
| attgctctct | ttatttcata | attttccgcg | cgcgataggc | cctagaccag cgttctcggt | 4200 |
| cgttagggt | gcggtgtatc | ttctccagga | cgtggtagag | gtggctctgg acgttgagat | 4260 |
| acatgggcat | gagcccgtcc | cgggggtgga | ggtagcacca | ctgcagagct tcatgctccg | 4320 |
| gggtggtgtt | gtagatgatc | cagtcgtagc | aggagcgctg | gcatggtgc ctaaaaatgt | 4380 |
| ccttcagcag | caggccgatg | ccaggggga | ggcccttggt | gtaagtgttt acaaaacggt | 4440 |
| taagttggga | agggtgcatt | cggggagaga | tgatgtgcat | cttggactgt attttagat | 4500 |
| tggcgatgtt | tcccgcccaga | tccccttctgg | gattcatgtt | gtgcaggacc accagtacag | 4560 |
| tgtatccggt | gcacttgggg | aatttgtcat | gcagcttaga | gggaaaagcg tggaagaact | 4620 |
| tggagacgcc | tttgtggcct | cccagattt | ccatgcattc | gtccatgatg atggcaatgg | 4680 |
| gccccgcggga | ggcagcttgg | gcaaagatat | ttctgggggtc | gctgacgtcg tagttgtgtt | 4740 |

```
ccagggtgag gtcgtcatag gccatttta caaagcgcgg gcggagggtg cccgactggg    4800
ggatgatggt cccctctggc cctggggcgt agttgccctc gcagatctgc atttcccagg    4860
ccttaatctc ggaggggga atcatatcca cctgcggggc gatgaagaaa acggtttccg    4920
gagccgggga gattaactgg gatgagagca ggtttctaag cagctgtgat tttccacaac    4980
cggtgggccc ataaataaca cctataaccg gttgcagctg gtagtttaga gagctgcagc    5040
tgccgtcgtc ccgaggaggg ggggccacct cgttgagcat gtccctgacg cgcatgttct    5100
ccccgaccag atccgccaga aggcgctcgc cgcccaggga cagcagctct tgcaaggaag    5160
caaagttttt cagcggcttg aggccgtccg ccgtgggcat gttttttcagg gtctggctca    5220
gcagctccag gcggtcccag agctcggtga cgtgctctac ggcatctcta tccagcatat    5280
ctcctcgttt cgcgggttgg ggcgactttc gctgtagggc accaagcggt ggtcgtccag    5340
cggggccaga gtcatgtcct tccatgggcg cagggtcctc gtcagggtgg tctgggtcac    5400
ggtgaagggg tgcgctccgg gctgagcgct tgccaaggtg cgcttgaggc tggttctgct    5460
ggtgctgaag cgctgccggt cttcgccctg cgcgtcggcc aggtagcatt tgaccatggt    5520
gtcatagtcc agcccctccg cggcgtgtcc cttggcgcgc agcttgccct tggaggtggc    5580
gccgcacgag gggcagagca ggctcttgag cgcgtagagc ttggggggcga ggaagaccga    5640
ttcgggggag taggcgtccg cgccgcagac cccgcacacg gtctcgcact ccaccagcca    5700
ggtgagctcg gggcgcgccg ggtcaaaaac caggtttccc ccatgctttt tgatgcgttt    5760
cttacctcgg gtctccatga ggtggtgtcc ccgctcggtg acgaagaggc tgtccgtgtc    5820
tccgtagacc gacttgaggg gtcttttctc caggggggtc cctcggtctt cctcgtagag    5880
gaactcggac cactctgaga cgaaggcccg cgtccaggcc aggacgaagg aggctatgtg    5940
ggaggggtag cggtcgttgt ccactagggg gtccaccttc tccaaggtgt gaagacacat    6000
gtcgccttcc tcggcgtcca ggaaggtgat tggcttgtag gtgtaggcca cgtgaccggg    6060
ggttcctgac gggggggtat aaaagggggt ggggcgcgc tcgtcgtcac tctcttccgc    6120
atcgctgtct gcgagggcca gctgctgggg tgagtattcc ctctcgaagg cgggcatgac    6180
ctccgcgctg aggttgtcag tttccaaaaa cgaggaggat ttgatgttca cctgtcccga    6240
ggtgatacct ttgagggtac ccgcgtccat ctggtcagaa aacacgatct ttttattgtc    6300
cagcttggtg gcgaacgacc cgtagagggc gttggagagc agcttggcga tggagcgcag    6360
ggtctggttc ttgtccctgt cggcgcgctc cttggccgcg atgttgagct gcacgtactc    6420
gcgcgcgacg cagcgccact cggggaagac ggtggtgcgc tcgtcgggca ccaggcgcac    6480
gcgccagccg cggttgtgca gggtgaccag gtccacgctg gtggcgacct cgccgcgcag    6540
gcgctcgttg gtccagcaga gacggccgcc cttgcgcgag cagaaggggg caggggggtc    6600
gagctgggtc tcgtccgggg ggtccgcgtc cacggtgaaa accccggggc gcaggcgcgc    6660
gtcgaagtag tctatcttgc aaccttgcat gtccagcgcc tgctgccagt cgcgggcggc    6720
gagcgcgcgc tcgtaggggt tgagcggcgg gccccaggga tggggtggg tgagtgcgga    6780
ggcgtacatg ccgcagatgt catagacgta gaggggctcc cgcaggaccc cgatgtaggt    6840
ggggtagcag cggccgccgc ggatgctggc gcgcacgtag tcatacagct cgtgcgaggg    6900
ggcgaggagg tcggggccca ggttggtgcg ggcggggcgc tccgcgcgga agacgatctg    6960
cctgaagatg gcatgcgagt tggaagagat ggtggggcgc tggaagacgt tgaagctggc    7020
gtcctgcagg ccgacggcgt cgcgcacgaa ggaggcgtag gagtcgcgca gcttgtgtac    7080
cagctcggcg gtgacctgca cgtcgagcgc gcagtagtcg agggtctcgc ggatgatgtc    7140
```

```
atatttagcc tgccccttct ttttccacag ctcgcggttg aggacaaact cttcgcggtc    7200
tttccagtac tcttggatcg ggaaaccgtc cggttccgaa cggtaagagc ctagcatgta    7260
gaactggttg acggcctggt aggcgcagca gcccttctcc acggggaggg cgtaggcctg    7320
cgcggccttg cggagcgagg tgtgggtcag ggcgaaggtg tccctgacca tgactttgag    7380
gtactggtgc ttgaagtcgg agtcgtcgca gccgccccgc tcccagagcg agaagtcggt    7440
gcgcttcttg gagcggggt tgggcagagc gaaggtgaca tcgttgaaga ggattttgcc     7500 cgcgcgggc atgaagttgc gggtgatgcg gaagggcccc ggcacttcag agcggttgtt     7560
gatgacctgg gcggcgagca cgatctcgtc gaagccgttg atgttgtggc ccacgatgta    7620
gagttccagg aagcggggcc ggcccttttac ggtgggcagc ttctttagct cttcgtaggt   7680
gagctcctcg ggcgaggcga ggccgtgctc ggccagggcc cagtccgcga ggtgcgggtt    7740
gtctctgagg aaggacttcc agaggtcgcg ggccaggagg gtctgcaggc ggtctctgaa    7800
ggtcctgaac tggcggccca cggccatttt ttcggggtg atgcagtaga aggtgagggg     7860
gtcttgctgc cagcggtccc agtcgagctg cagggcgagg tcgcgcgcgg cggtgaccag    7920
gcgctcgtcg cccccgaatt tcatgaccag catgaagggc acgagctgct ttccgaaggc    7980
ccccatccaa gtgtaggtct ctacatcgta ggtgacaaag aggcgctccg tgcgaggatg    8040
cgagccgatc gggaagaact ggatctcccg ccaccagttg gaggagtggc tgttgatgtg    8100
gtggaagtag aagtcccgtc gccgggccga acactcgtgc tggcttttgt aaaagcgagc    8160
gcagtactgg cagcgctgca cgggctgtac ctcatgcacg agatgcacct ttcgcccgcg    8220
cacgaggaag ccgaggggaa atctgagccc cccgcctggc tcgcggcatg gctggttctc    8280
ttctactttg gatgcgtgtc cgtctccgtc tggctcctcg aggggtgtta cggtggagcg    8340
gaccaccacg ccgcgcgagc cgcaggtcca gatatcggcg cgcggcggtc ggagtttgat    8400
gacgacatcg cgcagctggg agctgtccat ggtctggagc tcccgcggcg gcggcaggtc   8460
agccgggagt tcttgcaggt tcacctcgca gagtcgggcc agggcgcggg gcaggtctag    8520
gtggtacctg atctctaggg gcgtgttggt ggcggcgtcg atggcttgca ggagcccgca    8580
gccccggggg gcgacgacgg tgccccgcgg ggtggtggtg gtggtggcgg tgcagctcag    8640
aagcggtgcc gcgggcgggc ccccggaggt aggggggct ccggtcccgc gggcaggggc     8700
ggcagcggca cgtcggcgtg gagcgcgggc aggagttggt gctgtgcccg gaggttgctg    8760
gcgaaggcga cgacgcggcg gttgatctcc tggatctggc gcctctgcgt gaagacgacg    8820
ggcccggtga gcttgaacct gaaagagagt tcgacagaat caatctcggt gtcattgacc    8880
gcggcctggc gcaggatctc ctgcacgtct cccgagttgt cttggtaggc gatctcggcc    8940
atgaactgct cgatctcttc ctcctggagg tctccgcgtc cggcgcgttc cacggtggcc    9000
gccaggtcgt tggagatgcg ccccatgagc tgcgagaagg cgttgagtcc gccctcgttc    9060
cagactcggc tgtagaccac gccccctgg tcatcgcggg cgcgcatgac cacctgcgcg     9120
aggttgagct ccacgtgccg cgcgaagacg cgtagttgc gcagacgctg gaagaggtag     9180
ttgagggtgg tggcggtgtg ctcggccacg aagaagttca tgaccagcg cgcaacgtg      9240 gattcgttga tgtcccccaa ggcctccagc cgttccatgg cctcgtagaa gtccacggcg    9300
aagttgaaaa actgggagtt gcgcgccgac acggtcaact cctcctccag aagacggatg    9360
agctcggcga cggtgtcgcg cacctcgcgc tcgaaggcta tggggatctc ttcctccgct    9420
agcatcacca cctcctcctc ttcctcctct tctggcactt ccatgatggc ttcctcctct    9480
```

```
tcgggggtg gcggcggcgg cggtgggga gggggcgctc tgcgccggcg gcggcgcacc    9540
gggaggcggt ccacgaagcg cgcgatcatc tccccgcggc ggcggcgcat ggtctcggtg    9600
acggcgcggc cgttctcccg ggggcgcagt tggaagacgc cgccggacat ctggtgctgg    9660
ggcgggtggc cgtgaggcag cgagacggcg ctgacgatgc atctcaacaa ttgctgcgta    9720
ggtacgccgc cgagggacct gagggagtcc atatccaccg gatccgaaaa cctttcgagg    9780
aaggcgtcta accagtcgca gtcgcaaggt aggctgagca ccgtggcggg cggcggggg    9840
tgggggagt gtctggcgga ggtgctgctg atgatgtaat tgaagtaggc ggacttgaca    9900
cggcggatgg tcgacaggag caccatgtcc ttgggtccgg cctgctggat gcggaggcgg    9960
tcggctatgc cccaggcttc gttctggcat cggcgcaggt ccttgtagta gtcttgcatg   10020
agcctttcca ccggcacctc ttctccttcc tcttctgctt cttccatgtc tgcttcggcc   10080
ctggggcggc gccgcgcccc cctgccccc atgcgcgtga ccccgaaccc cctgagcggt   10140
tggagcaggg ccaggtcggc gacgacgcgc tcggccagga tggcctgctg cacctgcgtg   10200
agggtggttt ggaagtcatc caagtccacg aagcggtggt aggcgccgt gttgatggtg   10260
taggtgcagt tggccatgac ggaccagttg acggtctggt ggcccggttg cgacatctcg   10320
gtgtacctga gtcgcgagta ggcgcgggag tcgaagacgt agtcgttgca agtccgcacc   10380
aggtactggt agcccaccag gaagtgcggc ggcggctggc ggtagagggg ccagcgcagg   10440
gtggcggggg ctccggggc caggtcttcc agcatgaggc ggtggtaggc gtagatgtac   10500
ctggacatcc aggtgatacc cgcggcggtg gtggaggcgc gcgggaagtc gcgcacccgg   10560
ttccagatgt tgcgcagggg cagaaagtgc tccatggtag gcgtgctctg tccagtcaga   10620
cgcgcgcagt cgttgatact ctagaccagg gaaaacgaaa gccggtcagc gggcactctt   10680
ccgtggtctg gtgaatagat cgcaagggta tcatggcgga gggcctcggt tcgagccccg   10740
ggtccggggcc ggacggtccg ccatgatcca cgcggttacc gcccgcgtgt cgaacccagg   10800
tgtgcgacgc cagacaacgg tggagtgttc cttttggcgt ttttctggcc gggcgccggc   10860
gccgcgtaag agactaagcc gcgaaagcga agcagtaagg tggctcgctc cccgtagccg   10920
gagggatcct tgctaagggt tgcgttgcgg cgaaccccgg ttcgaatccc gtactcgggc   10980
cggccggacc cgcggctaag gtgttggatt ggcctccccc tcgtataaag accccgcttg   11040
cggattgact ccggacacgg ggacgagccc cttttatttt tgctttcccc agatgcatcc   11100
ggtgctgcgg cagatgcgcc ccccgcccca gcagcagcaa caacaccagc aagagcggca   11160
gcaacagcag cgggagtcat gcagggcccc ctcacccacc ctcggcgggc cggccacctc   11220
ggcgtccgcg gccgtgtctg gcgcctgcgg cggcggcggg gggccggctg acgaccccga   11280
ggagcccccg cggcgcaggg ccagacacta cctggacctg gaggagggcg agggcctggc   11340
gcggctgggg gcgccgtctc ccgagcgcca cccgcgggtg cagctgaagc gcgactcgcg   11400
cgaggcgtac gtgcctcggc agaacctgtt cagggaccgc gcgggcgagg agcccgagga   11460
gatgcgggac aggaggttca gcgcagggcg ggagctgcgg caggggctga ccgcgagcg   11520
gctgctgcgc gaggaggact ttgagcccga cgcgcggacg gggatcagcc ccgcgcgcgc   11580
gcacgtggcg gccgccgacc tggtgacggc gtacgagcag acggtgaacc aggagatcaa   11640
cttccaaaag agtttcaaca accacgtgcg cacgctggtg gcgcgcgagg aggtgaccat   11700
cgggctgatg cacctgtggg actttgtaag cgcgctggtg cagaaccccca acagcaagcc   11760
tctgacggcg cagctgttcc tgatagtgca gcacagcagg acaacgagg cgtttaggga   11820
cgcgctgctg aacatcaccg agcccgaggg tcggtggctg ctggacctga ttaacatcct   11880
```

```
gcagagcata gtggtgcagg agcgcagcct gagcctggcc gacaaggtgg cggccatcaa    11940
ctactcgatg ctgagcctgg gcaagtttta cgcgcgcaag atctaccaga cgccgtacgt    12000
gcccatagac aaggaggtga agatcgacgg tttttacatg cgcatggcgc tgaaggtgct    12060
caccctgagc gacgacctgg gcgtgtaccg caacgagcgc atccacaagg ccgtgagcgt    12120
gagccggcgg cgcgagctga gcgaccgcga gctgatgcac agcctgcagc gggcgctggc    12180
gggcgccgga gcggcgaca gggaggcgga gtcctacttc gatgcggggg cggacctgcg    12240
ctgggcgccc agccggcggg ccctggaggc cgcggggggtc cgcgaggact atgacgagga    12300
cggcgaggag gatgaggagt acgagctaga ggagggcgag tacctggact aaaccgcggg    12360
tggtgtttcc ggtagatgca agacccgaac gtggtggacc cggcgctgcg ggcggctctg    12420
cagagccagc cgtccggcct taactcctca gacgactggc gacaggtcat ggaccgcatc    12480
atgtcgctga cggcgcgtaa cccggacgcg ttccggcagc agccgcaggc caacaggctc    12540
tccgccatcc tggaggcggt ggtgcctgcg cgctcgaacc ccacgcacga aaggtgctg    12600 gccatagtga acgcgctggc cgagaacagg gccatccgcc cggacgaggc cgggctggtg    12660
tacgacgcgc tgctgcagcg cgtggcccgc tacaacagcg gcaacgtgca gaccaacctg    12720
gaccggctgg tggggacgt gcgcgaggcg gtggcgcagc gcgagcgcgc ggatcggcag    12780
ggcaacctgg gctccatggt ggcgctgaat gccttcctga gcacgcagcc ggccaacgtg    12840
ccgcgggggc aggaagacta caccaacttt gtgagcgcgc tgcggctgat ggtgaccgag    12900
accccccaga gcgaggtgta ccagtcgggc ccggactact tcttccagac cagcagacag    12960
ggcctgcaga cggtgaacct gagccaggct ttcaagaacc tgcggggggct gtggggcgtg    13020 aaggcgccca ccggcgaccg ggcgacggtg tccagcctgc tgacgcccaa ctcgcgcctg    13080
ctgctgctgc tgatcgcgcc gttcacggac agcggcagcg tgtcccggga cacctacctg    13140
gggcacctgc tgaccctgta ccgcgaggcc atcgggcagg cgcaggtgga cgagcacacc    13200
ttccaggaga tcaccagcgt gagccgcgcg ctggggcagg aggacacgag cagcctggag    13260
gcgactctga actacctgct gaccaaccgg cggcagaaga ttccctcgct gcacagcctg    13320
acctccgagg aggagcgcat cttgcgctac gtgcagcaga gcgtgagcct gaacctgatg    13380
cgcgacgggg tgacgcccag cgtggcgctg gacatgaccg cgcgcaacat ggaaccgggc    13440
atgtacgccg cgcaccggcc ttacatcaac cgcctgatgg actacctgca tcgcgcggcg    13500
gccgtgaacc ccgagtactt taccaacgcc atcctgaacc cgcactggct cccgccgccc    13560
gggttctaca gcggggggctt cgaggtcccg gagaccaacg atggcttcct gtgggacgac    13620
atggacgaca gcgtgttctc cccgcggccg caggcgctgg cggaagcgtc cctgctgcgt    13680
cccaagaagg aggaggagga ggaggcgagt cgccgccgcg gcagcagcgg cgtggcttct    13740
ctgtccgagc tgggggcggc agccgccgcg cgccccgggt ccctgggcgg cagccccttt    13800
ccgagcctgg tggggtctct gcacagcgag cgcaccaccc gccctcggct gctgggcgag    13860
gacgagtacc tgaataactc cctgctgcag ccggtgcggg agaaaaacct gcctcccgcc    13920
ttccccaaca acgggataga gagcctggtg gacaagatga gcagatggaa gacctatgcg    13980
caggagcaca gggacgcgcc tgcgctccgg ccgcccacgc ggcgccagcg ccacgaccgg    14040
cagcgggggc tggtgtggga tgacgaggac tccgcggacg atagcagcgt gctggacctg    14100
ggagggagcg gcaacccgtt cgcgcacctg cgccccccgcc tggggaggat gttttaaaaa    14160
aaaaaaaaaa aagcaagaag catgatgcaa aaattaaata aaactcacca aggccatggc    14220
```

-continued

```
gaccgagcgt tggtttcttg tgttcccttc agtatgcggc gcgcggcgat gtaccaggag    14280
ggacctcctc cctcttacga gagcgtggtg ggcgcggcgg cggcggcgcc ctcttctccc    14340
tttgcgtcgc agctgctgga gccgccgtac gtgcctccgc gctacctgcg gcctacgggg    14400
gggagaaaca gcatccgtta ctcggagctg gcgcccctgt tcgacaccac ccgggtgtac    14460
ctggtggaca acaagtcggc ggacgtggcc tccctgaact accagaacga ccacagcaat    14520
tttttgacca cggtcatcca gaacaatgac tacagcccga gcgaggccag cacccagacc    14580
atcaatctgg atgaccggtc gcactggggc ggcgacctga aaaccatcct gcacaccaac    14640
atgcccaacg tgaacgagtt catgttcacc aataagttca aggcgcgggt gatggtgtcg    14700
cgctcgcaca ccaaggaaga ccgggtggag ctgaagtacg agtgggtgga gttcgagctg    14760
ccagagggca actactccga gaccatgacc attgacctga tgaacaacgc gatcgtggag    14820
cactatctga aagtgggcag gcagaacggg gtcctggaga gcgacatcgg ggtcaagttc    14880
gacaccagga acttccgcct ggggctggac cccgtgaccg ggctggttat gcccggggtg    14940
tacaccaacg aggccttcca tcccgacatc atcctgctgc ccggctgcgg ggtggacttc    15000
acttacagcc gcctgagcaa cctcctgggc atccgcaagc ggcagcccct tccaggagggc    15060 ttcaggatca cctacgagga cctggagggg ggcaacatcc ccgcgctcct cgatgtggag    15120
gcctaccagg atagcttgaa ggaaaatgag gcgggacagg aggataccgc ccccgccgcc    15180
tccgccgccc ccgagcaggg cgaggatgct gctgacaccg cggccgcgga cggggcagag    15240
gccgaccccg ctatggtggt ggaggctccc gagcaggagg aggacatgaa tgacagtgcg    15300
gtgcgcggag acaccttcgt cacccggggg gaggaaaagc aagcggaggc cgaggccgcg    15360
gccgaggaaa agcaactggc ggcagcagcg gcggcggcgg cgttggccgc ggcggaggct    15420
gagtctgagg ggaccaagcc cgccaaggag cccgtgatta gcccctgac cgaagatagc    15480 aagaagcgca gttacaacct gctcaaggac agcaccaaca ccgcgtaccg cagctggtac    15540
ctggcctaca actacggcga cccgtcgacg ggggtgcgct cctggaccct gctgtgcacg    15600
ccggacgtga cctgcggctc ggagcaggtg tactggtcgc tgcccgacat gatgcaagac    15660
cccgtgacct tccgctccac gcggcaggtc agcaacttcc cggtggtggg cgccgagctg    15720
ctgcccgtgc actccaagag cttctacaac gaccaggccg tctactccca gctcatccgc    15780
cagttcacct ctctgaccca cgtgttcaat cgctttcctg agaaccagat tctggcgcgc    15840
ccgcccgccc ccaccatcac caccgtcagt gaaaacgttc ctgctctcac agatcacggg    15900
acgctaccgc tgcgcaacag catcggagga gtccagcgag tgaccgttac tgacgccaga    15960
cgccgcacct gcccctacgt ttacaaggcc ttgggcatag tctcgccgcg cgtcctttcc    16020
agccgcactt tttgagcaac accaccatca tgtccatcct gatctcaccc agcaataact    16080
ccggctgggg actgctgcgc gcgcccagca agatgttcgg aggggcgagg aagcgttccg    16140
agcagcaccc cgtgcgcgtg cgcgggcact tccgcgcccc ctggggagcg cacaaacgcg    16200
gccgcgcggg gcgcaccacc gtggacgacg ccatcgactc ggtggtggag caggcgcgca    16260
actacaggcc cgcggtctct accgtggacg cggccatcca gaccgtggtg cggggcgcgc    16320
ggcggtacgc caagctgaag agccgccgga agcgcgtggc ccgccgccac cgccgccgac    16380
ccggggccgc cgccaaacgc gccgccgcgg ccctgcttcg ccgggccaag cgcacgggcc    16440
gccgcgccgc catgagggcc gcgccgcgct tggccgccgg catcaccgcc gccaccatgg    16500 cccccgtac ccgaagacgc gcggccgccg ccgccgccgc cgccatcagt gacatggcca    16560
gcaggcgccg gggcaacgtg tactgggtgc gcgactcggt gaccggcacg cgcgtgcccg    16620
```

```
tgcgcttccg cccccccgcgg acttgagatg atgtgaaaaa acaacactga gtctcctgct   16680
gttgtgtgta tcccagcggc ggcggcgcgc gcagcgtcat gtccaagcgc aaaatcaaag   16740
aagagatgct ccaggtcgtc gcgccggaga tctatgggcc cccgaagaag aagagcagg    16800
attcgaagcc ccgcaagata aagcgggtca aaaagaaaaa gaaagatgat gacgatgccg   16860
atggggaggt ggagttcctg cgcgccacgg cgcccaggcg cccggtgcag tggaagggcc   16920
ggcgcgtaaa gcgcgtcctg cgccccggca ccgcggtggt cttcacgccc ggcgagcgct   16980
ccacccggac tttcaagcgc gtctatgacg aggtgtacgg cgacgaagac ctgctggagc   17040
aggccaacga gcgcttcgga gagtttgctt acgggaagcg tcagcgggcg ctggggaagg   17100
aggacctgct ggcgctgccg ctggaccagg gcaaccccac ccccagtctg aagcccgtga   17160
ccctgcagca ggtgctgccg agcagcgcac cctccgaggc gaagcggggt ctgaagcgcg   17220
agggcggcga cctggcgccc accgtgcagc tcatggtgcc caagcggcag aggctggagg   17280
atgtgctgga gaaaatgaaa gtagaccccg gtctgcagcc ggacatcagg gtccgcccca   17340
tcaagcaggt ggcgccgggc ctcggcgtgc agaccgtgga cgtggtcatc cccaccggca   17400
actccccgc cgccgccacc actaccgctg cctccacgga catggagaca cagaccgatc   17460
ccgccgcagc cgcagccgca gccgccgccg cgacctcctc ggcggaggtg cagacggacc   17520
cctggctgcc gccggcgatg tcagctcccc gcgcgcgtcg cgggcgcagg aagtacggcg   17580
ccgccaacgc gctcctgccc gagtacgcct tgcatccttc catcgcgccc acccccggct   17640
accgaggcta tacctaccgc ccgcgaagag ccaaggggttc caccccgccgt ccccgccgac   17700
gcgccgccgc caccacccgc cgccgccgcc gcagacgcca gccgcactg gctccagtct   17760
ccgtgaggaa agtggcgcgc gacggacaca ccctggtgct gccccagggcg cgctaccacc   17820
ccagcatcgt ttaaaagcct gttgtggttc ttgcagatat ggccctcact tgccgcctcc   17880
gtttcccggt gccgggatac cgaggaggaa gatcgcgccg caggagggggt ctggccggcc   17940
gcggcctgag cggaggcagc cgccgcgcgc accgcggcg acgcgccacc agccgacgca   18000
tgcgcggcgg ggtgctgccc ctgttaatcc ccctgatcgc cgcggcgatc ggcgccgtgc   18060
ccgggatcgc ctccgtggcc ttgcaagcgt cccagaggca ttgacagact tgcaaacttg   18120
caaatatgga aaaaaaaacc ccaataaaaa agtctagact ctcacgctcg cttggtcctg   18180
tgactatttt gtagaatgga agacatcaac tttgcgtcgc tggccccgcg tcacggctcg   18240
cgcccgttcc tgggacactg gaacgatatc ggcaccagca acatgagcgg tggcgccttc   18300
agttggggct ctctgtggag cggcattaaa agtatcgggt ctgccgttaa aaattacggc   18360
tcccgggcct ggaacagcag cacgggccag atgttgagag acaagttgaa agagcagaac   18420
ttccagcaga aggtggtgga gggcctggcc tccggcatca acggggtggt ggacctggcc   18480
aaccaggccg tgcagaataa gatcaacagc agactggacc cccggccgcc ggtggaggag   18540
gtgccgccgg cgctggagac ggtgtccccc gatgggcgtg gcgagaagcg cccgcggccc   18600
gatagggaag agaccactct ggtcacgcag accgatgagc cgcccccgta tgaggaggcc   18660
ctgaagcaag gtctgcccac cacgcggccc atcgcgccca tggccaccgg ggtggtgggc   18720
cgccacaccc ccgccacgct ggacttgcct ccgcccgccg atgtgccgca gcagcagaag   18780
gcggcacagc cggggcccgcc cgcgaccgcc tcccgttcct ccgccggtcc tctgcgccgc   18840
gcggccagcg gccccgcgg gggggtcgcg aggcacggca actggcagag cacgctgaac   18900
agcatcgtgg gtctgggggt gcggtccgtg aagcgccgcc gatgctactg aatagcttag   18960
```

```
ctaacgtgtt gtatgtgtgt atgcgcccta tgtcgccgcc agaggagctg ctgagtcgcc    19020
gccgttcgcg cgcccaccac caccgccact ccgcccctca agatggcgac cccatcgatg    19080
atgccgcagt ggtcgtacat gcacatctcg ggccaggacg cctcggagta cctgagcccc    19140
gggctggtgc agttcgcccg cgccaccgag agctacttca gcctgagtaa caagtttagg    19200
aaccccacgg tggcgcccac gcacgatgtg accaccgacc ggtctcagcg cctgacgctg    19260
cggttcattc ccgtggaccg cgaggacacc gcgtactcgt acaaggcgcg gttcaccctg    19320
gccgtgggcg acaaccgcgt gctggacatg gcctccacct actttgacat ccgcggggtg    19380
ctggaccggg gtcccacttt caagccctac tctggcaccg cctacaactc cctgcccccc    19440
aagggcgctc ccaactcctg cgagtgggag caagaggaaa ctcaggcagt tgaagaagca    19500
gcagaagagg aagaagaaga tgctgacggt caagctgagg aagagcaagc agctaccaaa    19560
aagactcatg tatatgctca ggctcccctt tctggcgaaa aaattagtaa agatggtctg    19620
caaataggaa cggacgctac agctacagaa caaaaaccta tttatgcaga ccctacattc    19680
cagcccgaac cccaaatcgg ggagtcccag tggaatgagg cagatgctac agtcgccggc    19740
ggtagagtgc taaagaaatc tactcccatg aaaccatgct atggttccta tgcaagaccc    19800
acaaatgcta atggaggtca gggtgtacta acggcaaatg cccagggaca gctagaatct    19860
caggttgaaa tgcaattctt ttcaacttct gaaaacgccc gtaacgaggc taacaacatt    19920
cagcccaaat tggtgctgta tagtgaggat gtgcacatgg agaccccgga tacgcacctt    19980
tcttacaagc ccgcaaaaag cgatgacaat tcaaaaatca tgctgggtca gcagtccatg    20040
cccaacagac ctaattacat cggcttcaga gacaacttta tcggcctcat gtattacaat    20100
agcactggca acatgggagt gcttgcaggt caggcctctc agttgaatgc agtggtggac    20160
ttgcaagaca gaaacacaga actgtcctac cagctcttgc ttgattccat gggtgacaga    20220
accagatact tttccatgtg gaatcaggca gtggacagtt atgacccaga tgttagaatt    20280
attgaaaatc atggaactga agacgagctc cccaactatt gtttccctct gggtggcata    20340
ggggtaactg acacttacca ggctgttaaa accaacaatg gcaataacgg gggccaggtg    20400
acttggacaa aagatgaaac ttttgcagat cgcaatgaaa taggggtggg aaacaatttc    20460
gctatggaga tcaacctcag tgccaacctg tggagaaact tcctgtactc caacgtggcg    20520
ctgtacctac cagacaagct taagtacaac ccctccaatg tggacatctc tgacaacccc    20580
aacacctacg attacatgaa caagcgagtg gtggcccggg gctggtgga ctgctacatc    20640
aacctgggcg cgcgctggtc gctggactac atggacaacg tcaaccccttt caaccaccac    20700
cgcaatgcgg gcctgcgcta ccgctccatg ctcctgggca cgggcgcta cgtgcccttc    20760
cacatccagg tgccccagaa gttctttgcc atcaagaacc tcctcctcct gccgggctcc    20820
tacacctacg agtggaactt caggaaggat gtcaacatgg tcctccagag ctctctgggt    20880
aacgatctca gggtggacgg ggccagcatc aagttcgaga gcatctgcct ctacgccacc    20940
ttcttcccca tggcccacaa cacggcctcc acgctcgagg ccatgctcag gaacgacacc    21000
aacgaccagt ccttcaatga ctacctctcc gccgccaaca tgctctaccc catacccgcc    21060
aacgccacca acgtccccat ctccatcccc tcgcgcaact gggcggcctt ccgcggctgg    21120
gccttcaccc gcctcaagac caaggagacc cctcctggg ctcgggatt cgaccctac    21180
tacacctact cgggctccat tccctacctg gacggcacct tctacctcaa ccacactttc    21240
aagaaggtct cggtcacctt cgactcctcg gtcagctggc cggcaacga ccgtctgctc    21300
acccccaacg agttcgagat caagcgctcg gtcgacgggg agggctacaa cgtggcccag    21360
```

```
tgcaacatga ccaaggactg gttcctggtc cagatgctgg ccaactacaa catcggctac    21420
cagggcttct acatcccaga gagctacaag gacaggatgt actccttctt caggaacttc    21480
cagcccatga gccggcaggt ggtggaccag accaagtaca aggactacca ggaggtgggc    21540
atcatccacc agcacaacaa ctcgggcttc gtgggctacc tcgcccccac catgcgcgag    21600
ggacaggcct accccgccaa cttccccta tccgctcatag gcaagaccgc ggtcgacagc    21660
atcacccaga aaaagttcct ctgcgaccgc accctctggc gcatcccctt ctccagcaac    21720
ttcatgtcca tgggtgcgct ctcggacctg gccagaact tgctctacgc caactccgcc    21780
cacgccctcg acatgacctt cgaggtcgac cccatggacg agcccaccct tctctatgtt    21840
ctgttcgaag tctttgacgt ggtccgggtc accagccgc accgcggcgt catcgagacc    21900
gtgtacctgc gtacgccctt ctcggccggc aacgccacca cctaaagaag caagccgcag    21960
tcatcgccgc ctgcatgccg tcgggttcca ccgagcaaga gctcagggcc atcgtcagag    22020
acctgggatg cgggccctat ttttggggca ccttcgacaa gcgcttccct ggctttgtct    22080
ccccacacaa gctggcctgc gccatcgtca acacggccgg ccgcgagacc ggggcgtgc    22140 actggctggc cttcgcctgg aacccgcgct ccaaaacatg cttcctcttt gacccttcg    22200 gcttttcgga ccagcggctc aagcaaatct acgagttcga gtacgagggc ttgctgcgtc    22260
gcagcgccat cgcctcctcg cccgaccgct gcgtcaccct cgaaaagtcc acccagaccg    22320
tgcaggggcc cgactcggcc gcctgcggtc tcttctgctg catgtttctg cacgcctttg    22380
tgcactggcc tcagagtccc atggaccgca accccaccat gaacttgctg acggggtgc    22440 ccaactccat gctccagagc cccaggtcg agcccaccct gcgccgcaac caggagcagc    22500
tctacagctt cctggagcgc cactcgcctt acttccgccg ccacagcgca cagatcagga    22560
gggccacctc cttctgccac ttgcaagaga tgcaagaagg gtaataacga tgtacacact    22620
ttttttctca ataaatggca tcttttat ttatacaagct ctctggggta ttcatttccc    22680
accaccaccc gccgttgtcg ccatctggct ctatttagaa atcgaaaggg ttctgccggg    22740
agtcgccgtg cgccacgggc agggacacgt tgcgatactg gtagcgggtg ccccacttga    22800
actcgggcac caccaggcga ggcagctcgg ggaagttttc gctccacagg ctgcgggtca    22860
gcaccagcgc gttcatcagg tcgggcgccg agatcttgaa gtcgcagttg gggccgccgc    22920
cctgcgcgcg cgagttgcgg tacaccgggt tgcagcactg gaacaccaac agcgccgggt    22980
gcttcacgct ggccagcacg ctgcggtcgg agatcagctc ggcgtccagg tcctccgcgt    23040
tgctcagcgc gaacgggtc atcttgggca cttgccgccc caggaagggc gcgtgccccg    23100
gtttcgagtt gcagtcgcag cgcagcggga tcagcaggtg cccgtgcccg gactcggcgt    23160
tggggtacag cgcgcgcatg aaggcctgca tctggcggaa ggccatctgg gccttggcgc    23220
cctccgagaa gaacatgccg caggacttgc ccgagaactg gtttgcgggg cagctggcgt    23280
cgtgcaggca gcgcgcgcg tcggtgttgg cgatctgcac cacgttgcgc ccccaccggt    23340
tcttcacgat cttggccttg gacgattgct ccttcagcgc gcgctgcccg ttctcgctgg    23400
tcacatccat ctcgatcaca tgttccttgt tcaccatgct gctgccgtgc agacacttca    23460
gctcgccctc cgtctcggtg cagcggtgct gccacagcgc gcagcccgtg ggctcgaaag    23520
acttgtaggt cacctccgcg aaggactgca ggtaccctg caaaaagcgg cccatcatgg    23580
tcacgaaggt cttgttgctg ctgaaggtca gctgcagccc gcggtgctcc tcgttcagcc    23640
aggtcttgca cacggccgcc agcgcctcca cctggtcggg cagcatcttg aagttcacct    23700
```

```
tcagctcatt ctccacgtgg tacttgtcca tcagcgtgcg cgccgcctcc atgcccttct   23760
cccaggccga caccagcggc aggctcacgg ggttcttcac catcaccgtg gccgccgcct   23820
ccgccgcgct ttcgctttcc gccccgctgt tctcttcctc ttcctcctct tcctcgccgc   23880
cgcccactcg cagcccccgc accacggggt cgtcttcctg caggcgctgc accttgcgct   23940
tgccgttgcg ccccctgcttg atgcgcacgg gcgggttgct gaagcccacc atcaccagcg   24000
cggcctcttc ttgctcgtcc tcgctgtcca gaatgacctc cggggagggg gggttggtca   24060
tcctcagtac cgaggcacgc ttctttttct tcctgggggc gttcgccagc tccgcggctg   24120
cggccgctgc cgaggtcgaa ggccgagggc tgggcgtgcg cggcaccagc gcgtcctgcg   24180
agccgtcctc gtcctcctcg gactcgagac ggaggcgggc ccgcttcttc ggggcgcgc    24240
ggggcggcgg aggcggcggc ggcgacgag acgggacga  gacatcgtcc agggtgggtg    24300
gacggcgggc cgcgccgcgt ccgcgctcgg gggtggtctc gcgctggtcc tcttcccgac   24360
tggccatctc ccactgctcc ttctcctata ggcagaaaga gatcatggag tctctcatgc   24420
gagtcgagaa ggaggaggac agcctaaccg cccctctga gccctccacc accgccgcca    24480
ccaccgccaa tgccgccgcg gacgacgcgc ccaccgagac caccgccagt accacctcc    24540
ccagcgacgc accccgctc gagaatgaag tgctgatcga gcaggacccg gttttgtga    24600
gcggagagga ggatgaggtg gatgagaagg agaaggagga ggtcgccgcc tcagtgccaa   24660
aagaggataa aaagcaagac caggacgacg cagataagga tgagacagca gtcgggcggg   24720
ggaacggaag ccatgatgct gatgacggct acctagacgt gggagacgac gtgctgctta   24780
agcacctgca ccgccagtgc gtcatcgtct gcgacgcgct gcaggagcgc tgcgaagtgc   24840
ccctggacgt ggcggaggtc agccgcgcct acgagcggca cctcttcgcg ccgcacgtgc   24900
cccccaagcg ccgggagaac ggcacctgcg agcccaaccc gcgtctcaac ttctacccgg   24960
tcttcgcggt acccgaggtg ctggccacct accacatctt tttccaaaac tgcaagatcc   25020
ccctctcctg ccgcgccaac cgcacccgcg ccgacaaaac cctgaccctg cggcagggcg   25080
cccacatacc tgatatcgcc tctctggagg aagtgcccaa gatcttcgag ggtctcggtc   25140
gcgacgagaa acgggcggcg aacgctctgc acggagacag cgaaaacgag agtcactcgg   25200
gggtgctggt ggagctcgag ggcgacaacg cgcgcctggc cgtactcaag cgcagcatag   25260
aggtcaccca ctttgcctac ccggcgctca acctgccccc caaggtcatg agtgtggtca   25320
tgggcgagct catcatgcgc cgcgcccagc cctggccgc ggatgcaaac ttgcaagagt    25380
cctccgagga aggcctgccc gcggtcagcg acgagcagct ggcgcgctgg ctggagaccc   25440
gcgaccccgc gcagctggag gagcggcgca agctcatgat ggccgcggtg ctggtcaccg   25500
tggagctcga gtgtctgcag cgcttcttcg cggaccccga gatgcagcgc aagctcgagg   25560
agaccctgca ctacaccttc cgccagggct acgtgcgcca ggcctgcaag atctccaacg   25620
tggagctctg caacctggtc tcctacctgg gcatcctgca cgagaaccgc ctcgggcaga   25680
acgtcctgca ctccaccctc aaaggggagg gcgccgcga ctacatccgc gactgcgcct    25740
acctcttcct ctgctacacc tggcagacgg ccatgggggt ctggcagcag tgcctggagg   25800
agcgcaacct caaggagctg aaaagctcc tcaagcgcac cctcagggac ctctggacgg    25860
gcttcaacga gcgctcggtg gccgccgcgc tggcggacat catctttccc gagcgcctgc   25920
tcaagaccct gcagcagggc ctgcccgact tcaccagcca gagcatgctg cagaacttca   25980
ggactttcat cctggagcgc tcgggcatcc tgccggccac ttgctgcgcg ctgcccagcg   26040
acttcgtgcc catcaagtac agggagtgcc cgccgccgct ctggggccac tgctacctct   26100
```

| | |
|---|---|
| tccagctggc caactacctc gcctaccact cggacctcat ggaagacgtg agcggcgagg | 26160 |
| gcctgctcga gtgccactgc cgctgcaacc tctgcacgcc ccaccgctct ctagtctgca | 26220 |
| acccgcagct gctcagcgag agtcagatta tcggtacctt cgagctgcag ggtccctcgc | 26280 |
| ctgacgagaa gtccgcggct ccagggctga aactcactcc ggggctgtgg acttccgcct | 26340 |
| acctacgcaa atttgtacct gaggactacc acgcccacga gatcaggttc tacgaagacc | 26400 |
| aatcccgccc gcccaaggcg gagctcaccg cctgcgtcat cacccagggg cacatcctgg | 26460 |
| gccaattgca agccatcaac aaagcccgcc gagagttctt gctgaaaaag ggtcgggggg | 26520 |
| tgtacctgga cccccagtcc ggcgaggagc taaacccgct accccgccg ccgcccagc | 26580 |
| agcgggacct tgcttcccag gatggcaccc agaaagaagc agcagccgcc gccgccgccg | 26640 |
| cagccataca tgcttctgga ggaagaggag gaggactggg acagtcaggc agaggaggtt | 26700 |
| tcggacgagg agcaggagga gatgatggaa gactgggagg aggacagcag cctagacgag | 26760 |
| gaagcttcag aggccgaaga ggtggcagac gcaacaccat cgccctcggt cgcagccccc | 26820 |
| tcgccggggc ccctgaaatc ctccgaaccc agcaccagcg ctataacctc cgctcctccg | 26880 |
| gcgccggcgc cacccgcccg cagacccaac cgtagatggg acaccacagg aaccggggtc | 26940 |
| ggtaagtcca agtgcccgcc gccgccaccg cagcagcagc agcagcagcg ccagggctac | 27000 |
| cgctcgtggc gcgggcacaa gaacgccata gtcgcctgct tgcaagactg cgggggcaac | 27060 |
| atctctttcg cccgccgctt cctgctattc caccacgggg tcgccttcc ccgcaatgtc | 27120 |
| ctgcattact accgtcatct ctacagcccc tactgcagcg gcgacccaga ggcggcagcg | 27180 |
| gcagccacag cggcgaccac cacctaggaa gatatcctcc gcgggcaaga cagcggcagc | 27240 |
| agcggccagg agaccgcgg cagcagcggc gggagcggtg ggcgcactgc gcctctcgcc | 27300 |
| caacgaaccc ctctcgaccc gggagctcag acacaggatc ttccccactt tgtatgccat | 27360 |
| cttccaacag agcagaggcc aggagcagga gctgaaaata aaaaacagat ctctgcgctc | 27420 |
| cctcacccgc agctgtctgt atcacaaaag cgaagatcag cttcggcgca cgctggagga | 27480 |
| cgcggaggca ctcttcagca aatactgcgc gctcactctt aaagactagc tccgcgccct | 27540 |
| tctcgaattt aggcgggaga aaactacgtc atcgccggcc gccgcccagc ccgcccagcc | 27600 |
| gagatgagca aagagattcc cacgccatac atgtggagct accagccgca gatgggactc | 27660 |
| gcggcgggag cggcccagga ctactccacc cgcatgaact acatgagcgc gggacccac | 27720 |
| atgatctcac aggtcaacgg gatccgcgcc cagcgaaacc aaatactgct ggaacaggcg | 27780 |
| gccatcaccg ccacgcccg ccataatctc aaccccgaa attggcccgc cgccctcgtg | 27840 |
| taccaggaaa cccctccgc caccaccgta ctacttccgc gtgacgccca ggccgaagtc | 27900 |
| cagatgacta actcagggc gcagctcgcg ggcggctttc gtcacgggc gcggccgctc | 27960 |
| cgaccaggta taagacacct gatgatcaga ggccgaggta tccagctcaa cgacgagtcg | 28020 |
| gtgagctctt cgctcggtct ccgtccggac ggaactttcc agctcgccgg atccggccgc | 28080 |
| tcttcgttca cgcccgcca ggcgtacctg actctgcaga cctcgtcctc ggagccccgc | 28140 |
| tccggcggca tcggaaccct ccagttcgtg gaggagttcg tgccctcggt ctacttcaac | 28200 |
| cccttctcgg gacctcccgg acgctacccc gaccagttca ttccgaactt tgacgcggtg | 28260 |
| aaggactcgg cggacggcta cgactgaatg tcaggtgtcg aggcagagca gcttcgcctg | 28320 |
| agacacctcg agcactgccg ccgccacaag tgcttcgccc gcggttctgg tgagttctgc | 28380 |
| tactttcagc tacccgagga gcataccgag gggccggcgc acggcgtccg cctgaccacc | 28440 |

```
cagggcgagg ttacctgttc cctcatccgg gagtttaccc tccgtcccct gctagtggag   28500
cgggagcggg gtccctgtgt cctaactatc gcctgcaact gccctaaccc tggattacat   28560
caagatcttt gctgtcatct ctgtgctgag tttaataaac gctgagatca gaatctactg   28620
gggctcctgt cgccatcctg tgaacgccac cgtcttcacc cacccgacc aggcccaggc    28680
gaacctcacc tgcggtctgc atcggagggc caagaagtac ctcacctggt acttcaacgg   28740
caccccttt gtggtttaca acagcttcga cggggacgga gtctccctga agaccagct    28800
ctccggtctc agctactcca tccacaagaa caccaccctc caactcttcc ctccctacct   28860
gccgggaacc tacgagtgcg tcaccggccg ctgcacccac ctcacccgcc tgatcgtaaa   28920
ccagagcttt ccgggaacag ataactccct cttccccaga acaggaggtg agctcaggaa   28980
actccccggg gaccagggcg gagacgtacc ttcgacccctt gtggggttag gattttttat   29040
taccgggttg ctggctcttt taatcaaagt ttccttgaga tttgttcttt ccttctacgt   29100
gtatgaacac ctcaacctcc aataactcta cccttctc ggaatcaggt gacttctctg      29160
aaatcgggct tggtgtgctg cttactctgt tgatttttt ccttatcata ctcagccttc     29220
tgtgcctcag gctcgccgcc tgctgcgcac acatctatat ctactgctgg ttgctcaagt   29280
gcaggggtcg ccacccaaga tgaacaggta catggtccta tcgatcctag gcctgctggc   29340
cctggcggcc tgcagcgccg ccaaaaaaga gattaccttt gaggagcccg cttgcaatgt   29400
aactttcaag cccgagggtg accaatgcac caccctcgtc aaatgcgtta ccaatcatga   29460
gaggctgcgc atcgactaca aaaacaaaac tggccagttt gcggtctata gtgtgtttac   29520
gcccggagac ccctctaact actctgtcac cgtcttccag ggcggacagt ctaagatatt    29580
caattacact ttccctttt atgagttatg cgatgcggtc atgtacatgt caaaacagta    29640
caacctgtgg cctccctctc cccaggcgtg tgtggaaaat actgggtctt actgctgtat   29700
ggctttcgca atcactacgc tcgctctaat ctgcacggtg ctatacataa aattcaggca   29760
gaggcgaatc tttatcgatg aaaagaaaat gccttgatcg ctaacaccgg cttctatct    29820
gcagaatgaa tgcaatcacc tccctactaa tcaccaccac cctccttgcg attgccatg    29880
ggttgacacg aatcgaagtg ccagtggggt ccaatgtcac catggtgggc cccgccggca   29940
attccacct catgtgggaa aaatttgtcc gcaatcaatg ggttcattc tgctctaacc      30000
gaatcagtat caagcccaga gccatctgcg atgggcaaaa tctaactctg atcaatgtgc   30060
aaatgatgga tgctgggtac tattacgggc agcggggaga aatcattaat tactggcgac   30120
cccacaagga ctacatgctg catgtagtcg aggcacttcc cactaccacc cccactacca   30180
cctctcccac caccaccacc actactacta ctactactac tactactact actaccacta   30240
ccgctgcccg ccatacccgc aaaagcacca tgattagcac aaagcccct cgtgctcact    30300
cccacgccgg cgggcccatc ggtgcgacct cagaaaccac cgagctttgc ttctgccaat   30360
gcactaacgc cagcgctcat gaactgttcg acctggagaa tgaggatgtc cagcagagct   30420
ccgcttgcct gacccaggag gctgtggagc ccgttgccct gaagcagatc ggtgattcaa   30480
taattgactc ttcttctttt gccactcccg aataccctcc cgattctact ttccacatca    30540
cgggtaccaa agaccctaac ctctctttct acctgatgct gctgctctgt atctctgtgg    30600
tctcttccgc gctgatgtta ctggggatgt tctgctgcct gatctgccgc agaaagagaa   30660
aagctcgctc tcagggccaa ccactgatgc ccttcccta cccccggat tttgcagata     30720
acaagatatg agctcgctgc tgacactaac cgctttacta gcctgcgctc taaccccttgt   30780
cgcttgcgac tcgagattcc acaatgtcac agctgtggca ggagaaaatg ttactttcaa    30840
```

```
ctccacggcc gatacccagt ggtcgtggag tggctcaggt agctacttaa ctatctgcaa    30900
tagctccact tcccccggca tatcccaac caagtaccaa tgcaatgcca gcctgttcac     30960
cctcatcaac gcttccaccc tggacaatgg actctatgta ggctatgtac cctttggtgg    31020
gcaaggaaag acccacgctt acaacctgga agttcgccag cccagaacca ctacccaagc    31080
ttctcccacc accaccacca ccaccaccat caccagcagc agcagcagca gcagccacag    31140
cagcagcagc agattattga ctttggtttt ggccagctca tctgccgcta cccaggccat    31200
ctacagctct gtgcccgaaa ccactcagat ccaccgccca gaaacgacca ccgccaccac    31260
cctacacacc tccagcgatc agatgccgac caacatcacc cccttggctc ttcaaatggg    31320
acttacaagc cccactccaa aaccagtgga tgcggccgag gtctccgccc tcgtcaatga    31380
ctgggcgggg ctgggaatgt ggtggttcgc cataggcatg atggcgctct gcctgcttct    31440
gctctggctc atctgctgcc tccaccgcag gcgagccaga cccccatct atagacccat      31500 cattgtcctg aaccccgata atgatgggat ccatagattg gatggcctga aaaacctact    31560 ttttctttt acagtatgat aaattgagac atgcctcgca ttttcttgta catgttcctt     31620
ctcccacctt ttctggggtg ttctacgctg gccgctgtgt ctcacctgga ggtagactgc    31680
ctctcaccct tcactgtcta cctgctttac ggattggtca ccctcactct catctgcagc    31740
ctaatcacag taatcatcgc cttcatccag tgcattgatt acatctgtgt gcgcctcgca    31800
tacttcagac accacccgca gtaccgagac aggaacattg cccaacttct aagactgctc    31860
taatcatgca taagactgtg atctgccttc tgatcctctg catcctgccc accctcacct    31920
cctgccagta caccacaaaa tctccgcgca aaagacatgc ctcctgccgc ttcacccaac    31980
tgtggaatat acccaaatgc tacaacgaaa agagcgagct ctccgaagct tggctgtatg    32040
gggtcatctg tgtcttagtt ttctgcagca ctgtctttgc cctcataatc taccctact     32100 ttgatttggg atggaacgcg atcgatgcca tgaattaccc cacctttccc gcacccgaga    32160
taattccact gcgacaagtt gtaccgttg tcgttaatca acgcccccca tccctacgc      32220 ccactgaaat cagctacttt aacctaacag gcggagatga ctgacgccct agatctagaa    32280
atggacggca tcagtaccga gcagcgtctc ctagagaggc gcaggcaggc ggctgagcaa    32340
gagcgcctca atcaggagct ccgagatctc gttaacctgc accagtgcaa aagaggcatc    32400
ttttgtctgg taaagcaggc caaagtcacc tacgagaaga ccggcaacag ccaccgcctc    32460
agttacaaat tgcccaccca gcgccagaag ctggtgctca tggtgggtga aatcccatc     32520 accgtcaccc agcactcggt agagaccgag gggtgtctgc actcccctg tcggggtcca     32580 gaagacctct gcaccctggt aaagaccctg tgcggtctca gagatttagt ccctttaac     32640 taatcaaaca ctggaatcaa taaaagaat cacttactta aaatcagaca gcaggtctct     32700
gtccagttta ttcagcagca cctccttccc ctcctcccaa ctctggtact ccaaacgcct    32760
tctggcggca aacttcctcc acaccctgaa gggaatgtca gattcttgct cctgtccctc    32820
cgcacccact atcttcatgt tgttgcagat gaagcgcacc aaaacgtctg acgagagctt    32880
caaccccgtg taccctatg acacggaaag cggccctccc tccgtccctt tcctcacccc     32940
tcccttcgtg tctcccgatg gattccaaga aagtcccccc ggggtcctgt ctctgaacct    33000
ggccgagccc ctggtcactt cccacggcat gctcgccctg aaaatgggaa gtggcctctc    33060 cctgacgac gctggcaacc tcacctctca agatatcacc accgctagcc ctcccctcaa    33120 aaaaccaag accaacctca gcctagaaac ctcatccccc ctaactgtga gcacctcagg    33180
```

```
cgccctcacc gtagcagccg ccgctcccct ggcggtggcc ggcacctccc tcaccatgca    33240
atcagaggcc cccctgacag tacaggatgc aaaactcacc ctggccacca aaggcccccct   33300 gaccgtgtct gaaggcaaac tggccttgca acatcggcc ccgctgacgg ccgctgacag     33360
cagcaccctc acagtcagtg ccacaccacc ccttagcaca agcaatggca gcttgggtat    33420
tgacatgcaa gcccccattt acaccaccaa tggaaaacta ggacttaact ttggcgctcc    33480
cctgcatgtg gtagacagcc taaatgcact gactgtagtt actggccaag gtcttacgat    33540
aaacggaaca gccctacaaa ctagagtctc aggtgccctc aactatgaca catcaggaaa    33600
cctagaattg agagctgcag ggggtatgcg agttgatgca aatggtcaac ttatccttga    33660
tgtagcttac ccatttgatg cacaaaacaa tctcagcctt aggcttggac agggacccct    33720
gtttgttaac tctgcccaca acttggatgt taactacaac agaggcctct acctgttcac    33780
atctggaaat accaaaaagc tagaagttaa tatcaaaaca gccaagggtc tcatttatga    33840
tgacactgct atagcaatca atgcgggtga tgggctacag tttgactcag gctcagatac    33900
aaatccatta aaaactaaac ttggattagg actggattat gactccagca gagccataat    33960
tgctaaactg ggaactggcc taagctttga caacacaggt gccatcacag taggcaacaa    34020
aaatgatgac aagcttacct tgtggaccac accagcccca tccctaact gtagaatcta     34080 ttcagagaaa gatgctaaat tcacacttgt tttgactaaa tgcggcagtc aggtgttggc    34140
cagcgtttct gttttatctg taaaaggtag ccttgcgccc atcagtggca cagtaactag    34200
tgctcagatt gtcctcagat ttgatgaaaa tggagttcta ctaagcaatt cttcccttga    34260
ccctcaatac tggaactaca gaaaaggtga ccttacagag ggcactgcat ataccaacgc    34320
agtgggattt atgcccaacc tcacagcata cccaaaaaca cagagccaaa ctgctaaaag    34380
caacattgta agtcaggttt acttgaatgg ggacaaatcc aaacccatga ccctcaccat    34440
taccctcaat ggaactaatg aaacaggaga tgccacagta agcacttact ccatgtcatt    34500
ctcatggaac tggaatggaa gtaattacat taatgaaacg ttccaaacca actccttcac    34560
cttctcctac atcgcccaag aataaaaagc atgacgctgt tgatttgatt caatgtgttt    34620
ctgttttatt ttcaagcaca acaaaatcat tcaagtcatt cttccatctt agcttaatag    34680
acacagtagc ttaatagacc cagtagtgca aagccccatt ctagcttata gatcagacag    34740
tgataattaa ccaccaccac caccatacct tttgattcag gaaatcatga tcatcacagg    34800
atcctagtct tcaggccgcc ccctccctcc caagacacag aatacacagt cctctccccc    34860
cgactggctt taaataacac catctggttg gtcacagaca tgttcttagg ggttatattc    34920
cacacggtct cctgccgcgc caggcgctcg tcggtgatgt tgataaactc tcccggcagc    34980
tcgctcaagt tcacgtcgct gtccagcggc tgaacctccg gctgacgcga taactgtgcg    35040
accggctgct ggacgaacgg aggccgcgcc tacaagggg tagagtcata atcctcggtc      35100
aggatagggc ggtgatgcag cagcagcgag cgaaacatct gctgccgccg ccgctccgtc    35160
cggcaggaaa acaacacgcc ggtggtctcc tccgcgataa tccgcaccgc ccgcagcatc    35220
agcttcctcg ttctccgcgc gcagcacctc acccttatct cgctcaaatc ggcgcagtag    35280
gtacagcaca gcaccacgat gttattcatg atcccacagt gcagggcgct gtatccaaag    35340
ctcatgccgg gaaccaccgc ccccacgtgg ccatcgtacc acaagcgcac gtaaatcaag    35400
tgtcgacccc tcatgaacgc gctggacaca acattactt ccttgggcat gttgtaattc      35460
accacctccc ggtaccagat aaacctctgg ttgaacaggg caccttccac caccatcctg    35520
aaccaagagg ccagaacctg cccaccggct atgcactgca gggaaccgg gttggaacaa      35580
```

```
tgacaatgca gactccaagg ctcgtaaccg tggatcatcc ggctgctgaa ggcatcgatg    35640
ttggcacaac acagacacac gtgcatgcac tttctcatga ttagcagctc ttccctcgtc    35700
aggatcatat cccaaggaat aacccattct tgaatcaacg taaaacccac acagcaggga    35760
aggcctcgca cataactcac gttgtgcatg gtcagcgtgt tgcattccgg aaacagcgga    35820
tgatcctcca gtatcgaggc gcgggtctcc ttctcacagg gaggtaaagg gtccctgctg    35880
tacggactgc gccgggacga ccgagatcgt gttgagcgta gtgtcatgga aaagggaacg    35940
ccggacgtgg tcatacttct tgaagcagaa ccaggttcgc gcgtggcagg cctccttgcg    36000
tctgcggtct cgccgtctag ctcgctccgt gtgatagttg tagtacagcc actcccgcag    36060
agcgtcgagg cgcaccctgg cttccggatc tatgtagact ccgtcttgca ccgcggccct    36120
gataatatcc accaccgtag aataagcaac acccagccaa gcaatacact cgctctgcga    36180
gcggcagaca ggaggagcgg gcagagatgg gagaaccatg ataaaaaact ttttttaaag    36240
aatattttcc aattcttcga aagtaagatc tatcaagtgg cagcgctccc ctccactggc    36300
gcggtcaaac tctacggcca agcacagac aacggcattt ctaagatgtt ccttaatggc    36360
gtccaaaaga cacaccgctc tcaagttgca gtaaactatg aatgaaaacc catccggctg    36420
attttccaat atagacgcgc cggcagcgtc caccaaaccc agataatttt cttctctcca    36480
gcggtttacg atctgtctaa gcaaatccct tatatcaagt ccgaccatgc caaaaatctg    36540
ctcaagagcg ccctccacct tcatgtacaa gcagcgcatc atgattgcaa aaattcaggt    36600
tcttcagaga cctgtataag attcaaaatg ggaacattaa caaaaattcc tctgtcgcgc    36660
agatcccttc gcagggcaag ctgaacataa tcagacaggt ccgaacggac cagtgaggcc    36720
aaatccccac caggaaccag atccagagac cctatactga ttatgacgcg catactcggg    36780
gctatgctga ccagcgtagc gccgatgtag gcgtgctgca tgggcggcga gataaaatgc    36840
aaagtgctgg ttaaaaaatc aggcaaagcc tcgcgcaaaa aagctaacac atcataatca    36900
tgctcatgca ggtagttgca ggtaagctca ggaaccaaaa cggaataaca cacgattttc    36960
ctctcaaaca tgacttcgcg gatactgcgt aaaacaaaaa attataaata aaaaattaat    37020
taaataactt aaacattgga agcctgtctc acaacaggaa aaaccacttt aatcaacata    37080
agacgggcca cgggcatgcc ggcatagccg taaaaaaatt ggtccccgtg attaacaagt    37140
accacagaca gctccccggt catgtcgggg gtcatcatgt gagactctgt atacacgtct    37200
ggattgtgaa catcagacaa acaaagaaat cgagccacgt agcccggagg tataatcacc    37260
cgcaggcgga ggtacagcaa aacgaccccc ataggaggaa tcacaaaatt agtaggagaa    37320
aaaaatacat aaacaccaga aaaccctgt tgctgaggca aaatagcgcc ctcccgatcc    37380
aaaacaacat aaagcgcttc cacaggagca gccataacaa agacccgagt cttaccagta    37440
aaagaaaaaa gatctctcaa cgcagcacca gcaccaacac ttcgcagtgt aaaaggccaa    37500
gtgccgagag agtatatata ggaataaaaa gtgacgtaaa cggcaaagt ccaaaaaacg    37560 cccagaaaaa ccgcacgcga acctacgccc cgaaacgaaa gccaaaaaac actagacact    37620
cccttccggc gtcaacttcc gctttcccac gctacgtcac ttccccggt caaacaaact    37680 acatatcccg aacttccaag tcgccacgcc caaaacaccg cctacacctc cccgcccgcc    37740
ggcccgcccc cggacccgcc tcccgccccg cgccgcccat ctcattatca tattggcttc    37800
aatccaaaat aaggtatatt attgatgatg                                     37830
```

<210> SEQ ID NO 11

<211> LENGTH: 37559
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 11

| | | | | | |
|---|---|---|---|---|---|
| catcatcaat | aatatacctt | attttggatt | gaagccaata | tgataatgag | atgggcggcg | 60 |
| cggggcgggg | cgcggggcgg | gaggcgggtt | tggggcggg | ccggcgggcg | ggcggtgtg | 120 |
| gcggaagtgg | actttgtaag | tgtggcggat | gtgacttgct | agtgccgggc | gcggtaaaag | 180 |
| tgacgttttc | cgtgcgcgac | aacgccccg | ggaagtgaca | ttttccccgc | ggttttacc | 240 |
| ggatgttgta | gtgaatttgg | gcgtaaccaa | gtaagatttg | gccattttcg | cgggaaaact | 300 |
| gaaacgggga | agtgaaatct | gattaatttt | gcgttagtca | taccgcgtaa | tatttgtcta | 360 |
| gggccgaggg | actttggccg | attacgtgga | ggactcgccc | aggtgttttt | tgaggtgaat | 420 |
| ttccgcgttc | cgggtcaaag | tctgcgtttt | attattatag | gatatcccat | tgcatacgtt | 480 |
| gtatccatat | cataatatgt | acatttatat | tggctcatgt | ccaacattac | cgccatgttg | 540 |
| acattgatta | ttgactagtt | attaatagta | atcaattacg | gggtcattag | ttcatagccc | 600 |
| atatatggag | ttccgcgtta | cataacttac | ggtaaatggc | ccgcctggct | gaccgcccaa | 660 |
| cgacccccgc | ccattgacgt | caataatgac | gtatgttccc | atagtaacgc | caatagggac | 720 |
| tttccattga | cgtcaatggg | tggagtattt | acggtaaact | gcccacttgg | cagtacatca | 780 |
| agtgtatcat | atgccaagta | cgccccctat | tgacgtcaat | gacggtaaat | ggcccgcctg | 840 |
| gcattatgcc | cagtacatga | ccttatggga | ctttcctact | tggcagtaca | tctacgtatt | 900 |
| agtcatcgct | attaccatgg | tgatgcggtt | ttggcagtac | atcaatgggc | gtggatagcg | 960 |
| gtttgactca | cggggatttc | caagtctcca | ccccattgac | gtcaatggga | gtttgttttg | 1020 |
| gcaccaaaat | caacgggact | ttccaaaatg | tcgtaacaac | tccgccccat | tgacgcaaat | 1080 |
| gggcggtagg | cgtgtacggt | gggaggtcta | tataagcaga | gctctcccta | tcagtgatag | 1140 |
| agatctccct | atcagtgata | gagatcgtcg | acgagctcgt | ttagtgaacc | gtcagatcgc | 1200 |
| ctggagacgc | catccacgct | gttttgacct | ccatagaaga | caccgggacc | gatccagcct | 1260 |
| ccgcggccgg | gaacggtgca | ttggaacgcg | gattccccgt | gccaagagtg | agatcttccg | 1320 |
| tttatctagg | taccagatat | cgccaccatg | gaactgctga | tcctgaaggc | caacgccatc | 1380 |
| accaccatcc | tgaccgccgt | gaccttctgc | ttcgccagcg | gccagaacat | caccgaggaa | 1440 |
| ttctaccaga | gcacctgtag | cgccgtgagc | aagggctacc | tgagcgccct | gagaaccggc | 1500 |
| tggtacacca | gcgtgatcac | catcgagctg | agcaacatca | agaaaacaa | gtgcaacggc | 1560 |
| accgacgcca | aagtgaagct | gatcaagcag | gaactggaca | agtacaagaa | cgccgtgacc | 1620 |
| gagctgcagc | tgctgatgca | gagcacccc | gccaccaaca | accgggccag | acgggagctg | 1680 |
| ccccggttca | tgaactacac | cctgaacaac | gccaaaaaga | ccaacgtgac | cctgagcaag | 1740 |
| aagcggaagc | ggcggttcct | gggctttctg | ctgggcgtgg | gcagcgccat | tgccagcggc | 1800 |
| gtggccgtgt | ctaaggtgct | gcacctggaa | ggcgaagtga | acaagatcaa | gagcgccctg | 1860 |
| ctgagcacca | acaaggccgt | ggtgtccctg | agcaacggcg | tgagcgtgct | gaccagcaag | 1920 |
| gtgctggatc | tgaagaacta | catcgacaag | cagctgctgc | ccatcgtgaa | caagcagagc | 1980 |
| tgcagcatca | gcaacatcga | gacagtgatc | gagttccagc | agaagaacaa | ccggctgctg | 2040 |
| gaaatcaccc | gggagttcag | cgtgaacgcc | ggcgtgacca | cccctgtgtc | cacctacatg | 2100 |

```
ctgaccaaca gcgagctgct gagcctgatc aacgacatgc ccatcaccaa cgaccagaaa    2160
aagctgatga gcaacaacgt gcagatcgtg cggcagcaga gctactccat catgtccatc    2220
atcaaagaag aggtgctggc ctacgtggtg cagctgcccc tgtacggcgt gatcgacacc    2280
ccctgctgga agctgcacac cagcccctg tgcaccacca acaccaaaga gggcagcaac     2340
atctgcctga cccggaccga cagaggctgg tactgcgaca acgccggcag cgtgtcattc    2400
tttccacagg ccgagacatg caaggtgcag agcaaccggg tgttctgcga caccatgaac    2460
agcctgaccc tgccctccga agtgaacctg tgcaacgtgg acatcttcaa ccccaagtac    2520
gactgcaaga tcatgacctc caagaccgac gtgtccagct ccgtgatcac ctccctgggc    2580
gccatcgtgt cctgctacgg caagaccaag tgcaccgcca gcaacaagaa ccggggcatc    2640
atcaagacct tcagcaacgg ctgcgactac gtgtccaaca aggggtggag caccgtgtcc    2700
gtgggcaaca ccctgtacta cgtgaacaaa caggaaggca agagcctgta cgtgaagggc    2760
gagcccatca tcaacttcta cgaccccctg gtgttcccca cgacgagtt cgacgccagc     2820 atcagccagg tgaacgagaa gatcaaccag agcctggcct tcatccggaa gtccgacgag    2880
ctgctgcaca atgtgaatgc cggcaagtcc accaccaacc ggaagcggag agcccctgtg    2940
aagcagaccc tgaacttcga cctgctgaag ctggccggcg acgtggagag caatcccggc    3000
cctatggccc tgagcaaagt gaaactgaac gatacactga acaaggacca gctgctgtcc    3060
agcagcaagt acaccatcca gcggagcacc ggcgacagca tcgataccc caactacgac     3120 gtgcagaagc acatcaacaa gctgtgcggc atgctgctga tcacagagga cgccaaccac    3180
aagttcaccg gcctgatcgg catgctgtac gccatgagcc ggctgggccg ggaggacacc    3240
atcaagatcc tgcgggacgc cggctaccac gtgaaggcca atggcgtgga cgtgaccaca    3300
caccggcagg acatcaacgg caaagaaatg aagttcgagg tgctgaccct ggccagcctg    3360
accaccgaga tccagatcaa tatcgagatc gagagccgga agtcctacaa gaaaatgctg    3420
aaagaaatgg gcgaggtggc ccccgagtac agacacgaca gccccgactg cggcatgatc    3480
atcctgtgta tcgccgccct ggtgatcaca aagctggccg ctggcgacag atctggcctg    3540
acagccgtga tcagacgggc caacaatgtg ctgaagaacg agatgaagcg gtacaagggc    3600
ctgctgccca aggacattgc caacagcttc tacgaggtgt tcgagaagta ccccacttc     3660 atcgacgtgt tcgtgcactt cggcattgcc cagagcagca ccagaggcgg ctccagagtg    3720
gagggcatct tcgccggcct gttcatgaac gcctacggcg ctggccaggt gatgctgaga    3780
tggggcgtgc tggccaagag cgtgaagaac atcatgctgg ccacgccag cgtgcaggcc     3840 gagatggaac aggtggtgga ggtgtacgag tacgcccaga gctgggcgg agaggccggc     3900 ttctaccaca tcctgaacaa ccctaaggcc tccctgctgt ccctgaccca gttccccac    3960 ttctccagcg tggtgctggg aaatgccgcc ggactgggca tcatgggcga gtaccggggc    4020 accccagaa accaggacct gtacgacgcc gccaaggcct acgccgagca gctgaaagaa     4080
aacggcgtga tcaactacag cgtgctggac ctgaccgctg aggaactgga agccatcaag    4140
caccagctga acccaagga caacgacgtg gagctgggag gcggaggatc tggcggcgga    4200
ggcatgagca cggaaccc ctgcaagttc gagatccggg ccactgcct gaacggcaag      4260 cggtgccact tcagccacaa ctacttcgag tggccccctc atgctctgct ggtgcgcag    4320 aacttcatgc tgaaccggat cctgaagtcc atggacaaga gcatcgacac cctgagcgag    4380
atcagcggag ccgccgagct ggacagaacc gaggaatatg cctgggcgt ggtgggagtg    4440
```

```
ctggaaagct acatcggctc catcaacaac atcacaaagc agagcgcctg cgtggccatg    4500
agcaagctgc tgacagagct gaacagcgac gacatcaaga agctgaggga caacgaggaa    4560
ctgaacagcc ccaagatccg ggtgtacaac accgtgatca gctacattga gagcaaccgc    4620
aagaacaaca agcagaccat ccatctgctg aagcggctgc ccgccgacgt gctgaaaaag    4680
accatcaaga cacccctgga catccacaag tccatcacca tcaacaatcc caaagaaagc    4740
accgtgtctg acaccaacga tcacgccaag aacaacgaca ccacctgatg agcggccgcg    4800
atctgctgtg ccttctagtt gccagccatc tgttgtttgc cctcccccg tgccttcctt     4860 gaccctggaa ggtgccactc ccactgtcct ttcctaataa aatgaggaaa ttgcatcgca    4920
ttgtctgagt aggtgtcatt ctattctggg gggtggggtg gggcaggaca gcaagggga     4980 ggattgggaa gacaatagca ggcatgctgg ggatgcggtg ggctctatgg ccgatcagcg    5040
atcgctgagg tgggtgagtg ggcgtggcct ggggtggtca tgaaaatata taagttgggg    5100
gtcttagggt ctctttattt gtgttgcaga gaccgccgga gccatgagcg ggagcagcag    5160
cagcagcagt agcagcagcg ccttggatgg cagcatcgtg agcccttatt tgacgacgcg    5220
gatgccccac tgggccgggg tgcgtcagaa tgtgatgggc tccagcatcg acggccgacc    5280
cgtcctgccc gcaaattccg ccacgctgac ctatgcgacc gtcgcgggga cgccgttgga    5340
cgccaccgcc gccgccgccc caccgcagc cgcctcggcc gtgcgcagcc tggccacgga    5400
ctttgcattc ctgggaccac tggcgacagg ggctacttct cgggccgctg ctgccgccgt    5460
tcgcgatgac aagctgaccg ccctgctggc gcagttggat gcgcttactc gggaactggg    5520 tgaccttttct cagcaggtca tggccctgcg ccagcaggtc tcctccctgc aagctggcgg    5580
gaatgcttct cccacaaatg ccgtttaaga taaataaaac cagactctgt ttggattaaa    5640
gaaaagtagc aagtgcattg ctctctttat ttcataattt tccgcgcgcg ataggcccta    5700
gaccagcgtt ctcggtcgtt gagggtgcgg tgtatcttct ccaggacgtg gtagaggtgg    5760
ctctggacgt tgagatacat gggcatgagc ccgtcccggg ggtggaggta gcaccactgc    5820
agagcttcat gctccggggt ggtgttgtag atgatccagt cgtagcagga gcgctgggca    5880
tggtgcctaa aaatgtcctt cagcagcagg ccgatggcca gggggaggcc cttggtgtaa    5940
gtgtttacaa aacggttaag ttgggaaggg tgcattcggg gagagatgat gtgcatcttg    6000 gactgtatttt ttagattggc gatgtttccg cccagatccc ttctgggatt catgttgtgc    6060
aggaccacca gtacagtgta tccggtgcac ttggggaatt tgtcatgcag cttagaggga    6120
aaagcgtgga gaacttgga gacgcctttg tggcctccca gattttccat gcattcgtcc    6180
atgatgatgg caatgggccc gcgggaggca gcttgggcaa agatatttct ggggtcgctg    6240
acgtcgtagt tgtgttccag ggtgaggtcg tcataggcca ttttttacaaa gcgcgggcgg    6300 agggtgcccg actgggggat gatggtcccc tctggccctg gggcgtagtt gccctcgcag    6360
atctgcattt cccaggcctt aatctcggag ggggaatca tatccacctg cggggcgatg     6420
aagaaaacgg tttccggagc cggggagatt aactgggatg agagcaggtt tctaagcagc    6480
tgtgattttc cacaaccggt gggcccataa ataacaccta taaccggttg cagctggtag    6540
tttagagagc tgcagctgcc gtcgtcccgg aggaggggg ccacctcgtt gagcatgtcc     6600
ctgacgcgca tgttctcccc gaccagatcc gccagaaggc gctcgccgcc cagggacagc    6660
agctcttgca aggaagcaaa gtttttcagc ggcttgaggc cgtccgccgt gggcatgttt    6720
ttcagggtct ggctcagcag ctccaggcgg tcccagagct cggtgacgtg ctctacggca    6780
tctctatcca gcatatctcc tcgtttcgcg ggttggggcg actttcgctg tagggcacca    6840
```

```
agcggtggtc gtccagcggg gccagagtca tgtccttcca tgggcgcagg gtcctcgtca    6900
gggtggtctg ggtcacggtg aagggtgcg ctccgggctg agcgcttgcc aaggtgcgct     6960
tgaggctggt tctgctggtg ctgaagcgct gccggtcttc gccctgcgcg tcggccaggt    7020
agcatttgac catggtgtca tagtccagcc cctccgcggc gtgtcccttg gcgcgcagct    7080
tgcccttgga ggtggcgccg cacgaggggc agagcaggct cttgagcgcg tagagcttgg    7140
gggcgaggaa gaccgattcg ggggagtagg cgtccgcgcc gcagacccca cacacgtct    7200
cgcactccac cagccaggtg agctcggggc gcgccgggtc aaaaaccagg tttccccccat    7260
gcttttgat gcgtttctta cctcgggtct ccatgaggtg gtgtccccgc tcggtgacga    7320
agaggctgtc cgtgtctccg tagaccgact tgaggggtct tttctccagg ggggtccctc    7380
ggtcttcctc gtagaggaac tcggaccact ctgagacgaa ggcccgcgtc caggccagga    7440
cgaaggaggc tatgtgggag gggtagcggt cgttgtccac tagggggtcc accttctcca    7500
aggtgtgaag acacatgtcg ccttcctcgg cgtccaggaa ggtgattggc ttgtaggtgt    7560
aggccacgtg accggggggtt cctgacgggg gggtataaaa ggggtgggg gcgcgctcgt    7620
cgtcactctc ttccgcatcg ctgtctgcga gggccagctg ctgggggtgag tattccctct    7680
cgaaggcggg catgacctcc gcgctgaggt tgtcagtttc caaaaacgag gaggatttga    7740
tgttcacctg tcccgaggtg ataccttga gggtacccgc gtccatctgg tcagaaaaca    7800
cgatctttt attgtccagc ttggtggcga acgaccccgta gagggcgttg gagagcagct    7860
tggcgatgga gcgcagggtc tggttcttgt ccctgtcggc gcgctccttg gccgcgatgt    7920
tgagctgcac gtactcgcgc gcgacgcagc gccactcggg gaagacggtg gtgcgctcgt    7980
cgggcaccag gcgcacgcgc cagccgcggt tgtgcagggt gaccaggtcc acgctggtgg    8040
cgacctcgcc gcgcaggcgc tcgttggtcc agcagagacg gccgcccttg cgcgagcaga    8100
aggggggcag ggggtcgagc tgggtctcgt ccgggggggtc cgcgtccacg gtgaaaaccc    8160
cggggcgcag gcgcgcgtcg aagtagtcta tcttgcaacc ttgcatgtcc agcgcctgct    8220
gccagtcgcg ggcggcgagc gcgcgctcgt aggggttgag cggcgggccc cagggcatgg    8280
ggtgggtgag tgcggaggcg tacatgccgc agatgtcata gacgtagagg ggctcccgca    8340
ggaccccgat gtaggtgggg tagcagcggc cgccgcggat gctggcgcgc acgtagtcat    8400
acagctcgtg cgagggggcg aggaggtcgg ggcccaggtt ggtgcgggcg gggcgctccg    8460
cgcggaagac gatctgcctg aagatggcat gcgagttgga agagatggtg gggcgctgga    8520
agacgttgaa gctggcgtcc tgcaggccga cggcgtcgcg cacgaaggag cgtaggagt    8580
cgcgcagctt gtgtaccagc tcggcggtga cctgcacgtc gagcgcgcag tagtcgaggg    8640
tctcgcggat gatgtcatat ttagcctgcc ccttcttttt ccacagctcg cggttgagga    8700
caaactcttc gcggtctttc cagtactctt ggatcgggaa accgtccggt tccgaacggt    8760
aagagcctag catgtagaac tggttgacgg cctggtaggc gcagcagccc ttctccacgg    8820
ggagggcgta ggcctgcgcg gccttgcgga gcgaggtgtg ggtcagggcg aaggtgtccc    8880
tgaccatgac tttgaggtac tggtgcttga agtcggagtc gtcgcagccg ccccgctccc    8940
agagcgagaa gtcggtgcgc ttcttggagc gggggttggg cagagcgaag gtgacatcgt    9000
tgaagaggat tttgcccgcg cggggcatga agttgcgggt gatgcggaag ggccccggca    9060
cttcagagcg gttgttgatg acctgggcgg cgagcacgat ctcgtcgaag ccgttgatgt    9120
tgtggcccac gatgtagagt tccaggaagc ggggccggcc ctttacggtg ggcagcttct    9180
```

```
ttagctcttc gtaggtgagc tcctcgggcg aggcgaggcc gtgctcggcc agggcccagt    9240
ccgcgaggtg cggttgtct ctgaggaagg acttccagag gtcgcgggcc aggagggtct     9300
gcaggcggtc tctgaaggtc ctgaactggc ggcccacggc cattttttcg ggggtgatgc    9360
agtagaaggt gaggggtct tgctgccagc ggtcccagtc gagctgcagg gcgaggtcgc     9420
gcgcggcggt gaccaggcgc tcgtcgcccc cgaatttcat gaccagcatg aagggcacga    9480
gctgctttcc gaaggccccc atccaagtgt aggtctctac atcgtaggtg acaaagaggc    9540
gctccgtgcg aggatgcgag ccgatcggga agaactggat ctcccgccac cagttggagg    9600
agtggctgtt gatgtggtgg aagtagaagt cccgtcgccg ggccgaacac tcgtgctggc    9660
tttgtaaaa gcgagcgcag tactggcagc gctgcacggg ctgtacctca tgcacgagat     9720
gcacctttcg cccgcgcacg aggaagccga ggggaaatct gagcccccg cctggctcgc     9780
ggcatggctg gttctcttct actttggatg cgtgtccgtc tccgtctggc tcctcgaggg    9840
gtgttacggt ggagcggacc accacgccgc gcgagccgca ggtccagata tcggcgcgcg    9900
gcggtcggag tttgatgacg acatcgcgca gctgggagct gtccatggtc tggagctccc    9960
gcggcggcgg caggtcagcc gggagttctt gcaggttcac ctcgcagagt cgggccaggg    10020
cgcggggcag gtctaggtgg tacctgatct ctaggggcgt gttggtggcg cgtcgatgg     10080
cttgcaggag cccgcagccc ggggggcga cgacggtgcc ccgcggggtg gtggtggtgg     10140
tggcggtgca gctcagaagc ggtgccgcgg gcgggccccc ggaggtaggg ggggctccgg    10200
tcccgcgggc aggggcggca gcggcacgtc ggcgtggagc gcgggcagga gttggtgctg    10260
tgcccggagg ttgctggcga aggcgacgac gcggcggttg atctcctgga tctggcgcct    10320
ctgcgtgaag acgacgggcc cggtgagctt gaacctgaaa gagagttcga cagaatcaat    10380
ctcggtgtca ttgaccgcgg cctggcgcag gatctcctgc acgtctcccg agttgtcttg    10440
gtaggcgatc tcggccatga actgctcgat ctcttcctcc tggaggtctc cgcgtccggc    10500
gcgttccacg gtgccgcca ggtcgttgga gatgcgcccc atgagctgcg agaaggcgtt    10560
gagtccgccc tcgttccaga ctcggctgta gaccacgccc ccctggtcat cgcgggcgcg    10620
catgaccacc tgcgcgaggt tgagctccac gtgccgcgcg aagacggcgt agttgcgcag    10680
acgctggaag aggtagttga gggtggtggc ggtgtgctcg gccacgaaga agttcatgac    10740
ccagcggcgc aacgtggatt cgttgatgtc ccccaaggcc tccagccgtt ccatggcctc    10800
gtagaagtcc acggcgaagt tgaaaaactg ggagttgcgc gccgacacgg tcaactcctc    10860
ctccagaaga cggatgagct cggcgacggt gtcgcgcacc tcgcgctcga aggctatggg    10920
gatctcttcc tccgctagca tcaccacctc ctcctcttcc tcctcttctg gcacttccat    10980
gatgccttcc tcctcttcgg ggggtggcgg cggcggcgt gggggagggg gcgctctgcg    11040
ccggcggcgg cgcaccggga ggcggtccac gaagcgcgcg atcatctccc cgcggcggcg    11100
gcgcatggtc tcggtgacgg cgcggccgtt ctcccgggg gcagttgga agacgccgcc     11160
ggacatctgg tgctggggcg ggtggccgtg aggcagcgag acggcgctga cgatgcatct    11220
caacaattgc tgcgtaggta cgccgccgag ggacctgagg gagtccatat ccaccggatc    11280
cgaaaacctt tcgaggaagg cgtctaacca gtcgcagtcg caaggtaggc tgagcaccgt    11340
ggcgggcggc ggggggtggg gggagtgtct ggcggaggtg ctgctgatga tgtaattgaa    11400
gtaggcggac ttgacacggc ggatggtcga caggagcacc atgtccttgg gtccggcctg    11460
ctggatgcgt aggcggtcgg ctatgcccca ggcttcgttc tggcatcggc gcaggtcctt    11520
gtagtagtct tgcatgagcc tttccaccgg cacctcttct ccttcctctt ctgcttcttc    11580
```

```
catgtctgct tcggccctgg ggcggcgccg cgccccctg cccccatgc gcgtgacccc    11640
gaaccccctg agcggttgga gcagggccag gtcggcgacg acgcgctcgg ccaggatggc    11700
ctgctgcacc tgcgtgaggg tggtttggaa gtcatccaag tccacgaagc ggtggtaggc    11760
gcccgtgttg atggtgtagg tgcagttggc catgacggac cagttgacgg tctggtggcc    11820
cggttgcgac atctcggtgt acctgagtcg cgagtaggcg cgggagtcga agacgtagtc    11880
gttgcaagtc cgcaccaggt actggtagcc caccaggaag tgcggcggcg gctggcggta    11940
gaggggccag cgcagggtgg cgggggctcc ggggccagg tcttccagca tgaggcggtg    12000
gtaggcgtag atgtacctgg acatccaggt gataccgcg gcggtggtgg aggcgcgcgg    12060
gaagtcgcgc acccggttcc agatgttgcg caggggcaga aagtgctcca tggtaggcgt    12120
gctctgtcca gtcagacgcg cgcagtcgtt gatactctag accagggaaa acgaaagccg    12180
gtcagcgggc actcttccgt ggtctggtga atagatcgca agggtatcat ggcggagggc    12240
ctcggttcga gccccgggtc cgggccgac ggtccgccat gatccacgcg gttaccgccc    12300
gcgtgtcgaa cccaggtgtg cgacgtcaga caacggtgga gtgttccttt tggcgttttt    12360
ctggccgggc gccggcgccg cgtaagagac taagccgcga aagcgaaagc agtaagtggc    12420
tcgctccccg tagccggagg gatccttgct aagggttgcg ttgcggcgaa ccccggttcg    12480
aatcccgtac tcgggccggc cggaccgcg gctaaggtgt tggattggcc tcccctcgt    12540
ataaagaccc cgcttgcgga ttgactccgg acacgggac gagccccttt tattttgct    12600
ttccccagat gcatccggtg ctgcggcaga tgcgcccccc gccccagcag cagcaacaac    12660
accagcaaga gcggcagcaa cagcagcggg agtcatgcag ggcccctca cccaccctcg    12720
gcgggccggc cacctcggcg tccgcggccg tgtctggcgc ctgcggcggc ggcgggggc    12780
cggctgacga ccccgaggag cccccgcggc gcagggccag acactacctg gacctggagg    12840
agggcgaggg cctggcgcgg ctgggggcgc cgtctcccga gcgccacccg cgggtgcagc    12900
tgaagcgcga ctcgcgcgag gcgtacgtgc ctcggcagaa cctgttcagg gaccgcgcgg    12960
gcgaggagcc cgaggagatg cgggacagga ggttcagcgc agggcgggag ctgcggcagg    13020
ggctgaaccg cgagcggctg ctgcgcgagg aggactttga gcccgacgcg cggacgggga    13080
tcagccccgc gcgcgcgcac gtggcggccg ccgacctggt gacggcgtac gagcagacgg    13140
tgaaccagga gatcaacttc caaaagagtt caacaacca cgtgcgcacg ctggtggcgc    13200
gcgaggaggt gaccatcggg ctgatgcacc tgtgggactt tgtaagcgcg ctggtgcaga    13260
accccaacag caagcctctg acggcgcagc tgttcctgat agtgcagcac agcagggaca    13320
acgaggcgtt tagggacgcg ctgctgaaca tcaccgagcc cgagggtcgg tggctgctgg    13380
acctgattaa catcctgcag agcatagtgg tgcaggagcc cagcctgagc ctggccgaca    13440
aggtggcggc catcaactac tcgatgctga gcctgggcaa gttttacgcg cgcaagatct    13500
accagacgcc gtacgtgccc atagacaagg aggtgaagat cgacggtttt tacatgcgca    13560
tggcgctgaa ggtgctcacc ctgagcgacg acctgggcgt gtaccgcaac gagcgcatcc    13620
acaaggccgt gagcgtgagc cggcggcgcg agctgagcga ccgcgagctg atgcacagcc    13680
tgcagcgggc gctggcgggc gccggcagcg gcgacaggga ggcggagtcc tacttcgatg    13740
cgggggcgga cctgcgctgg gcgcccagcc ggcgggccct ggaggccgcg gggtccgcg    13800
aggactatga cgaggacggc gaggaggatg aggagtacga gctagaggag ggcgagtacc    13860
tggactaaac cgcgggtggt gtttccggta gatgcaagac ccgaacgtgg tggaccccggc    13920
```

```
gctgcgggcg gctctgcaga gccagccgtc cggccttaac tcctcagacg actggcgaca    13980
ggtcatggac cgcatcatgt cgctgacggc gcgtaacccg gacgcgttcc ggcagcagcc    14040
gcaggccaac aggctctccg ccatcctgga ggcggtggtg cctgcgcgct cgaaccccac    14100
gcacgagaag gtgctggcca tagtgaacgc gctggccgag aacagggcca tccgcccgga    14160
cgaggccggg ctggtgtacg acgcgctgct gcagcgcgtg gcccgctaca acagcggcaa    14220
cgtgcagacc aacctggacc ggctggtggg ggacgtgcgc gaggcggtgg cgcagcgcga    14280
gcgcgcggat cggcagggca acctgggctc catggtggcg ctgaatgcct tcctgagcac    14340
gcagccggcc aacgtgccgc gggggcagga agactacacc aactttgtga gcgcgctgcg    14400
gctgatggtg accgagaccc cccagagcga ggtgtaccag tcgggcccgg actacttctt    14460
ccagaccagc agacagggcc tgcagacggt gaacctgagc caggctttca gaacctgcg    14520
ggggctgtgg ggcgtgaagg cgcccaccgg cgaccgggcg acggtgtcca gctgctgac    14580
gcccaactcg cgcctgctgc tgctgctgat cgcgccgttc acggacagcg gcagcgtgtc    14640
ccgggacacc tacctggggc acctgctgac cctgtaccgc gaggccatcg gcaggcgca    14700
ggtggacgag cacaccttcc aggagatcac cagcgtgagc cgcgcgctgg ggcaggagga    14760
cacgagcagc ctggaggcga ctctgaacta cctgctgacc aaccggcggc agaagattcc    14820
ctcgctgcac agcctgacct ccgaggagga gcgcatcttg cgctacgtgc agcagagcgt    14880
gagcctgaac ctgatgcgcg acggggtgac gcccagcgtg gcgctggaca tgaccgcgcg    14940
caacatggaa ccgggcatgt acgccgcgca ccggccttac atcaaccgcc tgatggacta    15000
cctgcatcgc gcggcggccg tgaaccccga gtactttacc aacgccatcc tgaacccgca    15060
ctggctcccg ccgcccgggt tctacagcgg gggcttcgag gtcccggaga ccaacgatgg    15120
cttcctgtgg gacgacatgg acgacagcgt gttctccccg cggccgcagg cgctggcgga    15180
agcgtccctg ctgcgtccca agaaggagga ggaggaggag gcgagtcgcc gccgcggcag    15240
cagcggcgtg gcttctctgt ccgagctggg ggcggcagcc gccgcgcgcc ccgggtccct    15300
gggcggcagc cccttccga gcctggtggg gtctctgcac agcgagcgca ccacccgccc    15360
tcggctgctg ggcgaggacg agtacctgaa taactccctg ctgcagccgg tgcgggagaa    15420
aaacctgcct cccgccttcc ccaacaacgg gatagagagc ctggtggaca agatgagcag    15480
atggaagacc tatgcgcagg agcacaggga cgcgcctgcg ctccggccgc ccacgcggcg    15540
ccagcgccac gaccggcagc gggggctggt gtgggatgac gaggactccg cggacgatag    15600
cagcgtgctg gacctgggag ggagcggcaa cccgttcgcg cacctgcgcc ccgcctggg    15660
gaggatgttt taaaaaaaaa aaaaaaagc aagaagcatg atgcaaaaat taaataaaac    15720
tcaccaaggc catggcgacc gagcgttggt ttcttgtgtt cccttcagta tgcggcgcgc    15780
ggcgatgtac caggagggac ctcctccctc ttacgagagc gtggtgggcg cggcggcggc    15840
ggcgccctct tctcccttg cgtcgcagct gctggagccg ccgtacgtgc ctccgcgcta    15900
cctgcggcct acgggggga gaaacagcat ccgttactcg gagctggcgc ccctgttcga    15960
caccacccgg gtgtacctgg tggacaacaa gtcggcggac gtggcctccc tgaactacca    16020
gaacgaccac agcaatttt tgaccacggt catccagaac aatgactaca gcccgagcga    16080
ggccagcacc cagaccatca atctggatga ccggtcgcac tggggcggcg acctgaaaac    16140
catcctgcac accaacatgc ccaacgtgaa cgagttcatg ttcaccaata agttcaaggc    16200
gcgggtgatg gtgtcgcgct cgcacaccaa ggaagaccgg gtggagctga agtacgagtg    16260
ggtggagttc gagctgccag agggcaacta ctccgagacc atgaccattg acctgatgaa    16320
```

```
caacgcgatc gtggagcact atctgaaagt gggcaggcag aacggggtcc tggagagcga    16380
catcggggtc aagttcgaca ccaggaactt ccgcctgggg ctggaccccg tgaccgggct    16440
ggttatgccc ggggtgtaca ccaacgaggc cttccatccc gacatcatcc tgctgcccgg    16500
ctgcggggtg gacttcactt acagccgcct gagcaacctc ctgggcatcc gcaagcggca    16560
gcccttccag gagggcttca ggatcaccta cgaggacctg ggggggggca acatccccgc    16620
gctcctcgat gtggaggcct accaggatag cttgaaggaa aatgaggcgg acaggagga    16680 taccgccccc gccgcctccg ccgccgccga gcagggcgag gatgctgctg acaccgcggc    16740
cgcggacggg gcagaggccg accccgctat ggtggtggag gctcccgagc aggaggagga    16800
catgaatgac agtgcggtgc gcggagacac cttcgtcacc cggggggagg aaaagcaagc    16860
ggaggccgag gccgcggccg aggaaaagca actggcggca gcagcggcgg cggcggcgtt    16920
ggccgcggcg gaggctgagt ctgaggggac caagcccgcc aaggagcccg tgattaagcc    16980
cctgaccgaa gatagcaaga agcgcagtta caacctgctc aaggacagca ccaacaccgc    17040
gtaccgcagc tggtacctgg cctacaacta cggcgacccg tcgacggggg tgcgctcctg    17100
gaccctgctg tgcacgccgg acgtgacctg cggctcggag caggtgtact ggtcgctgcc    17160
cgacatgatg caagaccccg tgaccttccg ctccacgcgg caggtcagca acttcccggt    17220
ggtgggcgcc gagctgctgc ccgtgcactc caagagcttc tacaacgacc aggccgtcta    17280
ctcccagctc atccgccagt tcacctctct gacccacgtg ttcaatcgct ttcctgagaa    17340
ccagattctg gcgcgcccgc ccgccccac catcaccacc gtcagtgaaa acgttcctgc    17400
tctcacagat cacgggacgc taccgctgcg caacagcatc ggaggagtcc agcgagtgac    17460
cgttactgac gccagacgcc gcacctgccc ctacgtttac aaggccttgg gcatagtctc    17520
gccgcgcgtc cttttccagcc gcacttttg agcaacacca ccatcatgtc catcctgatc    17580
tcacccagca ataactccgg ctggggactg ctgcgcgcgc ccagcaagat gttcggaggg    17640
gcgaggaagc gttccgagca gcaccccgtg cgcgtgcgcg ggcacttccg cgcccctgg    17700 ggagcgcaca aacgcggccg cgcggggcgc accaccgtgg acgacgccat cgactcggtg    17760
gtggagcagg cgcgcaacta caggcccgcg gtctctaccg tggacgcggc catccagacc    17820
gtggtgcggg gcgcgcggcg gtacgccaag ctgaagagcc gccggaagcg cgtggcccgc    17880
cgccaccgcc gccgacccgg ggccgccgcc aaacgcgccg ccgcggccct gcttcgccgg    17940
gccaagcgca cgggccgccg cgccgccatg agggccgcgc gccgcttggc cgccggcatc    18000
accgccgcca ccatggcccc ccgtacccga agacgcgcgg ccgccgccgc cgccgccgcc    18060
atcagtgaca tggccagcag gcgccggggc aacgtgtact gggtgcgcga ctcggtgacc    18120
ggcacgcgcg tgcccgtgcg cttccgcccc ccgcggactt gagatgatgt gaaaaaacaa    18180
cactgagtct cctgctgttg tgtgtatccc agcggcggcg gcgcgcgcag cgtcatgtcc    18240
aagcgcaaaa tcaaagaaga gatgctccag gtcgtcgcgc cggagatcta tgggcccccg    18300
aagaaggaag agcaggattc gaagcccgc aagataaagc gggtcaaaaa gaaaagaaa    18360 gatgatgacg atgccgatgg ggaggtggag ttcctgcgcg ccacggcgcc caggcgcccg    18420
gtgcagtgga agggccggcg cgtaaagcgc gtcctgcgcc ccggcaccgc ggtggtcttc    18480
acgcccggcg agcgctccac ccggactttc aagcgcgtct atgacgaggt gtacggcgac    18540
gaagacctgc tggagcaggc caacgagcgc ttcggagagt ttgcttacgg gaagcgtcag    18600
cgggcgctgg ggaaggagga cctgctggcg ctgccgctgg accagggcaa ccccacccc    18660
```

```
agtctgaagc cgtgaccct gcagcaggtg ctgccgagca gcgcaccctc cgaggcgaag    18720
cggggtctga agcgcgaggg cggcgacctg gcgcccaccg tgcagctcat ggtgcccaag    18780
cggcagaggc tggaggatgt gctggagaaa atgaaagtag accccggtct gcagccggac    18840
atcagggtcc gccccatcaa gcaggtggcg ccgggcctcg gcgtgcagac cgtggacgtg    18900
gtcatcccca ccggcaactc ccccgccgcc gccaccacta ccgctgcctc cacggacatg    18960
gagacacaga ccgatcccgc cgcagccgca gccgcagccg ccgccgcgac ctcctcggcg    19020
gaggtgcaga cggacccctg gctgccgccg gcgatgtcag ctccccgcgc gcgtcgcggg    19080
cgcaggaagt acggcgccgc caacgcgctc ctgcccgagt acgccttgca tccttccatc    19140
gcgcccaccc ccggctaccg aggctatacc taccgcccgc gaagagccaa gggttccacc    19200
cgccgtcccc gccgacgcgc cgccgccacc cccgccgcc gccgccgcag acgccagccc    19260
gcactggctc cagtctccgt gaggaaagtg gcgcgcgacg gacacaccct ggtgctgccc    19320
agggcgcgct accaccccag catcgtttaa aagcctgttg tggttcttgc agatatggcc    19380
ctcacttgcc gcctccgttt cccggtgccg ggataccgag gaggaagatc gcgccgcagg    19440
aggggtctgg ccggccgcgg cctgagcgga ggcagccgcc gcgcgcaccg gcggcgacgc    19500
gccaccagcc gacgcatgcg cggcggggtg ctgcccctgt taatccccct gatcgccgcg    19560
gcgatcggcg ccgtgcccgg gatcgcctcc gtggccttgc aagcgtccca gaggcattga    19620
cagacttgca aacttgcaaa tatggaaaaa aaaccccaa taaaaagtc tagactctca    19680 cgctcgcttg gtcctgtgac tattttgtag aatggaagac atcaactttg cgtcgctggc    19740
cccgcgtcac ggctcgcgcc cgttcctggg acactggaac gatatcggca ccagcaacat    19800
gagcggtggc gccttcagtt ggggctctct gtggagcggc attaaaagta tcgggtctgc    19860
cgttaaaaat tacggctccc gggctggaa cagcagcacg ggccagatgt tgagagacaa    19920
gttgaaagag cagaacttcc agcagaaggt ggtggagggc ctggcctccg gcatcaacgg    19980
ggtggtggac ctggccaacc aggccgtgca gaataagatc aacagcagac tggacccccg    20040
gccgccggtg gaggaggtgc cgccggcgct ggagacggtg tccccgatg ggcgtggcga    20100 gaagcgcccg cggcccgata gggaagagac cactctggtc acgcagaccg atgagccgcc    20160
cccgtatgag gaggccctga agcaaggtct gcccaccacg cggcccatcg cgcccatggc    20220
caccggggtg gtgggccgcc acaccccccgc cacgctggac ttgcctccgc ccgccgatgt    20280
gccgcagcag cagaaggcgg cacagccggg cccgcccgcg accgcctccc gttcctccgc    20340
cggtcctctg cgccgcgcgg ccagcggccc ccgcgggggg gtcgcgaggc acggcaactg    20400
gcagagcacg ctgaacagca tcgtgggtct ggggggtgcgg tccgtgaagc gccgccgatg    20460
ctactgaata gcttagctaa cgtgttgtat gtgtgtatgc gccctatgtc gccgccagag    20520
gagctgctga gtcgccgccg ttcgcgcgcc caccaccacc gccactccgc ccctcaagat    20580
ggcgacccca tcgatgatgc cgcagtggtc gtacatgcac atctcgggcc aggacgcctc    20640
ggagtacctg agccccgggc tggtgcagtt cgcccgcgcc accgagagct acttcagcct    20700
gagtaacaag tttaggaacc ccacggtggc gcccacgcac gatgtgacca ccgaccggtc    20760
tcagcgcctg acgctgcggt tcattcccgt ggaccgcgag gacaccgcgt actcgtacaa    20820
ggcgcggttc acccctggccg tgggcgacaa ccgcgtgctg gacatggcct ccacctactt    20880
tgacatccgc ggggtgctgg accggggtcc cactttcaag ccctactctg gcaccgccta    20940
caactccctg gcccccaagg gcgctcccaa ctcctgcgca tgggagcaag aggaaactca    21000
ggcagttgaa gaagcagcag aagaggaaga agaagatgct gacggtcaag ctgaggaaga    21060
```

```
gcaagcagct accaaaaaga ctcatgtata tgctcaggct cccctttctg gcgaaaaaat    21120
tagtaaagat ggtctgcaaa taggaacgga cgctacagct acagaacaaa aacctattta    21180
tgcagaccct acattccagc ccgaacccca atcggggag tcccagtgga atgaggcaga     21240
tgctacagtc gccggcggta gagtgctaaa gaaatctact cccatgaaac catgctatgg    21300
ttcctatgca agacccacaa atgctaatgg aggtcagggt gtactaacgg caaatgccca    21360
gggacagcta gaatctcagg ttgaaatgca attcttttca acttctgaaa cgcccgtaa    21420 cgaggctaac aacattcagc ccaaattggt gctgtatagt gaggatgtgc acatggagac    21480
cccggatacg caccttttctt acaagcccgc aaaaagcgat gacaattcaa aaatcatgct    21540
gggtcagcag tccatgccca acagacctaa ttacatcggc ttcagagaca actttatcgg    21600
cctcatgtat acaatagca ctggcaacat gggagtgctt gcaggtcagg cctctcagtt     21660
gaatgcagtg gtggacttgc aagacagaaa cacagaactg tcctaccagc tcttgcttga    21720
ttccatgggt gacagaacca gatacttttc catgtggaat caggcagtgg acagttatga    21780
cccagatgtt agaattattg aaaatcatgg aactgaagac gagctcccca actattgttt    21840
ccctctgggg ggcatagggg taactgacac ttaccaggct gttaaaacca acaatggcaa    21900
taacgggggc caggtgactt ggacaaaaga tgaaactttt gcagatcgca atgaaatagg    21960
ggtgggaaac aatttcgcta tggagatcaa cctcagtgcc aacctgtgga gaaacttcct    22020
gtactccaac gtggcgctgt acctaccaga caagcttaag tacaaccccct ccaatgtgga    22080 catctctgac aaccccaaca cctacgatta catgaacaag cgagtggtgg ccccggggct    22140
ggtggactgc tacatcaacc tgggcgcgcg ctggtcgctg gactacatgg acaacgtcaa    22200
ccccttcaac caccaccgca atgcgggcct gcgctaccgc tccatgctcc tgggcaacgg    22260
gcgctacgtg cccttccaca tccaggtgcc ccagaagttc tttgccatca gaacctcct    22320 cctcctgccg ggctcctaca cctacgagtg gaacttcagg aaggatgtca acatggtcct    22380
ccagagctct ctgggtaacg atctcagggt ggacggggcc agcatcaagt tcgagagcat    22440
ctgcctctac gccaccttct tccccatggc ccacaacacg gcctccacgc tcgaggccat    22500
gctcaggaac gacaccaacg accagtcctt caatgactac ctctccgccg ccaacatgct    22560
ctaccccata cccgccaacg ccaccaacgt cccccatctcc atcccctcgc gcaactgggc    22620
ggccttccgc ggctgggcct tcacccgcct caagaccaag gagacccct cctgggctc     22680 gggattcgac ccctactaca cctactcggg ctccattccc tacctggacg gcaccttcta    22740
cctcaaccac actttcaaga aggtctcggt caccttcgac tcctcggtca gctggccggg    22800
caacgaccgt ctgctcaccc ccaacgagtt cgagatcaag cgctcggtcg acgggagg     22860 ctacaacgtg gccagtgca acatgaccaa ggactggttc ctggtccaga tgctggccaa    22920
ctacaacatc ggctaccagg gcttctacat cccagagagc tacaaggaca ggatgtactc    22980
cttcttcagg aacttccagc ccatgagccg gcaggtggtg gaccagacca agtacaagga    23040
ctaccaggag gtgggcatca tccaccagca caacaactcg ggcttcgtgg gctacctcgc    23100
ccccaccatg cgcgagggac aggcctaccc cgccaacttc cctatccgc tcataggcaa    23160 gaccgcggtc gacagcatca cccagaaaaa gttcctctgc gaccgcaccc tctggcgcat    23220
ccccttctcc agcaacttca tgtccatggg tgcgctctcg gacctgggcc agaacttgct    23280
ctacgccaac tccgcccacg ccctcgacat gaccttcgag gtcgacccca tggacgagcc    23340
cacccttctc tatgttctgt tcgaagtctt tgacgtggtc cgggtccacc agccgcaccg    23400
```

```
cggcgtcatc gagaccgtgt acctgcgtac gcccttctcg gccggcaacg ccaccaccta   23460
aagaagcaag ccgcagtcat cgccgcctgc atgccgtcgg gttccaccga gcaagagctc   23520
agggccatcg tcagagacct gggatgcggg ccctattttt tgggcacctt cgacaagcgc   23580
ttccctggct ttgtctcccc acacaagctg gcctgcgcca tcgtcaacac ggccggccgc   23640
gagaccgggg gcgtgcactg gctggccttc gcctggaacc cgcgctccaa acatgcttc   23700 ctctttgacc ccttcggctt ttcggaccag cggctcaagc aaatctacga gttcgagtac   23760
gagggcttgc tgcgtcgcag cgccatcgcc tcctcgcccg accgctgcgt caccctcgaa   23820
aagtccaccc agaccgtgca ggggcccgac tcggccgcct gcggtctctt ctgctgcatg   23880
tttctgcacg ccttttgtgca ctggcctcag agtcccatgg accgcaaccc caccatgaac   23940
ttgctgacgg gggtgcccaa ctccatgctc cagagccccc aggtcgagcc caccctgcgc   24000
cgcaaccagg agcagctcta cagcttcctg gagcgccact cgccttactt ccgccgccac   24060
agcgcacaga tcaggagggc cacctccttc tgccacttgc aagagatgca agaagggtaa   24120
taacgatgta cacactttt ttctcaataa atggcatctt tttatttata caagctctct   24180
ggggtattca tttcccacca ccacccgccg ttgtcgccat ctggctctat ttagaaatcg   24240
aaagggttct gccgggagtc gccgtgcgcc acgggcaggg acacgttgcg atactggtag   24300
cgggtgcccc acttgaactc gggcaccacc aggcgaggca gctcggggaa gttttcgctc   24360
cacaggctgc gggtcagcac cagcgcgttc atcaggtcgg gcgccgagat cttgaagtcg   24420
cagttggggc cgccgccctg cgcgcgcgag ttgcggtaca ccgggttgca gcactggaac   24480
accaacagcg ccgggtgctt cacgctggcc agcacgctgc ggtcgagat cagctcggcg   24540 tccaggtcct ccgcgttgct cagcgcgaac ggggtcatct tgggcacttg ccgccccagg   24600
aagggcgcgt gccccggttt cgagttgcag tcgcagcgca gcgggatcag caggtgcccg   24660
tgcccggact cggcgttggg gtacagcgcg cgcatgaagg cctgcatctg gcggaaggcc   24720
atctgggcct tggcgccctc cgagaagaac atgccgcagg acttgcccga gaactggttt   24780
gcggggcagc tggcgtcgtg caggcagcag cgcgcgtcgg tgttggcgat ctgcaccacg   24840 ttgcgcccccc accggttctt cacgatcttg gccttggacg attgctcctt cagcgcgcgc   24900
tgcccgttct cgctggtcac atccatctcg atcacatgtt ccttgttcac catgctgctg   24960
ccgtgcagac acttcagctc gccctccgtc tcggtcagc ggtgctgcca cagcgcgcag   25020
cccgtgggct cgaaagactt gtaggtcacc tccgcgaagg actgcaggta cccctgcaaa   25080
aagcggccca tcatggtcac gaaggtcttg ttgctgctga aggtcagctg cagcccgcgg   25140
tgctcctcgt tcagccaggt cttgcacacg gccgccagcg cctccacctg gtcgggcagc   25200
atcttgaagt tcaccttcag ctcattctcc acgtggtact tgtccatcag cgtgcgcgcc   25260
gcctccatgc ccttctccca ggccgacacc agcggcaggc tcacggggtt cttcaccatc   25320
accgtggccg ccgcctccgc cgcgcttcg ctttccgccc cgctgttctc ttcctcttcc   25380
tcctcttcct cgccgccgcc cactcgcagc ccccgcacca cggggtcgtc ttcctgcagg   25440
cgctgcacct tgcgcttgcc gttgcgcccc tgcttgatgc gcacgggcgg gttgctgaag   25500
cccaccatca ccagcgcggc ctcttcttgc tcgtcctcgc tgtccagaat gacctccggg   25560
gagggggggt tggtcatcct cagtaccgag gcacgcttct tttcttcct gggggcgttc   25620 gccagctccg cggctgcggc cgctgccgag gtcgaaggcc gagggctggg cgtgcgcggc   25680
accagcgcgt cctgcgagcc gtcctcgtcc tcctcggact cgagacgag gcgggcccgc   25740 ttcttcgggg gcgcgcgggg cggcggaggc ggcggcggcg acggagacgg ggacgagaca   25800
```

```
tcgtccaggg tgggtggacg gcgggccgcg ccgcgtccgc gctcgggggt ggtctcgcgc   25860
tggtcctctt cccgactggc catctcccac tgctccttct cctataggca gaaagagatc   25920
atggagtctc tcatgcgagt cgagaaggag gaggacagcc taaccgcccc ctctgagccc   25980
tccaccaccg ccgccaccac cgccaatgcc gccgcgacg acgcgcccac cgagaccacc   26040
gccagtacca ccctccccag cgacgcaccc ccgctcgaga atgaagtgct gatcgagcag   26100
gacccgggtt ttgtgagcgg agaggaggat gaggtggatg agaaggagaa ggaggaggtc   26160
gccgcctcag tgccaaaaga ggataaaaag caagaccagg acgacgcaga taaggatgag   26220
acagcagtcg ggcgggggaa cggaagccat gatgctgatg acggctacct agacgtggga   26280
gacgacgtgc tgcttaagca cctgcaccgc cagtgcgtca tcgtctgcga cgcgctgcag   26340
gagcgctgcg aagtgcccct ggacgtggcg gaggtcagcc gcgcctacga gcggcacctc   26400
ttcgcgccgc acgtgccccc caagcgccgg gagaacggca cctgcgagcc caacccgcgt   26460
ctcaacttct acccggtctt cgcggtaccc gaggtgctgg ccacctacca catcttttc   26520 caaaactgca agatccccct ctcctgccgc gccaaccgca cccgcgccga caaaaccctg   26580
accctgcggc agggcgccca catacctgat atcgcctctc tggaggaagt gcccaagatc   26640
ttcgagggtc tcggtcgcga cgagaaacgg gcggcgaacg ctctgcacgg agacagcgaa   26700
aacgagagtc actcgggggt gctggtggag ctcgagggcg acaacgcgcg cctgccgta   26760 ctcaagcgca gcatagaggt cacccacttt gcctacccgg cgctcaacct gcccccaag   26820 gtcatgagtg tggtcatggg cgagctcatc atgcgccgcg cccagcccct ggccgcggat   26880
gcaaacttgc aagagtcctc cgaggaaggc ctgcccgcgg tcagcgacga gcagctggcg   26940
cgctggctgg agacccgcga ccccgcgcag ctggaggagc ggcgcaagct catgatggcc   27000
gcggtgctgg tcaccgtgga gctcgagtgt ctgcagcgct tcttcgcgga ccccgagatg   27060
cagcgcaagc tcgaggagac cctgcactac accttccgcc agggctacgt gcgccaggcc   27120
tgcaagatct ccaacgtgga gctctgcaac ctggtctcct acctgggcat cctgcacgag   27180
aaccgcctcg gcagaaacgt cctgcactcc accctcaaag gggaggcgcg ccgcgactac   27240
atccgcgact gcgcctacct cttcctctgc tacacctggc agacggccat gggggtctgg   27300
cagcagtgcc tggaggagcg caacctcaag gagctggaaa agctcctcaa gcgcaccctc   27360
agggacctct ggacgggctt caacgagcgc tcggtggccg ccgcgctggc ggacatcatc   27420
tttcccgagc gcctgctcaa gaccctgcag cagggcctgc ccgacttcac cagccagagc   27480
atgctgcaga acttcaggac tttcatcctg gagcgctcgg gcatcctgcc ggccacttgc   27540
tgcgcgctgc ccagcgactt cgtgcccatc aagtacaggg agtgcccgcc gccgctctgg   27600
ggccactgct acctcttcca gctggccaac tacctcgcct accactcgga cctcatggaa   27660
gacgtgagcg gcgagggcct gctcgagtgc cactgccgct gcaacctctg cacgccccac   27720
cgctctctag tctgcaaccc gcagctgctc agcgagagtc agattatcgg taccttcgag   27780
ctgcagggtc cctcgcctga cgagaagtcc gcggctccag ggctgaaact cactccgggg   27840
ctgtggactt ccgcctacct acgcaaattt gtacctgagg actaccacgc ccacgagatc   27900
aggttctacg aagaccaatc ccgcccgccc aaggcggagc tcaccgcctg cgtcatcacc   27960
caggggcaca tcctgggcca attgcaagcc atcaacaaag cccgccgaga gttcttgctg   28020
aaaaagggtc gggggtgtta cctggacccc cagtccggcg aggagctaaa cccgctaccc   28080
ccgccgccgc cccagcagcg ggaccttgct tcccaggatg gcacccagaa agaagcagca   28140
```

```
gccgccgccg ccgccgcagc catacatgct tctggaggaa gaggaggagg actgggacag    28200
tcaggcagag gaggtttcgg acgaggagca ggaggagatg atggaagact gggaggagga    28260
cagcagccta gacgaggaag cttcagaggc cgaagaggtg gcagacgcaa caccatcgcc    28320
ctcggtcgca gcccctcgc cggggcccct gaaatcctcc gaacccagca ccagcgctat     28380
aacctccgct cctccggcgc cggcgccacc cgcccgcaga cccaaccgta gatgggacac    28440
cacaggaacc ggggtcggta agtccaagtg cccgccgccg ccaccgcagc agcagcagca    28500
gcagcgccag ggctaccgct cgtggcgcgg gcacaagaac gccatagtcg cctgcttgca    28560
agactgcggg ggcaacatct cttccgcccg ccgcttcctg ctattccacc acggggtcgc    28620 cttccccgc aatgtcctgc attactaccg tcatctctac agcccctact gcagcggcga     28680
cccagaggcg gcagcggcag ccacagcggc gaccaccacc taggaagata tcctccgcgg    28740
gcaagacagc ggcagcagcg gccaggagac ccgcggcagc agcggcggga gcggtgggcg    28800
cactgcgcct ctcgcccaac gaacccctct cgacccggga gctcagacac aggatcttcc    28860
ccactttgta tgccatcttc caacagagca gaggccagga gcaggagctg aaaataaaaa    28920
acagatctct gcgctccctc acccgcagct gtctgtatca caaaagcgaa gatcagcttc    28980
ggcgcacgct ggaggacgcg gaggcactct tcagcaaata ctgcgcgctc actcttaaag    29040
actagctccg cgcccttctc gaatttaggc gggagaaaac tacgtcatcg ccggccgccg    29100
cccagcccgc ccagccgaga tgagcaaaga gattcccacg ccatacatgt ggagctacca    29160
gccgcagatg ggactcgcgg cgggagcggc ccaggactac tccacccgca tgaactacat    29220
gagcgcggga ccccacatga tctcacaggt caacgggatc cgcgcccagc gaaaccaaat    29280
actgctggaa caggcggcca tcaccgccac gccccgccat aatctcaacc cccgaaattg    29340
gcccgccgcc ctcgtgtacc aggaaacccc ctccgccacc accgtactac ttccgcgtga    29400
cgcccaggcc gaagtccaga tgactaactc aggggcgcag ctcgcgggcg gctttcgtca    29460
cggggcgcgg ccgctccgac caggtataag acacctgatg atcagaggcc gaggtatcca    29520
gctcaacgac gagtcggtga gctcttcgct cggtctccgt ccggacggaa cttccagct    29580 cgccggatcc ggccgctctt cgttcacgcc ccgccaggcg tacctgactc tgcagacctc    29640
gtcctcggag ccccgctccg gcggcatcgg aaccctccag ttcgtggagg agttcgtgcc    29700
ctcggtctac ttcaacccct tctcgggacc tccggacgc tacccgacc agttcattcc      29760 gaactttgac gcggtgaagg actcggcgga cggctacgac tgaatgtcag gtgtcgaggc    29820
agagcagctt cgcctgagac acctcgagca ctgccgccgc cacaagtgct tcgcccgcgg    29880
ttctggtgag ttctgctact ttcagctacc cgaggagcat accgaggggc cggcgcacgg    29940
cgtccgcctg accacccagg gcgaggttac ctgttccctc atccgggagt ttaccctccg    30000
tcccctgcta gtggagcggg agcggggtcc ctgtgtccta actatcgcct gcaactgccc    30060
taaccctgga ttcatcaag atctttgctg tcatctctgt gctgagttta ataaacgctg     30120
agatcagaat ctactggggc tcctgtcgcc atcctgtgaa cgccaccgtc ttcacccacc    30180
ccgaccaggc ccaggcgaac ctcacctgcg gtctgcatcg gagggccaag aagtacctca    30240
cctggtactt caacggcacc ccctttgtgg tttacaacag cttcgacggg gacggagtct    30300
ccctgaaaga ccagctctcc ggtctcagct actccatcca caagaacacc accctccaac    30360
tcttccctcc ctacctgccg ggaacctacg agtgcgtcac cggccgctgc acccaccta     30420 cccgcctgat cgtaaaccag agctttccgg gaacagataa ctccctcttc cccagaacag    30480
gaggtgagct caggaaactc cccggggacc agggcggaga cgtaccttcg acccttgtgg    30540
```

```
ggttaggatt ttttattacc gggttgctgg ctcttttaat caaagtttcc ttgagatttg   30600
ttctttcctt ctacgtgtat gaacacctca acctccaata actctaccct tcttcggaa    30660 tcaggtgact tctctgaaat cgggcttggt gtgctgctta ctctgttgat ttttttcctt   30720
atcatactca gccttctgtg cctcaggctc gccgcctgct gcgcacacat ctatatctac   30780
tgctggttgc tcaagtgcag gggtcgccac ccaagatgaa caggtacatg gtcctatcga   30840
tcctaggcct gctggccctg gcggcctgca gcgccgccaa aaaagagatt acctttgagg   30900
agcccgcttg caatgtaact ttcaagcccg agggtgacca atgcaccacc ctcgtcaaat   30960
gcgttaccaa tcatgagagg ctgcgcatcg actacaaaaa caaaactggc cagtttgcgg   31020
tctatagtgt gtttacgccc ggagacccct ctaactactc tgtcaccgtc ttccagggcg   31080
gacagtctaa gatattcaat tacactttcc cttttttatga gttatgcgat gcggtcatgt   31140
acatgtcaaa acagtacaac ctgtggcctc cctctcccca ggcgtgtgtg gaaaatactg   31200
ggtcttactg ctgtatggct ttcgcaatca ctacgctcgc tctaatctgc acggtgctat   31260
acataaaatt caggcagagg cgaatcttta tcgatgaaaa gaaaatgcct tgatcgctaa   31320
caccggcttt ctatctgcag aatgaatgca atcacctccc tactaatcac caccaccctc   31380
cttgcgattg cccatgggtt gacacgaatc gaagtgccag tggggtccaa tgtcaccatg   31440
gtgggccccg ccggcaattc cacccctcatg tgggaaaaat ttgtccgcaa tcaatgggtt   31500
catttctgct ctaaccgaat cagtatcaag cccagagcca tctgcgatgg gcaaaatcta   31560
actctgatca atgtgcaaat gatggatgct gggtactatt acgggcagcg gggagaaatc   31620
attaattact ggcgacccca caaggactac atgctgcatg tagtcgaggc acttcccact   31680 accacccca ctaccacctc tcccaccacc accaccacta ctactactac tactactact   31740
actactacta ccactaccgc tgcccgccat acccgcaaaa gcaccatgat tagcacaaag   31800
ccccctcgtg ctcactccca cgccggcggg cccatcggtg cgacctcaga accaccgag    31860 ctttgcttct gccaatgcac taacgccagc gctcatgaac tgttcgacct ggagaatgag   31920
gatgtccagc agagctccgc ttgcctgacc caggaggctg tggagcccgt tgccctgaag   31980
cagatcggtg attcaataat tgactcttct tcttttgcca ctcccgaata ccctcccgat   32040
tctactttcc acatcacggg taccaaagac cctaacctct cttctctacct gatgctgctg   32100 ctctgtatct ctgtggtctc ttccgcgctg atgttactgg ggatgttctg ctgcctgatc   32160
tgccgcagaa agagaaaagc tcgctctcag ggccaaccac tgatgcccct ccctacccc    32220 ccggattttg cagataacaa gatatgagct cgctgctgac actaaccgct ttactagcct   32280
gcgctctaac ccttgtcgct tgcgactcga gattccacaa tgtcacagct gtggcaggag   32340
aaaatgttac tttcaactcc acggccgata cccagtggtc gtggagtggc tcaggtagct   32400
acttaactat ctgcaatagc tccacttccc ccggcatatc cccaaccaag taccaatgca   32460
atgccagcct gttcaccctc atcaacgctt ccaccctgga caatggactc tatgtaggct   32520
atgtaccctt tggtgggcaa ggaaagaccc acgcttacaa cctggaagtt cgccagccca   32580
gaaccactac ccaagcttct cccaccacca ccaccaccac caccatcacc agcagcagca   32640
gcagcagcag ccacagcagc agcagcagat tattgacttt ggttttggcc agctcatctg   32700
ccgctaccca ggccatctac agctctgtgc ccgaaaccac tcagatccac cgcccagaaa   32760
cgaccaccgc caccaccta cacacctcca gcgatcagat gccgaccaac atcacccct    32820 tggctcttca aatgggactt acaagcccca ctccaaaacc agtggatgcg gccgaggtct   32880
```

-continued

```
ccgccctcgt caatgactgg gcggggctgg gaatgtggtg gttcgccata ggcatgatgg    32940
cgctctgcct gcttctgctc tggctcatct gctgcctcca ccgcaggcga gccagacccc    33000
ccatctatag acccatcatt gtcctgaacc ccgataatga tgggatccat agattggatg    33060
gcctgaaaaa cctactttt tcttttacag tatgataaat tgagacatgc ctcgcatttt    33120
cttgtacatg ttccttctcc cacctttct ggggtgttct acgctggccg ctgtgtctca    33180
cctggaggta gactgcctct cacccttcac tgtctacctg ctttacggat tggtcaccct    33240
cactctcatc tgcagcctaa tcacagtaat catcgccttc atccagtgca ttgattacat    33300
ctgtgtgcgc ctcgcatact tcagacacca cccgcagtac cgagacagga acattgccca    33360
acttctaaga ctgctctaat catgcataag actgtgatct gccttctgat cctctgcatc    33420
ctgcccaccc tcacctcctg ccagtacacc acaaaatctc cgcgcaaaag acatgcctcc    33480
tgccgcttca cccaactgtg aatataccc aaatgctaca cgaaaagag cgagctctcc    33540 gaagcttggc tgtatggggt catctgtgtc ttagttttct gcagcactgt ctttgccctc    33600
ataatctacc cctactttga tttgggatgg aacgcgatcg atgccatgaa ttaccccacc    33660
tttcccgcac ccgagataat tccactgcga caagttgtac ccgttgtcgt taatcaacgc    33720
cccccatccc ctacgcccac tgaaatcagc tactttaacc taacaggcgg agatgactga    33780
cgccctagat ctagaaatgg acggcatcag taccgagcag cgtctcctag agaggcgcag    33840
gcaggcggct gagcaagagc gcctcaatca ggagctccga gatctcgtta acctgccacca    33900 gtgcaaaaga ggcatctttt gtctggtaaa gcaggccaaa gtcacctacg agaagaccgg    33960
caacagccac cgcctcagtt acaaattgcc cacccagcgc cagaagctgg tgctcatggt    34020
gggtgagaat cccatcaccg tcacccagca ctcggtagag accgagggt gtctgcactc    34080 cccctgtcgg ggtccagaag acctctgcac cctggtaaag accctgtgcg gtctcagaga    34140
tttagtcccc tttaactaat caaacactgg aatcaataaa aagaatcact tacttaaaat    34200
cagacagcag gtctctgtcc agtttattca gcagcacctc cttcccctcc tcccaactct    34260
ggtactccaa acgccttctg gcggcaaact tcctccacac cctgaaggga atgtcagatt    34320
cttgctcctg tccctccgca cccactatct tcatgttgtt gcagatgaag cgcaccaaaa    34380
cgtctgacga gagcttcaac cccgtgtacc cctatgacac ggaaagcggc cctccctccg    34440 tcccttcct caccctccc ttcgtgtctc ccgatggatt ccaagaaagt cccccgggg    34500 tcctgtctct gaacctggcc gagcccctgg tcacttccca cggcatgctc gccctgaaaa    34560
tgggaagtgg cctctccctg gacgacgctg gcaacctcac ctctcaagat atcaccaccg    34620
ctagccctcc cctcaaaaaa accaagacca acctcagcct agaaacctca tcccccctaa    34680
ctgtgagcac ctcaggcgcc ctcaccgtag cagccgccgc tcccctggcg gtggccggca    34740
cctccctcac catgcaatca gaggcccccc tgacagtaca ggatgcaaaa ctcaccctgg    34800
ccaccaaagg cccctgacc gtgtctgaag gcaaactggc cttgcaaaca tcggcccgc    34860 tgacggccgc tgacagcagc accctcacag tcagtgccac accacccctt agcacaagca    34920
atggcagctt gggtattgac atgcaagccc ccatttacac caccaatgga aaactaggac    34980
ttaactttgg cgctccctg catgtggtag acagcctaaa tgcactgact gtagttactg    35040
gccaaggtct tacgataaac ggaacagccc tacaaactag agtctcaggt gccctcaact    35100
atgacacatc aggaaaccta gaattgagag ctgcagggg tatgcgagtt gatgcaaatg    35160
gtcaacttat ccttgatgta gcttacccat ttgatgcaca aaacaatctc agccttaggc    35220
ttggacaggg accctgttt gttaactctg cccacaactt ggatgttaac tacaacagag    35280
```

```
gcctctacct gttcacatct ggaaatacca aaaagctaga agttaatatc aaaacagcca    35340
agggtctcat ttatgatgac actgctatag caatcaatgc gggtgatggg ctacagtttg    35400
actcaggctc agatacaaat ccattaaaaa ctaaacttgg attaggactg gattatgact    35460
ccagcagagc cataattgct aaactgggaa ctggcctaag ctttgacaac acaggtgcca    35520
tcacagtagg caacaaaaat gatgacaagc ttaccttgtg gaccacacca gacccatccc    35580
ctaactgtag aatctattca gagaaagatg ctaaattcac acttgttttg actaaatgcg    35640
gcagtcaggt gttggccagc gtttctgttt tatctgtaaa aggtagcctt gcgcccatca    35700
gtggcacagt aactagtgct cagattgtcc tcagatttga tgaaaatgga gttctactaa    35760
gcaattcttc ccttgaccct caatactgga actacagaaa aggtgacctt acagagggca    35820
ctgcatatac caacgcagtg ggatttatgc ccaacctcac agcataccca aaaacacaga    35880
gccaaactgc taaaagcaac attgtaagtc aggtttactt gaatgggac aaatccaaac    35940 ccatgaccct caccattacc ctcaatggaa ctaatgaaac aggagatgcc acagtaagca    36000
cttactccat gtcattctca tggaactgga atggaagtaa ttacattaat gaaacgttcc    36060
aaaccaactc cttcacccttc tcctacatcg cccaagaata aaaagcatga cgctgttgat    36120
ttgattcaat gtgtttctgt tttattttca agcacaacaa aatcattcaa gtcattcttc    36180
catcttagct taatagacac agtagcttaa tagacccagt agtgcaaagc cccattctag    36240
cttataacta gtggagaagt actcgcctac atgggggtag agtcataatc gtgcatcagg    36300
atagggcggt ggtgctgcag cagcgcgcga ataaactgct gccgccgccg ctccgtcctg    36360
caggaataca acatggcagt ggtctcctca gcgatgattc gcaccgcccg cagcataagg    36420
cgccttgtcc tccgggcaca gcagcgcacc ctgatctcac ttaaatcagc acagtaactg    36480
cagcacagca ccacaatatt gttcaaaatc ccacagtgca aggcgctgta tccaaagctc    36540
atggcgggga ccacagaacc cacgtggcca tcataccaca agcgcaggta gattaagtgg    36600 cgaccoctca taaacacgct ggacataaac attacctctt ttggcatgtt gtaattcacc    36660
acctcccggt accatataaa cctctgatta aacatggcgc catccaccac catcctaaac    36720
cagctggcca aaacctgccc gccggctata cactgcaggg aaccgggact ggaacaatga    36780
cagtggagag cccaggactc gtaaccatgg atcatcatgc tcgtcatgat atcaatgttg    36840
gcacaacaca ggcacacgtg catacacttc ctcaggatta caagctcctc ccgcgttaga    36900
accatatccc agggaacaac ccattcctga atcagcgtaa atcccacact gcagggaaga    36960
cctcgcacgt aactcacgtt gtgcattgtc aaagtgttac attcgggcag cagcggatga    37020
tcctccagta tggtagcgcg ggtttctgtc tcaaaggag gtagacgatc cctactgtac    37080
ggagtgcgcc gagacaaccg agatcgtgtt ggtcgtagtg tcatgccaaa tggaacgccg    37140
gacgtagtca tatttcctga agtcttagat ctctcaacgc agcaccagca ccaacacttc    37200
gcagtgtaaa aggccaagtg ccgagagagt atatatagga ataaaagtg acgtaaacgg    37260 gcaaagtcca aaaacgcccc agaaaaaccg cacgcgaacc tacgccccga aacgaaagcc    37320
aaaaaacact agacactccc ttccggcgtc aacttccgct ttcccacgct acgtcacttg    37380
ccccagtcaa acaaactaca tatcccgaac ttccaagtcg ccacgccaaa acaccgcct    37440 acacctcccc gccgccggc ccgccccaa accgcctcc cgccccgcgc ccgccccgc    37500 gccgcccatc tcattatcat attggcttca atccaaaata aggtatatta ttgatgatg    37559
```

<210> SEQ ID NO 12

<211> LENGTH: 1109
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 12

```
ggagttccgc gttacataac ttacggtaaa tggcccgcct ggctgaccgc ccaacgaccc      60
ccgcccattg acgtcaataa tgacgtatgt tcccatagta acgccaatag ggactttcca     120
ttgacgtcaa tgggtggagt atttacggta aactgcccac ttggcagtac atcaagtgta     180
tcatatgcca agtacgcccc ctattgacgt caatgacggt aaatggcccg cctggcatta     240
tgcccagtac atgaccttat gggactttcc tacttggcag tacatctacg tattagtcat     300
cgctattacc atggtcgagg tgagccccac gttctgcttc actctcccca tctcccccc      360
ctccccaccc ccaattttgt atttatttat tttttaatta ttttgtgcag cgatggggc      420
gggggggggg ggggcgcgc gccaggcggg gcggggcggg gcgaggggcg gggcggggcg      480
aggcggagag gtgcggcggc agccaatcag agcggcgcgc tccgaaagtt cctttttatg     540
gcgaggcggc ggcggcggcg gccctataaa aagcgaagcg ctccctatca gtgatagaga     600
tctccctatc agtgatagag atcgtcgacg agctcgcggc gggcgggagt cgctgcgcgc     660
tgccttcgcc ccgtgccccg ctccgccgcc gcctcgcgcc gcccgcccg gctctgactg      720
accgcgttac taaaacaggt aagtccggcc tccgcgccgg gttttggcgc ctcccgcggg     780
cgcccccctc ctcacggcga gcgctgccac gtcagacgaa gggcgcagcg agcgtcctga     840
tccttccgcc cggacgctca ggacagcggc ccgctgctca taagactcgg ccttagaacc     900
ccagtatcag cagaaggaca ttttaggacg ggacttgggt gactctaggg cactggtttt     960
cttttccagag agcggaacag gcgaggaaaa gtagtcccctt ctcggcgatt ctgcggaggg    1020
atctccgtgg ggcggtgaac gccgatgatg cctctactaa ccatgttcat gttttctttt    1080
tttttctaca ggtcctgggt gacgaacag                                       1109
```

<210> SEQ ID NO 13
<211> LENGTH: 33
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 13

```
atacggacta gtggagaagt actcgcctac atg                                    33
```

<210> SEQ ID NO 14
<211> LENGTH: 36
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 14

```
atacggaaga tctaagactt caggaaatat gactac                                 36
```

<210> SEQ ID NO 15
<211> LENGTH: 46

<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 15
attcagtgta caggcgcgcc aaagcatgac gctgttgatt tgattc        46

<210> SEQ ID NO 16
<211> LENGTH: 35
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 16
actaggacta gttataagct agaatggggc tttgc                    35

<210> SEQ ID NO 17
<211> LENGTH: 79
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 17
ttaatagaca cagtagctta atagacccag tagtgcaaag ccccattcta gcttataacc    60
cctatttgtt tatttttct                                                 79

<210> SEQ ID NO 18
<211> LENGTH: 93
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 18
atatatactc tctcggcact tggccttta cactgcgaag tgttggtgct ggtgctgcgt    60
tgagagatct ttatttgtta actgttaatt gtc                                93

<210> SEQ ID NO 19
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 19
ttaatagaca cagtagctta ata                                 23

<210> SEQ ID NO 20
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:

```
                        Synthetic primer"

<400> SEQUENCE: 20
ggaagggagt gtctagtgtt                                            20

<210> SEQ ID NO 21
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 21
caatgggcgt ggatagcggt ttgac                                      25

<210> SEQ ID NO 22
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 22
cagcatgcct gctattgtc                                             19

<210> SEQ ID NO 23
<211> LENGTH: 29
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 23
catctacgta ttagtcatcg ctattacca                                  29

<210> SEQ ID NO 24
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 24
gacttggaaa tccccgtgag t                                          21

<210> SEQ ID NO 25
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic probe"

<400> SEQUENCE: 25
acatcaatgg gcgtggatag cggtt                                      25

<210> SEQ ID NO 26
<211> LENGTH: 592
```

```
<212> TYPE: DNA
<213> ORGANISM: Woodchuck hepatitis virus

<400> SEQUENCE: 26
taatcaacct ctggattaca aaatttgtga agattgact  ggtattctta actatgttgc      60
tccttttacg ctatgtggat acgctgcttt aatgcctttg tatcatgcta ttgcttcccg     120
tatggctttc attttctcct ccttgtataa atcctggttg ctgtctcttt atgaggagtt     180
gtggcccgtt gtcaggcaac gtggcgtggt gtgcactgtg tttgctgacg caaccccac      240
tggttgggc  attgccacca cctgtcagct cctttccggg actttcgctt tccccctccc     300
tattgccacg gcggaactca tcgccgcctg ccttgcccgc tgctggacag gggctcggct     360
gttgggcact gacaattccg tggtgttgtc ggggaaatca tcgtcctttc cttggctgct     420
cgcctgtgtt gccacctgga ttctgcgcgg gacgtcctc  tgctacgtcc cttcggccct     480
caatccagcg gaccttcctt cccgcggcct gctgccggct ctgcggcctc ttccgcgtct     540
tcgccttcgc cctcagacga gtcggatctc cctttgggcc gcctccccgc ct             592

<210> SEQ ID NO 27
<211> LENGTH: 543
<212> TYPE: PRT
<213> ORGANISM: Simian adenovirus

<400> SEQUENCE: 27

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Leu Thr Val
                165                 170                 175

Ser Ala Thr Pro Pro Ile Asn Val Ser Ser Gly Ser Leu Gly Leu Asp
            180                 185                 190

Met Glu Asp Pro Met Tyr Thr His Asp Gly Lys Leu Gly Ile Arg Ile
        195                 200                 205

Gly Gly Pro Leu Arg Val Val Asp Ser Leu His Thr Leu Thr Val Val
    210                 215                 220

Thr Gly Asn Gly Leu Thr Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
```

```
            245                 250                 255
Ala Gly Gly Met Arg Ile Asp Ala Asn Gly Gln Leu Ile Leu Asn Val
            260                 265                 270

Ala Tyr Pro Phe Asp Ala Gln Asn Asn Leu Ser Leu Arg Leu Gly Gln
            275                 280                 285

Gly Pro Leu Tyr Ile Asn Thr Asp His Asn Leu Asp Leu Asn Cys Asn
            290                 295                 300

Arg Gly Leu Thr Thr Thr Thr Asn Asn Thr Lys Lys Leu Glu Thr
305                 310                 315                 320

Lys Ile Ser Ser Gly Leu Asp Tyr Asp Thr Asn Gly Ala Val Ile Ile
            325                 330                 335

Lys Leu Gly Thr Gly Leu Ser Phe Asp Asn Thr Gly Ala Leu Thr Val
            340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
            370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
            405                 410                 415

Thr Ile Phe Leu Arg Phe Asp Gln Asn Gly Val Leu Met Glu Asn Ser
            420                 425                 430

Ser Leu Asp Arg Gln Tyr Trp Asn Phe Arg Asn Gly Asn Ser Thr Asn
            435                 440                 445

Ala Ala Pro Tyr Thr Asn Ala Val Gly Phe Met Pro Asn Leu Ala Ala
            450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
            485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
            515                 520                 525

Thr Phe Ala Thr Asn Ser Phe Thr Phe Ser Tyr Ile Ala Glu Gln
            530                 535                 540

<210> SEQ ID NO 28
<211> LENGTH: 541
<212> TYPE: PRT
<213> ORGANISM: Simian adenovirus

<400> SEQUENCE: 28

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Arg Leu Ser Glu Pro Leu Val Thr Ser His Gly Met Leu Ala Leu
            50                  55                  60

Lys Met Gly Asn Gly Leu Ser Leu Asp Asp Ala Gly Asn Leu Thr Ser
65                  70                  75                  80
```

```
Gln Asp Val Thr Thr Val Thr Pro Pro Leu Lys Lys Thr Lys Thr Asn
                85                  90                  95
Leu Ser Leu Gln Thr Ser Ala Pro Leu Thr Val Ser Ser Gly Ser Leu
            100                 105                 110
Thr Val Ala Ala Ala Ala Pro Leu Ala Val Ala Gly Thr Ser Leu Thr
        115                 120                 125
Met Gln Ser Gln Ala Pro Leu Thr Val Gln Asp Ala Lys Leu Gly Leu
    130                 135                 140
Ala Thr Gln Gly Pro Leu Thr Val Ser Glu Gly Lys Leu Thr Leu Gln
145                 150                 155                 160
Thr Ser Ala Pro Leu Thr Ala Ala Asp Ser Ser Thr Leu Thr Val Gly
                165                 170                 175
Thr Thr Pro Pro Ile Ser Val Ser Ser Gly Ser Leu Gly Leu Asp Met
            180                 185                 190
Glu Asp Pro Met Tyr Thr His Asp Gly Lys Leu Gly Ile Arg Ile Gly
        195                 200                 205
Gly Pro Leu Gln Val Val Asp Ser Leu His Thr Leu Thr Val Val Thr
    210                 215                 220
Gly Asn Gly Ile Thr Val Ala Asn Asn Ala Leu Gln Thr Lys Val Ala
225                 230                 235                 240
Gly Ala Leu Gly Tyr Asp Ser Ser Gly Asn Leu Glu Leu Arg Ala Ala
                245                 250                 255
Gly Gly Met Arg Ile Asn Thr Gly Gly Gln Leu Ile Leu Asp Val Ala
            260                 265                 270
Tyr Pro Phe Asp Ala Gln Asn Asn Leu Ser Leu Arg Leu Gly Gln Gly
        275                 280                 285
Pro Leu Tyr Val Asn Thr Asn His Asn Leu Asp Leu Asn Cys Asn Arg
    290                 295                 300
Gly Leu Thr Thr Thr Ser Ser Asn Thr Thr Lys Leu Glu Thr Lys
305                 310                 315                 320
Ile Asp Ser Gly Leu Asp Tyr Asn Ala Asn Gly Ala Ile Ile Ala Lys
                325                 330                 335
Leu Gly Thr Gly Leu Thr Phe Asp Asn Thr Gly Ala Ile Thr Val Gly
            340                 345                 350
Asn Thr Gly Asp Asp Lys Leu Thr Leu Trp Thr Thr Pro Asp Pro Ser
        355                 360                 365
Pro Asn Cys Arg Ile His Ala Asp Lys Asp Lys Phe Thr Leu Val Leu
    370                 375                 380
Thr Lys Cys Gly Ser Gln Ile Leu Ala Ser Val Ala Ala Leu Ala Val
385                 390                 395                 400
Ser Gly Asn Leu Ser Ser Met Thr Gly Thr Val Ser Ser Val Thr Ile
                405                 410                 415
Phe Leu Arg Phe Asp Gln Asn Gly Val Leu Met Glu Asn Ser Ser Leu
            420                 425                 430
Asp Lys Glu Tyr Trp Asn Phe Arg Asn Gly Asn Ser Thr Asn Ala Thr
        435                 440                 445
Pro Tyr Thr Asn Ala Val Gly Phe Met Pro Asn Leu Ser Ala Tyr Pro
    450                 455                 460
Lys Thr Gln Ser Gln Thr Ala Lys Asn Asn Ile Val Ser Glu Val Tyr
465                 470                 475                 480
Leu His Gly Asp Lys Ser Lys Pro Met Ile Leu Thr Ile Thr Leu Asn
                485                 490                 495
Gly Thr Asn Glu Ser Ser Glu Thr Ser Gln Val Ser His Tyr Ser Met
```

```
                        500                 505                 510
Ser Phe Thr Trp Ser Trp Asp Ser Gly Lys Tyr Ala Thr Glu Thr Phe
                515                 520                 525
Ala Thr Asn Ser Phe Thr Phe Ser Tyr Ile Ala Glu Gln
            530                 535                 540

<210> SEQ ID NO 29
<211> LENGTH: 543
<212> TYPE: PRT
<213> ORGANISM: Simian adenovirus

<400> SEQUENCE: 29

Met Lys Arg Thr Lys Thr Ser Asp Glu Ser Phe Asn Pro Val Tyr Pro
1               5                   10                  15
Tyr Asp Thr Glu Ser Gly Pro Pro Ser Val Pro Phe Leu Thr Pro Pro
                20                  25                  30
Phe Val Ser Pro Asp Gly Phe Gln Glu Ser Pro Pro Gly Val Leu Ser
            35                  40                  45
Leu Asn Leu Ala Glu Pro Leu Val Thr Ser His Gly Met Leu Ala Leu
        50                  55                  60
Lys Met Gly Ser Gly Leu Ser Leu Asp Asp Ala Gly Asn Leu Thr Ser
65                  70                  75                  80
Gln Asp Ile Thr Ser Thr Thr Pro Pro Leu Lys Lys Thr Lys Thr Asn
                85                  90                  95
Leu Ser Leu Glu Thr Ser Ser Pro Leu Thr Val Ser Thr Ser Gly Ala
            100                 105                 110
Leu Thr Val Ala Ala Ala Ala Pro Leu Ala Val Ala Gly Thr Ser Leu
        115                 120                 125
Thr Met Gln Ser Glu Ala Pro Leu Ala Val Gln Asp Ala Lys Leu Thr
130                 135                 140
Leu Ala Thr Lys Gly Pro Leu Thr Val Ser Glu Gly Lys Leu Ala Leu
145                 150                 155                 160
Gln Thr Ser Ala Pro Leu Thr Ala Ala Asp Ser Ser Thr Leu Thr Val
                165                 170                 175
Ser Ser Thr Pro Pro Ile Ser Val Ser Ser Gly Ser Leu Gly Leu Asp
            180                 185                 190
Met Glu Asp Pro Met Tyr Thr His Asp Gly Lys Leu Gly Ile Arg Ile
        195                 200                 205
Gly Gly Pro Leu Arg Val Val Asp Ser Leu His Thr Leu Thr Val Val
    210                 215                 220
Thr Gly Asn Gly Leu Thr Val Asp Asn Asn Ala Leu Gln Thr Arg Val
225                 230                 235                 240
Thr Gly Ala Leu Gly Tyr Asp Thr Ser Gly Asn Leu Gln Leu Arg Ala
                245                 250                 255
Ala Gly Gly Met Arg Ile Asp Ala Asn Gly Gln Leu Ile Leu Asp Val
            260                 265                 270
Ala Tyr Pro Phe Asp Ala Gln Asn Asn Leu Ser Leu Arg Leu Gly Gln
        275                 280                 285
Gly Pro Leu Tyr Val Asn Thr Asp His Asn Leu Asp Leu Asn Cys Asn
    290                 295                 300
Arg Gly Leu Thr Thr Thr Thr Asn Asn Thr Lys Lys Leu Glu Thr
305                 310                 315                 320
Lys Ile Ser Ser Gly Leu Asp Tyr Asp Thr Asn Gly Ala Val Ile Ile
                325                 330                 335
```

```
Lys Leu Gly Thr Gly Leu Ser Phe Asp Asn Thr Gly Ala Leu Thr Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
        370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ala Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Ala Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 30
<211> LENGTH: 543
<212> TYPE: PRT
<213> ORGANISM: Simian adenovirus

<400> SEQUENCE: 30

Met Lys Arg Thr Lys Thr Ser Asp Lys Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Val Thr Thr Thr Pro Pro Leu Lys Lys Thr Lys Thr Asn
                85                  90                  95

Leu Ser Leu Glu Thr Ser Ala Pro Leu Thr Val Ser Thr Ser Gly Ala
            100                 105                 110

Leu Thr Leu Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175
```

Ser Ala Thr Pro Pro Ile Ser Val Ser Ser Gly Ser Leu Gly Leu Asp
            180                 185                 190

Met Glu Asp Pro Met Tyr Thr His Asp Gly Lys Leu Gly Ile Arg Ile
            195                 200                 205

Gly Gly Pro Leu Arg Val Val Asp Ser Leu His Thr Leu Thr Val Val
        210                 215                 220

Thr Gly Asn Gly Ile Ala Val Asp Asn Ala Leu Gln Thr Arg Val
225                 230                 235                 240

Thr Gly Ala Leu Gly Tyr Asp Thr Ser Gly Asn Leu Gln Leu Arg Ala
                245                 250                 255

Ala Gly Gly Met Arg Ile Asp Ala Asn Gly Gln Leu Ile Leu Asp Val
                260                 265                 270

Ala Tyr Pro Phe Asp Ala Gln Asn Asn Leu Ser Leu Arg Leu Gly Gln
            275                 280                 285

Gly Pro Leu Tyr Val Asn Thr Asp His Asn Leu Asp Leu Asn Cys Asn
        290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
                325                 330                 335

Lys Leu Gly Thr Gly Val Ser Phe Asp Ser Thr Gly Ala Leu Ser Val
                340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
        370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                405                 410                 415

Thr Ile Phe Leu Arg Phe Asp Gln Asn Gly Val Leu Met Glu Asn Ser
            420                 425                 430

Ser Leu Asp Lys Gln Tyr Trp Asn Phe Arg Asn Gly Asn Ser Thr Asn
        435                 440                 445

Ala Thr Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Thr Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
        515                 520                 525

Thr Phe Ala Thr Asn Ser Phe Thr Phe Ser Tyr Ile Ala Glu Gln
    530                 535                 540

<210> SEQ ID NO 31
<211> LENGTH: 543
<212> TYPE: PRT
<213> ORGANISM: Simian adenovirus

<400> SEQUENCE: 31

Met Lys Arg Thr Lys Thr Ser Asp Glu Ser Phe Asn Pro Val Tyr Pro

```
1               5                   10                  15
Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Asn Leu Ala Glu Pro Leu Val Thr Ser His Gly Met Leu Ala Leu
            50                  55                  60

Lys Met Gly Ser Gly Leu Ser Leu Asp Asp Ala Gly Asn Leu Thr Ser
65                      70                  75                  80

Gln Asp Val Thr Thr Thr Thr Pro Pro Leu Lys Lys Thr Lys Thr Asn
                    85                  90                  95

Leu Ser Leu Glu Thr Ser Ala Pro Leu Thr Val Ser Thr Ser Gly Ala
            100                 105                 110

Leu Thr Leu Ala Ala Ala Ala Pro Leu Ala Val Ala Gly Thr Ser Leu
            115                 120                 125

Thr Met Gln Ser Glu Ala Pro Leu Thr Val Gln Asp Ala Lys Leu Thr
            130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                    165                 170                 175

Ser Ala Thr Pro Pro Ile Asn Val Ser Ser Gly Ser Leu Gly Leu Asp
                    180                 185                 190

Met Glu Asn Pro Met Tyr Thr His Asp Gly Lys Leu Gly Ile Arg Ile
                    195                 200                 205

Gly Gly Pro Leu Arg Val Val Asp Ser Leu His Thr Leu Thr Val Val
            210                 215                 220

Thr Gly Asn Gly Ile Ala Val Asp Asn Asn Ala Leu Gln Thr Arg Val
225                 230                 235                 240

Thr Gly Ala Leu Gly Tyr Asp Thr Ser Gly Asn Leu Gln Leu Arg Ala
                    245                 250                 255

Ala Gly Gly Met Arg Ile Asp Ala Asn Gly Gln Leu Ile Leu Asp Val
                    260                 265                 270

Ala Tyr Pro Phe Asp Ala Gln Asn Asn Leu Ser Leu Arg Leu Gly Gln
                    275                 280                 285

Gly Pro Leu Tyr Val Asn Thr Asp His Asn Leu Asp Leu Asn Cys Asn
            290                 295                 300

Arg Gly Leu Thr Thr Thr Thr Asn Asn Thr Lys Lys Leu Glu Thr
305                 310                 315                 320

Lys Ile Gly Ser Gly Leu Asp Tyr Asp Thr Asn Gly Ala Val Ile Ile
                    325                 330                 335

Lys Leu Gly Thr Gly Val Ser Phe Asp Ser Thr Gly Ala Leu Ser Val
            340                 345                 350

Gly Asn Thr Gly Asp Asp Lys Leu Thr Leu Trp Thr Thr Pro Asp Pro
            355                 360                 365

Ser Pro Asn Cys Arg Ile His Ser Asp Lys Asp Cys Lys Phe Thr Leu
            370                 375                 380

Val Leu Thr Lys Cys Gly Ser Gln Ile Leu Ala Ser Val Ala Ala Leu
385                 390                 395                 400

Ala Val Ser Gly Asn Leu Ala Ser Ile Thr Gly Thr Val Ser Ser Val
                    405                 410                 415

Thr Ile Phe Leu Arg Phe Asp Gln Asn Gly Val Leu Met Glu Asn Ser
            420                 425                 430
```

```
Ser Leu Asp Lys Gln Tyr Trp Asn Phe Arg Asn Gly Asn Ser Thr Asn
        435                 440                 445

Ala Thr Pro Tyr Thr Asn Ala Val Gly Phe Met Pro Asn Leu Ala Ala
    450                 455                 460

Tyr Pro Lys Thr Gln Ser Gln Thr Ala Lys Asn Asn Ile Val Ser Gln
465                 470                 475                 480

Val Tyr Leu Asn Gly Asp Lys Ser Lys Pro Met Ile Leu Thr Ile Thr
                485                 490                 495

Leu Asn Gly Thr Asn Glu Ser Ser Glu Thr Ser Gln Val Ser His Tyr
            500                 505                 510

Ser Met Ser Phe Thr Trp Ala Trp Glu Ser Gly Gln Tyr Ala Thr Glu
            515                 520                 525

Thr Phe Ala Thr Asn Ser Phe Thr Phe Ser Tyr Ile Ala Glu Gln
        530                 535                 540

<210> SEQ ID NO 32
<211> LENGTH: 578
<212> TYPE: PRT
<213> ORGANISM: Simian adenovirus

<400> SEQUENCE: 32

Met Lys Arg Thr Lys Thr Ser Asp Glu Ser Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65              70                  75                  80

Gln Asp Val Thr Thr Thr Pro Pro Leu Lys Lys Thr Lys Thr Asn
                85                  90                  95

Leu Ser Leu Glu Thr Ser Ala Pro Leu Thr Val Ser Thr Ser Gly Ala
            100                 105                 110

Leu Thr Leu Ala Ala Ala Val Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Ile
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Ser Ser Gly Asn Leu Glu Leu Arg Ala
                245                 250                 255

Ala Gly Gly Met Arg Val Asp Ala Asn Gly Lys Leu Ile Leu Asp Val
```

```
                260                 265                 270
Ala Tyr Pro Phe Asp Ala Gln Asn Asn Leu Ser Leu Arg Leu Gly Gln
            275                 280                 285

Gly Pro Leu Phe Val Asn Ser Ala His Asn Leu Asp Val Asn Tyr Asn
        290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Pro Gly Asp Gly Leu Glu Phe Gly Ser Gly Ser Asp Thr Asn
            340                 345                 350

Pro Leu Lys Thr Lys Leu Gly Leu Gly Leu Glu Tyr Asp Ser Ser Arg
        355                 360                 365

Ala Ile Ile Ala Lys Leu Gly Thr Gly Leu Ser Phe Asp Asn Thr Gly
    370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
        435                 440                 445

Val Thr Ser Ala Gln Ile Ile Leu Arg Phe Asp Glu Asn Gly Val Leu
    450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Ile
        515                 520                 525

Leu Thr Ile Thr Leu Asn Gly Thr Asn Glu Thr Gly Asp Ala Thr Val
    530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 33
<211> LENGTH: 578
<212> TYPE: PRT
<213> ORGANISM: Simian adenovirus

<400> SEQUENCE: 33

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
```

```
              50                  55                  60
Lys Met Gly Ser Gly Leu Ser Leu Asp Asp Ala Gly Asn Leu Thr Ser
 65                  70                  75                  80

Gln Asp Ile Thr Thr Ala Ser Pro Leu Lys Lys Thr Lys Thr Asn
                 85                  90                  95

Leu Ser Leu Glu Thr Ser Ser Pro Leu Thr Val Ser Thr Ser Gly Ala
                100                 105                 110

Leu Thr Val Ala Ala Ala Ala Pro Leu Ala Val Ala Gly Thr Ser Leu
                115                 120                 125

Thr Met Gln Ser Glu Ala Pro Leu Thr Val Gln Asp Ala Lys Leu Thr
130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
                180                 185                 190

Met Gln Ala Pro Ile Tyr Thr Thr Asn Gly Lys Leu Gly Leu Asn Phe
                195                 200                 205

Gly Ala Pro Leu His Val Val Asp Ser Leu Asn Ala Leu Thr Val Val
                210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
                260                 265                 270

Ala Tyr Pro Phe Asp Ala Gln Asn Asn Leu Ser Leu Arg Leu Gly Gln
                275                 280                 285

Gly Pro Leu Phe Val Asn Ser Ala His Asn Leu Asp Val Asn Tyr Asn
                290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Thr Ala Ile Ala
                325                 330                 335

Ile Asn Ala Gly Asp Gly Leu Gln Phe Asp Ser Gly Ser Asp Thr Asn
                340                 345                 350

Pro Leu Lys Thr Lys Leu Gly Leu Gly Leu Asp Tyr Asp Ser Ser Arg
                355                 360                 365

Ala Ile Ile Ala Lys Leu Gly Thr Gly Leu Ser Phe Asp Asn Thr Gly
370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
                420                 425                 430

Val Ser Val Leu Ser Val Lys Gly Ser Leu Ala Pro Ile Ser Gly Thr
                435                 440                 445

Val Thr Ser Ala Gln Ile Val Leu Arg Phe Asp Glu Asn Gly Val Leu
                450                 455                 460

Leu Ser Asn Ser Ser Leu Asp Pro Gln Tyr Trp Asn Tyr Arg Lys Gly
465                 470                 475                 480
```

-continued

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
        515                 520                 525

Leu Thr Ile Thr Leu Asn Gly Thr Asn Glu Thr Gly Asp Ala Thr Val
    530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 34
<211> LENGTH: 578
<212> TYPE: PRT
<213> ORGANISM: Simian adenovirus

<400> SEQUENCE: 34

Met Lys Arg Thr Lys Thr Ser Asp Glu Ser Phe Asn Pro Val Tyr Pro
1               5                   10                  15

Tyr Asp Thr Glu Ser Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Asn Leu Ala Glu Pro Leu Val Thr Ser His Gly Met Leu Ala Leu
    50                  55                  60

Lys Met Gly Ser Gly Leu Ser Leu Asp Asp Ala Gly Asn Leu Thr Ser
65                  70                  75                  80

Gln Asp Ile Thr Thr Ala Ser Pro Pro Leu Lys Lys Thr Lys Thr Asn
                85                  90                  95

Leu Ser Leu Glu Thr Ser Ser Pro Leu Thr Val Ser Thr Ser Gly Ala
            100                 105                 110

Leu Thr Val Ala Ala Ala Pro Leu Ala Val Ala Gly Thr Ser Leu
        115                 120                 125

Thr Met Gln Ser Glu Ala Pro Leu Thr Val Gln Asp Ala Lys Leu Thr
    130                 135                 140

Leu Ala Thr Lys Gly Pro Leu Thr Val Ser Glu Gly Lys Leu Ala Leu
145                 150                 155                 160

Gln Thr Ser Ala Pro Leu Thr Ala Ala Asp Ser Ser Thr Leu Thr Val
                165                 170                 175

Ser Ala Thr Pro Pro Leu Ser Thr Ser Asn Gly Ser Leu Gly Ile Asp
            180                 185                 190

Met Gln Ala Pro Ile Tyr Thr Thr Asn Gly Lys Leu Gly Leu Asn Phe
        195                 200                 205

Gly Ala Pro Leu His Val Val Asp Ser Leu Asn Ala Leu Thr Val Val
    210                 215                 220

Thr Gly Gln Gly Leu Thr Ile Asn Gly Thr Ala Leu Gln Thr Arg Val
225                 230                 235                 240

Ser Gly Ala Leu Asn Tyr Asp Thr Ser Gly Asn Leu Glu Leu Arg Ala
                245                 250                 255

Ala Gly Gly Met Arg Val Asp Ala Asn Gly Gln Leu Ile Leu Asp Val
            260                 265                 270

```
Ala Tyr Pro Phe Asp Ala Gln Asn Asn Leu Ser Leu Arg Leu Gly Gln
            275                 280                 285

Gly Pro Leu Phe Val Asn Ser Ala His Asn Leu Asp Val Asn Tyr Asn
        290                 295                 300

Arg Gly Leu Tyr Leu Phe Thr Ser Gly Asn Thr Lys Lys Leu Glu Val
305                 310                 315                 320

Asn Ile Lys Thr Ala Lys Gly Leu Ile Tyr Asp Asp Thr Ala Ile Ala
                325                 330                 335

Ile Asn Ala Gly Asp Gly Leu Gln Phe Asp Ser Gly Ser Asp Thr Asn
            340                 345                 350

Pro Leu Lys Thr Lys Leu Gly Leu Gly Leu Asp Tyr Asp Ser Ser Arg
            355                 360                 365

Ala Ile Ala Lys Leu Gly Thr Gly Leu Ser Phe Asp Asn Thr Gly
        370                 375                 380

Ala Ile Thr Val Gly Asn Lys Asn Asp Asp Lys Leu Thr Leu Trp Thr
385                 390                 395                 400

Thr Pro Asp Pro Ser Pro Asn Cys Arg Ile Tyr Ser Glu Lys Asp Ala
                405                 410                 415

Lys Phe Thr Leu Val Leu Thr Lys Cys Gly Ser Gln Val Leu Ala Ser
            420                 425                 430

Val Ser Val Leu Ser Val Lys Gly Ser Leu Ala Pro Ile Ser Gly Thr
            435                 440                 445

Val Thr Ser Ala Gln Ile Val Leu Arg Phe Asp Glu Asn Gly Val Leu
        450                 455                 460

Leu Ser Asn Ser Ser Leu Asp Pro Gln Tyr Trp Asn Tyr Arg Lys Gly
465                 470                 475                 480

Asp Leu Thr Glu Gly Thr Ala Tyr Thr Asn Ala Val Gly Phe Met Pro
                485                 490                 495

Asn Leu Thr Ala Tyr Pro Lys Thr Gln Ser Gln Thr Ala Lys Ser Asn
            500                 505                 510

Ile Val Ser Gln Val Tyr Leu Asn Gly Asp Lys Ser Lys Pro Met Thr
        515                 520                 525

Leu Thr Ile Thr Leu Asn Gly Thr Asn Glu Thr Gly Asp Ala Thr Val
    530                 535                 540

Ser Thr Tyr Ser Met Ser Phe Ser Trp Asn Trp Asn Gly Ser Asn Tyr
545                 550                 555                 560

Ile Asn Glu Thr Phe Gln Thr Asn Ser Phe Thr Phe Ser Tyr Ile Ala
                565                 570                 575

Gln Glu

<210> SEQ ID NO 35
<211> LENGTH: 577
<212> TYPE: PRT
<213> ORGANISM: Simian adenovirus

<400> SEQUENCE: 35

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
        35                  40                  45

Leu Arg Leu Ser Glu Pro Leu Val Thr Ser His Gly Met Leu Ala Leu
    50                  55                  60
```

```
Lys Met Gly Asn Gly Leu Ser Leu Asp Asp Ala Gly Asn Leu Thr Ser
 65              70                  75                  80

Gln Asp Val Thr Thr Val Thr Pro Pro Leu Lys Lys Thr Lys Thr Asn
                 85                  90                  95

Leu Ser Leu Gln Thr Ser Ala Pro Leu Thr Val Ser Ser Gly Ser Leu
                100                 105                 110

Thr Val Ala Ala Ala Ala Pro Leu Ala Val Ala Gly Thr Ser Leu Thr
                115                 120                 125

Met Gln Ser Gln Ala Pro Leu Thr Val Gln Asp Ala Lys Leu Gly Leu
130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
                165                 170                 175

Ala Thr Pro Pro Leu Ser Thr Ser Asn Gly Ser Leu Ser Ile Asp Met
                180                 185                 190

Gln Ala Pro Ile Tyr Thr Thr Asn Gly Lys Leu Ala Leu Asn Ile Gly
                195                 200                 205

Ala Pro Leu His Val Val Asp Thr Leu Asn Ala Leu Thr Val Val Thr
210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
                260                 265                 270

Tyr Pro Phe Asp Ala Gln Asn Asn Leu Ser Leu Arg Leu Gly Gln Gly
                275                 280                 285

Pro Leu Ile Val Asn Ser Ala His Asn Leu Asp Leu Asn Leu Asn Arg
290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
                340                 345                 350

Leu Gln Thr Lys Leu Gly Leu Gly Leu Glu Tyr Asp Ser Asn Lys Ala
                355                 360                 365

Ile Ile Thr Lys Leu Gly Thr Gly Leu Ser Phe Asp Asn Thr Gly Ala
                370                 375                 380

Ile Thr Val Gly Asn Lys Asn Asp Asp Lys Leu Thr Leu Trp Thr Thr
385                 390                 395                 400

Pro Asp Pro Ser Pro Asn Cys Arg Ile Asn Ser Glu Lys Asp Ala Lys
                405                 410                 415

Leu Thr Leu Val Leu Thr Lys Cys Gly Ser Gln Val Leu Ala Ser Val
                420                 425                 430

Ser Val Leu Ser Val Lys Gly Ser Leu Ala Pro Ile Ser Gly Thr Val
                435                 440                 445

Thr Ser Ala Gln Ile Val Leu Arg Phe Asp Glu Asn Gly Val Leu Leu
                450                 455                 460

Ser Asn Ser Ser Leu Asp Pro Gln Tyr Trp Asn Tyr Arg Lys Gly Asp
465                 470                 475                 480
```

```
Ser Thr Glu Gly Thr Ala Tyr Thr Asn Ala Val Gly Phe Met Pro Asn
                485                 490                 495

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
            515                 520                 525

Thr Ile Thr Leu Asn Gly Thr Asn Glu Thr Gly Asp Ala Thr Val Ser
        530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                565                 570                 575

Glu

<210> SEQ ID NO 36
<211> LENGTH: 577
<212> TYPE: PRT
<213> ORGANISM: Simian adenovirus

<400> SEQUENCE: 36

Met Lys Arg Ala Lys Thr Ser Asp Glu Thr Phe Asn Pro Val Tyr Pro
1               5                   10                  15

Tyr Asp Thr Glu Asn Gly Pro Pro Ser Val Pro Phe Leu Thr Pro Pro
            20                  25                  30

Phe Val Ser Pro Asp Gly Phe Gln Glu Ser Pro Pro Gly Val Leu Ser
            35                  40                  45

Leu Arg Leu Ser Glu Pro Leu Val Thr Ser His Gly Met Leu Ala Leu
50                  55                  60

Lys Met Gly Asn Gly Leu Ser Leu Asp Asp Ala Gly Asn Leu Thr Ser
65                  70                  75                  80

Gln Asp Val Thr Thr Val Thr Pro Pro Leu Lys Lys Thr Lys Thr Asn
                85                  90                  95

Leu Ser Leu Gln Thr Ser Ala Pro Leu Thr Val Ser Ser Gly Ser Leu
            100                 105                 110

Thr Val Ala Ala Ala Pro Leu Ala Val Ala Gly Thr Ser Leu Thr
            115                 120                 125

Met Gln Ser Gln Ala Pro Leu Thr Val Gln Asp Ala Lys Leu Gly Leu
130                 135                 140

Ala Thr Gln Gly Pro Leu Thr Val Ser Glu Gly Lys Leu Thr Leu Gln
145                 150                 155                 160

Thr Ser Ala Pro Leu Thr Ala Ala Asp Ser Ser Thr Leu Thr Val Ser
            165                 170                 175

Ala Thr Pro Pro Leu Ser Thr Ser Asn Gly Ser Leu Ser Ile Asp Met
            180                 185                 190

Gln Ala Pro Ile Tyr Thr Thr Asn Gly Lys Leu Ala Leu Asn Ile Gly
            195                 200                 205

Ala Pro Leu His Val Val Asp Thr Leu Asn Ala Leu Thr Val Val Thr
            210                 215                 220

Gly Gln Gly Leu Thr Ile Asn Gly Arg Ala Leu Gln Thr Arg Val Thr
225                 230                 235                 240

Gly Ala Leu Ser Tyr Asp Thr Glu Gly Asn Ile Gln Leu Gln Ala Gly
                245                 250                 255

Gly Gly Met Arg Ile Asp Asn Asn Gly Gln Leu Ile Leu Asn Val Ala
                260                 265                 270
```

```
Tyr Pro Phe Asp Ala Gln Asn Asn Leu Ser Leu Arg Leu Gly Gln Gly
            275                 280                 285

Pro Leu Ile Val Asn Ser Ala His Asn Leu Asp Leu Asn Leu Asn Arg
        290                 295                 300

Gly Leu Tyr Leu Phe Thr Ser Gly Asn Thr Lys Lys Leu Glu Val Asn
305                 310                 315                 320

Ile Lys Thr Ala Lys Gly Leu Phe Tyr Asp Gly Thr Ala Ile Ala Ile
                325                 330                 335

Asn Ala Gly Asp Gly Leu Gln Phe Gly Ser Gly Ser Asp Thr Asn Pro
            340                 345                 350

Leu Gln Thr Lys Leu Gly Leu Gly Leu Glu Tyr Asp Ser Asn Lys Ala
        355                 360                 365

Ile Ile Thr Lys Leu Gly Thr Gly Leu Ser Phe Asp Asn Thr Gly Ala
370                 375                 380

Ile Thr Val Gly Asn Lys Asn Asp Asp Lys Leu Thr Leu Trp Thr Thr
385                 390                 395                 400

Pro Asp Pro Ser Pro Asn Cys Arg Ile Asn Ser Glu Lys Asp Ala Lys
                405                 410                 415

Leu Thr Leu Val Leu Thr Lys Cys Gly Ser Gln Val Leu Ala Ser Val
            420                 425                 430

Ser Val Leu Ser Val Lys Gly Ser Leu Ala Pro Ile Ser Gly Thr Val
        435                 440                 445

Thr Ser Ala Gln Ile Val Leu Arg Phe Asp Glu Asn Gly Val Leu Leu
    450                 455                 460

Ser Asn Ser Ser Leu Asp Pro Gln Tyr Trp Asn Tyr Arg Lys Gly Asp
465                 470                 475                 480

Ser Thr Glu Gly Thr Ala Tyr Thr Asn Ala Val Gly Phe Met Pro Asn
                485                 490                 495

Leu Thr Ala Tyr Pro Lys Thr Gln Ser Gln Thr Ala Lys Ser Asn Ile
            500                 505                 510

Val Ser Gln Val Tyr Leu Asn Gly Asp Lys Thr Lys Pro Met Thr Leu
        515                 520                 525

Thr Ile Thr Leu Asn Gly Thr Asn Glu Thr Gly Asp Ala Thr Val Ser
    530                 535                 540

Thr Tyr Ser Met Ser Phe Ser Trp Asn Trp Asn Gly Ser Asn Tyr Ile
545                 550                 555                 560

Asn Asp Thr Phe Gln Thr Asn Ser Phe Thr Phe Ser Tyr Ile Ala Gln
                565                 570                 575

Glu

<210> SEQ ID NO 37
<211> LENGTH: 1145
<212> TYPE: PRT
<213> ORGANISM: Respiratory syncytial virus

<400> SEQUENCE: 37

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60
```

```
Lys Glu Asn Lys Cys Asn Gly Thr Asp Ala Lys Val Lys Leu Ile Lys
 65                  70                  75                  80

Gln Glu Leu Asp Lys Tyr Lys Asn Ala Val Thr Glu Leu Gln Leu Leu
             85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
                180                 185                 190

Leu Asp Leu Lys Asn Tyr Ile Asp Lys Gln Leu Leu Pro Ile Val Asn
            195                 200                 205

Lys Gln Ser Cys Ser Ile Ser Asn Ile Glu Thr Val Ile Glu Phe Gln
210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Asn Asp Met Pro Ile Thr Asn Asp Gln Lys Lys Leu
            260                 265                 270

Met Ser Asn Asn Val Gln Ile Val Arg Gln Gln Ser Tyr Ser Ile Met
            275                 280                 285

Ser Ile Ile Lys Glu Glu Val Leu Ala Tyr Val Val Gln Leu Pro Leu
290                 295                 300

Tyr Gly Val Ile Asp Thr Pro Cys Trp Lys Leu His Thr Ser Pro Leu
305                 310                 315                 320

Cys Thr Thr Asn Thr Lys Glu Gly Ser Asn Ile Cys Leu Thr Arg Thr
                325                 330                 335

Asp Arg Gly Trp Tyr Cys Asp Asn Ala Gly Ser Val Ser Phe Phe Pro
            340                 345                 350

Gln Ala Glu Thr Cys Lys Val Gln Ser Asn Arg Val Phe Cys Asp Thr
            355                 360                 365

Met Asn Ser Leu Thr Leu Pro Ser Glu Val Asn Leu Cys Asn Val Asp
        370                 375                 380

Ile Phe Asn Pro Lys Tyr Asp Cys Lys Ile Met Thr Ser Lys Thr Asp
385                 390                 395                 400

Val Ser Ser Ser Val Ile Thr Ser Leu Gly Ala Ile Val Ser Cys Tyr
                405                 410                 415

Gly Lys Thr Lys Cys Thr Ala Ser Asn Lys Asn Arg Gly Ile Ile Lys
            420                 425                 430

Thr Phe Ser Asn Gly Cys Asp Tyr Val Ser Asn Lys Gly Val Asp Thr
        435                 440                 445

Val Ser Val Gly Asn Thr Leu Tyr Tyr Val Asn Lys Gln Glu Gly Lys
    450                 455                 460

Ser Leu Tyr Val Lys Gly Glu Pro Ile Ile Asn Phe Tyr Asp Pro Leu
465                 470                 475                 480

Val Phe Pro Ser Asp Glu Phe Asp Ala Ser Ile Ser Gln Val Asn Glu
```

-continued

```
                485                 490                 495
Lys Ile Asn Gln Ser Leu Ala Phe Ile Arg Lys Ser Asp Glu Leu Leu
            500                 505                 510
His Asn Val Asn Ala Gly Lys Ser Thr Thr Asn Arg Lys Arg Arg Ala
            515                 520                 525
Pro Val Lys Gln Thr Leu Asn Phe Asp Leu Leu Lys Leu Ala Gly Asp
            530                 535                 540
Val Glu Ser Asn Pro Gly Pro Met Ala Leu Ser Lys Val Lys Leu Asn
545                 550                 555                 560
Asp Thr Leu Asn Lys Asp Gln Leu Leu Ser Ser Lys Tyr Thr Ile
            565                 570                 575
Gln Arg Ser Thr Gly Asp Ser Ile Asp Thr Pro Asn Tyr Asp Val Gln
            580                 585                 590
Lys His Ile Asn Lys Leu Cys Gly Met Leu Leu Ile Thr Glu Asp Ala
            595                 600                 605
Asn His Lys Phe Thr Gly Leu Ile Gly Met Leu Tyr Ala Met Ser Arg
            610                 615                 620
Leu Gly Arg Glu Asp Thr Ile Lys Ile Leu Arg Asp Ala Gly Tyr His
625                 630                 635                 640
Val Lys Ala Asn Gly Val Asp Val Thr Thr His Arg Gln Asp Ile Asn
            645                 650                 655
Gly Lys Glu Met Lys Phe Glu Val Leu Thr Leu Ala Ser Leu Thr Thr
            660                 665                 670
Glu Ile Gln Ile Asn Ile Glu Ile Glu Ser Arg Lys Ser Tyr Lys Lys
            675                 680                 685
Met Leu Lys Glu Met Gly Glu Val Ala Pro Glu Tyr Arg His Asp Ser
            690                 695                 700
Pro Asp Cys Gly Met Ile Ile Leu Cys Ile Ala Ala Leu Val Ile Thr
705                 710                 715                 720
Lys Leu Ala Ala Gly Asp Arg Ser Gly Leu Thr Ala Val Ile Arg Arg
            725                 730                 735
Ala Asn Asn Val Leu Lys Asn Glu Met Lys Arg Tyr Lys Gly Leu Leu
            740                 745                 750
Pro Lys Asp Ile Ala Asn Ser Phe Tyr Glu Val Phe Glu Lys Tyr Pro
            755                 760                 765
His Phe Ile Asp Val Phe Val His Phe Gly Ile Ala Gln Ser Ser Thr
            770                 775                 780
Arg Gly Gly Ser Arg Val Glu Gly Ile Phe Ala Gly Leu Phe Met Asn
785                 790                 795                 800
Ala Tyr Gly Ala Gly Gln Val Met Leu Arg Trp Gly Val Leu Ala Lys
            805                 810                 815
Ser Val Lys Asn Ile Met Leu Gly His Ala Ser Val Gln Ala Glu Met
            820                 825                 830
Glu Gln Val Val Glu Val Tyr Glu Tyr Ala Gln Lys Leu Gly Gly Glu
            835                 840                 845
Ala Gly Phe Tyr His Ile Leu Asn Asn Pro Lys Ala Ser Leu Leu Ser
            850                 855                 860
Leu Thr Gln Phe Pro His Phe Ser Ser Val Val Leu Gly Asn Ala Ala
865                 870                 875                 880
Gly Leu Gly Ile Met Gly Glu Tyr Arg Gly Thr Pro Arg Asn Gln Asp
            885                 890                 895
Leu Tyr Asp Ala Ala Lys Ala Tyr Ala Glu Gln Leu Lys Glu Asn Gly
            900                 905                 910
```

| Val | Ile | Asn | Tyr | Ser | Val | Leu | Asp | Leu | Thr | Ala | Glu | Glu | Leu | Glu | Ala |
| | | | 915 | | | | 920 | | | | 925 | | | | |

| Ile | Lys | His | Gln | Leu | Asn | Pro | Lys | Asp | Asn | Asp | Val | Glu | Leu | Gly | Gly |
| | 930 | | | | 935 | | | | 940 | | | | | | |

| Gly | Gly | Ser | Gly | Gly | Gly | Gly | Met | Ser | Arg | Arg | Asn | Pro | Cys | Lys | Phe |
| 945 | | | | | 950 | | | | 955 | | | | | 960 | |

| Glu | Ile | Arg | Gly | His | Cys | Leu | Asn | Gly | Lys | Arg | Cys | His | Phe | Ser | His |
| | | | 965 | | | | | 970 | | | | | 975 | | |

| Asn | Tyr | Phe | Glu | Trp | Pro | Pro | His | Ala | Leu | Leu | Val | Arg | Gln | Asn | Phe |
| | | | 980 | | | | 985 | | | | 990 | | | | |

| Met | Leu | Asn | Arg | Ile | Leu | Lys | Ser | Met | Asp | Lys | Ser | Ile | Asp | Thr | Leu |
| | | 995 | | | | | 1000 | | | | | 1005 | | | |

| Ser | Glu | Ile | Ser | Gly | Ala | Ala | Glu | Leu | Asp | Arg | Thr | Glu | Glu | Tyr |
| | 1010 | | | | | 1015 | | | | | 1020 | | | |

| Ala | Leu | Gly | Val | Val | Gly | Val | Leu | Glu | Ser | Tyr | Ile | Gly | Ser | Ile |
| | 1025 | | | | | 1030 | | | | | 1035 | | | |

| Asn | Asn | Ile | Thr | Lys | Gln | Ser | Ala | Cys | Val | Ala | Met | Ser | Lys | Leu |
| | 1040 | | | | | 1045 | | | | | 1050 | | | |

| Leu | Thr | Glu | Leu | Asn | Ser | Asp | Asp | Ile | Lys | Lys | Leu | Arg | Asp | Asn |
| | 1055 | | | | | 1060 | | | | | 1065 | | | |

| Glu | Glu | Leu | Asn | Ser | Pro | Lys | Ile | Arg | Val | Tyr | Asn | Thr | Val | Ile |
| | 1070 | | | | | 1075 | | | | | 1080 | | | |

| Ser | Tyr | Ile | Glu | Ser | Asn | Arg | Lys | Asn | Asn | Lys | Gln | Thr | Ile | His |
| | 1085 | | | | | 1090 | | | | | 1095 | | | |

| Leu | Leu | Lys | Arg | Leu | Pro | Ala | Asp | Val | Leu | Lys | Lys | Thr | Ile | Lys |
| | 1100 | | | | | 1105 | | | | | 1110 | | | |

| Asn | Thr | Leu | Asp | Ile | His | Lys | Ser | Ile | Thr | Ile | Asn | Asn | Pro | Lys |
| | 1115 | | | | | 1120 | | | | | 1125 | | | |

| Glu | Ser | Thr | Val | Ser | Asp | Thr | Asn | Asp | His | Ala | Lys | Asn | Asn | Asp |
| | 1130 | | | | | 1135 | | | | | 1140 | | | |

| Thr | Thr |
| | 1145 |

<210> SEQ ID NO 38
<211> LENGTH: 1502
<212> TYPE: DNA
<213> ORGANISM: Human immunodeficiency virus

<400> SEQUENCE: 38

```
atgggtgcta gggcttctgt gctgtctggt ggtgagctgg acaagtggga gaagatcagg     60
ctgaggcctg gtggcaagaa gaagtacaag ctaaagcaca ttgtgtgggc ctccagggag    120
ctggagaggt ttgctgtgaa ccctggcctg ctggagacct tgaggggtg caggcagatc    180 ctgggccagc tccagccctc cctgcaaaca ggctctgagg agctgaggtc cctgtacaac    240
acagtggcta ccctgtactg tgtgcaccag aagattgatg tgaaggacac caaggaggcc    300
ctggagaaga ttgaggagga gcagaacaag tccaagaaga ggcccagca ggctgctgct    360 ggcacaggca actccagcca ggtgtcccag aactaccca ttgtgcagaa cctccagggc    420
cagatggtgc accaggccat ctccccccgg accctgaatg cctgggtgaa ggtggtggag    480
gagaggcctt ctcccctgag gtgatcccca tgttctctgc cctgtctgag ggtgccaccc    540
cccaggacct gaacaccatg ctgaacacag tgggggcca tcaggctgcc atgcagatgc    600
tgaaggagac catcaatgag gaggctgctg agtgggacag gctgcatcct gtgcacgctg    660
```

-continued

```
gccccattgc ccccggccag atgagggagc ccagggctc tgacattgct ggcaccacct    720
ccaccctcca ggagcagatt ggctggatga ccaacaaccc ccccatcct gtggggaaa    780 tctacaagag gtggatcatc ctgggcctga acaagattgt gaggatgtac tcccccacct    840
ccatcctgga catcaggcag ggccccaagg agcccttcag ggactatgtg gacaggttct    900
acaagaccct gagggctgag caggcctccc aggaggtgaa gaactggatg acagagaccc    960
tgctggtgca gaatgccaac cctgactgca agaccatcct gaaggccctg ggccctgctg   1020
ccaccctgga ggagatgatg acagcctgcc aggggtggg gggccctggt cacaaggcca   1080
gggtgctggc tgaggccatg tcccaggtga ccaactccgc caccatcatg atgcagaggg   1140
gcaacttcag gaaccagagg aagacagtga agtgcttcaa ctgtggcaag gtgggccaca   1200
ttgccaagaa ctgtagggcc cccaggaaga agggctgctg gaagtgtggc aaggagggcc   1260
accagatgaa ggactgcaat gagaggcagg ccaacttcct gggcaaaatc tggccctccc   1320
acaagggcag gcctggcaac ttcctccagt ccaggcctga gcccacagcc cctcccgagg   1380
agtccttcag gtttggggag gagaagacca ccccagcca gaagcaggag cccattgaca   1440
aggagctgta cccctggcc tccctgaggt ccctgtttgg caacgacccc tcctcccagt   1500
aa                                                                1502
```

UNITED STATES PATENT AND TRADEMARK OFFICE
CERTIFICATE OF CORRECTION

PATENT NO. : 11,254,710 B2
APPLICATION NO. : 15/735839
DATED : February 22, 2022
INVENTOR(S) : Stefano Colloca et al.

It is certified that error appears in the above-identified patent and that said Letters Patent is hereby corrected as shown below:

On the Title Page

In the Foreign Application Priority Data, Item (30):
Change:
"(30) Foreign Application Priority Data
Jun. 12, 2015 (GB)................1510357
Aug. 19, 2015 (GB)................1514772"

To:
--(30) Foreign Application Priority Data
Jun. 12, 2015 (GB)................1510357
Aug. 19, 2015 (GB)................1514772
Jun. 12, 2015 (EP) ................PCT/EP2015/063248--

In the Claims

Column 367, Lines 59-67, Claim 5:
Change:
"(b) an adenoviral EIA region, or a fragment thereof selected from among the E1A_280R and E1A_243R regions;
(c) an adenoviral EIB or IX region, or a fragment thereof, selected from the group consisting of the EIB_19K, E1B_55K and IX regions;
(d) an adenoviral E2b region; or a fragment thereof, selected from the group consisting of the E2B pTP, E2B Polymerase and E2B_IVa2 regions;"

To:
--(b) an adenoviral E1A region, or a fragment thereof selected from among the E1A_280R and E1A_243R regions;
(c) an adenoviral E1B or IX region, or a fragment thereof, selected from the group consisting of the E1B_19K, E1B_55K and IX regions;

Signed and Sealed this
Thirtieth Day of January, 2024

Katherine Kelly Vidal
*Director of the United States Patent and Trademark Office*

(d) an adenoviral E2b region; or a fragment thereof, selected from the group consisting of the E2B_pTP, E2B_Polymerase and E2B_IVa2 regions;--

Column 368, Lines 29-36, Claim 5:
Change:
"(e) an adenoviral L1 region, or a fragment thereof, said fragment encoding an adenoviral protein selected from the group consisting of the L1_13.6k protein, L1_52k and L1_Ia protein;
(f) an adenoviral L2 region, or a fragment thereof, said fragment encoding an adenoviral protein selected from the group consisting of the L2_penton protein, L2_pVIIL, L2_V, and L2_pX protein;"

To:
--(e) an adenoviral L1 region, or a fragment thereof, said fragment encoding an adenoviral protein selected from the group consisting of the L1_13.6k protein, L1_52k and L1_IIIa protein;
(f) an adenoviral L2 region, or a fragment thereof, said fragment encoding an adenoviral protein selected from the group consisting of the L2_penton protein, L2_pVII, L2_V, and L2_pX protein;--

Column 368, Lines 42-49, Claim 5:
Change:
"(i) ara adenoviral L4 region, or a fragment thereof, said fragment encoding an adenoviral protein selected from the group consisting of the L4_100k protein, the L4_33k protein and protein L4_VIII;
(j) an adenoviral E3 region, or a fragment thereof, selected from the group consisting of E3 ORR1, E3 ORF2, E3 ORF3, E3 ORF4, E3 ORFS, E3 ORF6, E3 ORF7, E3 ORF8, and E3 ORF9;"

To:
--(i) an adenoviral L4 region, or a fragment thereof, said fragment encoding an adenoviral protein selected from the group consisting of the L4_100k protein, the L4_33k protein and protein L4_VIII;
(j) an adenoviral E3 region, or a fragment thereof, selected from the group consisting of E3 ORF1, E3 ORF2, E3 ORF3, E3 ORF4, E3 ORF5, E3 ORF6, E3 ORF7, E3 ORF8, and E3 ORF9;--

Column 368, Lines 53-55, Claim 5:
Change:
"(l) an adenoviral E4 region, or a fragment thereof selected from the group consisting of E4 ORF7, E4 ORF6, E4 ORF4, E4 d ORF3, E4 ORF2, and E4 ORF1; and"

To:
--(l) an adenoviral E4 region, or a fragment thereof selected from the group consisting of E4 ORF7, E4 ORF6, E4 ORF4, E4 ORF3, E4 ORF2, and E4 ORF1; and--